(12) United States Patent
Kuo et al.

(10) Patent No.: US 11,155,630 B2
(45) Date of Patent: *Oct. 26, 2021

(54) THERAPEUTIC ANTIBODIES AND THEIR USES

(71) Applicant: PFIZER INC., New York, NY (US)

(72) Inventors: Tracy Chia-Chien Kuo, San Mateo, CA (US); Javier Fernando Chaparro Riggers, San Mateo, CA (US); Wei Chen, Cupertino, CA (US); Amy Shaw-Ru Chen, San Jose, CA (US); Edward Derrick Pascua, Oakland, CA (US); Thomas John Van Blarcom, Oakland, CA (US); Leila Marie Boustany, Redwood City, CA (US); Weihsien Ho, Belmont, CA (US); Yik Andy Yeung, South San Francisco, CA (US); Pavel Strop, San Mateo, CA (US); Arvind Rajpal, San Francisco, CA (US)

(73) Assignee: PFIZER INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/129,833

(22) Filed: Dec. 21, 2020

(65) Prior Publication Data

US 2021/0188991 A1 Jun. 24, 2021

Related U.S. Application Data

(60) Continuation of application No. 17/005,073, filed on Aug. 27, 2020, which is a division of application No. 16/017,974, filed on Jun. 25, 2018, now Pat. No. 10,793,635, which is a division of application No. 15/878,344, filed on Jan. 23, 2018, now Pat. No. 10,040,860, which is a division of application No. 15/085,644, filed on Mar. 30, 2016, now Pat. No. 9,969,809.

(60) Provisional application No. 62/146,843, filed on Apr. 13, 2015, provisional application No. 62/146,504, filed on Apr. 13, 2015, provisional application No. 62/301,582, filed on Feb. 29, 2016.

(51) Int. Cl.
| | | |
|---|---|---|
| *C07K 16/28* | (2006.01) | |
| *C07K 16/30* | (2006.01) | |
| *A61K 39/395* | (2006.01) | |
| *A61K 31/454* | (2006.01) | |
| *A61K 31/704* | (2006.01) | |
| *A61K 31/69* | (2006.01) | |
| *A61K 47/68* | (2017.01) | |
| *A61K 39/00* | (2006.01) | |

(52) U.S. Cl.
CPC ........ *C07K 16/2878* (2013.01); *A61K 31/454* (2013.01); *A61K 31/69* (2013.01); *A61K 31/704* (2013.01); *A61K 39/3955* (2013.01); *A61K 39/39558* (2013.01); *A61K 47/6801* (2017.08); *A61K 47/6849* (2017.08); *C07K 16/2803* (2013.01); *C07K 16/2809* (2013.01); *A61K 2039/505* (2013.01); *C07K 2317/21* (2013.01); *C07K 2317/31* (2013.01); *C07K 2317/56* (2013.01); *C07K 2317/565* (2013.01); *C07K 2317/73* (2013.01); *C07K 2317/732* (2013.01); *C07K 2317/92* (2013.01)

(58) Field of Classification Search
CPC ............ C07K 16/2878; C07K 16/2803; C07K 16/2809; C07K 2317/31
See application file for complete search history.

(56) References Cited

U.S. PATENT DOCUMENTS

| | | | |
|---|---|---|---|
| 7,083,785 B2 | 8/2006 | Browning et al. | |
| 7,351,803 B2* | 4/2008 | Johnson | A61P 37/02 530/387.1 |
| 9,243,058 B2 | 1/2016 | Armitage et al. | |
| 2008/0267965 A1 | 10/2008 | Kalled et al. | |
| 2012/0082661 A1 | 4/2012 | Kalled et al. | |
| 2013/0115208 A1* | 5/2013 | Ho | C07K 16/468 424/133.1 |
| 2015/0051266 A1 | 2/2015 | Kochenderfer | |
| 2015/0284467 A1 | 10/2015 | Lipp et al. | |
| 2015/0368351 A1 | 12/2015 | Vu et al. | |
| 2016/0297884 A1 | 10/2016 | Kuo et al. | |

FOREIGN PATENT DOCUMENTS

| | | |
|---|---|---|
| EP | 2762497 A1 | 8/2014 |
| EP | 3023437 A1 | 5/2016 |
| EP | 3029068 A1 | 6/2016 |
| WO | 2010104949 A2 | 9/2010 |
| WO | 2012066058 A1 | 5/2012 |
| WO | 2013072406 A1 | 5/2013 |
| WO | 2013072415 A1 | 5/2013 |
| WO | 2013/154760 A1 | 10/2013 |
| WO | 2013158856 A2 | 10/2013 |
| WO | 2014068079 A1 | 5/2014 |
| WO | 2014122144 A1 | 8/2014 |
| WO | 2014140248 A1 | 9/2014 |
| WO | 2015052536 A1 | 4/2015 |
| WO | 2015166073 A1 | 11/2015 |

OTHER PUBLICATIONS

Paul, Fundamental Immunology, 3rd Edition, 1993, pp. 292-295.*

(Continued)

*Primary Examiner* — Hong Sang
(74) *Attorney, Agent, or Firm* — Pfizer Inc.; Ye Hua

(57) ABSTRACT

The present invention relates to bispecific antibodies that specific bind to BCMA (B-Cell Maturation Antigen) and CD3 (Cluster of Differentiation 3). Method of making the bispecific antibodies and method of using the bispecific antibodies for the treatment of multiple myeloma are also provided.

14 Claims, 24 Drawing Sheets
Specification includes a Sequence Listing.

(56) References Cited

OTHER PUBLICATIONS

Rudikoff et al., Proc. Natl. Acad. Sci. USA, 1982, 79(6):1979-1983.*
Colman, Research in Immunology, 1994, 145:33-36.*
Bendig, Methods: A Companion to Methods in Enzymology, 1995; 8:83-93.*
Khantasup et al., Monoclonal Antibodies in Immunodiagnosis and Immunotherapy, 2015, 34(6): 404-417.*
International Search Report for International Application No. PCT/IB2016/051801 completed on Jun. 6, 2016.
Ramadoss, N., et al., "An Anti-B Cell Maturation Antigen Bispecific Antibody for Multiple Myeloma," Journal of the American Chemical Society, 2015, 5288-5291, vol. 137, No. 16.
Written Opinion for International Application No. PCT/IB2016/051801 completed on Jun. 6, 2016.

* cited by examiner

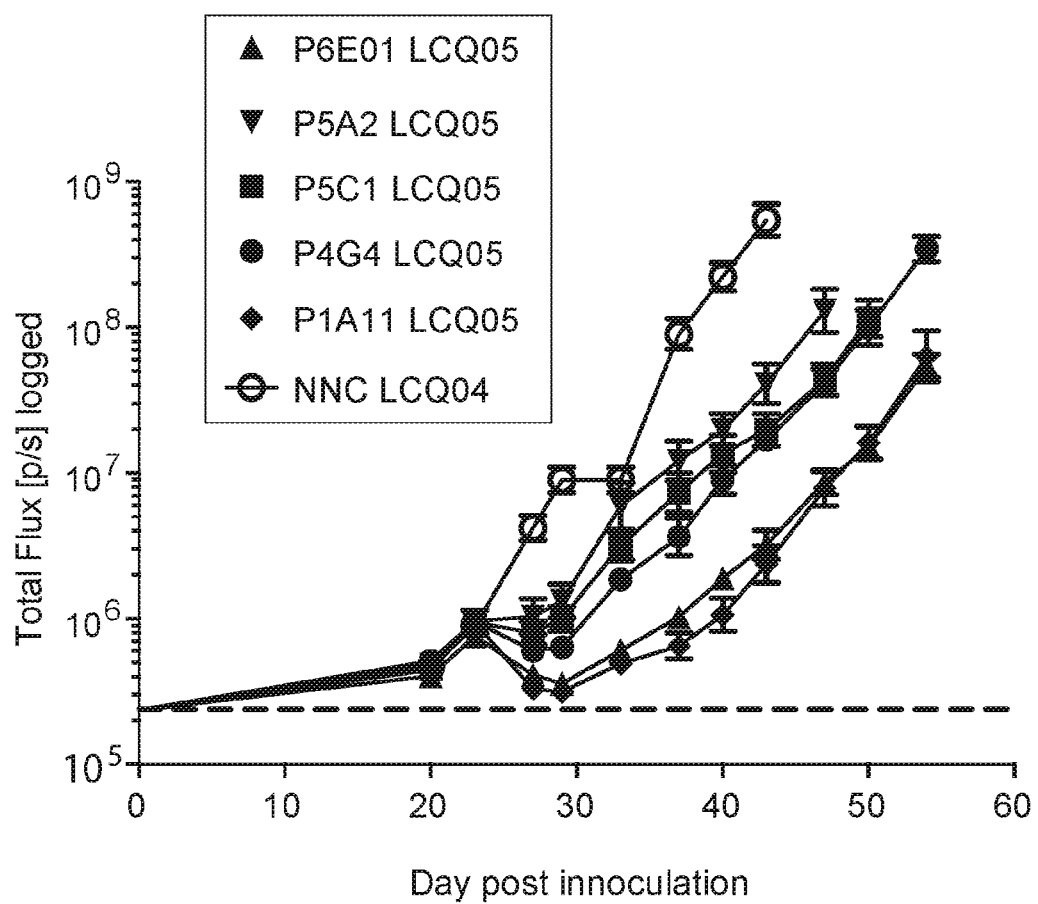

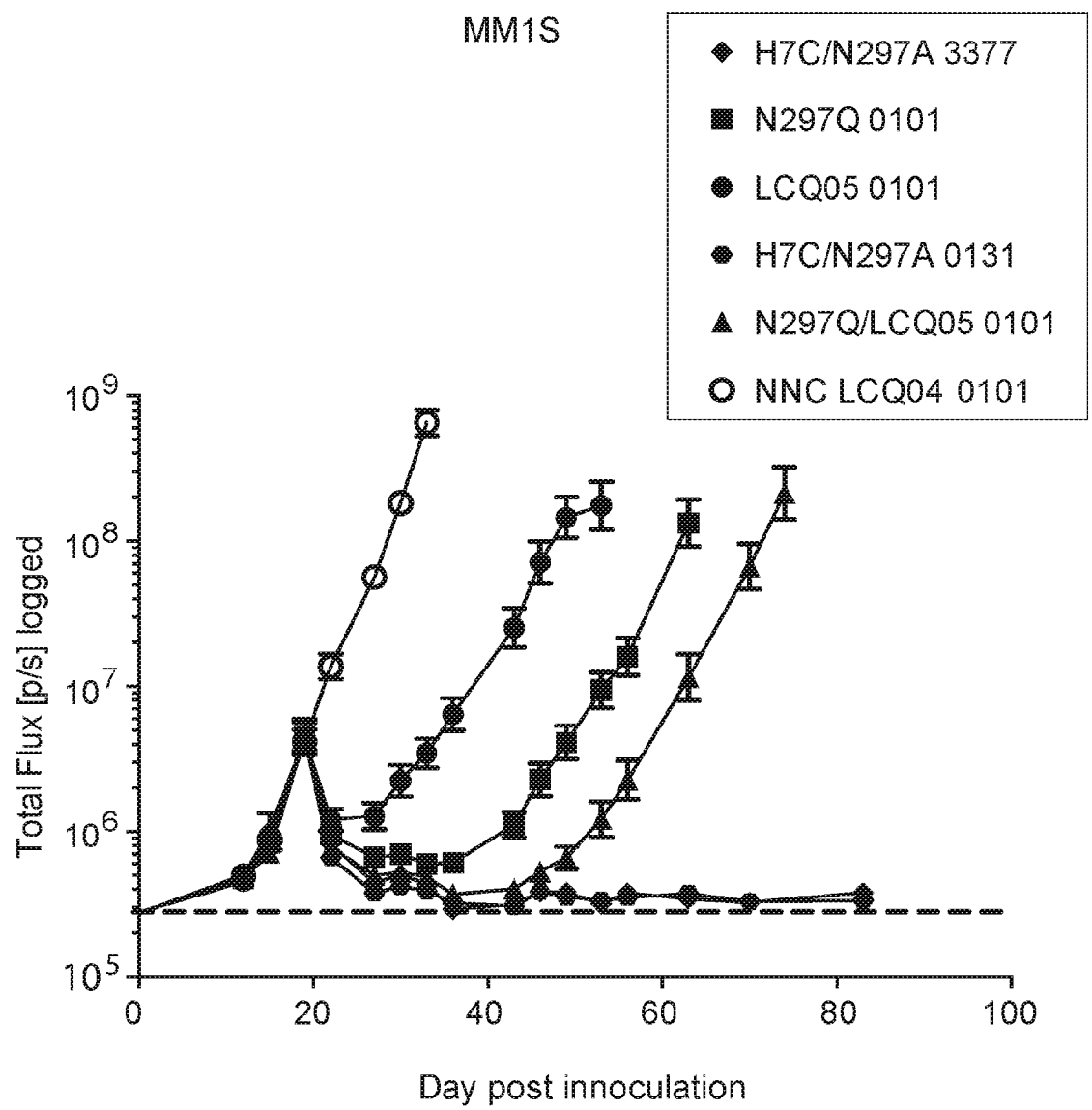

Cell Killing Comparison of h2B4 Variants; Day 2

Cell Killing Comparison of h2B4 Variants; Day 3

CD3: h2B4 vs. 25A8 Variants; Day 2
PanT as Effector/ SW480 as Target

CD3: h2B4 vs. 25A8 Variants; Day 3
PanT as Effector/ SW480 as Target

SEQUENCE LISTING

```
<160> NUMBER OF SEQ ID NOS: 504

<210> SEQ ID NO 1
<211> LENGTH: 109
<212> TYPE: PRT
<213> ORGANISM: Artificial Sequence
<220> FEATURE:
<223> OTHER INFORMATION: Synthetic Construct

<400> SEQUENCE: 1

Glu Ile Val Leu Thr Gln Ser Pro Gly Thr Leu Ser Leu Ser Pro Gly
1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Ser Pro Pro
                85                  90                  95

Ser Phe Thr Phe Gly Gln Gly Thr Lys Val Glu Ile Lys
            100                 105

<210> SEQ ID NO 2
<211> LENGTH: 119
<212> TYPE: PRT
<213> ORGANISM: Artificial Sequence
```

```
<220> FEATURE:
<223> OTHER INFORMATION: Synthetic Construct

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Ala Met Thr Trp Val Arg Gln Ala Pro Gly Lys Gly Leu Glu Trp Val
        35                  40                  45

Ser Ala Ile Ser Gly Ser Gly Gly Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ser Pro Ile Ala Ser Gly Met Asp Tyr Trp Gly Gln Gly
            100                 105                 110

Thr Leu Val Thr Val Ser Ser
        115

<210> SEQ ID NO 3
<211> LENGTH: 119
<212> TYPE: PRT
<213> ORGANISM: Artificial Sequence
<220> FEATURE:
<223> OTHER INFORMATION: Synthetic Construct

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Ala Met Thr Trp Val Arg Gln Ala Pro Gly Lys Gly Leu Glu Trp Val
        35                  40                  45

Ser Ala Ile Ser Gly Ser Gly Gly Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ser Pro Ile Ala Ala Gln Met Asp Tyr Trp Gly Gln Gly
            100                 105                 110

Thr Leu Val Thr Val Ser Ser
        115

<210> SEQ ID NO 4
<211> LENGTH: 109
<212> TYPE: PRT
<213> ORGANISM: Artificial Sequence
<220> FEATURE:
<223> OTHER INFORMATION: Synthetic Construct

<400> SEQUENCE: 4

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Phe
            20                  25                  30
```

```
Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Lys His Tyr Gly Trp Pro Pro
                 85                  90                  95

Ser Phe Thr Phe Gly Gln Gly Thr Lys Val Glu Ile Lys
            100                 105
```

<210> SEQ ID NO 5
<211> LENGTH: 109
<212> TYPE: PRT
<213> ORGANISM: Artificial Sequence
<220> FEATURE:
<223> OTHER INFORMATION: Synthetic Construct

<400> SEQUENCE: 5

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Leu Gly Ser Phe
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln His Tyr Asn Tyr Pro Pro
                 85                  90                  95

Ser Phe Thr Phe Gly Gln Gly Thr Lys Val Glu Ile Lys
            100                 105
```

<210> SEQ ID NO 6
<211> LENGTH: 109
<212> TYPE: PRT
<213> ORGANISM: Artificial Sequence
<220> FEATURE:
<223> OTHER INFORMATION: Synthetic Construct

<400> SEQUENCE: 6

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Gly Asp Phe
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln His Tyr Asn Tyr Pro Pro
                 85                  90                  95

Ser Phe Thr Phe Gly Gln Gly Thr Lys Val Glu Ile Lys
            100                 105
```

```
<210> SEQ ID NO 7
<211> LENGTH: 121
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Ala Met Thr Trp Val Arg Gln Ala Pro Gly Lys Gly Leu Glu Trp Val
        35                  40                  45

Ser Ala Ile Ser Gly Ser Gly Gly Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Arg Val Ser Pro Ile Ala Ala Leu Met Asp Tyr Trp Gly
            100                 105                 110

Gln Gly Thr Leu Val Thr Val Ser Ser
        115                 120

<210> SEQ ID NO 8
<211> LENGTH: 119
<212> TYPE: PRT
<213> ORGANISM: Artificial Sequence
<220> FEATURE:
<223> OTHER INFORMATION: Synthetic Construct

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Ala Met Thr Trp Val Arg Gln Ala Pro Gly Lys Gly Leu Glu Trp Val
        35                  40                  45

Ser Ala Ile Ser Gly Ser Gly Gly Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ser Pro Ile Ala Ala Pro Met Asp Tyr Trp Gly Gln Gly
            100                 105                 110

Thr Leu Val Thr Val Ser Ser
        115

<210> SEQ ID NO 9
<211> LENGTH: 109
<212> TYPE: PRT
<213> ORGANISM: Artificial Sequence
<220> FEATURE:
<223> OTHER INFORMATION: Synthetic Construct
```

```
<400> SEQUENCE: 9

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Phe
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Pro Tyr Pro Pro
                85                  90                  95

Ser Phe Thr Phe Gly Gln Gly Thr Lys Val Glu Ile Lys
            100                 105

<210> SEQ ID NO 10
<211> LENGTH: 109
<212> TYPE: PRT
<213> ORGANISM: Artificial Sequence
<220> FEATURE:
<223> OTHER INFORMATION: Synthetic Construct

<400> SEQUENCE: 10

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Phe
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Asn Tyr Pro Pro
                85                  90                  95

Ser Phe Thr Phe Gly Gln Gly Thr Lys Val Glu Ile Lys
            100                 105

<210> SEQ ID NO 11
<211> LENGTH: 109
<212> TYPE: PRT
<213> ORGANISM: Artificial Sequence
<220> FEATURE:
<223> OTHER INFORMATION: Synthetic Construct

<400> SEQUENCE: 11

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Asp Phe
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80
```

```
Pro Glu Asp Phe Ala Val Tyr Tyr Cys Lys His Tyr Gly Trp Pro Pro
                85                  90                  95

Ser Phe Thr Phe Gly Gln Gly Thr Lys Val Glu Ile Lys
                100                 105
```

<210> SEQ ID NO 12
<211> LENGTH: 109
<212> TYPE: PRT
<213> ORGANISM: Artificial Sequence
<220> FEATURE:
<223> OTHER INFORMATION: Synthetic Construct

<400> SEQUENCE: 12

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Asp Phe
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Pro Tyr Pro Pro
                85                  90                  95

Ser Phe Thr Phe Gly Gln Gly Thr Lys Val Glu Ile Lys
                100                 105
```

<210> SEQ ID NO 13
<211> LENGTH: 109
<212> TYPE: PRT
<213> ORGANISM: Artificial Sequence
<220> FEATURE:
<223> OTHER INFORMATION: Synthetic Construct

<400> SEQUENCE: 13

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Asp Phe
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Asn Tyr Pro Pro
                85                  90                  95

Ser Phe Thr Phe Gly Gln Gly Thr Lys Val Glu Ile Lys
                100                 105
```

<210> SEQ ID NO 14
<211> LENGTH: 109
<212> TYPE: PRT
<213> ORGANISM: Artificial Sequence
<220> FEATURE:
<223> OTHER INFORMATION: Synthetic Construct -continued

```
<400> SEQUENCE: 14

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Asp Phe
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Asn Tyr Pro Pro
                85                  90                  95

Ser Phe Thr Phe Gly Gln Gly Thr Lys Val Glu Ile Lys
            100                 105

<210> SEQ ID NO 15
<211> LENGTH: 109
<212> TYPE: PRT
<213> ORGANISM: Artificial Sequence
<220> FEATURE:
<223> OTHER INFORMATION: Synthetic Construct

<400> SEQUENCE: 15

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Lys His Tyr Gly Trp Pro Pro
                85                  90                  95

Ser Phe Thr Phe Gly Gln Gly Thr Lys Val Glu Ile Lys
            100                 105

<210> SEQ ID NO 16
<211> LENGTH: 109
<212> TYPE: PRT
<213> ORGANISM: Artificial Sequence
<220> FEATURE:
<223> OTHER INFORMATION: Synthetic Construct

<400> SEQUENCE: 16

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80
```

Pro Glu Asp Phe Ala Val Tyr Tyr Cys Gln His Tyr Pro Tyr Pro Pro
                85                  90                  95

Ser Phe Thr Phe Gly Gln Gly Thr Lys Val Glu Ile Lys
                100                 105

<210> SEQ ID NO 17
<211> LENGTH: 109
<212> TYPE: PRT
<213> ORGANISM: Artificial Sequence
<220> FEATURE:
<223> OTHER INFORMATION: Synthetic Construct

<400> SEQUENCE: 17

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Asn Tyr Pro Pro
                85                  90                  95

Ser Phe Thr Phe Gly Gln Gly Thr Lys Val Glu Ile Lys
                100                 105

<210> SEQ ID NO 18
<211> LENGTH: 109
<212> TYPE: PRT
<213> ORGANISM: Artificial Sequence
<220> FEATURE:
<223> OTHER INFORMATION: Synthetic Construct

<400> SEQUENCE: 18

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Pro Ser Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Pro Tyr Pro Pro
                85                  90                  95

Ser Phe Thr Phe Gly Gln Gly Thr Lys Val Glu Ile Lys
                100                 105

<210> SEQ ID NO 19
<211> LENGTH: 109
<212> TYPE: PRT
<213> ORGANISM: Artificial Sequence
<220> FEATURE:
<223> OTHER INFORMATION: Synthetic Construct

<400> SEQUENCE: 19

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ala His
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Pro Tyr Pro Pro
                85                  90                  95

Ser Phe Thr Phe Gly Gln Gly Thr Lys Val Glu Ile Lys
                100                 105
```

<210> SEQ ID NO 20
<211> LENGTH: 109
<212> TYPE: PRT
<213> ORGANISM: Artificial Sequence
<220> FEATURE:
<223> OTHER INFORMATION: Synthetic Construct

<400> SEQUENCE: 20

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Phe
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Pro Tyr Pro Pro
                85                  90                  95

Ser Phe Thr Phe Gly Gln Gly Thr Lys Val Glu Ile Lys
                100                 105
```

<210> SEQ ID NO 21
<211> LENGTH: 109
<212> TYPE: PRT
<213> ORGANISM: Artificial Sequence
<220> FEATURE:
<223> OTHER INFORMATION: Synthetic Construct

<400> SEQUENCE: 21

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Pro His
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80
```

```
Pro Glu Asp Phe Ala Val Tyr Tyr Cys Gln His Tyr Pro Tyr Pro Pro
                85                  90                  95

Ser Phe Thr Phe Gly Gln Gly Thr Lys Val Glu Ile Lys
            100                 105
```

<210> SEQ ID NO 22
<211> LENGTH: 109
<212> TYPE: PRT
<213> ORGANISM: Artificial Sequence
<220> FEATURE:
<223> OTHER INFORMATION: Synthetic Construct

<400> SEQUENCE: 22

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Lys Tyr Tyr Pro Tyr Pro Pro
                85                  90                  95

Ser Phe Thr Phe Gly Gln Gly Thr Lys Val Glu Ile Lys
            100                 105
```

<210> SEQ ID NO 23
<211> LENGTH: 109
<212> TYPE: PRT
<213> ORGANISM: Artificial Sequence
<220> FEATURE:
<223> OTHER INFORMATION: Synthetic Construct

<400> SEQUENCE: 23

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Lys Phe Tyr Pro Tyr Pro Pro
                85                  90                  95

Ser Phe Thr Phe Gly Gln Gly Thr Lys Val Glu Ile Lys
            100                 105
```

<210> SEQ ID NO 24
<211> LENGTH: 119
<212> TYPE: PRT
<213> ORGANISM: Artificial Sequence
<220> FEATURE:
<223> OTHER INFORMATION: Synthetic Construct

```
<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Ala Met Thr Trp Val Arg Gln Ala Pro Gly Lys Gly Leu Glu Trp Val
        35                  40                  45

Ser Ala Ile Ser Gly Ser Gly Asn Thr Phe Tyr Ala Asp Gln Arg
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ser Pro Ile Ala Ser Gly Met Asp Tyr Trp Gly Gln Gly
            100                 105                 110

Thr Leu Val Thr Val Ser Ser
        115

<210> SEQ ID NO 25
<211> LENGTH: 119
<212> TYPE: PRT
<213> ORGANISM: Artificial Sequence
<220> FEATURE:
<223> OTHER INFORMATION: Synthetic Construct

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Ala Met Thr Trp Val Arg Gln Ala Pro Gly Lys Gly Leu Glu Trp Val
        35                  40                  45

Ser Ala Ile Asp Tyr Ser Gly Gly Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ser Pro Ile Ala Ser Gly Met Asp Tyr Trp Gly Gln Gly
            100                 105                 110

Thr Leu Val Thr Val Ser Ser
        115

<210> SEQ ID NO 26
<211> LENGTH: 119
<212> TYPE: PRT
<213> ORGANISM: Artificial Sequence
<220> FEATURE:
<223> OTHER INFORMATION: Synthetic Construct

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Ala Met Thr Trp Val Arg Gln Ala Pro Gly Lys Gly Leu Glu Trp Val
        35                  40                  45
```

```
Ser Ala Ile Ser Tyr Gln Gly Gly Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ser Pro Ile Ala Ser Gly Met Asp Tyr Trp Gly Gln Gly
                100                 105                 110

Thr Leu Val Thr Val Ser Ser
        115
```

<210> SEQ ID NO 27
<211> LENGTH: 119
<212> TYPE: PRT
<213> ORGANISM: Artificial Sequence
<220> FEATURE:
<223> OTHER INFORMATION: Synthetic Construct

<400> SEQUENCE: 27

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
                20                  25                  30

Ala Met Thr Trp Val Arg Gln Ala Pro Gly Lys Gly Leu Glu Trp Val
            35                  40                  45

Ser Ala Ile Ser Leu Thr Gly Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ser Pro Ile Ala Ser Gly Met Asp Tyr Trp Gly Gln Gly
                100                 105                 110

Thr Leu Val Thr Val Ser Ser
        115
```

<210> SEQ ID NO 28
<211> LENGTH: 119
<212> TYPE: PRT
<213> ORGANISM: Artificial Sequence
<220> FEATURE:
<223> OTHER INFORMATION: Synthetic Construct

<400> SEQUENCE: 28

```
Glu Val Gln Leu Leu Glu Ser Gly Gly Gly Leu Val Gln Pro Gly Gly
1               5                   10                  15

Ser Leu Arg Leu Ser Cys Ala Ser Gly Phe Thr Phe Gly Ser Tyr
                20                  25                  30

Ala Met Thr Trp Val Arg Gln Ala Pro Gly Lys Gly Leu Glu Trp Val
            35                  40                  45

Ser Ala Ile Ser His Ala Gly Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Val Ser Pro Ile Ala Ser Gly Met Asp Tyr Trp Gly Gln Gly
            100                 105                 110

Thr Leu Val Thr Val Ser Ser
        115

<210> SEQ ID NO 29
<211> LENGTH: 119
<212> TYPE: PRT
<213> ORGANISM: Artificial Sequence
<220> FEATURE:
<223> OTHER INFORMATION: Synthetic Construct

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Ala Met Thr Trp Val Arg Gln Ala Pro Gly Lys Gly Leu Glu Trp Val
        35                  40                  45

Ser Ala Ile Ser Gly Ser Gly Gly Asn Thr Phe Tyr Ala Asp Gln Leu
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ser Pro Ile Ala Ser Gly Met Asp Tyr Trp Gly Gln Gly
            100                 105                 110

Thr Leu Val Thr Val Ser Ser
        115

<210> SEQ ID NO 30
<211> LENGTH: 119
<212> TYPE: PRT
<213> ORGANISM: Artificial Sequence
<220> FEATURE:
<223> OTHER INFORMATION: Synthetic Construct

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Ala Met Thr Trp Val Arg Gln Ala Pro Gly Lys Gly Leu Glu Trp Val
        35                  40                  45

Ser Ala Ile Ser Gly Ser Gly Gly Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ser Pro Ile Tyr Ala Gly Met Asp Tyr Trp Gly Gln Gly
            100                 105                 110

Thr Leu Val Thr Val Ser Ser
        115

<210> SEQ ID NO 31
<211> LENGTH: 119
<212> TYPE: PRT
<213> ORGANISM: Artificial Sequence

```
<220> FEATURE:
<223> OTHER INFORMATION: Synthetic Construct

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Ala Met Thr Trp Val Arg Gln Ala Pro Gly Lys Gly Leu Glu Trp Val
        35                  40                  45

Ser Ala Ile Ser Gly Ser Gly Gly Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ser Pro Ile Ala Ala Glu Met Asp Tyr Trp Gly Gln Gly
            100                 105                 110

Thr Leu Val Thr Val Ser Ser
        115

<210> SEQ ID NO 32
<211> LENGTH: 119
<212> TYPE: PRT
<213> ORGANISM: Artificial Sequence
<220> FEATURE:
<223> OTHER INFORMATION: Synthetic Construct

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Ala Met Thr Trp Val Arg Gln Ala Pro Gly Lys Gly Leu Glu Trp Val
        35                  40                  45

Ser Ala Ile Ser Gly Ser Gly Gly Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Val Ser Pro Ile Ala Ala Gln Met Asp Tyr Trp Gly Gln Gly
            100                 105                 110

Thr Leu Val Thr Val Ser Ser
        115

<210> SEQ ID NO 33
<211> LENGTH: 115
<212> TYPE: PRT
<213> ORGANISM: Artificial Sequence
<220> FEATURE:
<223> OTHER INFORMATION: Synthetic Construct

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Ala Met Asn Trp Val Arg Gln Ala Pro Gly Lys Gly Leu Glu Trp Val
        35                  40                  45

Ser Ala Ile Ser Asp Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ile Trp Gly Gln Gly Thr Leu Val Thr
            100                 105                 110

Val Ser Ser
        115

<210> SEQ ID NO 34
<211> LENGTH: 108
<212> TYPE: PRT
<213> ORGANISM: Artificial Sequence
<220> FEATURE:
<223> OTHER INFORMATION: Synthetic Construct

<400> SEQUENCE: 34

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Trp Pro
                85                  90                  95

Leu Thr Phe Gly Gln Gly Thr Lys Val Glu Ile Lys
            100                 105

<210> SEQ ID NO 35
<211> LENGTH: 115
<212> TYPE: PRT
<213> ORGANISM: Artificial Sequence
<220> FEATURE:
<223> OTHER INFORMATION: Synthetic Construct

<400> SEQUENCE: 35

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Asp Ser Gly Ser Ala Trp Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95
```

```
Ala Arg Tyr Trp Pro Met Ser Leu Trp Gly Gln Gly Thr Leu Val Thr
            100                 105                 110

Val Ser Ser
        115

<210> SEQ ID NO 36
<211> LENGTH: 108
<212> TYPE: PRT
<213> ORGANISM: Artificial Sequence
<220> FEATURE:
<223> OTHER INFORMATION: Synthetic Construct

<400> SEQUENCE: 36

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Val Leu
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gln Arg Trp Pro
                85                  90                  95

Leu Thr Phe Gly Gln Gly Thr Lys Val Glu Ile Lys
            100                 105

<210> SEQ ID NO 37
<211> LENGTH: 115
<212> TYPE: PRT
<213> ORGANISM: Artificial Sequence
<220> FEATURE:
<223> OTHER INFORMATION: Synthetic Construct

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Asp Ser Gly Gly Ser Met Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Ser Leu Trp Gly Gln Gly Thr Leu Val Thr
            100                 105                 110

Val Ser Ser
        115

<210> SEQ ID NO 38
<211> LENGTH: 108
<212> TYPE: PRT
<213> ORGANISM: Artificial Sequence
<220> FEATURE:
<223> OTHER INFORMATION: Synthetic Construct
```

<400> SEQUENCE: 38

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gln Ser Trp Pro
                85                  90                  95

Leu Thr Phe Gly Gln Gly Thr Lys Val Glu Ile Lys
            100                 105

<210> SEQ ID NO 39
<211> LENGTH: 115
<212> TYPE: PRT
<213> ORGANISM: Artificial Sequence
<220> FEATURE:
<223> OTHER INFORMATION: Synthetic Construct

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Asp Phe Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ile Trp Gly Gln Gly Thr Leu Val Thr
            100                 105                 110

Val Ser Ser
    115

<210> SEQ ID NO 40
<211> LENGTH: 108
<212> TYPE: PRT
<213> ORGANISM: Artificial Sequence
<220> FEATURE:
<223> OTHER INFORMATION: Synthetic Construct

<400> SEQUENCE: 40

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asp Leu
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

```
Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gln Thr Trp Pro
                85                  90                  95

Leu Thr Phe Gly Gln Gly Thr Lys Val Glu Ile Lys
            100                 105
```

<210> SEQ ID NO 41
<211> LENGTH: 108
<212> TYPE: PRT
<213> ORGANISM: Artificial Sequence
<220> FEATURE:
<223> OTHER INFORMATION: Synthetic Construct

<400> SEQUENCE: 41

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Leu
                20                  25                  30

Tyr Leu Ala Trp Tyr Gln Gln Lys Pro Gly Gln Ala Pro Arg Leu Leu
            35                  40                  45

Met Tyr Asp Ala Ser Ile Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gln Gly Trp Pro
                85                  90                  95

Leu Thr Phe Gly Gln Gly Thr Lys Val Glu Ile Lys
            100                 105
```

<210> SEQ ID NO 42
<211> LENGTH: 115
<212> TYPE: PRT
<213> ORGANISM: Artificial Sequence
<220> FEATURE:
<223> OTHER INFORMATION: Synthetic Construct

<400> SEQUENCE: 42

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Asn Trp Val Arg Gln Ala Pro Gly Lys Gly Leu Glu Trp Val
            35                  40                  45

Ser Ala Ile Thr Ala Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Ser Leu Trp Gly Gln Gly Thr Leu Val Thr
            100                 105                 110

Val Ser Ser
        115
```

<210> SEQ ID NO 43
<211> LENGTH: 108
<212> TYPE: PRT
<213> ORGANISM: Artificial Sequence

```
<220> FEATURE:
<223> OTHER INFORMATION: Synthetic Construct

<400> SEQUENCE: 43

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ala Tyr
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Glu Arg Trp Pro
                85                  90                  95

Leu Thr Phe Gly Gln Gly Thr Lys Val Glu Ile Lys
            100                 105

<210> SEQ ID NO 44
<211> LENGTH: 115
<212> TYPE: PRT
<213> ORGANISM: Artificial Sequence
<220> FEATURE:
<223> OTHER INFORMATION: Synthetic Construct

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Asp Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Ser Leu Trp Gly Gln Gly Thr Leu Val Thr
            100                 105                 110

Val Ser Ser
        115

<210> SEQ ID NO 45
<211> LENGTH: 108
<212> TYPE: PRT
<213> ORGANISM: Artificial Sequence
<220> FEATURE:
<223> OTHER INFORMATION: Synthetic Construct

<400> SEQUENCE: 45

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Leu
            20                  25                  30

Tyr Leu Ala Trp Tyr Gln Gln Lys Pro Gly Gln Ala Pro Arg Leu Leu
        35                  40                  45
```

Met Tyr Asp Ala Ser Ile Arg Ala Thr Gly Ile Pro Asp Arg Phe Ser
            50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gln Val Trp Pro
                 85                  90                  95

Leu Thr Phe Gly Gln Gly Thr Lys Val Glu Ile Lys
            100                 105

<210> SEQ ID NO 46
<211> LENGTH: 115
<212> TYPE: PRT
<213> ORGANISM: Artificial Sequence
<220> FEATURE:
<223> OTHER INFORMATION: Synthetic Construct

<400> SEQUENCE: 46

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
             20                  25                  30

Ala Met Asn Trp Val Arg Gln Ala Pro Gly Lys Gly Leu Glu Trp Val
         35                  40                  45

Ser Ala Ile Ser Asp Ser Gly Gly Ser Arg Trp Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Trp Pro Met Thr Pro Trp Gly Gln Gly Thr Leu Val Thr
            100                 105                 110

Val Ser Ser
        115

<210> SEQ ID NO 47
<211> LENGTH: 108
<212> TYPE: PRT
<213> ORGANISM: Artificial Sequence
<220> FEATURE:
<223> OTHER INFORMATION: Synthetic Construct

<400> SEQUENCE: 47

Glu Ile Val Leu Thr Gln Ser Pro Gly Thr Leu Ser Leu Ser Pro Gly
 1               5                   10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Met Tyr Asp Ala Ser Ile Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Leu Asp Trp Pro
                 85                  90                  95

Leu Thr Phe Gly Gln Gly Thr Lys Val Glu Ile Lys
            100                 105

<210> SEQ ID NO 48
<211> LENGTH: 115
<212> TYPE: PRT
<213> ORGANISM: Artificial Sequence
<220> FEATURE:
<223> OTHER INFORMATION: Synthetic Construct

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Val Leu Asp Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Thr Pro Trp Gly Gln Gly Thr Leu Val Thr
            100                 105                 110

Val Ser Ser
        115

<210> SEQ ID NO 49
<211> LENGTH: 108
<212> TYPE: PRT
<213> ORGANISM: Artificial Sequence
<220> FEATURE:
<223> OTHER INFORMATION: Synthetic Construct

<400> SEQUENCE: 49

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gln Val Trp Pro
                85                  90                  95

Leu Thr Phe Gly Gln Gly Thr Lys Val Glu Ile Lys
            100                 105

<210> SEQ ID NO 50
<211> LENGTH: 115
<212> TYPE: PRT
<213> ORGANISM: Artificial Sequence
<220> FEATURE:
<223> OTHER INFORMATION: Synthetic Construct

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

```
Ala Met Asn Trp Val Arg Gln Ala Pro Gly Lys Gly Leu Glu Trp Val
            35                  40                  45

Ser Ala Ile Ser Asp Ser Gly Gly Ser Arg Trp Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Trp Pro Met Ser Asp Trp Gly Gln Gly Thr Leu Val Thr
            100                 105                 110

Val Ser Ser
        115

<210> SEQ ID NO 51
<211> LENGTH: 108
<212> TYPE: PRT
<213> ORGANISM: Artificial Sequence
<220> FEATURE:
<223> OTHER INFORMATION: Synthetic Construct

<400> SEQUENCE: 51

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Val Leu
            20                  25                  30

Tyr Leu Ala Trp Tyr Gln Gln Lys Pro Gly Gln Ala Pro Arg Leu Leu
            35                  40                  45

Met Tyr Asp Ala Ser Ile Arg Ala Thr Gly Ile Pro Asp Arg Phe Ser
 50                      55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Leu Ala Trp Pro
                 85                  90                  95

Leu Thr Phe Gly Gln Gly Thr Lys Val Glu Ile Lys
            100                 105

<210> SEQ ID NO 52
<211> LENGTH: 115
<212> TYPE: PRT
<213> ORGANISM: Artificial Sequence
<220> FEATURE:
<223> OTHER INFORMATION: Synthetic Construct

<400> SEQUENCE: 52

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Ser Ala Ile Ser Asp Ser Gly Gly Ser Lys Trp Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

Ala Arg Tyr Trp Pro Met Ser Leu Trp Gly Gln Gly Thr Leu Val Thr
            100                 105                 110

Val Ser Ser
        115

<210> SEQ ID NO 53
<211> LENGTH: 108
<212> TYPE: PRT
<213> ORGANISM: Artificial Sequence
<220> FEATURE:
<223> OTHER INFORMATION: Synthetic Construct

<400> SEQUENCE: 53

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Phe Thr Trp Pro
                85                  90                  95

Leu Thr Phe Gly Gln Gly Thr Lys Val Glu Ile Lys
            100                 105

<210> SEQ ID NO 54
<211> LENGTH: 115
<212> TYPE: PRT
<213> ORGANISM: Artificial Sequence
<220> FEATURE:
<223> OTHER INFORMATION: Synthetic Construct

<400> SEQUENCE: 54

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Gly Gly Ser Gly Gly Ser Leu Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ser Trp Gly Gln Gly Thr Leu Val Thr
            100                 105                 110

Val Ser Ser
        115

<210> SEQ ID NO 55
<211> LENGTH: 108
<212> TYPE: PRT
<213> ORGANISM: Artificial Sequence
<220> FEATURE:
<223> OTHER INFORMATION: Synthetic Construct -continued

<400> SEQUENCE: 55

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Pro Tyr
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Glu Arg Trp Pro
                85                  90                  95

Leu Thr Phe Gly Gln Gly Thr Lys Val Glu Ile Lys
            100                 105

<210> SEQ ID NO 56
<211> LENGTH: 115
<212> TYPE: PRT
<213> ORGANISM: Artificial Sequence
<220> FEATURE:
<223> OTHER INFORMATION: Synthetic Construct

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Asp Ser Gly Gly Ser Gly Trp Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Ser Leu Trp Gly Gln Gly Thr Leu Val Thr
            100                 105                 110

Val Ser Ser
    115

<210> SEQ ID NO 57
<211> LENGTH: 108
<212> TYPE: PRT
<213> ORGANISM: Artificial Sequence
<220> FEATURE:
<223> OTHER INFORMATION: Synthetic Construct

<400> SEQUENCE: 57

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Val Glu
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
50                  55                  60

```
Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Arg Trp Pro
                85                  90                  95

Leu Thr Phe Gly Gln Gly Thr Lys Val Glu Ile Lys
            100                 105
```

<210> SEQ ID NO 58
<211> LENGTH: 115
<212> TYPE: PRT
<213> ORGANISM: Artificial Sequence
<220> FEATURE:
<223> OTHER INFORMATION: Synthetic Construct

<400> SEQUENCE: 58

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Val Leu Asp Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Ser Leu Trp Gly Gln Gly Thr Leu Val Thr
            100                 105                 110

Val Ser Ser
        115
```

<210> SEQ ID NO 59
<211> LENGTH: 108
<212> TYPE: PRT
<213> ORGANISM: Artificial Sequence
<220> FEATURE:
<223> OTHER INFORMATION: Synthetic Construct

<400> SEQUENCE: 59

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Glu Leu
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Phe Gly Trp Pro
                85                  90                  95

Leu Thr Phe Gly Gln Gly Thr Lys Val Glu Ile Lys
            100                 105
```

<210> SEQ ID NO 60
<211> LENGTH: 115
<212> TYPE: PRT
<213> ORGANISM: Artificial Sequence -continued

```
<220> FEATURE:
<223> OTHER INFORMATION: Synthetic Construct

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Asp Ser Gly Gly Ser Cys Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Thr Pro Trp Gly Gln Gly Thr Leu Val Thr
            100                 105                 110

Val Ser Ser
        115

<210> SEQ ID NO 61
<211> LENGTH: 108
<212> TYPE: PRT
<213> ORGANISM: Artificial Sequence
<220> FEATURE:
<223> OTHER INFORMATION: Synthetic Construct

<400> SEQUENCE: 61

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Glu Met Ser
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala His Trp Pro
                85                  90                  95

Leu Thr Phe Gly Gln Gly Thr Lys Val Glu Ile Lys
            100                 105

<210> SEQ ID NO 62
<211> LENGTH: 115
<212> TYPE: PRT
<213> ORGANISM: Artificial Sequence
<220> FEATURE:
<223> OTHER INFORMATION: Synthetic Construct

<400> SEQUENCE: 62

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45
```

```
Ser Ala Ile Phe Ala Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Thr Pro Trp Gly Gln Gly Thr Leu Val Thr
                100                 105                 110

Val Ser Ser
        115

<210> SEQ ID NO 63
<211> LENGTH: 108
<212> TYPE: PRT
<213> ORGANISM: Artificial Sequence
<220> FEATURE:
<223> OTHER INFORMATION: Synthetic Construct

<400> SEQUENCE: 63

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Met Tyr Asp Ala Ser Ile Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gln Arg Trp Pro
                85                  90                  95

Leu Thr Phe Gly Gln Gly Thr Lys Val Glu Ile Lys
                100                 105

<210> SEQ ID NO 64
<211> LENGTH: 115
<212> TYPE: PRT
<213> ORGANISM: Artificial Sequence
<220> FEATURE:
<223> OTHER INFORMATION: Synthetic Construct

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Asn Trp Val Arg Gln Ala Pro Gly Lys Gly Leu Glu Trp Val
            35                  40                  45

Ser Ala Ile Ser Gly Trp Gly Gly Ser Leu Pro Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ser Trp Gly Gln Gly Thr Leu Val Thr
                100                 105                 110

Val Ser Ser
        115
```

-continued

```
<210> SEQ ID NO 65
<211> LENGTH: 108
<212> TYPE: PRT
<213> ORGANISM: Artificial Sequence
<220> FEATURE:
<223> OTHER INFORMATION: Synthetic Construct

<400> SEQUENCE: 65

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ala Gln
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Arg Trp Pro
                85                  90                  95

Leu Thr Phe Gly Gln Gly Thr Lys Val Glu Ile Lys
            100                 105

<210> SEQ ID NO 66
<211> LENGTH: 115
<212> TYPE: PRT
<213> ORGANISM: Artificial Sequence
<220> FEATURE:
<223> OTHER INFORMATION: Synthetic Construct

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Met Ser Ser Gly Gly Pro Leu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Ala Leu Trp Gly Gln Gly Thr Leu Val Thr
            100                 105                 110

Val Ser Ser
        115

<210> SEQ ID NO 67
<211> LENGTH: 108
<212> TYPE: PRT
<213> ORGANISM: Artificial Sequence
<220> FEATURE:
<223> OTHER INFORMATION: Synthetic Construct

<400> SEQUENCE: 67

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ala Leu
            20                  25                  30
```

Tyr Leu Ala Trp Tyr Gln Gln Lys Pro Gly Gln Ala Pro Arg Leu Leu
            35                  40                  45

Met Tyr Asp Ala Ser Ile Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gln Val Trp Pro
                 85                  90                  95

Leu Thr Phe Gly Gln Gly Thr Lys Val Glu Ile Lys
            100                 105

<210> SEQ ID NO 68
<211> LENGTH: 115
<212> TYPE: PRT
<213> ORGANISM: Artificial Sequence
<220> FEATURE:
<223> OTHER INFORMATION: Synthetic Construct

<400> SEQUENCE: 68

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Asn Trp Val Arg Gln Ala Pro Gly Lys Gly Leu Glu Trp Val
         35                  40                  45

Ser Ala Ile Leu Met Ser Gly Gly Ser Thr Tyr Tyr Ala Asp Ser Val
 50                  55                  60

Lys Gly Arg Phe Thr Ile Ser Arg Asp Asn Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Trp Pro Met Ser Leu Trp Gly Gln Gly Thr Leu Val Thr
            100                 105                 110

Val Ser Ser
        115

<210> SEQ ID NO 69
<211> LENGTH: 108
<212> TYPE: PRT
<213> ORGANISM: Artificial Sequence
<220> FEATURE:
<223> OTHER INFORMATION: Synthetic Construct

<400> SEQUENCE: 69

Glu Ile Val Leu Thr Gln Ser Pro Gly Thr Leu Ser Leu Ser Pro Gly
 1               5                  10                  15

Glu Arg Ala Thr Leu Ser Cys Gly Pro Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Met Tyr Asp Ala Ser Ile Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gln Ser Trp Pro
                 85                  90                  95

Leu Thr Phe Gly Gln Gly Thr Lys Val Glu Ile Lys
            100                 105

<210> SEQ ID NO 70
<211> LENGTH: 115
<212> TYPE: PRT
<213> ORGANISM: Artificial Sequence
<220> FEATURE:
<223> OTHER INFORMATION: Synthetic Construct

<400> SEQUENCE: 70

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Asp Ser Gly Gly Tyr Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Ser Leu Trp Gly Gln Gly Thr Leu Val Thr
            100                 105                 110

Val Ser Ser
        115
```

<210> SEQ ID NO 71
<211> LENGTH: 108
<212> TYPE: PRT
<213> ORGANISM: Artificial Sequence
<220> FEATURE:
<223> OTHER INFORMATION: Synthetic Construct

<400> SEQUENCE: 71

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Trp Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Glu Ser Trp Pro
                85                  90                  95

Leu Thr Phe Gly Gln Gly Thr Lys Val Glu Ile Lys
            100                 105
```

<210> SEQ ID NO 72
<211> LENGTH: 115
<212> TYPE: PRT
<213> ORGANISM: Artificial Sequence
<220> FEATURE:
<223> OTHER INFORMATION: Synthetic Construct

<400> SEQUENCE: 72

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

Ala Met Asn Trp Val Arg Gln Ala Pro Gly Lys Gly Leu Glu Trp Val
         35                  40                  45

Ser Ala Ile Leu Ser Ser Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Tyr Trp Pro Met Asp Ile Trp Gly Gln Gly Thr Leu Val Thr
            100                 105                 110

Val Ser Ser
    115

<210> SEQ ID NO 73
<211> LENGTH: 108
<212> TYPE: PRT
<213> ORGANISM: Artificial Sequence
<220> FEATURE:
<223> OTHER INFORMATION: Synthetic Construct

<400> SEQUENCE: 73

Glu Ile Val Leu Thr Gln Ser Pro Gly Thr Leu Ser Leu Ser Pro Gly
 1               5                  10                  15

Glu Arg Ala Thr Leu Ser Cys Arg Gly Gly Gln Ser Val Ser Ser Ser
             20                  25                  30

Tyr Leu Ala Trp Tyr Gln Gln Lys Pro Gly Gln Ala Pro Arg Leu Leu
         35                  40                  45

Met Tyr Asp Ala Ser Ile Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gln Ser Trp Pro
             85                  90                  95

Leu Thr Phe Gly Gln Gly Thr Lys Val Glu Ile Lys
            100                 105

<210> SEQ ID NO 74
<211> LENGTH: 115
<212> TYPE: PRT
<213> ORGANISM: Artificial Sequence
<220> FEATURE:
<223> OTHER INFORMATION: Synthetic Construct

<400> SEQUENCE: 74

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Asn Trp Val Arg Gln Ala Pro Gly Lys Gly Leu Glu Trp Val
         35                  40                  45

Ser Ala Ile Leu Asp Ser Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

```
Ala Arg Tyr Trp Pro Met Ser Pro Trp Gly Gln Gly Thr Leu Val Thr
            100                 105                 110

Val Ser Ser
        115

<210> SEQ ID NO 75
<211> LENGTH: 108
<212> TYPE: PRT
<213> ORGANISM: Artificial Sequence
<220> FEATURE:
<223> OTHER INFORMATION: Synthetic Construct

<400> SEQUENCE: 75

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Phe Leu
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Trp Pro
                85                  90                  95

Leu Thr Phe Gly Gln Gly Thr Lys Val Glu Ile Lys
            100                 105

<210> SEQ ID NO 76
<211> LENGTH: 115
<212> TYPE: PRT
<213> ORGANISM: Artificial Sequence
<220> FEATURE:
<223> OTHER INFORMATION: Synthetic Construct

<400> SEQUENCE: 76

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Val
        35                  40                  45

Ser Ala Ile Gly Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Trp Gly Gln Gly Thr Leu Val Thr
            100                 105                 110

Val Ser Ser
        115

<210> SEQ ID NO 77
<211> LENGTH: 108
<212> TYPE: PRT
<213> ORGANISM: Artificial Sequence
<220> FEATURE:
<223> OTHER INFORMATION: Synthetic Construct
```

-continued

<400> SEQUENCE: 77

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Thr Ser Pro
                85                  90                  95

Leu Thr Phe Gly Gln Gly Thr Lys Val Glu Ile Lys
            100                 105

<210> SEQ ID NO 78
<211> LENGTH: 115
<212> TYPE: PRT
<213> ORGANISM: Artificial Sequence
<220> FEATURE:
<223> OTHER INFORMATION: Synthetic Construct

<400> SEQUENCE: 78

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Val
        35                  40                  45

Ser Ala Ile Gly Gly Ser Gly Gly Ser Leu Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ser Trp Gly Gln Gly Thr Leu Val Thr
            100                 105                 110

Val Ser Ser
        115

<210> SEQ ID NO 79
<211> LENGTH: 108
<212> TYPE: PRT
<213> ORGANISM: Artificial Sequence
<220> FEATURE:
<223> OTHER INFORMATION: Synthetic Construct

<400> SEQUENCE: 79

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Pro Glu
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Val Trp Pro
                85                  90                  95

Leu Thr Phe Gly Gln Gly Thr Lys Val Glu Ile Lys
                100                 105

<210> SEQ ID NO 80
<211> LENGTH: 109
<212> TYPE: PRT
<213> ORGANISM: Artificial Sequence
<220> FEATURE:
<223> OTHER INFORMATION: Synthetic Construct

<400> SEQUENCE: 80

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Tyr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Ser Pro Pro
                85                  90                  95

Leu Phe Thr Phe Gly Gln Gly Thr Lys Val Glu Ile Lys
                100                 105

<210> SEQ ID NO 81
<211> LENGTH: 108
<212> TYPE: PRT
<213> ORGANISM: Artificial Sequence
<220> FEATURE:
<223> OTHER INFORMATION: Synthetic Construct

<400> SEQUENCE: 81

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
                20                  25                  30

Tyr Leu Ala Trp Tyr Gln Gln Lys Pro Gly Gln Ala Pro Arg Leu Leu
            35                  40                  45

Ile Tyr Asp Ala Ser Ser Arg Ala Pro Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Arg Trp Pro
                85                  90                  95

Leu Thr Phe Gly Gln Gly Thr Lys Val Glu Ile Lys
                100                 105

<210> SEQ ID NO 82
<211> LENGTH: 108
<212> TYPE: PRT
<213> ORGANISM: Artificial Sequence
<220> FEATURE:
<223> OTHER INFORMATION: Synthetic Construct

```
<400> SEQUENCE: 82

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Pro Leu
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ala Phe Pro
                85                  90                  95

Leu Thr Phe Gly Gln Gly Thr Lys Val Glu Ile Lys
            100                 105

<210> SEQ ID NO 83
<211> LENGTH: 115
<212> TYPE: PRT
<213> ORGANISM: Artificial Sequence
<220> FEATURE:
<223> OTHER INFORMATION: Synthetic Construct

<400> SEQUENCE: 83

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Val
        35                  40                  45

Ser Ala Ile Gly Gly Ser Gly Gly Trp Ser Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ser Trp Gly Gln Gly Thr Leu Val Thr
            100                 105                 110

Val Ser Ser
        115

<210> SEQ ID NO 84
<211> LENGTH: 108
<212> TYPE: PRT
<213> ORGANISM: Artificial Sequence
<220> FEATURE:
<223> OTHER INFORMATION: Synthetic Construct

<400> SEQUENCE: 84

Glu Ile Val Leu Thr Gln Ser Pro Gly Thr Leu Ser Leu Ser Pro Gly
1               5                   10                  15

Glu Arg Ala Thr Leu Ser Cys Trp Leu Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Pro Gly Ile Pro Asp Arg Phe Ser
    50                  55                  60
```

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Glu Trp Pro
                85                  90                  95

Leu Thr Phe Gly Gln Gly Thr Lys Val Glu Ile Lys
            100                 105

<210> SEQ ID NO 85
<211> LENGTH: 108
<212> TYPE: PRT
<213> ORGANISM: Artificial Sequence
<220> FEATURE:
<223> OTHER INFORMATION: Synthetic Construct

<400> SEQUENCE: 85

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Trp Pro
                85                  90                  95

Leu Thr Phe Gly Gln Gly Thr Lys Val Glu Ile Lys
            100                 105

<210> SEQ ID NO 86
<211> LENGTH: 108
<212> TYPE: PRT
<213> ORGANISM: Artificial Sequence
<220> FEATURE:
<223> OTHER INFORMATION: Synthetic Construct

<400> SEQUENCE: 86

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Leu
            20                  25                  30

Phe Leu Ala Trp Tyr Gln Gln Lys Pro Gly Gln Ala Pro Arg Leu Leu
        35                  40                  45

Ile Tyr Asp Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ala Trp Pro
                85                  90                  95

Leu Thr Phe Gly Gln Gly Thr Lys Val Glu Ile Lys
            100                 105

<210> SEQ ID NO 87
<211> LENGTH: 115
<212> TYPE: PRT
<213> ORGANISM: Artificial Sequence
<220> FEATURE:
<223> OTHER INFORMATION: Synthetic Construct

<400> SEQUENCE: 87

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Val
        35                  40                  45

Ser Ala Thr Val Gly Ser Gly Gly Ser Ile Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ser Trp Gly Gln Gly Thr Leu Val Thr
            100                 105                 110

Val Ser Ser
        115

<210> SEQ ID NO 88
<211> LENGTH: 108
<212> TYPE: PRT
<213> ORGANISM: Artificial Sequence
<220> FEATURE:
<223> OTHER INFORMATION: Synthetic Construct

<400> SEQUENCE: 88

Glu Ile Val Leu Thr Gln Ser Pro Gly Thr Leu Ser Leu Ser Pro Gly
1               5                   10                  15

Glu Arg Ala Thr Leu Ser Cys Ala Cys Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ala Trp Pro
                85                  90                  95

Leu Thr Phe Gly Gln Gly Thr Lys Val Glu Ile Lys
            100                 105

<210> SEQ ID NO 89
<211> LENGTH: 108
<212> TYPE: PRT
<213> ORGANISM: Artificial Sequence
<220> FEATURE:
<223> OTHER INFORMATION: Synthetic Construct

<400> SEQUENCE: 89

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Cys Asp Val Ser Ser Thr
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Met Arg Ser Pro
                85                  90                  95

Leu Thr Phe Gly Gln Gly Thr Lys Val Glu Ile Lys
            100                 105

<210> SEQ ID NO 90
<211> LENGTH: 108
<212> TYPE: PRT
<213> ORGANISM: Artificial Sequence
<220> FEATURE:
<223> OTHER INFORMATION: Synthetic Construct

<400> SEQUENCE: 90

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Glu Ala Val Pro Ser Thr
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ala Phe Pro
                85                  90                  95

Leu Thr Phe Gly Gln Gly Thr Lys Val Glu Ile Lys
            100                 105

<210> SEQ ID NO 91
<211> LENGTH: 108
<212> TYPE: PRT
<213> ORGANISM: Artificial Sequence
<220> FEATURE:
<223> OTHER INFORMATION: Synthetic Construct

<400> SEQUENCE: 91

Glu Ile Val Leu Thr Gln Ser Pro Gly Thr Leu Ser Leu Ser Pro Gly
1               5                   10                  15

Glu Arg Ala Thr Leu Ser Cys Cys Ser Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ala Phe Pro
                85                  90                  95

Leu Thr Phe Gly Gln Gly Thr Lys Val Glu Ile Lys
            100                 105

<210> SEQ ID NO 92
<211> LENGTH: 115
<212> TYPE: PRT
<213> ORGANISM: Artificial Sequence
<220> FEATURE:
<223> OTHER INFORMATION: Synthetic Construct

```
<400> SEQUENCE: 92

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Asp Ser Gly Gly Ser Arg Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Tyr Trp Pro Met Asp Ile Trp Gly Gln Gly Thr Leu Val Thr
            100                 105                 110

Val Ser Ser
        115

<210> SEQ ID NO 93
<211> LENGTH: 108
<212> TYPE: PRT
<213> ORGANISM: Artificial Sequence
<220> FEATURE:
<223> OTHER INFORMATION: Synthetic Construct

<400> SEQUENCE: 93

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Val Arg Val Ser Ser Thr
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Met Lys Trp Pro
                85                  90                  95

Leu Thr Phe Gly Gln Gly Thr Lys Val Glu Ile Lys
            100                 105

<210> SEQ ID NO 94
<211> LENGTH: 108
<212> TYPE: PRT
<213> ORGANISM: Artificial Sequence
<220> FEATURE:
<223> OTHER INFORMATION: Synthetic Construct

<400> SEQUENCE: 94

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ala Ala
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60
```

```
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Met Cys Trp Pro
                 85                  90                  95

Leu Thr Phe Gly Gln Gly Thr Lys Val Glu Ile Lys
            100                 105
```

<210> SEQ ID NO 95
<211> LENGTH: 115
<212> TYPE: PRT
<213> ORGANISM: Artificial Sequence
<220> FEATURE:
<223> OTHER INFORMATION: Synthetic Construct

<400> SEQUENCE: 95

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Pro Met Ser Trp Val Arg Gln Ala Pro Gly Lys Gly Leu Glu Trp Val
         35                  40                  45

Ser Ala Ile Gly Gly Ser Gly Ser Ile His Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Trp Pro Met Asp Ser Trp Gly Gln Gly Thr Leu Val Thr
            100                 105                 110

Val Ser Ser
        115
```

<210> SEQ ID NO 96
<211> LENGTH: 108
<212> TYPE: PRT
<213> ORGANISM: Artificial Sequence
<220> FEATURE:
<223> OTHER INFORMATION: Synthetic Construct

<400> SEQUENCE: 96

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
             20                  25                  30

Tyr Trp Gly Trp Tyr Gln Gln Lys Pro Gly Gln Ala Pro Arg Leu Leu
         35                  40                  45

Met Tyr Asp Ala Ser Ile Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gln Cys Trp Pro
                 85                  90                  95

Leu Thr Phe Gly Gln Gly Thr Lys Val Glu Ile Lys
            100                 105
```

<210> SEQ ID NO 97
<211> LENGTH: 115
<212> TYPE: PRT
<213> ORGANISM: Artificial Sequence

```
<220> FEATURE:
<223> OTHER INFORMATION: Synthetic Construct

<400> SEQUENCE: 97

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Val
        35                  40                  45

Ser Ala His Ile Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ser Trp Gly Gln Gly Thr Leu Val Thr
            100                 105                 110

Val Ser Ser
        115

<210> SEQ ID NO 98
<211> LENGTH: 108
<212> TYPE: PRT
<213> ORGANISM: Artificial Sequence
<220> FEATURE:
<223> OTHER INFORMATION: Synthetic Construct

<400> SEQUENCE: 98

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gln Ser Trp Pro
                85                  90                  95

Leu Thr Phe Gly Gln Gly Thr Lys Val Glu Ile Lys
            100                 105

<210> SEQ ID NO 99
<211> LENGTH: 115
<212> TYPE: PRT
<213> ORGANISM: Artificial Sequence
<220> FEATURE:
<223> OTHER INFORMATION: Synthetic Construct

<400> SEQUENCE: 99

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Val
        35                  40                  45
```

Ser Ala Ile Gly Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Trp Pro Met Asp Pro Trp Gly Gln Gly Thr Leu Val Thr
                100                 105                 110

Val Ser Ser
        115

<210> SEQ ID NO 100
<211> LENGTH: 108
<212> TYPE: PRT
<213> ORGANISM: Artificial Sequence
<220> FEATURE:
<223> OTHER INFORMATION: Synthetic Construct

<400> SEQUENCE: 100

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Pro
                20                  25                  30

Tyr Leu Ala Trp Tyr Gln Gln Lys Pro Gly Gln Ala Pro Arg Leu Leu
            35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gln Ser Trp Pro
                 85                  90                  95

Leu Thr Phe Gly Gln Gly Thr Lys Val Glu Ile Lys
                100                 105

<210> SEQ ID NO 101
<211> LENGTH: 115
<212> TYPE: PRT
<213> ORGANISM: Artificial Sequence
<220> FEATURE:
<223> OTHER INFORMATION: Synthetic Construct

<400> SEQUENCE: 101

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Pro Met Ser Trp Val Arg Gln Ala Pro Gly Lys Gly Leu Glu Trp Val
            35                  40                  45

Ser Ala Ile Gly Gly Ser Gly Gly Ser Leu Gly Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Trp Pro Met Asp Ser Trp Gly Gln Gly Thr Leu Val Thr
                100                 105                 110

Val Ser Ser
        115

```
<210> SEQ ID NO 102
<211> LENGTH: 108
<212> TYPE: PRT
<213> ORGANISM: Artificial Sequence
<220> FEATURE:
<223> OTHER INFORMATION: Synthetic Construct

<400> SEQUENCE: 102
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Pro Leu
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Lys Ala Trp Pro
                85                  90                  95

Leu Thr Phe Gly Gln Gly Thr Lys Val Glu Ile Lys
            100                 105

```
<210> SEQ ID NO 103
<211> LENGTH: 108
<212> TYPE: PRT
<213> ORGANISM: Artificial Sequence
<220> FEATURE:
<223> OTHER INFORMATION: Synthetic Construct

<400> SEQUENCE: 103
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Tyr Leu
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Met Glu Trp Pro
                85                  90                  95

Leu Thr Phe Gly Gln Gly Thr Lys Val Glu Ile Lys
            100                 105

```
<210> SEQ ID NO 104
<211> LENGTH: 115
<212> TYPE: PRT
<213> ORGANISM: Artificial Sequence
<220> FEATURE:
<223> OTHER INFORMATION: Synthetic Construct

<400> SEQUENCE: 104
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Val
        35                  40                  45

```
Ser Ala Ile Phe Ala Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Trp Pro Met Asp Ser Trp Gly Gln Gly Thr Leu Val Thr
                100                 105                 110

Val Ser Ser
        115

<210> SEQ ID NO 105
<211> LENGTH: 108
<212> TYPE: PRT
<213> ORGANISM: Artificial Sequence
<220> FEATURE:
<223> OTHER INFORMATION: Synthetic Construct

<400> SEQUENCE: 105

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ala Gln
                 20                  25                  30

Tyr Leu Ala Trp Tyr Gln Gln Lys Pro Gly Gln Ala Pro Arg Leu Leu
             35                  40                  45

Met Tyr Asp Ala Ser Ile Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gln Ala Trp Pro
                 85                  90                  95

Leu Thr Phe Gly Gln Gly Thr Lys Val Glu Ile Lys
            100                 105

<210> SEQ ID NO 106
<211> LENGTH: 115
<212> TYPE: PRT
<213> ORGANISM: Artificial Sequence
<220> FEATURE:
<223> OTHER INFORMATION: Synthetic Construct

<400> SEQUENCE: 106

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Pro Met Ser Trp Val Arg Gln Ala Pro Gly Lys Gly Leu Glu Trp Val
             35                  40                  45

Ser Ala Ile Gly Gly Ser Gly Thr Trp Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Trp Pro Met Asp Ser Trp Gly Gln Gly Thr Leu Val Thr
                100                 105                 110

Val Ser Ser
        115
```

<210> SEQ ID NO 107
<211> LENGTH: 108
<212> TYPE: PRT
<213> ORGANISM: Artificial Sequence
<220> FEATURE:
<223> OTHER INFORMATION: Synthetic Construct

<400> SEQUENCE: 107

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gln Lys Trp Pro
                85                  90                  95

Leu Thr Phe Gly Gln Gly Thr Lys Val Glu Ile Lys
            100                 105

<210> SEQ ID NO 108
<211> LENGTH: 108
<212> TYPE: PRT
<213> ORGANISM: Artificial Sequence
<220> FEATURE:
<223> OTHER INFORMATION: Synthetic Construct

<400> SEQUENCE: 108

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ala Val
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Arg Ala Trp Pro
                85                  90                  95

Leu Thr Phe Gly Gln Gly Thr Lys Val Glu Ile Lys
            100                 105

<210> SEQ ID NO 109
<211> LENGTH: 108
<212> TYPE: PRT
<213> ORGANISM: Artificial Sequence
<220> FEATURE:
<223> OTHER INFORMATION: Synthetic Construct

<400> SEQUENCE: 109

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ile Ala Val Ser Ser Thr
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Met Val Trp Pro
                85                  90                  95

Leu Thr Phe Gly Gln Gly Thr Lys Val Glu Ile Lys
            100                 105

<210> SEQ ID NO 110
<211> LENGTH: 115
<212> TYPE: PRT
<213> ORGANISM: Artificial Sequence
<220> FEATURE:
<223> OTHER INFORMATION: Synthetic Construct

<400> SEQUENCE: 110

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Val
        35                  40                  45

Ser Ala Leu Phe Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ser Trp Gly Gln Gly Thr Leu Val Thr
            100                 105                 110

Val Ser Ser
        115

<210> SEQ ID NO 111
<211> LENGTH: 108
<212> TYPE: PRT
<213> ORGANISM: Artificial Sequence
<220> FEATURE:
<223> OTHER INFORMATION: Synthetic Construct

<400> SEQUENCE: 111

Glu Ile Val Leu Thr Gln Ser Pro Gly Thr Leu Ser Leu Ser Pro Gly
1               5                   10                  15

Glu Arg Ala Thr Leu Ser Cys Arg Pro Arg Gln Ser Val Ser Ser Ser
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gln Asp Trp Pro
                85                  90                  95

Leu Thr Phe Gly Gln Gly Thr Lys Val Glu Ile Lys
            100                 105

```
<210> SEQ ID NO 112
<211> LENGTH: 115
<212> TYPE: PRT
<213> ORGANISM: Artificial Sequence
<220> FEATURE:
<223> OTHER INFORMATION: Synthetic Construct

<400> SEQUENCE: 112
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Val
        35                  40                  45

Ser Ala Ile Gly Gly Ser Gly Gly Ser Leu Pro Tyr Ala Asp Ile Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ile Trp Gly Gln Gly Thr Leu Val Thr
            100                 105                 110

Val Ser Ser
        115

```
<210> SEQ ID NO 113
<211> LENGTH: 108
<212> TYPE: PRT
<213> ORGANISM: Artificial Sequence
<220> FEATURE:
<223> OTHER INFORMATION: Synthetic Construct

<400> SEQUENCE: 113
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gln Glu Trp Pro
                85                  90                  95

Leu Thr Phe Gly Gln Gly Thr Lys Val Glu Ile Lys
            100                 105

```
<210> SEQ ID NO 114
<211> LENGTH: 114
<212> TYPE: PRT
<213> ORGANISM: Artificial Sequence
<220> FEATURE:
<223> OTHER INFORMATION: Synthetic Construct

<400> SEQUENCE: 114
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

-continued

```
Pro Met Ser Trp Val Arg Gln Ala Pro Gly Lys Gly Leu Glu Trp Val
         35                  40                  45

Ser Ala Ala Leu Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Trp Pro Met Asp Ser Trp Gly Gln Gly Thr Leu Val Thr
             100                 105                 110

Val Ser

<210> SEQ ID NO 115
<211> LENGTH: 108
<212> TYPE: PRT
<213> ORGANISM: Artificial Sequence
<220> FEATURE:
<223> OTHER INFORMATION: Synthetic Construct

<400> SEQUENCE: 115

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ala Ser
             20                  25                  30

Tyr Leu Ala Trp Tyr Gln Gln Lys Pro Gly Gln Ala Pro Arg Leu Leu
         35                  40                  45

Met Tyr Asp Ala Ser Ile Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Met Ser Trp Pro
                 85                  90                  95

Leu Thr Phe Gly Gln Gly Thr Lys Val Glu Ile Lys
             100                 105

<210> SEQ ID NO 116
<211> LENGTH: 108
<212> TYPE: PRT
<213> ORGANISM: Artificial Sequence
<220> FEATURE:
<223> OTHER INFORMATION: Synthetic Construct

<400> SEQUENCE: 116

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Tyr Met
             20                  25                  30

Tyr Leu Ala Trp Tyr Gln Gln Lys Pro Gly Gln Ala Pro Arg Leu Leu
         35                  40                  45

Ile Tyr Asp Ala Ser Ile Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Lys Ser Trp Pro
                 85                  90                  95

Leu Thr Phe Gly Gln Gly Thr Lys Val Glu Ile Lys
             100                 105
```

-continued

```
<210> SEQ ID NO 117
<211> LENGTH: 108
<212> TYPE: PRT
<213> ORGANISM: Artificial Sequence
<220> FEATURE:
<223> OTHER INFORMATION: Synthetic Construct

<400> SEQUENCE: 117

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ala Leu
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Tyr Gly Trp Pro
                85                  90                  95

Leu Thr Phe Gly Gln Gly Thr Lys Val Glu Ile Lys
            100                 105

<210> SEQ ID NO 118
<211> LENGTH: 115
<212> TYPE: PRT
<213> ORGANISM: Artificial Sequence
<220> FEATURE:
<223> OTHER INFORMATION: Synthetic Construct

<400> SEQUENCE: 118

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Val
        35                  40                  45

Ser Ala Ile Gly Gly Ser Gly Gly Ser Leu Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Ala Asp Trp Gly Gln Gly Thr Leu Val Thr
            100                 105                 110

Val Ser Ser
        115

<210> SEQ ID NO 119
<211> LENGTH: 108
<212> TYPE: PRT
<213> ORGANISM: Artificial Sequence
<220> FEATURE:
<223> OTHER INFORMATION: Synthetic Construct

<400> SEQUENCE: 119

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Pro Ile Ser Ser Ser
            20                  25                  30
```

Tyr Leu Ala Trp Tyr Gln Gln Lys Pro Gly Gln Ala Pro Arg Leu Leu
              35                  40                  45

Met Tyr Asp Ala Ser Ile Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gln Gly Trp Pro
                 85                  90                  95

Leu Thr Phe Gly Gln Gly Thr Lys Val Glu Ile Lys
                100                 105

<210> SEQ ID NO 120
<211> LENGTH: 115
<212> TYPE: PRT
<213> ORGANISM: Artificial Sequence
<220> FEATURE:
<223> OTHER INFORMATION: Synthetic Construct

<400> SEQUENCE: 120

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Asn Trp Val Arg Gln Ala Pro Gly Lys Gly Leu Glu Trp Val
             35                  40                  45

Ser Ala Ile Ser Asp Ser Gly Gly Phe Val Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Trp Pro Met Asp Ser Trp Gly Gln Gly Thr Leu Val Thr
                100                 105                 110

Val Ser Ser
        115

<210> SEQ ID NO 121
<211> LENGTH: 108
<212> TYPE: PRT
<213> ORGANISM: Artificial Sequence
<220> FEATURE:
<223> OTHER INFORMATION: Synthetic Construct

<400> SEQUENCE: 121

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
              35                  40                  45

Met Tyr Asp Ala Ser Ile Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Glu Phe Trp Pro
                 85                  90                  95

Leu Thr Phe Gly Gln Gly Thr Lys Val Glu Ile Lys
                100                 105

```
<210> SEQ ID NO 122
<211> LENGTH: 115
<212> TYPE: PRT
<213> ORGANISM: Artificial Sequence
<220> FEATURE:
<223> OTHER INFORMATION: Synthetic Construct

<400> SEQUENCE: 122
```

| Glu | Val | Gln | Leu | Leu | Glu | Ser | Gly | Gly | Gly | Leu | Val | Gln | Pro | Gly |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Ser | Leu | Arg | Leu | Ser | Cys | Ala | Ala | Ser | Gly | Phe | Thr | Phe | Ser | Ser | Tyr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ala | Met | Asn | Trp | Val | Arg | Gln | Ala | Pro | Gly | Lys | Gly | Leu | Glu | Trp | Val |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Ser | Ala | Ile | Gly | Gly | Ser | Gly | Gly | Ser | Thr | Tyr | Tyr | Ala | Asp | Ser | Val |
|-----|-----|-----|-----|-----|-----|-----|-----|-----|-----|-----|-----|-----|-----|-----|-----|
| 50  |     |     |     |     | 55  |     |     |     |     | 60  |     |     |     |     |     |

| Lys | Gly | Arg | Phe | Thr | Ile | Ser | Arg | Asp | Asn | Ser | Lys | Asn | Thr | Leu | Tyr |
|-----|-----|-----|-----|-----|-----|-----|-----|-----|-----|-----|-----|-----|-----|-----|-----|
| 65  |     |     |     | 70  |     |     |     |     | 75  |     |     |     |     | 80  |     |

| Leu | Gln | Met | Asn | Ser | Leu | Arg | Ala | Glu | Asp | Thr | Ala | Val | Tyr | Tyr | Cys |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Ala | Arg | Tyr | Trp | Pro | Met | Ser | Leu | Trp | Gly | Gln | Gly | Thr | Leu | Val | Thr |
|-----|-----|-----|-----|-----|-----|-----|-----|-----|-----|-----|-----|-----|-----|-----|-----|
|     |     |     |     | 100 |     |     |     |     | 105 |     |     |     |     | 110 |     |

| Val | Ser | Ser |
|-----|-----|-----|
|     |     | 115 |

```
<210> SEQ ID NO 123
<211> LENGTH: 108
<212> TYPE: PRT
<213> ORGANISM: Artificial Sequence
<220> FEATURE:
<223> OTHER INFORMATION: Synthetic Construct

<400> SEQUENCE: 123
```

| Glu | Ile | Val | Leu | Thr | Gln | Ser | Pro | Gly | Thr | Leu | Ser | Leu | Ser | Pro | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Glu | Arg | Ala | Thr | Leu | Ser | Cys | Arg | Ala | Ser | Gln | Ser | Val | Ser | Ser | Thr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Tyr | Leu | Ala | Trp | Tyr | Gln | Gln | Lys | Pro | Gly | Gln | Ala | Pro | Arg | Leu | Leu |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Met | Tyr | Asp | Ala | Ser | Ile | Arg | Ala | Thr | Gly | Ile | Pro | Asp | Arg | Phe | Ser |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Gly | Ser | Gly | Ser | Gly | Thr | Asp | Phe | Thr | Leu | Thr | Ile | Ser | Arg | Leu | Glu |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Pro | Glu | Asp | Phe | Ala | Val | Tyr | Tyr | Cys | Gln | Gln | Tyr | Met | Ser | Trp | Pro |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Leu | Thr | Phe | Gly | Gln | Gly | Thr | Lys | Val | Glu | Ile | Lys |
|-----|-----|-----|-----|-----|-----|-----|-----|-----|-----|-----|-----|
|     |     |     | 100 |     |     |     |     | 105 |     |     |     |

```
<210> SEQ ID NO 124
<211> LENGTH: 108
<212> TYPE: PRT
<213> ORGANISM: Artificial Sequence
<220> FEATURE:
<223> OTHER INFORMATION: Synthetic Construct

<400> SEQUENCE: 124
```

| Glu | Ile | Val | Leu | Thr | Gln | Ser | Pro | Gly | Thr | Leu | Ser | Leu | Ser | Pro | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Glu | Arg | Ala | Thr | Leu | Ser | Cys | Arg | Ala | Ser | Gln | Gly | Ile | Ser | Ser | Thr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

```
Tyr Leu Ala Trp Tyr Gln Gln Lys Pro Gly Gln Ala Pro Arg Leu Leu
            35                  40                  45

Met Tyr Asp Ala Ser Ile Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Ala Tyr Trp Pro
                 85                  90                  95

Leu Thr Phe Gly Gln Gly Thr Lys Val Glu Ile Lys
             100                 105
```

```
<210> SEQ ID NO 125
<211> LENGTH: 115
<212> TYPE: PRT
<213> ORGANISM: Artificial Sequence
<220> FEATURE:
<223> OTHER INFORMATION: Synthetic Construct

<400> SEQUENCE: 125

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Asn Trp Val Arg Gln Ala Pro Gly Lys Gly Leu Glu Trp Val
         35                  40                  45

Ser Ala Cys Leu Asp Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Trp Pro Met Asp Ser Trp Gly Gln Gly Thr Leu Val Thr
             100                 105                 110

Val Ser Ser
    115
```

```
<210> SEQ ID NO 126
<211> LENGTH: 108
<212> TYPE: PRT
<213> ORGANISM: Artificial Sequence
<220> FEATURE:
<223> OTHER INFORMATION: Synthetic Construct

<400> SEQUENCE: 126

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Met Tyr Asp Ala Ser Ile Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gln Gly Trp Pro
                 85                  90                  95

Leu Thr Phe Gly Gln Gly Thr Lys Val Glu Ile Lys
             100                 105
```

```
<210> SEQ ID NO 127
<211> LENGTH: 115
<212> TYPE: PRT
<213> ORGANISM: Artificial Sequence
<220> FEATURE:
<223> OTHER INFORMATION: Synthetic Construct

<400> SEQUENCE: 127
```

| Glu | Val | Gln | Leu | Leu | Glu | Ser | Gly | Gly | Gly | Leu | Val | Gln | Pro | Gly |
|---|---|---|---|---|---|---|---|---|---|---|---|---|---|---|
| 1 |   |   |   | 5 |   |   |   |   | 10 |   |   |   |   | 15 |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
|   |   |   | 20 |   |   |   |   | 25 |   |   |   |   | 30 |   |   |

Pro Met Ser Trp Val Arg Gln Ala Pro Gly Lys Gly Leu Glu Trp Val
            35                  40                  45

Ser Ala Ala Leu Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Ser Leu Trp Gly Gln Gly Thr Leu Val Thr
            100                 105                 110

Val Ser Ser
        115

```
<210> SEQ ID NO 128
<211> LENGTH: 108
<212> TYPE: PRT
<213> ORGANISM: Artificial Sequence
<220> FEATURE:
<223> OTHER INFORMATION: Synthetic Construct

<400> SEQUENCE: 128
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Val Arg
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Trp Pro
                85                  90                  95

Ile Thr Phe Gly Gln Gly Thr Lys Val Glu Ile Lys
            100                 105

```
<210> SEQ ID NO 129
<211> LENGTH: 5
<212> TYPE: PRT
<213> ORGANISM: Artificial Sequence
<220> FEATURE:
<223> OTHER INFORMATION: Synthetic Construct

<400> SEQUENCE: 129
```

Ser Tyr Ala Met Thr
1               5

```
<210> SEQ ID NO 130
<211> LENGTH: 7
<212> TYPE: PRT
<213> ORGANISM: Artificial Sequence
<220> FEATURE:
<223> OTHER INFORMATION: Synthetic Construct

<400> SEQUENCE: 130

Gly Phe Thr Phe Gly Ser Tyr
1               5

<210> SEQ ID NO 131
<211> LENGTH: 10
<212> TYPE: PRT
<213> ORGANISM: Artificial Sequence
<220> FEATURE:
<223> OTHER INFORMATION: Synthetic Construct

<400> SEQUENCE: 131

Gly Phe Thr Phe Gly Ser Tyr Ala Met Thr
1               5                   10

<210> SEQ ID NO 132
<211> LENGTH: 17
<212> TYPE: PRT
<213> ORGANISM: Artificial Sequence
<220> FEATURE:
<223> OTHER INFORMATION: Synthetic Construct

<400> SEQUENCE: 132

Ala Ile Ser Gly Ser Gly Gly Asn Thr Phe Tyr Ala Asp Ser Val Lys
1               5                   10                  15

Gly

<210> SEQ ID NO 133
<211> LENGTH: 6
<212> TYPE: PRT
<213> ORGANISM: Artificial Sequence
<220> FEATURE:
<223> OTHER INFORMATION: Synthetic Construct

<400> SEQUENCE: 133

Ser Gly Ser Gly Gly Asn
1               5

<210> SEQ ID NO 134
<211> LENGTH: 10
<212> TYPE: PRT
<213> ORGANISM: Artificial Sequence
<220> FEATURE:
<223> OTHER INFORMATION: Synthetic Construct

<400> SEQUENCE: 134

Val Ser Pro Ile Ala Ser Gly Met Asp Tyr
1               5                   10

<210> SEQ ID NO 135
<211> LENGTH: 10
<212> TYPE: PRT
<213> ORGANISM: Artificial Sequence
<220> FEATURE:
<223> OTHER INFORMATION: Synthetic Construct

<400> SEQUENCE: 135

Val Ser Pro Ile Ala Ala Gln Met Asp Tyr
1               5                   10
```

```
<210> SEQ ID NO 136
<211> LENGTH: 10
<212> TYPE: PRT
<213> ORGANISM: Artificial Sequence
<220> FEATURE:
<223> OTHER INFORMATION: Synthetic Construct

<400> SEQUENCE: 136

Val Ser Pro Ile Ala Ala Leu Met Asp Tyr
1               5                   10

<210> SEQ ID NO 137
<211> LENGTH: 10
<212> TYPE: PRT
<213> ORGANISM: Artificial Sequence
<220> FEATURE:
<223> OTHER INFORMATION: Synthetic Construct

<400> SEQUENCE: 137

Val Ser Pro Ile Ala Ala Pro Met Asp Tyr
1               5                   10

<210> SEQ ID NO 138
<211> LENGTH: 17
<212> TYPE: PRT
<213> ORGANISM: Artificial Sequence
<220> FEATURE:
<223> OTHER INFORMATION: Synthetic Construct

<400> SEQUENCE: 138

Ala Ile Ser Gly Ser Gly Gly Asn Thr Phe Tyr Ala Asp Gln Arg Lys
1               5                   10                  15

Gly

<210> SEQ ID NO 139
<211> LENGTH: 17
<212> TYPE: PRT
<213> ORGANISM: Artificial Sequence
<220> FEATURE:
<223> OTHER INFORMATION: Synthetic Construct

<400> SEQUENCE: 139

Ala Ile Asp Tyr Ser Gly Gly Asn Thr Phe Tyr Ala Asp Ser Val Lys
1               5                   10                  15

Gly

<210> SEQ ID NO 140
<211> LENGTH: 6
<212> TYPE: PRT
<213> ORGANISM: Artificial Sequence
<220> FEATURE:
<223> OTHER INFORMATION: Synthetic Construct

<400> SEQUENCE: 140

Asp Tyr Ser Gly Gly Asn
1               5

<210> SEQ ID NO 141
<211> LENGTH: 17
<212> TYPE: PRT
<213> ORGANISM: Artificial Sequence
<220> FEATURE:
<223> OTHER INFORMATION: Synthetic Construct
```

```
<400> SEQUENCE: 141

Ala Ile Ser Tyr Gln Gly Gly Asn Thr Phe Tyr Ala Asp Ser Val Lys
1               5                   10                  15

Gly

<210> SEQ ID NO 142
<211> LENGTH: 6
<212> TYPE: PRT
<213> ORGANISM: Artificial Sequence
<220> FEATURE:
<223> OTHER INFORMATION: Synthetic Construct

<400> SEQUENCE: 142

Ser Tyr Gln Gly Gly Asn
1               5

<210> SEQ ID NO 143
<211> LENGTH: 17
<212> TYPE: PRT
<213> ORGANISM: Artificial Sequence
<220> FEATURE:
<223> OTHER INFORMATION: Synthetic Construct

<400> SEQUENCE: 143

Ala Ile Ser Leu Thr Gly Gly Asn Thr Phe Tyr Ala Asp Ser Val Lys
1               5                   10                  15

Gly

<210> SEQ ID NO 144
<211> LENGTH: 6
<212> TYPE: PRT
<213> ORGANISM: Artificial Sequence
<220> FEATURE:
<223> OTHER INFORMATION: Synthetic Construct

<400> SEQUENCE: 144

Ser Leu Thr Gly Gly Asn
1               5

<210> SEQ ID NO 145
<211> LENGTH: 17
<212> TYPE: PRT
<213> ORGANISM: Artificial Sequence
<220> FEATURE:
<223> OTHER INFORMATION: Synthetic Construct

<400> SEQUENCE: 145

Ala Ile Ser His Ala Gly Gly Asn Thr Phe Tyr Ala Asp Ser Val Lys
1               5                   10                  15

Gly

<210> SEQ ID NO 146
<211> LENGTH: 6
<212> TYPE: PRT
<213> ORGANISM: Artificial Sequence
<220> FEATURE:
<223> OTHER INFORMATION: Synthetic Construct

<400> SEQUENCE: 146

Ser His Ala Gly Gly Asn
1               5
```

```
<210> SEQ ID NO 147
<211> LENGTH: 17
<212> TYPE: PRT
<213> ORGANISM: Artificial Sequence
<220> FEATURE:
<223> OTHER INFORMATION: Synthetic Construct

<400> SEQUENCE: 147

Ala Ile Ser Gly Ser Gly Gly Asn Thr Phe Tyr Ala Asp Gln Leu Lys
1               5                   10                  15
Gly

<210> SEQ ID NO 148
<211> LENGTH: 10
<212> TYPE: PRT
<213> ORGANISM: Artificial Sequence
<220> FEATURE:
<223> OTHER INFORMATION: Synthetic Construct

<400> SEQUENCE: 148

Val Ser Pro Ile Tyr Ala Gly Met Asp Tyr
1               5                   10

<210> SEQ ID NO 149
<211> LENGTH: 10
<212> TYPE: PRT
<213> ORGANISM: Artificial Sequence
<220> FEATURE:
<223> OTHER INFORMATION: Synthetic Construct

<400> SEQUENCE: 149

Val Ser Pro Ile Ala Ala Glu Met Asp Tyr
1               5                   10

<210> SEQ ID NO 150
<211> LENGTH: 5
<212> TYPE: PRT
<213> ORGANISM: Artificial Sequence
<220> FEATURE:
<223> OTHER INFORMATION: Synthetic Construct

<400> SEQUENCE: 150

Ser Tyr Ala Met Asn
1               5

<210> SEQ ID NO 151
<211> LENGTH: 7
<212> TYPE: PRT
<213> ORGANISM: Artificial Sequence
<220> FEATURE:
<223> OTHER INFORMATION: Synthetic Construct

<400> SEQUENCE: 151

Gly Phe Thr Phe Ser Ser Tyr
1               5

<210> SEQ ID NO 152
<211> LENGTH: 10
<212> TYPE: PRT
<213> ORGANISM: Artificial Sequence
<220> FEATURE:
<223> OTHER INFORMATION: Synthetic Construct

<400> SEQUENCE: 152

Gly Phe Thr Phe Ser Ser Tyr Ala Met Asn
1               5                   10
```

```
<210> SEQ ID NO 153
<211> LENGTH: 17
<212> TYPE: PRT
<213> ORGANISM: Artificial Sequence
<220> FEATURE:
<223> OTHER INFORMATION: Synthetic Construct

<400> SEQUENCE: 153

Ala Ile Ser Asp Ser Gly Gly Ser Thr Tyr Tyr Ala Asp Ser Val Lys
1               5                   10                  15

Gly

<210> SEQ ID NO 154
<211> LENGTH: 6
<212> TYPE: PRT
<213> ORGANISM: Artificial Sequence
<220> FEATURE:
<223> OTHER INFORMATION: Synthetic Construct

<400> SEQUENCE: 154

Ser Asp Ser Gly Gly Ser
1               5

<210> SEQ ID NO 155
<211> LENGTH: 6
<212> TYPE: PRT
<213> ORGANISM: Artificial Sequence
<220> FEATURE:
<223> OTHER INFORMATION: Synthetic Construct

<400> SEQUENCE: 155

Tyr Trp Pro Met Asp Ile
1               5

<210> SEQ ID NO 156
<211> LENGTH: 5
<212> TYPE: PRT
<213> ORGANISM: Artificial Sequence
<220> FEATURE:
<223> OTHER INFORMATION: Synthetic Construct

<400> SEQUENCE: 156

Ser Tyr Pro Met Ser
1               5

<210> SEQ ID NO 157
<211> LENGTH: 10
<212> TYPE: PRT
<213> ORGANISM: Artificial Sequence
<220> FEATURE:
<223> OTHER INFORMATION: Synthetic Construct

<400> SEQUENCE: 157

Gly Phe Thr Phe Ser Ser Tyr Pro Met Ser
1               5                   10

<210> SEQ ID NO 158
<211> LENGTH: 17
<212> TYPE: PRT
<213> ORGANISM: Artificial Sequence
<220> FEATURE:
<223> OTHER INFORMATION: Synthetic Construct
```

```
<400> SEQUENCE: 158

Ala Ile Gly Gly Ser Gly Gly Ser Leu Pro Tyr Ala Asp Ile Val Lys
1               5                   10                  15

Gly

<210> SEQ ID NO 159
<211> LENGTH: 6
<212> TYPE: PRT
<213> ORGANISM: Artificial Sequence
<220> FEATURE:
<223> OTHER INFORMATION: Synthetic Construct

<400> SEQUENCE: 159

Gly Gly Ser Gly Gly Ser
1               5

<210> SEQ ID NO 160
<211> LENGTH: 17
<212> TYPE: PRT
<213> ORGANISM: Artificial Sequence
<220> FEATURE:
<223> OTHER INFORMATION: Synthetic Construct

<400> SEQUENCE: 160

Ala Ile Leu Asp Ser Gly Gly Ser Thr Tyr Tyr Ala Asp Ser Val Lys
1               5                   10                  15

Gly

<210> SEQ ID NO 161
<211> LENGTH: 6
<212> TYPE: PRT
<213> ORGANISM: Artificial Sequence
<220> FEATURE:
<223> OTHER INFORMATION: Synthetic Construct

<400> SEQUENCE: 161

Tyr Trp Pro Met Asp Ser
1               5

<210> SEQ ID NO 162
<211> LENGTH: 17
<212> TYPE: PRT
<213> ORGANISM: Artificial Sequence
<220> FEATURE:
<223> OTHER INFORMATION: Synthetic Construct

<400> SEQUENCE: 162

Ala Ile Gly Gly Ser Gly Gly Ser Thr Tyr Tyr Ala Asp Ser Val Lys
1               5                   10                  15

Gly

<210> SEQ ID NO 163
<211> LENGTH: 17
<212> TYPE: PRT
<213> ORGANISM: Artificial Sequence
<220> FEATURE:
<223> OTHER INFORMATION: Synthetic Construct

<400> SEQUENCE: 163

Ala Ile Ser Asp Ser Gly Gly Ser Ala Trp Tyr Ala Asp Ser Val Lys
1               5                   10                  15

Gly
```

```
<210> SEQ ID NO 164
<211> LENGTH: 6
<212> TYPE: PRT
<213> ORGANISM: Artificial Sequence
<220> FEATURE:
<223> OTHER INFORMATION: Synthetic Construct

<400> SEQUENCE: 164

Tyr Trp Pro Met Ser Leu
1               5

<210> SEQ ID NO 165
<211> LENGTH: 17
<212> TYPE: PRT
<213> ORGANISM: Artificial Sequence
<220> FEATURE:
<223> OTHER INFORMATION: Synthetic Construct

<400> SEQUENCE: 165

Ala Ile Ser Asp Phe Gly Gly Ser Thr Tyr Tyr Ala Asp Ser Val Lys
1               5                   10                  15

Gly

<210> SEQ ID NO 166
<211> LENGTH: 6
<212> TYPE: PRT
<213> ORGANISM: Artificial Sequence
<220> FEATURE:
<223> OTHER INFORMATION: Synthetic Construct

<400> SEQUENCE: 166

Ser Asp Phe Gly Gly Ser
1               5

<210> SEQ ID NO 167
<211> LENGTH: 17
<212> TYPE: PRT
<213> ORGANISM: Artificial Sequence
<220> FEATURE:
<223> OTHER INFORMATION: Synthetic Construct

<400> SEQUENCE: 167

Ala Ile Thr Ala Ser Gly Gly Ser Thr Tyr Tyr Ala Asp Ser Val Lys
1               5                   10                  15

Gly

<210> SEQ ID NO 168
<211> LENGTH: 6
<212> TYPE: PRT
<213> ORGANISM: Artificial Sequence
<220> FEATURE:
<223> OTHER INFORMATION: Synthetic Construct

<400> SEQUENCE: 168

Thr Ala Ser Gly Gly Ser
1               5

<210> SEQ ID NO 169
<211> LENGTH: 17
<212> TYPE: PRT
<213> ORGANISM: Artificial Sequence
<220> FEATURE:
<223> OTHER INFORMATION: Synthetic Construct
```

<400> SEQUENCE: 169

Ala Ile Ser Asp Ser Gly Gly Ser Arg Trp Tyr Ala Asp Ser Val Lys
1               5                   10                  15

Gly

<210> SEQ ID NO 170
<211> LENGTH: 6
<212> TYPE: PRT
<213> ORGANISM: Artificial Sequence
<220> FEATURE:
<223> OTHER INFORMATION: Synthetic Construct

<400> SEQUENCE: 170

Tyr Trp Pro Met Thr Pro
1               5

<210> SEQ ID NO 171
<211> LENGTH: 17
<212> TYPE: PRT
<213> ORGANISM: Artificial Sequence
<220> FEATURE:
<223> OTHER INFORMATION: Synthetic Construct

<400> SEQUENCE: 171

Ala Val Leu Asp Ser Gly Gly Ser Thr Tyr Tyr Ala Asp Ser Val Lys
1               5                   10                  15

Gly

<210> SEQ ID NO 172
<211> LENGTH: 6
<212> TYPE: PRT
<213> ORGANISM: Artificial Sequence
<220> FEATURE:
<223> OTHER INFORMATION: Synthetic Construct

<400> SEQUENCE: 172

Leu Asp Ser Gly Gly Ser
1               5

<210> SEQ ID NO 173
<211> LENGTH: 6
<212> TYPE: PRT
<213> ORGANISM: Artificial Sequence
<220> FEATURE:
<223> OTHER INFORMATION: Synthetic Construct

<400> SEQUENCE: 173

Tyr Trp Pro Met Ser Asp
1               5

<210> SEQ ID NO 174
<211> LENGTH: 17
<212> TYPE: PRT
<213> ORGANISM: Artificial Sequence
<220> FEATURE:
<223> OTHER INFORMATION: Synthetic Construct

<400> SEQUENCE: 174

Ala Ile Ser Asp Ser Gly Gly Ser Lys Trp Tyr Ala Asp Ser Val Lys
1               5                   10                  15

Gly

```
<210> SEQ ID NO 175
<211> LENGTH: 17
<212> TYPE: PRT
<213> ORGANISM: Artificial Sequence
<220> FEATURE:
<223> OTHER INFORMATION: Synthetic Construct

<400> SEQUENCE: 175

Ala Ile Ser Asp Ser Gly Gly Ser Gly Trp Tyr Ala Asp Ser Val Lys
1               5                   10                  15
Gly

<210> SEQ ID NO 176
<211> LENGTH: 17
<212> TYPE: PRT
<213> ORGANISM: Artificial Sequence
<220> FEATURE:
<223> OTHER INFORMATION: Synthetic Construct

<400> SEQUENCE: 176

Ala Ile Ser Asp Ser Gly Gly Ser Cys Trp Tyr Ala Asp Ser Val Lys
1               5                   10                  15
Gly

<210> SEQ ID NO 177
<211> LENGTH: 17
<212> TYPE: PRT
<213> ORGANISM: Artificial Sequence
<220> FEATURE:
<223> OTHER INFORMATION: Synthetic Construct

<400> SEQUENCE: 177

Ala Ile Phe Ala Ser Gly Gly Ser Thr Tyr Tyr Ala Asp Ser Val Lys
1               5                   10                  15
Gly

<210> SEQ ID NO 178
<211> LENGTH: 6
<212> TYPE: PRT
<213> ORGANISM: Artificial Sequence
<220> FEATURE:
<223> OTHER INFORMATION: Synthetic Construct

<400> SEQUENCE: 178

Phe Ala Ser Gly Gly Ser
1               5

<210> SEQ ID NO 179
<211> LENGTH: 6
<212> TYPE: PRT
<213> ORGANISM: Artificial Sequence
<220> FEATURE:
<223> OTHER INFORMATION: Synthetic Construct

<400> SEQUENCE: 179

Ser Gly Trp Gly Gly Ser
1               5

<210> SEQ ID NO 180
<211> LENGTH: 17
<212> TYPE: PRT
<213> ORGANISM: Artificial Sequence
<220> FEATURE:
<223> OTHER INFORMATION: Synthetic Construct
```

```
<400> SEQUENCE: 180

Ala Ile Met Ser Ser Gly Gly Pro Leu Tyr Tyr Ala Asp Ser Val Lys
1               5                   10                  15

Gly

<210> SEQ ID NO 181
<211> LENGTH: 6
<212> TYPE: PRT
<213> ORGANISM: Artificial Sequence
<220> FEATURE:
<223> OTHER INFORMATION: Synthetic Construct

<400> SEQUENCE: 181

Met Ser Ser Gly Gly Pro
1               5

<210> SEQ ID NO 182
<211> LENGTH: 6
<212> TYPE: PRT
<213> ORGANISM: Artificial Sequence
<220> FEATURE:
<223> OTHER INFORMATION: Synthetic Construct

<400> SEQUENCE: 182

Tyr Trp Pro Met Ala Leu
1               5

<210> SEQ ID NO 183
<211> LENGTH: 17
<212> TYPE: PRT
<213> ORGANISM: Artificial Sequence
<220> FEATURE:
<223> OTHER INFORMATION: Synthetic Construct

<400> SEQUENCE: 183

Ala Ile Leu Met Ser Gly Gly Ser Thr Tyr Tyr Ala Asp Ser Val Lys
1               5                   10                  15

Gly

<210> SEQ ID NO 184
<211> LENGTH: 6
<212> TYPE: PRT
<213> ORGANISM: Artificial Sequence
<220> FEATURE:
<223> OTHER INFORMATION: Synthetic Construct

<400> SEQUENCE: 184

Leu Met Ser Gly Gly Ser
1               5

<210> SEQ ID NO 185
<211> LENGTH: 17
<212> TYPE: PRT
<213> ORGANISM: Artificial Sequence
<220> FEATURE:
<223> OTHER INFORMATION: Synthetic Construct

<400> SEQUENCE: 185

Ala Ile Ser Asp Ser Gly Gly Tyr Arg Tyr Tyr Ala Asp Ser Val Lys
1               5                   10                  15

Gly
```

```
<210> SEQ ID NO 186
<211> LENGTH: 6
<212> TYPE: PRT
<213> ORGANISM: Artificial Sequence
<220> FEATURE:
<223> OTHER INFORMATION: Synthetic Construct

<400> SEQUENCE: 186

Ser Asp Ser Gly Gly Tyr
1               5

<210> SEQ ID NO 187
<211> LENGTH: 17
<212> TYPE: PRT
<213> ORGANISM: Artificial Sequence
<220> FEATURE:
<223> OTHER INFORMATION: Synthetic Construct

<400> SEQUENCE: 187

Ala Ile Leu Ser Ser Gly Gly Ser Thr Tyr Tyr Ala Asp Ser Val Lys
1               5                   10                  15

Gly

<210> SEQ ID NO 188
<211> LENGTH: 6
<212> TYPE: PRT
<213> ORGANISM: Artificial Sequence
<220> FEATURE:
<223> OTHER INFORMATION: Synthetic Construct

<400> SEQUENCE: 188

Leu Ser Ser Gly Gly Ser
1               5

<210> SEQ ID NO 189
<211> LENGTH: 6
<212> TYPE: PRT
<213> ORGANISM: Artificial Sequence
<220> FEATURE:
<223> OTHER INFORMATION: Synthetic Construct

<400> SEQUENCE: 189

Tyr Trp Pro Met Ser Pro
1               5

<210> SEQ ID NO 190
<211> LENGTH: 17
<212> TYPE: PRT
<213> ORGANISM: Artificial Sequence
<220> FEATURE:
<223> OTHER INFORMATION: Synthetic Construct

<400> SEQUENCE: 190

Ala Ile Gly Gly Ser Gly Gly Trp Ser Tyr Tyr Ala Asp Ser Val Lys
1               5                   10                  15

Gly

<210> SEQ ID NO 191
<211> LENGTH: 6
<212> TYPE: PRT
<213> ORGANISM: Artificial Sequence
<220> FEATURE:
<223> OTHER INFORMATION: Synthetic Construct
```

```
<400> SEQUENCE: 191

Gly Gly Ser Gly Gly Trp
1               5

<210> SEQ ID NO 192
<211> LENGTH: 17
<212> TYPE: PRT
<213> ORGANISM: Artificial Sequence
<220> FEATURE:
<223> OTHER INFORMATION: Synthetic Construct

<400> SEQUENCE: 192

Ala Thr Val Gly Ser Gly Gly Ser Ile Gly Tyr Ala Asp Ser Val Lys
1               5                   10                  15

Gly

<210> SEQ ID NO 193
<211> LENGTH: 6
<212> TYPE: PRT
<213> ORGANISM: Artificial Sequence
<220> FEATURE:
<223> OTHER INFORMATION: Synthetic Construct

<400> SEQUENCE: 193

Val Gly Ser Gly Gly Ser
1               5

<210> SEQ ID NO 194
<211> LENGTH: 17
<212> TYPE: PRT
<213> ORGANISM: Artificial Sequence
<220> FEATURE:
<223> OTHER INFORMATION: Synthetic Construct

<400> SEQUENCE: 194

Ala Ile Gly Gly Ser Gly Gly Ser Ile His Tyr Ala Asp Ser Val Lys
1               5                   10                  15

Gly

<210> SEQ ID NO 195
<211> LENGTH: 17
<212> TYPE: PRT
<213> ORGANISM: Artificial Sequence
<220> FEATURE:
<223> OTHER INFORMATION: Synthetic Construct

<400> SEQUENCE: 195

Ala His Ile Gly Ser Gly Gly Ser Thr Tyr Tyr Ala Asp Ser Val Lys
1               5                   10                  15

Gly

<210> SEQ ID NO 196
<211> LENGTH: 6
<212> TYPE: PRT
<213> ORGANISM: Artificial Sequence
<220> FEATURE:
<223> OTHER INFORMATION: Synthetic Construct

<400> SEQUENCE: 196

Ile Gly Ser Gly Gly Ser
1               5
```

```
<210> SEQ ID NO 197
<211> LENGTH: 6
<212> TYPE: PRT
<213> ORGANISM: Artificial Sequence
<220> FEATURE:
<223> OTHER INFORMATION: Synthetic Construct

<400> SEQUENCE: 197

Tyr Trp Pro Met Asp Pro
1               5

<210> SEQ ID NO 198
<211> LENGTH: 17
<212> TYPE: PRT
<213> ORGANISM: Artificial Sequence
<220> FEATURE:
<223> OTHER INFORMATION: Synthetic Construct

<400> SEQUENCE: 198

Ala Ile Gly Gly Ser Gly Gly Ser Leu Gly Tyr Ala Asp Ser Val Lys
1               5                   10                  15

Gly

<210> SEQ ID NO 199
<211> LENGTH: 17
<212> TYPE: PRT
<213> ORGANISM: Artificial Sequence
<220> FEATURE:
<223> OTHER INFORMATION: Synthetic Construct

<400> SEQUENCE: 199

Ala Ile Gly Gly Ser Gly Thr Trp Thr Tyr Tyr Ala Asp Ser Val Lys
1               5                   10                  15

Gly

<210> SEQ ID NO 200
<211> LENGTH: 6
<212> TYPE: PRT
<213> ORGANISM: Artificial Sequence
<220> FEATURE:
<223> OTHER INFORMATION: Synthetic Construct

<400> SEQUENCE: 200

Gly Gly Ser Gly Thr Trp
1               5

<210> SEQ ID NO 201
<211> LENGTH: 17
<212> TYPE: PRT
<213> ORGANISM: Artificial Sequence
<220> FEATURE:
<223> OTHER INFORMATION: Synthetic Construct

<400> SEQUENCE: 201

Ala Leu Phe Gly Ser Gly Gly Ser Thr Tyr Tyr Ala Asp Ser Val Lys
1               5                   10                  15

Gly

<210> SEQ ID NO 202
<211> LENGTH: 6
<212> TYPE: PRT
<213> ORGANISM: Artificial Sequence
<220> FEATURE:
<223> OTHER INFORMATION: Synthetic Construct
```

```
<400> SEQUENCE: 202

Phe Gly Ser Gly Gly Ser
1               5

<210> SEQ ID NO 203
<211> LENGTH: 17
<212> TYPE: PRT
<213> ORGANISM: Artificial Sequence
<220> FEATURE:
<223> OTHER INFORMATION: Synthetic Construct

<400> SEQUENCE: 203

Ala Ala Leu Gly Ser Gly Gly Ser Thr Tyr Tyr Ala Asp Ser Val Lys
1               5                   10                  15

Gly

<210> SEQ ID NO 204
<211> LENGTH: 6
<212> TYPE: PRT
<213> ORGANISM: Artificial Sequence
<220> FEATURE:
<223> OTHER INFORMATION: Synthetic Construct

<400> SEQUENCE: 204

Leu Gly Ser Gly Gly Ser
1               5

<210> SEQ ID NO 205
<211> LENGTH: 6
<212> TYPE: PRT
<213> ORGANISM: Artificial Sequence
<220> FEATURE:
<223> OTHER INFORMATION: Synthetic Construct

<400> SEQUENCE: 205

Tyr Trp Pro Met Ala Asp
1               5

<210> SEQ ID NO 206
<211> LENGTH: 17
<212> TYPE: PRT
<213> ORGANISM: Artificial Sequence
<220> FEATURE:
<223> OTHER INFORMATION: Synthetic Construct

<400> SEQUENCE: 206

Ala Ile Ser Asp Ser Gly Gly Phe Val Tyr Tyr Ala Asp Ser Val Lys
1               5                   10                  15

Gly

<210> SEQ ID NO 207
<211> LENGTH: 6
<212> TYPE: PRT
<213> ORGANISM: Artificial Sequence
<220> FEATURE:
<223> OTHER INFORMATION: Synthetic Construct

<400> SEQUENCE: 207

Ser Asp Ser Gly Gly Phe
1               5

<210> SEQ ID NO 208
<211> LENGTH: 17
<212> TYPE: PRT
<213> ORGANISM: Artificial Sequence
```

```
<220> FEATURE:
<223> OTHER INFORMATION: Synthetic Construct

<400> SEQUENCE: 208

Ala Cys Leu Asp Ser Gly Gly Ser Thr Tyr Tyr Ala Asp Ser Val Lys
1               5                   10                  15

Gly

<210> SEQ ID NO 209
<211> LENGTH: 12
<212> TYPE: PRT
<213> ORGANISM: Artificial Sequence
<220> FEATURE:
<223> OTHER INFORMATION: Synthetic Construct

<400> SEQUENCE: 209

Arg Ala Ser Gln Ser Val Ser Ser Ser Tyr Leu Ala
1               5                   10

<210> SEQ ID NO 210
<211> LENGTH: 7
<212> TYPE: PRT
<213> ORGANISM: Artificial Sequence
<220> FEATURE:
<223> OTHER INFORMATION: Synthetic Construct

<400> SEQUENCE: 210

Gly Ala Ser Ser Arg Ala Thr
1               5

<210> SEQ ID NO 211
<211> LENGTH: 10
<212> TYPE: PRT
<213> ORGANISM: Artificial Sequence
<220> FEATURE:
<223> OTHER INFORMATION: Synthetic Construct

<400> SEQUENCE: 211

Gln His Tyr Gly Ser Pro Pro Ser Phe Thr
1               5                   10

<210> SEQ ID NO 212
<211> LENGTH: 12
<212> TYPE: PRT
<213> ORGANISM: Artificial Sequence
<220> FEATURE:
<223> OTHER INFORMATION: Synthetic Construct

<400> SEQUENCE: 212

Arg Ala Ser Gln Ser Leu Gly Ser Phe Tyr Leu Ala
1               5                   10

<210> SEQ ID NO 213
<211> LENGTH: 10
<212> TYPE: PRT
<213> ORGANISM: Artificial Sequence
<220> FEATURE:
<223> OTHER INFORMATION: Synthetic Construct

<400> SEQUENCE: 213

Lys His Tyr Gly Trp Pro Pro Ser Phe Thr
1               5                   10
```

```
<210> SEQ ID NO 214
<211> LENGTH: 10
<212> TYPE: PRT
<213> ORGANISM: Artificial Sequence
<220> FEATURE:
<223> OTHER INFORMATION: Synthetic Construct

<400> SEQUENCE: 214

Gln His Tyr Asn Tyr Pro Pro Ser Phe Thr
1               5                   10

<210> SEQ ID NO 215
<211> LENGTH: 12
<212> TYPE: PRT
<213> ORGANISM: Artificial Sequence
<220> FEATURE:
<223> OTHER INFORMATION: Synthetic Construct

<400> SEQUENCE: 215

Arg Ala Ser Gln Ser Val Gly Asp Phe Tyr Leu Ala
1               5                   10

<210> SEQ ID NO 216
<211> LENGTH: 10
<212> TYPE: PRT
<213> ORGANISM: Artificial Sequence
<220> FEATURE:
<223> OTHER INFORMATION: Synthetic Construct

<400> SEQUENCE: 216

Gln His Tyr Pro Tyr Pro Pro Ser Phe Thr
1               5                   10

<210> SEQ ID NO 217
<211> LENGTH: 12
<212> TYPE: PRT
<213> ORGANISM: Artificial Sequence
<220> FEATURE:
<223> OTHER INFORMATION: Synthetic Construct

<400> SEQUENCE: 217

Arg Ala Ser Gln Ser Val Ser Ser Tyr Pro Ser
1               5                   10

<210> SEQ ID NO 218
<211> LENGTH: 12
<212> TYPE: PRT
<213> ORGANISM: Artificial Sequence
<220> FEATURE:
<223> OTHER INFORMATION: Synthetic Construct

<400> SEQUENCE: 218

Arg Ala Ser Gln Ser Val Ser Ala His Tyr Leu Ala
1               5                   10

<210> SEQ ID NO 219
<211> LENGTH: 12
<212> TYPE: PRT
<213> ORGANISM: Artificial Sequence
<220> FEATURE:
<223> OTHER INFORMATION: Synthetic Construct

<400> SEQUENCE: 219

Arg Ala Ser Gln Ser Val Ser Ser Phe Phe Leu Ala
1               5                   10
```

```
<210> SEQ ID NO 220
<211> LENGTH: 10
<212> TYPE: PRT
<213> ORGANISM: Artificial Sequence
<220> FEATURE:
<223> OTHER INFORMATION: Synthetic Construct

<400> SEQUENCE: 220

Lys Tyr Tyr Pro Tyr Pro Pro Ser Phe Thr
1               5                   10

<210> SEQ ID NO 221
<211> LENGTH: 7
<212> TYPE: PRT
<213> ORGANISM: Artificial Sequence
<220> FEATURE:
<223> OTHER INFORMATION: Synthetic Construct

<400> SEQUENCE: 221

Asp Ala Ser Ile Arg Ala Thr
1               5

<210> SEQ ID NO 222
<211> LENGTH: 9
<212> TYPE: PRT
<213> ORGANISM: Artificial Sequence
<220> FEATURE:
<223> OTHER INFORMATION: Synthetic Construct

<400> SEQUENCE: 222

Gln Gln Tyr Gly Ser Trp Pro Leu Thr
1               5

<210> SEQ ID NO 223
<211> LENGTH: 12
<212> TYPE: PRT
<213> ORGANISM: Artificial Sequence
<220> FEATURE:
<223> OTHER INFORMATION: Synthetic Construct

<400> SEQUENCE: 223

Arg Ala Ser Gln Ser Val Ser Val Leu Tyr Leu Ala
1               5                   10

<210> SEQ ID NO 224
<211> LENGTH: 9
<212> TYPE: PRT
<213> ORGANISM: Artificial Sequence
<220> FEATURE:
<223> OTHER INFORMATION: Synthetic Construct

<400> SEQUENCE: 224

Gln Gln Tyr Gln Arg Trp Pro Leu Thr
1               5

<210> SEQ ID NO 225
<211> LENGTH: 9
<212> TYPE: PRT
<213> ORGANISM: Artificial Sequence
<220> FEATURE:
<223> OTHER INFORMATION: Synthetic Construct

<400> SEQUENCE: 225

Gln Gln Tyr Gln Ser Trp Pro Leu Thr
1               5
```

```
<210> SEQ ID NO 226
<211> LENGTH: 12
<212> TYPE: PRT
<213> ORGANISM: Artificial Sequence
<220> FEATURE:
<223> OTHER INFORMATION: Synthetic Construct

<400> SEQUENCE: 226

Arg Ala Ser Gln Ser Val Ser Asp Leu Tyr Leu Ala
1               5                   10

<210> SEQ ID NO 227
<211> LENGTH: 9
<212> TYPE: PRT
<213> ORGANISM: Artificial Sequence
<220> FEATURE:
<223> OTHER INFORMATION: Synthetic Construct

<400> SEQUENCE: 227

Gln Gln Tyr Gln Thr Trp Pro Leu Thr
1               5

<210> SEQ ID NO 228
<211> LENGTH: 12
<212> TYPE: PRT
<213> ORGANISM: Artificial Sequence
<220> FEATURE:
<223> OTHER INFORMATION: Synthetic Construct

<400> SEQUENCE: 228

Arg Ala Ser Gln Ser Val Ser Asn Leu Tyr Leu Ala
1               5                   10

<210> SEQ ID NO 229
<211> LENGTH: 9
<212> TYPE: PRT
<213> ORGANISM: Artificial Sequence
<220> FEATURE:
<223> OTHER INFORMATION: Synthetic Construct

<400> SEQUENCE: 229

Gln Gln Tyr Gln Gly Trp Pro Leu Thr
1               5

<210> SEQ ID NO 230
<211> LENGTH: 12
<212> TYPE: PRT
<213> ORGANISM: Artificial Sequence
<220> FEATURE:
<223> OTHER INFORMATION: Synthetic Construct

<400> SEQUENCE: 230

Arg Ala Ser Gln Ser Val Ser Ala Tyr Tyr Leu Ala
1               5                   10

<210> SEQ ID NO 231
<211> LENGTH: 9
<212> TYPE: PRT
<213> ORGANISM: Artificial Sequence
<220> FEATURE:
<223> OTHER INFORMATION: Synthetic Construct

<400> SEQUENCE: 231

Gln Gln Tyr Glu Arg Trp Pro Leu Thr
1               5
```

```
<210> SEQ ID NO 232
<211> LENGTH: 12
<212> TYPE: PRT
<213> ORGANISM: Artificial Sequence
<220> FEATURE:
<223> OTHER INFORMATION: Synthetic Construct

<400> SEQUENCE: 232

Arg Ala Ser Gln Ser Val Ser Ser Leu Tyr Leu Ala
1               5                   10

<210> SEQ ID NO 233
<211> LENGTH: 9
<212> TYPE: PRT
<213> ORGANISM: Artificial Sequence
<220> FEATURE:
<223> OTHER INFORMATION: Synthetic Construct

<400> SEQUENCE: 233

Gln Gln Tyr Gln Val Trp Pro Leu Thr
1               5

<210> SEQ ID NO 234
<211> LENGTH: 9
<212> TYPE: PRT
<213> ORGANISM: Artificial Sequence
<220> FEATURE:
<223> OTHER INFORMATION: Synthetic Construct

<400> SEQUENCE: 234

Gln Gln Tyr Leu Asp Trp Pro Leu Thr
1               5

<210> SEQ ID NO 235
<211> LENGTH: 12
<212> TYPE: PRT
<213> ORGANISM: Artificial Sequence
<220> FEATURE:
<223> OTHER INFORMATION: Synthetic Construct

<400> SEQUENCE: 235

Arg Ala Ser Gln Ser Val Ser Ala Leu Tyr Leu Ala
1               5                   10

<210> SEQ ID NO 236
<211> LENGTH: 9
<212> TYPE: PRT
<213> ORGANISM: Artificial Sequence
<220> FEATURE:
<223> OTHER INFORMATION: Synthetic Construct

<400> SEQUENCE: 236

Gln Gln Tyr Leu Ala Trp Pro Leu Thr
1               5

<210> SEQ ID NO 237
<211> LENGTH: 9
<212> TYPE: PRT
<213> ORGANISM: Artificial Sequence
<220> FEATURE:
<223> OTHER INFORMATION: Synthetic Construct

<400> SEQUENCE: 237

Gln Gln Tyr Phe Thr Trp Pro Leu Thr
1               5
```

```
<210> SEQ ID NO 238
<211> LENGTH: 12
<212> TYPE: PRT
<213> ORGANISM: Artificial Sequence
<220> FEATURE:
<223> OTHER INFORMATION: Synthetic Construct

<400> SEQUENCE: 238

Arg Ala Ser Gln Ser Val Ser Pro Tyr Tyr Leu Ala
1               5                   10

<210> SEQ ID NO 239
<211> LENGTH: 12
<212> TYPE: PRT
<213> ORGANISM: Artificial Sequence
<220> FEATURE:
<223> OTHER INFORMATION: Synthetic Construct

<400> SEQUENCE: 239

Arg Ala Ser Gln Ser Val Ser Val Glu Tyr Leu Ala
1               5                   10

<210> SEQ ID NO 240
<211> LENGTH: 9
<212> TYPE: PRT
<213> ORGANISM: Artificial Sequence
<220> FEATURE:
<223> OTHER INFORMATION: Synthetic Construct

<400> SEQUENCE: 240

Gln Gln Tyr Ala Arg Trp Pro Leu Thr
1               5

<210> SEQ ID NO 241
<211> LENGTH: 12
<212> TYPE: PRT
<213> ORGANISM: Artificial Sequence
<220> FEATURE:
<223> OTHER INFORMATION: Synthetic Construct

<400> SEQUENCE: 241

Arg Ala Ser Gln Ser Val Ser Glu Leu Tyr Leu Ala
1               5                   10

<210> SEQ ID NO 242
<211> LENGTH: 9
<212> TYPE: PRT
<213> ORGANISM: Artificial Sequence
<220> FEATURE:
<223> OTHER INFORMATION: Synthetic Construct

<400> SEQUENCE: 242

Gln Gln Tyr Phe Gly Trp Pro Leu Thr
1               5

<210> SEQ ID NO 243
<211> LENGTH: 12
<212> TYPE: PRT
<213> ORGANISM: Artificial Sequence
<220> FEATURE:
<223> OTHER INFORMATION: Synthetic Construct

<400> SEQUENCE: 243

Arg Ala Ser Gln Ser Val Glu Met Ser Tyr Leu Ala
1               5                   10
```

```
<210> SEQ ID NO 244
<211> LENGTH: 9
<212> TYPE: PRT
<213> ORGANISM: Artificial Sequence
<220> FEATURE:
<223> OTHER INFORMATION: Synthetic Construct

<400> SEQUENCE: 244

Gln Gln Tyr Ala His Trp Pro Leu Thr
1               5

<210> SEQ ID NO 245
<211> LENGTH: 12
<212> TYPE: PRT
<213> ORGANISM: Artificial Sequence
<220> FEATURE:
<223> OTHER INFORMATION: Synthetic Construct

<400> SEQUENCE: 245

Arg Ala Ser Gln Ser Val Ser Ala Gln Tyr Leu Ala
1               5                   10

<210> SEQ ID NO 246
<211> LENGTH: 12
<212> TYPE: PRT
<213> ORGANISM: Artificial Sequence
<220> FEATURE:
<223> OTHER INFORMATION: Synthetic Construct

<400> SEQUENCE: 246

Gly Pro Ser Gln Ser Val Ser Ser Ser Tyr Leu Ala
1               5                   10

<210> SEQ ID NO 247
<211> LENGTH: 12
<212> TYPE: PRT
<213> ORGANISM: Artificial Sequence
<220> FEATURE:
<223> OTHER INFORMATION: Synthetic Construct

<400> SEQUENCE: 247

Arg Ala Ser Gln Ser Val Ser Ser Tyr Trp Ala
1               5                   10

<210> SEQ ID NO 248
<211> LENGTH: 9
<212> TYPE: PRT
<213> ORGANISM: Artificial Sequence
<220> FEATURE:
<223> OTHER INFORMATION: Synthetic Construct

<400> SEQUENCE: 248

Gln Gln Tyr Glu Ser Trp Pro Leu Thr
1               5

<210> SEQ ID NO 249
<211> LENGTH: 12
<212> TYPE: PRT
<213> ORGANISM: Artificial Sequence
<220> FEATURE:
<223> OTHER INFORMATION: Synthetic Construct

<400> SEQUENCE: 249

Arg Gly Gly Gln Ser Val Ser Ser Ser Tyr Leu Ala
1               5                   10
```

```
<210> SEQ ID NO 250
<211> LENGTH: 12
<212> TYPE: PRT
<213> ORGANISM: Artificial Sequence
<220> FEATURE:
<223> OTHER INFORMATION: Synthetic Construct

<400> SEQUENCE: 250

Arg Ala Ser Gln Ser Val Ser Phe Leu Tyr Leu Ala
1               5                   10

<210> SEQ ID NO 251
<211> LENGTH: 12
<212> TYPE: PRT
<213> ORGANISM: Artificial Sequence
<220> FEATURE:
<223> OTHER INFORMATION: Synthetic Construct

<400> SEQUENCE: 251

Arg Ala Ser Gln Ser Val Ser Ser Thr Tyr Leu Ala
1               5                   10

<210> SEQ ID NO 252
<211> LENGTH: 7
<212> TYPE: PRT
<213> ORGANISM: Artificial Sequence
<220> FEATURE:
<223> OTHER INFORMATION: Synthetic Construct

<400> SEQUENCE: 252

Asp Ala Ser Ser Arg Ala Pro
1               5

<210> SEQ ID NO 253
<211> LENGTH: 9
<212> TYPE: PRT
<213> ORGANISM: Artificial Sequence
<220> FEATURE:
<223> OTHER INFORMATION: Synthetic Construct

<400> SEQUENCE: 253

Gln Gln Tyr Ser Thr Ser Pro Leu Thr
1               5

<210> SEQ ID NO 254
<211> LENGTH: 12
<212> TYPE: PRT
<213> ORGANISM: Artificial Sequence
<220> FEATURE:
<223> OTHER INFORMATION: Synthetic Construct

<400> SEQUENCE: 254

Arg Ala Ser Gln Ser Val Ser Pro Glu Tyr Leu Ala
1               5                   10

<210> SEQ ID NO 255
<211> LENGTH: 9
<212> TYPE: PRT
<213> ORGANISM: Artificial Sequence
<220> FEATURE:
<223> OTHER INFORMATION: Synthetic Construct

<400> SEQUENCE: 255

Gln Gln Tyr Ser Val Trp Pro Leu Thr
1               5
```

```
<210> SEQ ID NO 256
<211> LENGTH: 9
<212> TYPE: PRT
<213> ORGANISM: Artificial Sequence
<220> FEATURE:
<223> OTHER INFORMATION: Synthetic Construct

<400> SEQUENCE: 256

Gln Gln Tyr Ser Ala Trp Pro Leu Thr
1               5

<210> SEQ ID NO 257
<211> LENGTH: 12
<212> TYPE: PRT
<213> ORGANISM: Artificial Sequence
<220> FEATURE:
<223> OTHER INFORMATION: Synthetic Construct

<400> SEQUENCE: 257

Arg Ala Ser Gln Ser Val Ser Ser Val Tyr Leu Ala
1               5                   10

<210> SEQ ID NO 258
<211> LENGTH: 9
<212> TYPE: PRT
<213> ORGANISM: Artificial Sequence
<220> FEATURE:
<223> OTHER INFORMATION: Synthetic Construct

<400> SEQUENCE: 258

Gln Gln Tyr Ser Thr Trp Pro Leu Thr
1               5

<210> SEQ ID NO 259
<211> LENGTH: 9
<212> TYPE: PRT
<213> ORGANISM: Artificial Sequence
<220> FEATURE:
<223> OTHER INFORMATION: Synthetic Construct

<400> SEQUENCE: 259

Gln Gln Tyr Ser Arg Trp Pro Leu Thr
1               5

<210> SEQ ID NO 260
<211> LENGTH: 12
<212> TYPE: PRT
<213> ORGANISM: Artificial Sequence
<220> FEATURE:
<223> OTHER INFORMATION: Synthetic Construct

<400> SEQUENCE: 260

Arg Ala Ser Gln Ser Val Ser Pro Leu Tyr Leu Ala
1               5                   10

<210> SEQ ID NO 261
<211> LENGTH: 9
<212> TYPE: PRT
<213> ORGANISM: Artificial Sequence
<220> FEATURE:
<223> OTHER INFORMATION: Synthetic Construct

<400> SEQUENCE: 261

Gln Gln Tyr Ser Ala Phe Pro Leu Thr
1               5
```

```
<210> SEQ ID NO 262
<211> LENGTH: 12
<212> TYPE: PRT
<213> ORGANISM: Artificial Sequence
<220> FEATURE:
<223> OTHER INFORMATION: Synthetic Construct

<400> SEQUENCE: 262

Trp Leu Ser Gln Ser Val Ser Thr Tyr Leu Ala
1               5                   10

<210> SEQ ID NO 263
<211> LENGTH: 9
<212> TYPE: PRT
<213> ORGANISM: Artificial Sequence
<220> FEATURE:
<223> OTHER INFORMATION: Synthetic Construct

<400> SEQUENCE: 263

Gln Gln Tyr Ser Glu Trp Pro Leu Thr
1               5

<210> SEQ ID NO 264
<211> LENGTH: 9
<212> TYPE: PRT
<213> ORGANISM: Artificial Sequence
<220> FEATURE:
<223> OTHER INFORMATION: Synthetic Construct

<400> SEQUENCE: 264

Gln Gln Tyr Ser Ser Trp Pro Leu Thr
1               5

<210> SEQ ID NO 265
<211> LENGTH: 12
<212> TYPE: PRT
<213> ORGANISM: Artificial Sequence
<220> FEATURE:
<223> OTHER INFORMATION: Synthetic Construct

<400> SEQUENCE: 265

Arg Ala Ser Gln Ser Val Ser Ser Leu Phe Leu Ala
1               5                   10

<210> SEQ ID NO 266
<211> LENGTH: 12
<212> TYPE: PRT
<213> ORGANISM: Artificial Sequence
<220> FEATURE:
<223> OTHER INFORMATION: Synthetic Construct

<400> SEQUENCE: 266

Ala Cys Ser Gln Ser Val Ser Ser Thr Tyr Leu Ala
1               5                   10

<210> SEQ ID NO 267
<211> LENGTH: 12
<212> TYPE: PRT
<213> ORGANISM: Artificial Sequence
<220> FEATURE:
<223> OTHER INFORMATION: Synthetic Construct

<400> SEQUENCE: 267

Arg Ala Ser Cys Asp Val Ser Ser Thr Tyr Leu Ala
1               5                   10
```

```
<210> SEQ ID NO 268
<211> LENGTH: 9
<212> TYPE: PRT
<213> ORGANISM: Artificial Sequence
<220> FEATURE:
<223> OTHER INFORMATION: Synthetic Construct

<400> SEQUENCE: 268

Gln Gln Tyr Met Arg Ser Pro Leu Thr
 1               5

<210> SEQ ID NO 269
<211> LENGTH: 12
<212> TYPE: PRT
<213> ORGANISM: Artificial Sequence
<220> FEATURE:
<223> OTHER INFORMATION: Synthetic Construct

<400> SEQUENCE: 269

Arg Ala Ser Glu Ala Val Pro Ser Thr Tyr Leu Ala
 1               5                  10

<210> SEQ ID NO 270
<211> LENGTH: 12
<212> TYPE: PRT
<213> ORGANISM: Artificial Sequence
<220> FEATURE:
<223> OTHER INFORMATION: Synthetic Construct

<400> SEQUENCE: 270

Cys Ser Ser Gln Ser Val Ser Ser Thr Tyr Leu Ala
 1               5                  10

<210> SEQ ID NO 271
<211> LENGTH: 12
<212> TYPE: PRT
<213> ORGANISM: Artificial Sequence
<220> FEATURE:
<223> OTHER INFORMATION: Synthetic Construct

<400> SEQUENCE: 271

Arg Ala Ser Val Arg Val Ser Ser Thr Tyr Leu Ala
 1               5                  10

<210> SEQ ID NO 272
<211> LENGTH: 9
<212> TYPE: PRT
<213> ORGANISM: Artificial Sequence
<220> FEATURE:
<223> OTHER INFORMATION: Synthetic Construct

<400> SEQUENCE: 272

Gln Gln Tyr Met Lys Trp Pro Leu Thr
 1               5

<210> SEQ ID NO 273
<211> LENGTH: 12
<212> TYPE: PRT
<213> ORGANISM: Artificial Sequence
<220> FEATURE:
<223> OTHER INFORMATION: Synthetic Construct

<400> SEQUENCE: 273

Arg Ala Ser Gln Ser Val Ser Ala Ala Tyr Leu Ala
 1               5                  10
```

```
<210> SEQ ID NO 274
<211> LENGTH: 9
<212> TYPE: PRT
<213> ORGANISM: Artificial Sequence
<220> FEATURE:
<223> OTHER INFORMATION: Synthetic Construct

<400> SEQUENCE: 274

Gln Gln Tyr Met Cys Trp Pro Leu Thr
1               5

<210> SEQ ID NO 275
<211> LENGTH: 12
<212> TYPE: PRT
<213> ORGANISM: Artificial Sequence
<220> FEATURE:
<223> OTHER INFORMATION: Synthetic Construct

<400> SEQUENCE: 275

Arg Ala Ser Gln Ser Val Ser Ser Ser Tyr Trp Gly
1               5                   10

<210> SEQ ID NO 276
<211> LENGTH: 9
<212> TYPE: PRT
<213> ORGANISM: Artificial Sequence
<220> FEATURE:
<223> OTHER INFORMATION: Synthetic Construct

<400> SEQUENCE: 276

Gln Gln Tyr Gln Cys Trp Pro Leu Thr
1               5

<210> SEQ ID NO 277
<211> LENGTH: 12
<212> TYPE: PRT
<213> ORGANISM: Artificial Sequence
<220> FEATURE:
<223> OTHER INFORMATION: Synthetic Construct

<400> SEQUENCE: 277

Arg Ala Ser Gln Ser Val Ser Ser Pro Tyr Leu Ala
1               5                   10

<210> SEQ ID NO 278
<211> LENGTH: 9
<212> TYPE: PRT
<213> ORGANISM: Artificial Sequence
<220> FEATURE:
<223> OTHER INFORMATION: Synthetic Construct

<400> SEQUENCE: 278

Gln Gln Tyr Lys Ala Trp Pro Leu Thr
1               5

<210> SEQ ID NO 279
<211> LENGTH: 12
<212> TYPE: PRT
<213> ORGANISM: Artificial Sequence
<220> FEATURE:
<223> OTHER INFORMATION: Synthetic Construct

<400> SEQUENCE: 279

Arg Ala Ser Gln Ser Val Ser Tyr Leu Tyr Leu Ala
1               5                   10
```

```
<210> SEQ ID NO 280
<211> LENGTH: 9
<212> TYPE: PRT
<213> ORGANISM: Artificial Sequence
<220> FEATURE:
<223> OTHER INFORMATION: Synthetic Construct

<400> SEQUENCE: 280

Gln Gln Tyr Met Glu Trp Pro Leu Thr
1               5

<210> SEQ ID NO 281
<211> LENGTH: 9
<212> TYPE: PRT
<213> ORGANISM: Artificial Sequence
<220> FEATURE:
<223> OTHER INFORMATION: Synthetic Construct

<400> SEQUENCE: 281

Gln Gln Tyr Gln Ala Trp Pro Leu Thr
1               5

<210> SEQ ID NO 282
<211> LENGTH: 9
<212> TYPE: PRT
<213> ORGANISM: Artificial Sequence
<220> FEATURE:
<223> OTHER INFORMATION: Synthetic Construct

<400> SEQUENCE: 282

Gln Gln Tyr Gln Lys Trp Pro Leu Thr
1               5

<210> SEQ ID NO 283
<211> LENGTH: 12
<212> TYPE: PRT
<213> ORGANISM: Artificial Sequence
<220> FEATURE:
<223> OTHER INFORMATION: Synthetic Construct

<400> SEQUENCE: 283

Arg Ala Ser Gln Ser Val Ser Ala Val Tyr Leu Ala
1               5                   10

<210> SEQ ID NO 284
<211> LENGTH: 9
<212> TYPE: PRT
<213> ORGANISM: Artificial Sequence
<220> FEATURE:
<223> OTHER INFORMATION: Synthetic Construct

<400> SEQUENCE: 284

Gln Gln Tyr Arg Ala Trp Pro Leu Thr
1               5

<210> SEQ ID NO 285
<211> LENGTH: 12
<212> TYPE: PRT
<213> ORGANISM: Artificial Sequence
<220> FEATURE:
<223> OTHER INFORMATION: Synthetic Construct

<400> SEQUENCE: 285

Arg Ala Ser Ile Ala Val Ser Ser Thr Tyr Leu Ala
1               5                   10
```

```
<210> SEQ ID NO 286
<211> LENGTH: 9
<212> TYPE: PRT
<213> ORGANISM: Artificial Sequence
<220> FEATURE:
<223> OTHER INFORMATION: Synthetic Construct

<400> SEQUENCE: 286

Gln Gln Tyr Met Val Trp Pro Leu Thr
1               5

<210> SEQ ID NO 287
<211> LENGTH: 12
<212> TYPE: PRT
<213> ORGANISM: Artificial Sequence
<220> FEATURE:
<223> OTHER INFORMATION: Synthetic Construct

<400> SEQUENCE: 287

Arg Pro Arg Gln Ser Val Ser Ser Ser Tyr Leu Ala
1               5                   10

<210> SEQ ID NO 288
<211> LENGTH: 9
<212> TYPE: PRT
<213> ORGANISM: Artificial Sequence
<220> FEATURE:
<223> OTHER INFORMATION: Synthetic Construct

<400> SEQUENCE: 288

Gln Gln Tyr Gln Asp Trp Pro Leu Thr
1               5

<210> SEQ ID NO 289
<211> LENGTH: 9
<212> TYPE: PRT
<213> ORGANISM: Artificial Sequence
<220> FEATURE:
<223> OTHER INFORMATION: Synthetic Construct

<400> SEQUENCE: 289

Gln Gln Tyr Gln Glu Trp Pro Leu Thr
1               5

<210> SEQ ID NO 290
<211> LENGTH: 12
<212> TYPE: PRT
<213> ORGANISM: Artificial Sequence
<220> FEATURE:
<223> OTHER INFORMATION: Synthetic Construct

<400> SEQUENCE: 290

Arg Ala Ser Gln Ser Val Ser Ala Ser Tyr Leu Ala
1               5                   10

<210> SEQ ID NO 291
<211> LENGTH: 9
<212> TYPE: PRT
<213> ORGANISM: Artificial Sequence
<220> FEATURE:
<223> OTHER INFORMATION: Synthetic Construct

<400> SEQUENCE: 291

Gln Gln Tyr Met Ser Trp Pro Leu Thr
1               5
```

```
<210> SEQ ID NO 292
<211> LENGTH: 12
<212> TYPE: PRT
<213> ORGANISM: Artificial Sequence
<220> FEATURE:
<223> OTHER INFORMATION: Synthetic Construct

<400> SEQUENCE: 292

Arg Ala Ser Gln Ser Val Ser Tyr Met Tyr Leu Ala
1               5                   10

<210> SEQ ID NO 293
<211> LENGTH: 9
<212> TYPE: PRT
<213> ORGANISM: Artificial Sequence
<220> FEATURE:
<223> OTHER INFORMATION: Synthetic Construct

<400> SEQUENCE: 293

Gln Gln Tyr Lys Ser Trp Pro Leu Thr
1               5

<210> SEQ ID NO 294
<211> LENGTH: 9
<212> TYPE: PRT
<213> ORGANISM: Artificial Sequence
<220> FEATURE:
<223> OTHER INFORMATION: Synthetic Construct

<400> SEQUENCE: 294

Gln Gln Tyr Tyr Gly Trp Pro Leu Thr
1               5

<210> SEQ ID NO 295
<211> LENGTH: 12
<212> TYPE: PRT
<213> ORGANISM: Artificial Sequence
<220> FEATURE:
<223> OTHER INFORMATION: Synthetic Construct

<400> SEQUENCE: 295

Arg Ala Ser Gln Pro Ile Ser Ser Tyr Leu Ala
1               5                   10

<210> SEQ ID NO 296
<211> LENGTH: 9
<212> TYPE: PRT
<213> ORGANISM: Artificial Sequence
<220> FEATURE:
<223> OTHER INFORMATION: Synthetic Construct

<400> SEQUENCE: 296

Gln Gln Tyr Glu Phe Trp Pro Leu Thr
1               5

<210> SEQ ID NO 297
<211> LENGTH: 12
<212> TYPE: PRT
<213> ORGANISM: Artificial Sequence
<220> FEATURE:
<223> OTHER INFORMATION: Synthetic Construct

<400> SEQUENCE: 297

Arg Ala Ser Gln Gly Ile Ser Thr Tyr Leu Ala
1               5                   10
```

```
<210> SEQ ID NO 298
<211> LENGTH: 9
<212> TYPE: PRT
<213> ORGANISM: Artificial Sequence
<220> FEATURE:
<223> OTHER INFORMATION: Synthetic Construct

<400> SEQUENCE: 298

Gln Gln Tyr Ala Tyr Trp Pro Leu Thr
1               5

<210> SEQ ID NO 299
<211> LENGTH: 12
<212> TYPE: PRT
<213> ORGANISM: Artificial Sequence
<220> FEATURE:
<223> OTHER INFORMATION: Synthetic Construct

<400> SEQUENCE: 299

Arg Ala Ser Gln Ser Val Ser Val Arg Tyr Leu Ala
1               5                   10

<210> SEQ ID NO 300
<211> LENGTH: 9
<212> TYPE: PRT
<213> ORGANISM: Artificial Sequence
<220> FEATURE:
<223> OTHER INFORMATION: Synthetic Construct

<400> SEQUENCE: 300

Gln Gln Tyr Gly Ser Trp Pro Ile Thr
1               5

<210> SEQ ID NO 301
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is A or P
<220> FEATURE:
<221> NAME/KEY: MISC_FEATURE
<222> LOCATION: (5)..(5)
<223> OTHER INFORMATION: Xaa is T, N, or S

<400> SEQUENCE: 301

Ser Tyr Xaa Met Xaa
1               5

<210> SEQ ID NO 302
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is G or S

<400> SEQUENCE: 302

Gly Phe Thr Phe Xaa Ser Tyr
1               5
```

```
<210> SEQ ID NO 303
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is G or S
<220> FEATURE:
<221> NAME/KEY: MISC_FEATURE
<222> LOCATION: (8)..(8)
<223> OTHER INFORMATION: Xaa is A or P
<220> FEATURE:
<221> NAME/KEY: MISC_FEATURE
<222> LOCATION: (10)..(10)
<223> OTHER INFORMATION: Xaa is T, N, or S

<400> SEQUENCE: 303

Gly Phe Thr Phe Xaa Ser Tyr Xaa Met Xaa
1               5                   10

<210> SEQ ID NO 304
<211> LENGTH: 17
<212> TYPE: PRT
<213> ORGANISM: Artificial Sequence
<220> FEATURE:
<223> OTHER INFORMATION: Synthetic Construct

<400> SEQUENCE: 304

Ala Ile Ser Gly Trp Gly Gly Ser Leu Pro Tyr Ala Asp Ser Val Lys
1               5                   10                  15

Gly

<210> SEQ ID NO 305
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is I, V, T, H, L, A, or C
<220> FEATURE:
<221> NAME/KEY: MISC_FEATURE
<222> LOCATION: (3)..(3)
<223> OTHER INFORMATION: Xaa is S, D, G, T, I, L, F, M, or V
<220> FEATURE:
<221> NAME/KEY: MISC_FEATURE
<222> LOCATION: (4)..(4)
<223> OTHER INFORMATION: Xaa is G, Y, L, H, D, A, S, or M
<220> FEATURE:
<221> NAME/KEY: MISC_FEATURE
<222> LOCATION: (5)..(5)
<223> OTHER INFORMATION: Xaa is S, Q, T, A, F, or W
<220> FEATURE:
<221> NAME/KEY: MISC_FEATURE
<222> LOCATION: (7)..(7)
<223> OTHER INFORMATION: Xaa is G or T
<220> FEATURE:
<221> NAME/KEY: MISC_FEATURE
<222> LOCATION: (8)..(8)
<223> OTHER INFORMATION: Xaa is N, S, P, Y, W, or F
<220> FEATURE:
<221> NAME/KEY: MISC_FEATURE
<222> LOCATION: (9)..(9)
<223> OTHER INFORMATION: Xaa is S, T, I, L, T, A, R, V, K, G, or C
<220> FEATURE:
<221> NAME/KEY: MISC_FEATURE
<222> LOCATION: (10)..(10)
<223> OTHER INFORMATION: Xaa is F, Y, P, W, H, or G
```

```
<220> FEATURE:
<221> NAME/KEY: MISC_FEATURE
<222> LOCATION: (14)..(14)
<223> OTHER INFORMATION: Xaa is V, R, or L
<220> FEATURE:
<221> NAME/KEY: MISC_FEATURE
<222> LOCATION: (15)..(15)
<223> OTHER INFORMATION: Xaa is G or T

<400> SEQUENCE: 305

Ala Xaa Xaa Xaa Xaa Gly Xaa Xaa Xaa Xaa Tyr Ala Asp Xaa Xaa Lys
1               5                   10                  15

Gly

<210> SEQ ID NO 306
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is S, V, I, D, G, T, L, F, or M
<220> FEATURE:
<221> NAME/KEY: MISC_FEATURE
<222> LOCATION: (2)..(2)
<223> OTHER INFORMATION: Xaa is G, Y, L, H, D, A, S, or M
<220> FEATURE:
<221> NAME/KEY: MISC_FEATURE
<222> LOCATION: (3)..(3)
<223> OTHER INFORMATION: Xaa is S, G, F, or W
<220> FEATURE:
<221> NAME/KEY: MISC_FEATURE
<222> LOCATION: (4)..(4)
<223> OTHER INFORMATION: Xaa is G or S
<220> FEATURE:
<221> NAME/KEY: MISC_FEATURE
<222> LOCATION: (5)..(5)
<223> OTHER INFORMATION: Xaa is G or T
<220> FEATURE:
<221> NAME/KEY: MISC_FEATURE
<222> LOCATION: (6)..(6)
<223> OTHER INFORMATION: Xaa is N, S, P, Y, or W

<400> SEQUENCE: 306

Xaa Xaa Xaa Xaa Xaa Xaa
1               5

<210> SEQ ID NO 307
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is A or Y
<220> FEATURE:
<221> NAME/KEY: MISC_FEATURE
<222> LOCATION: (6)..(6)
<223> OTHER INFORMATION: Xaa is A or S
<220> FEATURE:
<221> NAME/KEY: MISC_FEATURE
<222> LOCATION: (7)..(7)
<223> OTHER INFORMATION: Xaa is G, Q, L, P, or E

<400> SEQUENCE: 307

Val Ser Pro Ile Xaa Xaa Xaa Met Asp Tyr
1               5                   10
```

```
<210> SEQ ID NO 308
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is D, S, T, or A
<220> FEATURE:
<221> NAME/KEY: MISC_FEATURE
<222> LOCATION: (6)..(6)
<223> OTHER INFORMATION: Xaa is I, S, L, P, or D

<400> SEQUENCE: 308

Tyr Trp Pro Met Xaa Xaa
1               5

<210> SEQ ID NO 309
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is R, G, W, A, or C
<220> FEATURE:
<221> NAME/KEY: MISC_FEATURE
<222> LOCATION: (2)..(2)
<223> OTHER INFORMATION: Xaa is A, P, G, L, C, or S
<220> FEATURE:
<221> NAME/KEY: MISC_FEATURE
<222> LOCATION: (3)..(3)
<223> OTHER INFORMATION: Xaa is S, G, or R
<220> FEATURE:
<221> NAME/KEY: MISC_FEATURE
<222> LOCATION: (4)..(4)
<223> OTHER INFORMATION: Xaa is Q, C, E, V, or I
<220> FEATURE:
<221> NAME/KEY: MISC_FEATURE
<222> LOCATION: (5)..(5)
<223> OTHER INFORMATION: Xaa is S, P, G, A, R, or D
<220> FEATURE:
<221> NAME/KEY: MISC_FEATURE
<222> LOCATION: (6)..(6)
<223> OTHER INFORMATION: Xaa is V, G, I, or L
<220> FEATURE:
<221> NAME/KEY: MISC_FEATURE
<222> LOCATION: (7)..(7)
<223> OTHER INFORMATION: Xaa is S, E, D, P, or G
<220> FEATURE:
<221> NAME/KEY: MISC_FEATURE
<222> LOCATION: (8)..(8)
<223> OTHER INFORMATION: Xaa is S, P, F, A, M, E, V, N, D, or Y
<220> FEATURE:
<221> NAME/KEY: MISC_FEATURE
<222> LOCATION: (9)..(9)
<223> OTHER INFORMATION: Xaa is I, T, V, E, F, S, A, M, Q, Y, H, or R
<220> FEATURE:
<221> NAME/KEY: MISC_FEATURE
<222> LOCATION: (10)..(10)
<223> OTHER INFORMATION: Xaa is Y or F
<220> FEATURE:
<221> NAME/KEY: MISC_FEATURE
<222> LOCATION: (11)..(11)
<223> OTHER INFORMATION: Xaa is L, W, or P
<220> FEATURE:
<221> NAME/KEY: MISC_FEATURE
<222> LOCATION: (12)..(12)
<223> OTHER INFORMATION: Xaa is A, S, or G
```

```
<400> SEQUENCE: 309

Xaa Xaa Xaa Xaa Xaa Xaa Xaa Xaa Xaa Xaa Xaa Xaa
1               5                   10

<210> SEQ ID NO 310
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is G or D
<220> FEATURE:
<221> NAME/KEY: MISC_FEATURE
<222> LOCATION: (4)..(4)
<223> OTHER INFORMATION: Xaa is S or I
<220> FEATURE:
<221> NAME/KEY: MISC_FEATURE
<222> LOCATION: (7)..(7)
<223> OTHER INFORMATION: Xaa is T or P

<400> SEQUENCE: 310

Xaa Ala Ser Xaa Arg Ala Xaa
1               5

<210> SEQ ID NO 311
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Q or K
<220> FEATURE:
<221> NAME/KEY: MISC_FEATURE
<222> LOCATION: (2)..(2)
<223> OTHER INFORMATION: Xaa is H or Y
<220> FEATURE:
<221> NAME/KEY: MISC_FEATURE
<222> LOCATION: (4)..(4)
<223> OTHER INFORMATION: Xaa is G, N, or P
<220> FEATURE:
<221> NAME/KEY: MISC_FEATURE
<222> LOCATION: (5)..(5)
<223> OTHER INFORMATION: Xaa is S, W, or Y

<400> SEQUENCE: 311

Xaa Xaa Tyr Xaa Xaa Pro Pro Ser Phe Thr
1               5                   10

<210> SEQ ID NO 312
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is G, Q, E, L, F, A, S, M, K, R, or Y
<220> FEATURE:
<221> NAME/KEY: MISC_FEATURE
<222> LOCATION: (5)..(5)
<223> OTHER INFORMATION: Xaa is S, R, T, G, V, F, Y, D, A, H, V, E, K,
      or C
<220> FEATURE:
<221> NAME/KEY: MISC_FEATURE
<222> LOCATION: (6)..(6)
<223> OTHER INFORMATION: Xaa is W, F, or S
```

```
<220> FEATURE:
<221> NAME/KEY: MISC_FEATURE
<222> LOCATION: (8)..(8)
<223> OTHER INFORMATION: Xaa is L or I

<400> SEQUENCE: 312

Gln Gln Tyr Xaa Xaa Xaa Pro Xaa Thr
1               5

<210> SEQ ID NO 313
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (30)..(30)
<223> OTHER INFORMATION: Xaa is G or S
<220> FEATURE:
<221> NAME/KEY: MISC_FEATURE
<222> LOCATION: (33)..(33)
<223> OTHER INFORMATION: Xaa is A or P
<220> FEATURE:
<221> NAME/KEY: MISC_FEATURE
<222> LOCATION: (35)..(35)
<223> OTHER INFORMATION: Xaa is T, N, or S
<220> FEATURE:
<221> NAME/KEY: MISC_FEATURE
<222> LOCATION: (51)..(51)
<223> OTHER INFORMATION: Xaa is I, V, T, H, L, A, or C
<220> FEATURE:
<221> NAME/KEY: MISC_FEATURE
<222> LOCATION: (52)..(52)
<223> OTHER INFORMATION: Xaa is S, D, G, T, I, L, F, M, or V
<220> FEATURE:
<221> NAME/KEY: MISC_FEATURE
<222> LOCATION: (53)..(53)
<223> OTHER INFORMATION: Xaa is G, Y, L, H, D, A, S, or M
<220> FEATURE:
<221> NAME/KEY: MISC_FEATURE
<222> LOCATION: (54)..(54)
<223> OTHER INFORMATION: Xaa is S, Q, T, A, F, or W
<220> FEATURE:
<221> NAME/KEY: MISC_FEATURE
<222> LOCATION: (56)..(56)
<223> OTHER INFORMATION: Xaa is G or T
<220> FEATURE:
<221> NAME/KEY: MISC_FEATURE
<222> LOCATION: (57)..(57)
<223> OTHER INFORMATION: Xaa is N, S, P, Y, W, or F
<220> FEATURE:
<221> NAME/KEY: MISC_FEATURE
<222> LOCATION: (58)..(58)
<223> OTHER INFORMATION: Xaa is S, T, I, L, T, A, R, V, K, G, or C
<220> FEATURE:
<221> NAME/KEY: MISC_FEATURE
<222> LOCATION: (59)..(59)
<223> OTHER INFORMATION: Xaa is F, Y, P, W, H, or G
<220> FEATURE:
<221> NAME/KEY: MISC_FEATURE
<222> LOCATION: (63)..(63)
<223> OTHER INFORMATION: Xaa is V, R, or L
<220> FEATURE:
<221> NAME/KEY: MISC_FEATURE
<222> LOCATION: (64)..(64)
<223> OTHER INFORMATION: Xaa is G or T
<220> FEATURE:
<221> NAME/KEY: MISC_FEATURE
<222> LOCATION: (103)..(103)
<223> OTHER INFORMATION: Xaa is A or Y
<220> FEATURE:
<221> NAME/KEY: MISC_FEATURE
<222> LOCATION: (104)..(104)
<223> OTHER INFORMATION: Xaa is A or S
```

<220> FEATURE:
<221> NAME/KEY: MISC_FEATURE
<222> LOCATION: (105)..(105)
<223> OTHER INFORMATION: Xaa is G, Q, L, P, or E

<400> SEQUENCE: 313

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Xaa Ser Tyr
            20                  25                  30

Xaa Met Xaa Trp Val Arg Gln Ala Pro Gly Lys Gly Leu Glu Trp Val
        35                  40                  45

Ser Ala Xaa Xaa Xaa Xaa Gly Xaa Xaa Xaa Xaa Tyr Ala Asp Xaa Xaa
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Val Ser Pro Ile Xaa Xaa Xaa Met Asp Tyr Trp Gly Gln Gly
            100                 105                 110

Thr Leu Val Thr Val Ser Ser
        115

<210> SEQ ID NO 314
<211> LENGTH: 115
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (30)..(30)
<223> OTHER INFORMATION: Xaa is G or S
<220> FEATURE:
<221> NAME/KEY: MISC_FEATURE
<222> LOCATION: (33)..(33)
<223> OTHER INFORMATION: Xaa is A or P
<220> FEATURE:
<221> NAME/KEY: MISC_FEATURE
<222> LOCATION: (35)..(35)
<223> OTHER INFORMATION: Xaa is T, N, or S
<220> FEATURE:
<221> NAME/KEY: MISC_FEATURE
<222> LOCATION: (51)..(51)
<223> OTHER INFORMATION: Xaa is I, V, T, H, L, A, or C
<220> FEATURE:
<221> NAME/KEY: MISC_FEATURE
<222> LOCATION: (52)..(52)
<223> OTHER INFORMATION: Xaa is S, D, G, T, I, L, F, M, or V
<220> FEATURE:
<221> NAME/KEY: MISC_FEATURE
<222> LOCATION: (53)..(53)
<223> OTHER INFORMATION: Xaa is G, Y, L, H, D, A, S, or M
<220> FEATURE:
<221> NAME/KEY: MISC_FEATURE
<222> LOCATION: (54)..(54)
<223> OTHER INFORMATION: Xaa is S, Q, T, A, F, or W
<220> FEATURE:
<221> NAME/KEY: MISC_FEATURE
<222> LOCATION: (56)..(56)
<223> OTHER INFORMATION: Xaa is G or T
<220> FEATURE:
<221> NAME/KEY: MISC_FEATURE
<222> LOCATION: (57)..(57)
<223> OTHER INFORMATION: Xaa is N, S, P, Y, W, or F
<220> FEATURE:
<221> NAME/KEY: MISC_FEATURE
<222> LOCATION: (58)..(58)
<223> OTHER INFORMATION: Xaa is S, T, I, L, T, A, R, V, K, G, or C

```
<220> FEATURE:
<221> NAME/KEY: MISC_FEATURE
<222> LOCATION: (59)..(59)
<223> OTHER INFORMATION: Xaa is F, Y, P, W, H, or G
<220> FEATURE:
<221> NAME/KEY: MISC_FEATURE
<222> LOCATION: (63)..(63)
<223> OTHER INFORMATION: Xaa is V, R, or L
<220> FEATURE:
<221> NAME/KEY: MISC_FEATURE
<222> LOCATION: (64)..(64)
<223> OTHER INFORMATION: Xaa is G or T
<220> FEATURE:
<221> NAME/KEY: MISC_FEATURE
<222> LOCATION: (103)..(103)
<223> OTHER INFORMATION: Xaa is D, S, T, or A
<220> FEATURE:
<221> NAME/KEY: MISC_FEATURE
<222> LOCATION: (104)..(104)
<223> OTHER INFORMATION: Xaa is I, S, L, P, or D

<400> SEQUENCE: 314

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Xaa Ser Tyr
            20                  25                  30

Xaa Met Xaa Trp Val Arg Gln Ala Pro Gly Lys Gly Leu Glu Trp Val
        35                  40                  45

Ser Ala Xaa Xaa Xaa Xaa Gly Xaa Xaa Xaa Xaa Tyr Ala Asp Xaa Xaa
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Xaa Xaa Trp Gly Gln Gly Thr Leu Val Thr
            100                 105                 110

Val Ser Ser
        115

<210> SEQ ID NO 315
<211> LENGTH: 109
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (24)..(24)
<223> OTHER INFORMATION: Xaa is R, G, W, A, or C
<220> FEATURE:
<221> NAME/KEY: MISC_FEATURE
<222> LOCATION: (25)..(25)
<223> OTHER INFORMATION: Xaa is A, P, G, L, C, or S
<220> FEATURE:
<221> NAME/KEY: MISC_FEATURE
<222> LOCATION: (26)..(26)
<223> OTHER INFORMATION: Xaa is S, G, or R
<220> FEATURE:
<221> NAME/KEY: MISC_FEATURE
<222> LOCATION: (27)..(27)
<223> OTHER INFORMATION: Xaa is Q, C, E, V, or I
<220> FEATURE:
<221> NAME/KEY: MISC_FEATURE
<222> LOCATION: (28)..(28)
<223> OTHER INFORMATION: Xaa is S, P, G, A, R, or D
<220> FEATURE:
<221> NAME/KEY: MISC_FEATURE
<222> LOCATION: (29)..(29)
<223> OTHER INFORMATION: Xaa is V, G, I, or L
```

```
<220> FEATURE:
<221> NAME/KEY: MISC_FEATURE
<222> LOCATION: (30)..(30)
<223> OTHER INFORMATION: Xaa is S, E, D, P, or G
<220> FEATURE:
<221> NAME/KEY: MISC_FEATURE
<222> LOCATION: (31)..(31)
<223> OTHER INFORMATION: Xaa is S, P, F, A, M, E, V, N, D, or Y
<220> FEATURE:
<221> NAME/KEY: MISC_FEATURE
<222> LOCATION: (32)..(32)
<223> OTHER INFORMATION: Xaa is I, T, V, E, S, A, M, Q, Y, H, R, or F
<220> FEATURE:
<221> NAME/KEY: MISC_FEATURE
<222> LOCATION: (33)..(33)
<223> OTHER INFORMATION: Xaa is Y or F
<220> FEATURE:
<221> NAME/KEY: MISC_FEATURE
<222> LOCATION: (34)..(34)
<223> OTHER INFORMATION: Xaa is L, W, or P
<220> FEATURE:
<221> NAME/KEY: MISC_FEATURE
<222> LOCATION: (35)..(35)
<223> OTHER INFORMATION: Xaa is A, S, or G
<220> FEATURE:
<221> NAME/KEY: MISC_FEATURE
<222> LOCATION: (51)..(51)
<223> OTHER INFORMATION: Xaa is G or D
<220> FEATURE:
<221> NAME/KEY: MISC_FEATURE
<222> LOCATION: (54)..(54)
<223> OTHER INFORMATION: Xaa is S or I
<220> FEATURE:
<221> NAME/KEY: MISC_FEATURE
<222> LOCATION: (57)..(57)
<223> OTHER INFORMATION: Xaa is T or P
<220> FEATURE:
<221> NAME/KEY: MISC_FEATURE
<222> LOCATION: (90)..(90)
<223> OTHER INFORMATION: Xaa is Q or K
<220> FEATURE:
<221> NAME/KEY: MISC_FEATURE
<222> LOCATION: (91)..(91)
<223> OTHER INFORMATION: Xaa is H or Y
<220> FEATURE:
<221> NAME/KEY: MISC_FEATURE
<222> LOCATION: (93)..(93)
<223> OTHER INFORMATION: Xaa is G, N, or P
<220> FEATURE:
<221> NAME/KEY: MISC_FEATURE
<222> LOCATION: (94)..(94)
<223> OTHER INFORMATION: Xaa is S, W, or Y

<400> SEQUENCE: 315

Glu Ile Val Leu Thr Gln Ser Pro Gly Thr Leu Ser Leu Ser Pro Gly
1               5                   10                  15

Glu Arg Ala Thr Leu Ser Cys Xaa Xaa Xaa Xaa Xaa Xaa Xaa Xaa Xaa
            20                  25                  30

Xaa Xaa Xaa Trp Tyr Gln Gln Lys Pro Gly Gln Ala Pro Arg Leu Leu
        35                  40                  45

Met Tyr Xaa Ala Ser Xaa Arg Ala Xaa Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Xaa Xaa Tyr Xaa Xaa Pro Pro
                85                  90                  95

Ser Phe Thr Phe Gly Gln Gly Thr Lys Val Glu Ile Lys
                100                 105
```

```
<210> SEQ ID NO 316
<211> LENGTH: 107
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (24)..(24)
<223> OTHER INFORMATION: Xaa is R, G, W, A, or C
<220> FEATURE:
<221> NAME/KEY: MISC_FEATURE
<222> LOCATION: (25)..(25)
<223> OTHER INFORMATION: Xaa is A, P, G, L, C, or S
<220> FEATURE:
<221> NAME/KEY: MISC_FEATURE
<222> LOCATION: (26)..(26)
<223> OTHER INFORMATION: Xaa is S, G, or R
<220> FEATURE:
<221> NAME/KEY: MISC_FEATURE
<222> LOCATION: (27)..(27)
<223> OTHER INFORMATION: Xaa is Q, C, E, V, or I
<220> FEATURE:
<221> NAME/KEY: MISC_FEATURE
<222> LOCATION: (28)..(28)
<223> OTHER INFORMATION: Xaa is S, L, P, G, A, R, or D
<220> FEATURE:
<221> NAME/KEY: MISC_FEATURE
<222> LOCATION: (29)..(29)
<223> OTHER INFORMATION: Xaa is V, G, or I
<220> FEATURE:
<221> NAME/KEY: MISC_FEATURE
<222> LOCATION: (30)..(30)
<223> OTHER INFORMATION: Xaa is S, E, D, or P
<220> FEATURE:
<221> NAME/KEY: MISC_FEATURE
<222> LOCATION: (31)..(31)
<223> OTHER INFORMATION: Xaa is S, P, F, A, M, E, V, N, D, or Y
<220> FEATURE:
<221> NAME/KEY: MISC_FEATURE
<222> LOCATION: (32)..(32)
<223> OTHER INFORMATION: Xaa is I, T, V, E, S, A, M, Q, Y, H, or R
<220> FEATURE:
<221> NAME/KEY: MISC_FEATURE
<222> LOCATION: (33)..(33)
<223> OTHER INFORMATION: Xaa is Y or F
<220> FEATURE:
<221> NAME/KEY: MISC_FEATURE
<222> LOCATION: (34)..(34)
<223> OTHER INFORMATION: Xaa is L, W, or P
<220> FEATURE:
<221> NAME/KEY: MISC_FEATURE
<222> LOCATION: (35)..(35)
<223> OTHER INFORMATION: Xaa is A, S, or G
<220> FEATURE:
<221> NAME/KEY: MISC_FEATURE
<222> LOCATION: (51)..(51)
<223> OTHER INFORMATION: Xaa is G or D
<220> FEATURE:
<221> NAME/KEY: MISC_FEATURE
<222> LOCATION: (54)..(54)
<223> OTHER INFORMATION: Xaa is S or I
<220> FEATURE:
<221> NAME/KEY: MISC_FEATURE
<222> LOCATION: (57)..(57)
<223> OTHER INFORMATION: Xaa is T or P
<220> FEATURE:
<221> NAME/KEY: MISC_FEATURE
<222> LOCATION: (93)..(93)
<223> OTHER INFORMATION: Xaa is G, Q, E, L, F, A, S, M, R, K, or Y
<220> FEATURE:
<221> NAME/KEY: MISC_FEATURE
<222> LOCATION: (94)..(94)
<223> OTHER INFORMATION: Xaa is S, R, T, G, R, V, D, A, H, E, K, C, F,
      or Y
<220> FEATURE:
<221> NAME/KEY: MISC_FEATURE
<222> LOCATION: (95)..(95)
<223> OTHER INFORMATION: Xaa is W, S, or F
```

```
<220> FEATURE:
<221> NAME/KEY: MISC_FEATURE
<222> LOCATION: (97)..(97)
<223> OTHER INFORMATION: Xaa is L or I

<400> SEQUENCE: 316

Glu Ile Val Leu Thr Gln Ser Pro Gly Thr Leu Ser Leu Ser Pro Gly
1               5                   10                  15

Glu Arg Ala Thr Leu Ser Cys Xaa Xaa Xaa Xaa Xaa Xaa Xaa Xaa
            20                  25                  30

Xaa Xaa Xaa Trp Tyr Gln Gln Lys Pro Gly Gln Ala Pro Arg Leu Leu
        35                  40                  45

Met Tyr Xaa Ala Ser Xaa Arg Ala Xaa Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Xaa Xaa Xaa Pro
                85                  90                  95

Xaa Phe Gly Gln Gly Thr Lys Val Glu Ile Lys
            100                 105

<210> SEQ ID NO 317
<211> LENGTH: 108
<212> TYPE: PRT
<213> ORGANISM: Artificial Sequence
<220> FEATURE:
<223> OTHER INFORMATION: Synthetic Construct

<400> SEQUENCE: 317

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ala Leu
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ala Trp Pro
                85                  90                  95

Leu Thr Phe Gly Gln Gly Thr Lys Val Glu Ile Lys
            100                 105

<210> SEQ ID NO 318
<211> LENGTH: 5
<212> TYPE: PRT
<213> ORGANISM: Artificial Sequence
<220> FEATURE:
<223> OTHER INFORMATION: Synthetic Construct

<400> SEQUENCE: 318

Leu Leu Gln Gly Gly
1               5

<210> SEQ ID NO 319
<211> LENGTH: 112
<212> TYPE: PRT
<213> ORGANISM: Artificial Sequence
<220> FEATURE:
<223> OTHER INFORMATION: Synthetic Construct
```

<400> SEQUENCE: 319

Asp Ile Val Met Thr Gln Ser Pro Asp Ser Leu Ala Val Ser Leu Gly
1               5                   10                  15

Glu Arg Ala Thr Ile Asn Cys Thr Ser Ser Gln Ser Leu Phe Asn Val
            20                  25                  30

Arg Ser Arg Lys Asn Tyr Leu Ala Trp Tyr Gln Gln Lys Pro Gly Gln
        35                  40                  45

Pro Pro Lys Leu Leu Ile Ser Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asp Leu Phe Thr Phe Gly Ser Gly Thr Lys Leu Glu Ile Lys
            100                 105                 110

<210> SEQ ID NO 320
<211> LENGTH: 121
<212> TYPE: PRT
<213> ORGANISM: Artificial Sequence
<220> FEATURE:
<223> OTHER INFORMATION: Synthetic Construct

<400> SEQUENCE: 320

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Val Arg Gln Ala Pro Gly Lys Gly Leu Glu Trp Val
        35                  40                  45

Ala Phe Ile Arg Asn Arg Ala Arg Gly Tyr Thr Ser Asp His Asn Ala
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Pro Ser Tyr Tyr Val Leu Asp Tyr Trp Gly
            100                 105                 110

Gln Gly Thr Thr Val Thr Val Ser Ser
        115                 120

<210> SEQ ID NO 321
<211> LENGTH: 112
<212> TYPE: PRT
<213> ORGANISM: Artificial Sequence
<220> FEATURE:
<223> OTHER INFORMATION: Synthetic Construct

<400> SEQUENCE: 321

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Val
            20                  25                  30

Arg Ser Arg Lys Asn Tyr Leu Ala Trp Tyr Gln Gln Lys Pro Gly Gln
        35                  40                  45

Pro Pro Lys Leu Leu Ile Ser Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asp Leu Phe Thr Phe Gly Ser Gly Thr Lys Leu Glu Ile Lys
            100                 105                 110

<210> SEQ ID NO 322
<211> LENGTH: 121
<212> TYPE: PRT
<213> ORGANISM: Artificial Sequence
<220> FEATURE:
<223> OTHER INFORMATION: Synthetic Construct

<400> SEQUENCE: 322

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Tyr Met Thr Trp Val Arg Gln Ala Pro Gly Lys Gly Leu Glu Trp Val
            35                  40                  45

Ala Phe Ile Arg Asn Arg Ala Arg Gly Tyr Thr Ser Asp His Asn Ala
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Pro Ser Tyr Tyr Val Leu Asp Tyr Trp Gly
            100                 105                 110

Gln Gly Thr Thr Val Thr Val Ser Ser
        115                 120

<210> SEQ ID NO 323
<211> LENGTH: 112
<212> TYPE: PRT
<213> ORGANISM: Artificial Sequence
<220> FEATURE:
<223> OTHER INFORMATION: Synthetic Construct

<400> SEQUENCE: 323

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Val
                20                  25                  30

Arg Ser Arg Lys Asn Tyr Leu Ala Trp Tyr Gln Gln Lys Pro Gly Gln
            35                  40                  45

Pro Pro Lys Leu Leu Ile Ser Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asp Leu Phe Thr Phe Gly Ser Gly Thr Lys Leu Glu Ile Lys
            100                 105                 110

<210> SEQ ID NO 324
<211> LENGTH: 121
<212> TYPE: PRT
<213> ORGANISM: Artificial Sequence
<220> FEATURE:
<223> OTHER INFORMATION: Synthetic Construct

<400> SEQUENCE: 324

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Val Arg Gln Ala Pro Gly Lys Gly Leu Glu Trp Val
        35                  40                  45

Ala Phe Ile Arg Asn Arg Ala Arg Gly Tyr Thr Ser Asp His Asn Pro
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
            85                  90                  95

Tyr Cys Ala Arg Asp Arg Pro Ser Tyr Tyr Val Leu Asp Tyr Trp Gly
            100                 105                 110

Gln Gly Thr Thr Val Thr Val Ser Ser
            115                 120

<210> SEQ ID NO 325
<211> LENGTH: 112
<212> TYPE: PRT
<213> ORGANISM: Artificial Sequence
<220> FEATURE:
<223> OTHER INFORMATION: Synthetic Construct

<400> SEQUENCE: 325

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Val
            20                  25                  30

Arg Ser Arg Lys Asn Tyr Leu Ala Trp Tyr Gln Gln Lys Pro Gly Gln
            35                  40                  45

Pro Pro Lys Leu Leu Ile Ser Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
            85                  90                  95

Ser Tyr Asp Leu Phe Thr Phe Gly Ser Gly Thr Lys Leu Glu Ile Lys
            100                 105                 110

<210> SEQ ID NO 326
<211> LENGTH: 121
<212> TYPE: PRT
<213> ORGANISM: Artificial Sequence
<220> FEATURE:
<223> OTHER INFORMATION: Synthetic Construct

<400> SEQUENCE: 326

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Val Arg Gln Ala Pro Gly Lys Gly Leu Glu Trp Val
        35                  40                  45

Ala Phe Ile Arg Asn Arg Ala Arg Gly Tyr Thr Ser Asp Tyr Ala Glu
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Pro Ser Tyr Tyr Val Leu Asp Tyr Trp Gly
            100                 105                 110

Gln Gly Thr Thr Val Thr Val Ser Ser
            115                 120

<210> SEQ ID NO 327
<211> LENGTH: 112
<212> TYPE: PRT
<213> ORGANISM: Artificial Sequence
<220> FEATURE:
<223> OTHER INFORMATION: Synthetic Construct

<400> SEQUENCE: 327

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Val
            20                  25                  30

Arg Ser Arg Lys Asn Tyr Leu Ala Trp Tyr Gln Gln Lys Pro Gly Gln
        35                  40                  45

Pro Pro Lys Leu Leu Ile Ser Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asp Leu Phe Thr Phe Gly Ser Gly Thr Lys Leu Glu Ile Lys
            100                 105                 110

<210> SEQ ID NO 328
<211> LENGTH: 121
<212> TYPE: PRT
<213> ORGANISM: Artificial Sequence
<220> FEATURE:
<223> OTHER INFORMATION: Synthetic Construct

<400> SEQUENCE: 328

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Val Arg Gln Ala Pro Gly Lys Gly Leu Glu Trp Val
        35                  40                  45

Ala Phe Ile Arg Asn Arg Ala Arg Gly Tyr Thr Ser Asp Tyr Ala Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Pro Ser Tyr Tyr Val Leu Asp Tyr Trp Gly
            100                 105                 110

Gln Gly Thr Thr Val Thr Val Ser Ser
            115                 120

<210> SEQ ID NO 329
<211> LENGTH: 112
<212> TYPE: PRT
<213> ORGANISM: Artificial Sequence
<220> FEATURE:
<223> OTHER INFORMATION: Synthetic Construct

<400> SEQUENCE: 329

Asp Ile Val Met Thr Gln Ser Pro Asp Ser Leu Ala Val Ser Leu Gly
1               5                   10                  15

Glu Arg Ala Thr Ile Asn Cys Thr Ser Ser Gln Ser Leu Phe Asn Val
            20                  25                  30

Arg Ser Arg Lys Asn Tyr Leu Ala Trp Tyr Gln Gln Lys Pro Gly Gln
        35                  40                  45

Pro Pro Lys Leu Leu Ile Ser Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asp Leu Phe Thr Phe Gly Ser Gly Thr Lys Leu Glu Ile Lys
            100                 105                 110

<210> SEQ ID NO 330
<211> LENGTH: 121
<212> TYPE: PRT
<213> ORGANISM: Artificial Sequence
<220> FEATURE:
<223> OTHER INFORMATION: Synthetic Construct

<400> SEQUENCE: 330

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Val Arg Gln Ala Pro Gly Lys Gly Leu Glu Trp Val
        35                  40                  45

Ala Phe Ile Arg Asn Arg Ala Arg Gly Tyr Thr Ser Asp Tyr Ala Pro
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Pro Ser Tyr Tyr Val Leu Asp Tyr Trp Gly
            100                 105                 110

Gln Gly Thr Thr Val Thr Val Ser Ser
        115                 120

<210> SEQ ID NO 331
<211> LENGTH: 5
<212> TYPE: PRT
<213> ORGANISM: Artificial Sequence
<220> FEATURE:
<223> OTHER INFORMATION: Synthetic Construct

<400> SEQUENCE: 331

Asp Tyr Tyr Met Thr
1               5

```
<210> SEQ ID NO 332
<211> LENGTH: 7
<212> TYPE: PRT
<213> ORGANISM: Artificial Sequence
<220> FEATURE:
<223> OTHER INFORMATION: Synthetic Construct

<400> SEQUENCE: 332

Gly Phe Thr Phe Ser Asp Tyr
1               5

<210> SEQ ID NO 333
<211> LENGTH: 10
<212> TYPE: PRT
<213> ORGANISM: Artificial Sequence
<220> FEATURE:
<223> OTHER INFORMATION: Synthetic Construct

<400> SEQUENCE: 333

Gly Phe Thr Phe Ser Asp Tyr Tyr Met Thr
1               5                   10

<210> SEQ ID NO 334
<211> LENGTH: 19
<212> TYPE: PRT
<213> ORGANISM: Artificial Sequence
<220> FEATURE:
<223> OTHER INFORMATION: Synthetic Construct

<400> SEQUENCE: 334

Phe Ile Arg Asn Arg Ala Arg Gly Tyr Thr Ser Asp His Asn Ala Ser
1               5                   10                  15

Val Lys Gly

<210> SEQ ID NO 335
<211> LENGTH: 10
<212> TYPE: PRT
<213> ORGANISM: Artificial Sequence
<220> FEATURE:
<223> OTHER INFORMATION: Synthetic Construct

<400> SEQUENCE: 335

Asp Arg Pro Ser Tyr Tyr Val Leu Asp Tyr
1               5                   10

<210> SEQ ID NO 336
<211> LENGTH: 19
<212> TYPE: PRT
<213> ORGANISM: Artificial Sequence
<220> FEATURE:
<223> OTHER INFORMATION: Synthetic Construct

<400> SEQUENCE: 336

Phe Ile Arg Asn Arg Ala Arg Gly Tyr Thr Ser Asp His Asn Pro Ser
1               5                   10                  15

Val Lys Gly

<210> SEQ ID NO 337
<211> LENGTH: 19
<212> TYPE: PRT
<213> ORGANISM: Artificial Sequence
<220> FEATURE:
<223> OTHER INFORMATION: Synthetic Construct
```

```
<400> SEQUENCE: 337

Phe Ile Arg Asn Arg Ala Arg Gly Tyr Thr Ser Asp Tyr Ala Glu Ser
1               5                   10                  15

Val Lys Gly

<210> SEQ ID NO 338
<211> LENGTH: 19
<212> TYPE: PRT
<213> ORGANISM: Artificial Sequence
<220> FEATURE:
<223> OTHER INFORMATION: Synthetic Construct

<400> SEQUENCE: 338

Phe Ile Arg Asn Arg Ala Arg Gly Tyr Thr Ser Asp Tyr Ala Asp Ser
1               5                   10                  15

Val Lys Gly

<210> SEQ ID NO 339
<211> LENGTH: 19
<212> TYPE: PRT
<213> ORGANISM: Artificial Sequence
<220> FEATURE:
<223> OTHER INFORMATION: Synthetic Construct

<400> SEQUENCE: 339

Phe Ile Arg Asn Arg Ala Arg Gly Tyr Thr Ser Asp Tyr Ala Pro Ser
1               5                   10                  15

Val Lys Gly

<210> SEQ ID NO 340
<211> LENGTH: 17
<212> TYPE: PRT
<213> ORGANISM: Artificial Sequence
<220> FEATURE:
<223> OTHER INFORMATION: Synthetic Construct

<400> SEQUENCE: 340

Thr Ser Ser Gln Ser Leu Phe Asn Val Arg Ser Arg Lys Asn Tyr Leu
1               5                   10                  15

Ala

<210> SEQ ID NO 341
<211> LENGTH: 7
<212> TYPE: PRT
<213> ORGANISM: Artificial Sequence
<220> FEATURE:
<223> OTHER INFORMATION: Synthetic Construct

<400> SEQUENCE: 341

Trp Ala Ser Thr Arg Glu Ser
1               5

<210> SEQ ID NO 342
<211> LENGTH: 8
<212> TYPE: PRT
<213> ORGANISM: Artificial Sequence
<220> FEATURE:
<223> OTHER INFORMATION: Synthetic Construct

<400> SEQUENCE: 342

Lys Gln Ser Tyr Asp Leu Phe Thr
1               5
```

```
<210> SEQ ID NO 343
<211> LENGTH: 17
<212> TYPE: PRT
<213> ORGANISM: Artificial Sequence
<220> FEATURE:
<223> OTHER INFORMATION: Synthetic Construct

<400> SEQUENCE: 343

Lys Ser Ser Gln Ser Leu Phe Asn Val Arg Ser Arg Lys Asn Tyr Leu
1               5                   10                  15

Ala

<210> SEQ ID NO 344
<211> LENGTH: 112
<212> TYPE: PRT
<213> ORGANISM: Artificial Sequence
<220> FEATURE:
<223> OTHER INFORMATION: Synthetic Construct

<400> SEQUENCE: 344

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Val
            20                  25                  30

Arg Ser Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asp Leu Phe Thr Phe Gly Ser Gly Thr Lys Leu Glu Ile Lys
            100                 105                 110

<210> SEQ ID NO 345
<211> LENGTH: 121
<212> TYPE: PRT
<213> ORGANISM: Artificial Sequence
<220> FEATURE:
<223> OTHER INFORMATION: Synthetic Construct

<400> SEQUENCE: 345

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Val Arg Gln Ala Pro Gly Lys Gly Leu Glu Trp Val
        35                  40                  45

Ala Phe Ile Arg Asn Arg Ala Arg Gly Tyr Thr Ser Asp His Asn Pro
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Pro Ser Tyr Tyr Val Leu Asp Tyr Trp Gly
            100                 105                 110

Gln Gly Thr Thr Val Thr Val Ser Ser
        115                 120
```

<210> SEQ ID NO 346
<211> LENGTH: 112
<212> TYPE: PRT
<213> ORGANISM: Artificial Sequence
<220> FEATURE:
<223> OTHER INFORMATION: Synthetic Construct

<400> SEQUENCE: 346

```
Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Leu Phe Asn Val
            20                  25                  30
Arg Ser Arg Lys Asn Tyr Leu Ala Trp Tyr Gln Gln Lys Pro Gly Gln
        35                  40                  45
Pro Pro Lys Leu Leu Ile Ser Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Lys Gln
                85                  90                  95
Ser Tyr Asp Leu Phe Thr Phe Gly Gln Gly Thr Lys Leu Glu Ile Lys
            100                 105                 110
```

<210> SEQ ID NO 347
<211> LENGTH: 121
<212> TYPE: PRT
<213> ORGANISM: Artificial Sequence
<220> FEATURE:
<223> OTHER INFORMATION: Synthetic Construct

<400> SEQUENCE: 347

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asp Tyr
            20                  25                  30
Tyr Met Thr Trp Val Arg Gln Ala Pro Gly Lys Gly Leu Glu Trp Val
        35                  40                  45
Ala Phe Ile Arg Asn Arg Ala Arg Gly Tyr Thr Ser Asp His Asn Pro
    50                  55                  60
Ser Val Lys Gly Arg Phe Thr Ile Ser Arg Asp Asn Ala Lys Asn Ser
65                  70                  75                  80
Leu Tyr Leu Gln Met Asn Ser Leu Arg Ala Glu Asp Thr Ala Val Tyr
                85                  90                  95
Tyr Cys Ala Arg Asp Arg Pro Ser Tyr Tyr Val Leu Asp Tyr Trp Gly
            100                 105                 110
Gln Gly Thr Thr Val Thr Val Ser Ser
        115                 120
```

<210> SEQ ID NO 348
<211> LENGTH: 112
<212> TYPE: PRT
<213> ORGANISM: Artificial Sequence
<220> FEATURE:
<223> OTHER INFORMATION: Synthetic Construct

<400> SEQUENCE: 348

```
Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Leu Phe Asn Val
            20                  25                  30
```

```
Arg Ser Arg Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Lys Gln
                 85                  90                  95

Ser Tyr Asp Leu Phe Thr Phe Gly Gln Gly Thr Lys Leu Glu Ile Lys
            100                 105                 110
```

<210> SEQ ID NO 349
<211> LENGTH: 121
<212> TYPE: PRT
<213> ORGANISM: Artificial Sequence
<220> FEATURE:
<223> OTHER INFORMATION: Synthetic Construct

<400> SEQUENCE: 349

```
Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Asp Tyr
            20                  25                  30

Tyr Met Thr Trp Val Arg Gln Ala Pro Gly Lys Gly Leu Glu Trp Val
            35                  40                  45

Ala Phe Ile Arg Asn Arg Ala Arg Gly Tyr Thr Ser Asp His Asn Pro
 50                  55                  60

Ser Val Lys Gly Arg Phe Thr Ile Ser Arg Asp Asn Ala Lys Asn Ser
 65                  70                  75                  80

Leu Tyr Leu Gln Met Asn Ser Leu Arg Ala Glu Asp Thr Ala Val Tyr
                 85                  90                  95

Tyr Cys Ala Arg Asp Arg Pro Ser Tyr Tyr Val Leu Asp Tyr Trp Gly
            100                 105                 110

Gln Gly Thr Thr Val Thr Val Ser Ser
            115                 120
```

<210> SEQ ID NO 350
<211> LENGTH: 112
<212> TYPE: PRT
<213> ORGANISM: Artificial Sequence
<220> FEATURE:
<223> OTHER INFORMATION: Synthetic Construct

<400> SEQUENCE: 350

```
Asp Ile Val Met Ser Gln Ser Pro Ser Leu Ala Val Ser Val Gly
 1               5                   10                  15

Asp Lys Val Thr Met Ser Cys Thr Ser Ser Gln Ser Leu Phe Asn Ser
            20                  25                  30

Arg Ser Arg Lys Asn Tyr Leu Ala Trp Tyr Gln Gln Lys Ser Gly Gln
            35                  40                  45

Ser Pro Lys Leu Leu Ile Ser Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Lys Gln
                 85                  90                  95

Ser Tyr Asp Leu Phe Thr Phe Gly Ser Gly Thr Lys Leu Glu Ile Lys
            100                 105                 110
```

```
<210> SEQ ID NO 351
<211> LENGTH: 121
<212> TYPE: PRT
<213> ORGANISM: Artificial Sequence
<220> FEATURE:
<223> OTHER INFORMATION: Synthetic Construct

<400> SEQUENCE: 351

Glu Val Lys Leu Val Glu Ser Gly Gly Gly Leu Val Gln Pro Gly Gly
1               5                   10                  15

Ser Leu Arg Leu Ser Cys Ala Thr Phe Gly Phe Thr Phe Thr Asp Tyr
            20                  25                  30

Tyr Met Thr Trp Val Arg Gln Pro Pro Gly Lys Ala Leu Glu Trp Val
        35                  40                  45

Ala Phe Ile Arg Asn Arg Ala Arg Gly Tyr Thr Ser Asp His Asn Ala
    50                  55                  60

Ser Val Lys Gly Arg Phe Thr Ile Ser Arg Asp Asn Ser Gln Asn Ile
65                  70                  75                  80

Leu Tyr Leu Gln Met Asn Thr Leu Arg Ala Glu Asp Ser Ala Thr Tyr
                85                  90                  95

Tyr Cys Ala Arg Asp Arg Pro Ser Tyr Tyr Val Leu Asp Tyr Trp Gly
            100                 105                 110

Gln Gly Thr Thr Val Thr Val Ser Ser
        115                 120

<210> SEQ ID NO 352
<211> LENGTH: 112
<212> TYPE: PRT
<213> ORGANISM: Artificial Sequence
<220> FEATURE:
<223> OTHER INFORMATION: Synthetic Construct

<400> SEQUENCE: 352

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Asp Ser Val Gln Pro Glu Asp Leu Ala Val Tyr Tyr Cys Thr Gln
                85                  90                  95

Ser Phe Ile Leu Arg Thr Phe Gly Gly Gly Thr Lys Leu Glu Ile Lys
            100                 105                 110

<210> SEQ ID NO 353
<211> LENGTH: 184
<212> TYPE: PRT
<213> ORGANISM: Homo sapien

<400> SEQUENCE: 353

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30
```

```
Pro Pro Leu Thr Cys Gln Arg Tyr Cys Asn Ala Ser Val Thr Asn Ser
         35                  40                  45

Val Lys Gly Thr Asn Ala Ile Leu Trp Thr Cys Leu Gly Leu Ser Leu
 50                  55                  60

Ile Ile Ser Leu Ala Val Phe Val Leu Met Phe Leu Leu Arg Lys Ile
 65                  70                  75                  80

Asn Ser Glu Pro Leu Lys Asp Glu Phe Lys Asn Thr Gly Ser Gly Leu
                 85                  90                  95

Leu Gly Met Ala Asn Ile Asp Leu Glu Lys Ser Arg Thr Gly Asp Glu
                100                 105                 110

Ile Ile Leu Pro Arg Gly Leu Glu Tyr Thr Val Glu Glu Cys Thr Cys
                115                 120                 125

Glu Asp Cys Ile Lys Ser Lys Pro Lys Val Asp Ser Asp His Cys Phe
130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
                180

<210> SEQ ID NO 354
<211> LENGTH: 119
<212> TYPE: PRT
<213> ORGANISM: Artificial Sequence
<220> FEATURE:
<223> OTHER INFORMATION: Synthetic Construct

<400> SEQUENCE: 354

Gln Val Gln Leu Gln Gln Pro Gly Ser Glu Leu Val Arg Pro Gly Ala
 1               5                  10                  15

Ser Val Ile Leu Ser Cys Lys Ala Ser Gly Tyr Thr Phe Thr Ser Tyr
                 20                  25                  30

Trp Met His Trp Val Arg Gln Arg Pro Gly Gln Gly Leu Glu Trp Ile
             35                  40                  45

Gly Asn Ile Tyr Ser Gly Gly Asp Thr Ile Asn Tyr Asp Glu Lys Phe
 50                  55                  60

Lys Asn Lys Ala Ile Leu Thr Val Asp Thr Ser Ser Ser Thr Ala Tyr
 65                  70                  75                  80

Met His Leu Ser Ser Leu Thr Ser Glu Asp Ser Ala Val Tyr Tyr Cys
                 85                  90                  95

Thr Arg Asp Ala Thr Ser Arg Tyr Phe Phe Asp Tyr Trp Gly Gln Gly
                100                 105                 110

Thr Thr Val Thr Val Ser Ser
            115

<210> SEQ ID NO 355
<211> LENGTH: 112
<212> TYPE: PRT
<213> ORGANISM: Artificial Sequence
<220> FEATURE:
<223> OTHER INFORMATION: Synthetic Construct

<400> SEQUENCE: 355

Asp Ile Val Met Ser Gln Ser Pro Ser Ser Leu Ala Val Ser Ala Gly
 1               5                  10                  15

Glu Lys Val Thr Met Ser Cys Lys Ser Ser Gln Ser Leu Leu Asn Ser
                 20                  25                  30
```

```
Arg Thr Arg Lys Asn Tyr Leu Ala Trp Tyr Gln Gln Lys Pro Gly Gln
            35                  40                  45

Ser Pro Lys Leu Leu Ile Tyr Trp Ala Ser Thr Arg Ala Ser Gly Val
 50                  55                  60

Pro Asp Arg Phe Thr Gly Ser Gly Ser Gly Thr Asp Phe Thr Leu Thr
 65              70                  75                  80

Ile Ser Ser Val Gln Ala Glu Asp Leu Ala Ile Tyr Tyr Cys Lys Gln
                 85                  90                  95

Ser Phe Ile Leu Arg Thr Phe Gly Gly Gly Thr Lys Leu Glu Ile Lys
                100                 105                 110
```

<210> SEQ ID NO 356
<211> LENGTH: 117
<212> TYPE: PRT
<213> ORGANISM: Artificial Sequence
<220> FEATURE:
<223> OTHER INFORMATION: Synthetic Construct

<400> SEQUENCE: 356

```
Gln Val Gln Leu Gln Gln Ser Gly Pro Asp Leu Val Lys Pro Gly Ala
 1               5                  10                  15

Ser Val Glu Ile Ser Cys Lys Ala Ser Gly Tyr Ser Phe Thr Thr Tyr
             20                  25                  30

Tyr Leu His Trp Val Arg Gln Arg Pro Gly Gln Gly Leu Glu Trp Ile
             35                  40                  45

Gly Trp Ile Phe Pro Gly Ser Asp Asn Thr Lys Tyr Asn Glu Lys Phe
 50                  55                  60

Lys Gly Lys Ala Thr Leu Thr Ala Asp Thr Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Asn Arg Asp Tyr Tyr Phe Asp Tyr Trp Gly Gln Gly Thr Thr
                100                 105                 110

Val Thr Val Ser Ser
            115
```

<210> SEQ ID NO 357
<211> LENGTH: 215
<212> TYPE: PRT
<213> ORGANISM: Artificial Sequence
<220> FEATURE:
<223> OTHER INFORMATION: Synthetic Construct

<400> SEQUENCE: 357

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
             35                  40                  45

Met Tyr Asp Ala Ser Ile Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gln Ser Trp Pro
                 85                  90                  95

Leu Thr Phe Gly Gln Gly Thr Lys Val Glu Ile Lys Arg Thr Val Ala
                100                 105                 110
```

Ala Pro Ser Val Phe Ile Phe Pro Ser Asp Glu Gln Leu Lys Ser
115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
                210                 215

<210> SEQ ID NO 358
<211> LENGTH: 255
<212> TYPE: PRT
<213> ORGANISM: Artificial Sequence
<220> FEATURE:
<223> OTHER INFORMATION: Synthetic Construct

<400> SEQUENCE: 358

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Pro Met Ser Trp Val Arg Gln Ala Pro Gly Lys Gly Leu Glu Trp Val
                35                  40                  45

Ser Ala Ile Gly Gly Ser Gly Gly Ser Leu Pro Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ile Trp Gly Gln Gly Thr Leu Val Thr
                100                 105                 110

Val Ser Ser Ala Ser Thr Lys Gly Pro Ser Val Phe Pro Leu Ala Pro
                115                 120                 125

Ser Ser Lys Ser Thr Ser Gly Gly Thr Ala Ala Leu Gly Cys Leu Val
                130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
                195                 200                 205

Val Asp Lys Lys Val Glu Pro Lys Ser Cys Asp Lys Thr His Thr Cys
                210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro
                245                 250                 255

-continued

```
<210> SEQ ID NO 359
<211> LENGTH: 6
<212> TYPE: PRT
<213> ORGANISM: Artificial Sequence
<220> FEATURE:
<223> OTHER INFORMATION: Synthetic Construct

<400> SEQUENCE: 359

Ser Gly Ser Gly Gly Ser
1               5

<210> SEQ ID NO 360
<211> LENGTH: 17
<212> TYPE: PRT
<213> ORGANISM: Artificial Sequence
<220> FEATURE:
<223> OTHER INFORMATION: Synthetic Construct

<400> SEQUENCE: 360

Ala Ile Ser Gly Ser Gly Gly Ser Thr Phe Tyr Ala Asp Ser Val Lys
1               5                   10                  15

Gly

<210> SEQ ID NO 361
<211> LENGTH: 9
<212> TYPE: PRT
<213> ORGANISM: Artificial Sequence
<220> FEATURE:
<223> OTHER INFORMATION: Synthetic Construct

<400> SEQUENCE: 361

Val Gly Thr Ser Gly Ala Phe Gly Ile
1               5

<210> SEQ ID NO 362
<211> LENGTH: 7
<212> TYPE: PRT
<213> ORGANISM: Artificial Sequence
<220> FEATURE:
<223> OTHER INFORMATION: Synthetic Construct

<400> SEQUENCE: 362

Gly Ala Ser Ser Arg Ala Tyr
1               5

<210> SEQ ID NO 363
<211> LENGTH: 118
<212> TYPE: PRT
<213> ORGANISM: Artificial Sequence
<220> FEATURE:
<223> OTHER INFORMATION: Synthetic Construct

<400> SEQUENCE: 363

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ala Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                85                  90                  95

Ala Arg Leu Ser Trp Ser Gly Ala Phe Asp Asn Trp Gly Gln Gly Thr
            100                 105                 110

Leu Val Thr Val Ser Ser
        115

<210> SEQ ID NO 364
<211> LENGTH: 109
<212> TYPE: PRT
<213> ORGANISM: Artificial Sequence
<220> FEATURE:
<223> OTHER INFORMATION: Synthetic Construct

<400> SEQUENCE: 364

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Asn Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Tyr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Ser Pro Pro
                85                  90                  95

Ser Phe Thr Phe Gly Gln Gly Thr Lys Val Glu Ile Lys
            100                 105

<210> SEQ ID NO 365
<211> LENGTH: 118
<212> TYPE: PRT
<213> ORGANISM: Artificial Sequence
<220> FEATURE:
<223> OTHER INFORMATION: Synthetic Construct

<400> SEQUENCE: 365

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Val Gly Thr Ser Gly Ala Phe Gly Ile Trp Gly Gln Gly Thr
            100                 105                 110

Leu Val Thr Val Ser Ser
        115

<210> SEQ ID NO 366
<211> LENGTH: 5
<212> TYPE: PRT
<213> ORGANISM: Artificial Sequence

```
<220> FEATURE:
<223> OTHER INFORMATION: Synthetic Construct

<400> SEQUENCE: 366

Ser Tyr Ala Met Ser
1               5

<210> SEQ ID NO 367
<211> LENGTH: 10
<212> TYPE: PRT
<213> ORGANISM: Artificial Sequence
<220> FEATURE:
<223> OTHER INFORMATION: Synthetic Construct

<400> SEQUENCE: 367

Gly Phe Thr Phe Ser Ser Tyr Ala Met Ser
1               5                   10

<210> SEQ ID NO 368
<211> LENGTH: 6
<212> TYPE: PRT
<213> ORGANISM: Artificial Sequence
<220> FEATURE:
<223> OTHER INFORMATION: Synthetic Construct

<400> SEQUENCE: 368

Ser Ala Ser Gly Gly Ser
1               5

<210> SEQ ID NO 369
<211> LENGTH: 17
<212> TYPE: PRT
<213> ORGANISM: Artificial Sequence
<220> FEATURE:
<223> OTHER INFORMATION: Synthetic Construct

<400> SEQUENCE: 369

Ala Ile Ser Ala Ser Gly Gly Ser Thr Tyr Tyr Ala Asp Ser Val Lys
1               5                   10                  15

Gly

<210> SEQ ID NO 370
<211> LENGTH: 9
<212> TYPE: PRT
<213> ORGANISM: Artificial Sequence
<220> FEATURE:
<223> OTHER INFORMATION: Synthetic Construct

<400> SEQUENCE: 370

Leu Ser Trp Ser Gly Ala Phe Asp Asn
1               5

<210> SEQ ID NO 371
<211> LENGTH: 7
<212> TYPE: PRT
<213> ORGANISM: Artificial Sequence
<220> FEATURE:
<223> OTHER INFORMATION: Synthetic Construct

<400> SEQUENCE: 371

Gly Phe Thr Phe Arg Ser Tyr
1               5
```

```
<210> SEQ ID NO 372
<211> LENGTH: 10
<212> TYPE: PRT
<213> ORGANISM: Artificial Sequence
<220> FEATURE:
<223> OTHER INFORMATION: Synthetic Construct

<400> SEQUENCE: 372

Gly Phe Thr Phe Arg Ser Tyr Ala Met Ser
1               5                   10

<210> SEQ ID NO 373
<211> LENGTH: 112
<212> TYPE: PRT
<213> ORGANISM: Artificial Sequence
<220> FEATURE:
<223> OTHER INFORMATION: Synthetic Construct

<400> SEQUENCE: 373

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Asp Ser Val Gln Pro Glu Asp Leu Ala Val Tyr Tyr Cys Thr Gln
                85                  90                  95

Ser Phe Ile Leu Arg Thr Phe Gly Gly Gly Thr Lys Leu Glu Ile Lys
            100                 105                 110

<210> SEQ ID NO 374
<211> LENGTH: 119
<212> TYPE: PRT
<213> ORGANISM: Artificial Sequence
<220> FEATURE:
<223> OTHER INFORMATION: Synthetic Construct

<400> SEQUENCE: 374

Gln Val Gln Leu Gln Gln Pro Gly Ser Glu Leu Val Arg Pro Gly Ala
1               5                   10                  15

Ser Val Ile Leu Ser Cys Lys Ala Ser Gly Tyr Thr Phe Thr Ser Tyr
            20                  25                  30

Trp Met His Trp Val Arg Gln Arg Pro Gly Gln Gly Leu Glu Trp Ile
        35                  40                  45

Gly Asn Ile Tyr Ser Gly Gly Asp Thr Ile Asn Tyr Asp Glu Lys Phe
    50                  55                  60

Lys Asn Lys Ala Ile Leu Thr Val Asp Thr Ser Ser Ser Thr Ala Tyr
65                  70                  75                  80

Met His Leu Ser Ser Leu Thr Ser Glu Asp Ser Ala Val Tyr Tyr Cys
                85                  90                  95

Thr Arg Asp Ala Thr Ser Arg Tyr Phe Phe Asp Tyr Trp Gly Gln Gly
            100                 105                 110

Thr Thr Val Thr Val Ser Ser
            115
```

```
<210> SEQ ID NO 375
<211> LENGTH: 112
<212> TYPE: PRT
<213> ORGANISM: Artificial Sequence
<220> FEATURE:
<223> OTHER INFORMATION: Synthetic Construct

<400> SEQUENCE: 375

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Ala Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Ile Tyr Tyr Cys Lys Gln
                85                  90                  95

Ser Phe Ile Leu Arg Thr Phe Gly Gly Gly Thr Lys Leu Glu Ile Lys
            100                 105                 110

<210> SEQ ID NO 376
<211> LENGTH: 117
<212> TYPE: PRT
<213> ORGANISM: Artificial Sequence
<220> FEATURE:
<223> OTHER INFORMATION: Synthetic Construct

<400> SEQUENCE: 376

Gln Val Gln Leu Gln Gln Ser Gly Pro Asp Leu Val Lys Pro Gly Ala
1               5                   10                  15

Ser Val Glu Ile Ser Cys Lys Ala Ser Gly Tyr Ser Phe Thr Thr Tyr
            20                  25                  30

Tyr Leu His Trp Val Arg Gln Arg Pro Gly Gln Gly Leu Glu Trp Ile
        35                  40                  45

Gly Trp Ile Phe Pro Gly Ser Asp Asn Thr Lys Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Asn Arg Asp Tyr Tyr Phe Asp Tyr Trp Gly Gln Gly Thr Thr
            100                 105                 110

Val Thr Val Ser Ser
        115

<210> SEQ ID NO 377
<211> LENGTH: 109
<212> TYPE: PRT
<213> ORGANISM: Artificial Sequence
<220> FEATURE:
<223> OTHER INFORMATION: Synthetic Construct

<400> SEQUENCE: 377

Gln Ala Val Val Thr Gln Glu Ser Ala Leu Thr Thr Ser Pro Gly Glu
1               5                   10                  15

Ala Val Thr Leu Thr Cys Arg Ser Ser Thr Gly Ala Val Thr Thr Ser
            20                  25                  30
```

```
Asn Tyr Ala Asn Trp Val Gln Glu Lys Pro Asp His Leu Phe Thr Gly
             35                  40                  45

Leu Ile Gly Gly Thr Asn Thr Arg Ala Pro Gly Val Pro Ala Arg Phe
 50                  55                  60

Ser Gly Ser Leu Ile Gly Asp Lys Ala Ala Leu Thr Ile Thr Gly Ala
 65                  70                  75                  80

Gln Thr Glu Asp Glu Ala Ile Tyr Phe Cys Val Leu Trp Tyr Asn Asn
                 85                  90                  95

Tyr Trp Val Phe Gly Gly Gly Thr Lys Leu Thr Val Leu
                100                 105

<210> SEQ ID NO 378
<211> LENGTH: 124
<212> TYPE: PRT
<213> ORGANISM: Artificial Sequence
<220> FEATURE:
<223> OTHER INFORMATION: Synthetic Construct

<400> SEQUENCE: 378

Glu Val Gln Leu Val Glu Ser Gly Gly Gly Leu Val Arg Pro Glu Gly
 1               5                  10                  15

Ser Leu Arg Leu Ser Cys Ala Ala Ser Gly Phe Thr Phe Asn Thr Tyr
                 20                  25                  30

Ala Met Asn Trp Val Arg Gln Ala Pro Gly Lys Gly Leu Glu Trp Val
             35                  40                  45

Gly Arg Ile Arg Ser Lys Ile Asn Asn Tyr Ala Thr Tyr Tyr Ala Glu
 50                  55                  60

Ser Val Lys Gly Arg Phe Thr Leu Ser Arg Asp Ser Leu Ser Met
 65                  70                  75                  80

Val Tyr Leu Gln Met Asn Ser Leu Lys Asn Glu Asp Thr Ala Met Tyr
                 85                  90                  95

Tyr Cys Val Arg His Glu Thr Leu Arg Ser Gly Ile Ser Trp Phe Ala
                100                 105                 110

Ser Trp Gly Gln Gly Thr Leu Val Thr Val Ser Ser
            115                 120

<210> SEQ ID NO 379
<211> LENGTH: 109
<212> TYPE: PRT
<213> ORGANISM: Artificial Sequence
<220> FEATURE:
<223> OTHER INFORMATION: Synthetic Construct

<400> SEQUENCE: 379

Gln Ala Val Val Thr Gln Glu Ser Ala Leu Thr Thr Ser Pro Gly Glu
 1               5                  10                  15

Thr Val Thr Leu Thr Cys Arg Ser Ser Thr Gly Ala Val Thr Thr Ser
                 20                  25                  30

Asn Tyr Ala Asn Trp Val Gln Glu Lys Pro Asp His Leu Phe Thr Gly
             35                  40                  45

Leu Ile Gly Gly Thr Asn Asn Arg Ala Pro Gly Val Pro Ala Arg Phe
 50                  55                  60

Ser Gly Ser Leu Ile Gly Asp Lys Ala Ala Leu Thr Ile Thr Gly Ala
 65                  70                  75                  80

Gln Thr Glu Asp Glu Ala Ile Tyr Phe Cys Ala Leu Trp Tyr Ser Asn
                 85                  90                  95

His Trp Val Phe Gly Gly Gly Thr Lys Leu Thr Val Leu
                100                 105
```

```
<210> SEQ ID NO 380
<211> LENGTH: 124
<212> TYPE: PRT
<213> ORGANISM: Artificial Sequence
<220> FEATURE:
<223> OTHER INFORMATION: Synthetic Construct

<400> SEQUENCE: 380

Glu Val Gln Leu Val Asp Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Arg
65                  70                  75                  80

Leu Tyr Leu Gln Met Asn Asn Leu Lys Thr Glu Asp Thr Ala Met Tyr
                85                  90                  95

Tyr Cys Val Arg His Glu Thr Leu Arg Ser Gly Ile Ser Trp Phe Ala
            100                 105                 110

Asn Trp Gly Gln Gly Thr Leu Val Thr Val Ser Ser
        115                 120

<210> SEQ ID NO 381
<211> LENGTH: 109
<212> TYPE: PRT
<213> ORGANISM: Artificial Sequence
<220> FEATURE:
<223> OTHER INFORMATION: Synthetic Construct

<400> SEQUENCE: 381

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Thr Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Val Leu Trp Tyr Asn Asn
                85                  90                  95

Tyr Trp Val Phe Gly Gly Gly Thr Lys Leu Thr Val Leu
            100                 105

<210> SEQ ID NO 382
<211> LENGTH: 124
<212> TYPE: PRT
<213> ORGANISM: Artificial Sequence
<220> FEATURE:
<223> OTHER INFORMATION: Synthetic Construct

<400> SEQUENCE: 382

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30
```

```
Ala Met Asn Trp Val Arg Gln Ala Pro Gly Lys Gly Leu Glu Trp Val
        35                  40                  45

Gly Arg Ile Arg Ser Lys Ile Asn Asn Tyr Ala Thr Tyr Tyr Ala Glu
 50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Val Arg His Glu Thr Leu Arg Ser Gly Ile Ser Trp Phe Ala
            100                 105                 110

Ser Trp Gly Gln Gly Thr Leu Val Thr Val Ser Ser
        115                 120
```

<210> SEQ ID NO 383
<211> LENGTH: 109
<212> TYPE: PRT
<213> ORGANISM: Artificial Sequence
<220> FEATURE:
<223> OTHER INFORMATION: Synthetic Construct

<400> SEQUENCE: 383

```
Gln Ala Val Val Thr Gln Glu Pro Ser Leu Thr Val Ser Pro Gly Gly
 1               5                  10                  15

Thr Val Thr Leu Thr Cys Arg Ser Ser Thr Gly Ala Val Thr Thr Ser
                 20                  25                  30

Asn Tyr Ala Asn Trp Val Gln Gln Lys Pro Gly Gln Ala Pro Arg Gly
            35                  40                  45

Leu Ile Gly Gly Thr Asn Thr Arg Ala Pro Gly Thr Pro Ala Arg Phe
 50                  55                  60

Ser Gly Ser Leu Leu Gly Gly Lys Ala Ala Leu Thr Leu Ser Gly Ala
 65                  70                  75                  80

Gln Pro Glu Asp Glu Ala Glu Tyr Tyr Cys Val Leu Trp Tyr Asn Asn
                 85                  90                  95

His Trp Val Phe Gly Gly Gly Thr Lys Leu Thr Val Leu
            100                 105
```

<210> SEQ ID NO 384
<211> LENGTH: 124
<212> TYPE: PRT
<213> ORGANISM: Artificial Sequence
<220> FEATURE:
<223> OTHER INFORMATION: Synthetic Construct

<400> SEQUENCE: 384

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Thr Tyr
                 20                  25                  30

Ala Met Asn Trp Val Arg Gln Ala Pro Gly Lys Gly Leu Glu Trp Val
            35                  40                  45

Gly Arg Ile Arg Ser Lys Ile Asn Asn Tyr Ala Thr Tyr Tyr Ala Glu
 50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95
```

Tyr Cys Val Arg His Glu Thr Leu Arg Ser Gly Ile Ser Trp Phe Ala
                100                 105                 110

Ser Trp Gly Gln Gly Thr Leu Val Thr Val Ser Ser
        115                 120

<210> SEQ ID NO 385
<211> LENGTH: 109
<212> TYPE: PRT
<213> ORGANISM: Artificial Sequence
<220> FEATURE:
<223> OTHER INFORMATION: Synthetic Construct

<400> SEQUENCE: 385

Gln Ala Val Val Thr Gln Glu Pro Ser Leu Thr Val Ser Pro Gly Gly
1               5                   10                  15

Thr Val Thr Leu Thr Cys Arg Ala Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Thr Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Val Leu Trp Tyr Asn Asn
                85                  90                  95

His Trp Val Phe Gly Gly Gly Thr Lys Leu Thr Val Leu
            100                 105

<210> SEQ ID NO 386
<211> LENGTH: 124
<212> TYPE: PRT
<213> ORGANISM: Artificial Sequence
<220> FEATURE:
<223> OTHER INFORMATION: Synthetic Construct

<400> SEQUENCE: 386

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ile Asn Asn Tyr Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Val Arg His Glu Thr Leu Arg Ser Gly Ile Ser Trp Phe Ala
            100                 105                 110

Ser Trp Gly Gln Gly Thr Leu Val Thr Val Ser Ser
        115                 120

<210> SEQ ID NO 387
<211> LENGTH: 109
<212> TYPE: PRT
<213> ORGANISM: Artificial Sequence
<220> FEATURE:
<223> OTHER INFORMATION: Synthetic Construct

<400> SEQUENCE: 387

Gln Ala Val Val Thr Gln Glu Pro Ser Leu Thr Val Ser Pro Gly Gly
1               5                   10                  15

Thr Val Thr Leu Thr Cys Arg Thr Ser Thr Gly Ala Val Thr Thr Ser
            20                  25                  30

Asn Tyr Ala Asn Trp Val Gln Lys Pro Gly Gln Ala Pro Arg Gly
        35                  40                  45

Leu Ile Gly Gly Thr Asn Thr Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Val Leu Trp Tyr Asn Asn
                85                  90                  95

His Trp Val Phe Gly Gly Gly Thr Lys Leu Thr Val Leu
            100                 105

<210> SEQ ID NO 388
<211> LENGTH: 124
<212> TYPE: PRT
<213> ORGANISM: Artificial Sequence
<220> FEATURE:
<223> OTHER INFORMATION: Synthetic Construct

<400> SEQUENCE: 388

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ile Asn Asn Tyr Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Val Arg His Glu Thr Leu Arg Ser Gly Ile Ser Trp Phe Ala
            100                 105                 110

Ser Trp Gly Gln Gly Thr Leu Val Thr Val Ser Ser
        115                 120

<210> SEQ ID NO 389
<211> LENGTH: 109
<212> TYPE: PRT
<213> ORGANISM: Artificial Sequence
<220> FEATURE:
<223> OTHER INFORMATION: Synthetic Construct

<400> SEQUENCE: 389

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Thr Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Val Leu Trp Tyr Asn Asn
                85                  90                  95

Tyr Trp Val Phe Gly Gly Gly Thr Lys Leu Thr Val Leu
            100                 105

<210> SEQ ID NO 390
<211> LENGTH: 124
<212> TYPE: PRT
<213> ORGANISM: Artificial Sequence
<220> FEATURE:
<223> OTHER INFORMATION: Synthetic Construct

<400> SEQUENCE: 390

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ile Asn Asn Tyr Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Val Arg His Glu Thr Leu Arg Ser Gly Ile Ser Trp Phe Ala
            100                 105                 110

Ser Trp Gly Gln Gly Thr Leu Val Thr Val Ser Ser
        115                 120

<210> SEQ ID NO 391
<211> LENGTH: 109
<212> TYPE: PRT
<213> ORGANISM: Artificial Sequence
<220> FEATURE:
<223> OTHER INFORMATION: Synthetic Construct

<400> SEQUENCE: 391

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Thr Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Val Leu Trp Tyr Asn Asn
                85                  90                  95

His Trp Val Phe Gly Gly Gly Thr Lys Leu Thr Val Leu
            100                 105

<210> SEQ ID NO 392
<211> LENGTH: 124
<212> TYPE: PRT
<213> ORGANISM: Artificial Sequence
<220> FEATURE:
<223> OTHER INFORMATION: Synthetic Construct

<400> SEQUENCE: 392

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ile Asn Asn Tyr Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Val Arg His Glu Thr Leu Arg Ser Gly Ile Ser Trp Phe Ala
            100                 105                 110

Ser Trp Gly Gln Gly Thr Leu Val Thr Val Ser Ser
        115                 120

<210> SEQ ID NO 393
<211> LENGTH: 109
<212> TYPE: PRT
<213> ORGANISM: Artificial Sequence
<220> FEATURE:
<223> OTHER INFORMATION: Synthetic Construct

<400> SEQUENCE: 393

Gln Ala Val Val Thr Gln Glu Pro Ser Leu Thr Val Ser Pro Gly Gly
1               5                   10                  15

Thr Val Thr Leu Thr Cys Arg Thr Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Thr Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Val Leu Trp Tyr Asn Asn
                85                  90                  95

His Trp Val Phe Gly Gly Gly Thr Lys Leu Thr Val Leu
            100                 105

<210> SEQ ID NO 394
<211> LENGTH: 124
<212> TYPE: PRT
<213> ORGANISM: Artificial Sequence
<220> FEATURE:
<223> OTHER INFORMATION: Synthetic Construct

<400> SEQUENCE: 394

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser His Ile Asn Asn Tyr Ala Thr Tyr Tyr Ala Glu
            50                  55                  60

Ser Val Lys Gly Arg Phe Thr Ile Ser Arg Asp Asp Ser Lys Asn Thr
 65                 70                  75                  80

Leu Tyr Leu Gln Met Asn Ser Leu Lys Thr Glu Asp Thr Ala Val Tyr
                    85                  90                  95

Tyr Cys Val Arg His Glu Thr Leu Arg Ser Gly Ile Ser Trp Phe Ala
                100                 105                 110

Ser Trp Gly Gln Gly Thr Leu Val Thr Val Ser Ser
            115                 120

<210> SEQ ID NO 395
<211> LENGTH: 109
<212> TYPE: PRT
<213> ORGANISM: Artificial Sequence
<220> FEATURE:
<223> OTHER INFORMATION: Synthetic Construct

<400> SEQUENCE: 395

Gln Ala Val Val Thr Gln Glu Pro Ser Leu Thr Val Ser Pro Gly Gly
 1               5                  10                  15

Thr Val Thr Leu Thr Cys Arg Ser Thr Gly Ala Val Thr Thr Ser
            20                  25                  30

Asn Tyr Ala Asn Trp Val Gln Gln Lys Pro Gly Gln Ala Pro Arg Gly
                35                  40                  45

Leu Ile Gly Gly Thr Asn Thr Arg Ala Pro Gly Thr Pro Ala Arg Phe
        50                  55                  60

Ser Gly Ser Leu Leu Gly Lys Ala Ala Leu Thr Leu Ser Gly Ala
 65                 70                  75                  80

Gln Pro Glu Asp Glu Ala Glu Tyr Tyr Cys Val Leu Trp Tyr Asn Asn
                    85                  90                  95

His Trp Val Phe Gly Gly Gly Thr Lys Leu Thr Val Leu
                100                 105

<210> SEQ ID NO 396
<211> LENGTH: 124
<212> TYPE: PRT
<213> ORGANISM: Artificial Sequence
<220> FEATURE:
<223> OTHER INFORMATION: Synthetic Construct

<400> SEQUENCE: 396

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
                35                  40                  45

Gly Arg Ile Arg Ser Lys Tyr Asn Asn Tyr Ala Thr Tyr Tyr Ala Glu
        50                  55                  60

Ser Val Lys Gly Arg Phe Thr Ile Ser Arg Asp Asp Ser Lys Asn Thr
 65                 70                  75                  80

Leu Tyr Leu Gln Met Asn Ser Leu Lys Thr Glu Asp Thr Ala Val Tyr
                    85                  90                  95

Tyr Cys Val Arg His Glu Thr Leu Arg Ser Gly Ile Ser Trp Phe Ala
                100                 105                 110

Ser Trp Gly Gln Gly Thr Leu Val Thr Val Ser Ser
            115                 120

```
<210> SEQ ID NO 397
<211> LENGTH: 109
<212> TYPE: PRT
<213> ORGANISM: Artificial Sequence
<220> FEATURE:
<223> OTHER INFORMATION: Synthetic Construct

<400> SEQUENCE: 397
```

Gln Ala Val Val Thr Gln Glu Pro Ser Leu Thr Val Ser Pro Gly Gly
1               5                   10                  15

Thr Val Thr Leu Thr Cys Arg Thr Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Thr Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Val Leu Trp Tyr Asn Asn
                85                  90                  95

His Trp Val Phe Gly Gly Gly Thr Lys Leu Thr Val Leu
            100                 105

```
<210> SEQ ID NO 398
<211> LENGTH: 124
<212> TYPE: PRT
<213> ORGANISM: Artificial Sequence
<220> FEATURE:
<223> OTHER INFORMATION: Synthetic Construct

<400> SEQUENCE: 398
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Glu Arg Ser Lys Ile Asn Asn Tyr Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Val Arg His Glu Thr Leu Arg Ser Gly Ile Ser Trp Phe Ala
            100                 105                 110

Ser Trp Gly Gln Gly Thr Leu Val Thr Val Ser Ser
        115                 120

```
<210> SEQ ID NO 399
<211> LENGTH: 109
<212> TYPE: PRT
<213> ORGANISM: Artificial Sequence
<220> FEATURE:
<223> OTHER INFORMATION: Synthetic Construct

<400> SEQUENCE: 399
```

Gln Ala Val Val Thr Gln Glu Pro Ser Leu Thr Val Ser Pro Gly Gly
1               5                   10                  15

Thr Val Thr Leu Thr Cys Arg Ser Thr Gly Ala Val Thr Thr Ser
            20                  25                  30

Asn Tyr Ala Asn Trp Val Gln Gln Lys Pro Gly Gln Ala Pro Arg Gly
                35                  40                  45

Leu Ile Gly Gly Thr Asn Thr Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Val Leu Trp Tyr Asn Asn
                85                  90                  95

His Trp Val Phe Gly Gly Gly Thr Lys Leu Thr Val Leu
                100                 105

<210> SEQ ID NO 400
<211> LENGTH: 124
<212> TYPE: PRT
<213> ORGANISM: Artificial Sequence
<220> FEATURE:
<223> OTHER INFORMATION: Synthetic Construct

<400> SEQUENCE: 400

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
                20                  25                  30

Ala Met Asn Trp Val Arg Gln Ala Pro Gly Lys Gly Leu Glu Trp Val
                35                  40                  45

Gly Arg Ile Arg Ser Lys Ile Asn Asn Tyr Lys Thr Tyr Tyr Ala Glu
            50                  55                  60

Ser Val Lys Gly Arg Phe Thr Ile Ser Arg Asp Asp Ser Lys Asn Thr
65              70                  75                  80

Leu Tyr Leu Gln Met Asn Ser Leu Lys Thr Glu Asp Thr Ala Val Tyr
                85                  90                  95

Tyr Cys Val Arg His Glu Thr Leu Arg Ser Gly Ile Ser Trp Phe Ala
                100                 105                 110

Ser Trp Gly Gln Gly Thr Leu Val Thr Val Ser Ser
            115                 120

<210> SEQ ID NO 401
<211> LENGTH: 5
<212> TYPE: PRT
<213> ORGANISM: Artificial Sequence
<220> FEATURE:
<223> OTHER INFORMATION: Synthetic Construct

<400> SEQUENCE: 401

Thr Tyr Ala Met Asn
1               5

<210> SEQ ID NO 402
<211> LENGTH: 7
<212> TYPE: PRT
<213> ORGANISM: Artificial Sequence
<220> FEATURE:
<223> OTHER INFORMATION: Synthetic Construct

<400> SEQUENCE: 402

Gly Phe Thr Phe Asn Thr Tyr
1               5

```
<210> SEQ ID NO 403
<211> LENGTH: 10
<212> TYPE: PRT
<213> ORGANISM: Artificial Sequence
<220> FEATURE:
<223> OTHER INFORMATION: Synthetic Construct

<400> SEQUENCE: 403

Gly Phe Thr Phe Asn Thr Tyr Ala Met Asn
1               5                   10

<210> SEQ ID NO 404
<211> LENGTH: 8
<212> TYPE: PRT
<213> ORGANISM: Artificial Sequence
<220> FEATURE:
<223> OTHER INFORMATION: Synthetic Construct

<400> SEQUENCE: 404

Arg Ser Lys Ile Asn Asn Tyr Ala
1               5

<210> SEQ ID NO 405
<211> LENGTH: 19
<212> TYPE: PRT
<213> ORGANISM: Artificial Sequence
<220> FEATURE:
<223> OTHER INFORMATION: Synthetic Construct

<400> SEQUENCE: 405

Arg Ile Arg Ser Lys Ile Asn Asn Tyr Ala Thr Tyr Tyr Ala Glu Ser
1               5                   10                  15

Val Lys Gly

<210> SEQ ID NO 406
<211> LENGTH: 13
<212> TYPE: PRT
<213> ORGANISM: Artificial Sequence
<220> FEATURE:
<223> OTHER INFORMATION: Synthetic Construct

<400> SEQUENCE: 406

His Glu Thr Leu Arg Ser Gly Ile Ser Trp Phe Ala Ser
1               5                   10

<210> SEQ ID NO 407
<211> LENGTH: 7
<212> TYPE: PRT
<213> ORGANISM: Artificial Sequence
<220> FEATURE:
<223> OTHER INFORMATION: Synthetic Construct

<400> SEQUENCE: 407

Gly Phe Thr Phe Ser Thr Tyr
1               5

<210> SEQ ID NO 408
<211> LENGTH: 10
<212> TYPE: PRT
<213> ORGANISM: Artificial Sequence
<220> FEATURE:
<223> OTHER INFORMATION: Synthetic Construct

<400> SEQUENCE: 408

Gly Phe Thr Phe Ser Thr Tyr Ala Met Asn
1               5                   10
```

```
<210> SEQ ID NO 409
<211> LENGTH: 8
<212> TYPE: PRT
<213> ORGANISM: Artificial Sequence
<220> FEATURE:
<223> OTHER INFORMATION: Synthetic Construct

<400> SEQUENCE: 409

Arg Ser His Ile Asn Asn Tyr Ala
1               5

<210> SEQ ID NO 410
<211> LENGTH: 19
<212> TYPE: PRT
<213> ORGANISM: Artificial Sequence
<220> FEATURE:
<223> OTHER INFORMATION: Synthetic Construct

<400> SEQUENCE: 410

Arg Ile Arg Ser His Ile Asn Asn Tyr Ala Thr Tyr Tyr Ala Glu Ser
1               5                   10                  15

Val Lys Gly

<210> SEQ ID NO 411
<211> LENGTH: 8
<212> TYPE: PRT
<213> ORGANISM: Artificial Sequence
<220> FEATURE:
<223> OTHER INFORMATION: Synthetic Construct

<400> SEQUENCE: 411

Arg Ser Lys Tyr Asn Asn Tyr Ala
1               5

<210> SEQ ID NO 412
<211> LENGTH: 19
<212> TYPE: PRT
<213> ORGANISM: Artificial Sequence
<220> FEATURE:
<223> OTHER INFORMATION: Synthetic Construct

<400> SEQUENCE: 412

Arg Ile Arg Ser Lys Tyr Asn Asn Tyr Ala Thr Tyr Tyr Ala Glu Ser
1               5                   10                  15

Val Lys Gly

<210> SEQ ID NO 413
<211> LENGTH: 19
<212> TYPE: PRT
<213> ORGANISM: Artificial Sequence
<220> FEATURE:
<223> OTHER INFORMATION: Synthetic Construct

<400> SEQUENCE: 413

Arg Glu Arg Ser Lys Ile Asn Asn Tyr Ala Thr Tyr Tyr Ala Glu Ser
1               5                   10                  15

Val Lys Gly

<210> SEQ ID NO 414
<211> LENGTH: 19
<212> TYPE: PRT
<213> ORGANISM: Artificial Sequence
<220> FEATURE:
<223> OTHER INFORMATION: Synthetic Construct
```

<400> SEQUENCE: 414

Arg Ile Arg Ser Lys Ile Asn Asn Tyr Lys Thr Tyr Tyr Ala Glu Ser
1               5                   10                  15

Val Lys Gly

<210> SEQ ID NO 415
<211> LENGTH: 7
<212> TYPE: PRT
<213> ORGANISM: Artificial Sequence
<220> FEATURE:
<223> OTHER INFORMATION: Synthetic Construct

<400> SEQUENCE: 415

Gly Phe Thr Phe Thr Asp Tyr
1               5

<210> SEQ ID NO 416
<211> LENGTH: 10
<212> TYPE: PRT
<213> ORGANISM: Artificial Sequence
<220> FEATURE:
<223> OTHER INFORMATION: Synthetic Construct

<400> SEQUENCE: 416

Gly Phe Thr Phe Thr Asp Tyr Tyr Met Thr
1               5                   10

<210> SEQ ID NO 417
<211> LENGTH: 8
<212> TYPE: PRT
<213> ORGANISM: Artificial Sequence
<220> FEATURE:
<223> OTHER INFORMATION: Synthetic Construct

<400> SEQUENCE: 417

Arg Asn Arg Ala Arg Gly Tyr Thr
1               5

<210> SEQ ID NO 418
<211> LENGTH: 19
<212> TYPE: PRT
<213> ORGANISM: Artificial Sequence
<220> FEATURE:
<223> OTHER INFORMATION: Synthetic Construct

<400> SEQUENCE: 418

Phe Ile Arg Asn Arg Ala Arg Gly Tyr Thr Ser Asp His Asn Ala Ser
1               5                   10                  15

Val Lys Gly

<210> SEQ ID NO 419
<211> LENGTH: 7
<212> TYPE: PRT
<213> ORGANISM: Artificial Sequence
<220> FEATURE:
<223> OTHER INFORMATION: Synthetic Construct

<400> SEQUENCE: 419

Gly Tyr Thr Phe Thr Ser Tyr
1               5

<210> SEQ ID NO 420
<211> LENGTH: 10
<212> TYPE: PRT
<213> ORGANISM: Artificial Sequence

```
<220> FEATURE:
<223> OTHER INFORMATION: Synthetic Construct

<400> SEQUENCE: 420

Gly Tyr Thr Phe Thr Ser Tyr Trp Met His
1               5                   10

<210> SEQ ID NO 421
<211> LENGTH: 6
<212> TYPE: PRT
<213> ORGANISM: Artificial Sequence
<220> FEATURE:
<223> OTHER INFORMATION: Synthetic Construct

<400> SEQUENCE: 421

Tyr Ser Gly Gly Asp Thr
1               5

<210> SEQ ID NO 422
<211> LENGTH: 17
<212> TYPE: PRT
<213> ORGANISM: Artificial Sequence
<220> FEATURE:
<223> OTHER INFORMATION: Synthetic Construct

<400> SEQUENCE: 422

Asn Ile Tyr Ser Gly Gly Asp Thr Ile Asn Tyr Asp Glu Lys Phe Lys
1               5                   10                  15

Asn

<210> SEQ ID NO 423
<211> LENGTH: 10
<212> TYPE: PRT
<213> ORGANISM: Artificial Sequence
<220> FEATURE:
<223> OTHER INFORMATION: Synthetic Construct

<400> SEQUENCE: 423

Asp Ala Thr Ser Arg Tyr Phe Phe Asp Tyr
1               5                   10

<210> SEQ ID NO 424
<211> LENGTH: 5
<212> TYPE: PRT
<213> ORGANISM: Artificial Sequence
<220> FEATURE:
<223> OTHER INFORMATION: Synthetic Construct

<400> SEQUENCE: 424

Thr Tyr Tyr Leu His
1               5

<210> SEQ ID NO 425
<211> LENGTH: 8
<212> TYPE: PRT
<213> ORGANISM: Artificial Sequence
<220> FEATURE:
<223> OTHER INFORMATION: Synthetic Construct

<400> SEQUENCE: 425

Gly Tyr Ser Phe Thr Thr Tyr Tyr
1               5
```

```
<210> SEQ ID NO 426
<211> LENGTH: 10
<212> TYPE: PRT
<213> ORGANISM: Artificial Sequence
<220> FEATURE:
<223> OTHER INFORMATION: Synthetic Construct

<400> SEQUENCE: 426

Gly Tyr Ser Phe Thr Thr Tyr Tyr Leu His
1               5                   10

<210> SEQ ID NO 427
<211> LENGTH: 6
<212> TYPE: PRT
<213> ORGANISM: Artificial Sequence
<220> FEATURE:
<223> OTHER INFORMATION: Synthetic Construct

<400> SEQUENCE: 427

Phe Pro Gly Ser Asp Asn
1               5

<210> SEQ ID NO 428
<211> LENGTH: 17
<212> TYPE: PRT
<213> ORGANISM: Artificial Sequence
<220> FEATURE:
<223> OTHER INFORMATION: Synthetic Construct

<400> SEQUENCE: 428

Trp Ile Phe Pro Gly Ser Asp Asn Thr Lys Tyr Asn Glu Lys Phe Lys
1               5                   10                  15

Gly

<210> SEQ ID NO 429
<211> LENGTH: 8
<212> TYPE: PRT
<213> ORGANISM: Artificial Sequence
<220> FEATURE:
<223> OTHER INFORMATION: Synthetic Construct

<400> SEQUENCE: 429

Asn Arg Asp Tyr Tyr Phe Asp Tyr
1               5

<210> SEQ ID NO 430
<211> LENGTH: 17
<212> TYPE: PRT
<213> ORGANISM: Artificial Sequence
<220> FEATURE:
<223> OTHER INFORMATION: Synthetic Construct

<400> SEQUENCE: 430

Thr Ser Ser Gln Ser Leu Phe Asn Ser Arg Ser Arg Lys Asn Tyr Leu
1               5                   10                  15

Ala

<210> SEQ ID NO 431
<211> LENGTH: 15
<212> TYPE: PRT
<213> ORGANISM: Artificial Sequence
<220> FEATURE:
<223> OTHER INFORMATION: Synthetic Construct
```

-continued

```
<400> SEQUENCE: 431

Lys Ser Ser Gln Ser Leu Leu Asn Ser Arg Thr Arg Lys Asn Tyr
1               5                   10                  15

<210> SEQ ID NO 432
<211> LENGTH: 8
<212> TYPE: PRT
<213> ORGANISM: Artificial Sequence
<220> FEATURE:
<223> OTHER INFORMATION: Synthetic Construct

<400> SEQUENCE: 432

Thr Gln Ser Phe Ile Leu Arg Thr
1               5

<210> SEQ ID NO 433
<211> LENGTH: 7
<212> TYPE: PRT
<213> ORGANISM: Artificial Sequence
<220> FEATURE:
<223> OTHER INFORMATION: Synthetic Construct

<400> SEQUENCE: 433

Trp Ala Ser Thr Arg Ala Ser
1               5

<210> SEQ ID NO 434
<211> LENGTH: 8
<212> TYPE: PRT
<213> ORGANISM: Artificial Sequence
<220> FEATURE:
<223> OTHER INFORMATION: Synthetic Construct

<400> SEQUENCE: 434

Lys Gln Ser Phe Ile Leu Arg Thr
1               5

<210> SEQ ID NO 435
<211> LENGTH: 14
<212> TYPE: PRT
<213> ORGANISM: Artificial Sequence
<220> FEATURE:
<223> OTHER INFORMATION: Synthetic Construct

<400> SEQUENCE: 435

Arg Ser Ser Thr Gly Ala Val Thr Thr Ser Asn Tyr Ala Asn
1               5                   10

<210> SEQ ID NO 436
<211> LENGTH: 7
<212> TYPE: PRT
<213> ORGANISM: Artificial Sequence
<220> FEATURE:
<223> OTHER INFORMATION: Synthetic Construct

<400> SEQUENCE: 436

Gly Thr Asn Thr Arg Ala Pro
1               5

<210> SEQ ID NO 437
<211> LENGTH: 9
<212> TYPE: PRT
<213> ORGANISM: Artificial Sequence
<220> FEATURE:
<223> OTHER INFORMATION: Synthetic Construct
```

```
<400> SEQUENCE: 437

Val Leu Trp Tyr Asn Asn Tyr Trp Val
1               5

<210> SEQ ID NO 438
<211> LENGTH: 9
<212> TYPE: PRT
<213> ORGANISM: Artificial Sequence
<220> FEATURE:
<223> OTHER INFORMATION: Synthetic Construct

<400> SEQUENCE: 438

Ala Leu Trp Tyr Ser Asn His Trp Val
1               5

<210> SEQ ID NO 439
<211> LENGTH: 9
<212> TYPE: PRT
<213> ORGANISM: Artificial Sequence
<220> FEATURE:
<223> OTHER INFORMATION: Synthetic Construct

<400> SEQUENCE: 439

Val Leu Trp Tyr Asn Asn His Trp Val
1               5

<210> SEQ ID NO 440
<211> LENGTH: 14
<212> TYPE: PRT
<213> ORGANISM: Artificial Sequence
<220> FEATURE:
<223> OTHER INFORMATION: Synthetic Construct

<400> SEQUENCE: 440

Arg Ala Ser Thr Gly Ala Val Thr Thr Ser Asn Tyr Ala Asn
1               5                   10

<210> SEQ ID NO 441
<211> LENGTH: 14
<212> TYPE: PRT
<213> ORGANISM: Artificial Sequence
<220> FEATURE:
<223> OTHER INFORMATION: Synthetic Construct

<400> SEQUENCE: 441

Arg Thr Ser Thr Gly Ala Val Thr Thr Ser Asn Tyr Ala Asn
1               5                   10

<210> SEQ ID NO 442
<211> LENGTH: 117
<212> TYPE: PRT
<213> ORGANISM: Artificial Sequence
<220> FEATURE:
<223> OTHER INFORMATION: Synthetic Construct

<400> SEQUENCE: 442

Glu Val Gln Leu Gln Gln Ser Gly Ala Glu Leu Val Arg Pro Gly Ala
1               5                   10                  15

Leu Val Lys Leu Ser Cys Lys Gly Ser Gly Phe Asn Ile Lys Asp Tyr
            20                  25                  30

Tyr Ile His Trp Val Lys Gln Arg Pro Glu Gln Gly Leu Glu Trp Ile
        35                  40                  45

Gly Trp Ile Asp Pro Glu Asn Gly Asn Asn Lys Tyr Asp Pro Lys Phe
    50                  55                  60
```

Gln Gly Lys Ala Ser Ile Thr Ala Asp Thr Ser Ser Asn Ile Ala Tyr
65                  70                  75                  80

Leu Gln Leu Ser Ser Leu Thr Ser Glu Asp Thr Ala Val Tyr Tyr Cys
                85                  90                  95

Ala Arg Asn Asp Asn Tyr Ala Phe Asp Tyr Trp Gly Gln Gly Thr Thr
            100                 105                 110

Val Thr Val Ser Ser
        115

<210> SEQ ID NO 443
<211> LENGTH: 112
<212> TYPE: PRT
<213> ORGANISM: Artificial Sequence
<220> FEATURE:
<223> OTHER INFORMATION: Synthetic Construct

<400> SEQUENCE: 443

Asp Ile Val Val Ser Gln Ser Pro Ser Ser Leu Ala Val Ser Ala Gly
1               5                   10                  15

Glu Lys Val Ile Met Ser Cys Lys Ser Ser Gln Ser Leu Leu Asn Ser
            20                  25                  30

Arg Thr Arg Lys Asn Tyr Leu Ala Trp Tyr Gln Leu Lys Pro Gly Gln
        35                  40                  45

Ser Pro Lys Leu Leu Ile Tyr Ser Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Thr Glu Asp Leu Ala Val Tyr Tyr Cys Met Gln
                85                  90                  95

Ser Phe Thr Leu Arg Thr Phe Gly Gly Gly Thr Lys Leu Glu Ile Lys
            100                 105                 110

<210> SEQ ID NO 444
<211> LENGTH: 121
<212> TYPE: PRT
<213> ORGANISM: Artificial Sequence
<220> FEATURE:
<223> OTHER INFORMATION: Synthetic Construct

<400> SEQUENCE: 444

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Val Arg Gln Ala Pro Gly Lys Gly Leu Glu Trp Val
        35                  40                  45

Ala Phe Ile Arg Asn Arg Ala Arg Gly Tyr Thr Ser Asp His Asn Ala
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Pro Ser Tyr Tyr Val Leu Asp Tyr Trp Gly
            100                 105                 110

Gln Gly Thr Thr Val Thr Val Ser Ser
        115                 120

<210> SEQ ID NO 445
<211> LENGTH: 112
<212> TYPE: PRT
<213> ORGANISM: Artificial Sequence
<220> FEATURE:
<223> OTHER INFORMATION: Synthetic Construct

<400> SEQUENCE: 445

```
Asp Ile Val Met Thr Gln Ser Pro Asp Ser Leu Ala Val Ser Leu Gly
1               5                   10                  15

Glu Arg Ala Thr Ile Asn Cys Thr Ser Ser Gln Ser Leu Phe Asn Ser
            20                  25                  30

Arg Ser Arg Lys Asn Tyr Leu Ala Trp Tyr Gln Gln Lys Pro Gly Gln
        35                  40                  45

Pro Pro Lys Leu Leu Ile Ser Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Asp Thr Phe Thr Phe Gly Ser Gly Thr Lys Leu Glu Ile Lys
            100                 105                 110
```

<210> SEQ ID NO 446
<211> LENGTH: 5
<212> TYPE: PRT
<213> ORGANISM: Artificial Sequence
<220> FEATURE:
<223> OTHER INFORMATION: Synthetic Construct

<400> SEQUENCE: 446

```
Asp Tyr Tyr Ile His
1               5
```

<210> SEQ ID NO 447
<211> LENGTH: 7
<212> TYPE: PRT
<213> ORGANISM: Artificial Sequence
<220> FEATURE:
<223> OTHER INFORMATION: Synthetic Construct

<400> SEQUENCE: 447

```
Gly Phe Asn Ile Lys Asp Tyr
1               5
```

<210> SEQ ID NO 448
<211> LENGTH: 10
<212> TYPE: PRT
<213> ORGANISM: Artificial Sequence
<220> FEATURE:
<223> OTHER INFORMATION: Synthetic Construct

<400> SEQUENCE: 448

```
Gly Phe Asn Ile Lys Asp Tyr Tyr Ile His
1               5                   10
```

<210> SEQ ID NO 449
<211> LENGTH: 6
<212> TYPE: PRT
<213> ORGANISM: Artificial Sequence
<220> FEATURE:
<223> OTHER INFORMATION: Synthetic Construct

```
<400> SEQUENCE: 449

Asp Pro Glu Asn Gly Asn
1               5

<210> SEQ ID NO 450
<211> LENGTH: 17
<212> TYPE: PRT
<213> ORGANISM: Artificial Sequence
<220> FEATURE:
<223> OTHER INFORMATION: Synthetic Construct

<400> SEQUENCE: 450

Trp Ile Asp Pro Glu Asn Gly Asn Asn Lys Tyr Asp Pro Lys Phe Gln
1               5                   10                  15

Gly

<210> SEQ ID NO 451
<211> LENGTH: 8
<212> TYPE: PRT
<213> ORGANISM: Artificial Sequence
<220> FEATURE:
<223> OTHER INFORMATION: Synthetic Construct

<400> SEQUENCE: 451

Asn Asp Asn Tyr Ala Phe Asp Tyr
1               5

<210> SEQ ID NO 452
<211> LENGTH: 7
<212> TYPE: PRT
<213> ORGANISM: Artificial Sequence
<220> FEATURE:
<223> OTHER INFORMATION: Synthetic Construct

<400> SEQUENCE: 452

Ser Ala Ser Thr Arg Glu Ser
1               5

<210> SEQ ID NO 453
<211> LENGTH: 8
<212> TYPE: PRT
<213> ORGANISM: Artificial Sequence
<220> FEATURE:
<223> OTHER INFORMATION: Synthetic Construct

<400> SEQUENCE: 453

Met Gln Ser Phe Thr Leu Arg Thr
1               5

<210> SEQ ID NO 454
<211> LENGTH: 4
<212> TYPE: PRT
<213> ORGANISM: Artificial Sequence
<220> FEATURE:
<223> OTHER INFORMATION: Synthetic Construct

<400> SEQUENCE: 454

Leu Leu Gln Gly
1

<210> SEQ ID NO 455
<211> LENGTH: 6
<212> TYPE: PRT
<213> ORGANISM: Artificial Sequence
<220> FEATURE:
<223> OTHER INFORMATION: Synthetic Construct
```

```
<400> SEQUENCE: 455

Leu Ser Leu Ser Gln Gly
1               5

<210> SEQ ID NO 456
<211> LENGTH: 8
<212> TYPE: PRT
<213> ORGANISM: Artificial Sequence
<220> FEATURE:
<223> OTHER INFORMATION: Synthetic Construct

<400> SEQUENCE: 456

Gly Gly Gly Leu Leu Gln Gly Gly
1               5

<210> SEQ ID NO 457
<211> LENGTH: 5
<212> TYPE: PRT
<213> ORGANISM: Artificial Sequence
<220> FEATURE:
<223> OTHER INFORMATION: Synthetic Construct

<400> SEQUENCE: 457

Gly Leu Leu Gln Gly
1               5

<210> SEQ ID NO 458
<211> LENGTH: 10
<212> TYPE: PRT
<213> ORGANISM: Artificial Sequence
<220> FEATURE:
<223> OTHER INFORMATION: Synthetic Construct

<400> SEQUENCE: 458

Gly Ser Pro Leu Ala Gln Ser His Gly Gly
1               5                   10

<210> SEQ ID NO 459
<211> LENGTH: 7
<212> TYPE: PRT
<213> ORGANISM: Artificial Sequence
<220> FEATURE:
<223> OTHER INFORMATION: Synthetic Construct

<400> SEQUENCE: 459

Gly Leu Leu Gln Gly Gly Gly
1               5

<210> SEQ ID NO 460
<211> LENGTH: 6
<212> TYPE: PRT
<213> ORGANISM: Artificial Sequence
<220> FEATURE:
<223> OTHER INFORMATION: Synthetic Construct

<400> SEQUENCE: 460

Gly Leu Leu Gln Gly Gly
1               5

<210> SEQ ID NO 461
<211> LENGTH: 4
<212> TYPE: PRT
<213> ORGANISM: Artificial Sequence
<220> FEATURE:
<223> OTHER INFORMATION: Synthetic Construct
```

<400> SEQUENCE: 461

Gly Leu Leu Gln
1

<210> SEQ ID NO 462
<211> LENGTH: 8
<212> TYPE: PRT
<213> ORGANISM: Artificial Sequence
<220> FEATURE:
<223> OTHER INFORMATION: Synthetic Construct

<400> SEQUENCE: 462

Leu Leu Gln Leu Leu Gln Gly Ala
1               5

<210> SEQ ID NO 463
<211> LENGTH: 5
<212> TYPE: PRT
<213> ORGANISM: Artificial Sequence
<220> FEATURE:
<223> OTHER INFORMATION: Synthetic Construct

<400> SEQUENCE: 463

Leu Leu Gln Gly Ala
1               5

<210> SEQ ID NO 464
<211> LENGTH: 7
<212> TYPE: PRT
<213> ORGANISM: Artificial Sequence
<220> FEATURE:
<223> OTHER INFORMATION: Synthetic Construct

<400> SEQUENCE: 464

Leu Leu Gln Tyr Gln Gly Ala
1               5

<210> SEQ ID NO 465
<211> LENGTH: 6
<212> TYPE: PRT
<213> ORGANISM: Artificial Sequence
<220> FEATURE:
<223> OTHER INFORMATION: Synthetic Construct

<400> SEQUENCE: 465

Leu Leu Gln Gly Ser Gly
1               5

<210> SEQ ID NO 466
<211> LENGTH: 6
<212> TYPE: PRT
<213> ORGANISM: Artificial Sequence
<220> FEATURE:
<223> OTHER INFORMATION: Synthetic Construct

<400> SEQUENCE: 466

Leu Leu Gln Tyr Gln Gly
1               5

<210> SEQ ID NO 467
<211> LENGTH: 7
<212> TYPE: PRT
<213> ORGANISM: Artificial Sequence
<220> FEATURE:
<223> OTHER INFORMATION: Synthetic Construct

```
<400> SEQUENCE: 467

Leu Leu Gln Leu Leu Gln Gly
1               5

<210> SEQ ID NO 468
<211> LENGTH: 5
<212> TYPE: PRT
<213> ORGANISM: Artificial Sequence
<220> FEATURE:
<223> OTHER INFORMATION: Synthetic Construct

<400> SEQUENCE: 468

Ser Leu Leu Gln Gly
1               5

<210> SEQ ID NO 469
<211> LENGTH: 5
<212> TYPE: PRT
<213> ORGANISM: Artificial Sequence
<220> FEATURE:
<223> OTHER INFORMATION: Synthetic Construct

<400> SEQUENCE: 469

Leu Leu Gln Leu Gln
1               5

<210> SEQ ID NO 470
<211> LENGTH: 6
<212> TYPE: PRT
<213> ORGANISM: Artificial Sequence
<220> FEATURE:
<223> OTHER INFORMATION: Synthetic Construct

<400> SEQUENCE: 470

Leu Leu Gln Leu Leu Gln
1               5

<210> SEQ ID NO 471
<211> LENGTH: 5
<212> TYPE: PRT
<213> ORGANISM: Artificial Sequence
<220> FEATURE:
<223> OTHER INFORMATION: Synthetic Construct

<400> SEQUENCE: 471

Leu Leu Gln Gly Arg
1               5

<210> SEQ ID NO 472
<211> LENGTH: 6
<212> TYPE: PRT
<213> ORGANISM: Artificial Sequence
<220> FEATURE:
<223> OTHER INFORMATION: Synthetic Construct

<400> SEQUENCE: 472

Leu Leu Gln Gly Pro Pro
1               5

<210> SEQ ID NO 473
<211> LENGTH: 6
<212> TYPE: PRT
<213> ORGANISM: Artificial Sequence
<220> FEATURE:
<223> OTHER INFORMATION: Synthetic Construct
```

```
<400> SEQUENCE: 473

Leu Leu Gln Gly Pro Ala
1               5

<210> SEQ ID NO 474
<211> LENGTH: 8
<212> TYPE: PRT
<213> ORGANISM: Artificial Sequence
<220> FEATURE:
<223> OTHER INFORMATION: Synthetic Construct

<400> SEQUENCE: 474

Gly Gly Leu Leu Gln Gly Pro Pro
1               5

<210> SEQ ID NO 475
<211> LENGTH: 7
<212> TYPE: PRT
<213> ORGANISM: Artificial Sequence
<220> FEATURE:
<223> OTHER INFORMATION: Synthetic Construct

<400> SEQUENCE: 475

Gly Gly Leu Leu Gln Gly Ala
1               5

<210> SEQ ID NO 476
<211> LENGTH: 7
<212> TYPE: PRT
<213> ORGANISM: Artificial Sequence
<220> FEATURE:
<223> OTHER INFORMATION: Synthetic Construct

<400> SEQUENCE: 476

Leu Leu Gln Gly Pro Gly Lys
1               5

<210> SEQ ID NO 477
<211> LENGTH: 6
<212> TYPE: PRT
<213> ORGANISM: Artificial Sequence
<220> FEATURE:
<223> OTHER INFORMATION: Synthetic Construct

<400> SEQUENCE: 477

Leu Leu Gln Gly Pro Gly
1               5

<210> SEQ ID NO 478
<211> LENGTH: 5
<212> TYPE: PRT
<213> ORGANISM: Artificial Sequence
<220> FEATURE:
<223> OTHER INFORMATION: Synthetic Construct

<400> SEQUENCE: 478

Leu Leu Gln Gly Pro
1               5

<210> SEQ ID NO 479
<211> LENGTH: 4
<212> TYPE: PRT
<213> ORGANISM: Artificial Sequence
<220> FEATURE:
<223> OTHER INFORMATION: Synthetic Construct
```

```
<400> SEQUENCE: 479

Leu Leu Gln Pro
1

<210> SEQ ID NO 480
<211> LENGTH: 6
<212> TYPE: PRT
<213> ORGANISM: Artificial Sequence
<220> FEATURE:
<223> OTHER INFORMATION: Synthetic Construct

<400> SEQUENCE: 480

Leu Leu Gln Pro Gly Lys
1               5

<210> SEQ ID NO 481
<211> LENGTH: 7
<212> TYPE: PRT
<213> ORGANISM: Artificial Sequence
<220> FEATURE:
<223> OTHER INFORMATION: Synthetic Construct

<400> SEQUENCE: 481

Leu Leu Gln Ala Pro Gly Lys
1               5

<210> SEQ ID NO 482
<211> LENGTH: 7
<212> TYPE: PRT
<213> ORGANISM: Artificial Sequence
<220> FEATURE:
<223> OTHER INFORMATION: Synthetic Construct

<400> SEQUENCE: 482

Leu Leu Gln Gly Ala Pro Gly
1               5

<210> SEQ ID NO 483
<211> LENGTH: 6
<212> TYPE: PRT
<213> ORGANISM: Artificial Sequence
<220> FEATURE:
<223> OTHER INFORMATION: Synthetic Construct

<400> SEQUENCE: 483

Leu Leu Gln Gly Ala Pro
1               5

<210> SEQ ID NO 484
<211> LENGTH: 6
<212> TYPE: PRT
<213> ORGANISM: Artificial Sequence
<220> FEATURE:
<223> OTHER INFORMATION: Synthetic Construct

<400> SEQUENCE: 484

Leu Leu Gln Leu Gln Gly
1               5

<210> SEQ ID NO 485
<211> LENGTH: 324
<212> TYPE: DNA
<213> ORGANISM: Artificial Sequence
<220> FEATURE:
<223> OTHER INFORMATION: Synthetic Construct
```

<400> SEQUENCE: 485

```
gagatcgtgc tgactcagtc ccctggaacc ctgtccctgt cacctggcga aagagctacc    60
ttgtcctgtc gcgcatcaca atccgtgtcg tcgagctatc tcgcgtggta ccagcagaag   120
cccggacagg ccccaaggct gcttatgtac gacgcctcca tccgggccac tggtatcccc   180
gaccgcttct cgggctccgg aagcggcacc gacttcaccc tgactatttc ccggctcgaa   240
ccggaggatt tcgccgtgta ctactgccaa cagtaccaga gctggccgct gacgtttggg   300
caggggacca aggtcgaaat caaa                                           324
```

<210> SEQ ID NO 486
<211> LENGTH: 345
<212> TYPE: DNA
<213> ORGANISM: Artificial Sequence
<220> FEATURE:
<223> OTHER INFORMATION: Synthetic Construct

<400> SEQUENCE: 486

```
gaagtccaac tcctcgaatc cggtggcggc cttgtccagc ctggaggttc cttgcgcctg    60
tcatgtgccg ccagcggatt caccttctcg tcctacccga tgtcgtgggt ccgccaggct   120
ccgggaaagg gcctggaatg ggtgtcagcc atcggaggat cggggggctc cctgccctac   180
gccgatatcg tgaagggaag gttcaccatt agccgggaca actccaagaa cactctgtac   240
ctccaaatga acagcctgag agcggaggac accgcagtgt actattgcgc ccggtactgg   300
ccaatggaca tctggggcca ggggactctg gtcaccgtct cctca                   345
```

<210> SEQ ID NO 487
<211> LENGTH: 255
<212> TYPE: DNA
<213> ORGANISM: Artificial Sequence
<220> FEATURE:
<223> OTHER INFORMATION: Synthetic Construct

<400> SEQUENCE: 487

```
gagatcgtgc tgacacagag ccctggcacc ctgagcctgt ctccaggcga aagagccacc    60
ctgtcctgca gagccagcca gagcgtgtcc agcagctacc tggcctggta tcagcagaag   120
cccggccagg ctccccggct gctgatctat ggcgcctctt ctagagccac cggcatcccc   180
gatagattca gcggctctgg cagcggcacc gacttcaccc tgaccatcag cagactggaa   240
cccgaggact tcgcc                                                     255
```

<210> SEQ ID NO 488
<211> LENGTH: 255
<212> TYPE: DNA
<213> ORGANISM: Artificial Sequence
<220> FEATURE:
<223> OTHER INFORMATION: Synthetic Construct

<400> SEQUENCE: 488

```
gaagtgcagc tgctggaatc tggcggagga ctggtgcagc ctggcggctc tctgagactg    60
tcttgtgccg ccagcggctt caccttcggc agctacgcta tgacctgggt cgccaggcc   120 cctggcaaag gactggaatg ggtgtccgcc atctctggca gcggcggcaa taccttctac   180
gccgagagcg tgaagggccg gttcaccatc agccgggaca acagcaagaa caccctgtac   240
ctgcagatga acagc                                                     255
```

```
<210> SEQ ID NO 489
<211> LENGTH: 255
<212> TYPE: DNA
<213> ORGANISM: Artificial Sequence
<220> FEATURE:
<223> OTHER INFORMATION: Synthetic Construct

<400> SEQUENCE: 489
gagatcgtgc tgacacagag ccctggcacc ctgagcctgt ctcctggtga aagagctact      60
ttgtcttgta gagcttctca atccgtttcc gcgtattatt tggcttggta tcaacaaaaa     120
ccaggtcaag ctccaagatt attgatgtac gatgcttcta ttagagccac cggtattcca     180
gatagatttt ctggttctgg ttccggtact gatttcactt tgactatctc tagattggaa     240
ccagaagatt tcgct                                                      255

<210> SEQ ID NO 490
<211> LENGTH: 255
<212> TYPE: DNA
<213> ORGANISM: Artificial Sequence
<220> FEATURE:
<223> OTHER INFORMATION: Synthetic Construct

<400> SEQUENCE: 490
gaagttcaat tattggaatc tggtggagga ctggtgcagc ctggcggctc tctgagactg      60
tcttgtgccg ccagcggctt caccttcagc agctacgcca tgaactgggt gcgccaggcc     120
cctggtaaag gtttggaatg ggtttctgct attactgcgt ctggtggttc tacttactat     180
gccgatgtgg ttaagggtag attcaccatt tctagagaca actctaagaa caccttgtac     240
ttgcaaatga actcc                                                      255

<210> SEQ ID NO 491
<211> LENGTH: 255
<212> TYPE: DNA
<213> ORGANISM: Artificial Sequence
<220> FEATURE:
<223> OTHER INFORMATION: Synthetic Construct

<400> SEQUENCE: 491
gagatcgtgc tgacacagag ccctggcacc ctgagcctgt ctcctggtga aagagctact      60
ttgtcttgta gagcttctca atccgtttcc gatctgtatt tggcttggta tcaacaaaaa     120
ccaggtcaag ctccaagatt attgatgtac gatgcttcta ttagagccac cggtattcca     180
gatagatttt ctggttctgg ttccggtact gatttcactt tgactatctc tagattggaa     240
ccagaagatt tcgct                                                      255

<210> SEQ ID NO 492
<211> LENGTH: 255
<212> TYPE: DNA
<213> ORGANISM: Artificial Sequence
<220> FEATURE:
<223> OTHER INFORMATION: Synthetic Construct

<400> SEQUENCE: 492
gaagttcaat tattggaatc tggtggagga ctggtgcagc ctggcggctc tctgagactg      60
tcttgtgccg ccagcggctt caccttcagc agctacgcca tgaactgggt gcgccaggcc     120
cctggtaaag gtttggaatg ggtttctgct atttctgatt tggtggttc tacttactat     180 gccgatatcg ttaagggtag attcaccatt tctagagaca actctaagaa caccttgtac     240
ttgcaaatga actcc                                                      255
```

```
<210> SEQ ID NO 493
<211> LENGTH: 255
<212> TYPE: PRT
<213> ORGANISM: Homo sapien

<400> SEQUENCE: 493

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp
                245                 250                 255

<210> SEQ ID NO 494
<211> LENGTH: 255
<212> TYPE: PRT
<213> ORGANISM: Homo sapien

<400> SEQUENCE: 494

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe
            245                 250                 255

<210> SEQ ID NO 495
<211> LENGTH: 255
<212> TYPE: PRT
<213> ORGANISM: Homo sapien

<400> SEQUENCE: 495

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205
```

```
Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe
                245                 250                 255

<210> SEQ ID NO 496
<211> LENGTH: 326
<212> TYPE: PRT
<213> ORGANISM: Artificial Sequence
<220> FEATURE:
<223> OTHER INFORMATION: Synthetic Construct

<400> SEQUENCE: 496

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Arg Val Arg Cys Pro Arg Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Ala
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Arg
        275                 280                 285

Leu Thr Val Asp Lys Ser Arg Trp Gln Gln Gly Asn Val Phe Ser Cys
    290                 295                 300
```

Ser Val Met His Glu Ala Leu His Asn His Tyr Thr Gln Lys Ser Leu
305                 310                 315                 320

Ser Leu Ser Pro Gly Lys
                325

<210> SEQ ID NO 497
<211> LENGTH: 326
<212> TYPE: PRT
<213> ORGANISM: Artificial Sequence
<220> FEATURE:
<223> OTHER INFORMATION: Synthetic Construct

<400> SEQUENCE: 497

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Glu Val Glu Cys Pro Glu Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Ala
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Glu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

-continued

```
<210> SEQ ID NO 498
<211> LENGTH: 15
<212> TYPE: PRT
<213> ORGANISM: Artificial Sequence
<220> FEATURE:
<223> OTHER INFORMATION: Synthetic Construct

<400> SEQUENCE: 498

Gly Gly Gly Gly Ser Gly Gly Gly Ser Gly Gly Gly Gly Ser
1               5                   10                  15

<210> SEQ ID NO 499
<211> LENGTH: 10
<212> TYPE: PRT
<213> ORGANISM: Artificial Sequence
<220> FEATURE:
<223> OTHER INFORMATION: Synthetic Construct

<400> SEQUENCE: 499

Gln His Tyr Gly Ser Pro Pro Leu Phe Thr
1               5                   10

<210> SEQ ID NO 500
<211> LENGTH: 12
<212> TYPE: PRT
<213> ORGANISM: Artificial Sequence
<220> FEATURE:
<223> OTHER INFORMATION: Synthetic Construct

<400> SEQUENCE: 500

Arg Ala Ser Gln Asn Val Ser Ser Ser Tyr Leu Ala
1               5                   10

<210> SEQ ID NO 501
<211> LENGTH: 7
<212> TYPE: PRT
<213> ORGANISM: Artificial Sequence
<220> FEATURE:
<223> OTHER INFORMATION: Synthetic Construct

<400> SEQUENCE: 501

Gly Ala Ser Tyr Arg Ala Thr
1               5

<210> SEQ ID NO 502
<211> LENGTH: 198
<212> TYPE: PRT
<213> ORGANISM: Homo sapiens

<400> SEQUENCE: 502

Met Gln Ser Gly Thr Arg Trp Arg Val Leu Gly Leu Cys Leu Leu Ser
1               5                   10                  15

Ile Gly Val Trp Gly Gln Asp Gly Asn Glu Glu Met Gly Ser Ile Thr
                20                  25                  30

Gln Thr Pro Tyr Gln Val Ser Ile Ser Gly Thr Thr Val Ile Leu Thr
            35                  40                  45

Cys Ser Gln His Leu Gly Ser Glu Ala Gln Trp Gln His Asn Gly Lys
        50                  55                  60

Asn Lys Glu Asp Ser Gly Asp Arg Leu Phe Leu Pro Glu Phe Ser Glu
65                  70                  75                  80

Met Glu Gln Ser Gly Tyr Tyr Val Cys Tyr Pro Arg Gly Ser Asn Pro
                85                  90                  95

Glu Asp Ala Ser His His Leu Tyr Leu Lys Ala Arg Val Cys Glu Asn
            100                 105                 110
```

Cys Met Glu Met Asp Val Met Ala Val Ala Thr Ile Val Ile Val Asp
            115                 120                 125

Ile Cys Ile Thr Leu Gly Leu Leu Leu Val Tyr Tyr Trp Ser Lys
    130                 135                 140

Asn Arg Lys Ala Lys Ala Lys Pro Val Thr Arg Gly Ala Gly Ala Gly
145                 150                 155                 160

Gly Arg Gln Arg Gly Gln Asn Lys Glu Arg Pro Pro Val Pro Asn
                165                 170                 175

Pro Asp Tyr Glu Pro Ile Arg Lys Gly Gln Gln Asp Leu Tyr Ser Gly
            180                 185                 190

Leu Asn Gln Arg Arg Ile
        195

<210> SEQ ID NO 503
<211> LENGTH: 115
<212> TYPE: PRT
<213> ORGANISM: Artificial Sequence
<220> FEATURE:
<223> OTHER INFORMATION: Synthetic Construct

<400> SEQUENCE: 503

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Val
        35                  40                  45

Ser Ala Ile Gly Gly Ser Gly Gly Ser Leu Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ile Trp Gly Gln Gly Thr Leu Val Thr
            100                 105                 110

Val Ser Ser
        115

<210> SEQ ID NO 504
<211> LENGTH: 17
<212> TYPE: PRT
<213> ORGANISM: Artificial Sequence
<220> FEATURE:
<223> OTHER INFORMATION: Synthetic Construct

<400> SEQUENCE: 504

Ala Ile Gly Gly Ser Gly Gly Ser Leu Pro Tyr Ala Asp Ser Val Lys
1               5                   10                  15

Gly

THERAPEUTIC ANTIBODIES AND THEIR USES

RELATED APPLICATIONS

This application is a continuation application of U.S. patent application Ser. No. 17/005,073, filed Aug. 27, 2020, which is a divisional of U.S. patent application Ser. No. 16/017,974, filed Jun. 25, 2018, now U.S. Pat. No. 10,793,635, which is a divisional U.S. patent application Ser. No. 15/878,344, filed Jan. 23, 2018, now U.S. Pat. No. 10,040,860, which is a divisional of U.S. application Ser. No. 15/085,644, filed on Mar. 30, 2016, now U.S. Pat. No. 9,969,809, which claims the benefits of U.S. Provisional Application No. 62/146,843 filed Apr. 13, 2015, U.S. Provisional Application No. 62/146,504 filed Apr. 13, 2015, and U.S. Provisional Application No. 62/301,582 filed Feb. 29, 2016, all of which are hereby incorporated by reference in their entireties.

REFERENCE TO SEQUENCE LISTING

This application is being filed electronically via EFS-Web and includes an electronically submitted sequence listing in .txt format. The .txt file contains a sequence listing entitled "PC72209E_SUBSTITUTE_SEQListing_ST25.txt" created on Dec. 22, 2020 and having a size of 297 KB. The sequence listing contained in this .txt file is part of the specification and is incorporated herein by reference in its entirety.

FIELD

The present invention relates to antibodies, e.g., full length antibodies or antigen binding fragments thereof, that specifically bind to BCMA (B-Cell Maturation Antigen) and/or CD3 (Cluster of Differentiation 3). The invention also relates to antibody conjugates (e.g., antibody-drug-conjugates) comprising the BCMA antibodies, compositions comprising the BCMA antibodies, and methods of using the BCMA antibodies and their conjugates for treating conditions associated with cells expressing BCMA (e.g., cancer or autoimmune disease). The invention further relates to heteromultimeric antibodies that specifically bind to CD3 and a tumor cell antigen, (e.g., bispecific antibodies that specifically bind to CD3 and BCMA). Compositions comprising such heteromultimeric antibodies, methods for producing and purifying such heterodimeric antibodies, and their use in diagnostics and therapeutics are also provided.

BACKGROUND

B-cell maturation antigen (BCMA, CD269, or TNFRSF17) is a member of the tumor necrosis factor receptor (TNFR) superfamily. BCMA was identified in a malignant human T cell lymphoma containing a t(4; 16) translocation. The gene is selectively expressed in the B-cell lineage with the highest expression in plasma blasts and plasma cells, antibody secreting cells. BCMA binds two ligands, B-cell activation factor (BAFF) (also called B-lymphocyte stimulator (BLyS) and APOL-related leukocyte expressed ligand (TALL-1)) and a proliferation-inducing ligand (APRIL) with affinity of 1 uM and 16 nM, respectively. Binding of APRIL or BAFF to BCMA promotes a signaling cascade involving NF-kappa B, Elk-1, c-Jun N-terminal kinase and the p38 mitogen-activated protein kinase, which produce signals for cell survival and proliferation.

BCMA is also expressed on malignant B cells and several cancers that involve B lymphocytes including multiple myeloma, plasmacytoma, Hodgkin's Lymphoma, and chronic lymphocytic leukemia. In autoimmune diseases where plasmablasts are involved such as systemic lupus erythematosus (SLE) and rheumatoid arthritis, BCMA expressing antibody-producing cells secrete autoantibodies that attack self.

In the case of multiple myeloma, about 24,000 new cases are newly diagnosed in the United States each year, and this number represents about 15% of the newly diagnosed hematological cancers in the United States. An average of 11,000 deaths result from multiple myeloma each year, and the average 5-year survival rate is about 44%, with median survival of 50-55 months. Current treatment for multiple myeloma is focused on plasma cells apoptosis and/or decreasing osteoclast activity (e.g., chemotherapy, thalidomide, lenalidomide, bisphosphonates, and/or proteasome inhibitors such as bortezomib (VELCADE®) or carfilzomib). However, multiple myeloma remains an incurable disease, and almost all patients have developed resistance to these agents and eventually relapse. Accordingly, an alternative treatment to multiple myeloma, such as using an anti-BCMA antagonist including antibodies and other immunotherapeutic agents (e.g. bispecific antibodies or antibody-drug conjugates), would make a superior therapeutic agent.

SUMMARY

The invention disclosed herein is directed to therapeutic antibodies that bind to BCMA and/or CD3. Antibody conjugates (e.g., antibody-drug conjugates) comprising BCMA are also provided. Further, the heteromultimeric antibodies (e.g., bispecific antibodies) that specifically bind to CD3 and a tumor cell antigen (e.g., bispecific antibodies that specifically bind to CD3 and BCMA) are also provided.

In one aspect, the invention provides an isolated antibody, or an antigen binding fragment thereof, which specifically binds to B-Cell Maturation Antigen (BCMA), wherein the antibody comprises (a) a heavy chain variable (VH) region comprising (i) a VH complementary determining region one (CDR1) comprising the sequence $SYX_1MX_2$, wherein $X_1$ is A or P; and $X_2$ is T, N, or S (SEQ ID NO: 301), $GFTFX_1SY$, wherein $X_1$ is G or S (SEQ ID NO: 302), or $GFTFX_1SYX_2MX_3$, wherein $X_1$ is G or S, $X_2$ is A or P; and $X_3$ is T, N, or S (SEQ ID NO: 303); (ii) a VH CDR2 comprising the sequence $AX_1X_2X_3X_4GX_5X_6X_7X_8YADX_9X_{10}KG$, wherein $X_1$ is I, V, T, H, L, A, or C; $X_2$ is S, D, G, T, I, L, F, M, or V; $X_3$ is G, Y, L, H, D, A, S, or M; $X_4$ is S, Q, T, A, F, or W; $X_5$ is G or T; $X_6$ is N, S, P, Y, W, or F; $X_7$ is S, T, I, L, T, A, R, V, K, G, or C; $X_8$ is F, Y, P, W, H, or G; $X_9$ is V, R, or L; and $X_{10}$ is G or T (SEQ ID NO: 305), or $X_1X_2X_3X_4X_5X_6$, wherein $X_1$ is S, V, I, D, G, T, L, F, or M; $X_2$ is G, Y, L, H, D, A, S, or M; $X_3$ is S, G, F, or W; $X_4$ is G or S; $X_5$ is G or T; and $X_6$ is N, S, P, Y, or W (SEQ ID NO: 306); and iii) a VH CDR3 comprising the sequence $VSPIX_1X_2X_3X_4$, wherein $X_1$ is A or Y; $X_2$ is A or S; and $X_3$ is G, Q, L, P, or E (SEQ ID NO: 307), or $YWPMX_1X_2$, wherein $X_1$ is D, S, T, or A; and $X_2$ is I, S, L, P, or D (SEQ ID NO: 308); and/or (b) a light chain variable (VL) region comprising (i) a VL CDR1 comprising the sequence $X_1X_2X_3X_4X_5X_6X_7X_8X_9X_{10}X_{11}X_{12}$, wherein $X_1$ is R, G, W, A, or C; $X_2$ is A, P, G, L, C, or S; $X_3$ is S, G, or R; $X_4$ is Q, C, E, V, or I; $X_5$ is S, P, G, A, R, or D; $X_6$ is V, G, I, or L; $X_7$ is S, E, D, P, or G; $X_8$ is S, P, F, A, M, E, V, N, D, or Y;

$X_9$ is I, T, V, E, S, A, M, Q, Y, H, R, or F; $X_{10}$ is Y or F; $X_{11}$ is L, W, or P; and $X_{12}$ is A, S, or G (SEQ ID NO: 309); (ii) a VL CDR2 comprising the sequence $X_1ASX_2RAX_3$, wherein $X_1$ is G or D; $X_2$ is S or I; and $X_3$ is T or P (SEQ ID NO: 310); and (iii) a VL CDR3 comprising the sequence $QQYX_1X_2X_3PX_4T$, wherein $X_1$ is G, Q, E, L, F, A, S, M, K, R, or Y; $X_2$ is S, R, T, G, V, F, Y, D, A, H, V, E, K, or C; $X_3$ is W, F, or S; and $X_4$ is L or I (SEQ ID NO: 311), or $QQYX_1X_2X_3PX_4$, wherein $X_1$ is G, Q, E, L, F, A, S, M, R, K, or Y; $X_2$ is S, R, T, G, R, V, D, A, H, E, K, C, F, or Y; $X_3$ is W, S, or F; and $X_4$ is L or I (SEQ ID NO: 312).

In another aspect, the invention provides an isolated antibody, or an antigen binding fragment thereof, which specifically binds to BCMA, wherein the antibody comprises: a VH region comprising a VH CDR1, VH CDR2, and VH CDR3 of the VH sequence shown in SEQ ID NO: 2, 3, 7, 8, 24, 25, 26, 27, 28, 29, 30, 31, 32, 33, 35, 37, 39, 42, 44, 46, 48, 50, 52, 54, 56, 58, 60, 62, 64, 66, 68, 70, 72, 74, 76, 78, 83, 87, 92, 95, 97, 99, 101, 104, 106, 110, 112, 114, 118, 120, 122, 125, 127, 313, 314, 363, or 365; and/or a VL region comprising VL CDR1, VL CDR2, and VL CDR3 of the VL sequence shown in SEQ ID NO: 1, 4, 5, 6, 9, 10, 11, 12, 13, 14, 15, 16, 17, 18, 19, 20, 21, 22, 23, 34, 36, 38, 40, 41, 43, 45, 47, 49, 51, 53, 55, 57, 59, 61, 63, 65, 67, 69, 71, 73, 75, 77, 79, 317, 81, 82, 84, 85, 86, 88, 89, 90, 91, 93, 94, 96, 98, 100, 102, 103, 105, 107, 108, 109, 111, 113, 115, 116, 117, 119, 121, 123, 124, 126, 128, 315, 316, or 364. In some embodiments, the VH region comprises (i) a VH CDR1 comprising SEQ ID NO:150, 151, 152, 156, or 157; (ii) a VH CDR2 comprising SEQ ID NO: 169, 154, 194, 159, 195, 196, 162, 158, 198, 177, 178, 199, 200, 201, 202, 203, 204, 206, 207, 208, 172, 203, or 204; and (iii) a VH CDR3 comprising SEQ ID NO: 155, 161, 197, 205, or 164; and/or wherein the VL region comprises (i) a VL CDR1 comprising SEQ ID NO: 209, 271, 273, 275, 251, 277, 260, 279, 245, 283, 285, 287, 290, 292, 235, 297, or 299; (ii) a VL CDR2 comprising SEQ ID NO: 221; and (iii) a VL CDR3 comprising SEQ ID NO: 225, 272, 274, 276, 278, 280, 281, 282, 284, 286, 288, 289, 291, 293, 294, 229, 296, 298, or 300. In some embodiments, the VH region comprises the sequence shown in SEQ ID NO: 112 or a variant with one or several conservative amino acid substitutions in residues that are not within a CDR and/or the VL region comprises the amino acid sequence shown in SEQ ID NO: 38 or a variant thereof with one or several amino acid substitutions in amino acids that are not within a CDR. In some embodiments, the antibody comprises a light chain comprising the sequence shown in SEQ ID NO: 357 and a heavy chain comprising the sequence shown in SEQ ID NO: 358. In some embodiments, the antibody comprises a VH region produced by the expression vector with ATCC Accession No. PTA-122094. In some embodiments, the antibody comprises a VL region produced by the expression vector with ATCC Accession No. PTA-122093.

In another aspect, the invention provides an isolated antibody comprising an acyl donor glutamine-containing tag engineered at a specific site of the BCMA antibody of the present invention. In some embodiments, the tag comprises an amino acid sequence selected from the group consisting of Q, LQG, LLQGG (SEQ ID NO:318), LLQG (SEQ ID NO:454), LSLSQG (SEQ ID NO: 455), GGGLLQGG (SEQ ID NO: 456), GLLQG (SEQ ID NO: 457), LLQ, GSPLAQSHGG (SEQ ID NO: 458), GLLQGGG (SEQ ID NO: 459), GLLQGG (SEQ ID NO: 460), GLLQ (SEQ ID NO: 461), LLQLLQGA (SEQ ID NO: 462), LLQGA (SEQ ID NO: 463), LLQYQGA (SEQ ID NO: 464), LLQGSG (SEQ ID NO: 465), LLQYQG (SEQ ID NO: 466), LLQLLQG (SEQ ID NO: 467), SLLQG (SEQ ID NO: 468), LLQLQ (SEQ ID NO: 469), LLQLLQ (SEQ ID NO: 470), LLQGR (SEQ ID NO: 471), LLQGPP (SEQ ID NO: 472), LLQGPA (SEQ ID NO: 473), GGLLQGPP (SEQ ID NO: 474), GGLLQGA (SEQ ID NO: 475), LLQGPGK (SEQ ID NO: 476), LLQGPG (SEQ ID NO: 477), LLQGP (SEQ ID NO: 478), LLQP (SEQ ID NO: 479), LLQPGK (SEQ ID NO: 480), LLQAPGK (SEQ ID NO: 481), LLQGAPG (SEQ ID NO: 482), LLQGAP (SEQ ID NO: 483), and LLQLQG (SEQ ID NO: 484).

In one variation, the invention provides an isolated antibody comprising an acyl donor glutamine-containing tag and an amino acid modification at position 222, 340, or 370 of the BCMA antibody of the present invention. In some embodiments, the amino acid modification is a substitution from lysine to arginine.

In some embodiments, the BCMA antibody of the present invention further comprises a linker. In some embodiments, the linker is selected from the group consisting of Ac-Lys-Gly (acetyl-lysine-glycine), aminocaproic acid, Ac-Lys-β-Ala (acetyl-lysine-β-alanine), amino-PEG2 (polyethylene glycol)-C2, amino-PEG3-C2, amino-PEG6-C2, Ac-Lys-Val-Cit-PABC (acetyl-lysine-valine-citrulline-p-aminobenzyloxycarbonyl), amino-PEG6-C2-Val-Cit-PABC, aminocaproyl-Val-Cit-PABC, [(3R,5R)-1-{3-[2-(2-aminoethoxy)ethoxy]propanoyl}piperidine-3,5-diyl]bis-Val-Cit-PABC, [(3S,5S)-1-{3-[2-(2-aminoethoxy)ethoxy]propanoyl}piperidine-3,5-diyl]bis-Val-Cit-PABC, putrescine, and Ac-Lys-putrescine.

In another aspect, the invention provides a conjugate of the BCMA antibody or the antigen binding fragment as described herein, wherein the antibody or the antigen binding fragment is conjugated to an agent, wherein the agent is selected from the group consisting of a cytotoxic agent, an immunomodulating agent, an imaging agent, a therapeutic protein, a biopolymer, and an oligonucleotide. In some embodiments, the agent is a cytotoxic agent including, but not limited to, an anthracycline, an auristatin, a camptothecin, a combretastatin, a dolastatin, a duocarmycin, an enediyne, a geldanamycin, an indolino-benzodiazepine dimer, a maytansine, a puromycin, a pyrrolobenzodiazepine dimer, a taxane, a vinca alkaloid, a tubulysin, a hemiasterlin, a spliceostatin, a pladienolide, and stereoisomers, isosteres, analogs, or derivatives thereof. For example, the cytotoxic agent is MMAD (Monomethyl Auristatin D), 0101 (2-methylalanyl-N-[(3R,4S,5S)-3-methoxy-1-{(2 S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide), 3377 (N,2-dimethylalanyl-N-{(1S,2R)-4-{(2S)-2-[(1R,2R)-3-{[(1S)-1-carboxyl-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide), 0131 (2-methyl-L-proly-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide), or 0121 (2-methyl-L-proly-N-[(3R,4S,5S)-1-{(2S)-2-[(1R,2R)-3-{[(2S)-1-methoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide).

In some embodiments, the present invention provides a conjugate comprising the formula: antibody-(acyl donor glutamine-containing tag)-(linker)-(cytotoxic agent). In some embodiments, the acyl donor glutamine-containing tag comprises an amino acid sequence LLQG (SEQ ID NO:

319) and/or GGLLQGPP (SEQ ID NO: 339) and wherein the linker comprises acetyl-lysine-valine-citrulline-p-aminobenzyloxycarbonyl or amino-PEG6-C2. In some embodiments, the conjugate is selected from the group consisting of 1) antibody-GGLLQGPP (SEQ ID NO: 339)-(acetyl-lysine-valine-citrulline-p-aminobenzyloxycarbonyl (AcLys-VC-PABC))-0101; 2) antibody-LLQG (SEQ ID NO: 319)-amino-PEG6-C2-0131; and 3) antibody-LLQG (SEQ ID NO: 319)-amino-PEG6-C2-3377. In some embodiments, the conjugate further comprises an amino acid substitution from lysine to arginine at antibody position 222. In some embodiments, the conjugate further comprises amino acid substitutions at antibody position N297Q or N297A.

In another aspect, provided is a method of producing the BCMA antibody as described herein, comprising culturing the host cell under conditions that result in production of the BCMA antibody, and isolating the BCMA antibody from the host cell or culture.

In another aspect, the invention provides a use of the BCMA antibodies or the BCMA antibody conjugates as described herein in the manufacture of a medicament for treating a condition (e.g., cancer or autoimmune disorder) associated with BCMA expression. In some embodiments, provided is a use of the BCMA antibodies or the BCMA antibody conjugates as described herein in the manufacture of a medicament for inhibiting tumor growth or progression. In some embodiments, provided is a use of the BCMA antibodies or the BCMA antibody conjugates as described herein in the manufacture of a medicament for inhibiting metastasis of malignant cells expressing BCMA. In some embodiments, provided is a use of the BCMA antibodies or the BCMA antibody conjugates as described herein in the manufacture of a medicament for inducing tumor regression.

In another aspect, the invention provides an isolated antibody, or an antigen binding fragment thereof, which specifically binds to CD3, wherein the antibody comprises a VH CDR1, VH CDR2, and VH CDR3 of the VH sequence shown in SEQ ID NO: 320, 322, 324, 326, 328, 330, 345, 347, 349, 351, 444, 354, 356, 378, 442, 380, 382, 384 386, 388, 390, 392, 394, 396, 398, or 400; and/or a light chain variable (VL) region comprising VL CDR1, VL CDR2, and VL CDR3 of the VL sequence shown in SEQ ID NO: 319, 321, 323, 325, 327, 329, 344, 346, 348, 350, 352, 355, 377, 443, 445, 379, 381, 383, 385, 387, 389, 391, 393, 395, 397, or 399. In some embodiments, the antibody comprises a VH CDR1, VH CDR2, and VH CDR3 of the VH sequence shown in SEQ ID NO: 324 or 388; and/or a light chain variable (VL) region comprising VL CDR1, VL CDR2, and VL CDR3 of the VL sequence shown in SEQ ID NO: 323 or 387. In some embodiments, the VH region comprises (i) a VH complementarity determining region one (CDR1) comprising the sequence shown in SEQ ID NO: 331, 332, 333, 401, 402, 403, 407, 408, 415, 416, 418, 419, 420, 424, 425, 426, 446, 447, or 448 (ii) a VH CDR2 comprising the sequence shown in SEQ ID NO: 334, 336, 337, 338, 339, 404, 405, 409, 410, 411, 412, 413, 414, 417, 418, 421, 422, 427, 428, 449, or 450; and iii) a VH CDR3 comprising the sequence shown in SEQ ID NO: 335, 406, 423, 429, or 451; and/or a light chain variable (VL) region comprising (i) a VL CDR1 comprising the sequence shown in SEQ ID NO: 340, 343, 430, 431, 435, or 440, 441; (ii) a VL CDR2 comprising the sequence shown in SEQ ID NO: 341, 433, 452, or 436; and (iii) a VL CDR3 comprising the sequence shown in SEQ ID NO: 342, 432, 434, 437, 438, 439, 446, or 453. In some embodiments, the VH region comprises (i) a VH complementarity determining region one (CDR1) comprising the sequence shown in SEQ ID NO: 331, 332, 333, 401, 407, or 408 (ii) a VH CDR2 comprising the sequence shown in SEQ ID NO: 336, 404, 405, or 417; and iii) a VH CDR3 comprising the sequence shown in SEQ ID NO: 335 or 406; and/or a light chain variable (VL) region comprising (i) a VL CDR1 comprising the sequence shown in SEQ ID NO: 343 or 441; (ii) a VL CDR2 comprising the sequence shown in SEQ ID NO: 341 or 436; and (iii) a VL CDR3 comprising the sequence shown in SEQ ID NO: 342 or 439. In some embodiments, the antibody comprises a VH region produced by the expression vector with ATCC Accession No. PTA-122513. In some embodiments, the antibody comprises a VL region produced by the expression vector with ATCC Accession No. PTA-122512.

In another aspect, provided is an isolated antibody which specifically binds to CD3 and competes with the anti-CD3 antibody of the present invention as described herein.

In another aspect, the invention provides a bispecific antibody wherein the bispecific antibody is a full-length human antibody, comprising a first antibody variable domain of the bispecific antibody capable of recruiting the activity of a human immune effector cell by specifically binding to an effector antigen located on the human immune effector cell, and comprising a second antibody variable domain of the bispecific antibody capable of specifically binding to a target antigen, wherein the first antibody variable domain comprises a heavy chain variable (VH) region comprising a VH CDR1, VH CDR2, and VH CDR3 of the VH sequence shown in SEQ ID NO: 320, 322, 324, 326, 328, 330, 345, 347, 349, 351, 444, 354, 356, 378, 442, 380, 382, 384 386, 388, 390, 392, 394, 396, 398, or 400; and/or a light chain variable (VL) region comprising VL CDR1, VL CDR2, and VL CDR3 of the VL sequence shown in SEQ ID NO: 319, 321, 323, 325, 327, 329, 344, 346, 348, 350, 352, 355, 377, 443, 445, 379, 381, 383, 385, 387, 389, 391, 393, 395, 397, or 399. In some embodiments, the first antibody variable domain comprises a heavy chain variable (VH) region comprising (i) a VH CDR1-comprising the sequence shown in SEQ ID NO: 331, 332, 333, 401, 402, 403, 407, 408, 415, 416, 418, 419, 420, 424, 425, 426, 446, 447, or 448 (ii) a VH CDR2 comprising the sequence shown in SEQ ID NO: 334, 336, 337, 338, 339, 404, 405, 409, 410, 411, 412, 413, 414, 417, 418, 421, 422, 427, 428, 449, or 450; and iii) a VH CDR3 comprising the sequence shown in SEQ ID NO: 335, 406, 423, 429, or 451; and/or a light chain variable (VL) region comprising (i) a VL CDR1 comprising the sequence shown in SEQ ID NO: 340, 343, 430, 431, 435, or 440, 441; (ii) a VL CDR2 comprising the sequence shown in SEQ ID NO: 341, 433, 452, or 436; and (iii) a VL CDR3 comprising the sequence shown in SEQ ID NO: 342, 432, 434, 437, 438, 439, 446, or 453. In some embodiments, the first antibody variable domain comprises a heavy chain variable (VH) region comprising a VH CDR1, VH CDR2, and VH CDR3 of the VH sequence shown in SEQ ID NO: 324 or 388; and/or a light chain variable (VL) region comprising VL CDR1, VL CDR2, and VL CDR3 of the VL sequence shown in SEQ ID NO: 323 or 387; and the second antibody variable domain comprises a heavy chain variable (VH) region comprising a VH CDR1, VH CDR2, and VH CDR3 of the VH sequence shown in SEQ ID NO: 112; and/or a light chain variable (VL) region comprising VL CDR1, VL CDR2, and VL CDR3 of the VL sequence shown in SEQ ID NO: 38.

In some embodiments, the second antibody variable domain comprises (a) a heavy chain variable (VH) region comprising (i) a VH complementarity determining region one (CDR1) comprising the sequence $SYX_1MX_2$, wherein $X_1$ is A or P; and $X_2$ is T, N, or S (SEQ ID NO: 301), GFTFX$_1$SY, wherein X$_1$ is G or S (SEQ ID NO: 302), or GFTFX$_1$SYX$_2$MX$_3$, wherein X$_1$ is G or S, X$_2$ is A or P; and X$_3$ is T, N, or S (SEQ ID NO: 303); (ii) a VH CDR2 comprising the sequence AX$_1$X$_2$X$_3$X$_4$GX$_5$X$_6$X$_7$X$_8$YADX$_9$X$_{10}$KG, wherein X$_1$ is I, V, T, H, L, A, or C; X$_2$ is S, D, G, T, I, L, F, M, or V; X$_3$ is G, Y, L, H, D, A, S, or M; X$_4$ is S, Q, T, A, F, or W; X$_5$ is G or T; X$_6$ is N, S, P, Y, W, or F; X$_7$ is S, T, I, L, T, A, R, V, K, G, or C; X$_8$ is F, Y, P, W, H, or G; X$_9$ is V, R, or L; and X$_{10}$ is G or T (SEQ ID NO: 305), or X$_1$X$_2$X$_3$X$_4$X$_5$X$_6$, wherein X$_1$ is S, V, I, D, G, T, L, F, or M; X$_2$ is G, Y, L, H, D, A, S, or M; X$_3$ is S, G, F, or W; X$_4$ is G or S; X$_5$ is G or T; and X$_6$ is N, S, P, Y, or W (SEQ ID NO: 306); and iii) a VH CDR3 comprising the sequence VSPIX$_1$X$_2$X$_3$X$_4$ wherein X$_1$ is A or Y; X$_2$ is A or S; and X$_3$ is G, Q, L, P, or E (SEQ ID NO: 307), or YWPMX$_1$X$_2$, wherein X$_1$ is D, S, T, or A; and X$_2$ is I, S, L, P, or D (SEQ ID NO: 308); and/or (b) a light chain variable (VL) region comprising (i) a VL CDR1 comprising the sequence X$_1$X$_2$X$_3$X$_4$X$_5$X$_6$X$_7$X$_8$X$_9$X$_{10}$X$_{11}$X$_{12}$, wherein X$_1$ is R, G, W, A, or C; X$_2$ is A, P, G, L, C, or S; X$_3$ is S, G, or R; X$_4$ is Q, C, E, V, or I; X$_5$ is S, L, P, G, A, R, or D; X$_6$ is V, G, or I; X$_7$ is S, E, D, or P; X$_8$ is S, P, F, A, M, E, V, N, D, or Y; X$_9$ is I, T, V, E, S, A, M, Q, Y, H, or R; X$_{10}$ is Y or F; X$_{11}$ is L, W, or P; and X$_{12}$ is A, S, or G (SEQ ID NO: 309); (ii) a VL CDR2 comprising the sequence X$_1$ASX$_2$RAX$_3$, wherein X$_1$ is G or D; X$_2$ is S or I; and X$_3$ is T or P (SEQ ID NO: 310); and (iii) a VL CDR3 comprising the sequence QQYX$_1$X$_2$X$_3$PX$_4$T, wherein X$_1$ is G, Q, E, L, F, A, S, M, K, R, or Y; X$_2$ is S, R, T, G, V, F, Y, D, A, H, V, E, K, or C; X$_3$ is W, F, or S; and X$_4$ is L or I (SEQ ID NO: 311), or QQYX$_1$X$_2$X$_3$PX$_4$, wherein X$_1$ is G, Q, E, L, F, A, S, M, R, K, or Y; X$_2$ is S, R, T, G, R, V, D, A, H, E, K, C, F, or Y; X$_3$ is W, S, or F; and X$_4$ is L or I (SEQ ID NO: 312). In some embodiments, the second antibody variable domain comprises a heavy chain variable (VH) region comprising (i) a VH CDR1 comprising the sequence shown in SEQ ID NO:150, 151, 152, 156, 157, 348, 349, 353, 354, or 355; (ii) a VH CDR2 comprising the sequence shown in SEQ ID NO: 169, 154, 194, 159, 195, 196, 162, 158, 198, 177, 178, 199, 200, 201, 202, 203, 204, 206, 207, 208, 172, 203, 204, 350, 351, 356 or 357; and (iii) a VH CDR3 comprising the sequence shown in SEQ ID NO: 155, 161, 197, 205, 164, or 352, or 358; and/or wherein the light chain variable (VL) region comprises (i) a VL CDR1 comprising the sequence shown in SEQ ID NO: 209, 271, 273, 275, 251, 277, 260, 279, 245, 283, 285, 287, 290, 292, 235, 297, 299, or 361; (ii) a VL CDR2 comprising the sequence shown in SEQ ID NO: 221, 359 or 362; and (iii) a VL CDR3 comprising the sequence shown in SEQ ID NO: 211, 225, 272, 274, 276, 278, 280, 281, 282, 284, 286, 288, 289, 291, 293, 294, 229, 296, 298, 300 or 360.

In some embodiments, (a) the first antibody variable domain comprises a heavy chain variable (VH) region comprising (i) a VH complementarity determining region one (CDR1) comprising the sequence shown in SEQ ID NO: 331, 332, 333, 401, 407, or 408 (ii) a VH CDR2 comprising the sequence shown in SEQ ID NO: 336, 417, 404, or 405; and iii) a VH CDR3 comprising the sequence shown in SEQ ID NO: 335 or 406; and/or a light chain variable (VL) region comprising (i) a VL CDR1 comprising the sequence shown in SEQ ID NO: 343 or 441; (ii) a VL CDR2 comprising the sequence shown in SEQ ID NO: 341 or 436; and (iii) a VL CDR3 comprising the sequence shown in SEQ ID NO: 342 or 439; and (b) the second antibody variable domain comprises a heavy chain VH region comprising a heavy chain variable (VH) region comprising (i) a VH CDR1 comprising the sequence shown in SEQ ID NO: 151, 156, or 157; (ii) a VH CDR2 comprising the sequence shown in SEQ ID NO: 158 or 159; and (iii) a VH CDR3 comprising SEQ ID NO: 155; and/or wherein the light chain variable (VL) region comprises (i) a VL CDR1 comprising the sequence shown in SEQ ID NO: 209; (ii) a VL CDR2 comprising the sequence shown in SEQ ID NO: 221; and (iii) a VL CDR3 comprising the sequence shown in SEQ ID NO: 225.

In some embodiments, both the first and the second antibody variable domains of the bispecific antibody comprise amino acid modifications at positions 223, 225, and 228 in the hinge region and at position 409 or 368 (EU numbering scheme) in the CH3 region of a human IgG2 (SEQ ID NO: 493). In some embodiments, the bispecific antibody as described herein further comprises an amino acid modification at position 265 of the human IgG2.

In another aspect, the invention provides pharmaceutical compositions comprising any of the antibodies (e.g., BCMA, CD3, or bispecific) or the conjugates thereof (e.g., BCMA antibody-drug conjugate) described herein.

In another aspect, the invention also provides cell lines that recombinantly produce any of the antibodies (e.g., BCMA, CD3, or bispecific) or the conjugates thereof (e.g., BCMA antibody-drug conjugate) described herein.

In another aspect, the invention also provides nucleic acids encoding any of the antibodies (e.g., BCMA, CD3, or bispecific) or the conjugates thereof (e.g., BCMA antibody-drug conjugate) described herein. The invention also provides nucleic acids encoding a heavy chain variable region and/or a light chain variable region of any of these antibodies described herein.

The invention also provides kits comprising an effective amount of any of the antibodies (e.g., BCMA, CD3, or bispecific) or the conjugates thereof (e.g., BCMA antibody-drug conjugate) described herein.

The invention also provides methods of treating a condition (e.g., tumor growth/progression inhibition; metastasis of malignant cells expressing BCMA inhibition; tumor regression induction in subjects with malignant cells expressing BCMA) in subjects in need thereof comprising providing the isolated antibodies (e.g., BCMA) or binding fragments, bispecific antibodies (BCMA-CD3 bispecifics), or the conjugates thereof (e.g., BCMA antibody-drug conjugates) thereof described herein and administering said antibodies or conjugates to said subject.

Also provided are methods of treating a condition associated with malignant cells expressing a tumor antigen in a subject comprising administering to a subject in need thereof an effective amount of the pharmaceutical compositions of the invention. In some embodiments, the condition is cancer. In some embodiments, the cancer is a B-cell related cancer selecting from the group consisting of multiple myeloma, malignant plasma cell neoplasm, Hodgkin's lymphoma, nodular lymphocyte predominant Hodgkin's lymphoma, Kahler's disease and Myelomatosis, plasma cell leukemia, plasmacytoma, B-cell prolymphocytic leukemia, hairy cell leukemia, B-cell non-Hodgkin's lymphoma (NHL), acute myeloid leukemia (AML), chronic lymphocytic leukemia (CLL), acute lymphocytic leukemia (ALL), chronic myeloid leukemia (CML), follicular lymphoma, Burkitt's lymphoma, marginal zone lymphoma, mantle cell lymphoma, large cell lymphoma, precursor B-lymphoblastic lymphoma, myeloid leukemia, Waldenstrom's macroglobulienemia, diffuse large B cell lymphoma, follicular lymphoma, marginal zone lymphoma, mucosa-associated lymphatic tissue lymphoma, small cell lymphocytic lymphoma, mantle cell lymphoma, Burkitt lymphoma, primary mediastinal (thymic)

large B-cell lymphoma, lymphoplasmactyic lymphoma, Waldenström macroglobulinemia, nodal marginal zone B cell lymphoma, splenic marginal zone lymphoma, intravascular large B-cell lymphoma, primary effusion lymphoma, lymphomatoid granulomatosis, T cell/histiocyte-rich large B-cell lymphoma, primary central nervous system lymphoma, primary cutaneous diffuse large B-cell lymphoma (leg type), EBV positive diffuse large B-cell lymphoma of the elderly, diffuse large B-cell lymphoma associated with inflammation, intravascular large B-cell lymphoma, ALK-positive large B-cell lymphoma, plasmablastic lymphoma, large B-cell lymphoma arising in HHV8-associated multicentric Castleman disease, B-cell lymphoma unclassified with features intermediate between diffuse large B-cell lymphoma and Burkitt lymphoma, B-cell lymphoma unclassified with features intermediate between diffuse large B-cell lymphoma and classical Hodgkin lymphoma, and other B-cell related lymphoma. In some embodiments, the condition is an autoimmune disorder, such as systemic lupus erythematosus or rheumatoid arthritis.

In some embodiments, the antibodies described herein comprise a constant region. In some embodiments, the antibodies described herein are of the human IgG1, IgG2 or IgG2Δa, IgG3, or IgG4 subclass. In some embodiments, the antibodies described herein comprise a glycosylated constant region. In some embodiments, the antibodies described herein comprise a constant region having increased binding affinity to one or more human Fc gamma receptor(s).

BRIEF DESCRIPTION OF THE FIGURES/DRAWINGS

FIG. 1A-FIG. 1D depict the double-referenced sensorgrams with fit curves for interactions between selected anti-BCMA antibodies of the present invention and human BCMA.

FIG. 2 depicts in vivo efficacy studies of various anti-BCMA ADCs in the MM1S orthotopic multiple myeloma model, including P6E01_VHVL-AcLys-Val-Cit-PABC-Aur0101; P5A2_VHVL-AcLys-Val-Cit-PABC-Aur0101; P5C1_VHVL-AcLys-Val-Cit-PABC-Aur0101; P4G4-AcLys-Val-Cit-PABC-Aur0101; and P1A11-AcLys-Val-Cit-PABC-Aur0101. NNC is a negative control non-BCMA antibody. "LCQ05" and "LCQ04" correspond to glutamine-containing transglutaminase tag SEQ ID NOs: 474 and 475, respectively.

FIG. 3 depicts in vivo efficacy of the anti-BCMA ADCs in the MM1S orthotopic multiple myeloma model, including L3.PY/P6E01 antibody conjugated with 1) H7c/N297A/K222R-amino-PEG6-C2-3377, 2) N297Q/K222R-AcLys-Val-Cit-PABC-0101, 3) LCQ05/K222R-AcLys-Val-Cit-PABC-0101, 4) H7c/N297A/K222R-amino-PEG6-C2-0131, and 5) N297Q/K222R/LCQ05-AcLys-Val-Cit-PABC-Aur0101. NNC is a control non-BCMA antibody. "LCQ05" and H7c correspond to glutamine-containing transglutaminase tag SEQ ID NO: 474 and SEQ ID NO: 454, respectively FIG. 4 also depicts in vivo efficacy of the anti-BCMA ADCs in the MM1S orthotopic multiple myeloma model, including L3.PY/P6E01 antibody conjugated with 1) H7c/N297A/K222R-amino-PEG6-C2-3377, 2) N297Q/K222R-AcLys-Val-Cit-PABC-Aur0101, 3) LCQ05/K222R-AcLys-Val-Cit-PABC-Aur0101, 4) H7c/N297A/K222R-amino-PEG6-C2-0131, and 5) N297Q/K222R/LCQ05-AcLys-Val-Cit-PABC-Aur0101. NNC is a control non-BCMA antibody (antibody-N297Q/K222R-AcLys-VC-PABC-0101).

"LCQ05" and H7c correspond to glutamine-containing transglutaminase tag SEQ ID NO: 474 and SEQ ID NO: 454, respectively.

FIG. 5 also depicts in vivo efficacy of an anti-BCMA ADC in the MM1S orthotopic multiple myeloma model. Anti-BCMA antibody COMBO_Rd4_0.6 nM-C29 ("Combo C29 DI) is conjugated to H7c/N297A/K222R-amino-PEG6-C2-131 at doses ranging from 0.1 mg/kg, 0.38 mg/kg, 0.75 mg/kg, 1.5 mg/kg in comparison to NNC, a control non-BCMA antibody (antibody-N297Q/K222R-AcLys-VC-PABC-0101) at 3 mg/kg. H7c correspond to glutamine-containing transglutaminase tag SEQ ID NO: 454.

Figure 15A:
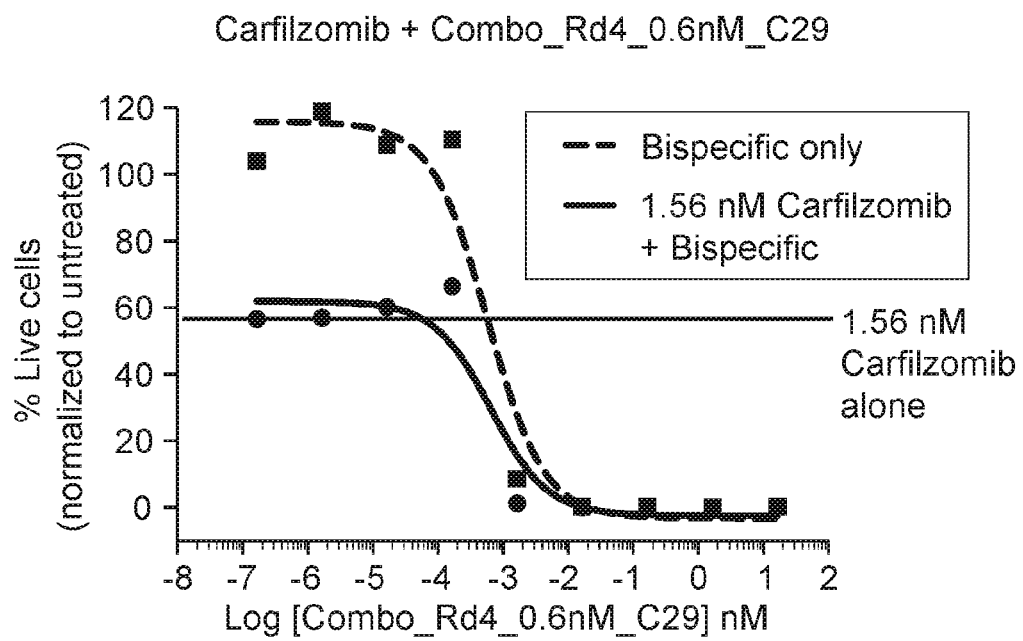
Figure 15B:
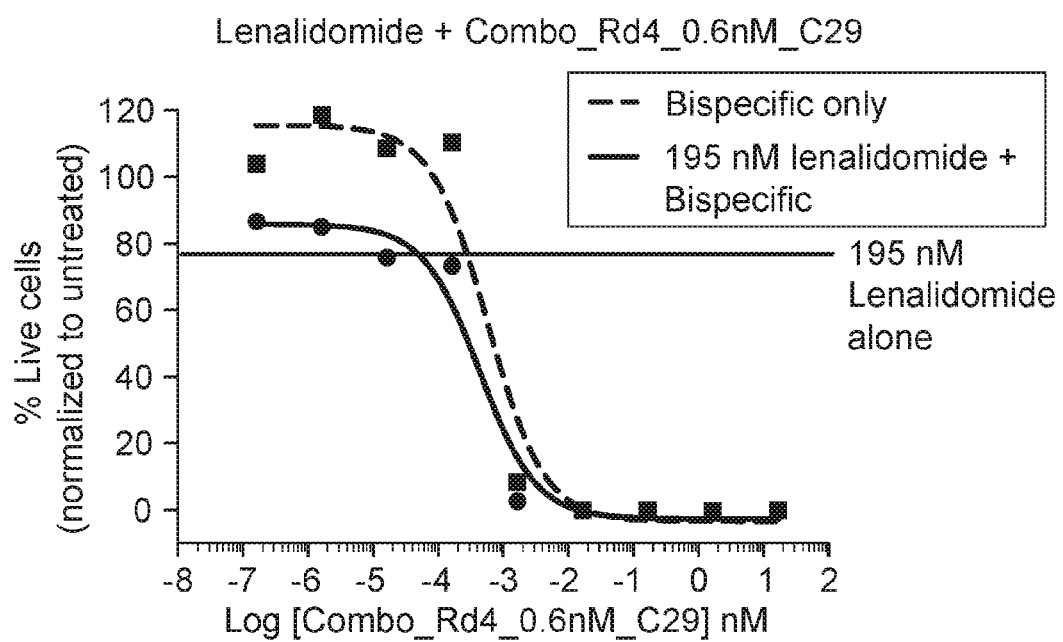
Figure 15C:
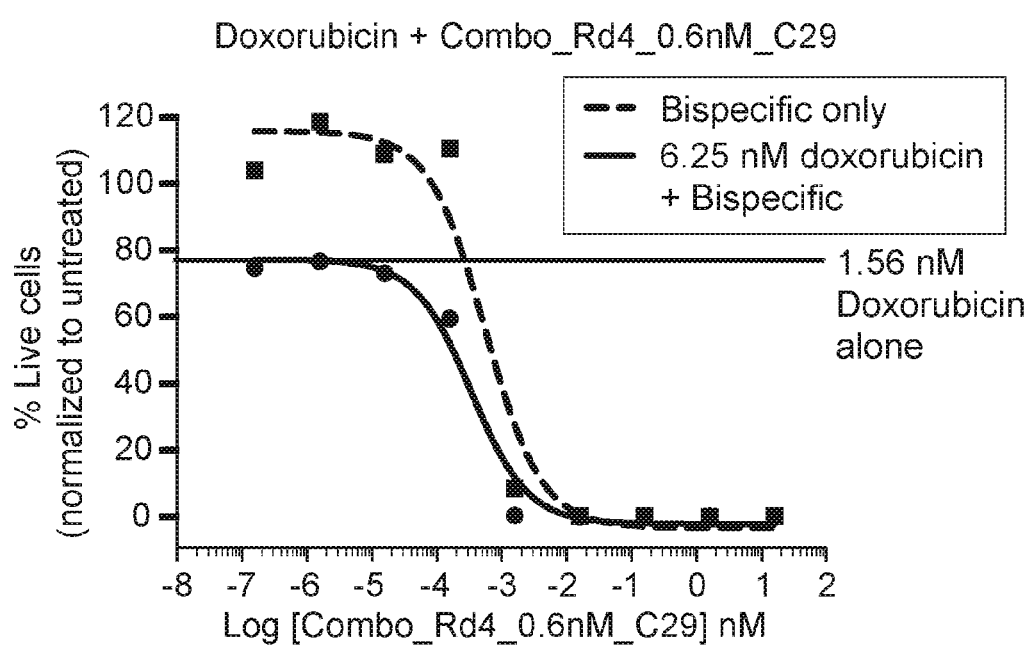

FIG. 15A-FIG. 15C, respectively, show that carfilzomib, lenalidomide, and doxorubicin do not have a negative effect on the function of the anti-BCMA/CD3 bispecific antibody on OPM2 cells as compared to the anti-BCMA/CD3 bispecific antibody alone.

Figure 16:
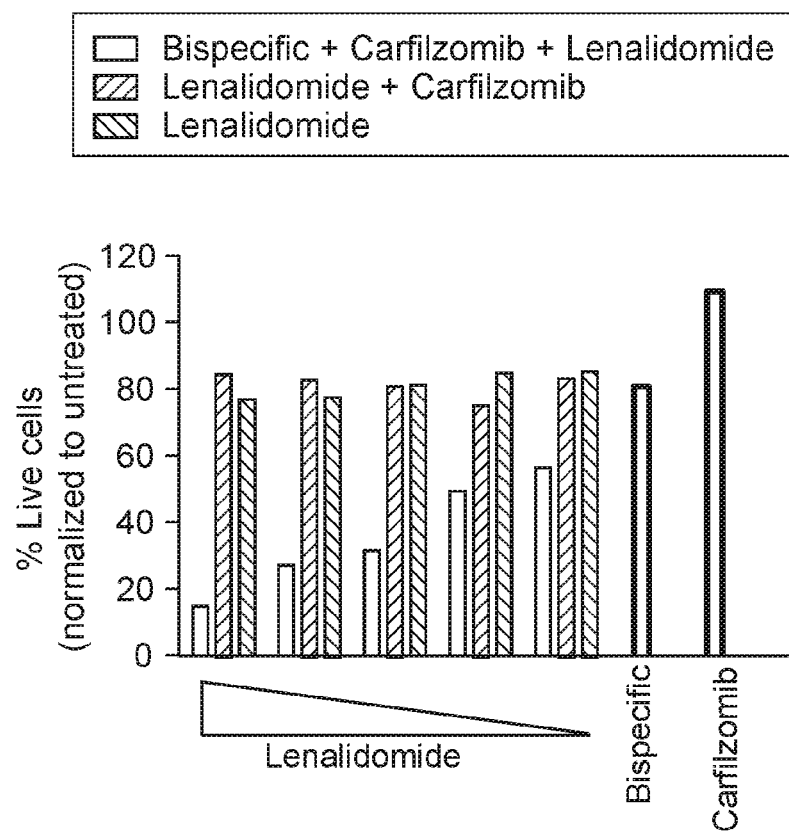

FIG. 16 shows synergistic effects on the function of anti-BCMA/CD3 bispecific antibody when combined with carfilzomib and lenalidomide in comparison to each molecule alone.

DETAILED DESCRIPTION

The invention disclosed herein provides antibodies and antibody conjugates (e.g., antibody-drug conjugates) that specifically bind to BCMA (e.g., human BCMA). The invention also provides polynucleotides encoding these antibodies and conjugates, compositions comprising these antibodies and conjugates, and methods of making these antibodies and conjugates. Further, the invention disclosed herein provides antibodies that specifically bind to CD3 (e.g., human CD3) as well as heterodimeric antibodies (e.g., bispecific antibodies) that specifically bind to CD3 and a tumor antigen (e.g., BCMA). The invention also provides polynucleotides encoding these antibodies, compositions comprising these antibodies, and methods of making and using these antibodies. The invention further provides methods for treating a condition associated with malignant BCMA expression in a subject, such as cancer or autoimmune disease, using the antibodies (e.g., BCMA, CD3, or bispecific antibody) or conjugates thereof (BCMA antibody-drug conjugates) as described herein.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Definitions

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv) and domain antibodies (including, for example, shark and camelid antibodies), and fusion proteins comprising an antibody, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

The term "antigen binding fragment" or "antigen binding portion" of an antibody, as used herein, refers to one or more fragments of an intact antibody that retain the ability to specifically bind to a given antigen (e.g., BCMA or CD3). Antigen binding functions of an antibody can be performed by fragments of an intact antibody. Examples of binding fragments encompassed within the term "antigen binding fragment" of an antibody include Fab; Fab'; F(ab')$_2$; an Fd fragment consisting of the VH and CH1 domains; an Fv fragment consisting of the VL and VH domains of a single arm of an antibody; a single domain antibody (dAb) fragment (Ward et al., Nature 341:544-546, 1989), and an isolated complementarity determining region (CDR).

An antibody, an antibody conjugate, or a polypeptide that "preferentially binds" or "specifically binds" (used interchangeably herein) to a target (e.g., BCMA protein or CD3 protein) is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a BCMA epitope or CD3 epitope is an antibody that binds this epitope with greater affinity, avidity, more readily, and/or with greater duration than it binds to other BCMA epitopes, non-BCMA epitopes, CD3 epitopes, or non-CD3 epitopes. It is also understood that by reading this definition, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

A "variable region" of an antibody refers to the variable region of the antibody light chain or the variable region of the antibody heavy chain, either alone or in combination. As known in the art, the variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al., 1997, J. Molec. Biol. 273:927-948). As used herein, a CDR may refer to CDRs defined by either approach or by a combination of both approaches.

A "CDR" of a variable domain are amino acid residues within the variable region that are identified in accordance with the definitions of the Kabat, Chothia, the accumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., Nature 342:877-883, 1989. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., J. Mol. Biol., 262:732-745, 1996. In another approach, referred to herein as the "conformational definition" of CDRs, the positions of the CDRs may be identified as the residues that make enthalpic contributions to antigen binding. See, e.g., Makabe et al., Journal of Biological Chemistry, 283:1156-1166, 2008. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature 256:495, 1975, or may be made by recombinant DNA methods such as described in U.S. Pat. No. 4,816,567. The monoclonal antibodies may also be isolated from phage libraries generated using the techniques described in McCafferty et al., Nature 348:552-554, 1990, for example.

As used herein, "humanized" antibody refers to forms of non-human (e.g. murine) antibodies that are chimeric immunoglobulins, immunoglobulin chains, or fragments thereof (such as Fv, Fab, Fab', F(ab')$_2$ or other antigen binding subsequences of antibodies) that contain minimal sequence derived from non-human immunoglobulin. Preferably, humanized antibodies are human immunoglobulins (recipient antibody) in which residues from a complementarity determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Preferred are antibodies having Fc regions modified as described in WO 99/58572. Other forms of humanized antibodies have one or more CDRs (CDR L1, CDR L2, CDR L3, CDR H1, CDR H2, or CDR H3) which are altered with respect to the original antibody, which are also termed one or more CDRs "derived from" one or more CDRs from the original antibody.

As used herein, "human antibody" means an antibody having an amino acid sequence corresponding to that of an antibody produced by a human and/or which has been made using any of the techniques for making human antibodies known to those skilled in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., Nature Biotechnology, 14:309-314, 1996; Sheets et al., Proc. Natl. Acad. Sci. (USA) 95:6157-6162, 1998; Hoogenboom and Winter, J. Mol. Biol., 227:381, 1991; Marks et al., J. Mol. Biol., 222:581, 1991). Human antibodies can also be made by immunization of animals into which human immunoglobulin loci have been transgenically introduced in place of the endogenous loci, e.g., mice in which the endogenous immunoglobulin genes have been partially or completely inactivated. This approach is described in U.S. Pat. Nos. 5,545,807; 5,545,806; 5,569, 825; 5,625,126; 5,633,425; and 5,661,016. Alternatively, the human antibody may be prepared by immortalizing human B lymphocytes that produce an antibody directed against a target antigen (such B lymphocytes may be recovered from an individual or from single cell cloning of the cDNA, or may have been immunized in vitro). See, e.g., Cole et al. Monoclonal Antibodies and Cancer Therapy, Alan R. Liss, p. 77, 1985; Boerner et al., J. Immunol., 147 (1):86-95, 1991; and U.S. Pat. No. 5,750,373.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

The terms "polypeptide", "oligopeptide", "peptide" and "protein" are used interchangeably herein to refer to chains of amino acids of any length, preferably, relatively short (e.g., 10-100 amino acids). The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

A "monovalent antibody" comprises one antigen binding site per molecule (e.g., IgG or Fab). In some instances, a monovalent antibody can have more than one antigen binding sites, but the binding sites are from different antigens.

A "monospecific antibody" comprises two identical antigen binding sites per molecule (e.g. IgG) such that the two binding sites bind identical epitope on the antigen. Thus, they compete with each other on binding to one antigen molecule. Most antibodies found in nature are monospecific. In some instances, a monospecific antibody can also be a monovalent antibody (e.g. Fab)

A "bivalent antibody" comprises two antigen binding sites per molecule (e.g., IgG). In some instances, the two binding sites have the same antigen specificities. However, bivalent antibodies may be bispecific.

A "bispecific" or "dual-specific" is a hybrid antibody having two different antigen binding sites. The two antigen binding sites of a bispecific antibody bind to two different epitopes, which may reside on the same or different protein targets.

A "bifunctional" is antibody is an antibody having identical antigen binding sites (i.e., identical amino acid sequences) in the two arms but each binding site can recognize two different antigens.

A "heteromultimer", "heteromultimeric complex", or "heteromultimeric polypeptide" is a molecule comprising at least a first polypeptide and a second polypeptide, wherein the second polypeptide differs in amino acid sequence from the first polypeptide by at least one amino acid residue. The heteromultimer can comprise a "heterodimer" formed by the first and second polypeptide or can form higher order tertiary structures where polypeptides in addition to the first and second polypeptide are present.

A "heterodimer," "heterodimeric protein," "heterodimeric complex," or "heteromultimeric polypeptide" is a molecule comprising a first polypeptide and a second polypeptide, wherein the second polypeptide differs in amino acid sequence from the first polypeptide by at least one amino acid residue.

The "hinge region," "hinge sequence", and variations thereof, as used herein, includes the meaning known in the art, which is illustrated in, for example, Janeway et al., ImmunoBiology: the immune system in health and disease, (Elsevier Science Ltd., NY) (4th ed., 1999); Bloom et al., *Protein Science* (1997), 6:407-415; Humphreys et al., *J. Immunol. Methods* (1997), 209:193-202.

The "immunoglobulin-like hinge region," "immunoglobulin-like hinge sequence," and variations thereof, as used herein, refer to the hinge region and hinge sequence of an immunoglobulin-like or an antibody-like molecule (e.g., immunoadhesins). In some embodiments, the immunoglobulin-like hinge region can be from or derived from any IgG1, IgG2, IgG3, or IgG4 subtype, or from IgA, IgE, IgD or IgM, including chimeric forms thereof, e.g., a chimeric IgG1/2 hinge region.

The term "immune effector cell" or "effector cell as used herein refers to a cell within the natural repertoire of cells in the human immune system which can be activated to affect the viability of a target cell. The viability of a target cell can include cell survival, proliferation, and/or ability to interact with other cells.

Antibodies of the invention can be produced using techniques well known in the art, e.g., recombinant technologies, phage display technologies, synthetic technologies or combinations of such technologies or other technologies readily known in the art (see, for example, Jayasena, S. D., Clin. Chem., 45: 1628-50, 1999 and Fellouse, F. A., et al, J. Mol. Biol., 373(4):924-40, 2007).

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As known in the art a "constant region" of an antibody refers to the constant region of the antibody light chain or the constant region of the antibody heavy chain, either alone or in combination.

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant regions, CH2 and CH3.

As used in the art, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, Ann. Rev. Immunol., 9:457-92, 1991; Capel et al., Immunomethods, 4:25-34, 1994; and de Haas et al., J. Lab. Clin. Med., 126:330-41, 1995. "FcR" also includes the neonatal receptor, FcRn, which is responsible for the transfer of maternal IgGs to the fetus (Guyer et al., J. Immunol., 117:587, 1976; and Kim et al., J. Immunol., 24:249, 1994).

The term "compete", as used herein with regard to an antibody, means that a first antibody, or an antigen binding fragment (or portion) thereof, binds to an epitope in a manner sufficiently similar to the binding of a second antibody, or an antigen binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

A "functional Fc region" possesses at least one effector function of a native sequence Fc region. Exemplary "effector functions" include C1q binding; complement dependent cytotoxicity; Fc receptor binding; antibody-dependent cell-mediated cytotoxicity; phagocytosis; down-regulation of cell surface receptors (e.g. B cell receptor), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. In some embodiments, the variant Fc region has at least one amino acid substitution compared to a native sequence Fc region or to the Fc region of a parent polypeptide, e.g. from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

The term "effector function" refers to the biological activities attributable to the Fc region of an antibody. Examples of antibody effector functions include, but are not limited to, antibody-dependent cell-mediated cytotoxicity (ADCC), Fc receptor binding, complement dependent cytotoxicity (CDC), phagocytosis, C1q binding, and down regulation of cell surface receptors (e.g., B cell receptor; BCR). See, e.g., U.S. Pat. No. 6,737,056. Such effector functions generally require the Fc region to be combined with a binding domain (e.g., an antibody variable domain) and can be assessed using various assays known in the art for evaluating such antibody effector functions. An exemplary measurement of effector function is through Fcγ3 and/or C1q binding.

As used herein "antibody-dependent cell-mediated cytotoxicity" or "ADCC" refers to a cell-mediated reaction in which nonspecific cytotoxic cells that express Fc receptors (FcRs) (e.g. natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. No. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in an animal model such as that disclosed in Clynes et al., 1998, PNAS (USA), 95:652-656.

"Complement dependent cytotoxicity" or "CDC" refers to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods,* 202: 163 (1996), may be performed.

As used herein, "treatment" is an approach for obtaining beneficial or desired clinical results. For purposes of this invention, beneficial or desired clinical results include, but are not limited to, one or more of the following: reducing the proliferation of (or destroying) neoplastic or cancerous cells, inhibiting metastasis of neoplastic cells, remission of a BCMA associated disease (e.g., cancer or autoimmune disease), decreasing symptoms resulting from a BCMA associated disease (e.g., cancer or autoimmune disease), increasing the quality of life of those suffering from a BCMA associated disease (e.g., cancer or autoimmune disease), decreasing the dose of other medications required to treat a BCMA associated disease (e.g., cancer or autoimmune disease), delaying the progression of a BCMA associated disease (e.g., cancer or autoimmune disease), curing a BCMA associated disease (e.g., cancer or autoimmune disease), and/or prolong survival of patients having a BCMA associated disease (e.g., cancer or autoimmune disease).

"Ameliorating" means a lessening or improvement of one or more symptoms as compared to not administering a BCMA antibody or a BCMA antibody conjugate. "Ameliorating" also includes shortening or reduction in duration of a symptom.

As used herein, an "effective dosage" or "effective amount" of drug, compound, or pharmaceutical composition is an amount sufficient to effect any one or more beneficial or desired results. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing incidence or amelioration of one or more symptoms of various BCMA associated diseases or conditions (such as multiple myeloma), decreasing the dose of other medications required to treat the disease, enhancing the effect of another medication, and/or delaying the progression of the BCMA associated disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably, a human. Mammals also include, but are not limited to, farm animals, sport animals, pets, primates, horses, dogs, cats, mice and rats.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 21st Ed. Mack Publishing, 2005).

The term "acyl donor glutamine-containing tag" or "glutamine tag" as used herein refers to a polypeptide or a protein containing one or more Gln residue(s) that acts as a transglutaminase amine acceptor. See, e.g., WO2012059882 and WO2015015448.

The term "$k_{on}$" or "$k_a$", as used herein, refers to the rate constant for association of an antibody to an antigen. Specifically, the rate constants ($k_{on}/k_a$ and $k_{off}/k_d$) and equilibrium dissociation constants are measured using whole antibody (i.e. bivalent) and monomeric BCMA proteins.

The term "$k_{off}$" or "$k_d$", as used herein, refers to the rate constant for dissociation of an antibody from the antibody/antigen complex.

The term "$K_D$", as used herein, refers to the equilibrium dissociation constant of an antibody-antigen interaction.

Reference to "about" a value or parameter herein includes (and describes) embodiments that are directed to that value or parameter per se. For example, description referring to "about X" includes description of "X." Numeric ranges are inclusive of the numbers defining the range.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular.

Exemplary methods and materials are described herein, although methods and materials similar or equivalent to those described herein can also be used in the practice or testing of the present invention. The materials, methods, and examples are illustrative only and not intended to be limiting.

BCMA Antibodies and Methods of Making Thereof

The present invention provides an antibody that binds to BCMA (e.g., human BCMA (e.g., SEQ ID NO: 353 or accession number: Q02223-2) and characterized by any one or more of the following characteristics: (a) treat, prevent, ameliorate one or more symptoms of a condition associated with malignant cells expressing BCMA in a subject (e.g., B-cell related cancer such as multiple myeloma); (b) inhibit tumor growth or progression in a subject (who has a malignant tumor expressing BCMA); (c) inhibit metastasis of cancer (malignant) cells expressing BCMA in a subject (who has one or more malignant cells expressing BCMA); (f) induce regression (e.g., long-term regression) of a tumor expressing BCMA; (d) exert cytotoxic activity in malignant cells expressing BCMA; and (e) block BCMA interaction with other yet to be identified factors.

In one aspect, provided is an isolated antibody, or an antigen binding fragment thereof, which specifically binds to B-Cell Maturation Antigen (BCMA), wherein the antibody comprises (a) a heavy chain variable (VH) region comprising (i) a VH complementary determining region one (CDR1) comprising the sequence $SYX_1MX_2$, wherein $X_1$ is A or P; and $X_2$ is T, N, or S (SEQ ID NO: 301), $GFTFX_1SY$, wherein $X_1$ is G or S (SEQ ID NO: 302), or $GFTFX_1SYX_2MX_3$, wherein $X_1$ is G or S, $X_2$ is A or P; and $X_3$ is T, N, or S (SEQ ID NO: 303); (ii) a VH CDR2 comprising the sequence $AX_1X_2X_3X_4GX_5X_6X_7X_8YADX_9X_{10}KG$, wherein $X_1$ is I, V, T, H, L, A, or C; $X_2$ is 5, D, G, T, I, L, F, M, or V; $X_3$ is G, Y, L, H, D, A, S, or M; $X_4$ is 5, Q, T, A, F, or W; $X_5$ is G or T; $X_6$ is N, S, P, Y, W, or F; $X_7$ is 5, T, I, L, T, A, R, V, K, G, or C; $X_8$ is F, Y, P, W, H, or G; $X_9$ is V, R, or L; and $X_{10}$ is G or T (SEQ ID NO: 305), or $X_1X_2X_3X_4X_5X_6$, wherein $X_1$ is S, V, I, D, G, T, L, F, or M; $X_2$ is G, Y, L, H, D, A, S, or M; $X_3$ is 5, G, F, or W; $X_4$ is G or S; $X_5$ is G or T; and $X_6$ is N, S, P, Y, or W (SEQ ID NO: 306); and iii) a VH CDR3 comprising the sequence $VSPIX_1X_2X_3X_4$, wherein $X_1$ is A or Y; $X_2$ is A or S; and $X_3$ is G, Q, L, P, or E (SEQ ID NO: 307), or $YWPMX_1X_2$, wherein $X_1$ is D, S, T, or A; and $X_2$ is I, S, L, P, or D (SEQ ID NO: 308); and/or a light chain variable (VL) region comprising (i) a VL CDR1 comprising the sequence $X_1X_2X_3X_4X_5X_6X_7X_8X_9X_{10}X_{11}X_{12}$, wherein $X_1$ is R, G, W, A, or C; $X_2$ is A, P, G, L, C, or S; $X_3$ is 5, G, or R; $X_4$ is Q, C, E, V, or I; $X_5$ is 5, P, G, A, R, or D; $X_6$ is V, G, I, or L; $X_7$ is 5, E, D, P, or G; $X_8$ is 5, P, F, A, M, E, V, N, D, or Y; $X_9$ is I, T, V, E, S, A, M, Q, Y, H, R, or F; $X_{10}$ is Y or F; $X_{11}$ is L, W, or P; and $X_{12}$ is A, S, or G (SEQ ID NO: 309); (ii) a VL CDR2 comprising the sequence $X_1ASX_2RAX_3$, wherein $X_1$ is G or D; $X_2$ is S or I; and $X_3$ is T or P (SEQ ID NO: 310); and (iii) a VL CDR3 comprising the sequence $QQYX_1X_2X_3PX_4T$, wherein $X_1$ is G, Q, E, L, F, A, S, M, K, R, or Y; $X_2$ is 5, R, T, G, V, F, Y, D, A, H, V, E, K, or C; $X_3$ is W, F, or S; and $X_4$ is L or I (SEQ ID NO: 311), or $QQYX_1X_2X_3PX_4$, wherein $X_1$ is G, Q, E, L, F, A, S, M, R, K, or Y; $X_2$ is 5, R, T, G, R, V, D, A, H, E, K, C, F, or Y; $X_3$ is W, 5, or F; and $X_4$ is L or I (SEQ ID NO: 312).

In another aspect, provided is an isolated antibody, or an antigen binding fragment thereof, which specifically binds to BCMA, wherein the antibody comprises: a VH region comprising a VH CDR1, VH CDR2, and VH CDR3 of the VH sequence shown in SEQ ID NO: 2, 3, 7, 8, 24, 25, 26, 27, 28, 29, 30, 31, 32, 33, 35, 37, 39, 42, 44, 46, 48, 50, 52, 54, 56, 58, 60, 62, 64, 66, 68, 70, 72, 74, 76, 78, 83, 87, 92, 95, 97, 99, 101, 104, 106, 110, 112, 114, 118, 120, 122, 112, 125, 127, 313, 314, 363, or 365; and/or a VL region comprising VL CDR1, VL CDR2, and VL CDR3 of the VL sequence shown in SEQ ID NO: 1, 4, 5, 6, 9, 10, 11, 12, 13, 14, 15, 16, 17, 18, 19, 20, 21, 22, 23, 34, 36, 38, 40, 41, 43, 45, 47, 49, 51, 53, 55, 57, 59, 61, 63, 65, 67, 69, 71, 73, 75, 77, 79, 317, 80, 81, 82, 84, 85, 86, 88, 89, 90, 91, 93, 94, 96, 98, 100, 102, 103, 105, 107, 108, 109, 111, 113, 115, 116, 117, 119, 121, 123, 124, 126, 128, 315, 316, or 364.

In some embodiments, provided is an antibody having any one of partial light chain sequence as listed in Table 1 and/or any one of partial heavy chain sequence as listed in Table 1.

TABLE 1

| mAb | Light Chain | Heavy Chain |
|---|---|---|
| P6E01/<br>P6E01 | EIVLTQSPGTLSLSPGERATLSCR<br>ASQSVSSSYLAWYQQKPGQAP<br>RLLIYGASSRATGIPDRFSGSGS<br>GTDFTLTISRLEPEDFAVYYCQH<br>YGSPPSFTFGQGTKVEIK (SEQ<br>ID NO: 1) | EVQLLESGGGLVQPGGSLRLSCA<br>ASGFTFGSYAMTWVRQAPGKGLE<br>WVSAISGSGGNTFYADSVKGRFTI<br>SRDNSKNTLYLQMNSLRAEDTAV<br>YYCARVSPIASGMDYWGQGTLVT<br>VSS (SEQ ID NO: 2) |
| P6E01/<br>H3.AQ | EIVLTQSPGTLSLSPGERATLSCR<br>ASQSVSSSYLAWYQQKPGQAP<br>RLLIYGASSRATGIPDRFSGSGS<br>GTDFTLTISRLEPEDFAVYYCQH<br>YGSPPSFTFGQGTKVEIK (SEQ<br>ID NO: 1) | EVQLLESGGGLVQPGGSLRLSCA<br>ASGFTFGSYAMTWVRQAPGKGLE<br>WVSAISGSGGNTFYADSVKGRFTI<br>SRDNSKNTLYLQMNSLRAEDTAV<br>YYCARVSPIAAQMDYWGQGTLVT<br>VSS (SEQ ID NO: 3) |

TABLE 1-continued

| mAb | Light Chain | Heavy Chain |
|---|---|---|
| L1.LGF/<br>L3.KW/<br>P6E01 | EIVLTQSPGTLSLSPGERATLSC<br>RASQSLGSFYLAWYQQKPGQA<br>PRLLIYGASSRATGIPDRFSGSG<br>SGTDFTLTISRLEPEDFAVYYCKH<br>YGWPPSFTFGQGTKVEIK (SEQ<br>ID NO: 4) | EVQLLESGGGLVQPGGSLRLSCA<br>ASGFTFGSYAMTWVRQAPGKGLE<br>WVSAISGSGGNTFYADSVKGRFTI<br>SRDNSKNTLYLQMNSLRAEDTAV<br>YYCARVSPIASGMDYWGQGTLVT<br>VSS (SEQ ID NO: 2) |
| L1.LGF/<br>L3.NY/<br>P6E01 | EIVLTQSPGTLSLSPGERATLSCR<br>ASQSLGSFYLAWYQQKPGQAP<br>RLLIYGASSRATGIPDRFSGSGS<br>GTDFTLTISRLEPEDFAVYYCQH<br>YNYPPSFTFGQGTKVEIK (SEQ<br>ID NO: 5) | EVQLLESGGGLVQPGGSLRLSCA<br>ASGFTFGSYAMTWVRQAPGKGLE<br>WVSAISGSGGNTFYADSVKGRFTI<br>SRDNSKNTLYLQMNSLRAEDTAV<br>YYCARVSPIASGMDYWGQGTLVT<br>VSS (SEQ ID NO: 2) |
| L1.GDF/<br>L3.NY/<br>P6E01 | EIVLTQSPGTLSLSPGERATLSCR<br>ASQSVGDFYLAWYQQKPGQAP<br>RLLIYGASSRATGIPDRFSGSGS<br>GTDFTLTISRLEPEDFAVYYCQH<br>YNYPPSFTFGQGTKVEIK (SEQ<br>ID NO: 6) | EVQLLESGGGLVQPGGSLRLSCA<br>ASGFTFGSYAMTWVRQAPGKGLE<br>WVSAISGSGGNTFYADSVKGRFTI<br>SRDNSKNTLYLQMNSLRAEDTAV<br>YYCARVSPIASGMDYWGQGTLVT<br>VSS (SEQ ID NO: 2) |
| L1.LGF/<br>L3.KW/<br>H3.AL | EIVLTQSPGTLSLSPGERATLSCR<br>ASQSLGSFYLAWYQQKPGQAP<br>RLLIYGASSRATGIPDRFSGSGS<br>GTDFTLTISRLEPEDFAVYYCKHY<br>GWPPSFTFGQGTKVEIK (SEQ ID<br>NO: 4) | EVQLLESGGGLVQPGGSLRLSCA<br>ASGFTFGSYAMTWVRQAPGKGLE<br>WVSAISGSGGNTFYADSVKGRFTI<br>SRDNSKNTLYLQMNSLRAEDTAV<br>YYCARARVSPIAALMDYWGQGTL<br>VTVSS (SEQ ID NO: 7) |
| L1.LGF/<br>L3.KW/<br>H3.AP | EIVLTQSPGTLSLSPGERATLSCR<br>ASQSLGSFYLAWYQQKPGQAP<br>RLLIYGASSRATGIPDRFSGSGS<br>GTDFTLTISRLEPEDFAVYYCKHY<br>GWPPSFTFGQGTKVEIK (SEQ<br>ID NO: 4) | EVQLLESGGGLVQPGGSLRLSCA<br>ASGFTFGSYAMTWVRQAPGKGE<br>WVSAISGSGGNTFYADSVKGRFTI<br>SRDNSKNTLYLQMNSLRAEDTAV<br>YYCARVSPIAAPMDYWGQGTLVT<br>VSS (SEQ ID NO: 8) |
| L1.LGF/<br>L3.KW/<br>H3.AQ | EIVLTQSPGTLSLSPGERATLSCR<br>ASQSLGSFYLAWYQQKPGQAP<br>RLLIYGASSRATGIPDRFSGSGS<br>GTDFTLTISRLEPEDFAVYYCKHY<br>GWPPSFTFGQGTKVEIK (SEQ ID<br>NO: 4) | EVQLLESGGGLVQPGGSLRLSCA<br>ASGFTFGSYAMTWVRQAPGKGLE<br>WVSAISGSGGNTFYADSVKGRFTI<br>SRDNSKNTLYLQMNSLRAEDTAV<br>YYCARVSPIAAQMDYWGQGTLVT<br>VSS (SEQ ID NO: 3) |
| L1.LGF/<br>L3.PY/<br>H3.AP | EIVLTQSPGTLSLSPGERATLSCR<br>ASQSLGSFYLAWYQQKPGQAP<br>RLLIYGASSRATGIPDRFSGSGS<br>GTDFTLTISRLEPEDFAVYYCQH<br>YPYPPSFTFGQGTKVEIK (SEQ<br>ID NO: 9) | EVQLLESGGGLVQPGGSLRLSCA<br>ASGFTFGSYAMTWVRQAPGKGLE<br>WVSAISGSGGNTFYADSVKGRFTI<br>SRDNSKNTLYLQMNSLRAEDTAV<br>YYCARVSPIAAPMDYWGQGTLVT<br>VSS (SEQ ID NO: 8) |
| L1.LGF/<br>L3.PY/<br>H3.AQ | EIVLTQSPGTLSLSPGERATLSCR<br>ASQSLGSFYLAWYQQKPGQAP<br>RLLIYGASSRATGIPDRFSGSGS<br>GTDFTLTISRLEPEDFAVYYCQH<br>YPYPPSFTFGQGTKVEIK (SEQ<br>ID NO: 9) | EVQLLESGGGLVQPGGSLRLSCA<br>ASGFTFGSYAMTWVRQAPGKGLE<br>WVSAISGSGGNTFYADSVKGRFTI<br>SRDNSKNTLYLQMNSLRAEDTAV<br>YYCARVSPIAAQMDYWGQGTLVT<br>VSS (SEQ ID NO: 3) |
| L1.LGF/<br>L3.NY/<br>H3.AL | EIVLTQSPGTLSLSPGERATLSCR<br>ASQSLGSFYLAWYQQKPGQAP<br>RLLIYGASSRATGIPDRFSGSGS<br>GTDFTLTISRLEPEDFAVYYCQH<br>YNYPPSFTFGQGTKVEIK (SEQ<br>ID NO: 10) | EVQLLESGGGLVQPGGSLRLSCA<br>ASGFTFGSYAMTWVRQAPGKGLE<br>WVSAISGSGGNTFYADSVKGRFTI<br>SRDNSKNTLYLQMNSLRAEDTAV<br>YYCARVSPIAALMDYWGQGTLVT<br>VSS (SEQ ID NO: 7) |
| L1.LGF/<br>L3.NY/<br>H3.AP | EIVLTQSPGTLSLSPGERATLSCR<br>ASQSLGSFYLAWYQQKPGQAP<br>RLLIYGASSRATGIPDRFSGSGS<br>GTDFTLTISRLEPEDFAVYYCQH<br>YNYPPSFTFGQGTKVEIK (SEQ<br>ID NO: 10) | EVQLLESGGGLVQPGGSLRLSCA<br>ASGFTFGSYAMTWVRQAPGKGLE<br>WVSAISGSGGNTFYADSVKGRFTI<br>SRDNSKNTLYLQMNSLRAEDTAV<br>YYCARVSPIAAPMDYWGQGTLVT<br>VSS (SEQ ID NO: 8) |
| L1.LGF/<br>L3.NY/<br>H3.AQ | EIVLTQSPGTLSLSPGERATLSCR<br>ASQSLGSFYLAWYQQKPGQAP<br>RLLIYGASSRATGIPDRFSGSGS<br>GTDFTLTISRLEPEDFAVYYCQH<br>YNYPPSFTFGQGTKVEIK (SEQ<br>ID NO: 10) | EVQLLESGGGLVQPGGSLRLSCA<br>ASGFTFGSYAMTWVRQAPGKGLE<br>WVSAISGSGGNTFYADSVKGRFTI<br>SRDNSKNTLYLQMNSLRAEDTAV<br>YYCARVSPIAAQMDYWGQGTLVT<br>VSS (SEQ ID NO: 3) |

TABLE 1-continued

| mAb | Light Chain | Heavy Chain |
|---|---|---|
| L1.GDF/ L3.KW/ H3.AL | EIVLTQSPGTLSLSPGERATLSCR ASQSVGDFYLAWYQQKPGQAP RLLIYGASSRATGIPDRFSGSGS GTDFTLTISRLEPEDFAVYYCKHY GWPPSFTFGQGTKVEIK (SEQ ID NO: 11) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIAALMDYWGQGTLVT VSS (SEQ ID NO: 7) |
| L1.GDF/ L3.KW/ H3.AP | EIVLTQSPGTLSLSPGERATLSCR ASQSVGDFYLAWYQQKPGQAP RLLIYGASSRATGIPDRFSGSGS GTDFTLTISRLEPEDFAVYYCKHY GWPPSFTFGQGTKVEIK (SEQ ID NO: 11) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIAAPMDYWGQGTLVT VSS (SEQ ID NO: 8) |
| L1.GDF/ L3.KW/ H3.AQ | EIVLTQSPGTLSLSPGERATLSCR ASQSVGDFYLAWYQQKPGQAP RLLIYGASSRATGIPDRFSGSGS GTDFTLTISRLEPEDFAVYYCKHY GWPPSFTFGQGTKVEIK (SEQ ID NO: 11) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIAAQMDYWGQGTLVT VSS (SEQ ID NO: 3) |
| L1.GDF/ L3.PY/ H3.AQ | EIVLTQSPGTLSLSPGERATLSCR ASQSVGDFYLAWYQQKPGQAP RLLIYGASSRATGIPDRFSGSGS GTDFTLTISRLEPEDFAVYYCQH YPYPPSFTFGQGTKVEIK (SEQ ID NO: 12) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIAAQMDYWGQGTLVT VSS (SEQ ID NO: 3) |
| L1.GDF/ L3.NY/ H3.AL | EIVLTQSPGTLSLSPGERATLSCR ASQSVGDFYLAWYQQKPGQAP RLLIYGASSRATGIPDRFSGSGS GTDFTLTISRLEPEDFAVYYCQH YNYPPSFTFGQGTKVEIK (SEQ ID NO: 13) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIAALMDYWGQGTLVT VSS (SEQ ID NO: 7) |
| L1.GDF/ L3.NY/ H3.AP | EIVLTQSPGTLSLSPGERATLSCR ASQSVGDFYLAWYQQKPGQAP RLLIYGASSRATGIPDRFSGSGS GTDFTLTISRLEPEDFAVYYCQH YNYPPSFTFGQGTKVEIK (SEQ ID NO: 13) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIAAPMDYWGQGTLVT VSS (SEQ ID NO: 8) |
| L1.GDF/ L3.NY/ H3.AQ | EIVLTQSPGTLSLSPGERATLSCR ASQSVGDFYLAWYQQKPGQAP RLLIYGASSRATGIPDRFSGSGS GTDFTLTISRLEPEDFAVYYCQH YNYPPSFTFGQGTKVEIK (SEQ ID NO: 14) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIAAQMDYWGQGTLVT VSS (SEQ ID NO: 3) |
| L3.KW/ P6E01 | EIVLTQSPGTLSLSPGERATLSCR ASQSVSSSYLAWYQQKPGQAP RLLIYGASSRATGIPDRFSGSGS GTDFTLTISRLEPEDFAVYYCKHY GWPPSFTFGQGTKVEIK (SEQ ID NO: 15) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIASGMDYWGQGTLVT VSS (SEQ ID NO: 2) |
| L3.PY/ P6E01 | EIVLTQSPGTLSLSPGERATLSCR ASQSVSSSYLAWYQQKPGQAP RLLIYGASSRATGIPDRFSGSGS GTDFTLTISRLEPEDFAVYYCQH YPYPPSFTFGQGTKVEIK (SEQ ID NO: 16) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIASGMDYWGQGTLVT VSS (SEQ ID NO: 2) |
| L3.NY/ P6E01 | EIVLTQSPGTLSLSPGERATLSCR ASQSVSSSYLAWYQQKPGQAP RLLIYGASSRATGIPDRFSGSGS GTDFTLTISRLEPEDFAVYYCQH YNYPPSFTFGQGTKVEIK (SEQ ID NO: 17) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIASGMDYWGQGTLVT VSS (SEQ ID NO: 2) |
| L3.PY/ L1.PS/ P6E01 | EIVLTQSPGTLSLSPGERATLSCR ASQSVSSSYPSWYQQKPGQAP RLLIYGASSRATGIPDRFSGSGS GTDFTLTISRLEPEDFAVYYCQH YPYPPSFTFGQGTKVEIK (SEQ ID NO: 18) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIASGMDYWGQGTLVT VSS (SEQ ID NO: 2) |

TABLE 1-continued

| mAb | Light Chain | Heavy Chain |
|---|---|---|
| L3.PY/ L1.AH/ P6E01 | EIVLTQSPGTLSLSPGERATLSCR ASQSVSAHYLAWYQQKPGQAP RLLIYGASSRATGIPDRFSGSGS GTDFTLTISRLEPEDFAVYYCQH YPYPPSFTFGQGTKVEIK (SEQ ID NO: 19) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIASGMDYWGQGTLVT VSS (SEQ ID NO: 2) |
| L3.PY/ L1.FF/ P6E01 | EIVLTQSPGTLSLSPGERATLSCR ASQSVSSFFLAWYQQKPGQAPR LLIYGASSRATGIPDRFSGSGSG TDFTLTISRLEPEDFAVYYCQHYP YPPSFTFGQGTKVEIK (SEQ ID NO: 20) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIASGMDYWGQGTLVT VSS (SEQ ID NO: 2) |
| L3.PY/ L1.PH/ P6E01 | EIVLTQSPGTLSLSPGERATLSCR ASQSVSPHYLAWYQQKPGQAP RLLIYGASSRATGIPDRFSGSGS GTDFTLTISRLEPEDFAVYYCQH YPYPPSFTFGQGTKVEIK (SEQ ID NO: 21) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIASGMDYWGQGTLVT VSS (SEQ ID NO: 2) |
| L3.PY/ L3.KY/ P6E01 | EIVLTQSPGTLSLSPGERATLSCR ASQSVSSSYLAWYQQKPGQAP RLLIYGASSRATGIPDRFSGSGS GTDFTLTISRLEPEDFAVYYCKYY PYPPSFTFGQGTKVEIK (SEQ ID NO: 22) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIASGMDYWGQGTLVT VSS (SEQ ID NO: 2) |
| L3.PY/ L3.KF/ P6E01 | EIVLTQSPGTLSLSPGERATLSCR ASQSVSSSYLAWYQQKPGQAP RLLIYGASSRATGIPDRFSGSGS GTDFTLTISRLEPEDFAVYYCKFY PYPPSFTFGQGTKVEIK (SEQ ID NO: 23) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIASGMDYWGQGTLVT VSS (SEQ ID NO: 2) |
| L3.PY/ H2.QR | EIVLTQSPGTLSLSPGERATLSCR ASQSVSSSYLAWYQQKPGQAP RLLIYGASSRATGIPDRFSGSGS GTDFTLTISRLEPEDFAVYYCQH YPYPPSFTFGQGTKVEIK (SEQ ID NO: 16) | EVQLLESGGGLVQPGGSLRLSCA ASGFTFGSYAMTWVRQAPGKGLE WVSAISGSGGNTFYADQRKGRFTI SRDNSKNTLYLQMNSLRAEDTAV YYCARVSPIASGMDYWGQGTLVT VSS (SEQ ID NO: 24) |
| L3.PY/ H2.DY | EIVLTQSPGTLSLSPGERATLSCR ASQSVSSSYLAWYQQKPGQAP RLLIYGASSRATGIPDRFSGSGS GTDFTLTISRLEPEDFAVYYCQH YPYPPSFTFGQGTKVEIK (SEQ ID NO: 16) | EVQLLESGGGLVQPGGSLRLSCA ASGFTFGSYAMTWVRQAPGKGLE WVSAIDYSGGNTFYADSVKGRFTI SRDNSKNTLYLQMNSLRAEDTAV YYCARVSPIASGMDYWGQGTLVT VSS (SEQ ID NO: 25) |
| L3.PY/ H2.YQ | EIVLTQSPGTLSLSPGERATLSCR ASQSVSSSYLAWYQQKPGQAP RLLIYGASSRATGIPDRFSGSGS GTDFTLTISRLEPEDFAVYYCQH YPYPPSFTFGQGTKVEIK (SEQ ID NO: 16) | EVQLLESGGGLVQPGGSLRLSCA ASGFTFGSYAMTWVRQAPGKGLE WVSAISYQGGNTFYADSVKGRFTI SRDNSKNTLYLQMNSLRAEDTAV YYCARVSPIASGMDYWGQGTLVT VSS (SEQ ID NO: 26) |
| L3.PY/ H2.LT | EIVLTQSPGTLSLSPGERATLSCR ASQSVSSSYLAWYQQKPGQAP RLLIYGASSRATGIPDRFSGSGS GTDFTLTISRLEPEDFAVYYCQH YPYPPSFTFGQGTKVEIK (SEQ ID NO: 16) | EVQLLESGGGLVQPGGSLRLSCA ASGFTFGSYAMTWVRQAPGKGLE WVSAISLTGGNTFYADSVKGRFTI SRDNSKNTLYLQMNSLRAEDTAV YYCARVSPIASGMDYWGQGTLVT VSS (SEQ ID NO: 27) |
| L3.PY/ H2.HA | EIVLTQSPGTLSLSPGERATLSCR ASQSVSSSYLAWYQQKPGQAP RLLIYGASSRATGIPDRFSGSGS GTDFTLTISRLEPEDFAVYYCQH YPYPPSFTFGQGTKVEIK (SEQ ID NO: 16) | EVQLLESGGGLVQPGGSLRLSCA ASGFTFGSYAMTWVRQAPGKGLE WVSAISHAGGNTFYADSVKGRFTI SRDNSKNTLYLQMNSLRAEDTAV YYCARVSPIASGMDYWGQGTLVT VSS (SEQ ID NO: 28) |
| L3.PY/ H2.QL | EIVLTQSPGTLSLSPGERATLSCR ASQSVSSSYLAWYQQKPGQAPRLLI YGASSRATGIPDRFSGSGSGTDFT LTISRLEPEDFAVYYCQHYPYPPSFT FGQGTKVEIK (SEQ ID NO: 16) | EVQLLESGGGLVQPGGSLRLSCA ASGFTFGSYAMTWVRQAPGKGLE WVSAISGSGGNTFYADQLKGRFTI SRDNSKNTLYLQMNSLRAEDTAV YYCARVSPIASGMDYWGQGTLVT VSS (SEQ ID NO: 29) |

TABLE 1-continued

| mAb | Light Chain | Heavy Chain |
|---|---|---|
| L3.PY/ H3.YA | EIVLTQSPGTLSLSPGERATLSCR ASQSVSSSYLAWYQQKPGQAP RLLIYGASSRATGIPDRFSGSGS GTDFTLTISRLEPEDFAVYYCQH YPYPPSFTFGQGTKVEIK (SEQ ID NO: 16) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIYAGMDYWGQGTLVT VSS (SEQ ID NO: 30) |
| L3.PY/ H3.AE | EIVLTQSPGTLSLSPGERATLSCR ASQSVSSSYLAWYQQKPGQAP RLLIYGASSRATGIPDRFSGSGS GTDFTLTISRLEPEDFAVYYCQH YPYPPSFTFGQGTKVEIK (SEQ ID NO: 16) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIAAEMDYWGQGTLVT VSS (SEQ ID NO: 31) |
| L3.PY/ H3.AQ | EIVLTQSPGTLSLSPGERATLSCR ASQSVSSSYLAWYQQKPGQAP RLLIYGASSRATGIPDRFSGSGS GTDFTLTISRLEPEDFAVYYCQH YPYPPSFTFGQGTKVEIK (SEQ ID NO: 16) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIAAQMDYWGQGTLVT VSS (SEQ ID NO: 3) |
| L3.PY/ H3.TAQ | EIVLTQSPGTLSLSPGERATLSCR ASQSVSSSYLAWYQQKPGQAP RLLIYGASSRATGIPDRFSGSGS GTDFTLTISRLEPEDFAVYYCQH YPYPPSFTFGQGTKVEIK (SEQ ID NO: 16) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCTRVSPIAAQMDYWGQGTLVT VSS (SEQ ID NO: 32) |
| L3.PY/ P6E01 | EIVLTQSPGTLSLSPGERATLSCR ASQSVSSSYLAWYQQKPGQAP RLLIYGASSRATGIPDRFSGSGS GTDFTLTISRLEPEDFAVYYCQH YPYPPSFTFGQGTKVEIK (SEQ ID NO: 16) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIASGMDYWGQGTLVT VSS (SEQ ID NO: 2) |
| L3.PY/ L1.PS/ H2.QR | EIVLTQSPGTLSLSPGERATLSCR ASQSVSSSYPSWYQQKPGQAP RLLIYGASSRATGIPDRFSGSGS GTDFTLTISRLEPEDFAVYYCQH YPYPPSFTFGQGTKVEIK (SEQ ID NO: 18) | EVQLLESGGGLVQPGGSLRLSCA ASGFTFGSYAMTWVRQAPGKGLE WVSAISGSGGNTFYADQRKGRFTI SRDNSKNTLYLQMNSLRAEDTAV YYCARVSPIASGMDYWGQGTLVT VSS (SEQ ID NO: 24) |
| L3.PY/ L1.PS/ H2.DY | EIVLTQSPGTLSLSPGERATLSCR ASQSVSSSYPSWYQQKPGQAP RLLIYGASSRATGIPDRFSGSGS GTDFTLTISRLEPEDFAVYYCQH YPYPPSFTFGQGTKVEIK (SEQ ID NO: 18) | EVQLLESGGGLVQPGGSLRLSCA ASGFTFGSYAMTWVRQAPGKGLE WVSAIDYSGGNTFYADSVKGRFTI SRDNSKNTLYLQMNSLRAEDTAV YYCARVSPIASGMDYWGQGTLVT VSS (SEQ ID NO: 25) |
| L3.PY/ L1.PS/ H2.YQ | EIVLTQSPGTLSLSPGERATLSCR ASQSVSSSYPSWYQQKPGQAP RLLIYGASSRATGIPDRFSGSGS GTDFTLTISRLEPEDFAVYYCQH YPYPPSFTFGQGTKVEIK (SEQ ID NO: 18) | EVQLLESGGGLVQPGGSLRLSCA ASGFTFGSYAMTWVRQAPGKGLE WVSAISYQGGNTFYADSVKGRFTI SRDNSKNTLYLQMNSLRAEDTAV YYCARVSPIASGMDYWGQGTLVT VSS (SEQ ID NO: 26) |
| L3.PY/ L1.PS/ H2.LT | EIVLTQSPGTLSLSPGERATLSCR ASQSVSSSYPSWYQQKPGQAP RLLIYGASSRATGIPDRFSGSGS GTDFTLTISRLEPEDFAVYYCQH YPYPPSFTFGQGTKVEIK (SEQ ID NO: 18) | EVQLLESGGGLVQPGGSLRLSCA ASGFTFGSYAMTWVRQAPGKGLE WVSAISLTGGNTFYADSVKGRFTI SRDNSKNTLYLQMNSLRAEDTAV YYCARVSPIASGMDYWGQGTLVT VSS (SEQ ID NO: 27) |
| L3.PY/ L1.PS/ H2.HA | EIVLTQSPGTLSLSPGERATLSCR ASQSVSSSYPSWYQQKPGQAP RLLIYGASSRATGIPDRFSGSGS GTDFTLTISRLEPEDFAVYYCQH YPYPPSFTFGQGTKVEIK (SEQ ID NO: 18) | EVQLLESGGGLVQPGGSLRLSCA ASGFTFGSYAMTWVRQAPGKGLE WVSAISHAGGNTFYADSVKGRFTI SRDNSKNTLYLQMNSLRAEDTAV YYCARVSPIASGMDYWGQGTLVT VSS (SEQ ID NO: 28) |
| L3.PY/ L1.PS/ H2.QL | EIVLTQSPGTLSLSPGERATLSCR ASQSVSSSYPSWYQQKPGQAP RLLIYGASSRATGIPDRFSGSGS GTDFTLTISRLEPEDFAVYYCQH YPYPPSFTFGQGTKVEIK (SEQ ID NO: 18) | EVQLLESGGGLVQPGGSLRLSCA ASGFTFGSYAMTWVRQAPGKGLE WVSAISGSGGNTFYADQLKGRFTI SRDNSKNTLYLQMNSLRAEDTAV YYCARVSPIASGMDYWGQGTLVT VSS (SEQ ID NO: 29) |

TABLE 1-continued

| mAb | Light Chain | Heavy Chain |
|---|---|---|
| L3.PY/ L1.PS/ H3.YA | EIVLTQSPGTLSLSPGERATLSCR ASQSVSSSYPSWYQQKPGQAP RLLIYGASSRATGIPDRFSGSGS GTDFTLTISRLEPEDFAVYYCQH YPYPPSFTFGQGTKVEIK (SEQ ID NO: 18) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIYAGMDYWGQGTLVT VSS (SEQ ID NO: 30) |
| L3.PY/ L1.PS/ H3.AE | EIVLTQSPGTLSLSPGERATLSCR ASQSVSSSYPSWYQQKPGQAP RLLIYGASSRATGIPDRFSGSGS GTDFTLTISRLEPEDFAVYYCQH YPYPPSFTFGQGTKVEIK (SEQ ID NO: 18) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIAAEMDYWGQGTLVT VSS (SEQ ID NO: 31) |
| L3.PY/ L1.PS/ H3.AQ | EIVLTQSPGTLSLSPGERATLSCR ASQSVSSSYPSWYQQKPGQAP RLLIYGASSRATGIPDRFSGSGS GTDFTLTISRLEPEDFAVYYCQH YPYPPSFTFGQGTKVEIK (SEQ ID NO: 18) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIAAQMDYWGQGTLVT VSS (SEQ ID NO: 3) |
| L3.PY/ L1.PS/ H3.TAQ | EIVLTQSPGTLSLSPGERATLSCR ASQSVSSSYPSWYQQKPGQAP RLLIYGASSRATGIPDRFSGSGS GTDFTLTISRLEPEDFAVYYCQH YPYPPSFTFGQGTKVEIK (SEQ ID NO: 18) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCTRVSPIAAQMDYWGQGTLVT VSS (SEQ ID NO: 32) |
| L3.PY/ L1.AH/ H2.QR | EIVLTQSPGTLSLSPGERATLSCR ASQSVSAHYLAWYQQKPGQAP RLLIYGASSRATGIPDRFSGSGS GTDFTLTISRLEPEDFAVYYCQH YPYPPSFTFGQGTKVEIK (SEQ ID NO: 19) | EVQLLESGGGLVQPGGSLRLSCA ASGFTFGSYAMTWVRQAPGKGLE WVSAISGSGGNTFYADQRKGRFTI SRDNSKNTLYLQMNSLRAEDTAV YYCARVSPIASGMDYWGQGTLVT VSS (SEQ ID NO: 24) |
| L3.PY/ L1.AH/ H2.DY | EIVLTQSPGTLSLSPGERATLSCR ASQSVSAHYLAWYQQKPGQAP RLLIYGASSRATGIPDRFSGSGS GTDFTLTISRLEPEDFAVYYCQH YPYPPSFTFGQGTKVEIK (SEQ ID NO: 19) | EVQLLESGGGLVQPGGSLRLSCA ASGFTFGSYAMTWVRQAPGKGLE WVSAIDYSGGNTFYADSVKGRFTI SRDNSKNTLYLQMNSLRAEDTAV YYCARVSPIASGMDYWGQGTLVT VSS (SEQ ID NO: 25) |
| L3.PY/ L1.AH/ H2.YQ | EIVLTQSPGTLSLSPGERATLSCR ASQSVSAHYLAWYQQKPGQAP RLLIYGASSRATGIPDRFSGSGS GTDFTLTISRLEPEDFAVYYCQH YPYPPSFTFGQGTKVEIK (SEQ ID NO: 19) | EVQLLESGGGLVQPGGSLRLSCA ASGFTFGSYAMTWVRQAPGKGLE WVSAISYQGGNTFYADSVKGRFTI SRDNSKNTLYLQMNSLRAEDTAV YYCARVSPIASGMDYWGQGTLVT VSS (SEQ ID NO: 26) |
| L3.PY/ L1.AH/ H2.LT | EIVLTQSPGTLSLSPGERATLSCR ASQSVSAHYLAWYQQKPGQAP RLLIYGASSRATGIPDRFSGSGS GTDFTLTISRLEPEDFAVYYCQH YPYPPSFTFGQGTKVEIK (SEQ ID NO: 19) | EVQLLESGGGLVQPGGSLRLSCA ASGFTFGSYAMTWVRQAPGKGLE WVSAISLTGGNTFYADSVKGRFTI SRDNSKNTLYLQMNSLRAEDTAV YYCARVSPIASGMDYWGQGTLVT VSS (SEQ ID NO: 27) |
| L3.PY/ L1.AH/ H2.HA | EIVLTQSPGTLSLSPGERATLSCR ASQSVSAHYLAWYQQKPGQAP RLLIYGASSRATGIPDRFSGSGS GTDFTLTISRLEPEDFAVYYCQH YPYPPSFTFGQGTKVEIK (SEQ ID NO: 19) | EVQLLESGGGLVQPGGSLRLSCA ASGFTFGSYAMTWVRQAPGKGLE WVSAISHAGGNTFYADSVKGRFTI SRDNSKNTLYLQMNSLRAEDTAV YYCARVSPIASGMDYWGQGTLVT VSS (SEQ ID NO: 28) |
| L3.PY/ L1.AH/ H2.QL | EIVLTQSPGTLSLSPGERATLSCR ASQSVSAHYLAWYQQKPGQAP RLLIYGASSRATGIPDRFSGSGS GTDFTLTISRLEPEDFAVYYCQH YPYPPSFTFGQGTKVEIK (SEQ ID NO: 19) | EVQLLESGGGLVQPGGSLRLSCA ASGFTFGSYAMTWVRQAPGKGLE WVSAISGSGGNTFYADQLKGRFTI SRDNSKNTLYLQMNSLRAEDTAV YYCARVSPIASGMDYWGQGTLVT VSS (SEQ ID NO: 29) |
| L3.PY/ L1.AH/ H3.YA | EIVLTQSPGTLSLSPGERATLSCR ASQSVSAHYLAWYQQKPGQAP RLLIYGASSRATGIPDRFSGSGS GTDFTLTISRLEPEDFAVYYCQH YPYPPSFTFGQGTKVEIK (SEQ ID NO: 19) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIYAGMDYWGQGTLVT VSS (SEQ ID NO: 30) |

TABLE 1-continued

| mAb | Light Chain | Heavy Chain |
|---|---|---|
| L3.PY/<br>L1.AH/<br>H3.AE | EIVLTQSPGTLSLSPGERATLSCR<br>ASQSVSAHYLAWYQQKPGQAP<br>RLLIYGASSRATGIPDRFSGSGS<br>GTDFTLTISRLEPEDFAVYYCQH<br>YPYPPSFTFGQGTKVEIK (SEQ<br>ID NO: 19) | EVQLLESGGGLVQPGGSLRLSCA<br>ASGFTFGSYAMTWVRQAPGKGLE<br>WVSAISGSGGNTFYADSVKGRFTI<br>SRDNSKNTLYLQMNSLRAEDTAV<br>YYCARVSPIAAEMDYWGQGTLVT<br>VSS (SEQ ID NO: 31) |
| L3.PY/<br>L1.AH/<br>H3.AQ | EIVLTQSPGTLSLSPGERATLSCR<br>ASQSVSAHYLAWYQQKPGQAP<br>RLLIYGASSRATGIPDRFSGSGS<br>GTDFTLTISRLEPEDFAVYYCQH<br>YPYPPSFTFGQGTKVEIK (SEQ<br>ID NO: 19) | EVQLLESGGGLVQPGGSLRLSCA<br>ASGFTFGSYAMTWVRQAPGKGLE<br>WVSAISGSGGNTFYADSVKGRFTI<br>SRDNSKNTLYLQMNSLRAEDTAV<br>YYCARVSPIAAQMDYWGQGTLVT<br>VSS (SEQ ID NO: 3) |
| L3.PY/<br>L1.AH/<br>H3.TAQ | EIVLTQSPGTLSLSPGERATLSCR<br>ASQSVSAHYLAWYQQKPGQAP<br>RLLIYGASSRATGIPDRFSGSGS<br>GTDFTLTISRLEPEDFAVYYCQH<br>YPYPPSFTFGQGTKVEIK (SEQ<br>ID NO: 19) | EVQLLESGGGLVQPGGSLRLSCA<br>ASGFTFGSYAMTWVRQAPGKGLE<br>WVSAISGSGGNTFYADSVKGRFTI<br>SRDNSKNTLYLQMNSLRAEDTAV<br>YYCTRVSPIAAQMDYWGQGTLVT<br>VSS (SEQ ID NO: 32) |
| L3.PY/<br>L1.FF/<br>H2.QR | EIVLTQSPGTLSLSPGERATLSCR<br>ASQSVSSFFLAWYQQKPGQAPR<br>LLIYGASSRATGIPDRFSGSGSG<br>TDFTLTISRLEPEDFAVYYCQHYP<br>YPPSFTFGQGTKVEIK (SEQ ID<br>NO: 20) | EVQLLESGGGLVQPGGSLRLSCA<br>ASGFTFGSYAMTWVRQAPGKGLE<br>WVSAISGSGGNTFYADQRKGRFTI<br>SRDNSKNTLYLQMNSLRAEDTAV<br>YYCARVSPIASGMDYWGQGTLVT<br>VSS (SEQ ID NO: 24) |
| L3.PY/<br>L1.FF/<br>H2.DY | EIVLTQSPGTLSLSPGERATLSCR<br>ASQSVSSFFLAWYQQKPGQAPR<br>LLIYGASSRATGIPDRFSGSGSG<br>TDFTLTISRLEPEDFAVYYCQHYP<br>YPPSFTFGQGTKVEIK (SEQ ID<br>NO: 20) | EVQLLESGGGLVQPGGSLRLSCA<br>ASGFTFGSYAMTWVRQAPGKGLE<br>WVSAIDYSGGNTFYADSVKGRFTI<br>SRDNSKNTLYLQMNSLRAEDTAV<br>YYCARVSPIASGMDYWGQGTLVT<br>VSS (SEQ ID NO: 25) |
| L3.PY/<br>L1.FF/<br>H2.YQ | EIVLTQSPGTLSLSPGERATLSCR<br>ASQSVSSFFLAWYQQKPGQAPR<br>LLIYGASSRATGIPDRFSGSGSG<br>TDFTLTISRLEPEDFAVYYCQHYP<br>YPPSFTFGQGTKVEIK (SEQ ID<br>NO: 20) | EVQLLESGGGLVQPGGSLRLSCA<br>ASGFTFGSYAMTWVRQAPGKGLE<br>WVSAISYQGGNTFYADSVKGRFTI<br>SRDNSKNTLYLQMNSLRAEDTAV<br>YYCARVSPIASGMDYWGQGTLVT<br>VSS (SEQ ID NO: 26) |
| L3.PY/<br>L1.FF/<br>H2.LT | EIVLTQSPGTLSLSPGERATLSCR<br>ASQSVSSFFLAWYQQKPGQAPR<br>LLIYGASSRATGIPDRFSGSGSG<br>TDFTLTISRLEPEDFAVYYCQHYP<br>YPPSFTFGQGTKVEIK (SEQ ID<br>NO: 20) | EVQLLESGGGLVQPGGSLRLSCA<br>ASGFTFGSYAMTWVRQAPGKGLE<br>WVSAISLTGGNTFYADSVKGRFTI<br>SRDNSKNTLYLQMNSLRAEDTAV<br>YYCARVSPIASGMDYWGQGTLVT<br>VSS (SEQ ID NO: 27) |
| L3.PY/<br>L1.FF/<br>H2.HA | EIVLTQSPGTLSLSPGERATLSCR<br>ASQSVSSFFLAWYQQKPGQAPR<br>LLIYGASSRATGIPDRFSGSGSG<br>TDFTLTISRLEPEDFAVYYCQHYP<br>YPPSFTFGQGTKVEIK (SEQ ID<br>NO: 20) | EVQLLESGGGLVQPGGSLRLSCA<br>ASGFTFGSYAMTWVRQAPGKGLE<br>WVSAISHAGGNTFYADSVKGRFTI<br>SRDNSKNTLYLQMNSLRAEDTAV<br>YYCARVSPIASGMDYWGQGTLVT<br>VSS (SEQ ID NO: 28) |
| L3.PY/<br>L1.FF/<br>H2.QL | EIVLTQSPGTLSLSPGERATLSCR<br>ASQSVSSFFLAWYQQKPGQAPR<br>LLIYGASSRATGIPDRFSGSGSG<br>TDFTLTISRLEPEDFAVYYCQHYP<br>YPPSFTFGQGTKVEIK (SEQ ID<br>NO: 20) | EVQLLESGGGLVQPGGSLRLSCA<br>ASGFTFGSYAMTWVRQAPGKGLE<br>WVSAISGSGGNTFYADQLKGRFTI<br>SRDNSKNTLYLQMNSLRAEDTAV<br>YYCARVSPIASGMDYWGQGTLVT<br>VSS (SEQ ID NO: 29) |
| L3.PY/<br>L1.FF/<br>H3.YA | EIVLTQSPGTLSLSPGERATLSCR<br>ASQSVSSFFLAWYQQKPGQAPR<br>LLIYGASSRATGIPDRFSGSGSG<br>TDFTLTISRLEPEDFAVYYCQHYP<br>YPPSFTFGQGTKVEIK (SEQ ID<br>NO: 20) | EVQLLESGGGLVQPGGSLRLSCA<br>ASGFTFGSYAMTWVRQAPGKGLE<br>WVSAISGSGGNTFYADSVKGRFTI<br>SRDNSKNTLYLQMNSLRAEDTAV<br>YYCARVSPIYAGMDYWGQGTLVT<br>VSS (SEQ ID NO: 30) |
| L3.PY/<br>L1.FF/<br>H3.AE | EIVLTQSPGTLSLSPGERATLSCR<br>ASQSVSSFFLAWYQQKPGQAPR<br>LLIYGASSRATGIPDRFSGSGSG<br>TDFTLTISRLEPEDFAVYYCQHYP<br>YPPSFTFGQGTKVEIK (SEQ ID<br>NO: 20) | EVQLLESGGGLVQPGGSLRLSCA<br>ASGFTFGSYAMTWVRQAPGKGLE<br>WVSAISGSGGNTFYADSVKGRFTI<br>SRDNSKNTLYLQMNSLRAEDTAV<br>YYCARVSPIAAEMDYWGQGTLVT<br>VSS (SEQ ID NO: 31) |

TABLE 1-continued

| mAb | Light Chain | Heavy Chain |
|---|---|---|
| L3.PY/ L1.FF/ H3.AQ | EIVLTQSPGTLSLSPGERATLSCR ASQSVSSFFLAWYQQKPGQAPR LLIYGASSRATGIPDRFSGSGSG TDFTLTISRLEPEDFAVYYCQHYP YPPSFTFGQGTKVEIK (SEQ ID NO: 20) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIAAQMDYWGQGTLVT VSS (SEQ ID NO: 3) |
| L3.PY/ L1.FF/ H3.TAQ | EIVLTQSPGTLSLSPGERATLSCR ASQSVSSFFLAWYQQKPGQAPR LLIYGASSRATGIPDRFSGSGSG TDFTLTISRLEPEDFAVYYCQHYP YPPSFTFGQGTKVEIK (SEQ ID NO: 20) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCTRVSPIAAQMDYWGQGTLVT VSS (SEQ ID NO: 32) |
| L3.PY/ L1.PH/ H2.QR | EIVLTQSPGTLSLSPGERATLSCR ASQSVSPHYLAWYQQKPGQAP RLLIYGASSRATGIPDRFSGSGS GTDFTLTISRLEPEDFAVYYCQH YPYPPSFTFGQGTKVEIK (SEQ ID NO: 21) | EVQLLESGGGLVQPGGSLRLSCA ASGFTFGSYAMTWVRQAPGKGLE WVSAISGSGGNTFYADQRKGRFTI SRDNSKNTLYLQMNSLRAEDTAV YYCARVSPIASGMDYWGQGTLVT VSS (SEQ ID NO: 24) |
| L3.PY/ L1.PH/ H2.HA | EIVLTQSPGTLSLSPGERATLSCR ASQSVSPHYLAWYQQKPGQAP RLLIYGASSRATGIPDRFSGSGS GTDFTLTISRLEPEDFAVYYCQH YPYPPSFTFGQGTKVEIK (SEQ ID NO: 21) | EVQLLESGGGLVQPGGSLRLSCA ASGFTFGSYAMTWVRQAPGKGLE WVSAISHAGGNTFYADSVKGRFTI SRDNSKNTLYLQMNSLRAEDTAV YYCARVSPIASGMDYWGQGTLVT VSS (SEQ ID NO: 28) |
| L3.PY/ L1.PH/ H3.AE | EIVLTQSPGTLSLSPGERATLSCR ASQSVSPHYLAWYQQKPGQAP RLLIYGASSRATGIPDRFSGSGS GTDFTLTISRLEPEDFAVYYCQH YPYPPSFTFGQGTKVEIK (SEQ ID NO: 21) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIAAEMDYWGQGTLVT VSS (SEQ ID NO: 31) |
| L3.PY/ L1.PH/ H3.AQ | EIVLTQSPGTLSLSPGERATLSCR ASQSVSPHYLAWYQQKPGQAP RLLIYGASSRATGIPDRFSGSGS GTDFTLTISRLEPEDFAVYYCQH YPYPPSFTFGQGTKVEIK (SEQ ID NO: 21) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIAAQMDYWGQGTLVT VSS (SEQ ID NO: 3) |
| L3.PY/ L1.PH/ H3.TAQ | EIVLTQSPGTLSLSPGERATLSCR ASQSVSPHYLAWYQQKPGQAP RLLIYGASSRATGIPDRFSGSGS GTDFTLTISRLEPEDFAVYYCQH YPYPPSFTFGQGTKVEIK (SEQ ID NO: 21) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCTRVSPIAAQMDYWGQGTLVT VSS (SEQ ID NO: 32) |
| L3.PY/ L3.KY/ H2.QR | EIVLTQSPGTLSLSPGERATLSCR ASQSVSSSYLAWYQQKPGQAP RLLIYGASSRATGIPDRFSGSGS GTDFTLTISRLEPEDFAVYYCKYY PYPPSFTFGQGTKVEIK (SEQ ID NO: 22) | EVQLLESGGGLVQPGGSLRLSCA ASGFTFGSYAMTWVRQAPGKGLE WVSAISGSGGNTFYADQRKGRFTI SRDNSKNTLYLQMNSLRAEDTAV YYCARVSPIASGMDYWGQGTLVT VSS (SEQ ID NO: 24) |
| L3.PY/ L3.KY/ H2.DY | EIVLTQSPGTLSLSPGERATLSCR ASQSVSSSYLAWYQQKPGQAP RLLIYGASSRATGIPDRFSGSGS GTDFTLTISRLEPEDFAVYYCKYY PYPPSFTFGQGTKVEIK (SEQ ID NO: 22) | EVQLLESGGGLVQPGGSLRLSCA ASGFTFGSYAMTWVRQAPGKGLE WVSAIDYSGGNTFYADSVKGRFTI SRDNSKNTLYLQMNSLRAEDTAV YYCARVSPIASGMDYWGQGTLVT VSS (SEQ ID NO: 25) |
| L3.PY/ L3.KY/ H2.YQ | EIVLTQSPGTLSLSPGERATLSCR ASQSVSSSYLAWYQQKPGQAP RLLIYGASSRATGIPDRFSGSGS GTDFTLTISRLEPEDFAVYYCKYY PYPPSFTFGQGTKVEIK (SEQ ID NO: 22) | EVQLLESGGGLVQPGGSLRLSCA ASGFTFGSYAMTWVRQAPGKGLE WVSAISYQGGNTFYADSVKGRFTI SRDNSKNTLYLQMNSLRAEDTAV YYCARVSPIASGMDYWGQGTLVT VSS (SEQ ID NO: 26) |
| L3.PY/ L3.KY/ H2.LT | EIVLTQSPGTLSLSPGERATLSCR ASQSVSSSYLAWYQQKPGQAP RLLIYGASSRATGIPDRFSGSGS GTDFTLTISRLEPEDFAVYYCKYY PYPPSFTFGQGTKVEIK (SEQ ID NO: 22) | EVQLLESGGGLVQPGGSLRLSCA ASGFTFGSYAMTWVRQAPGKGLE WVSAISLTGGNTFYADSVKGRFTI SRDNSKNTLYLQMNSLRAEDTAV YYCARVSPIASGMDYWGQGTLVT VSS (SEQ ID NO: 27) |

TABLE 1-continued

| mAb | Light Chain | Heavy Chain |
|---|---|---|
| L3.PY/ L3.KY/ H2.HA | EIVLTQSPGTLSLSPGERATLSCR ASQSVSSSYLAWYQQKPGQAP RLLIYGASSRATGIPDRFSGSGS GTDFTLTISRLEPEDFAVYYCKYY PYPPSFTFGQGTKVEIK (SEQ ID NO: 22) | EVQLLESGGGLVQPGGSLRLSCA ASGFTFGSYAMTWVRQAPGKGLE WVSAISHAGGNTFYADSVKGRFTI SRDNSKNTLYLQMNSLRAEDTAV YYCARVSPIASGMDYWGQGTLVT VSS (SEQ ID NO: 28) |
| L3.PY/ L3.KY/ H2.QL | EIVLTQSPGTLSLSPGERATLSCR ASQSVSSSYLAWYQQKPGQAP RLLIYGASSRATGIPDRFSGSGS GTDFTLTISRLEPEDFAVYYCKYY PYPPSFTFGQGTKVEIK (SEQ ID NO: 22) | EVQLLESGGGLVQPGGSLRLSCA ASGFTFGSYAMTWVRQAPGKGLE WVSAISGSGGNTFYADQLKGRFTI SRDNSKNTLYLQMNSLRAEDTAV YYCARVSPIASGMDYWGQGTLVT VSS (SEQ ID NO: 29) |
| L3.PY/ L3.KY/ H3.YA | EIVLTQSPGTLSLSPGERATLSCR ASQSVSSSYLAWYQQKPGQAP RLLIYGASSRATGIPDRFSGSGS GTDFTLTISRLEPEDFAVYYCKYY PYPPSFTFGQGTKVEIK (SEQ ID NO: 22) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIYAGMDYWGQGTLVT VSS (SEQ ID NO: 30) |
| L3.PY/ L3.KY/ H3.TAQ | EIVLTQSPGTLSLSPGERATLSCR ASQSVSSSYLAWYQQKPGQAP RLLIYGASSRATGIPDRFSGSGS GTDFTLTISRLEPEDFAVYYCKYY PYPPSFTFGQGTKVEIK (SEQ ID NO: 22) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCTRVSPIAAQMDYWGQGTLVT VSS (SEQ ID NO: 32) |
| L3.PY/ L3.KF/ H2.DY | EIVLTQSPGTLSLSPGERATLSCR ASQSVSSSYLAWYQQKPGQAP RLLIYGASSRATGIPDRFSGSGS GTDFTLTISRLEPEDFAVYYCKFY PYPPSFTFGQGTKVEIK (SEQ ID NO: 23) | EVQLLESGGGLVQPGGSLRLSCA ASGFTFGSYAMTWVRQAPGKGLE WVSAIDYSGGNTFYADSVKGRFTI SRDNSKNTLYLQMNSLRAEDTAV YYCARVSPIASGMDYWGQGTLVT VSS (SEQ ID NO: 25) |
| L3.PY/ L3.KF/ H2.YQ | EIVLTQSPGTLSLSPGERATLSCR ASQSVSSSYLAWYQQKPGQAP RLLIYGASSRATGIPDRFSGSGS GTDFTLTISRLEPEDFAVYYCKFY PYPPSFTFGQGTKVEIK (SEQ ID NO: 23) | EVQLLESGGGLVQPGGSLRLSCA ASGFTFGSYAMTWVRQAPGKGLE WVSAISYQGGNTFYADSVKGRFTI SRDNSKNTLYLQMNSLRAEDTAV YYCARVSPIASGMDYWGQGTLVT VSS (SEQ ID NO: 26) |
| L3.PY/ L3.KF/ H2.LT | EIVLTQSPGTLSLSPGERATLSCR ASQSVSSSYLAWYQQKPGQAP RLLIYGASSRATGIPDRFSGSGS GTDFTLTISRLEPEDFAVYYCKFY PYPPSFTFGQGTKVEIK (SEQ ID NO: 23) | EVQLLESGGGLVQPGGSLRLSCA ASGFTFGSYAMTWVRQAPGKGLE WVSAISLTGGNTFYADSVKGRFTI SRDNSKNTLYLQMNSLRAEDTAV YYCARVSPIASGMDYWGQGTLVT VSS (SEQ ID NO: 27) |
| L3.PY/ L3.KF/ H2.QL | EIVLTQSPGTLSLSPGERATLSCR ASQSVSSSYLAWYQQKPGQAP RLLIYGASSRATGIPDRFSGSGS GTDFTLTISRLEPEDFAVYYCKFY PYPPSFTFGQGTKVEIK (SEQ ID NO: 23) | EVQLLESGGGLVQPGGSLRLSCA ASGFTFGSYAMTWVRQAPGKGLE WVSAISGSGGNTFYADQLKGRFTI SRDNSKNTLYLQMNSLRAEDTAV YYCARVSPIASGMDYWGQGTLVT VSS (SEQ ID NO: 29) |
| L3.PY/ L3.KF/ H3.YA | EIVLTQSPGTLSLSPGERATLSCR ASQSVSSSYLAWYQQKPGQAP RLLIYGASSRATGIPDRFSGSGS GTDFTLTISRLEPEDFAVYYCKFY PYPPSFTFGQGTKVEIK (SEQ ID NO: 23) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIYAGMDYWGQGTLVT VSS (SEQ ID NO: 30) |
| L3.PY/ L3.KF/ H3.AE | EIVLTQSPGTLSLSPGERATLSCR ASQSVSSSYLAWYQQKPGQAP RLLIYGASSRATGIPDRFSGSGS GTDFTLTISRLEPEDFAVYYCKFY PYPPSFTFGQGTKVEIK (SEQ ID NO: 23) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIAAEMDYWGQGTLVT VSS (SEQ ID NO: 31) |
| L3.PY/ L3.KF/ H3.AQ | EIVLTQSPGTLSLSPGERATLSCR ASQSVSSSYLAWYQQKPGQAP RLLIYGASSRATGIPDRFSGSGS GTDFTLTISRLEPEDFAVYYCKFY PYPPSFTFGQGTKVEIK (SEQ ID NO: 23) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCARVSPIAAQMDYWGQGTLVT VSS (SEQ ID NO: 3) |

TABLE 1-continued

| mAb | Light Chain | Heavy Chain |
|---|---|---|
| L3.PY/ L3.KF/ H3.TAQ | EIVLTQSPGTLSLSPGERATLSCR ASQSVSSSYLAWYQQKPGQAP RLLIYGASSRATGIPDRFSGSGS GTDFTLTISRLEPEDFAVYYCKFY PYPPSFTFGQGTKVEIK (SEQ ID NO: 23) | EVQLLESGGGLVQPGGSLRLSCA ASGFTFGSYAMTWVRQAPGKGLE WVSAISGSGGNTFYADSVKGRFTI SRDNSKNTLYLQMNSLRAEDTAV YYCTRVSPIAAQMDYWGQGTLVT VSS (SEQ ID NO: 32) |
| P5A2 VHVL | EIVLTQSPGTLSLSPGERATLSCR ASQSVSSSYLAWYQQKPGQAP RLLMYDASIRATGIPDRFSGSGS GTDFTLTISRLEPEDFAVYYCQQ YGSWPLTFGQGTKVEIK (SEQ ID NO: 34) | EVQLLESGGGLVQPGGSLRLSCA ASGFTFSSYAMNWVRQAPGKGLE WVSAISDSGGSTYYADSVKGRFTI SRDNSKNTLYLQMNSLRAEDTAV YYCARYWPMDIWGQGTLVTVSS (SEQ ID NO: 33) |
| A02_ Rd4_0.6 nM_C06 | EIVLTQSPGTLSLSPGERATLSCR ASQSVSVIYLAWYQQKPGQAPR LLMYDASIRATGIPDRFSGSGSG TDFTLTISRLEPEDFAVYYCQQY QRWPLTFGQGTKVEIK (SEQ ID NO: 36) | EVQLLESGGGLVQPGGSLRLSCA ASGFTFSSYAMNWVRQAPGKGLE WVSAISDSGGSAWYADSVKGRFT ISRDNSKNTLYLQMNSLRAEDTAV YYCARYWPMSLWGQGTLVTVSS (SEQ ID NO: 35) |
| A02_ Rd4_0.6 nM_C09 | EIVLTQSPGTLSLSPGERATLSCR ASQSVSSSYLAWYQQKPGQAP RLLMYDASIRATGIPDRFSGSGS GTDFTLTISRLEPEDFAVYYCQQ YQSWPLTFGQGTKVEIK (SEQ ID NO: 38) | EVQLLESGGGLVQPGGSLRLSCA ASGFTFSSYAMNWVRQAPGKGLE WVSAISDSGGSMWYADSVKGRF TISRDNSKNTLYLQMNSLRAEDTA VYYCARYWPMSLWGQGTLVTVS S (SEQ ID NO: 37) |
| A02_ Rd4_6 nM_C16 | EIVLTQSPGTLSLSPGERATLSCR ASQSVSDIYLAWYQQKPGQAPR LLMYDASIRATGIPDRFSGSGSG TDFTLTISRLEPEDFAVYYCQQY QTWPLTFGQGTKVEIK (SEQ ID NO: 40) | EVQLLESGGGLVQPGGSLRLSCA ASGFTFSSYAMNWVRQAPGKGLE WVSAISdFGGSTYYADSVKGRFTI SRDNSKNTLYLQMNSLRAEDTAV YYCARYWPMDIWGQGTLVTVSS (SEQ ID NO: 39) |
| A02_ Rd4_6 nM_C03 | EIVLTQSPGTLSLSPGERATLSCR ASQSVSNLYLAWYQQKPGQAP RLLMYDASIRATGIPDRFSGSGS GTDFTLTISRLEPEDFAVYYCQQ YQGWPLTFGQGTKVEIK (SEQ ID NO: 41) | EVQLLESGGGLVQPGGSLRLSCA ASGFTFSSYAMNWVRQAPGKGLE WVSAISDSGGSTYYADSVKGRFTI SRDNSKNTLYLQMNSLRAEDTAV YYCARYWPMDIWGQGTLVTVSS (SEQ ID NO: 33) |
| A02_ Rd4_6 nM_C01 | EIVLTQSPGTLSLSPGERATLSCR ASQSVSAYYLAWYQQKPGQAP RLLMYDASIRATGIPDRFSGSGS GTDFTLTISRLEPEDFAVYYCQQ YERWPLTFGQGTKVEIK (SEQ ID NO: 43) | EVQLLESGGGLVQPGGSLRLSCA ASGFTFSSYAMNWVRQAPGKGLE WVSAITASGGSTYYADSVKGRFTI SRDNSKNTLYLQMNSLRAEDTAV YYCARYWPMSLWGQGTLVTVSS (SEQ ID NO: 42) |
| A02_ Rd4_6 nM_C26 | EIVLTQSPGTLSLSPGERATLSCR ASQSVSSLYLAWYQQKPGQAPR LLMYDASIRATGIPDRFSGSGSG TDFTLTISRLEPEDFAVYYCQQY QVWPLTFGQGTKVEIK (SEQ ID NO: 45) | EVQLLESGGGLVQPGGSLRLSCA ASGFTFSSYAMNWVRQAPGKGLE WVSAISDSGGSTYYADSVKGRFTI SRDNSKNTLYLQMNSLRAEDTAV YYCARYWPMSLWGQGTLVTVSS (SEQ ID NO: 44) |
| A02_ Rd4_6 nM_C25 | EIVLTQSPGTLSLSPGERATLSCR ASQSVSSSYLAWYQQKPGQAP RLLMYDASIRATGIPDRFSGSGS GTDFTLTISRLEPEDFAVYYCQQ YLDWPLTFGQGTKVEIK (SEQ ID NO: 47) | EVQLLESGGGLVQPGGSLRLSCA ASGFTFSSYAMNWVRQAPGKGLE WVSAISdSGGSRWYADSVKGRFT ISRDNSKNTLYLQMNSLRAEDTAV YYCARYWPMTPWGQGTLVTVSS (SEQ ID NO: 46) |
| A02_ Rd4_6 nM_C22 | EIVLTQSPGTLSLSPGERATLSCR ASQSVSSSYLAWYQQKPGQAP RLLMYDASIRATGIPDRFSGSGS GTDFTLTISRLEPEDFAVYYCQQ YQVWPLTFGQGTKVEIK (SEQ ID NO: 49) | EVQLLESGGGLVQPGGSLRLSCA ASGFTFSSYAMNWVRQAPGKGLE WVSAVLdSGGSTYYADSVKGRFT ISRDNSKNTLYLQMNSLRAEDTAV YYCARYWPMTPWGQGTLVTVSS (SEQ ID NO: 48) |
| A02_ Rd4_6 nM_C19 | EIVLTQSPGTLSLSPGERATLSCR ASQSVSVIYLAWYQQKPGQAPR LLMYDASIRATGIPDRFSGSGSG TDFTLTISRLEPEDFAVYYCQQL AWPLTFGQGTKVEIK (SEQ ID NO: 51) | EVQLLESGGGLVQPGGSLRLSCA ASGFTFSSYAMNWVRQAPGKGLE WVSAISdSGGSRWYADSVKGRFT ISRDNSKNTLYLQMNSLRAEDTAV YYCARYWPMSDWGQGTLVTVSS (SEQ ID NO: 50) |

TABLE 1-continued

| mAb | Light Chain | Heavy Chain |
|---|---|---|
| A02_Rd4_0.6 nM_C03 | EIVLTQSPGTLSLSPGERATLSCR ASQSVSSSYLAWYQQKPGQAP RLLMYDASIRATGIPDRFSGSGS GTDFTLTISRLEPEDFAVYYCQQ YFTWPLTFGQGTKVEIK (SEQ ID NO: 53) | EVQLLESGGGLVQPGGSLRLSCA ASGFTFSSYAMNWVRQAPGKGLE WVSAISdSGGSKWYADSVKGRFT ISRDNSKNTLYLQMNSLRAEDTAV YYCARYWPMSLWGQGTLVTVSS (SEQ ID NO: 52) |
| A02_Rd4_6 nM_C07 | EIVLTQSPGTLSLSPGERATLSCR ASQSVSPyYLAWYQQKPGQAPR LLMYDASIRATGIPDRFSGSGSG TDFTLTISRLEPEDFAVYYCQQYE RWPLTFGQGTKVEIK (SEQ ID NO: 55) | EVQLLESGGGLVQPGGSLRLSCA ASGFTFSSYAMNWVRQAPGKGLE WVSAIGGSGGSLPYADSVKGRFT ISRDNSKNTLYLQMNSLRAEDTAV YYCARYWPMDSWGQGTLVTVSS (SEQ ID NO: 54) |
| A02_Rd4_6 nM_C23 | EIVLTQSPGTLSLSPGERATLSCR ASQSVSVEYLAWYQQKPGQAP RLLMYDASIRATGIPDRFSGSGS GTDFTLTISRLEPEDFAVYYCQQ YARWPLTFGQGTKVEIK (SEQ ID NO: 57) | EVQLLESGGGLVQPGGSLRLSCA ASGFTFSSYAMNWVRQAPGKGLE WVSDASIRATdSGGGSWYADSVKGRFT ISRDNSKNTLYLQMNSLRAEDTAV YYCARYWPMSLWGQGTLVTVSS (SEQ ID NO: 56) |
| A02_Rd4_0.6 nM_C18 | EIVLTQSPGTLSLSPGERATLSCR ASQSVSEIYLAWYQQKPGQAPR LLMYDASIRATGIPDRFSGSGSG TDFTLTISRLEPEDFAVYYCQQYF GWPLTFGQGTKVEIK (SEQ ID NO: 59) | EVQLLESGGGLVQPGGSLRLSCA ASGFTFSSYAMNWVRQAPGKGLE WVSAVLdSGGSTYYADSVKGRFT ISRDNSKNTLYLQMNSLRAEDTAV YYCARYWPMSLWGQGTLVTVSS (SEQ ID NO: 58) |
| A02_Rd4_6 nM_C10 | EIVLTQSPGTLSLSPGERATLSCR ASQSVEMSYLAWYQQKPGQAP RLLMYDASIRATGIPDRFSGSGS GTDFTLTISRLEPEDFAVYYCQQ YAHWPLTFGQGTKVEIK (SEQ ID NO: 61) | EVQLLESGGGLVQPGGSLRLSCA ASGFTFSSYAMNWVRQAPGKGLE WVSAISdSGGSCWYADSVKGRFT ISRDNSKNTLYLQMNSLRAEDTAV YYCARYWPMTPWGQGTLVTVSS (SEQ ID NO: 60) |
| A02_Rd4_6 nM_C05 | EIVLTQSPGTLSLSPGERATLSCR ASQSVSSSYLAWYQQKPGQAP RLLMYDASIRATGIPDRFSGSGS GTDFTLTISRLEPEDFAVYYCQQ YQRWPLTFGQGTKVEIK (SEQ ID NO: 63) | EVQLLESGGGLVQPGGSLRLSCA ASGFTFSSYAMNWVRQAPGKGLE WVSAIFaSGGSTYYADSVKGRFTI SRDNSKNTLYLQMNSLRAEDTAV YYCARYWPMTPWGQGTLVTVSS (SEQ ID NO: 62) |
| A02_Rd4_0.6 nM_C10 | EIVLTQSPGTLSLSPGERATLSCR ASQSVSAQYLAWYQQKPGQAP RLLMYDASIRATGIPDRFSGSGS GTDFTLTISRLEPEDFAVYYCQQ YQRWPLTFGQGTKVEIK (SEQ ID NO: 65) | EVQLLESGGGLVQPGGSLRLSCA ASGFTFSSYAMNWVRQAPGKGLE WVSAISgWGGSLPYADSVKGRFT ISRDNSKNTLYLQMNSLRAEDTAV YYCARYWPMDSWGQGTLVTVSS (SEQ ID NO: 64) |
| A02_Rd4_6 nM_C04 | EIVLTQSPGTLSLSPGERATLSCR ASQSVSAIYLAWYQQKPGQAPR LLMYDASIRATGIPDRFSGSGSG TDFTLTISRLEPEDFAVYYCQQY QVWPLTFGQGTKVEIK (SEQ ID NO: 67) | EVQLLESGGGLVQPGGSLRLSCA ASGFTFSSYAMNWVRQAPGKGLE WVSAIMsSGGPLYYADSVKGRFTI SRDNSKNTLYLQMNSLRAEDTAV YYCARYWPMALWGQGTLVTVSS (SEQ ID NO: 66) |
| A02_Rd4_0.6 nM_C26 | EIVLTQSPGTLSLSPGERATLSCG PSQSVSSSYLAWYQQKPGQAPR LLMYDASIRATGIPDRFSGSGSG TDFTLTISRLEPEDFAVYYCQQY QSWPLTFGQGTKVEIK (SEQ ID NO: 69) | EVQLLESGGGLVQPGGSLRLSCA ASGFTFSSYAMNWVRQAPGKGLE WVSAILmSGGSTYYADSVKGRFTI SRDNSKNTLYLQMNSLRAEDTAV YYCARYWPMSLWGQGTLVTVSS (SEQ ID NO: 68) |
| A02_Rd4_0.6 nM_C13 | EIVLTQSPGTLSLSPGERATLSCR ASQSVSSSYWAWYQQKPGQAP RLLMYDASIRATGIPDRFSGSGS GTDFTLTISRLEPEDFAVYYCQQ YESWPLTFGQGTKVEIK (SEQ ID NO: 71) | EVQLLESGGGLVQPGGSLRLSCA ASGFTFSSYAMNWVRQAPGKGLE WVSAISdSGGYRYYADSVKGRFTI SRDNSKNTLYLQMNSLRAEDTAV YYCARYWPMSLWGQGTLVTVSS (SEQ ID NO: 70) |
| A02_Rd4_0.6 nM_C01 | EIVLTQSPGTLSLSPGERATLSCR GGQSVSSSYLAWYQQKPGQAP RLLMYDASIRATGIPDRFSGSGS GTDFTLTISRLEPEDFAVYYCQQ YQSWPLTFGQGTKVEIK (SEQ ID NO: 73) | EVQLLESGGGLVQPGGSLRLSCA ASGFTFSSYAMNWVRQAPGKGLE WVSAILsSGGSTYYADSVKGRFTI SRDNSKNTLYLQMNSLRAEDTAV YYCARYWPMDIWGQGTLVTVSS (SEQ ID NO: 72) |

TABLE 1-continued

| mAb | Light Chain | Heavy Chain |
|---|---|---|
| A02_Rd4_6 nM_C08 | EIVLTQSPGTLSLSPGERATLSCR ASQSVSFIYLAWYQQKPGQAPR LLMYDASIRATGIPDRFSGSGSG TDFTLTISRLEPEDFAVYYCQQY GSWPLTFGQGTKVEIK (SEQ ID NO: 75) | EVQLLESGGGLVQPGGSLRLSCA ASGFTFSSYAMNWVRQAPGKGLE WVSAILdSGGSTYYADSVKGRFTI SRDNSKNTLYLQMNSLRAEDTAV YYCARYWPMSPWGQGTLVTVSS (SEQ ID NO: 74) |
| P5C1_VHVL | EIVLTQSPGTLSLSPGERATLSCR ASQSVSSTYLAWYQQKPGQAPR LLIYDASSRAPGIPDRFSGSGSG TDFTLTISRLEPEDFAVYYCQQYS TSPLTFGQGTKVEIK (SEQ ID NO: 77) | EVQLLESGGGLVQPGGSLRLSCA ASGFTFSSYPMSWVRQAPGKGLE WVSAIGGSGGSTYYADSVKGRFT ISRDNSKNTLYLQMNSLRAEDTAV YYCARYWPMDSWGQGTLVTVSS (SEQ ID NO: 76) |
| C01_Rd4_6 nM_C24 | EIVLTQSPGTLSLSPGERATLSCR ASQSVSPEYLAWYQQKPGQAP RLLIYDASSRAPGIPDRFSGSGS GTDFTLTISRLEPEDFAVYYCQQ YSVWPLTFGQGTKVEIK (SEQ ID NO: 79) | EVQLLESGGGLVQPGGSLRLSCA ASGFTFSSYPMSWVRQAPGKGLE WVSAIGGSGGSLPYADSVKGRFT ISRDNSKNTLYLQMNSLRAEDTAV YYCARYWPMDSWGQGTLVTVSS (SEQ ID NO: 78) |
| C01_Rd4_6 nM_C26 | EIVLTQSPGTLSLSPGERATLSCR ASQSVSAIYLAWYQQKPGQAPR LLIYDASSRAPGIPDRFSGSGSG TDFTLTISRLEPEDFAVYYCQQYS AWPLTFGQGTKVEIK (SEQ ID NO: 317) | EVQLLESGGGLVQPGGSLRLSCA ASGFTFSSYPMSWVRQAPGKGLE WVSAIGGSGGSLPYADSVKGRFT ISRDNSKNTLYLQMNSLRAEDTAV YYCARYWPMDSWGQGTLVTVSS (SEQ ID NO: 78) |
| C01_Rd4_6 nM_C10 | EIVLTQSPGTLSLSPGERATLSCR ASQSVSSvYLAWYQQKPGQAPR LLIYDASSRAPGIPDRFSGSGSG TDFTLTISRLEPEDFAVYYCQQYS TWPLTFGQGTKVEIK (SEQ ID NO: 79) | EVQLLESGGGLVQPGGSLRLSCA ASGFTFSSYPMSWVRQAPGKGLE WVSAIGgSGGSLPYADSVKGRFTI SRDNSKNTLYLQMNSLRAEDTAV YYCARYWPMDSWGQGTLVTVSS (SEQ ID NO: 78) |
| C01_Rd4_0.6 nM_C27 | EIVLTQSPGTLSLSPGERATLSCR ASQSVSSTYLAWYQQKPGQAPR LLIYDASSRAPGIPDRFSGSGSG TDFTLTISRLEPEDFAVYYCQQYS RWPLTFGQGTKVEIK (SEQ ID NO: 81) | EVQLLESGGGLVQPGGSLRLSCA ASGFTFSSYPMSWVRQAPGKGLE WVSAIGgSGGSLPYADSVKGRFTI SRDNSKNTLYLQMNSLRAEDTAV YYCARYWPMDSWGQGTLVTVSS (SEQ ID NO: 78) |
| C01_Rd4_6 nM_C20 | EIVLTQSPGTLSLSPGERATLSCR ASQSVSPIYLAWYQQKPGQAPR LLIYDASSRAPGIPDRFSGSGSG TDFTLTISRLEPEDFAVYYCQQYS AFPLTFGQGTKVEIK (SEQ ID NO: 82) | EVQLLESGGGLVQPGGSLRLSCA ASGFTFSSYPMSWVRQAPGKGLE WVSAIGgSGGSLPYADSVKGRFTI SRDNSKNTLYLQMNSLRAEDTAV YYCARYWPMDSWGQGTLVTVSS (SEQ ID NO: 78) |
| C01_Rd4_6 nM_C12 | EIVLTQSPGTLSLSPGERATLSC WLSQSVSSTYLAWYQQKPGQA PRLLIYDASSRAPGIPDRFSGSG SGTDFTLTISRLEPEDFAVYYCQ QYSEWPLTFGQGTKVEIK (SEQ ID NO: 84) | EVQLLESGGGLVQPGGSLRLSCA ASGFTFSSYPMSWVRQAPGKGLE WVSAIGSGGWSYYADSVKGRFT ISRDNSKNTLYLQMNSLRAEDTAV YYCARYWPMDSWGQGTLVTVSS (SEQ ID NO: 83) |
| C01_Rd4_0.6 nM_C16 | EIVLTQSPGTLSLSPGERATLSCR ASQSVSSTYLAWYQQKPGQAPR LLIYDASSRAPGIPDRFSGSGSG TDFTLTISRLEPEDFAVYYCQQYS SWPLTFGQGTKVEIK (SEQ ID NO: 85) | EVQLLESGGGLVQPGGSLRLSCA ASGFTFSSYPMSWVRQAPGKGLE WVSAIGgSGGSLPYADSVKGRFTI SRDNSKNTLYLQMNSLRAEDTAV YYCARYWPMDSWGQGTLVTVSS (SEQ ID NO: 78) |
| C01_Rd4_0.6 nM_C09 | EIVLTQSPGTLSLSPGERATLSCR ASQSVSSIFLAWYQQKPGQAPR LLIYDASSRAPGIPDRFSGSGSG TDFTLTISRLEPEDFAVYYCQQYS AWPLTFGQGTKVEIK (SEQ ID NO: 86) | EVQLLESGGGLVQPGGSLRLSCA ASGFTFSSYPMSWVRQAPGKGLE WVSAIGgSGGSLPYADSVKGRFTI SRDNSKNTLYLQMNSLRAEDTAV YYCARYWPMDSWGQGTLVTVSS (SEQ ID NO: 78) |
| C01_Rd4_6 nM_C09 | EIVLTQSPGTLSLSPGERATLSCA CSQSVSSTYLAWYQQKPGQAPR LLIYDASSRAPGIPDRFSGSGSG TDFTLTISRLEPEDFAVYYCQQYS AWPLTFGQGTKVEIK (SEQ ID NO: 88) | EVQLLESGGGLVQPGGSLRLSCA ASGFTFSSYPMSWVRQAPGKGLE WVSATVgSGGSIGYADSVKGRFTI SRDNSKNTLYLQMNSLRAEDTAV YYCARYWPMDSWGQGTLVTVSS (SEQ ID NO: 87) |

TABLE 1-continued

| mAb | Light Chain | Heavy Chain |
|---|---|---|
| C01_Rd4_0.6 nM_C03 | EIVLTQSPGTLSLSPGERATLSCR ASCDVSSTYLAWYQQKPGQAPR LLIYDASSRAPGIPDRFSGSGSG TDFTLTISRLEPEDFAVYYCQQY MRSPLTFGQGTKVEIK (SEQ ID NO: 89) | EVQLLESGGGLVQPGGSLRLSCA ASGFTFSSYPMSWVRQAPGKGLE WVSAIGgSGGSLPYADSVKGRFTI SRDNSKNTLYLQMNSLRAEDTAV YYCARYWPMDSWGQGTLVTVSS (SEQ ID NO: 78) |
| C01_Rd4_0.6 nM_C06 | EIVLTQSPGTLSLSPGERATLSCR ASEAVPSTYLAWYQQKPGQAPR LLIYDASSRAPGIPDRFSGSGSG TDFTLTISRLEPEDFAVYYCQQYS AFPLTFGQGTKVEIK (SEQ ID NO: 90) | EVQLLESGGGLVQPGGSLRLSCA ASGFTFSSYPMSWVRQAPGKGLE WVSAIGgSGGSLPYADSVKGTISR DNSKNTLYLQMNSLRAEDTAVYY CARYWPMDSWGQGTLVTVSS (SEQ ID NO: 78) |
| C01_Rd4_6 nM_C04 | EIVLTQSPGTLSLSPGERATLSCC SSQSVSSTYLAWYQQKPGQAPR LLIYDASSRAPGIPDRFSGSGSG TDFTLTISRLEPEDFAVYYCQQYS AFPLTFGQGTKVEIK (SEQ ID NO: 91) | EVQLLESGGGLVQPGGSLRLSCA ASGFTFSSYPMSWVRQAPGKGLE WVSAIGgSGGSLPYADSVKGRFTI SRDNSKNTLYLQMNSLRAEDTAV YYCARYWPMDSWGQGTLVTVSS (SEQ ID NO: 78) |
| COMBO_Rd4_0.6 nM_C22 | EIVLTQSPGTLSLSPGERATLSCR ASVRVSSTYLAWYQQKPGQAPR LLMYDASIRATGIPDRFSGSGSG TDFTLTISRLEPEDFAVYYCQQY MKWPLTFGQGTKVEIK (SEQ ID NO: 93) | EVQLLESGGGLVQPGGSLRLSCA ASGFTFSSYAMNWVRQAPGKGLE WVSAISdSGGSRWYADSVKGRFT ISRDNSKNTLYLQMNSLRAEDTAV YYCTRYWPMDIWGQGTLVTVSS (SEQ ID NO: 92) |
| COMBO_Rd4_6 nM_C21 | EIVLTQSPGTLSLSPGERATLSCR ASQSVSAAYLAWYQQKPGQAP RLLMYDASIRATGIPDRFSGSGS GTDFTLTISRLEPEDFAVYYCQQ YMCWPLTFGQGTKVEIK (SEQ ID NO: 94) | EVQLLESGGGLVQPGGSLRLSCA ASGFTFSSYPMSWVRQAPGKGLE WVSAIGgSGGSLPYADSVKGRFTI SRDNSKNTLYLQMNSLRAEDTAV YYCARYWPMDSWGQGTLVTVSS (SEQ ID NO: 78) |
| COMBO_Rd4_6 nM_C10 | EIVLTQSPGTLSLSPGERATLSCR ASQSVSSSYWGWYQQKPGQAP RLLMYDASIRATGIPDRFSGSGS GTDFTLTISRLEPEDFAVYYCQQ YQCWPLTFGQGTKVEIK (SEQ ID NO: 96) | EVQLLESGGGLVQPGGSLRLSCA ASGFTFSSYPMSWVRQAPGKGLE WVSAIGgSGGSIHYADSVKGRFTI SRDNSKNTLYLQMNSLRAEDTAV YYCARYWPMDSWGQGTLVTVSS (SEQ ID NO: 95) |
| COMBO_Rd4_0.6 nM_C04 | EIVLTQSPGTLSLSPGERATLSCR ASQSVSSTYLAWYQQKPGQAPR LLMYDASIRATGIPDRFSGSGSG TDFTLTISRLEPEDFAVYYCQQY QSWPLTFGQGTKVEIK (SEQ ID NO: 98) | EVQLLESGGGLVQPGGSLRLSCA ASGFTFSSYPMSWVRQAPGKGLE WVSAHIgSGGSTYYADSVKGRFTI SRDNSKNTLYLQMNSLRAEDTAV YYCARYWPMDSWGQGTLVTVSS (SEQ ID NO: 97) |
| COMBO_Rd4_6 nM_C25 | EIVLTQSPGTLSLSPGERATLSCR ASQSVSSpYLAWYQQKPGQAPR LLMYDASIRATGIPDRFSGSGSG TDFTLTISRLEPEDFAVYYCQQY QSWPLTFGQGTKVEIK (SEQ ID NO: 100) | EVQLLESGGGLVQPGGSLRLSCA ASGFTFSSYPMSWVRQAPGKGLE WVSAIGgSGGSTYYADSVKGRFTI SRDNSKNTLYLQMNSLRAEDTAV YYCARYWPMDPWGQGTLVTVSS (SEQ ID NO: 99) |
| COMBO_Rd4_0.6 nM_C21 | EIVLTQSPGTLSLSPGERATLSCR ASQSVSSSYLAWYQQKPGQAP RLLMYDASIRATGIPDRFSGSGS GTDFTLTISRLEPEDFAVYYCQQ YQSWPLTFGQGTKVEIK (SEQ ID NO: 38) | EVQLLESGGGLVQPGGSLRLSCA ASGFTFSSYPMSWVRQAPGKGLE WVSAIGgSGGSLPYADSVKGRFTI SRDNSKNTLYLQMNSLRAEDTAV YYCARYWPMDSWGQGTLVTVSS (SEQ ID NO: 78) |
| COMBO_Rd4_6 nM_C11 | EIVLTQSPGTLSLSPGERATLSCR ASQSVSPIYLAWYQQKPGQAPR LLMYDASIRATGIPDRFSGSGSG TDFTLTISRLEPEDFAVYYCQQY KAWPLTFGQGTKVEIK (SEQ ID NO: 102) | EVQLLESGGGLVQPGGSLRLSCA ASGFTFSSYPMSWVRQAPGKGLE WVSAIGGSGGSLGYADSVKGRFT ISRDNSKNTLYLQMNSLRAEDTAV YYCARYWPMDSWGQGTLVTVSS (SEQ ID NO: 101) |
| COMBO_Rd4_0.6 nM_C20 | EIVLTQSPGTLSLSPGERATLSCR ASQSVSYLYLAWYQQKPGQAPR LLMYDASIRATGIPDRFSGSGSG TDFTLTISRLEPEDFAVYYCQQY MEWPLTFGQGTKVEIK (SEQ ID NO: 103) | EVQLLESGGGLVQPGGSLRLSCA ASGFTFSSYPMSWVRQAPGKGLE WVSAIGGSGGSLPYADSVKGRFT ISRDNSKNTLYLQMNSLRAEDTAV YYCARYWPMDSWGQGTLVTVSS (SEQ ID NO: 78) |

TABLE 1-continued

| mAb | Light Chain | Heavy Chain |
| --- | --- | --- |
| COMBO_Rd4_6 nM_C09 | EIVLTQSPGTLSLSPGERATLSCR ASQSVSAQYLAWYQQKPGQAP RLLMYDASIRATGIPDRFSGSGS GTDFTLTISRLEPEDFAVYYCQQ YQAWPLTFGQGTKVEIK (SEQ ID NO: 105) | EVQLLESGGGLVQPGGSLRLSCA ASGFTFSSYPMSWVRQAPGKGLE WVSAIFASGGSTYYADSVKGRFTI SRDNSKNTLYLQMNSLRAEDTAV YYCARYWPMDSWGQGTLVTVSS (SEQ ID NO: 104) |
| COMBO_Rd4_6 nM_C08 | EIVLTQSPGTLSLSPGERATLSCR ASQSVSSSYLAWYQQKPGQAP RLLMYDASIRATGIPDRFSGSGS GTDFTLTISRLEPEDFAVYYCQQ YQKWPLTFGQGTKVEIK (SEQ ID NO: 107) | EVQLLESGGGLVQPGGSLRLSCA ASGFTFSSYPMSWVRQAPGKGLE WVSAIGGSGTWTYYADSVKGRFT ISRDNSKNTLYLQMNSLRAEDTAV YYCARYWPMDSWGQGTLVTVSS (SEQ ID NO: 106) |
| COMBO_Rd4_0.6 nM_C19 | EIVLTQSPGTLSLSPGERATLSCR ASQSVSAVYLAWYQQKPGQAP RLLMYDASIRATGIPDRFSGSGS GTDFTLTISRLEPEDFAVYYCQQ YRAWPLTFGQGTKVEIK (SEQ ID NO: 108) | EVQLLESGGGLVQPGGSLRLSCA ASGFTFSSYPMSWVRQAPGKGLE WVSAIGGSGGSLPYADSVKGRFT ISRDNSKNTLYLQMNSLRAEDTAV YYCARYWPMDSWGQGTLVTVSS (SEQ ID NO: 78) |
| COMBO_Rd4_0.6 nM_C02 | EIVLTQSPGTLSLSPGERATLSCR ASIAVSSTYLAWYQQKPGQAPR LLMYDASIRATGIPDRFSGSGSG TDFTLTISRLEPEDFAVYYCQQY MVWPLTFGQGTKVEIK (SEQ ID NO: 109) | EVQLLESGGGLVQPGGSLRLSCA ASGFTFSSYPMSWVRQAPGKGLE WVSAIGGSGGSLPYADSVKGRFT ISRDNSKNTLYLQMNSLRAEDTAV YYCARYWPMDSWGQGTLVTVSS (SEQ ID NO: 78) |
| COMBO_Rd4_0.6 nM_C23 | EIVLTQSPGTLSLSPGERATLSCR PRQSVSSSYLAWYQQKPGQAP RLLMYDASIRATGIPDRFSGSGS GTDFTLTISRLEPEDFAVYYCQQ YQDWPLTFGQGTKVEIK (SEQ ID NO: 111) | EVQLLESGGGLVQPGGSLRLSCA ASGFTFSSYPMSWVRQAPGKGLE WVSALFGSGGSTYYADSVKGRFT ISRDNSKNTLYLQMNSLRAEDTAV YYCARYWPMDSWGQGTLVTVSS (SEQ ID NO: 110) |
| COMBO_Rd4_0.6 nM_C29 | EIVLTQSPGTLSLSPGERATLSCR ASQSVSSSYLAWYQQKPGQAP RLLMYDASIRATGIPDRFSGSGS GTDFTLTISRLEPEDFAVYYCQQ YQSWPLTFGQGTKVEIK (SEQ ID NO: 38) | EVQLLESGGGLVQPGGSLRLSCA ASGFTFSSYPMSWVRQAPGKGLE WVSAIGGSGGSLPYADSVKGRFT ISRDNSKNTLYLQMNSLRAEDTAV YYCARYWPMDIWGQGTLVTVSS (SEQ ID NO: 112) |
| COMBO_Rd4_0.6 nM_C09 | EIVLTQSPGTLSLSPGERATLSCR ASQSVSSTYLAWYQQKPGQAPR LLMYDASIRATGIPDRFSGSGSG TDFTLTISRLEPEDFAVYYCQQY QEWPLTFGQGTKVEIK (SEQ ID NO: 113) | EVQLLESGGGLVQPGGSLRLSCA ASGFTFSSYPMSWVRQAPGKGLE WVSAIGGSGGSLPYADSVKGRFT ISRDNSKNTLYLQMNSLRAEDTAV YYCARYWPMDIWGQGTLVTVSS (SEQ ID NO: 112) |
| COMBO_Rd4_6 nM_C12 | EIVLTQSPGTLSLSPGERATLSCR ASQSVSASYLAWYQQKPGQAP RLLMYDASIRATGIPDRFSGSGS GTDFTLTISRLEPEDFAVYYCQQ YMSWPLTFGQGTKVEIK (SEQ ID NO: 115) | EVQLLESGGGLVQPGGSLRLSCA ASGFTFSSYPMSWVRQAPGKGLE WVSAALGSGGSTYYADSVKGRF TISRDNSKNTLYLQMNSLRAEDTA VYYCARYWPMDSWGQGTLVTVS S (SEQ ID NO: 114) |
| COMBO_Rd4_0.6 nM_C30 | EIVLTQSPGTLSLSPGERATLSCR ASQSVSYMYLAWYQQKPGQAP RLLIYDASIRATGIPDRFSGSGSG TDFTLTISRLEPEDFAVYYCQQY KSWPLTFGQGTKVEIK (SEQ ID NO: 116) | EVQLLESGGGLVQPGGSLRLSCA ASGFTFSSYPMSWVRQAPGKGLE WVSAIGGSGGSTYYADSVKGRFT ISRDNSKNTLYLQMNSLRAEDTAV YYCARYWPMDSWGQGTLVTVSS (SEQ ID NO: 76) |
| COMBO_Rd4_0.6 nM_C14 | EIVLTQSPGTLSLSPGERATLSCR ASQSVSALYLAWYQQKPGQAP RLLMYDASIRATGIPDRFSGSGS GTDFTLTISRLEPEDFAVYYCQQ YYGWPLTFGQGTKVEIK (SEQ ID NO: 117) | EVQLLESGGGLVQPGGSLRLSCA ASGFTFSSYPMSWVRQAPGKGLE WVSAIGGSGGSLPYADSVKGRFT ISRDNSKNTLYLQMNSLRAEDTAV YYCARYWPMDIWGQGTLVTVSS (SEQ ID NO: 112) |
| COMBO_Rd4_6 nM_C07 | EIVLTQSPGTLSLSPGERATLSCR ASQPISSSYLAWYQQKPGQAPR LLMYDASIRATGIPDRFSGSGSG TDFTLTISRLEPEDFAVYYCQQY QGWPLTFGQGTKVEIK (SEQ ID NO: 119) | EVQLLESGGGLVQPGGSLRLSCA ASGFTFSSYPMSWVRQAPGKGLE WVSAIGGSGGSLPYADSVKGRFT ISRDNSKNTLYLQMNSLRAEDTAV YYCARYWPMADWGQGTLVTVSS (SEQ ID NO: 118) |

TABLE 1-continued

| mAb | Light Chain | Heavy Chain |
| --- | --- | --- |
| COMBO_Rd4_6nM_C02 | EIVLTQSPGTLSLSPGERATLSCRASQSVSSSYLAWYQQKPGQAPRLLMYDASIRATGIPDRFSGSGSGTDFTLTISRLEPEDFAVYYCQQYEFWPLTFGQGTKVEIK (SEQ ID NO: 121) | EVQLLESGGGLVQPGGSLRLSCASGFTFSSYAMNWVRQAPGKGLEWVSAISDSGGFVYYADSVKGRFTISRDNSKNTLYLQMNSLRAEDTAVYYCARYWPMDSWGQGTLVTVSS (SEQ ID NO: 120) |
| COMBO_Rd4_0.6nM_C05 | EIVLTQSPGTLSLSPGERATLSCRASQSVSSTYLAWYQQKPGQAPRLLMYDASIRATGIPDRFSGSGSGTDFTLTISRLEPEDFAVYYCQQYMSWPLTFGQGTKVEIK (SEQ ID NO: 123) | EVQLLESGGGLVQPGGSLRLSCASGFTFSSYAMNWVRQAPGKGLEWVSAIGGSGGSTYYADSVKGRFTISRDNSKNTLYLQMNSLRAEDTAVYYCARYWPMSLWGQGTLVTVSS (SEQ ID NO: 122) |
| COMBO_Rd4_0.6nM_C17 | EIVLTQSPGTLSLSPGERATLSCRASQGISSTYLAWYQQKPGQAPRLLMYDASIRATGIPDRFSGSGSGTDFTLTISRLEPEDFAVYYCQQYAYWPLTFGQGTKVEIK (SEQ ID NO: 124) | EVQLLESGGGLVQPGGSLRLSCASGFTFSSYPMSWVRQAPGKGLEWVSAIGGSGGSLPYADSVKGRFTISRDNSKNTLYLQMNSLRAEDTAVYYCARYWPMDIWGQGTLVTVSS (SEQ ID NO: 112) |
| COMBO_Rd4_6nM_C22 | EIVLTQSPGTLSLSPGERATLSCRASQSVSSSYLAWYQQKPGQAPRLLMYDASIRATGIPDRFSGSGSGTDFTLTISRLEPEDFAVYYCQQYQGWPLTFGQGTKVEIK (SEQ ID NO: 126) | EVQLLESGGGLVQPGGSLRLSCASGFTFSSYAMNWVRQAPGKGLEWVSACLDSGGSTYYADSVKGRFTISRDNSKNTLYLQMNSLRAEDTAVYYCARYWPMDSWGQGTLVTVSS (SEQ ID NO: 125) |
| COMBO_Rd4_0.6nM_C11 | EIVLTQSPGTLSLSPGERATLSCRASQSVSVRYLAWYQQKPGQAPRLLMYDASIRATGIPDRFSGSGSGTDFTLTISRLEPEDFAVYYCQQYGSWPITFGQGTKVEIK (SEQ ID NO: 128) | EVQLLESGGGLVQPGGSLRLSCASGFTFSSYPMSWVRQAPGKGLEWVSAALGSGGSTYYADSVKGRFTISRDNSKNTLYLQMNSLRAEDTAVYYCARYWPMSLWGQGTLVTVSS (SEQ ID NO: 127) |
| Consensus | EIVLTQSPGTLSLSPGERATLSCX$_1$X$_2$X$_3$X$_4$X$_5$X$_6$X$_7$X$_8$X$_9$X$_{10}$X$_{11}$X$_{12}$WYQQKPGQAPRLLMYX$_{13}$ASX$_{14}$RAX$_{15}$GIPDRFSGSGSGTDFTLTISRLEPEDFAVYYCX$_{16}$X$_{17}$YX$_{18}$X$_{19}$PPSFTFGQGTKVEIK, wherein X$_1$ is R, G, W, A, or C; X$_2$ is A, P, G, L, C, or S; X$_3$ is S, G, or R; X$_4$ is Q, C, E, V, or I; X$_5$ is S, P, G, A, R, or D; X$_6$ is V, G, I, or L; X$_7$ is S, E, D, P, or G; X$_8$ is S, P, F, A, M, E, V, D, or Y; X$_9$ is I, T, V, E, S, A, M, Q, Y, H, R, or F; X$_{10}$ is Y or F; X$_{11}$ is L, W, or P; X$_{12}$ is A, S, or G, X$_{13}$ is G or D; X$_{14}$ is S or I; X$_{15}$ is T or P; X$_{16}$ is Q or K; X$_{17}$ is H or Y; X$_{18}$ is G, N, or P; and X$_{19}$ is S, W, or Y (SEQ ID NO: 315); or EIVLTQSPGTLSLSPGERATLSCX$_1$X$_2$X$_3$X$_4$X$_5$X$_6$X$_7$X$_8$X$_9$X$_{10}$X$_{11}$X$_{12}$WYQQKPGQAPRLLMYX$_{13}$ASX$_{14}$RAX$_{15}$GIPDRFSGSGSGTDFTLTISRLEPEDFAVYYCX$_{16}$X$_{17}$YX$_{18}$PX$_{19}$FGQGTKVEIK, wherein X$_1$ is R, G, W, A, or C; X$_2$ is A, P, G, L, C, or S; X$_3$ is S, G, or R; X$_4$ is Q, C, E, V, or I; X$_5$ is S, L, P, G, A, R, or D; X$_6$ is V, G, or I; X$_7$ is S, E, D, or P; X$_8$ is S, P, F, A, M, E, V, N, D, or Y; X$_9$ is I, T, V, E, S, A, M, Q, Y, H, or R; X$_{10}$ is Y or F; X$_{11}$ is L, W, or P; X$_{12}$ is A, S, or G, X$_{13}$ is G or D; X14 is S or I; X15 is T or P; X16 is G, Q, E, L, F, A, S, M, R, K, or Y; X$_{17}$ is S, R, T, G, R, V, D, A, H, E, K, C, F, or Y; X$_{18}$ is W, S, or F; and X$_{19}$ is L or I (SEQ ID NO: 316) | EVQLLESGGGLVQPGGSLRLSCASGFTFX$_1$SYX$_2$MX$_3$WVRQAPGKGLEWVSAX$_4$X$_5$X$_6$X$_7$GX$_8$X$_9$X$_{10}$X$_{11}$YADX$_{12}$X$_{13}$XGRFTISRDNSKNTLYLQMNSLRAEDTAVYYCARVSPIX$_{14}$X$_{15}$X$_{16}$MDYWGQGTLVTVSS, wherein X$_1$ is G or S, X$_2$ is A or P; X$_3$ is T, N, or S; X$_4$ is I, V, T, H, L, A, or C; X$_5$ is S, D, G, T, I, L, F, M, or V; X$_6$ is G, Y, L, H, D, A, S, or M; X$_7$ is S, Q, T, A, N, F, or W; X$_8$ is G or T; X$_9$ is N, S, P, Y, W, or F; X$_{10}$ is S, T, I, L, T, A, R, V, K, G, or C; X$_{11}$ is F, Y, P, W, H, or G; X$_{12}$ is V, R, or L; X$_{13}$ is G or T; X$_{14}$ is A or Y; X$_{15}$ is A or S; and X$_{16}$ is G, Q, L, P, or E (SEQ ID NO: 313); or EVQLLESGGGLVQPGGSLRLSCASGFTFX$_1$SYX$_2$MX$_3$WVRQAPGKGLEWVSAX$_4$X$_5$X$_6$X$_7$GX$_8$X$_9$X$_{10}$X$_{11}$YADX$_{12}$X$_{13}$KGRFTISRDNSKNTLYLQMNSLRAEDTAVYYCARYWPMX$_{14}$X$_{15}$WGQGTLVTVSS, wherein X$_1$ is G or S, X$_2$ is A or P; X$_3$ is T, N, or S; X$_4$ is I, V, T, H, L, A, or C; X$_5$ is S, D, G, T, I, L, F, M, or V; X$_6$ is G, Y, L, H, D, A, S, or M; X$_7$ is S, Q, T, A, F, or W; X$_8$ is G or T; X$_9$ is N, S, P, Y, W, or F; X$_{10}$ is S, T, I, L, T, A, R, V, K, G, or C; X$_{11}$ is F, Y, P, W, H, or G; X$_{12}$ is V, R, or L; X$_{13}$ is G or T; X$_{14}$ is D, S, T, or A; and X$_{15}$ is I, S, L, P, or D (SEQ ID NO: 314) |

TABLE 1-continued

| mAb | Light Chain | Heavy Chain |
|---|---|---|
| P4G4 | EIVLTQSPGTLSLSPGERATLSCR ASQSVSSSYLAWYQQKPGQAP RLLIYGASSRAYGIPDRFSGSGS GTDFTLTISRLEPEDFAVYYCQH YGSPPLFTFGQGTKVEIK (SEQ ID NO: 80) | EVQLLESGGGLVQPGGSLRLSCA ASGFTFSSYAMSWVRQAPGKGLE WVSAISASGGSTYYADSVKGRFTI SRDNSKNTLYLQMNSLRAEDTAV YYCARLSWSGAFDNWGQGTLVT VSS (SEQ ID NO: 363) |
| P1A11 | EIVLTQSPGTLSLSPGERATLSCR ASQNVSSSYLAWYQQKPGQAP RLLIYGASYRATGIPDRFSGSGS GTDFTLTISRLEPEDFAVYYCQH YGSPPSFTFGQGTKVEIK (SEQ ID NO: 364) | EVQLLESGGGLVQPGGSLRLSCA ASGFTFRSYAMSWVRQAPGKGLE WVSAISGSGGSTFYADSVKGRFTI SRDNSKNTLYLQMNSLRAEDTAV YYCATVGTSGAFGIWGQGTLVTV SS (SEQ ID NO: 365) |

In Table 1, the underlined sequences are CDR sequences according to Kabat and in bold according to Chothia, except for the following heavy chain CDR2 sequences, in which the Chothia CDR sequences are underlined and the Kabat CDR sequences are in bold:
P5A2_VHVL, A02_Rd4_0.6nM_C06, A02_Rd4_0.6nM_C09
A02_Rd4_6nM_C16, A02_Rd4_6nM_C03, A02_Rd4_6nM_C01, A02_Rd4_6nM_C26
A02_Rd4_6nM_C25, A02_Rd4_6nM_C22, A02_Rd4_6nM_C19, A02_Rd4_0.6nM_C03
A02_Rd4_6nM_C07, A02_Rd4_6nM_C23, A02_Rd4_0.6nM_C18, A02_Rd4_6nM_C10
A02_Rd4_6nM_C05, A02_Rd4_0.6nM_C10, A02_Rd4_6nM_C04, A02_Rd4_0.6nM_C26
A02_Rd4_0.6nM_C1 A02_Rd4_0.6nM_C01, A02_Rd4_6nM_C08, P5C1_VHVL, C01_Rd4_6nM_C24, C01_Rd4_6nM_C26, C01_Rd4_6nM_C10, C01_Rd4_0.6nM_C27 C01_Rd4_6nM_C20, C01_Rd4_6nM_C12, C01_Rd4_0.6nM_C16, C01_Rd4_0.6nM_C09
C01_Rd4_6nM_C09, C01_Rd4_0.6nM_C03, C01_Rd4_0.6nM_C06, C01_Rd4_6nM_C04 COMBO_Rd4_0.6nM_C22, COMBO_Rd4_6nM_C21, COMBO_Rd4_6nM_C1 COMBO_Rd4_0.6nM_C04, COMBO_Rd4_6nM_C25, COMBO_Rd4_0.6nM_C21, COMBO_Rd4_6nM_C11, COMBO_Rd4_0.6nM_C20, COMBO_Rd4_6nM_C09, COMBO_Rd4_6nM_C08, COMBO_Rd4_0.6nM_C1 COMBO_Rd4_0.6nM_C02, COMBO_Rd4_0.6nM_C23, COMBO_Rd4_0.6nM_C29, COMBO_Rd4_0.6nM_C09, COMBO_Rd4_6nM_C12, COMBO_Rd4_0.6nM_C30, COMBO_Rd4_0.6nM_C14, COMBO_Rd4_6nM_C07, COMBO_Rd4_6nM_C02, COMBO_Rd4_0.6nM_C05, COMBO_Rd4_0.6nM_C17, COMBO_Rd4_6nM_C22, and COMBO_Rd4_0.6nM_C11.

The invention also provides CDR portions of antibodies to BCMA (including Chothia, Kabat CDRs, and CDR contact regions). Determination of CDR regions is well within the skill of the art. It is understood that in some embodiments, CDRs can be a combination of the Kabat and Chothia CDR (also termed "combined CRs" or "extended CDRs"). In some embodiments, the CDRs are the Kabat CDRs. In other embodiments, the CDRs are the Chothia CDRs. In other words, in embodiments with more than one CDR, the CDRs may be any of Kabat, Chothia, combination CDRs, or combinations thereof. Table 2 provides examples of CDR sequences provided herein.

TABLE 2

| | Heavy Chain | | |
|---|---|---|---|
| mAb | CDRH1 | CDRH2 | CDRH3 |
| P6E01 For the following mAbs: P6E01/P6E 01; L1.LGF/ L3.KW/P6E 01; L1.LGF/L3. NY/P6E01; L1.GDF/L3. NY/P6E01; L3.KW/P6E 01; L3.PY/P6E 01; L3.NY/P6E 01; L3.PY/L1.P S/P6E01; L3.PY/L1.A H/P6E01; L3.PY/L1.F F/P6E01; L3.PY/L1.P | SYAMT (SEQ ID NO: 129) (Kabat); GFTFGSY (SEQ ID NO: 130) (Chothia); GFTFGSYAMT (SEQ ID NO: 131) (extended) | AISGSGGNTFYADSVKG (SEQ ID NO: 132) (Kabat); SGSGGN (SEQ ID NO: 133) (Chothia) | VSPIASGMDY (SEQ ID NO: 134) |

TABLE 2-continued

| | | | |
|---|---|---|---|
| H/P6E01:<br>L3.PY/L3.K<br>Y/P6E01;<br>L3.PY/L3.K<br>F/P6E01;<br>and<br>L3.PY/P6E<br>1 | | | |
| H3.AQ<br>For the<br>following<br>mAbs:<br>P6E01/H3.<br>AQ;<br>L1.LGF/L3.<br>KW/H3.AQ;<br>L1.LGF/L3.<br>PY/H3.AQ;<br>L1.LGF/L3.<br>NY/H3.AQ;<br>L1.GDF/L3.<br>KW/H3.AQ;<br>L1.GDF/L3.<br>PY/H3.AQ;<br>L1.GDF/L3.<br>NY/H3.AQ;<br>L3.PY/H3.A<br>Q;<br>L3.PY/L1.P<br>S/H3.AQ;<br>L3.PY/L1.A<br>H/H3.AQ;<br>L3.PY/L1.F<br>F/H3.AQ;<br>L3.PY/L1.P<br>H/H3.AQ;<br>and<br>L3.PY/L3.K<br>F/H3.AQ. | SYAMT (SEQ ID NO: 129) (Kabat);<br>GFTFGSY (SEQ ID NO: 130) (Chothia);<br>GFTFGSYAMT (SEQ ID NO: 131) (extended) | AISGSGGNTFYADSVKG (SEQ ID NO: 132) (Kabat)<br>SGSGGN (SEQ ID NO: 133) (Chothia) | VSPIAAQMDY (SEQ ID NO: 135) |
| H3.AL<br>For the<br>following<br>mAbs:<br>L1.LGF/L3.<br>KW/H3.AL;<br>L1.LGF/L3.<br>NY/H3.AL;<br>and<br>L1.GDF/L3.<br>NY/H3.AL. | SYAMT (SEQ ID NO: 129) (Kabat);<br>GFTFGSY (SEQ ID NO: 130) (Chothia);<br>GFTFGSYAMT (SEQ ID NO: 131) (extended) | AISGSGGNTFYADSVKG (SEQ ID NO: 132) (Kabat)<br>SGSGGN (SEQ ID NO:133) (Chothia) | VSPIAALMDY (SEQ ID NO: 136) |
| H3.AP<br>For the<br>following<br>mAbs:<br>L1.LGF/L3.<br>KW/H3.AP;<br>L1.LGF/L3.<br>PY/H3.AP;<br>L1.LGF/L3<br>NY/H3.AP:<br>L1.GDF/L3.<br>KW/H3.AP;<br>and<br>L1.GDF/L3<br>NY/H3.AP. | SYAMT (SEQ ID NO: 129) (Kabat);<br>GFTFGSY (SEQ ID NO: 130) (Chothia);<br>GFTFGSYAMT (SEQ ID NO: 131) (extended) | AISGSGGNTFYADSVKG (SEQ ID NO: 132) (Kabat)<br>SGSGGN (SEQ ID NO: 133) (Chothia) | VSPIAAPMDY (SEQ ID NO: 137) |
| H2.QR<br>For the<br>following<br>mAbs:<br>L3.PY/H2.<br>QR;<br>L3.PY/L1.P<br>S/H2.QR;<br>L3.PY/ L1.A<br>H/H2.QR;<br>L3.PY/L1.F | SYAMT (SEQ ID NO: 129) (Kabat);<br>GFTFGSY (SEQ ID NO: 130) (Chothia);<br>GFTFGSYAMT (SEQ ID NO: 131) (extended) | AISGSGGNTFYADQRKG (SEQ ID NO: 138) (Kabat)<br>SGSGGN (SEQ ID NO: 133) (Chothia) | VSPIASGMDY (SEQ ID NO: 134) |

TABLE 2-continued

| | | | |
|---|---|---|---|
| F/H2.QR;<br>L3.PY/L1.P<br>H/H2.QR;<br>and<br>L3.PY/L3.K<br>Y/H2.QR. | | | |
| H2.DY<br>For the<br>following<br>mAbs:<br>L3.PY/H2.DY;<br>L3.PY/L1.P<br>S/H2.DY;<br>L3.PY/L1.A<br>H/H2.DY;<br>L3.PY/L1.F<br>F/H2.DY;<br>L3.PY/L3.K<br>Y/H2.DY;<br>and<br>L3.PY/L3.K<br>F/H2.DY. | SYAMT (SEQ ID NO:<br>129) (Kabat);<br>GFTFGSY (SEQ ID<br>NO: 130) (Chothia);<br>GFTFGSYAMT (SEQ<br>ID NO: 131)<br>(extended) | AIDYSGGNTFYADSVKG<br>(SEQ ID NO: 139) (Kabat)<br>DYSGGN (SEQ ID NO: 140)<br>(Chothia) | VSPIASGMDY<br>(SEQ ID NO: 134) |
| H2.YQ<br>For the<br>following<br>mAbs:<br>L3.PY/H2.YQ;<br>L3.PY/L1.P<br>S/H2.YQ;<br>L3.PY/L1.A<br>H/H2.YQ;<br>L3.PY/L1.F<br>F/H2.YQ;<br>L3.PY/L3.K<br>Y/H2.YQ;<br>and<br>L3.PY/L3.K<br>F/H2.YQ. | SYAMT (SEQ ID NO:<br>129) (Kabat);<br>GFTFGSY (SEQ ID<br>NO: 130) (Chothia);<br>GFTFGSYAMT (SEQ<br>ID NO: 131)<br>(extended) | AISYQGGNTFYADSVKG<br>(SEQ ID NO: 141) (Kabat)<br>SYQGGN (SEQ ID NO: 142)<br>(Chothia) | VSPIASGMDY<br>(SEQ ID NO: 134) |
| H2.LT<br>For the<br>following<br>mAbs:<br>L3.PY/H2.L<br>T;<br>L3.PY/L1.P<br>S/H2.LT;<br>L3.PY/L1.A<br>H/H2.LT;<br>L3.PY/L1.F<br>F/H2.LT<br>L3.PY/L3.K<br>Y/H2.LT;<br>and<br>L3.PY/L3.K<br>F/H2.LT. | SYAMT (SEQ ID NO:<br>129) (Kabat);<br>GFTFGSY (SEQ ID<br>NO: 130) (Chothia);<br>GFTFGSYAMT (SEQ<br>ID NO: 131)<br>(extended) | AISLTGGNTFYADSVKG<br>(SEQ ID NO: 143)<br>(Kabat)<br>SLTGGN<br>(SEQ ID NO: 144)<br>(Chothia) | VSPIASGMDY<br>(SEQ ID NO: 134) |
| H2.HA<br>For the<br>following<br>mAbs:<br>L3.PY/H2.<br>HA;<br>L3.PY/L1.<br>AH/H2.HA;<br>L3.PY/L1.F<br>F/H2.HA;<br>L3.PY/L1.P<br>H/H2.HA;<br>and<br>L3.PY/L3.K<br>Y/H2.HA. | SYAMT (SEQ ID NO:<br>129) (Kabat);<br>GFTFGSY (SEQ ID<br>NO: 130) (Chothia);<br>GFTFGSYAMT (SEQ<br>ID NO: 131)<br>(extended) | AISHAGGNTFYADSVKG<br>(SEQ ID NO: 145)<br>(Kabat)<br>SHAGGN<br>(SEQ ID NO: 146)<br>(Chothia) | VSPIASGMDY<br>(SEQ ID NO: 134) |

TABLE 2-continued

| | | | |
|---|---|---|---|
| H2.QL For the following mAbs: L3.PY/H2.QL; L3.PY/L1.PS/H2.QL; L3.PY/L1.AH/H2.QL; L3.PY/L1.FF/H2.QL; L3.PY/L3.KY/H2.QL; and L3.PY/L3.KF/H2.QL. | SYAMT (SEQ ID NO: 129) (Kabat); GFTFGSY (SEQ ID NO: 130) (Chothia); GFTFGSYAMT (SEQ ID NO: 131) (extended) | AISGSGGNTFYADQLKG (SEQ ID NO: 147) (Kabat) SGSGGN (SEQ ID NO: 133) (Chothia) | VSPIASGMDY (SEQ ID NO: 134) |
| H3.YA For the following mAbs: L3.PY/H3.YA; L3.PY/L1.PS/H3.YA; L3.PY/L1.AH/H3.YA; L3.PY/L1.FF/H3.YA; L3.PY/L3.KY/H3.YA; and L3.PY/L3.KF/H3.YA. | SYAMT (SEQ ID NO: 129) (Kabat); GFTFGSY (SEQ ID NO: 130) (Chothia); GFTFGSYAMT (SEQ ID NO: 131) (extended) | AISGSGGNTFYADSVKG (SEQ ID NO: 132) (Kabat) SGSGGN (SEQ ID NO: 133) (Chothia) | VSPIYAGMDY (SEQ ID NO: 148) |
| H3.AE For the following mAbs: L3.PY/H3.AE; L3.PY/L1.AH/H3.AE; L3.PY/L1.FF/H3.AE; L3.PY/L1.PH/H3.AE; and L3.PY/L3.KF/H3.AE. | SYAMT (SEQ ID NO: 129) (Kabat); GFTFGSY (SEQ ID NO: 130) (Chothia); GFTFGSYAMT (SEQ ID NO: 131) (extended) | AISGSGGNTFYADSVKG (SEQ ID NO: 132) (Kabat) SGSGGN (SEQ ID NO: 133) (Chothia) | VSPIAAEMDY (SEQ ID NO: 149) |
| H3.TAQ For the following mAbs: L3.PY/H3.TAQ; L3.PY/L1.PS/H3.TAQ; L3.PY/L1.AH/H3.TAQ; L3.PY/L1.FF/H3.TAQ; L3.PY/L1.PH/H3.TAQ; and L3.PY/L3.KF/H3.TAQ. | SYAMT (SEQ ID NO: 129) (Kabat); GFTFGSY (SEQ ID NO: 130) (Chothia); GFTFGSYAMT (SEQ ID NO: 131) (extended) | AISGSGGNTFYADSVKG (SEQ ID NO: 132) (Kabat) SGSGGN (SEQ ID NO: 133) (Chothia) | VSPIAAQMDY (SEQ ID NO: 135) |
| P5A2_VH VL and A02_Rd4_6nM_C03 | SYAMN (SEQ ID NO: 150) (Kabat); GFTFSSY (SEQ ID NO: 151) (Chothia); GFTFSSYAMN (SEQ ID NO: 152) (extended) | AISDSGGSTYYADSVKG (SEQ ID NO: 153) (Kabat) SDSGGS (SEQ ID NO: 154) (Chothia) | YWPMDI (SEQ ID NO: 155) |

TABLE 2-continued

| | | | |
|---|---|---|---|
| COMBO_Rd4_0.6nM_C17; COMBO_Rd4_0.6nM_C14; COMBO_Rd4_0.6nM_C29; and COMBO_Rd4_0.6nM_C09 | SYPMS (SEQ ID NO: 156) (Kabat); GFTFSSY (SEQ ID NO: 151) (Chothia); GFTFSSYPMS (SEQ ID NO: 157) (extended) | AIGGSGGSLPYADSVKG (SEQ ID NO: 158) (Kabat) GGSGGS (SEQ ID NO: 159) (Chothia) | YWPMDI (SEQ ID NO: 155) |
| C01_Rd4_6nM_C04; C01_Rd4_0.6nM_C03; C01_Rd4_0.6nM_C06; COMBO_Rd4_0.6nM_C02; COMBO_Rd4_6nM_C21; C01_Rd4_6nM_C26; COMBO_Rd4_0.6nM_C19; C01_Rd4_6nM_C24; C01_Rd4_6nM_C20; C01_Rd4_0.6nM_C09; COMBO_Rd4_0.6nM_C21; C01_Rd4_0.6nM_C04_C27 C01_Rd4_0.6nM_C16; C01_Rd4_6nM_C10; COMBO Rd4_0.6nM_C20 | SYPMS (SEQ ID NO: 156) (Kabat); GFTFSSY (SEQ ID NO: 151) (Chothia); GFTFSSYPMS (SEQ ID NO: 157) (extended) | AIGGSGGSLPYADSVKG (SEQ ID NO: 158) (Kabat) GGSGGS (SEQ ID NO: 159) (Chothia) | YWPMDS (SEQ ID NO: 161) |
| P5C1_VHVL and COMBO_Rd4_0.6nM_C30 | SYPMS (SEQ ID NO: 156) (Kabat); GFTFSSY (SEQ ID NO: 151) (Chothia); GFTFSSYPMS (SEQ ID NO: 157) (extended) | AIGGSGGSTYYADSVKG (SEQ ID NO: 162) (Kabat) GGSGGS (SEQ ID NO: 159) (Chothia) | YWPMDS (SEQ ID NO: 161) |
| A02_Rd4_0.6nM_C06 | SYAMN (SEQ ID NO: 150) (Kabat); GFTFSSY (SEQ ID NO: 151) (Chothia); GFTFSSYAMN (SEQ ID NO: 152) (extended) | AISDSGGSAWYADSVKG (SEQ ID NO: 163) (Kabat) SDSGGS (SEQ ID NO: 154) (Chothia) | YWPMSL (SEQ ID NO: 164) |

TABLE 2-continued

| | | | |
|---|---|---|---|
| A02_Rd4_ 0.6nM_ C09 | SYAMN (SEQ ID NO: 150) (Kabat); GFTFSSY (SEQ ID NO: 151) (Chothia); GFTFSSYAMN (SEQ ID NO: 152) (extended) | AISDSGGSAWYADSVKG (SEQ ID NO: 163) (Kabat) SDSGGS (SEQ ID NO: 154) (Chothia) | YWPMSL (SEQ ID NO: 164) |
| A02_Rd4_ 0.6nM_ C16 | SYAMN (SEQ ID NO: 150) (Kabat); GFTFSSY (SEQ ID NO: 151) (Chothia); GFTFSSYAMN (SEQ ID NO: 152) (extended) | AISDFGGSTYYADSVKG (SEQ ID NO: 165) (Kabat) SDFGGS (SEQ ID NO: 166) (Chothia) | YWPMDI (SEQ ID NO: 155) |
| A02_Rd4_ 6nM_ C01 | SYAMN (SEQ ID NO: 150) (Kabat); GFTFSSY (SEQ ID NO: 151) (Chothia); GFTFSSYAMN (SEQ ID NO: 152) (extended) | AITASGGSTYYADSVKG (SEQ ID NO: 167) (Kabat) TASGGS (SEQ ID NO: 168) (Chothia) | YWPMSL (SEQ ID NO: 164) |
| A02_Rd4_ 6nM_C26 | SYAMN (SEQ ID NO: 150) (Kabat); GFTFSSY (SEQ ID NO: 151) (Chothia); GFTFSSYAMN (SEQ ID NO: 152) (extended) | AISDSGGSTYYADSVKG (SEQ ID NO: 153) (Kabat) SDSGGS (SEQ ID NO: 154) (Chothia) | YWPMSL (SEQ ID NO: 164) |
| A02_Rd4_ 6nM_C25 | SYAMN (SEQ ID NO: 150) (Kabat); GFTFSSY (SEQ ID NO: 151) (Chothia); GFTFSSYAMN (SEQ ID NO: 152) (extended) | AISDSGGSRWYADSVKG (SEQ ID NO: 169) (Kabat) SDSGGS (SEQ ID NO: 154) (Chothia) | YWPMTP (SEQ ID NO: 170) |
| A02_Rd4_ 6nM_C22 | SYAMN (SEQ ID NO: 150) (Kabat); GFTFSSY (SEQ ID NO: 151) (Chothia); GFTFSSYAMN (SEQ ID NO: 152) (extended) | AVLDSGGSTYYADSVKG (SEQ ID NO: 171) (Kabat) LDSGGS (SEQ ID NO: 172) (Chothia) | YWPMTP (SEQ ID NO: 170) |
| A02_Rd4_ 6nM_C19 | SYAMN (SEQ ID NO: 150) (Kabat); GFTFSSY (SEQ ID NO: 151) (Chothia); GFTFSSYAMN (SEQ ID NO: 152) (extended) | AISDSGGSRWYADSVKG (SEQ ID NO: 169) (Kabat) SDSGGS (SEQ ID NO: 154) (Chothia) | YWPMSD (SEQ ID NO: 173) |
| A02_Rd4_ 0.6nM_ C03 | SYAMN (SEQ ID NO: 150) (Kabat); GFTFSSY (SEQ ID NO: 151) (Chothia); GFTFSSYAMN (SEQ ID NO: 152) (extended) | AISDSGGSKWYADSVKG (SEQ ID NO: 174) (Kabat) SDSGGS (SEQ ID NO: 154) (Chothia) | YWPMSL (SEQ ID NO: 164) |
| A02_Rd4_ 6nM_C07 | SYAMN (SEQ ID NO: 150) (Kabat); GFTFSSY (SEQ ID NO: 151) (Chothia); GFTFSSYAMN (SEQ ID NO: 152) (extended) | AIGGSGGSLPYADSVKG (SEQ ID NO: 158) (Kabat) GGSGGS (SEQ ID NO: 159) (Chothia) | YWPMDS (SEQ ID NO: 161) |
| A02_Rd4_ 6nM_C23 | SYAMN (SEQ ID NO: 150) (Kabat); GFTFSSY (SEQ ID NO: 151) (Chothia); GFTFSSYAMN (SEQ ID NO: 152) (extended) | AISDSGGSGWYADSVKG (SEQ ID NO: 175) (Kabat) SDSGGS (SEQ ID NO: 154) (Chothia) | YWPMSL (SEQ ID NO: 164) |

TABLE 2-continued

| | | | |
|---|---|---|---|
| A02_Rd4_0.6nM_C18 | SYAMN (SEQ ID NO: 150) (Kabat); GFTFSSY (SEQ ID NO: 151) (Chothia); GFTFSSYAMN (SEQ ID NO: 152) (extended) | AVLDSGGSTYYADSVKG (SEQ ID NO: 171) (Kabat) LDSGGS (SEQ ID NO: 172) (Chothia) | YWPMSL (SEQ ID NO: 164) |
| A02_Rd4_6nM_C10 | SYAMN (SEQ ID NO: 150) (Kabat); GFTFSSY (SEQ ID NO: 151) (Chothia); GFTFSSYAMN (SEQ ID NO: 152) (extended) | AISDSGGSCWYADSVKG (SEQ ID NO: 176) (Kabat) SDSGGS (SEQ ID NO: 154) (Chothia) | YWPMTP (SEQ ID NO: 170) |
| A02_Rd4_6nM_C05 | SYAMN (SEQ ID NO: 150) (Kabat); GFTFSSY (SEQ ID NO: 151) (Chothia); GFTFSSYAMN (SEQ ID NO: 152) (extended) | AIFASGGSTYYADSVKG (SEQ ID NO: 177) (Kabat) FASGGS (SEQ ID NO: 178) (Chothia) | YWPMTP (SEQ ID NO: 170) |
| A02_Rd4_0.6nM_C10 | SYAMN (SEQ ID NO: 150) (Kabat); GFTFSSY (SEQ ID NO: 151) (Chothia); GFTFSSYAMN (SEQ ID NO: 152) (extended) | AISGWGGSLPYADSVKG (SEQ ID NO: 304) (Kabat) SGWGGS (SEQ ID NO: 179) (Chothia) | YWPMDS (SEQ ID NO: 161) |
| A02_Rd4_6nM_C04 | SYAMN (SEQ ID NO: 150) (Kabat); GFTFSSY (SEQ ID NO: 151) (Chothia); GFTFSSYAMN (SEQ ID NO: 152) (extended) | AIMSSGGPLYYADSVKG (SEQ ID NO: 180) (Kabat) MSSGGP (SEQ ID NO: 181) (Chothia) | YWPMAL (SEQ ID NO: 182) |
| A02_Rd4_0.6nM_C26 | SYAMN (SEQ ID NO: 150) (Kabat); GFTFSSY (SEQ ID NO: 151) (Chothia); GFTFSSYAMN (SEQ ID NO: 152) (extended) | AILMSGGSTYYADSVKG (SEQ ID NO: 183) (Kabat) LMSGGS (SEQ ID NO: 184) (Chothia) | YWPMSL (SEQ ID NO: 164) |
| A02_Rd4_0.6nM_C13 | SYAMN (SEQ ID NO: 150) (Kabat); GFTFSSY (SEQ ID NO: 151) (Chothia); GFTFSSYAMN (SEQ ID NO: 152) (extended) | AISDSGGYRYYADSVKG (SEQ ID NO: 185) (Kabat) SDSGGY (SEQ ID NO: 186) (Chothia) | YWPMSL (SEQ ID NO: 164) |
| A02_Rd4_0.6nM_C01 | SYAMN (SEQ ID NO: 150) (Kabat); GFTFSSY (SEQ ID NO: 151) (Chothia); GFTFSSYAMN (SEQ ID NO: 152) (extended) | AILSSGGSTYYADSVKG (SEQ ID NO: 187) (Kabat) LSSGGS (SEQ ID NO: 188) (Chothia) | YWPMDI (SEQ ID NO: 155) |
| A02_Rd4_6nM_C08 | SYAMN (SEQ ID NO: 150) (Kabat); GFTFSSY (SEQ ID NO: 151) (Chothia); GFTFSSYAMN (SEQ ID NO: 152) (extended) | AILDSGGSTYYADSVKG (SEQ ID NO: 160) (Kabat) LDSGGS (SEQ ID NO: 172) (Chothia) | YWPMSP (SEQ ID NO: 189) |
| C01_Rd4_6nM_C12 | SYPMS (SEQ ID NO: 156) (Kabat); GFTFSSY (SEQ ID NO: 151) (Chothia); GFTFSSYPMS (SEQ ID NO: 157) (extended) | AIGGSGGWSYYADSVKG (SEQ ID NO: 190) (Kabat) GGSGGW (SEQ ID NO: 191) (Chothia) | YWPMDS (SEQ ID NO: 161) |

TABLE 2-continued

| | | | |
|---|---|---|---|
| C01_Rd4_6nM_C09 | SYPMS (SEQ ID NO: 156) (Kabat); GFTFSSY (SEQ ID NO: 151) (Chothia); GFTFSSYPMS (SEQ ID NO: 157) (extended) | ATVGGGSIGYADSVKG (SEQ ID NO: 192) (Kabat) VGSGGS (SEQ ID NO: 193) (Chothia) | YWPMDS (SEQ ID NO: 161) |
| COMBO_Rd4_0.6nM_C22 | SYAMN (SEQ ID NO: 150) (Kabat); GFTFSSY (SEQ ID NO: 151) (Chothia); GFTFSSYAMN (SEQ ID NO: 152) (extended) | AISDSGGSRWYADSVKG (SEQ ID NO: 169) (Kabat) SDSGGS (SEQ ID NO: 154) (Chothia) | YWPMDI (SEQ ID NO: 155) |
| COMBO_Rd4_0.6nM_C10 | SYPMS (SEQ ID NO: 156) (Kabat); GFTFSSY (SEQ ID NO: 151) (Chothia); GFTFSSYPMS (SEQ ID NO: 157) (extended) | AIGGSGGSIHYADSVKG (SEQ ID NO: 194) (Kabat) GGSGGS (SEQ ID NO: 159) (Chothia) | YWPMDS (SEQ ID NO: 161) |
| COMBO_Rd4_0.6nM_C04 | SYPMS (SEQ ID NO: 156) (Kabat); GFTFSSY (SEQ ID NO: 151) (Chothia); GFTFSSYPMS (SEQ ID NO: 157) (extended) | AHIGSGGSTYYADSVKG (SEQ ID NO: 195) (Kabat) IGSGGS (SEQ ID NO: 196) (Chothia) | YWPMDS (SEQ ID NO: 161) |
| COMBO_Rd4_0.6nM_C25 | SYPMS (SEQ ID NO: 156) (Kabat); GFTFSSY (SEQ ID NO: 151) (Chothia); GFTFSSYPMS (SEQ ID NO: 157) (extended) | AIGGSGGSTYYADSVKG (SEQ ID NO: 162) (Kabat) GGSGGS (SEQ ID NO: 159) (Chothia) | YWPMDP (SEQ ID NO: 197) |
| COMBO_Rd4_6nM_C21 | SYPMS (SEQ ID NO: 156) (Kabat); GFTFSSY (SEQ ID NO: 151) (Chothia); GFTFSSYPMS (SEQ ID NO: 157) (extended) | AIGGSGGSLPYADSVKG (SEQ ID NO: 158) (Kabat) GGSGGS (SEQ ID NO: 159) (Chothia) | YWPMDS (SEQ ID NO: 161) |
| COMBO_Rd4_6nM_C11 | SYPMS (SEQ ID NO: 156) (Kabat); GFTFSSY (SEQ ID NO: 151) (Chothia); GFTFSSYPMS (SEQ ID NO: 157) (extended) | AIGGSGGSLGYADSVKG (SEQ ID NO: 198) (Kabat) GGSGGS (SEQ ID NO: 159) (Chothia) | YWPMDS (SEQ ID NO: 161) |
| COMBO_Rd4_6nM_C09 | SYPMS (SEQ ID NO: 156) (Kabat); GFTFSSY (SEQ ID NO: 151) (Chothia); GFTFSSYPMS (SEQ ID NO: 157) (extended) | AIFASGGSTYYADSVKG (SEQ ID NO: 177) (Kabat) FASGGS (SEQ ID NO: 178) (Chothia) | YWPMDS (SEQ ID NO: 161) |
| COMBO_Rd4_6nM_C08 | SYPMS (SEQ ID NO: 156) (Kabat); GFTFSSY (SEQ ID NO: 151) (Chothia); GFTFSSYPMS (SEQ ID NO: 157) (extended) | AIGGSGTWTYYADSVKG (SEQ ID NO: 199) (Kabat) GGSGTW (SEQ ID NO: 200) (Chothia) | YWPMDS (SEQ ID NO: 161) |
| COMBO_Rd4_0.6nM_C23 | SYPMS (SEQ ID NO: 156) (Kabat); GFTFSSY (SEQ ID NO: 151) (Chothia); GFTFSSYPMS (SEQ ID NO: 157) (extended) | ALFGSGGSTYYADSVKG (SEQ ID NO: 201) (Kabat) FGSGGS (SEQ ID NO: 202) (Chothia) | YWPMDS (SEQ ID NO: 161) |

TABLE 2-continued

| | | | |
|---|---|---|---|
| COMBO_Rd4_0.6n M_C12 | SYPMS (SEQ ID NO: 156) (Kabat); GFTFSSY (SEQ ID NO: 151) (Chothia); GFTFSSYPMS (SEQ ID NO: 157) (extended) | AALGSGGSTYYADSVKG (SEQ ID NO: 203) (Kabat) LGSGGS (SEQ ID NO: 204) (Chothia) | YWPMDS (SEQ ID NO: 161) |
| COMBO_Rd4_6nM_ C07 | SYPMS (SEQ ID NO: 156) (Kabat); GFTFSSY (SEQ ID NO: 151) (Chothia); GFTFSSYPMS (SEQ ID NO: 157) (extended) | AIGGSGGSLPYADSVKG (SEQ ID NO: 158) (Kabat) GGSGGS (SEQ ID NO: 159) (Chothia) | YWPMAD (SEQ ID NO: 205) |
| COMBO_Rd4_6nM_ C02 | SYAMN (SEQ ID NO: 150) (Kabat); GFTFSSY (SEQ ID NO: 151) (Chothia); GFTFSSYAMN (SEQ ID NO: 152) (extended) | AISDSGGFVYYADSVKG (SEQ ID NO: 206) (Kabat) SDSGGF (SEQ ID NO: 207) (Chothia) | YWPMDS (SEQ ID NO: 161) |
| COMBO_Rd4_6nM_ C05 | SYAMN (SEQ ID NO: 150) (Kabat); GFTFSSY (SEQ ID NO: 151) (Chothia); GFTFSSYAMN (SEQ ID NO: 152) (extended) | AIGGSGGSTYYADSVKG (SEQ ID NO: 162) (Kabat) GGSGGS (SEQ ID NO: 159) (Chothia) | YWPMSL (SEQ ID NO: 164) |
| COMBO_Rd4_6nM_ C22 | SYAMN (SEQ ID NO: 150) (Kabat); GFTFSSY (SEQ ID NO: 151) (Chothia); GFTFSSYAMN (SEQ ID NO: 152) (extended) | ACLDSGGSTYYADSVKG (SEQ ID NO: 208) (Kabat) LDSGGS (SEQ ID NO: 172) (Chothia) | YWPMDS (SEQ ID NO: 161) |
| COMBO_Rd4_6nM_ C11 | SYPMS (SEQ ID NO 156) (Kabat); GFTFSSY (SEQ ID NO: 151) (Chothia); GFTFSSYPMS (SEQ ID NO: 157) (extended) | AALGSGGSTYYADSVKG (SEQ ID NO: 203) (Kabat) LGSGGS (SEQ ID NO: 204) (Chothia) | YWPMSL (SEQ ID NO: 164) |
| Heavy chain consensus | SYX$_1$MX$_2$, wherein X$_1$ is A or P; and X$_2$ is T, N, or S (Kabat) (SEQ ID NO: 301) GFTFX$_1$SY, wherein X$_1$ is G or S (Chothia) (SEQ ID NO: 302) GFTFX$_1$SYX$_2$MX$_3$, wherein X$_1$ is G or S, X$_2$ is A or P; and X$_3$ is T, N, or S (SEQ ID NO: 303) (extended) | AX$_1$X$_2$X$_3$X$_4$GX$_5$X$_6$X$_7$ X$_8$YADX$_9$X$_{10}$KG, wherein X$_1$ is I, V, T, H, L, A, or C; X$_2$ is S, D, G, T, I, L, F, M, or V; X$_3$ is G, Y, L, H, D, A, S, or M; X$_4$ is S, Q, T, A, F, or W; X$_5$ is G or T; X$_6$ is N, S, P, Y, W, or F; X$_7$ is S, T, I, L, A, R, V, K, G, or C; X$_8$ is F, Y, P, W, H, or G; X$_9$ is V, R, or L; and X$_{10}$ is G or T (Kabat) (SEQ ID NO: 305) X$_1$X$_2$X$_3$X$_4$X$_5$X$_6$ wherein X$_1$ is S, V, I, D, G, T, L, F, or M; X$_2$ is G, Y, L, H, D, A, S, or M; X$_3$ is S, G, F, or W; X$_4$ is G or S; X$_5$ is G or T; and X$_6$ is N, S, P, Y, or W (Chothia) (SEQ ID NO: 306) | VSPIX$_1$X$_2$X$_3$MDY wherein X$_1$ is A or Y; X$_2$ is A or S; and X$_3$ is G, Q, L, P, or E (SEQ ID NO: 307) YWPMX$_1$X$_2$, wherein X$_1$ is D, S, T, or A; and X$_2$ is I, S, L, P, or D (SEQ ID NO: 308) |

TABLE 2-continued

| mAb | | | |
|---|---|---|---|
| P4G4 | SYAMS (SEQ ID NO: 366) (Kabat); GFTFSSY (SEQ ID NO: 151) (Chothia); GFTFSSYAMS (SEQ ID NO: 367) (extended) | SASGGS (SEQ ID NO: 368) (Chothia) AISASGGSTYYADSVKG (SEQ ID NO: 369) (Kabat) | LSWSGAFDN (SEQ ID NO: 370) |
| P1A11 | SYAMS (SEQ ID NO: 366) (Kabat); GFTFRSY (SEQ ID NO: 371) GFTFRSYAMS (SEQ ID NO: 372) | SGSGGS (SEQ ID NO: 359) (Chothia) AISGSGGSTFYADSVKG (SEQ ID NO: 360) (Kabat) | VGTSGAFGI (SEQ ID NO: 361) |

Light Chain

| mAb | CDRL1 | CDRL2 | CDRL3 |
|---|---|---|---|
| P6E01 For the following mAbs: P6E01/P6E01; and P6E01/H3.AQ. | RASQSVSSSYLA (SEQ ID NO: 209) | GASSRAT (SEQ ID NO: 210) | QHYGSPPSFT (SEQ ID NO: 211) |
| L1.LGF/L3.KW For the following mAbs: L1.LGF/L3.KW/P6E0 L1.LGF/L3.KW/H3.A L1.LGF/L3.KW/H3.AP; and L1.LGF/L3.KW/H3.AQ | RASQSLGSFYLA (SEQ ID NO: 212) | GASSRAT (SEQ ID NO: 210) | KHYGWPPSFT (SEQ ID NO: 213) |
| L1.LGF/L3.NY For the following mAbs: L1.LGF/L3.NY/P6E0 L1.LGF/L3.NY/H3.AL | RASQSLGSFYLA (SEQ ID NO: 212) | GASSRAT (SEQ ID NO: 210) | QHYNYPPSFT (SEQ ID NO: 214) |
| L1.LGF/L3.NY/H3.AP; and L1.LGF/L3.NY/H3AQ L1.GDF/L3.NY For the following mAbs: L1.GDF/L3.NY/P6E01; L1.GDF/L3.NY/H3.A1. | RASQSVGDFYLA (SEQ ID NO: 215) | GASSRAT (SEQ ID NO: 210) | QHYNYPPSFT (SEQ ID NO: 214) |

TABLE 2-continued

| | | | |
|---|---|---|---|
| L,<br>L1.GDF/L<br>3.NY/H3.A<br>P; and<br>L1.GDF/L<br>3.NY/H3.<br>AQ | | | |
| L1.LGF/<br>L3.PY<br>For the<br>following<br>mAbs:<br>L1.LGF/L3.<br>PY/H3.<br>AP; and<br>L1.LGF/L3.<br>PY/H3.<br>AQ | RASQSLGSFYLA<br>(SEQ ID NO: 212)<br>RASQSVGDFYLA<br>(SEQ ID NO: 215) | GASSRAT (SEQ ID NO:<br>210)<br>GASSRAT (SEQ ID NO:<br>210) | QHYPYPPSFT<br>(SEQ ID NO: 216)<br>KHYGWPPSFT<br>(SEQ ID NO: 213) |
| L1.GDF/<br>L3.KW<br>For the<br>following<br>mAbs:<br>L1.GDF<br>/L3.KW/H3<br>.AL;<br>L1.GDF<br>/L3.KW/H3<br>AP; and<br>L1.GDF<br>/L3.KW/<br>H3.AQ | | | |
| L1.GDF/<br>L3.PY/<br>H3.AQ | RASQSVGDFYLA<br>(SEQ ID NO: 215) | GASSRAT (SEQ ID NO:<br>210) | QHYPYPPSFT<br>(SEQ ID NO: 216) |
| L3.KW/P<br>6E01 | RASQSVSSSYLA<br>(SEQ ID NO: 209) | GASSRAT (SEQ ID NO:<br>210) | KHYGWPPSFT<br>(SEQ ID NO: 213) |
| L3.PY<br>For the<br>following<br>mAbs:<br>L3.PY/P6<br>E01;<br>L3.PY/H2.<br>QR:<br>L3.PY/H2.<br>DY;<br>L3.PY/H2.<br>YQ;<br>L3.PY/H2.<br>LT;<br>L3.PY/H2.<br>HA;<br>L3.PY/H2.<br>QL;<br>L3.PY/H3.<br>YA;<br>L3.PY/H3.<br>AE;<br>L3.PY/H3.<br>AQ;<br>L3.PY/H3.<br>TAQ | RASQSVSSSYLA<br>(SEQ ID NO: 209) | GASSRAT (SEQ ID NO:<br>210) | QHYPYPPSFT<br>(SEQ ID NO: 216) |
| L3.NY/P<br>6E01 | RASQSVSSSYLA<br>(SEQ ID NO: 209) | GASSRAT (SEQ ID NO:<br>210) | QHYNYPPSFT<br>(SEQ ID NO: 214) |
| L3.PY/<br>L1.PS<br>For the<br>following<br>mAbs:<br>L3.PY/L1.<br>PS/<br>P6E01;<br>L3.PY/L1. | RASQSVSSSYPS<br>(SEQ ID NO: 217) | GASSRAT (SEQ ID NO:<br>210) | QHYPYPPSFT<br>(SEQ ID NO: 216) |

TABLE 2-continued

| | | | |
|---|---|---|---|
| PS/H2.QR L3.PY/L1. PS/H2.DY; L3.PY/L1. PS/H2.YQ L3.PY/L1. PS/H2.LT; L3.PY/L1. PS/H2.HA; L3.PY/L1. PS/H2.QL; L3.PY/L1. PS/H3.YA; L3.PY/L1. PS/H3.AE; L3.PY/L1. PS/H3.AQ L3.PY/L1. PS/H3.TAQ | | | |
| L3.PY/ L1.AH For the following mAbs: L3.PY/L1. AH/P6E01 L3.PY/L1. AH/H2.QR; L3.PY/L1. AH/H2.DY L3.PY/L1. AH/H2.YQ L3.PY/L1. AH/H2.LT; L3.PY/L1. AH/H2.HA; L3.PY/L1. AH/H2.QL; L3.PY/L1. AH/H3.YA; L3.PY/L1. AH/H3.AE; L3.PY/L1. AH/H3.AQ; L3.PY/L1. AH/H3.TAQ | RASQSVSAHYLA (SEQ ID NO: 218) | GASSRAT (SEQ ID NO: 210) | QHYPYPPSFT (SEQ ID NO: 216) |
| L3.PY/L1. FF For the following mAbs: L3.PY/L1. FF/P6E01; L3.PY/L1. FF/H2.QR; L3.PY/L1. FF/H2.DY; L3.PY/L1. FF/H2.YQ; L3.PY/L1. FF/H2.LT; L3.PY/L1. FF/H2.HA; L3.PY/L1. FF/H2.QL; L3.PY/L1. FF/H3.YA; L3.PY/L1. FF/H3.AE; L3.PY/L1. FF/H3.AQ; and L3.PY/L1. FF/H3.TAQ | RASQSVSSFFLA (SEQ ID NO: 219) | GASSRAT (SEQ ID NO: 210) | QHYPYPPSFT (SEQ ID NO: 216) |

TABLE 2-continued

| | | | |
|---|---|---|---|
| L3.PY/ L1.PH For the following mAbs: L3.PY/L1. PH/P6E01; L3.PY/L1. PH/H2.QR L3.PY/L1. PH/H2.HA; L3.PY/L1. PH/H3.AE; L3.PY/L1. PH/H3.AQ; and L3.PY/L1. PH/H3.TA Q | RASQSVSPHYLA (SEQ ID NO: 219) | GASSRAT (SEQ ID NO: 210) | QHYPYPPSFT (SEQ ID NO: 216) |
| L3.PY/L 3.KY For the following mAbs: L3.PY/L3. KY/P6E01 L3.PY/L3. KY/H2.QR L3.PY/L3. KY/H2.DY; L3.PY/L3. KY/H2. YQ; L3.PY/L3. KY/H2.LT L3.PY/L3. KY/H2. HA; L3.PY/L3. KY/H2. QL; L3.PY/L3. KY/H3.Y A; and L3.PY/L3. KY/H3.T AQ | RASQSVSSSYLA (SEQ ID NO: 209) | GASSRAT (SEQ ID NO: 210) | KYYPYPPSFT (SEQ ID NO: 220) |
| L3.PY/L3. KF For the following mAbs: L3.PY/L3. KF/H2.DY; L3.PY/L3. KF/H2.YQ; L3.PY/L3. KF/H2.LT; L3.PY/L3. KF/H2.QL; L3.PY/L3. KF/H3.YA; L3.PY/L3. KF/H3.AE; L3.PY/L3. KF/H3.AQ; and L3.PY/L3. KF/H3.TA Q | RASQSVSSSYLA (SEQ ID NO: 209) | GASSRAT (SEQ ID NO: 210) | KFYPYPPSFT(SEQ ID NO: 220) |
| P5A2_V HVL | RASQSVSSSYLA (SEQ ID NO: 209) | DASIRAT (SEQ ID NO: 221) | QQYGSWPLT (SEQ ID NO: 222) |
| A02_Rd 4_0.6nM_ C06 | RASQSVSVIYLA (SEQ ID NO: 223) | DASIRAT (SEQ ID NO: 221) | QQYQRWPLT (SEQ ID NO: 224) |

TABLE 2-continued

| | | | |
|---|---|---|---|
| A02_Rd4_0.6nM_C09; COMBO_Rd_0.6nM_C29; and COMBO_Rd4_0.6nM_C21 | RASQSVSSSYLA (SEQ ID NO: 209) | DASIRAT (SEQ ID NO: 221) | QQYQSWPLT (SEQ ID NO: 225) |
| A02_Rd4_6nM_C16 | RASQSVSDIYLA (SEQ ID NO: 226) | DASIRAT (SEQ ID NO: 221) | QQYQTWPLT (SEQ ID NO: 227) |
| A02_Rd4_6nM_C03 | RASQSVSNIYLA (SEQ ID NO: 228) | DASIRAT (SEQ ID NO: 221) | QQYQGWPLT (SEQ ID NO: 229) |
| A02_Rd4_6nM_C01 | RASQSVSAYYLA (SEQ ID NO: 230) | DASIRAT (SEQ ID NO: 221) | QQYERWPLT (SEQ ID NO: 231) |
| A02_Rd4_6nM_C26 | RASQSVSSIYLA (SEQ ID NO: 232) | DASIRAT (SEQ ID NO: 221) | QQYQVWPLT (SEQ ID NO: 233) |
| A02_Rd4_6nM_C25 | RASQSVSSSYLA (SEQ ID NO: 209) | DASIRAT (SEQ ID NO: 221) | QQYLDWPLT (SEQ ID NO: 234) |
| A02_Rd4_6nM_C22 | RASQSVSSSYLA (SEQ ID NO: 209) | DASIRAT (SEQ ID NO: 221) | QQYQVWPLT (SEQ ID NO: 233) |
| A02_Rd4_6nM_C19 | RASQSVSVIYLA (SEQ ID NO: 223) | DASIRAT (SEQ ID NO: 221) | QQYLAWPLT (SEQ ID NO: 236) |
| A02_Rd4_0.6nM_C03 | RASQSVSSSYLA (SEQ ID NO: 209) | DASIRAT (SEQ ID NO: 221) | QQYFTWPLT (SEQ ID NO: 237) |
| A02_Rd4_6nM_C07 | RASQSVSPYYLA (SEQ ID NO: 238) | DASIRAT (SEQ ID NO: 221) | QQYERWPLT (SEQ ID NO: 231) |
| A02_Rd4_6nM_C23 | RASQSVSVEYLA (SEQ ID NO: 239) | DASIRAT (SEQ ID NO: 221) | QQYARWPLT (SEQ ID NO: 240) |
| A02_Rd4_0.6nM_C18 | RASQSVSEIYLA (SEQ ID NO: 241) | DASIRAT (SEQ ID NO: 221) | QQYFGWPLT (SEQ ID NO: 242) |
| A02_Rd4_6nM_C10 | RASQSVEMSYLA (SEQ ID NO: 243) | DASIRAT (SEQ ID NO: 221) | QQYAHWPLT (SEQ ID NO: 244) |
| A02_Rd4_6nM_C05 | RASQSVSSSYLA (SEQ ID NO: 209) | DASIRAT (SEQ ID NO: 221) | QQYQRWPLT (SEQ ID NO: 224) |
| A02_Rd4_0.6nM_C10 | RASQSVSAQYLA (SEQ ID NO: 245) | DASIRAT (SEQ ID NO: 221) | QQYQRWPLT (SEQ ID NO: 224) |
| A02_Rd4_6nM_C04 | RASQSVSAIYLA (SEQ ID NO: 235) | DASIRAT (SEQ ID NO: 221) | QQYQVWPLT (SEQ ID NO: 233) |
| A02_Rd4_0.6nM_C26 | GPSQSVSSSYLA (SEQ ID NO: 246) | DASIRAT (SEQ ID NO: 221) | QQYQSWPLT (SEQ ID NO: 225) |
| A02_Rd4_0.6nM_C13 | RASQSVSSSYWA (SEQ ID NO: 247) | DASIRAT (SEQ ID NO: 221) | QQYESWPLT (SEQ ID NO: 248) |
| A02_Rd4_0.6nM_C01 | RGGQSVSSSYLA (SEQ ID NO: 249) | DASIRAT (SEQ ID NO: 221) | QQYQSWPLT (SEQ ID NO: 225) |

TABLE 2-continued

| | | | |
|---|---|---|---|
| A02_Rd4_6nM_C08 | RASQSVSFIYLA (SEQ ID NO: 250) | DASIRAT (SEQ ID NO: 221) | QQYGSWPLT (SEQ ID NO: 222) |
| P5C1_VHVL | RASQSVSSTYLA (SEQ ID NO: 251) | DASSRAP (SEQ ID NO: 252) | QQYSTSPLT (SEQ ID NO: 253) |
| C01_Rd4_6nM_C24 | RASQSVSPEYLA (SEQ ID NO: 254) | DASSRAP (SEQ ID NO: 252) | QQYSVWPLT (SEQ ID NO: 255) |
| C01_Rd4_6nM_C26 | RASQSVSAIYLA (SEQ ID NO: 235) | DASSRAP (SEQ ID NO: 252) | QQYSAWPLT (SEQ ID NO: 256) |
| C01_Rd4_6nM_C10 | RASQSVSSVYLA (SEQ ID NO: 257) | DASSRAP (SEQ ID NO: 252) | QQYSTWPLT (SEQ ID NO: 258) |
| C01_Rd4_0.6nM_C27 | RASQSVSSTYLA (SEQ ID NO: 251) | DASSRAP (SEQ ID NO: 252) | QQYSRWPLT (SEQ ID NO: 259) |
| C01_Rd4_6nM_C20 | RASQSVSPIYLA (SEQ ID NO: 260) | DASSRAP (SEQ ID NO: 252) | QQYSAFPLT (SEQ ID NO: 261) |
| C01_Rd4_6nM_C12 | WLSQSVSSTYLA (SEQ ID NO: 262) | DASSRAP (SEQ ID NO: 252) | QQYSEWPLT (SEQ ID NO: 263) |
| C01_Rd4_0.6nM_C16 | RASQSVSSTYLA (SEQ ID NO: 251) | DASSRAP (SEQ ID NO: 252) | QQYSSWPLT (SEQ ID NO: 264) |
| C01_Rd4_0.6nM_C09 | RASQSVSSIFLA (SEQ ID NO: 265) | DASSRAP (SEQ ID NO: 252) | QQYSAWPLT (SEQ ID NO: 256) |
| C01_Rd4_6nM_C09 | ACSQSVSSTYLA (SEQ ID NO: 266) | DASSRAP (SEQ ID NO: 252) | QQYSAWPLT (SEQ ID NO: 256) |
| C01_Rd4_0.6nM_C03 | RASCDVSSTYLA (SEQ ID NO: 267) | DASSRAP (SEQ ID NO: 252) | QQYMRSPLT (SEQ ID NO: 268) |
| C01_Rd4_0.6nM_C06 | RASEAVPSTYLA (SEQ ID NO: 269) | DASSRAP (SEQ ID NO: 252) | QQYSAFPLT (SEQ ID NO: 261) |
| C01_Rd4_0.6nM_C04 | CSSQSVSSTYLA (SEQ ID NO: 270) | DASSRAP (SEQ ID NO: 252) | QQYSAFPLT (SEQ ID NO: 261) |
| COMBO_Rd4_0.6nM_C22 | RASVRVSSTYLA (SEQ ID NO: 271) | DASIRAT (SEQ ID NO: 221) | QQYMKWPLT (SEQ ID NO: 272) |
| COMBO_Rd4_6nM_C21 | RASQSVSAAYLA (SEQ ID NO: 273) | DASIRAT (SEQ ID NO: 221) | QQYMCWPLT (SEQ ID NO: 274) |
| COMBO_Rd4_6nM_C10 | RASQSVSSSYWG (SEQ ID NO: 275) | DASIRAT (SEQ ID NO: 221) | QQYQCWPLT (SEQ ID NO: 276) |
| COMBO_Rd4_0.6nM_C04 | RASQSVSSTYLA (SEQ ID NO: 251) | DASIRAT (SEQ ID NO: 221) | QQYQSWPLT (SEQ ID NO: 225) |
| COMBO_Rd4_6nM_C25 | RASQSVSSPYLA (SEQ ID NO: 277) | DASIRAT (SEQ ID NO: 221) | QQYQSWPLT (SEQ ID NO: 225) |
| COMBO_Rd4_6nM_C11 | RASQSVSPIYLA (SEQ ID NO: 260) | DASIRAT (SEQ ID NO: 221) | QQYKAWPLT (SEQ ID NO: 278) |

TABLE 2-continued

| | | | |
|---|---|---|---|
| COMBO_Rd4_0.6nM_C20 | RASQSVSYLYLA (SEQ ID NO: 279) | DASIRAT (SEQ ID NO: 221) | QQYMEWPLT (SEQ ID NO: 280) |
| COMBO_Rd4_6nM_C09 | RASQSVSAQYLA (SEQ ID NO: 245) | DASIRAT (SEQ ID NO: 221) | QQYQAWPLT (SEQ ID NO: 281) |
| COMBO_Rd4_6nM_C08 | RASQSVSSSYLA (SEQ ID NO: 209) | DASIRAT (SEQ ID NO: 221) | QQYKWPLT (SEQ ID NO: 282) |
| COMBO_Rd4_0.6nM_C19 | RASQSVSAVYLA (SEQ ID NO: 283) | DASIRAT (SEQ ID NO: 221) | QQYRAWPLT (SEQ ID NO: 284) |
| COMBO_Rd4_0.6nM_C02 | RASIAVSSTYLA (SEQ ID NO: 285) | DASIRAT (SEQ ID NO: 221) | QQYMVWPLT (SEQ ID NO: 286) |
| COMBO_Rd4_0.6nM_C23 | RPRQSVSSSYLA (SEQ ID NO: 287) | DASIRAT (SEQ ID NO: 221) | QQYQDWPLT (SEQ ID NO: 288) |
| COMBO_Rd4_0.6nM_C09 | RASQSVSSTYLA (SEQ ID NO: 251) | DASIRAT (SEQ ID NO: 221) | QQYQEWPLT (SEQ ID NO: 289) |
| COMBO_Rd4_6nM_C12 | RASQSVSASYLA (SEQ ID NO: 290) | DASIRAT (SEQ ID NO: 221) | QQYMSWPLT (SEQ ID NO: 291) |
| COMBO_Rd4_0.6nM_C30 | RASQSVSYMYLA (SEQ ID NO: 292) | DASIRAT (SEQ ID NO: 221) | QQYKSWPLT (SEQ ID NO: 293) |
| COMBO_Rd4_0.6nM_C14 | RASQSVSAIYLA (SEQ ID NO: 235) | DASIRAT (SEQ ID NO: 221) | QQYYGWPLT (SEQ ID NO: 294) |
| COMBO_Rd4_6nM_C07 | RASQPISSSYLA (SEQ ID NO: 295) | DASIRAT (SEQ ID NO: 221) | QQYQGWPLT (SEQ ID NO: 229) |
| COMBO_Rd4_6nM_C02 | RASQSVSSSYLA (SEQ ID NO: 209) | DASIRAT (SEQ ID NO: 221) | QQYEFWPLT (SEQ ID NO: 296) |
| COMBO_Rd4_0.6nM_C05 | RASQSVSSTYLA (SEQ ID NO: 251) | DASIRAT (SEQ ID NO: 221) | QQYMSWPLT (SEQ ID NO: 291) |
| COMBO_Rd4_0.6nM_C17 | RASQGISSTYLA (SEQ ID NO: 297) | DASIRAT (SEQ ID NO: 221) | QQYAYWPLT (SEQ ID NO: 298) |
| COMBO_Rd4_6nM_C22 | RASQSVSSSYLA (SEQ ID NO: 209) | DASIRAT (SEQ ID NO: 221) | QQYQGWPLT (SEQ ID NO: 229) |
| COMBO_Rd4_0.6nM_C11 | RASQSVSVRYLA (SEQ ID NO: 299) | DASIRAT (SEQ ID NO: 221) | QQYGSWPIT (SEQ ID NO: 300) |
| Light chain consensus | $X_1X_2X_3X_4X_5X_6X_7X_8X_9X_{10}X_{11}X_{12}$, wherein $X_1$ is R, G, W, A, or C; $X_2$ is A, P, G, L, C, or S; and $X_3$ is S, G, or R; $X_4$ is Q, C, E, V, or I; $X_5$ is P, G, A, R, or D; $X_6$ is V, G, I, or L; $X_7$ is S, E, D, P, or G; $X_8$ is S, P, F, A, M, E, V, N, D, or Y; $X_9$ is I, T, V, E, F, S, | $X_1ASX_2RAX_3$, wherein $X_1$ is G or D; $X_2$ is S or I; and $X_3$ is T or P (SEQ ID NO: 310) | $X_1X_2YX_3X_4PPSFT$, wherein $X_1$ is Q or K; $X_2$ is H or Y; $X_3$ is G, N, or P; and $X_4$ is S, W, or Y (SEQ ID NO: 311) $QQYX_1X_2X_3PX_4T$, wherein $X_1$ is G, Q, E, L, F, A, S, M, K, R, or Y; $X_2$ is S, R, T, G, V, F, Y, D, A, H, V, E, K, or C; $X_3$ is W, F, or |

TABLE 2-continued

| | A, M, Q, Y, H, or R; X₁₀ is Y or F; X₁₁ is L, W, or P; and X₁₂ is A, S, or G (SEQ ID NO: 309) | | S; and X₄ is L or I (SEQ ID NO: 312) |
|---|---|---|---|
| P4G4 | RASQSVSSSYLA (SEQ ID NO: 209) | GASSRAY (SEQ ID NO: 362) | QHYGSPPLFT (SEQ ID NO: 499) |
| P1A11 | RASQNVSSSYLA (SEQ ID NO: 500) | GASYRAT (SEQ ID NO: 501) | QHYGSPPSFT (SEQ ID NO: 211) |

In some embodiments, the present invention provides an antibody that binds to BCMA and competes with the antibody as described herein, including P6E01/P6E01, P6E01/H3.AQ, L1.LGF/L3.KW/P6E01; L1.LGF/L3.NY/P6E01, L1.GDF/L3.NY/P6E01, L1.LGF/L3.KW/H3.AL, L1.LGF/L3.KW/H3.AP, L1.LGF/L3.KW/H3.AQ, L1.LGF/L3.PY/H3.AP, L1.LGF/L3.PY/H3.AQ, L1.LGF/L3.NY/H3.AL, L1.LGF/L3.NY/H3.AP, L1.LGF/L3.NY/H3.AQ, L1.GDF/L3.KW/H3.AL, L1.GDF/L3.KW/H3.AP, L1.GDF/L3.KW/H3.AQ, L1.GDF/L3.PY/H3.AQ, L1.GDF/L3.NY/H3.AL, L1.GDF/L3.NY/H3.AP, L1.GDF/L3.NY/H3.AQ, L3.KW/P6E01, L3.PY/P6E01, L3.NY/P6E01, L3.PY/L1.PS/P6E01, L3.PY/L1.AH/P6E01, L3.PY/L1.FF/P6E01, L3.PY/L1.PH/P6E01, L3.PY/L3.KY/P6E01, L3.PY/L3.KF/P6E01, L3.PY/H2.QR, L3.PY/H2.DY, L3.PY/H2.YQ, L3.PY/H2.LT, L3.PY/H2.HA, L3.PY/H2.QL, L3.PY/H3.YA, L3.PY/H3.AE, L3.PY/H3.AQ, L3.PY/H3.TAQ, L3.PY/P6E01, L3.PY/L1.PS/H2.QR, L3.PY/L1.PS/H2.DY, L3.PY/L1.PS/H2.YQ, L3.PY/L1.PS/H2.LT, L3.PY/L1.PS/H2.HA, L3.PY/L1.PS/H2.QL, L3.PY/L1.PS/H3.YA, L3.PY/L1.PS/H3.AE, L3.PY/L1.PS/H3.AQ, L3.PY/L1.PS/H3.TAQ, L3.PY/L1.AH/H2.QR, L3.PY/L1.AH/H2.DY, L3.PY/L1.AH/H2.YQ, L3.PY/L1.AH/H2.LT, L3.PY/L1.AH/H2.HA, L3.PY/L1.AH/H2.QL, L3.PY/L1.AH/H3.YA, L3.PY/L1.AH/H3.AE, L3.PY/L1.AH/H3.AQ, L3.PY/L1.AH/H3.TAQ, L3.PY/L1.FF/H2.QR, L3.PY/L1.FF/H2.DY, L3.PY/L1.FF/H2.YQ, L3.PY/L1.FF/H2.LT, L3.PY/L1.FF/H2.HA, L3.PY/L1.FF/H2.QL, L3.PY/L1.FF/H3.YA, L3.PY/L1.FF/H3.AE, L3.PY/L1.FF/H3.AQ, L3.PY/L1.FF/H3.TAQ, L3.PY/L1.PH/H2.QR, L3.PY/L1.PH/H2.DY, L3.PY/L1.PH/H2.HA, L3.PY/L1.PH/H2.QL, L3.PY/L1.PH/H3.YA, L3.PY/L1.PH/H3.AE, L3.PY/L1.PH/H3.AQ, L3.PY/L1.PH/H3.TAQ, L3.PY/L3.KY/H2.QR, L3.PY/L3.KY/H2.DY, L3.PY/L3.KY/H2.YQ L3.PY/L3.KY/H2.LT, L3.PY/L3.KY/H2.HA, L3.PY/L3.KY/H2.QL, L3.PY/L3.KY/H3.YA L3.PY/L3.KY/H3.TAQ, L3.PY/L3.KF/H2.DY, L3.PY/L3.KF/H2.YQ, L3.PY/L3.KF/H2.LT L3.PY/L3.KF/H2.QL, L3.PY/L3.KF/H3.YA, L3.PY/L3.KF/H3.AE, L3.PY/L3.KF/H3.AQ L3.PY/L3.KF/H3.TAQ, P5A2_VHVL, A02_Rd4_0.6nM_C06, A02_Rd4_0.6nM_C09 A02_Rd4_6nM_C16, A02_Rd4_6nM_C03, A02_Rd4_6nM_C01, A02_Rd4_6nM_C26 A02_Rd4_6nM_C25, A02_Rd4_6nM_C22, A02_Rd4_6nM_C1 A02_Rd4_0.6nM_C03 A02_Rd4_6nM_C07, A02_Rd4_6nM_C23, A02_Rd4_0.6nM_C18, A02_Rd4_6nM_C10 A02_Rd4_6nM_C05, A02_Rd4_0.6nM_C10, A02_Rd4_6nM_C04, A02_Rd4_0.6nM_C26 A02_Rd4_0.6nM_C1 A02_Rd4_6nM_C01, A02_Rd4_6nM_C08, P5C1_VHVL, C01_Rd4_6nM_C24, C01_Rd4_6nM_C26, C01_Rd4_6nM_C10, C01_Rd4_0.6nM_C27 C01_Rd4_6nM_C20, C01_Rd4_6nM_C12, C01_Rd4_0.6nM_C16, C01_Rd4_0.6nM_C09 C01_Rd4_6nM_C09, C01_Rd4_0.6nM_C03, C01_Rd4_0.6nM_C06, C01_Rd4_6nM_C04 COMBO_Rd4_0.6nM_C22, COMBO_Rd4_6nM_C21, COMBO_Rd4_6nM_C10, COMBO_Rd4_0.6nM_C04, COMBO_Rd4_6nM_C25, COMBO_Rd4_0.6nM_C21, COMBO_Rd4_6nM_C11, COMBO_Rd4_0.6nM_C20, COMBO_Rd4_6nM_C09, COMBO_Rd4_6nM_C08, COMBO_Rd4_0.6nM_C19, COMBO_Rd4_0.6nM_C02, COMBO_Rd4_0.6nM_C23, COMBO_Rd4_0.6nM_C29, COMBO_Rd4_0.6nM_C09, COMBO_Rd4_6nM_C12, COMBO_Rd4_0.6nM_C30, COMBO_Rd4_0.6nM_C14, COMBO_Rd4_6nM_C07, COMBO_Rd4_6nM_C02, COMBO_Rd4_0.6nM_C05, COMBO_Rd4_0.6nM_C17, COMBO_Rd4_6nM_C22, COMBO_Rd4_0.6nM_C11, COMBO_Rd4_0.6nM_C29, P4G4, or P1A11.

In some embodiments, the present invention provides an antibody or an antigen binding fragment, which specifically binds to BCMA, wherein the antibody comprises a VH region comprising a sequence shown in SEQ ID NO: 112; and/or a VL region comprising a sequence shown in SEQ ID NO: 38. In some embodiments, the antibody comprises a light chain comprising the sequence
(SEQ ID NO: 357)
EIVLTQSPGTLSLSPGERATLSCRASQSVSSSYLAWYQQKPGQAPRLLM

YDASIRATGIPDRFSGSGSGTDFTLTISRLEPEDFAVYYCQQYQSWPLT

FGQGTKVEIKRTVAAPSVFIFPPSDEQLKSGTASVVCLLNNFYPREAKV

QWKVDNALQSGNSQESVTEQDSKDSTYSLSSTLTLSKADYEKHKVYACE

VTHQGLSSPVTKSFNRGEC
and a heavy chain comprising the sequence
(SEQ ID NO: 358)
EVQLLESGGGLVQPGGSLRLSCAASGFTFSSYPMSWVRQAPGKGLEWVS

AIGGSGGSLPYADSVKGRFTISRDNSKNTLYLQMNSLRAEDTAVYYCAR

YWPMDIWGQGTLVTVSSASTKGPSVFPLAPSSKSTSGGTAALGCLVKDY

FPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTT

PPVLDSDGSFFLYSKLTVDKSRWQQGNVFSCSVMHEALHNHYTQKSLSL

SPGK.

In some embodiments, the present invention provides an antibody or an antigen binding fragment, which specifically bind to BCMA, wherein the antibody comprises a VH region comprising a sequence shown in SEQ ID NO: 2, 32, 42, or 78; and/or a VL region comprising a sequence shown in SEQ ID NO: 6, 16, 43, or 85.

In some embodiments, the invention also provides CDR portions of antibodies to BCMA antibodies based on CDR contact regions. CDR contact regions are regions of an antibody that imbue specificity to the antibody for an antigen. In general, CDR contact regions include the residue positions in the CDRs and Vernier zones which are constrained in order to maintain proper loop structure for the antibody to bind a specific antigen. See, e.g., Makabe et al., J. Biol. Chem., 283:1156-1166, 2007. Determination of CDR contact regions is well within the skill of the art.

The binding affinity ($K_D$) of the BCMA antibody as described herein to BCMA (such as human BCMA (e.g., (SEQ ID NO: 353) can be about 0.002 nM to about 6500 nM. In some embodiments, the binding affinity is about any of 6500 nm, 6000 nm, 5986 nm, 5567 nm, 5500 nm, 4500 nm, 4000 nm, 3500 nm, 3000 nm, 2500 nm, 2134 nm, 2000 nm, 1500 nm, 1000 nm, 750 nm, 500 nm, 400 nm, 300 nm, 250 nm, 200 nM, 193 nM, 100 nM, 90 nM, 50 nM, 45 nM, 40 nM, 35 nM, 30 nM, 25 nM, 20 nM, 19 nm, 18 nm, 17 nm, 16 nm, 15 nM, 10 nM, 8 nM, 7.5 nM, 7 nM, 6.5 nM, 6 nM, 5.5 nM, 5 nM, 4 nM, 3 nM, 2 nM, 1 nM, 0.5 nM, 0.3 nM, 0.1 nM, 0.01 nM, or 0.002 nM. In some embodiments, the binding affinity is less than about any of 6500 nm, 6000 nm, 5500 nm, 5000 nm, 4000 nm, 3000 nm, 2000 nm, 1000 nm, 900 nm, 800 nm, 250 nM, 200 nM, 100 nM, 50 nM, 30 nM, 20 nM, 10 nM, 7.5 nM, 7 nM, 6.5 nM, 6 nM, 5 nM, 4.5 nM, 4 nM, 3.5 nM, 3 nM, 2.5 nM, 2 nM, 1.5 nM, 1 nM, or 0.5 nM.

In some embodiments, the invention encompasses compositions, including pharmaceutical compositions, comprising antibodies described herein or made by the methods and having the characteristics described herein. As used herein, compositions comprise one or more antibodies that bind to BCMA, and/or one or more polynucleotides comprising sequences encoding one or more these antibodies. These compositions may further comprise suitable excipients, such as pharmaceutically acceptable excipients including buffers, which are well known in the art.

The invention also provides methods of making any of these antibodies. The antibodies of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an antibody could be produced by an automated polypeptide synthesizer employing the solid phase method. See also, U.S. Pat. Nos. 5,807,715; 4,816,567; and 6,331,415.

The invention also encompasses fusion proteins comprising one or more fragments or regions from the antibodies of this invention. In one embodiment, a fusion polypeptide is provided that comprises at least 10 contiguous amino acids of the variable light chain region shown in SEQ ID NOs: 1, 4, 5, 6, 9, 10, 11, 12, 13, 14, 15, 16, 17, 18, 19, 20, 21, 22, 23, 34, 36, 38, 40, 41, 43, 45, 47, 49, 51, 53, 55, 57, 59, 61, 63, 65, 67, 69, 71, 73, 75, 77, 79, 317, 81, 82, 84, 85, 86, 88, 89, 90, 91, 93, 94, 96, 98, 100, 102, 103, 105, 107, 108, 109, 111, 113, 115, 116, 117, 119, 121, 123, 124, 126, 128, 80, 315, 36, or 364, and/or at least 10 amino acids of the variable heavy chain region shown in SEQ ID NOs: 2, 3, 7, 8, 24, 25, 26, 27, 28, 29, 30, 31, 32, 33, 35, 37, 39, 42, 44, 46, 48, 50, 52, 54, 56, 58, 60, 62, 64, 66, 68, 70, 72, 74, 76, 78, 83, 87, 92, 95, 97, 99, 101, 104, 106, 110, 112, 114, 118, 120, 122, 112, 125, 127, 313, 314, 363, or 365. In other embodiments, a fusion polypeptide is provided that comprises at least about 10, at least about 15, at least about 20, at least about 25, or at least about 30 contiguous amino acids of the variable light chain region and/or at least about 10, at least about 15, at least about 20, at least about 25, or at least about 30 contiguous amino acids of the variable heavy chain region. In another embodiment, the fusion polypeptide comprises a light chain variable region and/or a heavy chain variable region, as shown in any of the sequence pairs selected from among SEQ ID NOs: 1 and 2, 1 and 3, 4 and 2, 5 and 2, 6 and 2, 4 and 7, 4 and 8, 4 and 3, 9 and 8, 9 and 3, 10 and 7, 10 and 8, 10 and 3, 11 and 7, 11 and 8, 11 and 3, 12 and 3, 13 and 7, 13 and 8, 14 and 3, 15 and 2, 16 and 2, 17 and 2, 18 and 2, 19 and 2, 20 and 2, 21 and 2, 22 and 2, 23 and 2, 16 and 24, 16 and 25, 16 and 26, 16 and 27, 16 and 28, 16 and 29, 16 and 30, 16 and 31, 16 and 3, 16 and 32, 16 and 2, 18 and 24, 18 and 25, 18 and 26, 18 and 27, 18 and 28, 18 and 29, 18 and 30, 18 and 31, 18 and 3, 18 and 32, 19 and 24, 19 and 25, 19 and 26, 19 and 27, 19 and 28, 19 and 29, 19 and 30, 19 and 31, 19 and 3, 19 and 32, 20 and 24, 20 and 25, 20 and 26, 20 and 27, 20 and 28, 20 and 29, 20 and 30, 20 and 31, 20 and 3, 20 and 32, 21 and 24, 21 and 28, 21 and 31, 21 and 3, 21 and 32, 22 and 24, 22 and 25, 22 and 26, 22 and 27, 22 and 28, 22 and 29, 22 and 30, 22 and 32, 23 and 25, 23 and 26, 23 and 27, 23 and 29, 23 and 30, 23 and 31, 23 and 3, 23 and 32, 34 and 33, 36 and 35, 38 and 37, 40 and 39, 41 and 33, 43 and 42, 45 and 44, 47 and 46, 49 and 48, 51 and 50, 53 and 52, 55 and 54, 57 and 56, 59 and 58, 61 and 60, 63 and 62, 65 and 64, 67 and 66, 69 and 68, 71 and 70, 73 and 72, 75 and 74, 77 and 76, 79 and 78, 317 and 78, 79 and 78, 81 and 78, 82 and 78, 84 and 83, 85 and 78, 86 and 78, 88 and 87, 89 and 78, 90 and 78, 91 and 78, 93 and 92, 94 and 78, 96 and 95, 98 and 97, 38 and 78, 102 and 101, 103 and 78, 105 and 104, 107 and 106, 108 and 78, 109 and 78, 111 and 110, 38 and 112, 113 and 112, 115 and 114, 116 and 76, 117 and 112, 119 and 118, 121 and 120, 123 and 122, 124 and 112, 126 and 125, 128 and 127, 80 and 363, or 364 and 365. In another embodiment, the fusion polypeptide comprises one or more CDR(s). In still other embodiments, the fusion polypeptide comprises CDR H3 (VH CDR3) and/or CDR L3 (VL CDR3). For purposes of this invention, a fusion protein contains one or more antibodies and another amino acid sequence to which it is not attached in the native molecule, for example, a heterologous sequence or a homologous sequence from another region. Exemplary heterologous sequences include, but are not limited to a "tag" such as a FLAG tag or a 6His tag. Tags are well known in the art.

The invention also provides isolated polynucleotides encoding the antibodies of the invention, and vectors and host cells comprising the polynucleotide.

In one embodiment, a polynucleotide comprises a sequence encoding the heavy chain and/or the light chain variable regions of antibody P6E01/P6E01, P6E01/H3.AQ, L1.LGF/L3.KW/P6E01; L1.LGF/L3.NY/P6E01, L1.GDF/L3.NY/P6E01, L1.LGF/L3.KW/H3.AL, L1.LGF/L3.KW/H3.AP, L1.LGF/L3.KW/H3.AQ, L1.LGF/L3.PY/H3.AP, L1.LGF/L3.PY/H3.AQ, L1.LGF/L3.NY/H3.AL, L1.LGF/L3.NY/H3.AP, L1.LGF/L3.NY/H3.AQ, L1.GDF/L3.KW/H3.AL, L1.GDF/L3.KW/H3.AP, L1.GDF/L3.KW/H3.AQ, L1.GDF/L3.PY/H3.AQ, L1.GDF/L3.NY/H3.AL, L1.GDF/L3.NY/H3.AP, L1.GDF/L3.NY/H3.AQ, L3.KW/P6E01, L3.PY/P6E01, L3.NY/P6E01, L3.PY/L1.PS/P6E01, L3.PY/L1.AH/P6E01, L3.PY/L1.FF/P6E01, L3.PY/L1.PH/P6E01, L3.PY/L3.KY/P6E01, L3.PY/L3.KF/P6E01, L3.PY/H2.QR, L3.PY/H2.DY, L3.PY/H2.YQ, L3.PY/H2.LT, L3.PY/H2.HA, L3.PY/H2.QL, L3.PY/H3.YA, L3.PY/H3.AE, L3.PY/H3.AQ, L3.PY/H3.TAQ, L3.PY/P6E01, L3.PY/L1.PS/H2.QR, L3.PY/L1.PS/H2.DY, L3.PY/L1.PS/H2.YQ, L3.PY/L1.PS/H2.LT, L3.PY/L1.PS/H2.HA, L3.PY/L1.PS/H2.QL, L3.PY/L1.PS/H3.YA, L3.PY/L1.PS/H3.AE, L3.PY/L1.PS/H3.AQ, L3.PY/L1.PS/H3.TAQ, L3.PY/L1.AH/H2.QR, L3.PY/L1.AH/H2.DY, L3.PY/L1.AH/H2.YQ, L3.PY/L1.AH/H2.LT, L3.PY/L1.AH/H2.HA, L3.PY/L1.AH/H2.QL, L3.PY/L1.AH/H3.YA, L3.PY/L1.AH/H3.AE, L3.PY/L1.AH/H3.AQ, L3.PY/L1.AH/H3.TAQ, L3.PY/L1.FF/H2.QR, L3.PY/L1.FF/H2.DY, L3.PY/L1.FF/H2.YQ, L3.PY/L1.FF/H2.LT, L3.PY/L1.FF/H2.HA, L3.PY/L1.FF/H2.QL, L3.PY/L1.FF/H3.YA, L3.PY/L1.FF/H3.AE, L3.PY/L1.FF/H3.AQ, L3.PY/L1.FF/H3.TAQ, L3.PY/L1.PH/H2.QR, L3.PY/L1.PH/H2.HA, L3.PY/L1.PH/H3.AE, L3.PY/L1.PH/H3.AQ, L3.PY/L1.PH/H3.TAQ, L3.PY/L3.KY/H2.QR, L3.PY/L3.KY/H2.DY, L3.PY/L3.KY/H2.YQ L3.PY/L3.KY/H2.LT, L3.PY/L3.KY/H2.HA, L3.PY/L3.KY/H2.QL, L3.PY/L3.KY/H3.YA L3.PY/L3.KY/H3.TAQ, L3.PY/L3.KF/H2.DY, L3.PY/L3.KF/H2.YQ, L3.PY/L3.KF/H2.LT L3.PY/L3.KF/H2.QL, L3.PY/L3.KF/H3.YA, L3.PY/L3.KF/H3.AE, L3.PY/L3.KF/H3.AQ L3.PY/L3.KF/H3.TAQ, P5A2_VHVL, A02_Rd4_0.6nM_C06, A02_Rd4_0.6nM_C09 A02_Rd4_6nM_C16, A02_Rd4_6nM_C03, A02_Rd4_6nM_C01, A02_Rd4_6nM_C26 A02_Rd4_6nM_C25, A02_Rd4_6nM_C22, A02_Rd4_6nM_C19, A02_Rd4_0.6nM_C03 A02_Rd4_6nM_C07, A02_Rd4_6nM_C23, A02_Rd4_0.6nM_C18, A02_Rd4_6nM_C10 A02_Rd4_6nM_C05, A02_Rd4_0.6nM_C10, A02_Rd4_6nM_C04, A02_Rd4_0.6nM_C26 A02_Rd4_0.6nM_C13, A02_Rd4_0.6nM_C01, A02_Rd4_6nM_C08, P5C1_VHVL, C01_Rd4_6nM_C24, C01_Rd4_6nM_C26, C01_Rd4_6nM_C10, C01_Rd4_0.6nM_C27 C01_Rd4_6nM_C20, C01_Rd4_6nM_C12, C01_Rd4_6nM_C16, C01_Rd4_0.6nM_C09 C01_Rd4_6nM_C09, C01_Rd4_6nM_C03, C01_Rd4_0.6nM_C06, C01_Rd4_6nM_C04 COMBO_Rd4_0.6nM_C22, COMBO_Rd4_6nM_C21, COMBO_Rd4_6nM_C1 COMBO_Rd4_0.6nM_C04, COMBO_Rd4_6nM_C25, COMBO_Rd4_0.6nM_C21, COMBO_Rd4_6nM_C11, COMBO_Rd4_0.6nM_C20, COMBO_Rd4_6nM_C09, COMBO_Rd4_0.6nM_C08, COMBO_Rd4_0.6nM_C1 COMBO_Rd4_0.6nM_C02, COMBO_Rd4_0.6nM_C23, COMBO_Rd4_0.6nM_C29, COMBO_Rd4_0.6nM_C09, COMBO_Rd4_6nM_C12, COMBO_Rd4_0.6nM_C30, COMBO_Rd4_6nM_C14, COMBO_Rd4_6nM_C07, COMBO_Rd4_6nM_C02, COMBO_Rd4_0.6nM_C05, COMBO_Rd4_0.6nM_C17, COMBO_Rd4_6nM_C22, COMBO_Rd4_0.6nM_C11, COMBO_Rd4_0.6nM_C29, P4G4, or P1A11. The sequence encoding the antibody of interest may be maintained in a vector in a host cell and the host cell can then be expanded and frozen for future use. Vectors (including expression vectors) and host cells are further described herein.

The invention also encompasses scFv of antibodies of this invention. Single chain variable region fragments are made by linking light and/or heavy chain variable regions by using a short linking peptide (Bird et al., Science 242:423-426, 1988). An example of a linking peptide is (GGGGS)$_3$ (SEQ ID NO: 498), which bridges approximately 3.5 nm between the carboxy terminus of one variable region and the amino terminus of the other variable region. Linkers of other sequences have been designed and used (Bird et al., 1988, supra). Linkers should be short, flexible polypeptides and preferably comprised of less than about 20 amino acid residues. Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

Other forms of single chain antibodies, such as diabodies or minibodies are also encompassed. Diabodies are bivalent, bispecific antibodies in which heavy chain variable (VH) and light chain variable (VL) domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., Proc. Natl. Acad Sci. USA 90:6444-6448, 1993; Poljak, R. J., et al., Structure 2:1121-1123, 1994). Minibody includes the VL and VH domains of a native antibody fused to the hinge region and CH3 domain of the immunoglobulin molecule. See, e.g., U.S. Pat. No. 5,837,821.

In another aspect, the invention provides compositions (such as a pharmaceutical compositions) comprising any of the polynucleotides of the invention. In some embodiments, the composition comprises an expression vector comprising a polynucleotide encoding any of the antibodies described herein. In still other embodiments, the composition comprises either or both of the polynucleotides shown in SEQ ID NO: 486 and SEQ ID NO: 485 below:

COMBO_Rd4_0.6 nM_C29 heavy chain variable region
(SEQ ID NO: 486)
GAAGTCCAACTCCTCGAATCCGGTGGCGGCCTTGTCCAGCCTGGAGGTTC

CTTGCGCCTGTCATGTGCCGCCAGCGGATTCACCTTCTCGTCCTACCCGA

TGTCGTGGGTCCGCCAGGCTCCGGGAAAGGGCCTGGAATGGGTGTCAGCC

ATCGGAGGATCGGGGGGCTCCCTGCCCTACGCCGATATCGTGAAGGGAAG

GTTCACCATTAGCCGGGACAACTCCAAGAACACTCTGTACCTCCAAATGA

ACAGCCTGAGAGCGGAGGACACCGCAGTGTACTATTGCGCCCGGTACTGG

CCAATGGACATCTGGGGCCAGGGGACTCTGGTCACCGTCTCCTCA

COMBO_Rd4_0.6 nM_C29 light chain variable region
(SEQ ID NO: 485)
GAGATCGTGCTGACTCAGTCCCCTGGAACCCTGTCCCTGTCACCTGGCGA

AAGAGCTACCTTGTCCTGTCGCGCATCACAATCCGTGTCGTCGAGCTATC

TCGCGTGGTACCAGCAGAAGCCCGGACAGGCCCCAAGGCTGCTTATGTAC

GACGCCTCCATCCGGGCCACTGGTATCCCCGACCGCTTCTCGGGCTCCGG

AAGCGGCACCGACTTCACCCTGACTATTTCCCGGCTCGAACCGGAGGATT

TCGCCGTGTACTACTGCCAACAGTACCAGAGCTGGCCGCTGACGTTTGGG

CAGGGGACCAAGGTCGAAATCAAA

In other embodiments, the composition comprises either or both of the polynucleotides shown in SEQ ID NO: 488 and SEQ ID NO: 487 below:

L3.PY/H3TAQ heavy chain variable region
(SEQ ID NO: 488)
GAAGTGCAGCTGCTGGAATCTGGCGGAGGACTGGTGCAGCCTGGCGGCTC

TCTGAGACTGTCTTGTGCCGCCAGCGGCTTCACCTTCGGCAGCTACGCTA

TGACCTGGGTGCGCCAGGCCCCTGGCAAAGGACTGGAATGGGTGTCCGCC

ATCTCTGGCAGCGGCGGCAATACCTTCTACGCCGAGAGCGTGAAGGGCCG

GTTCACCATCAGCCGGGACAACAGCAAGAACACCCTGTACCTGCAGATGA

ACAGCCTGCGGGCCGAGGACACCGCCGTGTACTATTGTACACGGGTGTCC

CCTATCGCCGCGCAGATGGATTATTGGGGCCAGGGCACTCTGGTCACCGT

CTCCTCA

L3.PY/H3TAQ heavy chain variable region
(SEQ ID NO: 487)
GAGATCGTGCTGACACAGAGCCCTGGCACCCTGAGCCTGTCTCCAGGCGA

AAGAGCCACCCTGTCCTGCAGAGCCAGCCAGAGCGTGTCCAGCAGCTACC

TGGCCTGGTATCAGCAGAAGCCCGGCCAGGCTCCCCGGCTGCTGATCTAT

GGCGCCTCTTCTAGAGCCACCGGCATCCCCGATAGATTCAGCGGCTCTGG

CAGCGGCACCGACTTCACCCTGACCATCAGCAGACTGGAACCCGAGGACT

TCGCCGTGTACTACTGCCAGCACTACCCTTATCCCCCCAGCTTCACATTT

GGCCAGGGCACCAAGGTGGAGATCAAA

In still other embodiments, the composition comprises either or both of the polynucleotides shown in SEQ ID NO: 490 and SEQ ID NO: 489 below:

A02_Rd4_0.6 nM_C01 heavy chain variable region
(SEQ ID NO: 490)
GAAGTTCAATTATTGGAATCTGGTGGAGGACTGGTGCAGCCTGGCGGCT

CTCTGAGACTGTCTTGTGCCGCCAGCGGCTTCACCTTCAGCAGCTACGC

CATGAACTGGGTGCGCCAGGCCCCTGGTAAAGGTTTGGAATGGGTTTCT

GCTATTACTGCGTCTGGTGGTTCTACTTACTATGCCGATGTGGTTAAGG

GTAGATTCACCATTTCTAGAGACAACTCTAAGAACACCTTGTACTTGCA

AATGAACTCCTTGAGAGCTGAAGATACTGCTGTTTATTACTGTGCTAGA

TACTGGCCAATGTCGTTGTGGGGTCAAGGTACTCTGGTCACCGTCTCCT

CA

A02_Rd4_0.6 nM_C01 light chain variable region
(SEQ ID NO: 489)
GAGATCGTGCTGACACAGAGCCCTGGCACCCTGAGCCTGTCTCCTGGTG

AAAGAGCTACTTTGTCTTGTAGAGCTTCTCAATCCGTTTCCGCGTATTA

TTTGGCTTGGTATCAACAAAAACCAGGTCAAGCTCCAAGATTATTGATG

TACGATGCTTCTATTAGAGCCACCGGTATTCCAGATAGATTTTCTGGTT

CTGGTTCCGGTACTGATTTCACTTTGACTATCTCTAGATTGGAACCAGA

AGATTTCGCTGTTTACTACTGTCAACAATATGAGCGTTGGCCATTGACT

TTTGGTCAAGGTACAAAGGTTGAAATCAAACGTGAG

In other embodiments, the composition comprises either or both of the polynucleotides shown in SEQ ID NO: 492 and SEQ ID NO: 491 below:

A02_Rd4_0.6 nM_C16 heavy chain variable region
(SEQ ID NO: 492)
GAAGTTCAATTATTGGAATCTGGTGGAGGACTGGTGCAGCCTGGCGGCT

CTCTGAGACTGTCTTGTGCCGCCAGCGGCTTCACCTTCAGCAGCTACGC

CATGAACTGGGTGCGCCAGGCCCCTGGTAAAGGTTTGGAATGGGTTTCT

GCTATTTCTGATTTTGGTGGTTCTACTTACTATGCCGATATCGTTAAGG

GTAGATTCACCATTTCTAGAGACAACTCTAAGAACACCTTGTACTTGCA

AATGAACTCCTTGAGAGCTGAAGATACTGCTGTTTATTACTGTGCTAGA

TACTGGCCAATGGATATTTGGGGTCAAGGTACTCTGGTCACCGTCTCCT

CA

A02_Rd4_0.6 nM_C16 light chain variable region
(SEQ ID NO: 491)
GAGATCGTGCTGACACAGAGCCCTGGCACCCTGAGCCTGTCTCCTGGTG

AAAGAGCTACTTTGTCTTGTAGAGCTTCTCAATCCGTTTCCGATCTGTA

TTTGGCTTGGTATCAACAAAAACCAGGTCAAGCTCCAAGATTATTGATG

TACGATGCTTCTATTAGAGCCACCGGTATTCCAGATAGATTTTCTGGTT

CTGGTTCCGGTACTGATTTCACTTTGACTATCTCTAGATTGGAACCAGA

AGATTTCGCTGTTTACTACTGTCAACAATATCAGACTTGGCCATTGACT

TTTGGTCAAGGTACAAAGGTTGAAATCAAACGTGAG.

Expression vectors, and administration of polynucleotide compositions are further described herein.

In another aspect, the invention provides a method of making any of the polynucleotides described herein.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratgene, and Invitrogen.

Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasm ids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*). Preferably, the host cells express the cDNAs at a level of about 5 fold higher, more preferably, 10 fold higher, even more preferably, 20 fold higher than that of the corresponding endogenous antibody or protein of interest, if present, in the host cells. Screening the host cells for a specific binding to BCMA or an BCMA domain (e.g., domains 1-4) is effected by an immunoassay or FACS. A cell overexpressing the antibody or protein of interest can be identified.

Representative materials of the present invention were deposited in the American Type Culture Collection (ATCC) on Apr. 15, 2015. Vector having ATCC Accession No. PTA-122094 is a polynucleotide encoding a humanized BCMA antibody heavy chain variable region, and vector having ATCC Accession No. PTA-122093 is a polynucleotide encoding a humanized BCMA antibody light chain variable region. The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. Section 122 and the Commissioner's rules pursuant thereto (including 37 C.F.R. Section 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

BCMA Antibody Conjugates

The present invention also provides a conjugate (or immunoconjugate) of the BCMA antibody as described herein, or of the antigen binding fragment thereof, wherein the antibody or the antigen binding fragment is conjugated to an agent (e.g., a cytotoxic agent) for targeted immunotherapy (e.g., antibody-drug conjugates) either directly or indirectly via a linker. For example, a cytotoxic agent can be linked or conjugated to the BCMA antibody or the antigen binding fragment thereof as described herein for targeted local delivery of the cytotoxic agent moiety to tumors (e.g., BCMA expressing tumor).

Methods for conjugating cytotoxic agent or other therapeutic agents to antibodies have been described in various publications. For example, chemical modification can be made in the antibodies either through lysine side chain amines or through cysteine sulfhydryl groups activated by reducing interchain disulfide bonds for the conjugation reaction to occur. See, e.g., Tanaka et al., FEBS Letters 579:2092-2096, 2005, and Gentle et al., Bioconjugate Chem. 15:658-663, 2004. Reactive cysteine residues engineered at specific sites of antibodies for specific drug conjugation with defined stoichiometry have also been described. See, e.g., Junutula et al., Nature Biotechnology, 26:925-932, 2008. Conjugation using an acyl donor glutamine-containing tag or an endogenous glutamine made reactive (i.e., the ability to form a covalent bond as an acyl donor) by polypeptide engineering in the presence of transglutaminase and an amine (e.g., a cytotoxic agent comprising or attached to a reactive amine) is also described in international applications WO2012/059882 and WO2015015448.

In some embodiments, the BCMA antibody or the conjugate as described herein comprises an acyl donor glutamine-containing tag engineered at a specific site of the antibody (e.g., a carboxyl terminus, an amino terminus, or at another site in the BCMA antibody). In some embodiments, the tag comprises an amino acid glutamine (Q) or an amino acid sequence LQG, LLQGG (SEQ ID NO:318), LLQG (SEQ ID NO:454), LSLSQG (SEQ ID NO: 455), GGGLLQGG (SEQ ID NO: 456), GLLQG (SEQ ID NO: 457), LLQ, GSPLAQSHGG (SEQ ID NO: 458), GLLQGGG (SEQ ID NO: 459), GLLQGG (SEQ ID NO: 460), GLLQ (SEQ ID NO: 461), LLQLLQGA (SEQ ID NO: 462), LLQGA (SEQ ID NO: 463), LLQYQGA (SEQ ID NO: 464), LLQGSG (SEQ ID NO: 465), LLQYQG (SEQ ID NO: 466), LLQLLQG (SEQ ID NO: 467), SLLQG (SEQ ID NO: 468), LLQLQ (SEQ ID NO: 469), LLQLLQ (SEQ ID NO: 470), LLQGR (SEQ ID NO: 471), LLQGPP (SEQ ID NO: 472), LLQGPA (SEQ ID NO: 473), GGLLQGPP (SEQ ID NO: 474), GGLLQGA (SEQ ID NO: 475), LLQGPGK (SEQ ID NO: 476), LLQGPG (SEQ ID NO: 477), LLQGP (SEQ ID NO: 478), LLQP (SEQ ID NO: 479), LLQPGK (SEQ ID NO: 480), LLQAPGK (SEQ ID NO:

481), LLQGAPG (SEQ ID NO: 482), LLQGAP (SEQ ID NO: 483), and LLQLQG (SEQ ID NO: 484).

In some embodiments, the BCMA antibody or the conjugate as described herein comprises an acyl donor glutamine-containing tag engineered at a specific site of the antibody, wherein the tag comprises an amino acid sequence GGLLQGPP (SEQ ID NO: 474) or GGLLQGA (SEQ ID NO: 475) engineered at the light chain carboxyl terminus of the BCMA antibody. In some embodiments, the BCMA antibody or the conjugate as described herein comprises an acyl donor glutamine-containing tag engineered at a specific site of the antibody, wherein the tag comprises an amino acid sequence LLQG (SEQ ID NO: 454) engineered after residue T135 in the heavy chain of the BCMA antibody. In other embodiments, the BCMA antibody or the conjugate as described herein comprises an acyl donor glutamine-containing tag engineered at a specific site of the antibody, wherein the tag comprises an amino acid sequence LLQGA (SEQ ID NO: 463) or LLQGPP (SEQ ID NO: 472) engineered at the heavy chain carboxyl terminus of the BCMA antibody and wherein the lysine residue at the heavy chain carboxyl terminus is deleted. In some embodiments, the BCMA antibody or the conjugate as described herein comprises an amino acid substitution at position 297 of the BCMA antibody (EU numbering scheme). For example, the amino acid asparagine (N) can be substituted with glutamine (Q) or alanine (A) at position 297 of the BCMA antibody.

Also provided is an isolated antibody comprising an acyl donor glutamine-containing tag and an amino acid modification at position 222, 340, or 370 of the antibody (EU numbering scheme) wherein the modification is an amino acid deletion, insertion, substitution, mutation, or any combination thereof. Accordingly, in some embodiments, provided is the BCMA antibody or the conjugate as described herein comprising the acyl donor glutamine-containing tag (e.g., Q, LQG, LLQGG (SEQ ID NO:318), LLQG (SEQ ID NO:454), LSLSQG (SEQ ID NO: 455), GGGLLQGG (SEQ ID NO: 456), GLLQG (SEQ ID NO: 457), LLQ, GSPLAQSHGG (SEQ ID NO: 458), GLLQGGG (SEQ ID NO: 459), GLLQGG (SEQ ID NO: 460), GLLQ (SEQ ID NO: 461), LLQLLQGA (SEQ ID NO: 462), LLQGA (SEQ ID NO: 463), LLQYQGA (SEQ ID NO: 464), LLQGSG (SEQ ID NO: 465), LLQYQG (SEQ ID NO: 466), LLQLLQG (SEQ ID NO: 467), SLLQG (SEQ ID NO: 468), LLQLQ (SEQ ID NO: 469), LLQLLQ (SEQ ID NO: 470), LLQGR (SEQ ID NO: 471), LLQGPP (SEQ ID NO: 472), LLQGPA (SEQ ID NO: 473), GGLLQGPP (SEQ ID NO: 474), GGLLQGA (SEQ ID NO: 475), LLQGPGK (SEQ ID NO: 476), LLQGPG (SEQ ID NO: 477), LLQGP (SEQ ID NO: 478), LLQP (SEQ ID NO: 479), LLQPGK (SEQ ID NO: 480), LLQAPGK (SEQ ID NO: 481), LLQGAPG (SEQ ID NO: 482), LLQGAP (SEQ ID NO: 483), and LLQLQG (SEQ ID NO: 484)) conjugated at a specific site (e.g., at a carboxyl terminus of the heavy or light chain, residue T135 in the antibody heavy chain, or at another site) of the BCMA antibody and an amino acid modification at position 222, 340, or 370 of the antibody (EU numbering scheme). In some embodiments, the amino acid modification is a substitution from lysine to arginine (e.g., K222R, K340R, or K370R).

In some embodiments, the BCMA antibody or the conjugate as described herein comprises an acyl donor glutamine-containing tag comprising the sequence GGLLQGPP (SEQ ID NO: 474) engineered at the C-terminus of the BCMA antibody light chain and an amino acid substitution from lysine to arginine at position 222 of the antibody (EU numbering scheme). In some embodiments, the BCMA antibody or the conjugate as described herein comprises an acyl donor glutamine-containing tag comprising the sequence GGLLQGA (SEQ ID NO: 475) engineered at the C-terminus of the BCMA antibody light chain and an amino acid substitution from lysine to arginine at position 222 of the antibody (EU numbering scheme). In some embodiments, the BCMA antibody or the conjugate as described herein comprises an acyl donor glutamine-containing tag comprising the sequence LLQGA (SEQ ID NO: 463) engineered at the C-terminus of the BCMA antibody heavy chain and an amino acid substitution from lysine to arginine at position 222 of the antibody (EU numbering scheme), wherein the lysine residue at the heavy chain carboxyl terminus is deleted. In some embodiments, the BCMA antibody or the conjugate as described herein comprises an acyl donor glutamine-containing tag comprising the sequence LLQG (SEQ ID NO: 454) engineered after residue T135 in the heavy chain of the BCMA antibody and an amino acid substitution from lysine to arginine at position 222 of the antibody (EU numbering scheme).

In some embodiments, the BCMA antibody or the conjugate as described herein comprises an acyl donor glutamine-containing tag comprising a glutamine engineered at position 297 or an amino acid substitution at position 297 from asparagine (N) to another amino acid in the BCMA antibody and an amino acid substitution from lysine to arginine at position 222 of the antibody (EU numbering scheme). For example, in some embodiments, the BCMA antibody or the conjugate as described herein comprises an acyl donor glutamine-containing tag comprising the sequence GGLLQGPP (SEQ ID NO: 474) engineered at the C-terminus of the BCMA antibody light chain, an amino acid substitution at position 297 of the BCMA antibody from asparagine (N) to glutamine (Q), and an amino acid substitution from lysine to arginine at position 222 of the antibody (EU numbering scheme). In some embodiments, the BCMA antibody or the conjugate as described herein comprises an acyl donor glutamine-containing tag comprising the sequence LLQG (SEQ ID NO: 454) engineered after residue T135 in the heavy chain of the BCMA antibody, an amino acid substitution at position 297 of the BCMA antibody from asparagine (N) to alanine (A), and an amino acid substitution from lysine to arginine at position 222 of the antibody (EU numbering scheme).

The agents that can be conjugated to the BCMA antibodies or the antigen binding fragments of the present invention include, but are not limited to, cytotoxic agents, immunomodulating agents, imaging agents, therapeutic proteins, biopolymers, or oligonucleotides.

Examples of a cytotoxic agent include, but are not limited to, anthracycline, an auristatin, a dolastatin, a combretastatin, a duocarmycin, a pyrrolobenzodiazepine dimer, an indolino-benzodiazepine dimer, an enediyne, a geldanamycin, a maytansine, a puromycin, a taxane, a vinca alkaloid, a camptothecin, a tubulysin, a hemiasterlin, a spliceostatin, a pladienolide, and stereoisomers, isosteres, analogs, or derivatives thereof.

The anthracyclines are derived from bacteria *Strepomyces* and have been used to treat a wide range of cancers, such as leukemias, lymphomas, breast, uterine, ovarian, and lung cancers. Exemplary anthracyclines include, but are not limited to, daunorubicin, doxorubicin (i.e., adriamycin), epirubicin, idarubicin, valrubicin, and mitoxantrone.

Dolastatins and their peptidic analogs and derivatives, auristatins, are highly potent antimitotic agents that have been shown to have anticancer and antifungal activity. See, e.g., U.S. Pat. No. 5,663,149 and Pettit et al., *Antimicrob. Agents Chemother.* 42:2961-2965, 1998. Exemplary dolastatins and auristatins include, but are not limited to, dolastatin 10, auristatin E, auristatin EB (AEB), auristatin EFP (AEFP), MMAD (Monomethyl Auristatin D or monomethyl dolastatin 10), MMAF (Monomethyl Auristatin F or N-methylvaline-valine-dolaisoleuine-dolaproine-phenylalanine), MMAE (Monomethyl Auristatin E or N-methylvaline-valine-dolaisoleuine-dolaproine-norephedrine), 5-benzoylvaleric acid-AE ester (AEVB), and other novel auristatins (such as the ones described in U.S. Publication No. 2013/0129753). In some embodiments, the auristatin is 0101 (2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide) having the following structure:

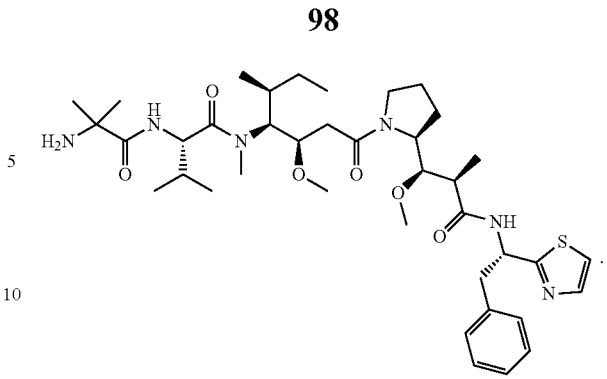

In some embodiments, the auristatin is 3377 (N,2-dimethylalanyl-N-{(1S,2R)-4-{(2S)-2-[(1R,2R)-3-{[(1S)-1-carboxyl-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide) having the following structure:

In some embodiments, the auristatin is 0131-OMe (N,2-dimethylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methylL-valinamide) having the following structure:

In other embodiments, the auristatin is 0131 (2-methyl-L-proly-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide) having the following structure:

In other embodiments, the auristatin is 0121 (2-methyl-L-proly-N-[(3R,4S,5S)-1-{(2S)-2-[(1R,2R)-3-{[(2S)-1-methoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide) having the following structure:

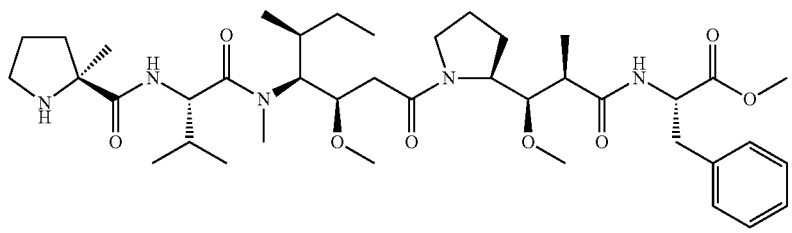 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@]1(C)CCCN1)C(C)C]

Camptothecin is a cytotoxic quinoline alkaloid which inhibits the enzyme topoisomerase I. Examples of camptothecin and its derivatives include, but are not limited to, topotecan and irinotecan, and their metabolites, such as SN-38.

Combretastatins are natural phenols with vascular disruption properties in tumors. Exemplary combretastatins and their derivatives include, but are not limited to, combretastatin A-4 (CA-4) and ombrabulin.

Duocarmycin and CC-1065 are DNA alkylating agents with cytotoxic potency. See Boger and Johnson, PNAS 92:3642-3649 (1995). Exemplary duocarmycin and CC-1065 include, but are not limited to, (+)-duocarmycin A and (+)-duocarmycin SA, (+)-CC-1065, and the compounds as disclosed in the international application PCT/IB2015/050280 including, but not limited to, N~2~-acetyl-L-lysyl-L-valyl-N~5~-carbamoyl-N-[4-({[(2-{[({(1S)-1-(chloromethyl)-3-[(5-{[(1S)-1-(chloromethyl)-5-(phosphonooxy)-1,2-dihydro-3H-benzo[e]indol-3-yl]carbonyl}thiophen-2-yl)carbonyl]-2,3-dihydro-1H-benzo[e]indol-5-yl}oxy)carbonyl]methyl)amino}ethyl)(methyl)carbamoyl]oxy}methyl)phenyl]-L-ornithinamide having the structure:

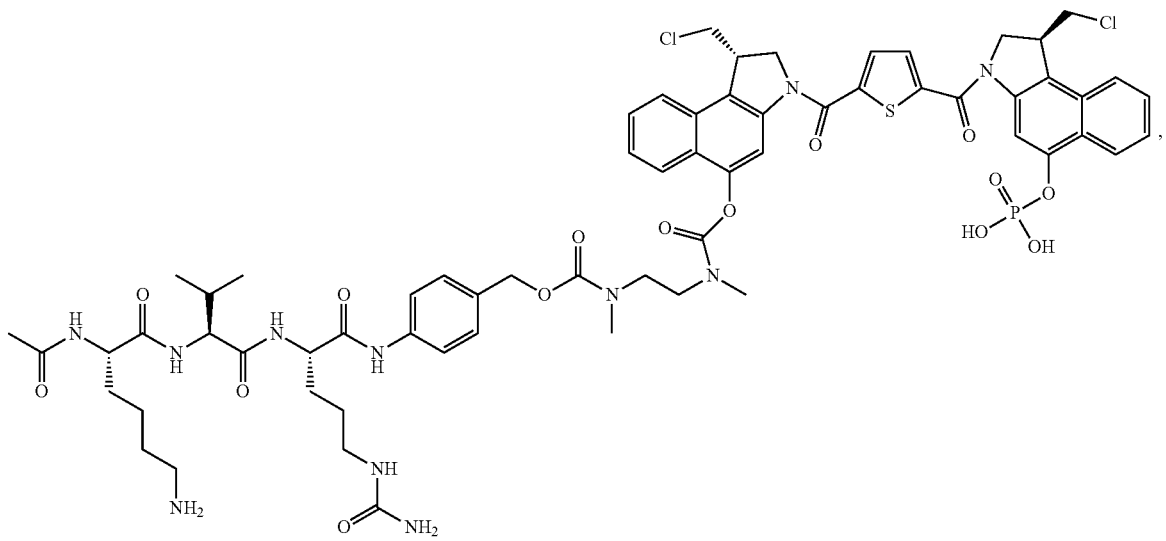

N~2~-acetyl-L-lysyl-L-valyl-N~5~-carbamoyl-N-[4-({[(2-{[({(8S)-8-(chloromethyl)-6-[(3-{[(1S)-1-(chloromethyl)-8-methyl-5-(phosphonooxy)-1,6-dihydropyrrolo[3,2-e]indol-3(2H)-yl]carbonyl}bicyclo[1.1.1]pent-1-yl)carbonyl]-1-methyl-3,6,7,8-tetrahydropyrrolo[3,2-e]indol-4-yl}oxy)carbonyl](methyl)amino}ethyl)(methyl)carbamoyl]oxy}methyl)phenyl]-L-ornithinamide having the structure:

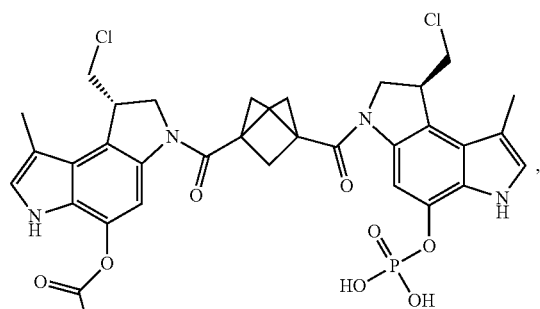
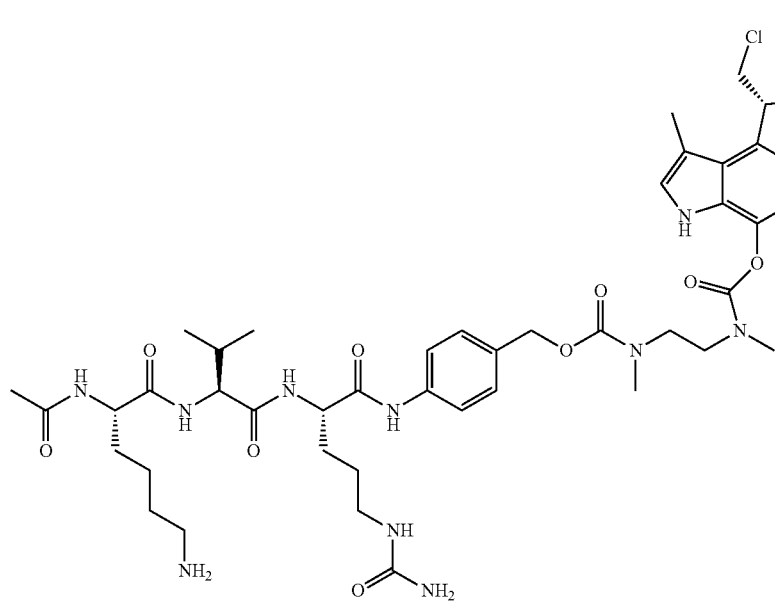

N~2~-acetyl-L-lysyl-L-valyl-N~5~-carbamoyl-N-[4-({[(2-{[({(8S)-8-(chloromethyl)-6-[(4-{[(1S)-1-(chloromethyl)-8-methyl-5-(phosphonooxy)-1,6-dihydropyrrolo[3,2-e]indol-3(2H)-yl]carbonyl}pentacyclo[4.2.0.0~2,5~0.0~3,8~0.0~4,7~]oct-1-yl)carbonyl]-1-methyl-3,6,7,8-tetrahydropyrrolo[3,2-e]indol-4-yl}oxy)carbonyl](methyl)amino}ethyl)(methyl)carbamoyl]oxy}methyl)phenyl]-L-ornithinamide having the structure:

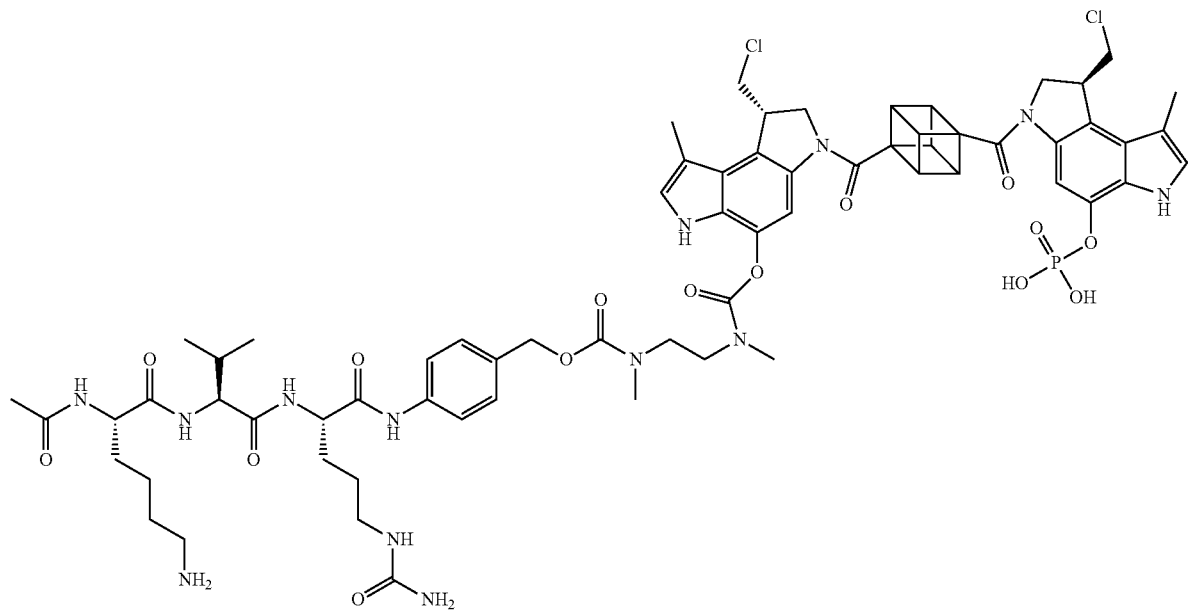 [SMILES: CC(=O)N[C@@H](CCCCN)C(=O)N[C@H](C(=O)N[C@@H](CCCNC(N)=O)C(=O)Nc1ccc(COC(=O)N(C)CCN(C)C(=O)Oc2cc3c(c4c(C)c[nH]c24)[C@H](CCl)CN3C(=O)C23C4C5C2C2C3C4C52C(=O)N2C[C@@H](CCl)c3c2cc(OP(=O)(O)O)c2[nH]cc(C)c32)cc1)C(C)C]

Enediynes are a class of anti-tumor bacterial products characterized by either nine- and ten-membered rings or the presence of a cyclic system of conjugated triple-double-triple bonds. Exemplary enediynes include, but are not limited to, calicheamicin, esperamicin, uncialamicin, dynemicin, and their derivatives.

Geldanamycins are benzoquinone ansamycin antibiotic that bind to Hsp90 (Heat Shock Protein 90) and have been used antitumor drugs. Exemplary geldanamycins include, but are not limited to, 17-AAG (17-N-Allylamino-17-Demethoxygeldanamycin) and 17-DMAG (17-Dimethyl-aminoethylamino-17-demethoxygeldanamycin).

Hemiasterlin and its analogues (e.g., HTI-286) bind to the tubulin, disrupt normal microtubule dynamics, and, at stoichiometric amounts, depolymerize microtubules.

Maytansines or their derivatives maytansinoids inhibit cell proliferation by inhibiting the microtubules formation during mitosis through inhibition of polymerization of tubulin. See Remillard et al., Science 189:1002-1005, 1975. Exemplary maytansines and maytansinoids include, but are not limited to, mertansine (DM1) and its derivatives as well as ansamitocin.

Pyrrolobenzodiazepine dimers (PBDs) and indolino-benzodiazepine dimers (IGNs) are anti-tumor agents that contain one or more immine functional groups, or their equivalents, that bind to duplex DNA. PBD and IGN molecules are based on the natural product athramycin, and interact with DNA in a sequence-selective manner, with a preference for purine-guanine-purine sequences. Exemplary PBDs and their analogs include, but are not limited to, SJG-136.

Spliceostatins and pladienolides are anti-tumor compounds which inhibit splicing and interacts with spliceosome, SF3b. Examples of spliceostatins include, but are not limited to, spliceostatin A, FR901464, and (2S,3Z)-5-{[(2R,3R,5S,6S)-6-{(2E,4E)-5-[(3R,4R,5R,7S)-7-(2-hydrazinyl-2-oxoethyl)-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate having the structure of

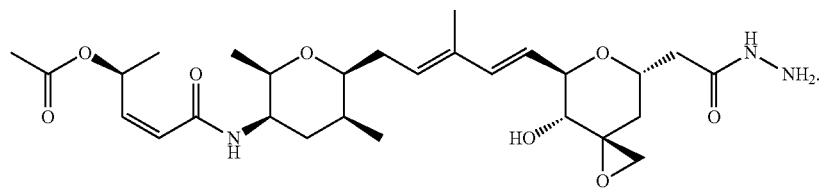 [SMILES: CC(=O)O[C@@H](C)/C=C\C(=O)N[C@@H]1C[C@H](C)[C@H](C/C=C(C)/C=C/[C@H]2O[C@H](CC(=O)NN)C[C@@]3(CO3)[C@@H]2O)O[C@@H]1C]

Examples of pladienolides include, but are not limited to, Pladienolide B, Pladienolide D, or E7107.

Taxanes are diterpenes that act as anti-tubulin agents or mitotic inhibitors. Exemplary taxanes include, but are not limited to, paclitaxel (e.g., TAXOL®) and docetaxel (TAXOTERE®).

Tubulysins are natural products isolated from a strain of myxobacteria that has been shown to depolymerize microtubules and induce mitotic arrest. Exemplary tubulysins include, but are not limited to, tubulysin A, tubulysin B, and tubulysin D.

Vinca alkyloids are also anti-tubulin agents. Exemplary vinca alkyloids include, but are not limited to, vincristine, vinblastine, vindesine, and vinorelbine.

Accordingly, in some embodiments, the cytotoxic agent is selected from the group consisting of MMAD (Monomethyl Auristatin D), 0101 (2-methylalanyl-N-[(3R,4S,5S)-3-methoxy-1-{(2 S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide), 3377 (N,2-dimethylalanyl-N-{(1S,2R)-4-{(2S)-2-[(1R,2R)-3-{[(1S)-1-carboxyl-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide), 0131 (2-methyl-L-proly-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide), 0131-OMe (N,2-dimethylalanyl-N-[(3R,4S, 5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methylL-valinamide), 0121(2-methyl-L-proly-N-[(3R,4S, 5S)-1-{(2S)-2-[(1R,2R)-3-{[(2S)-1-methoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide), and (2S,3Z)-5-{[(2R,3R,5S,6S)-6-{(2E,4E)-5-[(3R,4R,5R,7S)-7-(2-hydrazinyl-2-oxoethyl)-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate.

In some embodiments, the agent is an immunomodulating agent. Examples of an immunomodulating agent include, but are not limited to, gancyclovier, etanercept, tacrolimus, sirolimus, voclosporin, cyclosporine, rapamycin, cyclophosphamide, azathioprine, mycophenolgate mofetil, methotrextrate, glucocorticoid and its analogs, cytokines, stem cell growth factors, lymphotoxins, tumor necrosis factor (TNF), hematopoietic factors, interleukins (e.g., interleukin-1 (IL-1), IL-2, IL-3, IL-6, IL-10, IL-12, IL-18, and IL-21), colony stimulating factors (e.g., granulocyte-colony stimulating factor (G-CSF) and granulocyte macrophage-colony stimulating factor (GM-CSF)), interferons (e.g., interferons-α, -β and -γ), the stem cell growth factor designated "S 1 factor," erythropoietin and thrombopoietin, or a combination thereof.

In some embodiments, the agent moiety is an imaging agent (e.g., a fluorophore or a chelator), such as fluorescein, rhodamine, lanthanide phosphors, and their derivatives thereof, or a radioisotope bound to a chelator. Examples of fluorophores include, but are not limited to, fluorescein isothiocyanate (FITC) (e.g., 5-FITC), fluorescein amidite (FAM) (e.g., 5-FAM), eosin, carboxyfluorescein, erythrosine, Alexa Fluor® (e.g., Alexa 350, 405, 430, 488, 500, 514, 532, 546, 555, 568, 594, 610, 633, 647, 660, 680, 700, or 750), carboxytetramethylrhodamine (TAMRA) (e.g., 5-TAMRA), tetramethylrhodamine (TMR), and sulforhodamine (SR) (e.g., SR101). Examples of chelators include, but are not limited to, 1,4,7,10-tetraazacyclododecane-N, N',N",N'''-tetraacetic acid (DOTA), 1,4,7-triazacyclononane-1,4,7-triacetic acid (NOTA), 1,4,7-triazacyclononane, 1-glutaric acid-4,7-acetic acid (deferoxamine), diethylenetriaminepentaacetic acid (DTPA), and 1,2-bis(o-aminophenoxy)ethane-N,N,N',N'-tetraacetic acid) (BAPTA).

Examples of fluorophores include, but are not limited to, fluorescein isothiocyanate (FITC) (e.g., 5-FITC), fluorescein amidite (FAM) (e.g., 5-FAM), eosin, carboxyfluorescein, erythrosine, Alexa Fluor® (e.g., Alexa 350, 405, 430, 488, 500, 514, 532, 546, 555, 568, 594, 610, 633, 647, 660, 680, 700, or 750), carboxytetramethylrhodamine (TAMRA) (e.g., 5-TAMRA), tetramethylrhodamine (TMR), and sulforhodamine (SR) (e.g., SR101).

In some embodiments, therapeutic or diagnostic radioisotopes or other labels (e.g., PET or SPECT labels) can be incorporated in the agent for conjugation to the BCMA antibodies or the antigen binding fragments as described herein. Examples of a radioisotope or other labels include, but are not limited to, $^{3}$H, $^{11}$C, $^{13}$N, $^{14}$C, $^{15}$N, $^{15}$O, $^{35}$S, $^{18}$F, $^{32}$P, $^{33}$P, $^{47}$Sc, $^{51}$Cr, $^{57}$Co, $^{58}$Co, $^{59}$Fe, $^{62}$Cu, $^{64}$Cu, $^{67}$Cu, $^{67}$Ga, $^{68}$Ga, $^{75}$Se, $^{76}$Br, $^{77}$Br, $^{86}$Y, $^{89}$Zr, $^{90}$Y, $^{94}$Tc, $^{95}$Ru, $^{97}$Ru, $^{99}$Tc, $^{103}$Ru, $^{105}$Rh, $^{105}$Ru, $^{107}$Hg, $^{109}$Pd, $^{111}$Ag, $^{111}$In, $^{113}$In, $^{121}$Te, $^{122}$Te, $^{123}$I, $^{124}$I, $^{125}$I, $^{125}$Te, $^{126}$I, $^{131}$I, $^{131}$In, $^{133}$I, $^{142}$Pr, $^{143}$Pr, $^{153}$Pb, $^{153}$Sm, $^{161}$Tb, $^{165}$Tm, $^{166}$Dy, $^{166}$H, $^{167}$Tm, $^{168}$Tm, $^{169}$Yb, $^{177}$Lu, $^{186}$Re, $^{188}$Re, $^{189}$Re, $^{197}$Pt, $^{198}$Au, $^{199}$Au, $^{201}$Tl, $^{203}$Hg, $^{211}$At, $^{212}$Bi, $^{212}$Pb, $^{213}$Bi, $^{223}$Rd, $^{224}$Ac, or $^{225}$Ac.

In some embodiments, the agent is a therapeutic protein including, but is not limited to, a toxin, a hormone, an enzyme, and a growth factor.

Examples of a toxin protein (or polypeptide) include, but are not limited to, diphtheria (e.g., diphtheria A chain), *Pseudomonas* exotoxin and endotoxin, ricin (e.g., ricin A chain), abrin (e.g., abrin A chain), modeccin (e.g., modeccin A chain), alpha-sarcin, *Aleurites fordii* proteins, dianthin proteins, ribonuclease (RNase), DNase *Staphylococcal* enterotoxin-A, pokeweed antiviral protein, gelonin, diphtherin toxin, *Phytolaca americana* proteins (PAPI, PAPII, and PAP-S), *Momordica charantia* inhibitor, curcin, crotin, *Sapaonaria officinalis* inhibitor, mitogellin, restrictocin, phenomycin, enomycin, tricothecenes, inhibitor cystine knot (ICK) peptides (e.g., ceratotoxins), and conotoxin (e.g., KIIIA or SmIIIa).

In some embodiments, the agent is a biocompatible polymer. The BCMA antibodies or the antigen binding fragments as described herein can be conjugated to the biocompatible polymer to increase serum half-life and bioactivity, and/or to extend in vivo half-lives. Examples of biocompatible polymers include water-soluble polymer, such as polyethylene glycol (PEG) or its derivatives thereof and zwitterion-containing biocompatible polymers (e.g., a phosphorylcholine containing polymer).

In some embodiments, the agent is an oligonucleotide, such as anti-sense oligonucleotides.

In another aspect, the invention provides a conjugate of the antibody or the antigen binding fragment as described herein, wherein the conjugate comprises the formula: antibody-(acyl donor glutamine-containing tag)-(linker)-(cytotoxic agent), wherein the acyl donor glutamine-containing tag is engineered at a specific site of the antibody or the antigen binding fragment (e.g., at a carboxyl terminus of the heavy or light chain, after residue T135 in the antibody heavy chain, or at an another site), wherein the tag is conjugated to a linker (e.g., a linker containing one or more reactive amines (e.g., primary amine $NH_2$)), and wherein the linker is conjugated to a cytotoxic agent (e.g., MMAD or other auristatins such as 0101, 0131, or 3377).

Examples of a linker containing one or more reactive amines include, but are not limited to, Ac-Lys-Gly (acetyl-lysine-glycine), aminocaproic acid, Ac-Lys-β-Ala (acetyl-lysine-β-alanine), amino-PEG2 (polyethylene glycol)-C2, amino-PEG3-C2, amino-PEG6-C2 (or amino PEG6-propionyl), Ac-Lys-Val-Cit-PABC (acetyl-lysine-valine-citrulline-p-aminobenzyloxycarbonyl), amino-PEG6-C2-Val-Cit-PABC, aminocaproyl-Val-Cit-PABC, [(3R,5R)-1-{3-[2-(2-aminoethoxy)ethoxy]propanoyl}piperidine-3,5-diyl]bis-Val-Cit-PABC, [(3S,5S)-1-{3-[2-(2-aminoethoxy)ethoxy]propanoyl}piperidine-3,5-diyl]bis-Val-Cit-PABC, putrescine, or Ac-Lys-putrescine.

In some embodiments, the conjugate is 1) antibody-GGLLQGPP (SEQ ID NO: 474)-AcLys-VC-PABC-0101; 2) antibody-AcLys-VC-PABC-0101 and comprises N297Q; 3) antibody-GGLLQGPP (SEQ ID NO: 474)-AcLys-VC-PABC-0101 and comprises N297Q; 4) antibody-LLQG (SEQ ID NO: 454)-amino-PEG6-C2-0131 and comprises N297A; 5) antibody-LLQG (SEQ ID NO: 454)-amino-PEG6-C2-3377 and comprises N297A; 6) antibody-GGLLQGA (SEQ ID NO: 475)-AcLys-VC-PABC-0101. In some embodiments, the acyl donor glutamine-containing tag comprising, e.g., GGLLQGPP (SEQ ID NO: 474) or GGLLQGA (SEQ ID NO: 475), is engineered at the C-terminus of the light chain of the antibody. In other embodiments, the acyl donor glutamine-containing tag (e.g., LLQGA (SEQ ID NO: 463) or LLQGPP (SEQ ID NO: 472)) is engineered at the C-terminus of the heavy chain of the antibody, wherein the lysine residue at the C-terminus is deleted. In some embodiments, the acyl donor glutamine-containing tag comprising, e.g., LLQG (SEQ ID NO: 454) is engineered after residue T135 in the antibody heavy chain or replaces amino acid residues E294-N297 in the antibody heavy chain. Examples of the antibody include, but are not limited to, P6E01/P6E01, P6E01/H3.AQ, L1.LGF/L3.KW/P6E01; L1.LGF/L3.NY/P6E01, L1.GDF/L3.NY/P6E01, L1.LGF/L3.KW/H3.AL, L1.LGF/L3.KW/H3.AP, L1.LGF/L3.KW/H3.AQ, L1.LGF/L3.PY/H3.AP, L1.LGF/L3.PY/H3.AQ, L1.LGF/L3.NY/H3.AL, L1.LGF/L3.NY/H3.AP, L1.LGF/L3.NY/H3.AQ, L1.GDF/L3.KW/H3.AL, L1.GDF/L3.KW/H3.AP, L1.GDF/L3.KW/H3.AQ, L1.GDF/L3.PY/H3.AQ, L1.GDF/L3.NY/H3.AL, L1.GDF/L3.NY/H3.AP, L1.GDF/L3.NY/H3.AQ, L3.KW/P6E01, L3.PY/P6E01, L3.NY/P6E01, L3.PY/L1.PS/P6E01, L3.PY/L1.AH/P6E01, L3.PY/L1.FF/P6E01, L3.PY/L1.PH/P6E01, L3.PY/L3.KY/P6E01, L3.PY/L3.KF/P6E01, L3.PY/H2.QR, L3.PY/H2.DY, L3.PY/H2.YQ, L3.PY/H2.LT, L3.PY/H2.HA, L3.PY/H2.QL, L3.PY/H3.YA, L3.PY/H3.AE, L3.PY/H3.AQ, L3.PY/H3.TAQ, L3.PY/P6E01, L3.PY/L1.PS/H2.QR, L3.PY/L1.PS/H2.DY, L3.PY/L1.PS/H2.YQ, L3.PY/L1.PS/H2.LT, L3.PY/L1.PS/H2.HA, L3.PY/L1.PS/H2.QL, L3.PY/L1.PS/H3.YA, L3.PY/L1.PS/H3.AE, L3.PY/L1.PS/H3.AQ, L3.PY/L1.PS/H3.TAQ, L3.PY/L1.AH/H2.QR, L3.PY/L1.AH/H2.DY, L3.PY/L1.AH/H2.YQ, L3.PY/L1.AH/H2.LT, L3.PY/L1.AH/H2.HA, L3.PY/L1.AH/H2.QL, L3.PY/L1.AH/H3.YA, L3.PY/L1.AH/H3.AE, L3.PY/L1.AH/H3.AQ, L3.PY/L1.AH/H3.TAQ, L3.PY/L1.FF/H2.QR, L3.PY/L1.FF/H2.DY, L3.PY/L1.FF/H2.YQ, L3.PY/L1.FF/H2.LT, L3.PY/L1.FF/H2.HA, L3.PY/L1.FF/H2.QL, L3.PY/L1.FF/H3.YA, L3.PY/L1.FF/H3.AE, L3.PY/L1.FF/H3.AQ, L3.PY/L1.FF/H3.TAQ, L3.PY/L1.PH/H2.QR, L3.PY/L1.PH/H2.HA, L3.PY/L1.PH/H3.AE, L3.PY/L1.PH/H3.AQ, L3.PY/L1.PH/H3.TAQ, L3.PY/L3.KY/H2.QR, L3.PY/L3.KY/H2.DY, L3.PY/L3.KY/H2.YQ L3.PY/L3.KY/H2.LT, L3.PY/L3.KY/H2.HA, L3.PY/L3.KY/H2.QL, L3.PY/L3.KY/H3.YA L3.PY/L3.KY/H3.TAQ, L3.PY/L3.KF/H2.DY, L3.PY/L3.KF/H2.YQ, L3.PY/L3.KF/H2.LT L3.PY/L3.KF/H2.QL, L3.PY/L3.KF/H3.YA, L3.PY/L3.KF/H3.AE, L3.PY/L3.KF/H3.AQ L3.PY/L3.KF/H3.TAQ, P5A2_VHVL, A02_Rd4_0.6nM_C06, A02_Rd4_0.6nM_C09 A02_Rd4_6nM_C16, A02_Rd4_6nM_C03, A02_Rd4_6nM_C01, A02_Rd4_6nM_C26 A02_Rd4_6nM_C25, A02_Rd4_6nM_C22, A02_Rd4_6nM_C19, A02_Rd4_0.6nM_C03 A02_Rd4_6nM_C07, A02_Rd4_6nM_C23, A02_Rd4_0.6nM_C18, A02_Rd4_6nM_C10 A02_Rd4_6nM_C05, A02_Rd4_0.6nM_C10, A02_Rd4_6nM_C04, A02_Rd4_0.6nM_C26 A02_Rd4_0.6nM_C1 A02_Rd4_0.6nM_C01, A02_Rd4_6nM_C08, P5C1_VHVL, C01_Rd4_6nM_C24, C01_Rd4_6nM_C26, C01_Rd4_6nM_C10, C01_Rd4_0.6nM_C27 C01_Rd4_6nM_C20, C01_Rd4_6nM_C12, C01_Rd4_0.6nM_C16, C01_Rd4_0.6nM_C09 C01_Rd4_6nM_C09, C01_Rd4_0.6nM_C03, C01_Rd4_0.6nM_C06, C01_Rd4_6nM_C04

COMBO_Rd4_0.6nM_C22, COMBO_Rd4_6nM_C21, COMBO_Rd4_6nM_C10, COMBO_Rd4_0.6nM_C04, COMBO_Rd4_6nM_C25, COMBO_Rd4_0.6nM_C21, COMBO_Rd4_6nM_C11, COMBO_Rd4_0.6nM_C20, COMBO_Rd4_6nM_C09, COMBO_Rd4_6nM_C08, COMBO_Rd4_0.6nM_C1 COMBO_Rd4_0.6nM_C02, COMBO_Rd4_0.6nM_C23, COMBO_Rd4_0.6nM_C29, COMBO_Rd4_0.6nM_C09, COMBO_Rd4_6nM_C12, COMBO_Rd4_0.6nM_C30, COMBO_Rd4_0.6nM_C14, COMBO_Rd4_6nM_C07, COMBO_Rd4_6nM_C02, COMBO_Rd4_0.6nM_C05, COMBO_Rd4_0.6nM_C17, COMBO_Rd4_6nM_C22, COMBO_Rd4_0.6nM_C11, COMBO_Rd4_0.6nM_C29, P4G4, or P1A11.

In one variation, the conjugate further comprises an amino acid substitution from lysine to arginine at position 222. Accordingly, for example, the conjugate is 1) antibody-GGLLQGPP (SEQ ID NO: 474)-AcLys-VC-PABC-0101 and comprises K222R; 2) antibody-AcLys-VC-PABC-0101 and comprises N297Q and K222R; 3) antibody-GGLLQGPP (SEQ ID NO: 474)-AcLys-VC-PABC-0101 and comprises N297Q and K222R; 4) antibody-LLQG (SEQ ID NO: 454)-amino-PEG6-C2-0131 and comprises N297A and K222R; 5) antibody-LLQG (SEQ ID NO: 454)-amino-PEG6-C2-3377 and comprises N297A and K222R; and 6) antibody-GGLLQGA (SEQ ID NO: 475)-AcLys-VC-PABC-0101 and comprises K222R. In some embodiments, the acyl donor glutamine-containing tag comprising, e.g., GGLLQGPP (SEQ ID NO: 474) or GGLLQGA (SEQ ID NO: 475) is engineered at the C-terminus of the light chain of the antibody. In other embodiments, the acyl donor glutamine-containing tag (e.g., LLQGA (SEQ ID NO: 473) or LLQGPP (SEQ ID NO: 472)) is engineered at the C-terminus of the heavy chain of the antibody, wherein the lysine residue at the C-terminus is deleted. In some embodiments, the acyl donor glutamine-containing tag comprising, e.g., LLQG (SEQ ID NO: 454) is engineered after residue T135 in the antibody heavy chain or replaces amino acid residues E294-N297 in the antibody heavy chain. Examples of the antibody include, but are not limited to, P6E01, P6E01, P6E01/H3.AQ, L1.LGF/L3.KW/P6E01; L1.LGF/L3.NY/P6E01, L1.GDF/L3.NY/P6E01, L1.LGF/L3.KW/H3.AL, L1.LGF/L3.KW/H3.AP, L1.LGF/L3.KW/H3.AQ, L1.LGF/L3.PY/H3.AP, L1.LGF/L3.PY/H3.AQ, L1.LGF/L3.NY/H3.AL, L1.LGF/L3.NY/H3.AP, L1.LGF/L3.NY/H3.AQ, L1.GDF/L3.KW/H3.AL, L1.GDF/L3.KW/H3.AP, L1.GDF/L3.KW/H3.AQ, L1.GDF/L3.PY/H3.AQ, L1.GDF/L3.NY/H3.AL, L1.GDF/L3.NY/H3.AP, L1.GDF/L3.NY/H3.AQ, L3.KW/P6E01, L3.PY/P6E01, L3.NY/P6E01, L3.PY/L1.PS/P6E01, L3.PY/L1.AH/P6E01, L3.PY/L1.FF/P6E01, L3.PY/L1.PH/P6E01, L3.PY/L3.KY/P6E01, L3.PY/L3.KF/P6E01, L3.PY/H2.QR, L3.PY/H2.DY, L3.PY/H2.YQ, L3.PY/H2.LT, L3.PY/H2.HA, L3.PY/H2.QL, L3.PY/H3.YA, L3.PY/H3.AE, L3.PY/H3.AQ, L3.PY/H3.TAQ, L3.PY/P6E01, L3.PY/L1.PS/H2.QR, L3.PY/L1.PS/H2.DY, L3.PY/L1.PS/H2.YQ, L3.PY/L1.PS/H2.LT, L3.PY/L1.PS/H2.HA, L3.PY/L1.PS/H2.QL, L3.PY/L1.PS/H3.YA, L3.PY/L1.PS/H3.AE, L3.PY/L1.PS/H3.AQ, L3.PY/L1.PS/H3.TAQ, L3.PY/L1.AH/H2.QR, L3.PY/L1.AH/H2.DY, L3.PY/L1.AH/H2.YQ, L3.PY/L1.AH/H2.LT, L3.PY/L1.AH/H2.HA, L3.PY/L1.AH/H2.QL, L3.PY/L1.AH/H3.YA, L3.PY/L1.AH/H3.AE, L3.PY/L1.AH/H3.AQ, L3.PY/L1.AH/H3.TAQ, L3.PY/L1.FF/H2.QR, L3.PY/L1.FF/H2.DY, L3.PY/L1.FF/H2.YQ, L3.PY/L1.FF/H2.LT, L3.PY/L1.FF/H2.HA, L3.PY/L1.FF/H2.QL, L3.PY/L1.FF/H3.YA, L3.PY/L1.FF/H3.AE, L3.PY/L1.FF/H3.AQ, L3.PY/L1.FF/H3.TAQ, L3.PY/L1.PH/H2.QR, L3.PY/L1.PH/H2.HA, L3.PY/L1.PH/H3.AE, L3.PY/L1.PH/H3.AQ, L3.PY/L1.PH/H3.TAQ, L3.PY/L3.KY/H2.QR, L3.PY/L3.KY/H2.DY, L3.PY/L3.KY/H2.YQ L3.PY/L3.KY/H2.LT, L3.PY/L3.KY/H2.HA, L3.PY/L3.KY/H2.QL, L3.PY/L3.KY/H3.YA L3.PY/L3.KY/H3.TAQ, L3.PY/L3.KF/H2.DY, L3.PY/L3.KF/H2.YQ, L3.PY/L3.KF/H2.LT L3.PY/L3.KF/H2.QL, L3.PY/L3.KF/H3.YA, L3.PY/L3.KF/H3.AE, L3.PY/L3.KF/H3.AQ L3.PY/L3.KF/H3.TAQ, P5A2_VHVL, A02_Rd4_0.6nM_C06, A02_Rd4_0.6nM_C09 A02_Rd4_6nM_C16, A02_Rd4_6nM_C03, A02_Rd4_6nM_C01, A02_Rd4_6nM_C26 A02_Rd4_6nM_C25, A02_Rd4_6nM_C22, A02_Rd4_6nM_C19, A02_Rd4_0.6nM_C03 A02_Rd4_6nM_C07, A02_Rd4_6nM_C23, A02_Rd4_0.6nM_C18, A02_Rd4_6nM_C10 A02_Rd4_6nM_C05, A02_Rd4_0.6nM_C10, A02_Rd4_6nM_C04, A02_Rd4_0.6nM_C26 A02_Rd4_0.6nM_C13, A02_Rd4_0.6nM_C01, A02_Rd4_6nM_C08, P5C1_VHVL, C01_Rd4_6nM_C24, C01_Rd4_6nM_C26, C01_Rd4_6nM_C10, C01_Rd4_0.6nM_C27 C01_Rd4_6nM_C20, C01_Rd4_6nM_C12, C01_Rd4_0.6nM_C16, C01_Rd4_0.6nM_C09 C01_Rd4_6nM_C09, C01_Rd4_0.6nM_C03, C01_Rd4_0.6nM_C06, C01_Rd4_6nM_C04

COMBO_Rd4_0.6nM_C22, COMBO_Rd4_6nM_C21, COMBO_Rd4_6nM_C10, COMBO_Rd4_0.6nM_C04, COMBO_Rd4_6nM_C25, COMBO_Rd4_0.6nM_C21, COMBO_Rd4_6nM_C11, COMBO_Rd4_0.6nM_C20, COMBO_Rd4_6nM_C09, COMBO_Rd4_6nM_C08, COMBO_Rd4_0.6nM_C19, COMBO_Rd4_0.6nM_C02, COMBO_Rd4_0.6nM_C23, COMBO_Rd4_0.6nM_C29, COMBO_Rd4_0.6nM_C09, COMBO_Rd4_6nM_C12, COMBO_Rd4_0.6nM_C30, COMBO_Rd4_0.6nM_C14, COMBO_Rd4_6nM_C07, COMBO_Rd4_6nM_C02, COMBO_Rd4_0.6nM_C05, COMBO_Rd4_0.6nM_C17, COMBO_Rd4_6nM_C22, COMBO_Rd4_0.6nM_C11, COMBO_Rd4_0.6nM_C29, or P4G4, or P1A11.

CD3 Antibodies and Methods of Making Thereof

The present invention further provides an antibody that binds to CD3 (e.g., human CD3 (SEQ ID NO: 502; or accession number: NM_000733.3).

In one aspect, provided is an isolated antibody, or an antigen binding fragment thereof, which specifically binds to CD3, wherein the antibody comprises a VH CDR1, VH CDR2, and VH CDR3 of the VH sequence shown in SEQ ID NO: 320, 322, 324, 326, 328, 330, 345, 347, 349, 351, 444, 354, 356, 378, 442, 380, 382, 384 386, 388, 390, 392, 394, 396, 398, or 400; and/or a light chain variable (VL) region comprising VL CDR1, VL CDR2, and VL CDR3 of the VL sequence shown in SEQ ID NO: 319, 321, 323, 325, 327, 329, 344, 346, 348, 350, 352, 355, 377, 443, 445, 379, 381, 383, 385, 387, 389, 391, 393, 395, 397, or 399.

In another aspect, provided is an isolated antibody, or an antigen binding fragment thereof, which specifically binds to CD3, wherein the VH region comprises (i) a VH complementarity determining region one (CDR1) comprising the sequence shown in SEQ ID NO: 331, 332, 333, 401, 402, 403, 407, 408, 415, 416, 418, 419, 420, 424, 425, 426, 446, 447, or 448 (ii) a VH CDR2 comprising the sequence shown in SEQ ID NO: 334, 336, 337, 338, 339, 404, 405, 409, 410, 411, 412, 413, 414, 417, 418, 421, 422, 427, 428, 449, or 450; and iii) a VH CDR3 comprising the sequence shown in SEQ ID NO: 335, 406, 423, 429, or 451; and/or a light chain variable (VL) region comprising (i) a VL CDR1 comprising the sequence shown in SEQ ID NO: 340, 343, 430, 431, 435, or 440, 441; (ii) a VL CDR2 comprising the sequence shown in SEQ ID NO: 341, 433, 452, or 436; and (iii) a VL CDR3 comprising the sequence shown in SEQ ID NO: 342, 432, 434, 437, 438, 439, 446, or 453.

In some embodiments, provided is an antibody having any one of partial light chain sequence as listed in Table 3 and/or any one of partial heavy chain sequence as listed in Table 3.

TABLE 3

| mAb | Light Chain | Heavy Chain |
| --- | --- | --- |
| h2B4 | DIVMTQSPDSLAVSLGERATINCT SSQSLFNVRSRKNYLAWYQQKP GQPPKLLISWASTRESGVPDRFS GSGSGTDFTLTISSLQAEDVAVY YCKQSYDLFTFGSGTKLEIK (SEQ ID NO: 319) | EVQLVESGGGLVQPGGSLRLSCA ASGFTFSDYYMTWVRQAPGKGLE WVAFIRNRARGYTSDHNASVKGR FTISRDNAKNSLYLQMNSLRAEDT AVYYCARDRPSYYVLDYWGQGTT VTVSS (SEQ ID NO: 320) |
| h2B4-VH-wt VL_TK | DIVMTQSPDSLAVSLGERATINCKSSQSLFNVRSRKNYLAWYQQK PGQPPKLLISWASTRESGVPDRF SGSGSGTDFTLTISSLQAEDVAV YYCKQSYDLFTFGSGTKLEIK (SEQ ID NO: 321) | EVQLVESGGGLVQPGGSLRLSCA ASGFTFSDYYMTWVRQAPGKGLE WVAFIRNRARGYTSDHNASVKGR FTISRDNAKNSLYLQMNSLRAEDT AVYYCARDRPSYYVLDYWGQGTT VTVSS (SEQ ID NO: 322) |
| h2B4-VH-hnps VL_TK | DIVMTQSPDSLAVSLGERATINCKSSQSLFNVRSRKNYLAWYQQK PGQPPKLLISWASTRESGVPDRF SGSGSGTDFTLTISSLQAEDVAV YYCKQSYDLFTFGSGTKLEIK (SEQ ID NO: 323) | EVQLVESGGGLVQPGGSLRLSCA ASGFTFSDYYMTWVRQAPGKGLE WVAFIRNRARGYTSDHNPSVKGR FTISRDNAKNSLYLQMNSLRAEDT AVYYCARDRPSYYVLDYWGQGTT VTVSS (SEQ ID NO: 324) |
| h2B4-VH-yaes VL_TK | DIVMTQSPDSLAVSLGERATINCKSSQSLFNVRSRKNYLAWYQQK PGQPPKLLISWASTRESGVPDRF SGSGSGTDFTLTISSLQAEDVAV YYCKQSYDLFTFGSGTKLEIK (SEQ ID NO: 325) | EVQLVESGGGLVQPGGSLRLSCA ASGFTFSDYYMTWVRQAPGKGLE WVAFIRNRARGYTSDYAESVKGR FTISRDNAKNSLYLQMNSLRAEDT AVYYCARDRPSYYVLDYWGQGTT VTVSS (SEQ ID NO: 326) |
| h2B4-VH-yads VL_TK | DIVMTQSPDSLAVSLGERATINCKSSQSLFNVRSRKNYLAWYQQK PGQPPKLLISWASTRESGVPDRF SGSGSGTDFTLTISSLQAEDVAV YYCKQSYDLFTFGSGTKLEIK (SEQ ID NO: 327) | EVQLVESGGGLVQPGGSLRLSCA ASGFTFSDYYMTWVRQAPGKGLE WVAFIRNRARGYTSDYADSVKGR FTISRDNAKNSLYLQMNSLRAEDT AVYYCARDRPSYYVLDYWGQGTT VTVSS (SEQ ID NO: 328) |
| h2B4-VH-yaps VL_TK | DIVMTQSPDSLAVSLGERATINCT SSQSLFNVRSRKNYLAWYQQKP GQPPKLLISWASTRESGVPDRFS GSGSGTDFTLTISSLQAEDVAVY YCKQSYDLFTFGSGTKLEIK (SEQ ID NO: 329) | EVQLVESGGGLVQPGGSLRLSCA ASGFTFSDYYMTWVRQAPGKGLE WVAFIRNRARGYTSDYAPSVKGR FTISRDNAKNSLYLQMNSLRAEDT AVYYCARDRPSYYVLDYWGQGTT VTVSS (SEQ ID NO: 330) |
| h2B4-VH-hnps VL_TK-S55Y | DIVMTQSPDSLAVSLGERATINCKSSQSLFNVRSRKNYLAWYQQK PGQPPKLLIYWASTRESGVPDRF SGSGSGTDFTLTISSLQAEDVAV YYCKQSYDLFTFGSGTKLEIK (SEQ ID NO: 344) | EVQLVESGGGLVQPGGSLRLSCA ASGFTFSDYYMTWVRQAPGKGLE WVAFIRNRARGYTSDHNPSVKGR FTISRDNAKNSLYLQMNSLRAEDT AVYYCARDRPSYYVLDYWGQGTT VTVSS (SEQ ID NO: 345) |
| h2B4-VH-hnps VL_TK-S105Q | DIVMTQSPDSLAVSLGERATINCKSSQSLFNVRSRKNYLAWYQQK PGQPPKLLISWASTRESGVPDRF SGSGSGTDFTLTISSLQAEDVAV YYCKQSYDLFTFGQGTKLEIK (SEQ ID NO: 346) | EVQLVESGGGLVQPGGSLRLSCA ASGFTFSDYYMTWVRQAPGKGLE WVAFIRNRARGYTSDHNPSVKGR FTISRDNAKNSLYLQMNSLRAEDT AVYYCARDRPSYYVLDYWGQGTT VTVSS (SEQ ID NO: 347) |
| h2B4-VH-hnps VL_TK-S55Y/ S105Q | DIVMTQSPDSLAVSLGERATINCKSSQSLFNVRSRKNYLAWYQQK PGQPPKLLIYWASTRESGVPDRF SGSGSGTDFTLTISSLQAEDVAV YYCKQSYDLFTFGQGTKLEIK (SEQ ID NO: 348) | EVQLVESGGGLVQPGGSLRLSCA ASGFTFSDYYMTWVRQAPGKGLE WVAFIRNRARGYTSDHNPSVKGR FTISRDNAKNSLYLQMNSLRAEDT AVYYCARDRPSYYVLDYWGQGTT VTVSS (SEQ ID NO: 349) |

TABLE 3-continued

| mAb | Light Chain | Heavy Chain |
|---|---|---|
| 2B4 | DIVMSQSPPSLAVSVGDKVTMSCTSSQSLFNSRSRKNYLAWYQQKSGQSPKLLISWASTRESGVPDRFTGSGSGTDFTLTISSVQAEDLAVYYCKQSYDLFTFGSGTKLEIK (SEQ ID NO: 350) | EVKLVESGGGLVQPGGSLRLSCATFGFTFTDYYMTWVRQPPGKALEWVAFIRNRARGYTSDHNASVKGRFTISRDNSQNILYLQMNTLRAEDSATYYCARDRPSYYVLDYWGQGTTVTVSS (SEQ ID NO: 351) |
| h2B4-11 | DIVMTQSPDSLAVSLGERATINCTSSQSLFNSRSRKNYLAWYQQKPGQPPKLLISWASTRESGVPDRFSGSGSGTDFTLTISSLQAEDVAVYCQQSYDTFTFGSGTKLEIK (SEQ ID NO: 445) | EVQLVESGGGLVQPGGSLRLSCAASGFTFSDYYMTWVRQAPGKGLEWVAFIRNRARGYTSDHNASVKGRFTISRDNAKNSLYLQMNSLRAEDTAVYYCARDRPSYYVLDYWGQGTTVTVSS (SEQ ID NO: 444) |
| 1C10 | DIVMSQSPSSLAVSAGEKVTMSCKSSQSLLNSRTRKNYLAWYQQKPGQSPKLLIYWASTRESGVPDRFTGSGSGTDFTLTIDSVQPEDLAVYYCTQSFILRTFGGGTKLEIK (SEQ ID NO: 352) | QVQLQQPGSELVRPGASVILSCKASGYTFTSYWMHWVRQRPGQGLEWIGNIYSGGDTINYDEKFKNKAILTVDTSSSTAYMHLSSLTSEDSAVYYCTRDATSRYFFDYWGQGTTVTVSS (SEQ ID NO: 354) |
| 1A4 | DIVMSQSPSSLAVSAGEKVTMSCKSSQSLLNSRTRKNYLAWYQQKPGQSPKLLIYWASTRASGVPDRFTGSGSGTDFTLTISSVQAEDLAIYYCKQSFILRTFGGGTKLEIK (SEQ ID NO: 355) | QVQLQQSGPDLVKPGASVEISCKASGYSFTTYYLHWVRQRPGQGLEWIGWIFPGSDNTKYNEKFKGKATLTADTSSSTAYMQLSSLTSEDSAVYFCARNRDYYFDYWGQGTTVTVSS (SEQ ID NO: 356) |
| 7A3 | DIVVSQSPSSLAVSAGEKVIMSCKSSQSLLNSRTRKNYLAWYQLKPGQSPKLLIYSASTRESGVPDRFTGSGSGTDFTLTISSVQTEDLAVYYCMQSFTLRTFGGGTKLEIK (SEQ ID NO: 443) | EVQLQQSGAELVRPGALVKLSCKGSGFNIKDYYIHWVKQRPEQGLEWIGWIDPENGNNKYDPKFQGKASITADTSSNIAYLQLSSLTSEDTAVYYCARNDNYAFDYWGQGTTVTVSS (SEQ ID NO: 442) |
| 25A8 | QAVVTQESALTTSPGEAVTLTCRSSTGAVTTSNYANWVQEKPDHTFTGLIGGTNTRAPGVPARFSGSLIGDKAALTITGAQTEDEAIYFCVLWYNNYWVFGGGTKLTVL (SEQ ID NO: 377) | EVQLVESGGGLVRPEGSLRLSCAASGFTFNTYAMNWVRQAPGKGLEWVGRIRSKINNYATYYAESVKGRFTLSRDDSLSMVYLQMNSLKNEDTAMYYCVRHETLRSGISWFASWGQGTLVTVSS (SEQ ID NO: 378) |
| 16G7 | QAVVTQESALTTSPGETVTLTCRSSTGAVTTSNYANWVQEKPDHLFTGLIGGTNNRAPGVPARFSGSLIGDKAALTITGAQTEDEAIYFCALWYSNHWVFGGGTKLTVL (SEQ ID NO: 379) | EVQLVDSGGGLVQPKGSLKLSCAASGFTFNTYAMNWVRQAPGKGLEWVARIRSKSNNYATYYADSVKDRFTISRDDSQSRLYLQMNNLKTEDTAMYYCVRHETLRSGISWFANWGQGTLVTVSS (SEQ ID NO: 380) |
| h25A8-B5 | QAVVTQEPSLTVSPGGTVTLTCRSSTGAVTTSNYANWVQQKPGQAPRGLIGGTNTRAPGTPARFSGSLLGGKAALTLSGAQPEDEAEYYCVLWYNNYWVFGGGTKLTVL (SEQ ID NO: 381) | EVQLVESGGGLVKPGGSLRLSCAASGFTFSTYAMNWVRQAPGKGLEWVGRIRSKINNYATYYAESVKGRFTISRDDSKNTLYLQMNSLKTEDTAVYYCVRHETLRSGISWFASWGQGTLVTVSS (SEQ ID NO: 382) |
| h25A8-B8 | QAVVTQEPSLTVSPGGTVTLTCRSSTGAVTTSNYANWVQQKPGQAPRGLIGGTNTRAPGTPARFSGSLLGGKAALTLSGAQPEDEAEYYCVLWYNNHWVFGGGTKLTVL (SEQ ID NO: 383) | EVQLVESGGGLVKPGGSLRLSCAASGFTFSTYAMNWVRQAPGKGLEWVGRIRSKINNYATYYAESVKGRFTISRDDSKNTLYLQMNSLKTEDTAVYYCVRHETLRSGISWFASWGQGTLVTVSS (SEQ ID NO: 384) |
| h25A8-B12 | QAVVTQEPSLTVSPGGTVTLTCRASTGAVTTSNYANWVQQKPGQAPRGLIGGTNTRAPGTPARFSGSLLGGKAALTLSGAQPEDEAEYYCVLWYNNHWVFGGGTKLTVL (SEQ ID NO: 385) | EVQLVESGGGLVKPGGSLRLSCAASGFTFSTYAMNWVRQAPGKGLEWVGRIRSKINNYATYYAESVKGRFTISRDDSKNTLYLQMNSLKTEDTAVYYCVRHETLRSGISWFASWGQGTLVTVSS (SEQ ID NO: 386) |
| h25A8-B13 | QAVVTQEPSLTVSPGGTVTLTCRTSTGAVTTSNYANWVQQKPGQAPRGLIGGTNTRAPGTPARFSGSLLGGKAALTLSGAQPEDEAEYYCVLWYNNHWVFGGGTKLTVL (SEQ ID NO: 387) | EVQLVESGGGLVKPGGSLRLSCAASGFTFSTYAMNWVRQAPGKGLEWVGRIRSKINNYATYYAESVKGRFTISRDDSKNTLYLQMNSLKTEDTAVYYCVRHETLRSGISWFASWGQGTLVTVSS (SEQ ID NO: 388) |

TABLE 3-continued

| mAb | Light Chain | Heavy Chain |
|---|---|---|
| h25A8-C5 | QAVVTQEPSLTVSPGGTVTLTCR SSTGAVTTSNYANWVQQKPGQA PRGLIGGTNTRAPGTPARFSGSL LGGKAALTLSGAQPEDEAEYYCV LWYNNYWVFGGGTKLTVL (SEQ ID NO: 389) | EVQLVESGGGLVKPGGSRLSCA ASGFTFNTYAMNWVRQAPGQGLE WVGRIRSKINNYATYYAESVKGRF TISRDDSKNTLYLQMNSLKTEDTA VYYCVRHETLRSGISWFASWGQG TLVTVSS (SEQ ID NO: 390) |
| h25A8-C8 | QAVVTQEPSLTVSPGGTVTLTCR SSTGAVTTSNYANWVQQKPGQA PRGLIGGTNTRAPGTPARFSGSL LGGKAALTLSGAQPEDEAEYYCV LWYNNHWVFGGGTKLTVL (SEQ ID NO: 391) | EVQLVESGGGLVKPGGSRLSCA ASGFTFNTYAMNWVRQAPGKGLE WVGRIRSKINNYATYYAESVKGRF TISRDDSKNTLYLQMNSLKTEDTA VYYCVRHETLRSGISWFASWGQG TLVTVSS (SEQ ID NO: 392) |
| h25A8-D13 | QAVVTQEPSLTVSPGGTVTLTCR TSTGAVTTSNYANWVQQKPGQA PRGLIGGTNTRAPGTPARFSGSL LGGKAALTLSGAQPEDEAEYYCV LWYNNHWVFGGGTKLTVL (SEQ ID NO: 393) | EVQLVESGGGLVKPGGSRLSCA ASGFTFSTYAMNWVRQAPGKGLE WVGRIRSHINNYATYYAESVKGRF TISRDDSKNTLYLQMNSLKTEDTA VYYCVRHETLRSGISWFASWGQG TLVTVSS (SEQ ID NO: 394) |
| h25A8-E13 | QAVVTQEPSLTVSPGGTVTLTCR TSTGAVTTSNYANWVQQKPGQA PRGLIGGTNTRAPGTPARFSGSL LGGKAALTLSGAQPEDEAEYYCV LWYNNHWVFGGGTKLTVL (SEQ ID NO: 395) | EVQLVESGGGLVKPGGSRLSCA ASGFTFSTYAMNWVRQAPGKGLE WVGRIRSKYNNYATYYAESVKGR FTISRDDSKNTLYLQMNSLKTEDT AVYYCVRHETLRSGISWFASWGQ GTLVTVSS (SEQ ID NO: 396) |
| h25A8-F13 | QAVVTQEPSLTVSPGGTVTLTCR TSTGAVTTSNYANWVQQKPGQA PRGLIGGTNTRAPGTPARFSGSL LGGKAALTLSGAQPEDEAEYYCV LWYNNHWVFGGGTKLTVL (SEQ ID NO: 397) | EVQLVESGGGLVKPGGSRLSCA ASGFTFSTYAMNWVRQAPGKGLE WVGRERSKINNYATYYAESVKGR FTISRDDSKNTLYLQMNSLKTEDT AVYYCVRHETLRSGISWFASWGQ GTLVTVSS (SEQ ID NO: 398) |
| h25A8-G13 | QAVVTQEPSLTVSPGGTVTLTCR TSTGAVTTSNYANWVQQKPGQA PRGLIGGTNTRAPGTPARFSGSL LGGKAALTLSGAQPEDEAEYYCV LWYNNHWVFGGGTKLTVL (SEQ ID NO: 399) | EVQLVESGGGLVKPGGSRLSCA ASGFTFSTYAMNWVRQAPGKGLE WVGRIRSKINNYKTYYAESVKGRF TISRDDSKNTLYLQMNSLKTEDTA VYYCVRHETLRSGISWFASWGQG TLVTVSS (SEQ ID NO: 400) |

In Table 3, the underlined sequences are CDR sequences according to Kabat and in bold according to Chothia.

The invention also provides CDR portions of antibodies to CD3 (including Chothia, Kabat CDRs, and CDR contact regions). Determination of CDR regions is well within the skill of the art. It is understood that in some embodiments, CDRs can be a combination of the Kabat and Chothia CDR (also termed "combined CRs" or "extended CDRs"). In some embodiments, the CDRs are the Kabat CDRs. In other embodiments, the CDRs are the Chothia CDRs. In other words, in embodiments with more than one CDR, the CDRs may be any of Kabat, Chothia, combination CDRs, or combinations thereof. Table 4 provides examples of CDR sequences provided herein.

TABLE 4

| | Heavy Chain | | |
|---|---|---|---|
| mAb | CDRH1 | CDRH2 | CDRH3 |
| h2B4 | DYYMT (SEQ ID NO: 331) (Kabat); GFTFSDY (SEQ ID NO: 332) (Chothia); GFTFSDYYMT (SEQ ID NO: 333) (Extended) | RNRARGYT (SEQ ID NO: 417) (Chothia) FIRNRARGYTSDHNASVKG (SEQ ID NO: 334) (Kabat) | DRPSYYVLDY (SEQ ID NO: 335) |
| h2B4-VH-wt VL_TK | DYYMT (SEQ ID NO: 331) (Kabat); GFTFSDY (SEQ ID NO: 332) (Chothia); GFTFSDYYMT (SEQ ID NO: 333) (Extended) | RNRARGYT (SEQ ID NO: 417) (Chothia) FIRNRARGYTSDHNASVKG (SEQ ID NO: 334) (Kabat) | DRPSYYVLDY (SEQ ID NO: 335) |

TABLE 4-continued

| | | | |
|---|---|---|---|
| h2B4-VH-hnps VL_TK | DYYMT (SEQ ID NO: 331) (Kabat); GFTFSDY (SEQ ID NO: 332) (Chothia); GFTFSDYYMT (SEQ ID NO: 333) (Extended) | RNRARGYT (SEQ ID NO: 417) (Chothia) FIRNRARGYTSDHNPSVKG (SEQ ID NO: 336) (Kabat) | DRPSYYVLDY (SEQ ID NO: 335) |
| h2B4-VH-yaes VL_TK | DYYMT (SEQ ID NO: 331) (Kabat); GFTFSDY (SEQ ID NO: 332) (Chothia); GFTFSDYYMT (SEQ ID NO: 333) (Extended) | RNRARGYT (SEQ ID NO: 417) (Chothia) FIRNRARGYTSDYAESVKG (SEQ ID NO: 337) (Kabat) | DRPSYYVLDY (SEQ ID NO: 335) |
| h2B4-VH-yads VL_TK | DYYMT (SEQ ID NO: 331) (Kabat); GFTFSDY (SEQ ID NO: 332) (Chothia); GFTFSDYYMT (SEQ ID NO: 333) (Extended) | RNRARGYT (SEQ ID NO: 417) (Chothia) FIRNRARGYTSDYADSVKG (SEQ ID NO: 338) (Kabat) | DRPSYYVLDY (SEQ ID NO: 335) |
| h2B4-VH-yaps VL_TK | DYYMT (SEQ ID NO: 331) (Kabat); GFTFSDY (SEQ ID NO: 332) (Chothia); GFTFSDYYMT (SEQ ID NO: 333) (Extended) | RNRARGYT (SEQ ID NO: 417) (Chothia) FIRNRARGYTSDYAPSVKG (SEQ ID NO: 339) (Kabat) | DRPSYYVLDY (SEQ ID NO: 335) |
| h2B4-VH-hnps VL_TK-S55Y | DYYMT (SEQ ID NO: 331) (Kabat); GFTFSDY (SEQ ID NO: 332) (Chothia); GFTFSDYYMT (SEQ ID NO: 333) (Extended) | RNRARGYT (SEQ ID NO: 417) (Chothia) FIRNRARGYTSDHNPSVKG (SEQ ID NO: 336) (Kabat) | DRPSYYVLDY (SEQ ID NO: 335) |
| h2B4-VH-hnps VL_TK-S105Q | DYYMT (SEQ ID NO: 331) (Kabat); GFTFSDY (SEQ ID NO: 332) (Chothia); GFTFSDYYMT (SEQ ID NO: 333) (Extended) | RNRARGYT (SEQ ID NO: 417) (Chothia) FIRNRARGYTSDHNPSVKG (SEQ ID NO: 336) (Kabat) | DRPSYYVLDY (SEQ ID NO: 335) |
| h2B4-VH-hnps VL_TK-S55Y/S105Q | DYYMT (SEQ ID NO: 331) (Kabat); GFTFSDY (SEQ ID NO: 332) (Chothia); GFTFSDYYMT (SEQ ID NO: 333) (Extended) | RNRARGYT (SEQ ID NO: 417) (Chothia) FIRNRARGYTSDHNPSVKG (SEQ ID NO: 336) (Kabat) | DRPSYYVLDY (SEQ ID NO: 335) |
| 2B4 | DYYMT (SEQ ID NO: 331) (Kabat); GFTFTDY (SEQ ID NO: 415) (Chothia); GFTFTDYYMT (SEQ ID NO: 416) (Extended) | RNRARGYT (SEQ ID NO: 417) (Chothia) FIRNRARGYTSDHNASVKG (SEQ ID NO: 418) (Kabat) | DRPSYYVLDY (SEQ ID NO: 335) |
| h2B4-11 | DYYMT (SEQ ID NO: 331) (Kabat); GFTFSDY (SEQ ID NO: 332) (Chothia); GFTFSDYYMT (SEQ ID NO: 333) (Extended) | RNRARGYT (SEQ ID NO: 417) (Chothia) FIRNRARGYTSDHNASVKG (SEQ ID NO: 418) (Kabat) | DRPSYYVLDY (SEQ ID NO: 335) |
| 1C10 | SYWMH (SEQ ID NO: 418) (Kabat) GYTFTSY (SEQ ID NO: 419) (Chothia) GYTFTSYWMH (SEQ ID NO: 420) (Extended) | YSGGDT (SEQ ID NO: 421) (Chothia) NIYSGGDTINYDEKFKN (SEQ ID NO: 422) (Kabat) | DATSRYFFDY (SEQ ID NO: 423) |

TABLE 4-continued

| | | | |
|---|---|---|---|
| 1A4 | TYYLH (SEQ ID NO: 424) (Kabat) GYSFTTYY (SEQ ID NO: 425) (Chothia) GYSFTTYYLH (SEQ ID NO: 426) (Extended) | FPGSDN (SEQ ID NO: 427) (Chothia) WIFPGSDNTKYNEKFKG (SEQ ID NO: 428) (Kabat) | NRDYYFDY (SEQ ID NO: 429) |
| 7A3 | DYYIH (SEQ ID NO: 446) (Kabat) GFNIKDY (SEQ ID NO: 447) (Chothia) GFNIKDYYIH (SEQ ID NO: 448) (Extended) | DPENGN (SEQ ID NO: 449) (Chothia) WIDPENGNNKYDPKFQG (SEQ ID NO: 450) (Kabat) | NDNYAFDY (SEQ ID NO: 451) |
| 25A8 | TYAMN (SEQ ID NO: 401) (Kabat); GFTFNTY (SEQ ID NO: 402) (Chothia); GFTFNTYAMN (SEQ ID NO: 403) (Extended) | RSKINNYA (SEQ ID NO: 404) (Chothia) RIRSKINNYATYYAESVKG (SEQ ID NO: 405) (Kabat) | HETLRSGISWFA S (SEQ ID NO: 406) |
| 16G7 | TYAMN (SEQ ID NO: 401) (Kabat); GFTFNTY (SEQ ID NO: 402) (Chothia); GFTFNTYAMN (SEQ ID NO: 403) (Extended) | RSKSNNYA (SEQ ID NO: 404) (Chothia) RIRSKSNNYATYYADSVKD (SEQ ID NO: 405) (Kabat) | HETLRSGISWFA N (SEQ ID NO: 406) |
| h25A8-B5 | TYAMN (SEQ ID NO: 401) (Kabat); GFTFSTY (SEQ ID NO: 407) (Chothia); GFTFSTYAMN (SEQ ID NO: 408) (Extended) | RSKINNYA (SEQ ID NO: 404) (Chothia) RIRSKINNYATYYAESVKG (SEQ ID NO: 405) (Kabat) | HETLRSGISWFA S (SEQ ID NO: 406) |
| h25A8-B8 | TYAMN (SEQ ID NO: 401) (Kabat); GFTFSTY (SEQ ID NO: 407) (Chothia); GFTFSTYAMN (SEQ ID NO: 408) (Extended) | RSKINNYA (SEQ ID NO: 404) (Chothia) RIRSKINNYATYYAESVKG (SEQ ID NO: 405) (Kabat) | HETLRSGISWFA S (SEQ ID NO: 406) |
| h25A8-B12 | TYAMN (SEQ ID NO: 401) (Kabat); GFTFSTY (SEQ ID NO: 407) (Chothia); GFTFSTYAMN (SEQ ID NO: 408) (Extended) | RSKINNYA (SEQ ID NO: 404) (Chothia) RIRSKINNYATYYAESVKG (SEQ ID NO: 405) (Kabat) | HETLRSGISWFA S (SEQ ID NO: 406) |
| h25A8-B13 | TYAMN (SEQ ID NO: 401) (Kabat); GFTFSTY (SEQ ID NO: 407) (Chothia); GFTFSTYAMN (SEQ ID NO: 408) (Extended) | RSKINNYA (SEQ ID NO: 404) (Chothia) RIRSKINNYATYYAESVKG (SEQ ID NO: 405) (Kabat) | HETLRSGISWFA S (SEQ ID NO: 406) |
| h25A8-C5 | TYAMN (SEQ ID NO: 401) (Kabat); GFTFNTY (SEQ ID NO: 402) (Chothia); GFTFNTYAMN (SEQ ID NO: 403) (Extended) | RSKINNYA (SEQ ID NO: 404) (Chothia) RIRSKINNYATYYAESVKG (SEQ ID NO: 405) (Kabat) | HETLRSGISWFA S (SEQ ID NO: 406) |
| h25A8-C8 | TYAMN (SEQ ID NO: 401) (Kabat); GFTFNTY (SEQ ID NO: 402) (Chothia); GFTFNTYAMN (SEQ ID NO: 403) | RSKINNYA (SEQ ID NO: 404) (Chothia) RIRSKINNYATYYAESVKG (SEQ ID NO: 405) (Kabat) | HETLRSGISWFA S (SEQ ID NO: 406) |

TABLE 4-continued

| mAb | | | |
|---|---|---|---|
| h25A8-D13 | TYAMN (SEQ ID NO: 401) (Kabat); GFTFSTY (SEQ ID NO: 407) (Chothia); GFTFSTYAMN (SEQ ID NO: 408) (Extended) | RSHINNYA (SEQ ID NO: 409) (Chothia) RIRSHINNYATYYAESVKG (SEQ ID NO: 410) (Kabat) | HETLRSGISWFAS (SEQ ID NO: 406) |
| h25A8-E13 | TYAMN (SEQ ID NO: 401) (Kabat); GFTFSTY (SEQ ID NO: 407) (Chothia); GFTFSTYAMN (SEQ ID NO: 408) (Extended) | RSKYNNYA (SEQ ID NO: 411) (Chothia) RIRSKYNNYATYYAESVKG (SEQ ID NO: 412) (Kabat) | HETLRSGISWFAS (SEQ ID NO: 406) |
| h25A8-F13 | TYAMN (SEQ ID NO: 401) (Kabat); GFTFSTY (SEQ ID NO: 407) (Chothia); GFTFSTYAMN (SEQ ID NO: 408) (Extended) | RSKINNYA (SEQ ID NO: 404) (Chothia) RERSKINNYATYYAESVKG (SEQ ID NO: 413) (Kabat) | HETLRSGISWFAS (SEQ ID NO: 406) |
| h25A8-G13 | TYAMN (SEQ ID NO: 401) (Kabat); GFTFSTY (SEQ ID NO: 407) (Chothia); GFTFSTYAMN (SEQ ID NO: 408) (Extended) | RSKINNYA (SEQ ID NO: 404) (Chothia) RIRSKINNYKTYYAESVKG (SEQ ID NO: 414) (Kabat) | HETLRSGISWFAS (SEQ ID NO: 406) |

| Light Chain | | | |
|---|---|---|---|
| mAb | CDRH1 | CDRH2 | CDRH3 |
| h2B4 | TSSQSLFNVRSRKNYLA (SEQ ID NO: 340) | WASTRES (SEQ ID NO: 341) | KQSYDLFT (SEQ ID NO: 342) |
| h2B4-VH-wt VL_TK | KSSQSLFNVRSRKNYLA (SEQ ID NO: 343) | WASTRES (SEQ ID NO: 341) | KQSYDLFT (SEQ ID NO: 342) |
| h2B4-VH-hnps VL_TK | KSSQSLFNVRSRKNYLA (SEQ ID NO: 343) | WASTRES (SEQ ID NO: 341) | KQSYDLFT (SEQ ID NO: 342) |
| h2B4-VH-yaes VL_TK | KSSQSLFNVRSRKNYLA (SEQ ID NO: 343) | WASTRES (SEQ ID NO: 341) | KQSYDLFT (SEQ ID NO: 342) |
| h2B4-VH-yads VL_TK | KSSQSLFNVRSRKNYLA (SEQ ID NO: 343) | WASTRES (SEQ ID NO: 341) | KQSYDLFT (SEQ ID NO: 342) |
| h2B4-VH-yaps VL_TK | KSSQSLFNVRSRKNYLA (SEQ ID NO: 343) | WASTRES (SEQ ID NO: 341) | KQSYDLFT (SEQ ID NO: 342) |
| 2B4 | TSSQSLFNSRSRKNYLA (SEQ ID NO: 430) | WASTRES (SEQ ID NO: 341) | KQSYDLFT (SEQ ID NO: 342) |
| h2B4-11 | TSSQSLFNSRSRKNYLA (SEQ ID NO: 430) | WASTRES (SEQ ID NO: 341) | QQSYDTFT (SEQ ID NO: 446) |
| 1C10 | KSSQSLLNSRTRKNY (SEQ ID NO: 431) | WASTRES (SEQ ID NO: 341) | TQSFILRT (SEQ ID NO: 432) |
| 1A4 | KSSQSLLNSRTRKNY (SEQ ID NO: 431) | WASTRAS (SEQ ID NO: 433) | KQSFILRT (SEQ ID NO: 434) |
| 7A3 | KSSQSLLNSRTRKNY (SEQ ID NO: 431) | SASTRES (SEQ ID NO: 452) | MQSFTLRT (SEQ ID NO: 453) |

TABLE 4-continued

| | | | |
|---|---|---|---|
| h2B4-VH-hnps VL_TK-S55Y | KSSQSLFNVRSRKN YLA (SEQ ID NO: 343) | WASTRES (SEQ ID NO: 341) | KQSYDLFT (SEQ ID NO: 342) |
| h2B4-VH-hnps VL_TK-S105Q | KSSQSLFNVRSRKN YLA (SEQ ID NO: 343) | WASTRES (SEQ ID NO: 341) | KQSYDLFT (SEQ ID NO: 342) |
| h2B4-VH-hnps VL_TK-S55Y/ S105Q | KSSQSLFNVRSRKN YLA (SEQ ID NO: 343) | WASTRES (SEQ ID NO: 341) | KQSYDLFT (SEQ ID NO: 342) |
| 25A8 | RSSTGAVTTSNYAN (SEQ ID NO: 435) | GTNTRAP (SEQ ID NO: 436) | VLWYNNYWV (SEQ ID NO: 437) |
| 16G7 | RSSTGAVTTSNYAN (SEQ ID NO: 435) | GTNTRAP (SEQ ID NO: 436) | ALWYSNHWV (SEQ ID NO: 438) |
| h25A8-B5 | RSSTGAVTTSNYAN (SEQ ID NO: 435) | GTNTRAP (SEQ ID NO: 436) | VLWYNNYWV (SEQ ID NO: 437) |
| h25A8-B8 | RSSTGAVTTSNYAN (SEQ ID NO: 435) | GTNTRAP (SEQ ID NO: 436) | VLWYNNHWV (SEQ ID NO: 439) |
| h25A8-B12 | RASTGAVTTSNYAN (SEQ ID NO: 440) | GTNTRAP (SEQ ID NO: 436) | VLWYNNHWV (SEQ ID NO: 439) |
| h25A8-B13 | RTSTGAVTTSNYAN (SEQ ID NO: 441) | GTNTRAP (SEQ ID NO: 436) | VLWYNNHWV (SEQ ID NO: 439) |
| h25A8-C5 | RSSTGAVTTSNYAN (SEQ ID NO: 435) | GTNTRAP (SEQ ID NO: 436) | VLWYNNYWV (SEQ ID NO: 437) |
| h25A8-C8 | RSSTGAVTTSNYAN (SEQ ID NO: 435) | GTNTRAP (SEQ ID NO: 436) | VLWYNNHWV (SEQ ID NO: 439) |
| h25A8-D13 | RTSTGAVTTSNYAN (SEQ ID NO: 441) | GTNTRAP (SEQ ID NO: 436) | VLWYNNHWV (SEQ ID NO: 439) |
| h25A8-E13 | RTSTGAVTTSNYAN (SEQ ID NO: 441) | GTNTRAP (SEQ ID NO: 436) | VLWYNNHWV (SEQ ID NO: 439) |
| h25A8-F13 | RTSTGAVTTSNYAN (SEQ ID NO: 441) | GTNTRAP (SEQ ID NO: 436) | VLWYNNHWV (SEQ ID NO: 439) |
| h25A8-G13 | RTSTGAVTTSNYAN (SEQ ID NO: 441) | GTNTRAP (SEQ ID NO: 436) | VLWYNNHWV (SEQ ID NO: 439) |

The invention also provides isolated polynucleotides encoding the antibodies of the invention, and vectors and host cells comprising the polynucleotide.

In one embodiment, a polynucleotide comprises a sequence encoding the heavy chain and/or the light chain variable regions of antibody h2B4, h2B4-VH-wt VL_TK, h2B4-VH-hnps VL_TK, h2B4-VH-yaes VL_TK, h2B4-VH-yads VL_TK, h2B4-VH-yaps VL_TK, h2B4-VH-hnps VL_TK-S55Y, h2B4-VH-hnps VL_TK-S105Q, h2B4-vH-hnps VL_TK-S55Y/S105Q, 2B4, h2B4-11, 1C10, 1A4, 7A3, 25A8, 16G7, h25A8-B5, h25A8-B8, h25A8-612, h25A8-613, h25A8-C5, h25A8-C8, h25A8-D13, h25A8-E13, h25A8-F13, or h25A8-G13. The sequence encoding the antibody of interest may be maintained in a vector in a host cell and the host cell can then be expanded and frozen for future use. Vectors (including expression vectors) and host cells are further described herein.

The invention also encompasses fusion proteins comprising one or more fragments or regions from the antibodies of this invention. In one embodiment, a fusion polypeptide is provided that comprises at least 10 contiguous amino acids of the variable light chain region shown in SEQ ID NOs: 319, 321, 323, 325, 327, 329, 344, 346, 348, 350, 445, 352, 355, 443, 377, 379, 381, 383, 385, 387, 389, 391, 393, 395, 397, or 399, and/or at least 10 amino acids of the variable heavy chain region shown in SEQ ID NOs: 320, 322, 324, 326, 328, 330, 345, 347, 349, 351, 354, 356, 444, 442, 378, 380, 382, 384, 386, 388, 390, 392, 394, 396, 398, or 400. In other embodiments, a fusion polypeptide is provided that comprises at least about 10, at least about 15, at least about 20, at least about 25, or at least about 30 contiguous amino acids of the variable light chain region and/or at least about 10, at least about 15, at least about 20, at least about 25, or at least about 30 contiguous amino acids of the variable heavy chain region. In another embodiment, the fusion polypeptide comprises a light chain variable region and/or a heavy chain variable region, as shown in any of the sequence pairs selected from among SEQ ID NOs: 319 and 320, 321 and 322, 323 and 324, 325 and 326, 327 and 328, 329 and 330, 344 and 345, 346 and 347, 348 and 349, 350 and 351, 445 and 444, 352 and 354, 355 and 356, 443 and 442, 377 and 378, 379 and 380, 381 and 382, 383 and 384, 385 and 386, 387 and 388, 389 and 390, 391 and 392, 393 and 394, 395 and 396, 397 and 398, or 399 and 400. In another embodiment, the fusion polypeptide comprises one or more CDR(s). In still other embodiments, the fusion polypeptide comprises CDR H3 (VH CDR3) and/or CDR L3 (VL CDR3). For purposes of this invention, a fusion protein contains one or more antibodies and another amino acid sequence to which it is not attached in the native molecule, for example, a heterologous sequence or a homologous sequence from another region. Exemplary heterologous sequences include, but are not limited to a "tag" such as a FLAG tag or a 6His tag. Tags are well known in the art.

A fusion polypeptide can be created by methods known in the art, for example, synthetically or recombinantly. Typically, the fusion proteins of this invention are made by preparing an expressing a polynucleotide encoding them using recombinant methods described herein, although they may also be prepared by other means known in the art, including, for example, chemical synthesis.

Representative materials of the CD3 antibody in the present invention were deposited in the American Type Culture Collection (ATCC) on Sep. 11, 2015. Vector having ATCC Accession No. PTA-122513 is a polynucleotide encoding a humanized CD3 antibody heavy chain variable region, and vector having ATCC Accession No. PTA-122512 is a polynucleotide encoding a humanized CD3 antibody light chain variable region. The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. Section 122 and the Commissioner's rules pursuant thereto (including 37 C.F.R. Section 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

Bispecific Antibodies and Methods of Making

Bispecific antibodies, monoclonal antibodies that have binding specificities for at least two different antigens, can be prepared using the antibodies disclosed herein. Methods for making bispecific antibodies are known in the art (see, e.g., Suresh et al., Methods in Enzymology 121:210, 1986). Traditionally, the recombinant production of bispecific antibodies was based on the coexpression of two immunoglobulin heavy chain-light chain pairs, with the two heavy chains having different specificities (Millstein and Cuello, Nature 305, 537-539, 1983).

According to one approach to making bispecific antibodies, antibody variable domains with the desired binding specificities (antibody-antigen combining sites) are fused to immunoglobulin constant region sequences. The fusion preferably is with an immunoglobulin heavy chain constant region, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690.

In another approach, the bispecific antibodies are composed of amino acid modification in the first hinge region in one arm, and the substituted/replaced amino acid in the first hinge region has an opposite charge to the corresponding amino acid in the second hinge region in another arm. This approach is described in International Patent Application No. PCT/US2011/036419 (WO2011/143545).

In another approach, the formation of a desired heteromultimeric or heterodimeric protein (e.g., bispecific antibody) is enhanced by altering or engineering an interface between a first and a second immunoglobulin-like Fc region (e.g., a hinge region and/or a CH3 region). In this approach, the bispecific antibodies may be composed of a CH3 region, wherein the CH3 region comprises a first CH3 polypeptide and a second CH3 polypeptide which interact together to form a CH3 interface, wherein one or more amino acids within the CH3 interface destabilize homodimer formation and are not electrostatically unfavorable to homodimer formation. This approach is described in International Patent Application No. PCT/US2011/036419 (WO2011/143545).

In another approach, the bispecific antibodies can be generated using a glutamine-containing peptide tag engineered to the antibody directed to an epitope (e.g., BCMA) in one arm and another peptide tag (e.g., a Lys-containing peptide tag or a reactive endogenous Lys) engineered to a second antibody directed to a second epitope in another arm in the presence of transglutaminase. This approach is described in International Patent Application No. PCT/IB2011/054899 (WO2012/059882).

In another aspect of the invention, the heterodimeric protein (e.g., bispecific antibody) as described herein comprises a full-length human antibody, wherein a first antibody variable domain of the heterodimeric protein is capable of recruiting the activity of a human immune effector cell by specifically binding to an effector antigen located on the human immune effector cell, and wherein a second antibody variable domain of the heterodimeric protein is capable of specifically binding to a target antigen. In some embodiments, the human antibody has an IgG1, IgG2, IgG3, or IgG4 isotype. In some embodiments, the heterodimeric protein comprises an immunologically inert Fc region.

The human immune effector cell can be any of a variety of immune effector cells known in the art. For example, the immune effector cell can be a member of the human lymphoid cell lineage, including, but not limited to, a T cell (e.g., a cytotoxic T cell), a B cell, and a natural killer (NK) cell. The immune effector cell can also be, for example without limitation, a member of the human myeloid lineage, including, but not limited to, a monocyte, a neutrophilic granulocyte, and a dendritic cell. Such immune effector cells may have either a cytotoxic or an apoptotic effect on a target cell or other desired effect upon activation by binding of an effector antigen.

The effector antigen is an antigen (e.g., a protein or a polypeptide) that is expressed on the human immune effector cell. Examples of effector antigens that can be bound by the heterodimeric protein (e.g., a heterodimeric antibody or a bispecific antibody) include, but are not limited to, human CD3 (or CD3 (Cluster of Differentiation) complex), CD16, NKG2D, NKp46, CD2, CD28, CD25, CD64, and CD89.

The target cell can be a cell that is native or foreign to humans. In a native target cell, the cell may have been transformed to be a malignant cell or pathologically modified (e.g., a native target cell infected with a virus, a plasmodium, or a bacterium). In a foreign target cell, the cell is an invading pathogen, such as a bacterium, a plasmodium, or a virus.

The target antigen is expressed on a target cell in a diseased condition (e.g., an inflammatory disease, a proliferative disease (e.g., cancer), an immunological disorder, a neurological disease, a neurodegenerative disease, an autoimmune disease, an infectious disease (e.g., a viral infection or a parasitic infection), an allergic reaction, a graft-versus-host disease or a host-versus-graft disease). A target antigen is not effector antigen. Examples of the target antigens include, but are not limited to, BCMA, EpCAM (Epithelial Cell Adhesion Molecule), CCR5 (Chemokine Receptor type 5), CD19, HER (Human Epidermal Growth Factor Receptor)-2/neu, HER-3, HER-4, EGFR (Epidermal Growth Factor Receptor), PSMA, CEA, MUC-1 (Mucin), MUC2, MUC3, MUC4, MUC5AC, MUC5B, MUC7, CIhCG, Lewis-Y, CD20, CD33, CD30, ganglioside GD3, 9-O-Acetyl-GD3, GM2, Globo H, fucosyl GM1, Poly SA, GD2, Carboanhydrase IX (MN/CA IX), CD44v6, Shh (Sonic Hedgehog), Wue-1, Plasma Cell Antigen, (membrane-bound) IgE, MCSP (Melanoma Chondroitin Sulfate Proteoglycan), CCR8, TNF-alpha precursor, STEAP, mesothelin, A33 Antigen, PSCA (Prostate Stem Cell Antigen), Ly-6; desmoglein 4, E-cadherin neoepitope, Fetal Acetylcholine Receptor, CD25, CA19-9 marker, CA-125 marker and MIS (Muellerian Inhibitory Substance) Receptor type II, sTn (sialylated Tn antigen; TAG-72), FAP (fibroblast activation antigen), endosialin, EGFRvIII, LG, SAS and CD63.

In some embodiments, the heterodimeric protein (e.g., bispecific antibody) as described herein comprises a full-length human antibody, wherein a first antibody variable domain of the heterodimeric protein is capable of recruiting the activity of a human immune effector cell by specifically binding to an effector antigen (e.g., CD3 antigen) located on the human immune effector cell, wherein a second antibody variable domain of the heterodimeric protein is capable of specifically binding to a target antigen (e.g., CD20 antigen or EpCAM), wherein the first and second antibody variable domain of the heterodimeric protein comprise amino acid modifications at positions 223, 225, and 228 (e.g., (C223E or C223R), (E225R), and (P228E or P228R)) in the hinge region and at position 409 or 368 (e.g., K409R or L368E (EU numbering scheme)) in the CH3 region of human IgG2 (SEQ ID NO: 493).

In some embodiments, the first and second antibody variable domains of the heterodimeric protein comprise amino acid modifications at positions 221 and 228 (e.g., (D221R or D221E) and (P228R or P228E)) in the hinge region and at position 409 or 368 (e.g., K409R or L368E (EU numbering scheme)) in the CH3 region of human IgG1 (SEQ ID NO: 494).

In some embodiments, the first and second antibody variable domains of the heterodimeric protein comprise amino acid modifications at positions 228 (e.g., (P228E or P228R)) in the hinge region and at position 409 or 368 (e.g., R409 or L368E (EU numbering scheme)) in the CH3 region of human IgG4 (SEQ ID NO: 495).

In another embodiment, the first antibody variable domain of the heterodimeric protein comprises a VH region comprising a VH CDR1, VH CDR2, and VH CDR3 of the VH sequence shown in SEQ ID NO: 320, 322, 324, 326, 328, 330, 345, 347, 349, 351, 444, 354, 356, 378, 442, 380, 382, 384 386, 388, 390, 392, 394, 396, 398, or 400; and/or a light chain variable (VL) region comprising VL CDR1, VL CDR2, and VL CDR3 of the VL sequence shown in SEQ ID NO: 319, 321, 323, 325, 327, 329, 344, 346, 348, 350, 352, 355, 377, 443, 445, 379, 381, 383, 385, 387, 389, 391, 393, 395, 397, or 399, and the second antibody variable domain of the heterodimeric protein comprises VH region comprising the VH sequence shown in SEQ ID NO: 2, 3, 7, 8, 24, 25, 26, 27, 28, 29, 30, 31, 32, 33, 35, 37, 39, 42, 44, 46, 48, 50, 52, 54, 56, 58, 60, 62, 64, 66, 68, 70, 72, 74, 76, 78, 83, 87, 92, 95, 97, 99, 101, 104, 106, 110, 112, 114, 118, 120, 122, 125, 127, 313, 314, 363, or 365; and/or a VL region comprising VL CDR1, VL CDR2, and VL CDR3 of the VL sequence shown in SEQ ID NO: 1, 4, 5, 6, 9, 10, 11, 12, 13, 14, 15, 16, 17, 18, 19, 20, 21, 22, 23, 34, 36, 38, 40, 41, 43, 45, 47, 49, 51, 53, 55, 57, 59, 61, 63, 65, 67, 69, 71, 73, 75, 77, 79, 317, 81, 82, 84, 85, 86, 88, 89, 90, 91, 93, 94, 96, 98, 100, 102, 103, 105, 107, 108, 109, 111, 113, 115, 116, 117, 119, 121, 123, 124, 126, 128, 315, or 364.

In another embodiment, the first antibody variable domain comprises a heavy chain variable (VH) region comprising a VH CDR1, VH CDR2, and VH CDR3 of the VH sequence shown in SEQ ID NO: 324 or 388; and/or a light chain variable (VL) region comprising VL CDR1, VL CDR2, and VL CDR3 of the VL sequence shown in SEQ ID NO: 323 or 387; and the second antibody variable domain comprises a heavy chain variable (VH) region comprising a VH CDR1, VH CDR2, and VH CDR3 of the VH sequence shown in SEQ ID NO: 112; and/or a light chain variable (VL) region comprising VL CDR1, VL CDR2, and VL CDR3 of the VL sequence shown in SEQ ID NO: 38.

In another embodiment, the first antibody variable domain comprises a heavy chain variable (VH) region comprising (i) a VH complementarity determining region one (CDR1) comprising the sequence shown in SEQ ID NO: 331 (ii) a VH CDR2 comprising the sequence shown in SEQ ID NO: 417; and iii) a VH CDR3 comprising the sequence shown in SEQ ID NO: 335; and a light chain variable (VL) region comprising (i) a VL CDR1 comprising the sequence shown in SEQ ID NO: 343; (ii) a VL CDR2 comprising the sequence shown in SEQ ID NO: 341; and (iii) a VL CDR3 comprising the sequence shown in SEQ ID NO: 342; and the second antibody variable domain comprises a heavy chain VH region comprising a heavy chain variable (VH) region comprising (i) a VH CDR1 comprising the sequence shown in SEQ ID NO: 156; (ii) a VH CDR2 comprising the sequence shown in SEQ ID NO: 159; and (iii) a VH CDR3 comprising SEQ ID NO: 155; and a light chain variable (VL) region comprising (i) a VL CDR1 comprising the sequence shown in SEQ ID NO: 209; (ii) a VL CDR2 comprising the sequence shown in SEQ ID NO: 221; and (iii) a VL CDR3 comprising the sequence shown in SEQ ID NO: 225. The VH CDR1 of the first antibody variable domain may further comprise the sequence of S, FS, TFS, FTFS or GFTFS immediately preceding the sequence shown in SEQ ID NO: 331. For example, the VH CDR1 of the first antibody variable domain may comprise the sequence shown in SEQ ID NO: 333. The VH CDR2 of the first antibody variable domain may further comprise the sequence of F or FI immediately preceding the sequence shown in SEQ ID NO: 417 and/or the sequence of S, SD, SDH, SDHN, SDHNP, SDHNPS, SDHNPSV, SDHNPSVK, or SDHNPSVKG immediately following the sequence shown in SEQ ID NO: 417. For example, the VH CDR2 of the first antibody variable domain may comprise the sequence shown in SEQ ID NO: 336. The VH CDR1 of the second antibody variable domain may further comprise the sequence of S, FS, TFS, FTFS or GFTFS immediately preceding the sequence shown in SEQ ID NO: 156. For example, the VH CDR1 of the second antibody variable domain may comprise the sequence shown in SEQ ID NO: 157. The VH CDR2 of the second antibody variable domain may further comprise the sequence of A or AI immediately preceding the sequence shown in SEQ ID NO: 159 and/or the sequence of L, LP, LPY, LPYA, LPYAD, LPYADS, LPYADSV, LPYADSVK, or LPYADSVKG immediately following the sequence shown in SEQ ID NO: 159. For example, the VH CDR2 of the second antibody variable domain may comprise the sequence shown in SEQ ID NO: 158.

In another embodiment, the first antibody variable domain comprises a heavy chain variable (VH) region comprising (i) a VH complementarity determining region one (CDR1) comprising the sequence shown in SEQ ID NO: 332 (ii) a VH CDR2 comprising the sequence shown in SEQ ID NO: 336; and iii) a VH CDR3 comprising the sequence shown in SEQ ID NO: 335; and a light chain variable (VL) region comprising (i) a VL CDR1 comprising the sequence shown in SEQ ID NO: 343; (ii) a VL CDR2 comprising the sequence shown in SEQ ID NO: 341; and (iii) a VL CDR3 comprising the sequence shown in SEQ ID NO: 342; and the second antibody variable domain comprises a heavy chain VH region comprising a heavy chain variable (VH) region comprising (i) a VH CDR1 comprising the sequence shown in SEQ ID NO: 151; (ii) a VH CDR2 comprising the sequence shown in SEQ ID NO: 158; and (iii) a VH CDR3 comprising SEQ ID NO: 155; and a light chain variable (VL) region comprising (i) a VL CDR1 comprising the sequence shown in SEQ ID NO: 209; (ii) a VL CDR2 comprising the sequence shown in SEQ ID NO: 221; and (iii) a VL CDR3 comprising the sequence shown in SEQ ID NO: 225. The VH CDR1 of the first antibody variable domain may further comprise the sequence of Y, YM or YMT immediately following the sequence shown in SEQ ID NO: 332. For example, the VH CDR1 of the first antibody variable domain may comprise the sequence shown in SEQ ID NO: 333. The VH CDR1 of the second antibody variable domain may further comprise the sequence P, PM, or PMS immediately following the sequence shown in SEQ ID NO: 151. For example, the VH CDR1 of the second antibody variable domain may comprise the sequence shown in SEQ ID NO: 157.

In another embodiment, the first antibody variable domain comprises a heavy chain variable (VH) region comprising (i) a VH complementarity determining region one (CDR1) comprising the sequence shown in SEQ ID NO: 401 (ii) a VH CDR2 comprising the sequence shown in SEQ ID NO: 404; and iii) a VH CDR3 comprising the sequence shown in SEQ ID NO: 406; and a light chain variable (VL) region comprising (i) a VL CDR1 comprising the sequence shown in SEQ ID NO: 441; (ii) a VL CDR2 comprising the sequence shown in SEQ ID NO: 436; and (iii) a VL CDR3 comprising the sequence shown in SEQ ID NO: 439; and the second antibody variable domain comprises a heavy chain VH region comprising a heavy chain variable (VH) region comprising (i) a VH CDR1 comprising the sequence shown in SEQ ID NO: 156; (ii) a VH CDR2 comprising the sequence shown in SEQ ID NO: 159; and (iii) a VH CDR3 comprising SEQ ID NO: 155; and a light chain variable (VL) region comprising (i) a VL CDR1 comprising the sequence shown in SEQ ID NO: 209; (ii) a VL CDR2 comprising the sequence shown in SEQ ID NO: 221; and (iii) a VL CDR3 comprising the sequence shown in SEQ ID NO: 225. The VH CDR1 of the first antibody variable domain may further comprise the sequence of S, FS, TFS, FTFS or GFTFS immediately preceding the sequence shown in SEQ ID NO: 401. For example, the VH CDR1 of the first antibody variable domain comprises the sequence shown in SEQ ID NO: 408. The VH CDR2 of the first antibody variable domain may further comprise the sequence of R or RI immediately preceding the sequence shown in SEQ ID NO: 404 and/or the sequence of T, TY, TYY, TYYA, TYYAE, TYYAES, TYYAESV, TYYAESVK, or TYYAESVKG immediately following the sequence shown in SEQ ID NO: 404. For example, the bispecific antibody of claim 49, wherein the VH CDR2 of the first antibody variable domain comprises the sequence shown in SEQ ID NO: 405. The VH CDR1 of the second antibody variable domain may further comprise the sequence of S, FS, TFS, FTFS or GFTFS immediately preceding the sequence shown in SEQ ID NO: 156. For example, the VH CDR1 of the second antibody variable domain comprises the sequence shown in SEQ ID NO: 157. The VH CDR2 of the second antibody variable domain may further comprise the sequence of A or AI immediately preceding the sequence shown in SEQ ID NO: 159 and/or the sequence of L, LP, LPY, LPYA, LPYAD, LPYADS, LPYADSV, LPYADSVK, or LPYADSVKG immediately following the sequence shown in SEQ ID NO: 159. For example, the VH CDR2 of the second antibody variable domain may comprise the sequence shown in SEQ ID NO: 158.

In another embodiment, the first antibody variable domain comprises a heavy chain variable (VH) region comprising (i) a VH complementarity determining region one (CDR1) comprising the sequence shown in SEQ ID NO: 407 (ii) a VH CDR2 comprising the sequence shown in SEQ ID NO: 405; and iii) a VH CDR3 comprising the sequence shown in SEQ ID NO: 406; and a light chain variable (VL) region comprising (i) a VL CDR1 comprising the sequence shown in SEQ ID NO: 441; (ii) a VL CDR2 comprising the sequence shown in SEQ ID NO: 436; and (iii) a VL CDR3 comprising the sequence shown in SEQ ID NO: 439; and the second antibody variable domain comprises a heavy chain VH region comprising a heavy chain variable (VH) region comprising (i) a VH CDR1 comprising the sequence shown in SEQ ID NO: 151; (ii) a VH CDR2 comprising the sequence shown in SEQ ID NO: 158; and (iii) a VH CDR3 comprising SEQ ID NO: 155; and a light chain variable (VL) region comprising (i) a VL CDR1 comprising the sequence shown in SEQ ID NO: 209; (ii) a VL CDR2 comprising the sequence shown in SEQ ID NO: 221; and (iii) a VL CDR3 comprising the sequence shown in SEQ ID NO: 225. The VH CDR1 of the first antibody variable domain may further comprise the sequence of A, AM or AMN immediately following the sequence shown in SEQ ID NO: 407. For example, the VH CDR1 of the first antibody variable domain may comprise the sequence shown in SEQ ID NO: 408. The VH CDR1 of the second antibody variable domain may further comprise the sequence P, PM, or PMS immediately following the sequence shown in SEQ ID NO: 151. For example, the VH CDR1 of the second antibody variable domain may comprise the sequence shown in SEQ ID NO: 157.

The antibodies useful in the present invention can encompass monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv), mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies).

In some embodiments, the BCMA or CD3 antibody as described herein is a monoclonal antibody. For example, the BCMA or CD3 antibody is a humanized monoclonal antibody or a chimeric monoclonal antibody.

In some embodiments, the antibody comprises a modified constant region, such as, for example without limitation, a constant region that has increased potential for provoking an immune response. For example, the constant region may be modified to have increased affinity to an Fc gamma receptor such as, e.g., FcγRI, FcγRIIA, or FcγIII.

In some embodiments, the antibody comprises a modified constant region, such as a constant region that is immunologically inert, that is, having a reduced potential for provoking an immune response. In some embodiments, the constant region is modified as described in Eur. J. Immunol., 29:2613-2624, 1999; PCT Application No. PCT/GB99/01441; and/or UK Patent Application No. 98099518. The Fc can be human IgG1, human IgG2, human IgG3, or human IgG4. The Fc can be human IgG2 containing the mutation A330P331 to S330S331 (IgG2Δa), in which the amino acid residues are numbered with reference to the wild type IgG2 sequence. Eur. J. Immunol., 29:2613-2624, 1999. In some embodiments, the antibody comprises a constant region of IgG4 comprising the following mutations (Armour et al., Molecular Immunology 40 585-593, 2003): E233F234L235 to P233V234A235 (IgG4Δc), in which the numbering is with reference to wild type IgG4. In yet another embodiment, the Fc is human IgG4 E233F234L235 to P233V234A235 with deletion G236 (IgG4Δb). In another embodiment, the Fc is any human IgG4 Fc (IgG4, IgG4Δb or IgG4Δc) containing hinge stabilizing mutation S228 to P228 (Aalberse et al., Immunology 105, 9-19, 2002). In another embodiment, the Fc can be aglycosylated Fc.

In some embodiments, the constant region is aglycosylated by mutating the oligosaccharide attachment residue (such as Asn297) and/or flanking residues that are part of the glycosylation recognition sequence in the constant region. In some embodiments, the constant region is aglycosylated for N-linked glycosylation enzymatically. The constant region may be aglycosylated for N-linked glycosylation enzymatically or by expression in a glycosylation deficient host cell.

In some embodiments, the constant region has a modified constant region that removes or reduces Fc gamma receptor binding. For example, the Fc can be human IgG2 containing the mutation D265, in which the amino acid residues are numbered with reference to the wild type IgG2 sequence (SEQ ID NO: 493). Accordingly, in some embodiments, the constant region has a modified constant region having the sequence shown in SEQ ID NO: 496:

ASTKGPSVFPLAPCSRSTSESTAALGCLVKDYFPEPVTVSWNSGALTSG

VHTFPAVLQSSGLYSLSSVVTVPSSNFGTQTYTCNVDHKPSNTKVDKTV

ERKCRVRCPRCPAPPVAGPSVFLFPPKPKDTLMISRTPEVTCVVVAVSH

EDPEVQFNWYVDGVEVHNAKTKPREEQFNSTFRVVSVLTVVHQDWLNGK

EYKCKVSNKGLPSSIEKTISKTKGQPREPQVYTLPPSREEMTKNQVSLT

CLVKGFYPSDIAVEWESNGQPENNYKTTPPMLDSDGSFFLYSRLTVDKS

RWQQGNVFSCSVMHEALHNHYTQKSLSLSPGK.

In some embodiments, the constant region has a modified constant region having the sequence shown in SEQ ID NO: 497:

ASTKGPSVFPLAPCSRSTSESTAALGCLVKDYFPEPVTVSWNSGALTSG

VHTFPAVLQSSGLYSLSSVVTVPSSNFGTQTYTCNVDHKPSNTKVDKTV

ERKCEVECPECPAPPVAGPSVFLFPPKPKDTLMISRTPEVTCVVVAVSH

EDPEVQFNWYVDGVEVHNAKTKPREEQFNSTFRVVSVLTVVHQDWLNGK

EYKCKVSNKGLPSSIEKTISKTKGQPREPQVYTLPPSREEMTKNQVSLT

CEVKGFYPSDIAVEWESNGQPENNYKTTPPMLDSDGSFFLYSKLTVDKS

RWQQGNVFSCSVMHEALHNHYTQKSLSLSPGK.

One way of determining binding affinity of antibodies to BCMA or CD3 is by measuring binding affinity of monofunctional Fab fragments of the antibody. To obtain monofunctional Fab fragments, an antibody (for example, IgG) can be cleaved with papain or expressed recombinantly. The affinity of a BCMA Fab fragment of an antibody can be determined by surface plasmon resonance (Biacore™3000™ surface plasmon resonance (SPR) system, Biacore™, INC, Piscataway N.J.) equipped with pre-immobilized streptavidin sensor chips (SA) or anti-mouse Fc or anti-human Fc using HBS-EP running buffer (0.01M HEPES, pH 7.4, 0.15 NaCl, 3 mM EDTA, 0.005% v/v Surfactant P20). Biotinylated or Fc fusion human BCMA can be diluted into HBS-EP buffer to a concentration of less than 0.5 μg/mL and injected across the individual chip channels using variable contact times, to achieve two ranges of antigen density, either 50-200 response units (RU) for detailed kinetic studies or 800-1,000 RU for screening assays. Regeneration studies have shown that 25 mM NaOH in 25% v/v ethanol effectively removes the bound Fab while keeping the activity of BCMA on the chip for over 200 injections. Typically, serial dilutions (spanning concentrations of 0.1-10× estimated $K_D$) of purified Fab samples are injected for 1 min at 100 μL/minute and dissociation times of up to 2 hours are allowed. The concentrations of the Fab proteins are determined by ELISA and/or SDS-PAGE electrophoresis using a Fab of known concentration (as determined by amino acid analysis) as a standard. Kinetic association rates ($k_{on}$) and dissociation rates ($k_{off}$) are obtained simultaneously by fitting the data globally to a 1:1 Langmuir binding model (Karlsson, R. Roos, H. Fagerstam, L. Petersson, B. (1994). Methods Enzymology 6. 99-110) using the BIAevaluation program. Equilibrium dissociation constant ($K_D$) values are calculated as $k_{off}/k_{on}$. This protocol is suitable for use in determining binding affinity of an antibody to any BCMA, including human BCMA, BCMA of another mammal (such as mouse BCMA, rat BCMA, or primate BCMA), as well as different forms of BCMA (e.g., glycosylated BCMA). Binding affinity of an antibody is generally measured at 25° C., but can also be measured at 37° C.

The antibodies as described herein may be made by any method known in the art. For the production of hybridoma cell lines, the route and schedule of immunization of the host animal are generally in keeping with established and conventional techniques for antibody stimulation and production, as further described herein. General techniques for production of human and mouse antibodies are known in the art and/or are described herein.

It is contemplated that any mammalian subject including humans or antibody producing cells therefrom can be manipulated to serve as the basis for production of mammalian, including human and hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C., Nature 256:495-497, 1975 or as modified by Buck, D. W., et al., In Vitro, 18:377-381, 1982. Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies specific for BCMA, CD3, or portions thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity, if present, can be removed, for example, by running the preparation over adsorbents made of the immunogen attached to a solid phase and eluting or releasing the desired antibodies off the immunogen. Immunization of a host animal with a human BCMA or CD3, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups, can yield a population of antibodies (e.g., monoclonal antibodies).

If desired, the antibody (monoclonal or polyclonal) of interest may be sequenced and the polynucleotide sequence may then be cloned into a vector for expression or propagation. The sequence encoding the antibody of interest may be maintained in vector in a host cell and the host cell can then be expanded and frozen for future use. Production of recombinant monoclonal antibodies in cell culture can be carried out through cloning of antibody genes from B cells by means known in the art. See, e.g. Tiller et al., J. Immunol. Methods 329, 112, 2008; U.S. Pat. No. 7,314,622.

In an alternative, the polynucleotide sequence may be used for genetic manipulation to "humanize" the antibody or to improve the affinity, or other characteristics of the antibody. For example, the constant region may be engineered to more nearly resemble human constant regions to avoid immune response if the antibody is used in clinical trials and treatments in humans. It may be desirable to genetically manipulate the antibody sequence to obtain greater affinity to BCMA or CD3 and greater efficacy in inhibiting BCMA.

There are four general steps to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; and 6,180,370.

A number of "humanized" antibody molecules comprising an antigen binding site derived from a non-human immunoglobulin have been described, including chimeric antibodies having rodent or modified rodent V regions and their associated CDRs fused to human constant regions. See, for example, Winter et al. Nature 349:293-299, 1991, Lobuglio et al. Proc. Nat. Acad. Sci. USA 86:4220-4224, 1989, Shaw et al. J Immunol. 138:4534-4538, 1987, and Brown et al. Cancer Res. 47:3577-3583, 1987. Other references describe rodent CDRs grafted into a human supporting framework region (FR) prior to fusion with an appropriate human antibody constant region. See, for example, Riechmann et al. Nature 332:323-327, 1988, Verhoeyen et al. Science 239:1534-1536, 1988, and Jones et al. Nature 321: 522-525, 1986. Another reference describes rodent CDRs supported by recombinantly engineered rodent framework regions. See, for example, European Patent Publication No. 0519596. These "humanized" molecules are designed to minimize unwanted immunological response toward rodent anti-human antibody molecules which limits the duration and effectiveness of therapeutic applications of those moieties in human recipients. For example, the antibody constant region can be engineered such that it is immunologically inert (e.g., does not trigger complement lysis). See, e.g. PCT Publication No. PCT/GB99/01441; UK Patent Application No. 9809951.8. Other methods of humanizing antibodies that may also be utilized are disclosed by Daugherty et al., Nucl. Acids Res. 19:2471-2476, 1991, and in U.S. Pat.

Nos. 6,180,377; 6,054,297; 5,997,867; 5,866,692; 6,210,671; and 6,350,861; and in PCT Publication No. WO 01/27160.

The general principles related to humanized antibodies discussed above are also applicable to customizing antibodies for use, for example, in dogs, cats, primate, equines and bovines. Further, one or more aspects of humanizing an antibody described herein may be combined, e.g., CDR grafting, framework mutation and CDR mutation.

In one variation, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

In an alternative, antibodies may be made recombinantly and expressed using any method known in the art. In another alternative, antibodies may be made recombinantly by phage display technology. See, for example, U.S. Pat. Nos. 5,565,332; 5,580,717; 5,733,743; and 6,265,150; and Winter et al., Annu. Rev. Immunol. 12:433-455, 1994. Alternatively, the phage display technology (McCafferty et al., Nature 348: 552-553, 1990) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S. and Chiswell, David J., Current Opinion in Structural Biology 3:564-571, 1993. Several sources of V-gene segments can be used for phage display. Clackson et al., Nature 352:624-628, 1991, isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Mark et al., J. Mol. Biol. 222:581-597, 1991, or Griffith et al., EMBO J. 12:725-734, 1993. In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." (Marks et al., Bio/Technol. 10:779-783, 1992). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., Nucl. Acids Res. 21:2265-2266, 1993. Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen binding site, i.e., the epitope governs (imprints) the choice of partner. When the process is repeated in order to replace the remaining rodent V domain, a human antibody is obtained (see PCT Publication No. WO 93/06213). Unlike traditional humanization of rodent antibodies by CDR grafting, this technique provides completely human antibodies, which have no framework or CDR residues of rodent origin.

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al. Vaccine 19:2756, 2001; Lonberg, N. and D. Huszar Int. Rev. Immunol 13:65, 1995; and Pollock, et al., J Immunol Methods 231:147, 1999. Methods for making derivatives of antibodies, e.g., humanized, single chain, etc. are known in the art.

Immunoassays and flow cytometry sorting techniques such as fluorescence activated cell sorting (FACS) can also be employed to isolate antibodies that are specific for BCMA, CD3, or tumor antigens of interest.

The antibodies as described herein can be bound to many different carriers. Carriers can be active and/or inert. Examples of well-known carriers include polypropylene, polystyrene, polyethylene, dextran, nylon, amylases, glass, natural and modified celluloses, polyacrylamides, agaroses, and magnetite. The nature of the carrier can be either soluble or insoluble for purposes of the invention. Those skilled in the art will know of other suitable carriers for binding antibodies, or will be able to ascertain such, using routine experimentation. In some embodiments, the carrier comprises a moiety that targets the myocardium.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors (such as expression vectors disclosed in PCT Publication No. WO 87/04462), which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA also may be modified, for example, by substituting the coding sequence for human heavy and light chain constant regions in place of the homologous murine sequences, Morrison et al., Proc. Nat. Acad. Sci. 81:6851, 1984, or by covalently joining to the immunoglobulin coding sequence all or part of the coding sequence for a non-immunoglobulin polypeptide. In that manner, "chimeric" or "hybrid" antibodies are prepared that have the binding specificity of a monoclonal antibody herein.

The BCMA or tumor antigen of interest antibodies as described herein can be identified or characterized using methods known in the art, whereby reduction of BCMA or other tumor antigen expression levels are detected and/or measured. In some embodiments, a BCMA antibody is identified by incubating a candidate agent with BCMA and monitoring binding and/or attendant reduction of BCMA expression levels. The binding assay may be performed with purified BCMA polypeptide(s), or with cells naturally expressing, or transfected to express, BCMA polypeptide(s). In one embodiment, the binding assay is a competitive binding assay, where the ability of a candidate antibody to compete with a known BCMA antibody for BCMA binding is evaluated. The assay may be performed in various formats, including the ELISA format.

Following initial identification, the activity of a candidate BCMA, CD3, or other tumor antigen antibody can be further confirmed and refined by bioassays, known to test the targeted biological activities. Alternatively, bioassays can be used to screen candidates directly. Some of the methods for identifying and characterizing antibodies are described in detail in the Examples.

BCMA, CD3, or other tumor antigen antibodies may be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with a BCMA, CD3, or other tumor antigen antibody. In another example, the epitope to which the BCMA, CD3, or other tumor antigen antibody binds can be determined in a systematic screening by using overlapping peptides derived from the BCMA, CD3, or other tumor antigen sequence and determining binding by the BCMA, CD3, or other tumor antigen antibody. According to the gene fragment expression assays, the open reading frame encoding BCMA, CD3, or other tumor antigen is fragmented either randomly or by specific genetic constructions and the reactivity of the expressed fragments of BCMA, CD3, or other tumor antigen with the antibody to be tested is determined. The gene fragments may, for example, be produced by PCR and then transcribed and translated into protein in vitro, in the presence of radioactive amino acids. The binding of the antibody to the radioactively labeled BCMA, CD3, or other tumor antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant BCMA, CD3, or other tumor antigen in which various fragments of the BCMA, CD3, or other tumor antigen protein have been replaced (swapped) with sequences from BCMA from another species (e.g., mouse), or a closely related, but antigenically distinct protein (e.g., Trop-1). By assessing binding of the antibody to the mutant BCMA, CD3, or other tumor antigen, the importance of the particular BCMA, CD3, or other tumor antigen fragment to antibody binding can be assessed.

Yet another method which can be used to characterize a BCMA, CD3, or other tumor antigen antibody is to use competition assays with other antibodies known to bind to the same antigen, i.e., various fragments on BCMA, CD3, or other tumor antigen, to determine if the BCMA, CD3, or other tumor antigen antibody binds to the same epitope as other antibodies. Competition assays are well known to those of skill in the art.

An expression vector can be used to direct expression of a BCMA, CD3, or other tumor antigen antibody. One skilled in the art is familiar with administration of expression vectors to obtain expression of an exogenous protein in vivo. See, e.g., U.S. Pat. Nos. 6,436,908; 6,413,942; and 6,376,471. Administration of expression vectors includes local or systemic administration, including injection, oral administration, particle gun or catheterized administration, and topical administration. In another embodiment, the expression vector is administered directly to the sympathetic trunk or ganglion, or into a coronary artery, atrium, ventrical, or pericardium.

Targeted delivery of therapeutic compositions containing an expression vector, or subgenomic polynucleotides can also be used. Receptor-mediated DNA delivery techniques are described in, for example, Findeis et al., Trends Biotechnol., 1993, 11:202; Chiou et al., Gene Therapeutics: Methods And Applications Of Direct Gene Transfer, J. A. Wolff, ed., 1994; Wu et al., J. Biol. Chem., 263:621, 1988; Wu et al., J. Biol. Chem., 269:542, 1994; Zenke et al., Proc. Natl. Acad. Sci. USA, 87:3655, 1990; and Wu et al., J. Biol. Chem., 266:338, 1991. Therapeutic compositions containing a polynucleotide are administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol. The therapeutic polynucleotides and polypeptides can be delivered using gene delivery vehicles. The gene delivery vehicle can be of viral or non-viral origin (see generally, Jolly, Cancer Gene Therapy, 1:51, 1994; Kimura, Human Gene Therapy, 5:845, 1994; Connelly, Human Gene Therapy, 1995, 1:185; and Kaplitt, Nature Genetics, 6:148, 1994). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698;

WO 93/25234; WO 93/11230; WO 93/10218; WO 91/02805; U.S. Pat. Nos. 5,219,740 and 4,777,127; GB Pat. No. 2,200,651; and EP Pat. No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther., 1992, 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther., 3:147, 1992); ligand-linked DNA (see, e.g., Wu, J. Biol. Chem., 264:16985, 1989); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip, Mol. Cell Biol., 14:2411, 1994 and in Woffendin, Proc. Natl. Acad. Sci., 91:1581, 1994.

In some embodiments, the invention encompasses compositions, including pharmaceutical compositions, comprising antibodies described herein or made by the methods and having the characteristics described herein. As used herein, compositions comprise one or more antibodies that bind to CD3 and a tumor antigen (e.g BCMA), and/or one or more polynucleotides comprising sequences encoding one or more these antibodies. These compositions may further comprise suitable excipients, such as pharmaceutically acceptable excipients including buffers, which are well known in the art.

The invention also provides methods of making any of these antibodies. The antibodies of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an antibody could be produced by an automated polypeptide synthesizer employing the solid phase method. See also, U.S. Pat. Nos. 5,807,715; 4,816,567; and 6,331, 415.

Heteroconjugate antibodies, comprising two covalently joined antibodies, are also within the scope of the invention. Such antibodies have been used to target immune system cells to unwanted cells (U.S. Pat. No. 4,676,980), and for treatment of HIV infection (PCT Publication Nos. WO 91/00360 and WO 92/200373; EP 03089). Heteroconjugate antibodies may be made using any convenient cross-linking methods. Suitable cross-linking agents and techniques are well known in the art, and are described in U.S. Pat. No. 4,676,980.

Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

In the recombinant humanized antibodies, the Fcγ portion can be modified to avoid interaction with Fcγ receptor and the complement and immune systems. The techniques for preparation of such antibodies are described in WO 99/58572. For example, the constant region may be engineered to more resemble human constant regions to avoid immune response if the antibody is used in clinical trials and treatments in humans. See, for example, U.S. Pat. Nos. 5,997,867 and 5,866,692.

The invention encompasses modifications to the antibodies and polypeptides of the invention variants as described herein, including functionally equivalent antibodies which do not significantly affect their properties and variants which have enhanced or decreased activity and/or affinity. For example, the amino acid sequence may be mutated to obtain an antibody with the desired binding affinity to BCMA and/or CD3. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table 5 under the heading of "conservative substitutions." If such substitutions result in a change in biological activity, then more substantial changes, denominated "exemplary substitutions" in Table 5, or as further described below in reference to amino acid classes, may be introduced and the products screened.

TABLE 5

Amino Acid Substitutions

| Original Residue (naturally occurring amino acid) | Conservative Substitutions | Exemplary Substitutions |
| --- | --- | --- |
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |

TABLE 5-continued

Amino Acid Substitutions

| Original Residue (naturally occurring amino acid) | Conservative Substitutions | Exemplary Substitutions |
|---|---|---|
| Gly (G) | Ala | Ala |
| His (H) | Arg | Asn; Gln; Lys; Arg |
| Ile (I) | Leu | Leu; Val; Met; Ala, Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring amino acid residues are divided into groups based on common side-chain properties:

(1) Non-polar: Norleucine, Met, Ala, Val, Leu, Ile;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

Amino acid modifications can range from changing or modifying one or more amino acids to complete redesign of a region, such as the variable region. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. In still other embodiments, the CDR domain is CDR H3 and/or CDR L3.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, Chem. Immunol. 65:111-128, 1997; Wright and Morrison, TibTECH15:26-32, 1997). The oligosaccharide side chains of the immunoglobulins affect the protein's function (Boyd et al., Mol. Immunol. 32:1311-1318, 1996; Wittwe and Howard, Biochem. 29:4175-4180, 1990) and the intramolecular interaction between portions of the glycoprotein, which can affect the conformation and presented three-dimensional surface of the glycoprotein (Jefferis and Lund, supra; Wyss and Wagner, Current Opin. Biotech. 7:409-416, 1996). Oligosaccharides may also serve to target a given glycoprotein to certain molecules based upon specific recognition structures. Glycosylation of antibodies has also been reported to affect antibody-dependent cellular cytotoxicity (ADCC). In particular, CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., Mature Biotech. 17:176-180, 1999).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., J. Biol. Chem. 272:9062-9070, 1997).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example, using endoglycosidase H (Endo H), N-glycosidase F, endoglycosidase F1, endoglycosidase F2, endoglycosidase F3. In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation. Modifications can be used, for example, for attachment of labels for immunoassay. Modified polypeptides are made using established procedures in the art and can be screened using standard assays known in the art, some of which are described below and in the Examples.

In some embodiments of the invention, the antibody comprises a modified constant region, such as a constant region that has increased affinity to a human Fc gamma receptor, is immunologically inert or partially inert, e.g., does not trigger complement mediated lysis, does not stimulate antibody-dependent cell mediated cytotoxicity (ADCC), or does not activate macrophages; or has reduced activities (compared to the unmodified antibody) in any one or more of the following: triggering complement mediated lysis, stimulating antibody-dependent cell mediated cytotoxicity (ADCC), or activating microglia. Different modifications of the constant region may be used to achieve optimal level and/or combination of effector functions. See, for example, Morgan et al., Immunology 86:319-324, 1995; Lund et al., J. Immunology 157:4963-9 157:4963-4969, 1996; Idusogie et al., J. Immunology 164:4178-4184, 2000; Tao et al., J. Immunology 143: 2595-2601, 1989; and Jefferis et al., Immunological Reviews 163:59-76, 1998. In some embodiments, the constant region is modified as described in Eur. J. Immunol., 1999, 29:2613-2624; PCT Application No. PCT/GB99/01441; and/or UK Patent Application No. 9809951.8. In other embodiments, the antibody comprises a human heavy chain IgG2 constant region comprising the following mutations: A330P331 to S330S331 (amino acid numbering with reference to the wild type IgG2 sequence). Eur. J. Immunol., 1999, 29:2613-2624. In still other embodiments, the constant region is aglycosylated for N-linked glycosylation. In some embodiments, the constant region is aglycosylated for N-linked glycosylation by mutating the glycosylated amino acid residue or flanking residues that are part of the N-glycosylation recognition sequence in the constant region. For example, N-glycosylation site N297 may be mutated to A, Q, K, or H. See, Tao et al., J. Immunology 143: 2595-2601, 1989; and Jefferis et al., Immunological Reviews 163:59-76, 1998. In some embodiments, the constant region is aglycosylated for N-linked glycosylation. The constant region may be aglycosylated for N-linked glycosylation enzymatically (such as removing carbohydrate by enzyme PNGase), or by expression in a glycosylation deficient host cell.

Other antibody modifications include antibodies that have been modified as described in PCT Publication No. WO 99/58572. These antibodies comprise, in addition to a binding domain directed at the target molecule, an effector domain having an amino acid sequence substantially homologous to all or part of a constant region of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain CH2 domains. Antibodies modified in this manner are particularly suitable for use in chronic antibody therapy, to avoid inflammatory and other adverse reactions to conventional antibody therapy.

The invention includes affinity matured embodiments. For example, affinity matured antibodies can be produced by procedures known in the art (Marks et al., Bio/Technology, 10:779-783, 1992; Barbas et al., Proc Nat. Acad. Sci, USA 91:3809-3813, 1994; Schier et al., Gene, 169:147-155, 1995; Yelton et al., J. Immunol., 155:1994-2004, 1995; Jackson et al., J. Immunol., 154(7):3310-9, 1995, Hawkins et al., J. Mol. Biol., 226:889-896, 1992; and PCT Publication No. WO2004/058184).

The following methods may be used for adjusting the affinity of an antibody and for characterizing a CDR. One way of characterizing a CDR of an antibody and/or altering (such as improving) the binding affinity of a polypeptide, such as an antibody, termed "library scanning mutagenesis". Generally, library scanning mutagenesis works as follows. One or more amino acid positions in the CDR are replaced with two or more (such as 3, 4, 5, 6, 7, 8, 9, 10, 11, 12, 13, 14, 15, 16, 17, 18, 19, or 20) amino acids using art recognized methods. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased, or no binding are identified. Methods for determining binding affinity are well-known in the art. Binding affinity may be determined using Biacore™ surface plasmon resonance analysis, which detects differences in binding affinity of about 2-fold or greater. Biacore™ is particularly useful when the starting antibody already binds with a relatively high affinity, for example a $K_D$ of about 10 nM or lower. Screening using Biacore™ surface plasmon resonance is described in the Examples, herein.

Binding affinity may be determined using Kinexa Biocensor, scintillation proximity assays, ELISA, ORIGEN immunoassay (IGEN), fluorescence quenching, fluorescence transfer, and/or yeast display. Binding affinity may also be screened using a suitable bioassay.

In some embodiments, every amino acid position in a CDR is replaced (in some embodiments, one at a time) with all 20 natural amino acids using art recognized mutagenesis methods (some of which are described herein). This generates small libraries of clones (in some embodiments, one for every amino acid position that is analyzed), each with a complexity of 20 members (if all 20 amino acids are substituted at every position).

In some embodiments, the library to be screened comprises substitutions in two or more positions, which may be in the same CDR or in two or more CDRs. Thus, the library may comprise substitutions in two or more positions in one CDR. The library may comprise substitution in two or more positions in two or more CDRs. The library may comprise substitution in 3, 4, 5, or more positions, said positions found in two, three, four, five or six CDRs. The substitution may be prepared using low redundancy codons. See, e.g., Table 2 of Balint et al., Gene 137(1):109-18, 1993.

The CDR may be CDRH3 and/or CDRL3. The CDR may be one or more of CDRL1, CDRL2, CDRL3, CDRH1, CDRH2, and/or CDRH3. The CDR may be a Kabat CDR, a Chothia CDR, or an extended CDR.

Candidates with improved binding may be sequenced, thereby identifying a CDR substitution mutant which results in improved affinity (also termed an "improved" substitution). Candidates that bind may also be sequenced, thereby identifying a CDR substitution which retains binding.

Multiple rounds of screening may be conducted. For example, candidates (each comprising an amino acid substitution at one or more position of one or more CDR) with improved binding are also useful for the design of a second library containing at least the original and substituted amino acid at each improved CDR position (i.e., amino acid position in the CDR at which a substitution mutant showed improved binding). Preparation, and screening or selection of this library is discussed further below.

Library scanning mutagenesis also provides a means for characterizing a CDR, in so far as the frequency of clones with improved binding, the same binding, decreased binding or no binding also provide information relating to the importance of each amino acid position for the stability of the antibody-antigen complex. For example, if a position of the CDR retains binding when changed to all 20 amino acids, that position is identified as a position that is unlikely to be required for antigen binding. Conversely, if a position of CDR retains binding in only a small percentage of substitutions, that position is identified as a position that is important to CDR function. Thus, the library scanning mutagenesis methods generate information regarding positions in the CDRs that can be changed to many different amino acids (including all 20 amino acids), and positions in the CDRs which cannot be changed or which can only be changed to a few amino acids.

Candidates with improved affinity may be combined in a second library, which includes the improved amino acid, the original amino acid at that position, and may further include additional substitutions at that position, depending on the complexity of the library that is desired, or permitted using the desired screening or selection method. In addition, if desired, adjacent amino acid position can be randomized to at least two or more amino acids. Randomization of adjacent amino acids may permit additional conformational flexibility in the mutant CDR, which may in turn, permit or facilitate the introduction of a larger number of improving mutations. The library may also comprise substitution at positions that did not show improved affinity in the first round of screening.

The second library is screened or selected for library members with improved and/or altered binding affinity using any method known in the art, including screening using Biacore™ surface plasmon resonance analysis, and selection using any method known in the art for selection, including phage display, yeast display, and ribosome display.

This invention also provides compositions comprising antibodies conjugated (for example, linked) to an agent that facilitate coupling to a solid support (such as biotin or avidin). For simplicity, reference will be made generally to antibodies with the understanding that these methods apply to any of the BCMA antibody embodiments described herein. Conjugation generally refers to linking these components as described herein. The linking (which is generally fixing these components in proximate association at least for administration) can be achieved in any number of ways. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

In another aspect, the invention provides a method of making any of the polynucleotides described herein.

Polynucleotides complementarity to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementarity sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as E. coli or B. subtillis) and yeast (such as S. cerevisae, S. pombe; or K. lactis). Preferably, the host cells express the cDNAs at a level of about 5 fold higher, more preferably, 10 fold higher, even more preferably, 20 fold higher than that of the corresponding endogenous antibody or protein of interest, if present, in the host cells. Screening the host cells for a specific binding to BCMA or an BCMA domain (e.g., domains 1-4) is effected by an immunoassay or FACS. A cell overexpressing the antibody or protein of interest can be identified.

Methods of Using the Bispecific Antibodies

The antibodies (e.g., BCMA, CD3, or bispecific) and the antibody conjugates (e.g., BCMA antibody-drug conjugates) of the present invention are useful in various applications including, but are not limited to, therapeutic treatment methods and diagnostic treatment methods.

In one aspect, the invention provides a method for treating a condition associated with BCMA expression in a subject. In some embodiments, the method of treating a condition associated with BCMA expression in a subject comprises administering to the subject in need thereof an effective amount of a composition (e.g., pharmaceutical composition) comprising the BCMA antibodies or the BCMA antibody conjugates as described herein. The conditions associated with BCMA expression include, but are not limited to, abnormal BCMA expression, altered or aberrant BCMA expression, malignant cells expressing BCMA, and a proliferative disorder (e.g., cancer) or autoimmune disorder.

In another aspect, the invention provides a method for treating a B-cell related cancer or malignant cells expressing a tumor antigen. In some embodiments, provided is a method of treating a B-cell related cancer in a subject in need thereof comprising a) providing the bispecific antibody as described herein, and b) administering said bispecific antibody to said patient. In some embodiments, provided is a method of treating a condition associated with malignant cells expressing a tumor antigen in a subject comprising administering to the subject in need thereof an effective amount of a pharmaceutical composition comprising the bispecific antibody as described herein.

Accordingly, in some embodiments, provided is a method of treating a cancer in a subject comprising administering to the subject in need thereof an effective amount of a composition comprising the antibodies (e.g., BCMA, or CD3-BCMA bispecific antibodies) or the BCMA antibody conjugates as described herein. As used herein, cancer can be a B-cell related cancer including, but are not limited to, multiple myeloma, malignant plasma cell neoplasm, Hodgkin's lymphoma, nodular lymphocyte predominant Hodgkin's lymphoma, Kahler's disease and Myelomatosis, plasma cell leukemia, plasmacytoma, B-cell prolymphocytic leukemia, hairy cell leukemia, B-cell non-Hodgkin's lymphoma (NHL), acute myeloid leukemia (AML), chronic lymphocytic leukemia (CLL), acute lymphocytic leukemia (ALL), chronic myeloid leukemia (CML), follicular lymphoma, Burkitt's lymphoma, marginal zone lymphoma, mantle cell lymphoma, large cell lymphoma, precursor B-lymphoblastic lymphoma, myeloid leukemia, Waldenstrom's macroglobulienemia, diffuse large B cell lymphoma, follicular lymphoma, marginal zone lymphoma, mucosa-associated lymphatic tissue lymphoma, small cell lymphocytic lymphoma, mantle cell lymphoma, Burkitt lymphoma, primary mediastinal (thymic) large B-cell lymphoma, lymphoplasmactyic lymphoma, Waldenström macroglobulinemia, nodal marginal zone B cell lymphoma, splenic marginal zone lymphoma, intravascular large B-cell lymphoma, primary effusion lymphoma, lymphomatoid granulomatosis, T cell/histiocyte-rich large B-cell lymphoma, primary central nervous system lymphoma, primary cutaneous diffuse large B-cell lymphoma (leg type), EBV positive diffuse large B-cell lymphoma of the elderly, diffuse large B-cell lymphoma associated with inflammation, intravascular large B-cell lymphoma, ALK-positive large B-cell lymphoma, plasmablastic lymphoma, large B-cell lymphoma arising in HHV8-associated multicentric Castleman disease, B-cell lymphoma unclassified with features intermediate between diffuse large B-cell lymphoma and Burkitt lymphoma, B-cell lymphoma unclassified with features intermediate between diffuse large B-cell lymphoma and classical Hodgkin lymphoma, and other B-cell related lymphoma.

In some embodiments, provided is a method of inhibiting tumor growth or progression in a subject who has malignant cells expressing BCMA, comprising administering to the subject in need thereof an effective amount of a composition comprising the BCMA antibodies, CD3-BCMA bispecific antibodies, or the BCMA antibody conjugates as described herein. In other embodiments, provided is a method of inhibiting metastasis cells expressing BCMA in a subject, comprising administering to the subject in need thereof an effective amount of a composition comprising the BCMA antibodies, CD3-BCMA bispecific antibodies, or the BCMA antibody conjugates as described herein. In other embodiments, provided is a method of inducing tumor regression in malignant cells in a subject, comprising administering to the subject in need thereof an effective amount of a composition comprising the BCMA antibodies, CD3-BCMA bispecific antibodies, or the BCMA antibody conjugates as described herein.

In some embodiments, provided is a method of treating an autoimmune disorder in a subject comprising administering to the subject in need thereof an effective amount of a composition comprising the BCMA antibodies, CD3-BCMA bispecific antibodies, or the BCMA antibody conjugates as described herein.

As used herein, autoimmune disorders include, but are not limited to, systemic lupus erythematosus, rheumatoid arthritis, diabetes (Type I), multiple sclerosis, Addison's disease, celiac disease, dermatomyositis, Graves' disease, hashimoto's thyroiditis, hashimoto's encephalopathy, Myasthenia gravis, pernicious anemia, reactive arthritis, Sjogren syndrome, acute disseminated encephalomyelitis, agammaglobulinemia, amyotrophic lateral sclerosis, ankylosing spondylitis, antiphospholipid syndrome, antisynthetase syndrome, atopic allergy, atopic dermatitis, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendorcrine syndrome, autoimmune progesterone dermatitis, autoimmune thrombocytopenic purpura, autoimmune urticarial, autoimmune uveitis, Bechet's disease, Castleman's disease, cold agglutinin disease, Crohn's disease, dermatomyositis, eosinophilic fasciitis, gastrointestinal pemphigoid, Goodpasture's syndrome, Guillain-Barré syndrome, hidradenitis suppurativa, idiopathic thrombocytopenic purpura, narcolepsy, pemphigus vulgaris, pernicious anaemia, polymyositis, primary binary cirrhosis, relapsing polychrondritis, rheumatic fever, temporal arteritis, transverse myelitis, ulcerative colitis, undifferentiated connective tissue disease, vasculitis, and Wegener's granulomatosis.

In another aspect, the invention provides an effective amount of a composition (e.g., pharmaceutical composition) comprising the antibodies (e.g., BCMA or CD3-BCMA bispecific) or the BCMA antibody conjugates as described herein for treating a condition (e.g., cancer or autoimmune disorder) associated with BCMA expression in a subject in need thereof. In some embodiments, provided is an effective amount of a composition (e.g., pharmaceutical composition)

comprising the antibodies (e.g., BCMA or CD3-BCMA bispecific) or the BCMA antibody conjugates as described herein for inhibiting tumor growth or progression in a subject who has malignant cells expressing BCMA. In some embodiments, provided is an effective amount of a composition (e.g., pharmaceutical composition) comprising the antibodies (e.g., BCMA or CD3-BCMA bispecific) or the BCMA antibody conjugates as described herein for inhibiting metastasis of malignant cells expressing BCMA in a subject in need thereof. In some embodiments, provided is an effective amount of a composition (e.g., pharmaceutical composition) comprising the antibodies (e.g., BCMA or CD3-BCMA bispecific) or the BCMA antibody conjugates as described herein for inducing tumor regression in a subject who has malignant cells expressing BCMA.

In another aspect, the invention provides the antibodies (e.g., BCMA or CD3-BCMA bispecific) or the BCMA antibody conjugates as described herein for use in treating a condition (e.g., cancer or autoimmune disorder) associated with BCMA expression in a subject in need thereof. In some embodiments, provided is the antibodies (e.g., BCMA or CD3-BCMA bispecific) or the BCMA antibody conjugates as described herein for inhibiting tumor growth or progression in a subject who has malignant cells expressing BCMA. In some embodiments, provided is the antibodies (e.g., BCMA or CD3-BCMA bispecific) or the BCMA antibody conjugates as described herein for inhibiting metastasis of malignant cells expressing BCMA in a subject in need thereof. In some embodiments, provided is the antibodies (e.g., BCMA or CD3-BCMA bispecific) or the BCMA antibody conjugates as described herein for inducing tumor regression in a subject who has malignant cells expressing BCMA.

In another aspect, the invention provides a use of the antibodies (e.g., BCMA or CD3-BCMA bispecific) or the BCMA antibody conjugates as described herein in the manufacture of a medicament for treating a condition (e.g., cancer or autoimmune disorder) associated with BCMA expression. In some embodiments, provided is a use of the antibodies (e.g., BCMA or CD3-BCMA bispecific) or the BCMA antibody conjugates as described herein in the manufacture of a medicament for inhibiting tumor growth or progression. In some embodiments, provided is a use of the antibodies (e.g., BCMA or CD3-BCMA bispecific) or the BCMA antibody conjugates as described herein in the manufacture of a medicament for inhibiting metastasis of malignant cells expressing BCMA. In some embodiments, provided is a use of the antibodies (e.g., BCMA or CD3-BCMA bispecific) or the BCMA antibody conjugates as described herein in the manufacture of a medicament for inducing tumor regression.

In another aspect, provided is a method of detecting, diagnosing, and/or monitoring a condition associated with BCMA expression. For example, the antibodies (e.g., BCMA or CD3-BCMA bispecific) as described herein can be labeled with a detectable moiety such as an imaging agent and an enzyme-substrate label. The antibodies as described herein can also be used for in vivo diagnostic assays, such as in vivo imaging (e.g., PET or SPECT), or a staining reagent.

In some embodiments, the methods described herein further comprise a step of treating a subject with an additional form of therapy. In some embodiments, the additional form of therapy is an additional anti-cancer therapy including, but not limited to, chemotherapy, radiation, surgery, hormone therapy, and/or additional immunotherapy.

In some embodiments, the additional form of therapy comprises administering one or more therapeutic agent in addition to the antibodies (e.g., BCMA or CD3-BCMA bispecific) or the BCMA antibody conjugates as described herein. The one or more therapeutic agent can be a chemotherapeutic agents including, but not limited to, a second antibody (e.g., an anti-VEGF (Vascular Endothelial Growth Factor) antibody (e.g., AVASTIN®), an anti-HER2 antibody (e.g., HERCEPTIN®), an anti-CD25 antibody, an anti-CD33 antibody, an anti-CD20 antibody (e.g., RITUXAN®), an anti-mucin-like glycoprotein antibody, an anti-TNF antibody, and/or an epidermal growth factor receptor (EGFR) antibody (e.g., ERBITUX®)), an angiogenesis inhibitor, a cytotoxic agent (e.g., anthracyclines (e.g., daunorubicin, doxorubicin, epirubicin, idarubicin, valrubicin, and mitoxantrone), taxane (e.g., paclitaxel and docetaxel), dolastatin, duocarmycin, enediyne, geldanamycin, maytansine, puromycin, vinca alkaloid (e.g., vincristine), a topoisomerase inhibitor (e.g., etoposide), tubulysin, a pyrimidine analog (e.g., fluorouracil), platinum-containing agents (e.g., cisplatin, carboplatin, and oxaliplatin), alkylating agents (e.g., melphalan, cyclophosphamide, or carmustine) and hemiasterlin), immunomodulating agent (e.g., prednisone and lenalidomide (REVLIMID®)), an anti-inflammatory agent (e.g., dexamethasone), an aromatase inhibitor (e.g., anastrozole, exemestane, letrozole, vorozole, formestane, or testolactone), a proteasome inhibitor (e.g., bortezomib such as VELCADE® ([(1R)-3-methyl-1-[[(2S)-1-oxo-3-phenyl-2-[(pyrazinylcarbonyl)amino]propy-I]amino]butyl] boronic acid or carfilzomib), and other agents such as tamoxifen.

For example, in some embodiments, provided is a method of treating multiple myeloma comprising administering to a patient need thereof an effective amount of a composition comprising the antibodies (e.g., BCMA or CD3-BCMA bispecific) or the BCMA antibody conjugates as described herein and one or more other therapeutic agent such as a chemotherapeutic agent (e.g., doxorubicin or carfilzomib) or thalidomide or its derivative thereof (e.g., lenalidomide (REVLIMID®)). In some embodiments, the one or more other therapeutic agent is selecting from the group consisting of bortezomib (e.g., VELCADE®), melphalan, prednisone, doxorubicin, lenalidomide, thalidomide, prednisone, carmustine, etoposide, cisplatin, cyclophosphamide, carfilzomib, and vincristine. In some embodiments, the other therapeutic agent is bortezomib (e.g., VELCADE®), melphalan, lenalidomide (REVLIMID®), carfilzomib, doxorubicin, or prednisone. Accordingly, provided is a method of treating multiple myeloma comprising administering to a patient need thereof an effective amount of a composition comprising the antibodies (e.g., BCMA or CD3-BCMA bispecific) or the BCMA antibody conjugates as described herein and one or more other therapeutic agent selecting from the group consisting of bortezomib, lenalidomide, carfilzomib, and doxorubicin. In some embodiments, the patient is relapsing or refractory to previous multiple myeloma therapy.

The antibodies (e.g., BCMA or CD3-BCMA bispecific) or the BCMA antibody conjugates can be administered to an individual via any suitable route. It should be understood by persons skilled in the art that the examples described herein are not intended to be limiting but to be illustrative of the techniques available. Accordingly, in some embodiments, the antibody (e.g., BCMA or CD3-BCMA bispecific) or the BCMA antibody conjugate is administered to an individual in accord with known methods, such as intravenous administration, e.g., as a bolus or by continuous infusion over a period of time, by intramuscular, intraperitoneal, intracerebrospinal, intracranial, transdermal, subcutaneous, intra-articular, sublingually, intrasynovial, via insufflation, intrathecal, oral, inhalation or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, the antibody (e.g., BCMA or CD3-BCMA bispecific) or the BCMA antibody conjugate can be aerosolized using a fluorocarbon formulation and a metered dose inhaler, or inhaled as a lyophilized and milled powder.

In one embodiment, the antibody (e.g., BCMA or CD3-BCMA bispecific) or the BCMA antibody conjugate is administered via site-specific or targeted local delivery techniques. Examples of site-specific or targeted local delivery techniques include various implantable depot sources of the antibody (e.g., BCMA or CD3-BCMA bispecific) or the BCMA antibody conjugate or local delivery catheters, such as infusion catheters, indwelling catheters, or needle catheters, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Various formulations of the antibody (e.g., BCMA or CD3-BCMA bispecific) or the BCMA antibody conjugate may be used for administration. In some embodiments, the antibody (e.g., BCMA or CD3-BCMA bispecific) or the BCMA antibody conjugate may be administered neat. In some embodiments, the antibody (e.g., BCMA or CD3-BCMA bispecific) or the BCMA antibody conjugate and a pharmaceutically acceptable excipient may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 21st Ed. Mack Publishing, 2005.

In some embodiments, these agents are formulated for administration by injection (e.g., intraperitoneally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history.

The antibodies (e.g., BCMA or CD3-BCMA bispecific) or the BCMA antibody conjugates as described herein can be administered using any suitable method, including by injection (e.g., intraperitoneally, intravenously, subcutaneously, intramuscularly, etc.). The antibody (e.g., BCMA or CD3-BCMA bispecific) or the BCMA antibody conjugate can also be administered via inhalation, as described herein. Generally, for administration of an antibody (e.g., BCMA or CD3-BCMA bispecific) and a BCMA antibody conjugate, an initial candidate dosage can be about 2 mg/kg. For the purpose of the present invention, a typical daily dosage might range from about any of 3 µg/kg to 30 µg/kg to 300 µg/kg to 3 mg/kg, to 30 mg/kg, to 100 mg/kg or more, depending on the factors mentioned above. For example, dosage of about 1 mg/kg, about 2.5 mg/kg, about 5 mg/kg, about 10 mg/kg, and about 25 mg/kg may be used. For repeated administrations over several days or longer, depending on the condition, the treatment is sustained until a desired suppression of symptoms occurs or until sufficient therapeutic levels are achieved, for example, to inhibit or delay tumor growth/progression or metatstasis of cancer cells. An exemplary dosing regimen comprises administering an initial dose of about 2 mg/kg, followed by a weekly maintenance dose of about 1 mg/kg of the antibody (e.g., BCMA or CD3-BCMA bispecific) or BCMA antibody conjugate, or followed by a maintenance dose of about 1 mg/kg every other week. Other exemplary dosing regimen comprises administering increasing doses (e.g., initial dose of 1 mg/kg and gradual increase to one or more higher doses every week or longer time period). Other dosage regimens may also be useful, depending on the pattern of pharmacokinetic decay that the practitioner wishes to achieve. For example, in some embodiments, dosing from one to four times a week is contemplated. In other embodiments, dosing once a month or once every other month or every three months is contemplated. The progress of this therapy is easily monitored by conventional techniques and assays. The dosing regimen (including the antibody (e.g., BCMA or CD3-BCMA bispecific) or the BCMA antibody conjugate used) can vary over time.

For the purpose of the present invention, the appropriate dosage of an antibody (e.g., BCMA or CD3-BCMA bispecific) or a BCMA antibody conjugate will depend on the antibody (e.g., BCMA or CD3-BCMA bispecific) or the BCMA antibody conjugate (or compositions thereof) employed, the type and severity of symptoms to be treated, whether the agent is administered for therapeutic purposes, previous therapy, the patient's clinical history and response to the agent, the patient's clearance rate for the administered agent, and the discretion of the attending physician. Typically the clinician will administer an antibody (e.g., BCMA or CD3-BCMA bispecific) or a BCMA antibody conjugate until a dosage is reached that achieves the desired result. Dose and/or frequency can vary over course of treatment. Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of symptoms, e.g., tumor growth inhibition or delay, etc. Alternatively, sustained continuous release formulations of antibodies (e.g., BCMA or CD3-BCMA bispecific) or BCMA antibody conjugates may be appropriate. Various formulations and devices for achieving sustained release are known in the art.

In one embodiment, dosages for an antibody (e.g., BCMA or CD3-BCMA bispecific) or a BCMA antibody conjugate may be determined empirically in individuals who have been given one or more administration(s) of the antibody (e.g., BCMA or CD3-BCMA bispecific) or the BCMA antibody conjugate. Individuals are given incremental dosages of an antibody (e.g., BCMA or CD3-BCMA bispecific) or a BCMA antibody conjugate. To assess efficacy, an indicator of the disease can be followed.

Administration of an antibody (e.g., BCMA or CD3-BCMA bispecific) or an BCMA antibody conjugate in accordance with the method in the present invention can be continuous or intermittent, depending, for example, upon the recipient's physiological condition, whether the purpose of the administration is therapeutic or prophylactic, and other factors known to skilled practitioners. The administration of an antibody (e.g., BCMA or CD3-BCMA bispecific) or a BCMA antibody conjugate may be essentially continuous over a preselected period of time or may be in a series of spaced doses.

In some embodiments, more than one antibody (e.g., BCMA or CD3-BCMA bispecific) or BCMA antibody conjugate may be present. At least one, at least two, at least three, at least four, at least five different or more antibody (e.g., BCMA or CD3-BCMA bispecific) or BCMA antibody conjugate can be present. Generally, those antibodies (e.g., BCMA or CD3-BCMA bispecific) or BCMA antibody conjugates may have complementary activities that do not adversely affect each other. For example, one or more of the following antibody may be used: a first BCMA or CD3 antibody directed to one epitope on BCMA or CD3 and a second BCMA or CD3 antibody directed to a different epitope on BCMA or CD3.

Therapeutic formulations of the antibody (e.g., BCMA or CD3-BCMA bispecific) or the BCMA antibody conjugate used in accordance with the present invention are prepared for storage by mixing an antibody having the desired degree of purity with optional pharmaceutically acceptable carriers, excipients or stabilizers (Remington, The Science and Practice of Pharmacy 21st Ed. Mack Publishing, 2005), in the form of lyophilized formulations or aqueous solutions. Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Liposomes containing the antibody (e.g., BCMA or CD3-BCMA bispecific) or the BCMA antibody conjugate are prepared by methods known in the art, such as described in Epstein, et al., Proc. Natl. Acad. Sci. USA 82:3688, 1985; Hwang, et al., Proc. Natl Acad. Sci. USA 77:4030, 1980; and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy 21st Ed. Mack Publishing, 2005.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or 'poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(-)-3-hydroxybutyric acid.

The formulations to be used for in vivo administration must be sterile. This is readily accomplished by, for example, filtration through sterile filtration membranes. Therapeutic antibody (e.g., BCMA or CD3-BCMA bispecific) or BCMA antibody conjugate compositions are generally placed into a container having a sterile access port, for example, an intravenous solution bag or vial having a stopper pierceable by a hypodermic injection needle.

The compositions according to the present invention may be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 µm, particularly 0.1 and 0.5 µm, and have a pH in the range of 5.5 to 8.0.

The emulsion compositions can be those prepared by mixing an antibody (e.g., BCMA or CD3-BCMA bispecific) or a BCMA antibody conjugate with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Compositions

The compositions used in the methods of the invention comprise an effective amount of an antibody (e.g., BCMA or CD3-BCMA bispecific) or a BCMA antibody conjugate as described herein. Examples of such compositions, as well as how to formulate, are also described in an earlier section and below. In some embodiments, the composition comprises one or more antibodies (e.g., BCMA or CD3-BCMA bispecific) or BCMA antibody conjugates. For example, BCMA antibody or CD3-BCMA bispecific antibody recognizes human BCMA or CD3-BCMA. In some embodiments, the BCMA or CD3-BCMA antibody is a human antibody, a humanized antibody, or a chimeric antibody. In some embodiments, the BCMA antibody or CD3-BCMA antibody comprises a constant region that is capable of triggering a desired immune response, such as antibody-mediated lysis or ADCC. In other embodiments, the BCMA antibody or CD3-BCMA antibody comprises a constant region that does not trigger an unwanted or undesirable immune response, such as antibody-mediated lysis or ADCC.

It is understood that the compositions can comprise more than one antibody (e.g., BCMA or CD3-BCMA bispecific) or BCMA antibody conjugate (e.g., a mixture of BCMA antibodies or CD3-BCMA bispecific antibodies that recognize different epitopes of BCMA or CD3 and BCMA). Other exemplary compositions comprise more than one BCMA antibody, CD3-BCMA antibody, or BCMA antibody conjugate that recognize the same epitope(s), or different species of BCMA antibodies, CD3-BCMA bispecific antibodies, or BCMA antibody conjugate that bind to different epitopes of BCMA (e.g., human BCMA) or CD3 and BCMA (human CD3 and BCMA).

The composition used in the present invention can further comprise pharmaceutically acceptable carriers, excipients, or stabilizers (Remington: The Science and practice of Pharmacy 21st Ed., 2005, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

Kits

The invention also provides kits for use in the instant methods. Kits of the invention include one or more containers comprising the BCMA antibody, CD3-BCMA bispecific antibody, or the BCMA antibody conjugate as described herein and instructions for use in accordance with any of the methods of the invention described herein. Generally, these instructions comprise a description of administration of the BCMA antibody, CD3-BCMA bispecific antibody, or the BCMA antibody conjugate for the above described therapeutic treatments.

The instructions relating to the use of the BCMA antibodies, CD3-BCMA bispecific antibodies, or the BCMA antibody conjugates as described herein generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a BCMA antibody, CD3-BCMA bispecific antibody, or a BCMA antibody conjugate. The container may further comprise a second pharmaceutically active agent.

Kits may optionally provide additional components such as buffers and interpretive information. Normally, the kit comprises a container and a label or package insert(s) on or associated with the container.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

Example 1: Determination of Kinetics and Affinity of hBCMA/Human IgG Interactions at 25° C. and/or 37° C.

This example determines the kinetics and affinity of various anti-BCMA antibodies at 25° C. and 37° C.

All experiments were performed on a Bio-Rad Proteon XPR36 surface Plasmon resonance biosensor (Bio-Rad, Hercules, Calif.). An array of anti-BCMA antibodies was prepared using an amine-coupling method on a Bio-Rad GLC Sensor Chip similar to that described in Abdiche, et al., Anal. Biochem. 411, 139-151 (2011). The analysis temperature for the immobilization was 25° C. and the running buffer was HBS-T+ (10 mM HEPES, 150 mM NaCl, 0.05% Tween-20, pH 7.4). Channels were activated in the analyte (horizontal) direction by injecting a mixture of 1 mM ECD and 0.25 mM NHS for 3 minutes at a flow rate of 30 µL/m in. IgGs were immobilized on the activated spots by injecting them in the ligand (vertical) direction at 20 µg/mL in 10 mM Acetate pH 4.5 buffer for 1.5 minutes at 30 µg/mL. The activated surfaces were blocked by injecting 1M ethanolamine, pH 8.5 in the analyte direction for 3 minutes at 30 µL/min.

The analysis temperature for the hBCMA binding analysis was 37° C. or 25° C. in a running buffer of HBS-T+, supplemented with 1 mg/mL BSA. A kinetic titration method was employed for the interaction analysis as described in Abdiche, et al. The hBCMA (human BCMA) analyte was injected in the analyte direction using a series of injections from low to high concentration. The concentrations used were 0.08 nM, 0.4 nM, 2 nM, 10 nM and 50 nM (a 5-membered series, with a 5-fold dilution factor and top concentration of 50 nM). The association time for a given analyte dilution was two minutes. Immediately after the 50 nM hBCMA injection, dissociation was monitored for 2 hours. Prior to the hBCMA analyte injections, buffer was injected 5 times using the same association and dissociation times at the hBCMA analyte cycles to prepare a buffer blank sensorgram for double-referencing purposes (double referencing as described in Myszka, J. Mol. Recognit. 12, 279-284 (1999).

The sensorgrams were double-referenced and fit to a 1:1 Langmuir with mass transport kinetic titration model in BIAevaluation Software version 4.1.1 (GE Lifesciences, Piscataway, N.J.). The sensorgrams and fits are shown in FIG. 1, and the kinetics and affinity parameters for various anti-BCMA antibodies of the present invention are shown in Tables 6A-6C.

TABLE 6A

| Sample | $k_a$ (1/Ms) | $k_d$ (1/s) | $t_{1/2}$ (min) | $K_D$ (pM) |
|---|---|---|---|---|
| A02_Rd4_6 nM_C01 | 1.2E+06 | 2.8E−05 | 411 | 24 |
| A02_Rd4_6 nM_C16 | 1.1E+06 | 6.2E−05 | 187 | 59 |
| Combo_Rd4_0.6 nM_C29 | 6.6E+06 | 1.4E−04 | 83 | 21 |
| L3PY/H3TAQ | 2.6E+06 | 1.4E−04 | 84 | 53 |

TABLE 6B

| Antibody | ka (1/Ms) huBCMA @ 25° C. | kd (1/s) huBCMA @25° C. | T½ (min) to huBCMA @25° C. | KD (nM) to huBCMA @ 25° C. |
|---|---|---|---|---|
| P6E01/P6E01 | 1.04E+06 | 4.15E−03 | 2.8 | 4.0 |
| P6E01/H3.AQ | 8.35E+05 | 3.45E−04 | 33.53 | 0.41 |
| L1.LGF/L3.KW/P6E01 | 8.31E+05 | 7.55E−03 | 1.53 | 9.08 |
| L1.LGF/L3.NY/P6E01 | 1.33E+06 | 4.40E−03 | 2.63 | 3.32 |
| L1.GDF/L3.NY/P6E01 | 1.60E+06 | 5.92E−03 | 1.95 | 3.70 |
| L1.LGF/L3.KW/H3.AL | 4.28E+05 | 1.23E−03 | 9.40 | 2.87 |
| L1.LGF/L3.KW/H3.AP | 9.28E+05 | 2.27E−03 | 5.10 | 2.44 |
| L1.LGF/L3.KW/H3.AQ | 5.24E+05 | 9.56E−04 | 12.09 | 1.82 |
| L1.LGF/L3.PY/H3.AP | 4.57E+05 | 9.69E−04 | 11.92 | 2.12 |
| L1.LGF/L3.PY/H3.AQ | 9.31E+05 | 8.86E−04 | 13.04 | 0.95 |
| L1.LGF/L3.NY/H3.AL | 7.63E+05 | 9.70E−04 | 11.91 | 1.27 |
| L1.LGF/L3.NY/H3.AP | 9.36E+05 | 5.33E−04 | 21.67 | 0.57 |
| L1.LGF/L3.NY/H3.AQ | 6.66E+05 | 2.99E−04 | 38.61 | 0.45 |
| L1.GDF/L3.KW/H3.AL | 4.45E+05 | 3.90E−03 | 2.96 | 8.76 |
| L1.GDF/L3.KW/H3.AP | 1.17E+06 | 4.61E−03 | 2.51 | 3.93 |
| L1.GDF/L3.KW/H3.AQ | 7.97E+05 | 3.48E−03 | 3.32 | 4.37 |
| L1.GDF/L3.PY/H3.AQ | 1.42E+06 | 1.35E−02 | 0.86 | 9.49 |
| L1.GDF/L3.NY/H3.AL | 9.07E+05 | 4.03E−03 | 2.87 | 4.44 |
| L1.GDF/L3.NY/H3.AP | 1.41E+06 | 1.41E−03 | 8.21 | 1.00 |
| L1.GDF/L3.NY/H3.AQ | 9.84E+05 | 7.22E−04 | 16.00 | 0.73 |
| L3.KW/P6E01 | 7.40E+05 | 3.15E−04 | 36.66 | 0.43 |
| L3.PY/P6E01 | 7.12E+05 | 2.28E−04 | 50.74 | 0.32 |
| L3.NY/P6E01 | 8.76E+05 | 3.84E−04 | 30.08 | 0.44 |

| Antibody | ka (1/Ms) huBCMA @ 37° C. | kd (1/s) huBCMA @37° C. | T½ (min) to huBCMA @37° C. | KD (nM) to huBCMA @ 37° C. |
|---|---|---|---|---|
| L3.PY/L1.PS/P6E01 | 2.49E+06 | 1.13E−03 | 10.21 | 0.45 |
| L3.PY/L1.AH/P6E01 | 2.55E+06 | 1.26E−03 | 9.19 | 0.49 |
| L3.PY/L1.FF/P6E01 | 2.39E+06 | 1.41E−03 | 8.18 | 0.59 |

TABLE 6B-continued

| | | | | |
|---|---|---|---|---|
| L3.PY/L1.PH/P6E01 | 2.81E+06 | 9.13E−04 | 12.65 | 0.32 |
| L3.PY/L3.KY/P6E01 | 3.18E+06 | 1.09E−03 | 10.65 | 0.34 |
| L3.PY/L3.KF/P6E01 | 2.88E+06 | 2.08E−03 | 5.56 | 0.72 |
| L3.PY/H2.QR | 2.56E+06 | 1.19E−03 | 9.75 | 0.46 |
| L3.PY/H2.DY | 2.60E+06 | 1.38E−03 | 8.37 | 0.53 |
| L3.PY/H2.YQ | 2.58E+06 | 1.56E−03 | 7.41 | 0.60 |
| L3.PY/H2.LT | 2.40E+06 | 1.29E−03 | 8.95 | 0.54 |
| L3.PY/H2.HA | 2.43E+06 | 1.47E−03 | 7.89 | 0.60 |
| L3.PY/H2.QL | 2.64E+06 | 2.18E−03 | 5.31 | 0.82 |
| L3.PY/H3.YA | 3.15E+06 | 1.18E−03 | 9.82 | 0.37 |
| L3.PY/H3.AE | 3.29E+06 | 1.39E−03 | 8.32 | 0.42 |
| L3.PY/H3.AQ | 3.08E+06 | 1.73E−03 | 6.69 | 0.56 |
| L3.PY/H3.TAQ | 3.08E+06 | 1.14E−03 | 10.13 | 0.37 |
| L3.PY/P6E01 | 2.65E+06 | 1.96E−03 | 5.91 | 0.74 |
| L3.PY/L1.PS/H2.QR | 3.97E+06 | 1.03E−01 | 0.11 | 25.85 |
| L3.PY/L1.PS/H2.DY | 3.22E+06 | 3.61E−03 | 3.20 | 1.12 |
| L3.PY/L1.PS/H2.YQ | 3.35E+06 | 4.30E−03 | 2.69 | 1.28 |
| L3.PY/L1.PS/H2.LT | 3.40E+06 | 4.65E−03 | 2.49 | 1.37 |
| L3.PY/L1.PS/H2.HA | 3.30E+06 | 1.06E−02 | 1.09 | 3.21 |
| L3.PY/L1.PS/H2.QL | 1.52E+07 | 3.14E−01 | 0.04 | 20.64 |
| L3.PY/L1.PS/H3.YA | 3.07E+06 | 9.05E−03 | 1.28 | 2.95 |
| L3.PY/L1.PS/H3.AE | 3.14E+06 | 1.46E−03 | 7.93 | 0.46 |
| L3.PY/L1.PS/H3.AQ | 3.26E+06 | 1.79E−03 | 6.46 | 0.55 |
| L3.PY/L1.PS/H3.TAQ | 3.25E+06 | 2.46E−03 | 4.70 | 0.76 |
| L3.PY/L1.AH/H2.QR | 3.13E+06 | 1.81E−03 | 6.39 | 0.58 |
| L3.PY/L1.AH/H2.DY | 3.05E+06 | 1.52E−03 | 7.62 | 0.50 |
| L3.PY/L1.AH/H2.YQ | 2.42E+06 | 1.93E−03 | 6.00 | 0.80 |
| L3.PY/L1.AH/H2.LT | 3.16E+06 | 1.23E−03 | 9.38 | 0.39 |
| L3.PY/L1.AH/H2.HA | 3.33E+06 | 1.81E−03 | 6.37 | 0.54 |
| L3.PY/L1.AH/H2.QL | 3.04E+06 | 1.60E−03 | 7.22 | 0.53 |
| L3.PY/L1.AH/H3.YA | 3.00E+06 | 1.50E−03 | 7.73 | 0.50 |
| L3.PY/L1.AH/H3.AE | 3.32E+06 | 1.73E−03 | 6.70 | 0.52 |
| L3.PY/L1.AH/H3.AQ | 3.03E+06 | 1.97E−03 | 5.85 | 0.65 |
| L3.PY/L1.AH/H3.TAQ | 3.27E+06 | 1.19E−03 | 9.68 | 0.37 |
| L3.PY/L1.FF/H2.QR | 3.47E+06 | 1.77E−03 | 6.54 | 0.51 |
| L3.PY/L1.FF/H2.DY | 4.14E+06 | 2.71E−03 | 4.27 | 0.65 |
| L3.PY/L1.FF/H2.YQ | 3.32E+06 | 1.52E−03 | 7.61 | 0.46 |
| L3.PY/L1.FF/H2.LT | 3.30E+06 | 1.67E−03 | 6.92 | 0.51 |
| L3.PY/L1.FF/H2.HA | 3.49E+06 | 2.19E−03 | 5.29 | 0.63 |
| L3.PY/L1.FF/H2.QL | 3.48E+06 | 1.40E−03 | 8.28 | 0.40 |
| L3.PY/L1.FF/H3.YA | 3.50E+06 | 1.80E−03 | 6.41 | 0.51 |
| L3.PY/L1.FF/H3.AE | 3.82E+06 | 2.63E−03 | 4.39 | 0.69 |
| L3.PY/L1.FF/H3.AQ | 3.32E+06 | 1.54E−03 | 7.51 | 0.46 |
| L3.PY/L1.FF/H3.TAQ | 3.52E+06 | 1.89E−03 | 6.12 | 0.54 |
| L3.PY/L1.PH/H2.QR | 3.69E+06 | 2.36E−03 | 4.89 | 0.64 |
| L3.PY/L1.PH/H2.HA | 2.37E+06 | 1.16E−03 | 9.99 | 0.49 |
| L3.PY/L1.PH/H3.AE | 3.68E+06 | 1.34E−03 | 8.61 | 0.36 |
| L3.PY/L1.PH/H3.AQ | 3.08E+06 | 1.59E−03 | 7.27 | 0.52 |
| L3.PY/L1.PH/H3.TAQ | 3.58E+06 | 2.13E−03 | 5.43 | 0.59 |
| L3.PY/L3.KY/H2.QR | 2.95E+06 | 9.90E−04 | 11.67 | 0.34 |
| L3.PY/L3.KY/H2.DY | 3.19E+06 | 6.42E−04 | 18.00 | 0.20 |
| L3.PY/L3.KY/H2.YQ | 2.14E+06 | 1.65E−03 | 7.02 | 0.77 |
| L3.PY/L3.KY/H2.LT | 2.92E+06 | 9.06E−04 | 12.75 | 0.31 |
| L3.PY/L3.KY/H2.HA | 3.29E+06 | 1.63E−03 | 7.10 | 0.49 |
| L3.PY/L3.KY/H2.QL | 3.65E+06 | 2.08E−03 | 5.56 | 0.57 |
| L3.PY/L3.KY/H3.YA | 3.30E+06 | 9.12E−04 | 12.67 | 0.28 |
| L3.PY/L3.KY/H3.TAQ | 2.79E+06 | 6.49E−04 | 17.79 | 0.23 |
| L3.PY/L3.KF/H2.DY | 2.74E+06 | 1.82E−03 | 6.35 | 0.67 |
| L3.PY/L3.KF/H2.YQ | 1.96E+06 | 2.23E−03 | 5.18 | 1.14 |
| L3.PY/L3.KF/H2.LT | 2.75E+06 | 1.91E−03 | 6.05 | 0.69 |
| L3.PY/L3.KF/H2.QL | 2.07E+06 | 1.25E−03 | 9.26 | 0.60 |
| L3.PY/L3.KF/H3.YA | 3.12E+06 | 1.47E−03 | 7.85 | 0.47 |
| L3.PY/L3.KF/H3.AE | 3.07E+06 | 1.55E−03 | 7.44 | 0.51 |
| L3.PY/L3.KF/H3.AQ | 3.48E+06 | 2.27E−03 | 5.09 | 0.65 |
| L3.PY/L3.KF/H3.TAQ | 2.82E+06 | 1.62E−03 | 7.12 | 0.58 |

| Antibody | ka (1/Ms) to cyBCMA @ 25° C. | kd (1/s) to cyBCMA @25° C. | T½ (min) to cyBCMA @25° C. | KD (nM) to cyBCMA @ 25° C. |
|---|---|---|---|---|
| P6E01/P6E01 | | 7.02E−02 | 0.16 | 115.4 |
| P6E01/H3.AQ | 1.08E+06 | 7.40E−03 | 1.6 | 6.9 |
| L1.LGF/L3.KW/P6E01 | 4.55E+05 | 1.95E−02 | 0.6 | 42.8 |
| L1.LGF/L3.NY/P6E01 | 9.20E+05 | 1.05E−02 | 1.1 | 11.4 |
| L1.GDF/L3.NY/P6E01 | 1.20E+06 | 7.67E−03 | 1.5 | 6.4 |
| L1.LGF/L3.KW/H3.AL | 2.90E+05 | 1.21E−02 | 1.0 | 41.8 |
| L1.LGF/L3.KW/H3.AP | 5.54E+05 | 1.54E−02 | 0.7 | 27.8 |
| L1.LGF/L3.KW/H3.AQ | 5.27E+05 | 3.55E−03 | 3.3 | 6.7 |
| L1.LGF/L3.PY/H3.AP | 3.64E+05 | 1.30E−02 | 0.9 | 35.8 |
| L1.LGF/L3.PY/H3.AQ | 1.00E+06 | 4.77E−03 | 2.4 | 4.8 |

TABLE 6B-continued

| | | | | |
|---|---|---|---|---|
| L1.LGF/L3.NY/H3.AL | 6.35E+05 | 1.48E−02 | 0.8 | 23.2 |
| L1.LGF/L3.NY/H3.AP | 8.30E+05 | 5.57E−03 | 2.1 | 6.7 |
| L1.LGF/L3.NY/H3.AQ | 7.51E+05 | 1.48E−03 | 7.8 | 2.0 |
| L1.GDF/L3.KW/H3.AL | 3.18E+05 | 1.80E−02 | 0.6 | 56.7 |
| L1.GDF/L3.KW/H3.AP | 8.14E+05 | 2.03E−02 | 0.6 | 24.9 |
| L1.GDF/L3.KW/H3.AQ | 8.02E+05 | 5.65E−03 | 2.0 | 7.0 |
| L1.GDF/L3.PY/H3.AQ | 1.55E+06 | 1.66E−02 | 0.7 | 10.7 |
| L1.GDF/L3.NY/H3.AL | 9.00E+05 | 2.19E−02 | 0.5 | 24.3 |
| L1.GDF/L3.NY/H3.AP | 1.36E+06 | 7.02E−03 | 1.6 | 5.2 |
| L1.GDF/L3.NY/H3.AQ | 1.18E+06 | 1.36E−03 | 8.5 | 1.2 |
| L3.KW/P6E01 | 7.63E+05 | 2.57E−03 | 4.5 | 3.4 |
| L3.PY/P6E01 | 8.55E+05 | 2.93E−03 | 3.9 | 3.4 |
| L3.NY/P6E01 | 1.01E+06 | 2.87E−03 | 4.0 | 2.8 |

| Antibody | ka (1/Ms) cyBCMA @ 37° C. | kd (1/s) cyBCMA @37° C. | T½ (min) to cyBCMA @37° C. | KD (nM) to cyBCMA @ 37° C. |
|---|---|---|---|---|
| L3.PY/L1.PS/P6E01 | 2.17E+06 | 6.06E−03 | 1.91 | 2.79 |
| L3.PY/L1.AH/P6E01 | 2.16E+06 | 5.72E−03 | 2.02 | 2.65 |
| L3.PY/L1.FF/P6E01 | 2.45E+06 | 5.91E−03 | 1.96 | 2.41 |
| L3.PY/L1.PH/P6E01 | 2.17E+06 | 7.89E−03 | 1.46 | 3.63 |
| L3.PY/L3.KY/P6E01 | 2.27E+06 | 5.02E−03 | 2.30 | 2.21 |
| L3.PY/L3.KF/P6E01 | 2.39E+06 | 8.30E−03 | 1.39 | 3.48 |
| L3.PY/H2.QR | 2.18E+06 | 6.58E−03 | 1.76 | 3.02 |
| L3.PY/H2.DY | 2.24E+06 | 6.18E−03 | 1.87 | 2.76 |
| L3.PY/H2.YQ | 2.46E+06 | 6.21E−03 | 1.86 | 2.53 |
| L3.PY/H2.LT | 2.09E+06 | 7.57E−03 | 1.53 | 3.63 |
| L3.PY/H2.HA | 1.99E+06 | 7.55E−03 | 1.53 | 3.79 |
| L3.PY/H2.QL | 2.05E+06 | 1.26E−02 | 0.91 | 6.16 |
| L3.PY/H3.YA | 2.87E+06 | 5.40E−03 | 2.14 | 1.88 |
| L3.PY/H3.AE | 2.82E+06 | 5.04E−03 | 2.29 | 1.79 |
| L3.PY/H3.AQ | 2.77E+06 | 5.39E−03 | 2.14 | 1.94 |
| L3.PY/H3.TAQ | 2.57E+06 | 4.37E−03 | 2.64 | 1.70 |
| L3.PY/P6E01 | 2.20E+06 | 1.31E−02 | 0.88 | 5.96 |
| L3.PY/L1.PS/H2.QR | 5.25E+05 | 6.70E−04 | 17.23 | 1.28 |
| L3.PY/L1.PS/H2.DY | 1.90E+06 | 3.78E−03 | 3.06 | 1.99 |
| L3.PY/L1.PS/H2.YQ | 2.00E+06 | 3.74E−03 | 3.09 | 1.87 |
| L3.PY/L1.PS/H2.LT | 2.17E+06 | 4.11E−03 | 2.81 | 1.89 |
| L3.PY/L1.PS/H2.HA | 1.45E+06 | 2.69E−03 | 4.30 | 1.86 |
| L3.PY/L1.PS/H2.QL | 6.57E+05 | 6.36E−04 | 18.17 | 0.97 |
| L3.PY/L1.PS/H3.YA | 1.77E+06 | 9.98E−03 | 1.16 | 5.65 |
| L3.PY/L1.PS/H3.AE | 2.46E+06 | 4.13E−03 | 2.80 | 1.68 |
| L3.PY/L1.PS/H3.AQ | 2.52E+06 | 4.33E−03 | 2.67 | 1.72 |
| L3.PY/L1.PS/H3.TAQ | 2.58E+06 | 5.52E−03 | 2.09 | 2.14 |
| L3.PY/L1.AH/H2.QR | 2.20E+06 | 4.91E−03 | 2.35 | 2.23 |
| L3.PY/L1.AH/H2.DY | 2.32E+06 | 4.51E−03 | 2.56 | 1.95 |
| L3.PY/L1.AH/H2.YQ | 1.58E+06 | 4.31E−03 | 2.68 | 2.74 |
| L3.PY/L1.AH/H2.LT | 2.19E+06 | 2.96E−03 | 3.91 | 1.35 |
| L3.PY/L1.AH/H2.HA | 2.58E+06 | 4.39E−03 | 2.63 | 1.70 |
| L3.PY/L1.AH/H2.QL | 2.62E+06 | 9.55E−03 | 1.21 | 3.65 |
| L3.PY/L1.AH/H3.YA | 2.37E+06 | 5.26E−03 | 2.20 | 2.22 |
| L3.PY/L1.AH/H3.AE | 2.25E+06 | 3.56E−03 | 3.25 | 1.58 |
| L3.PY/L1.AH/H3.AQ | 2.24E+06 | 3.99E−03 | 2.90 | 1.78 |
| L3.PY/L1.AH/H3.TAQ | 2.28E+06 | 3.02E−03 | 3.83 | 1.32 |
| L3.PY/L1.FF/H2.QR | 2.55E+06 | 4.21E−03 | 2.75 | 1.65 |
| L3.PY/L1.FF/H2.DY | 2.66E+06 | 5.00E−03 | 2.31 | 1.88 |
| L3.PY/L1.FF/H2.YQ | 2.19E+06 | 3.26E−03 | 3.55 | 1.49 |
| L3.PY/L1.FF/H2.LT | 2.19E+06 | 3.41E−03 | 3.38 | 1.56 |
| L3.PY/L1.FF/H2.HA | 2.33E+06 | 4.17E−03 | 2.77 | 1.79 |
| L3.PY/L1.FF/H2.QL | 2.36E+06 | 4.49E−03 | 2.57 | 1.91 |
| L3.PY/L1.FF/H3.YA | 2.46E+06 | 4.16E−03 | 2.77 | 1.69 |
| L3.PY/L1.FF/H3.AE | 2.85E+06 | 5.01E−03 | 2.31 | 1.76 |
| L3.PY/L1.FF/H3.AQ | 2.18E+06 | 3.29E−03 | 3.51 | 1.51 |
| L3.PY/L1.FF/H3.TAQ | 2.32E+06 | 3.76E−03 | 3.07 | 1.62 |
| L3.PY/L1.PH/H2.QR | 2.42E+06 | 4.36E−03 | 2.65 | 1.80 |
| L3.PY/L1.PH/H2.HA | 1.61E+06 | 5.53E−03 | 2.09 | 3.44 |
| L3.PY/L1.PH/H3.AE | 2.61E+06 | 2.02E−03 | 5.72 | 0.77 |
| L3.PY/L1.PH/H3.AQ | 2.28E+06 | 3.41E−03 | 3.39 | 1.50 |
| L3.PY/L1.PH/H3.TAQ | 2.51E+06 | 3.20E−03 | 3.61 | 1.28 |
| L3.PY/L3.KY/H2.QR | 2.05E+06 | 7.74E−03 | 1.49 | 3.78 |
| L3.PY/L3.KY/H2.DY | 1.96E+06 | 2.43E−03 | 4.75 | 1.24 |
| L3.PY/L3.KY/H2.YQ | 1.27E+06 | 2.58E−03 | 4.47 | 2.04 |
| L3.PY/L3.KY/H2.LT | 1.82E+06 | 2.32E−03 | 4.98 | 1.27 |
| L3.PY/L3.KY/H2.HA | 2.28E+06 | 3.18E−03 | 3.63 | 1.40 |
| L3.PY/L3.KY/H2.QL | 2.75E+06 | 4.09E−03 | 2.83 | 1.49 |
| L3.PY/L3.KY/H3.YA | 1.84E+06 | 4.28E−03 | 2.70 | 2.33 |
| L3.PY/L3.KY/H3.TAQ | 1.81E+06 | 1.92E−03 | 6.03 | 1.06 |
| L3.PY/L3.KF/H2.DY | 2.08E+06 | 3.68E−03 | 3.14 | 1.77 |
| L3.PY/L3.KF/H2.YQ | 1.41E+06 | 5.01E−03 | 2.30 | 3.55 |

TABLE 6B-continued

| | | | | |
|---|---|---|---|---|
| L3.PY/L3.KF/H2.LT | 1.91E+06 | 4.13E−03 | 2.80 | 2.16 |
| L3.PY/L3.KF/H2.QL | 1.42E+06 | 3.10E−03 | 3.73 | 2.18 |
| L3.PY/L3.KF/H3.YA | 2.10E+06 | 7.96E−03 | 1.45 | 3.78 |
| L3.PY/L3.KF/H3.AE | 1.85E+06 | 5.64E−03 | 2.05 | 3.05 |
| L3.PY/L3.KF/H3.AQ | 2.55E+06 | 2.38E−03 | 4.85 | 0.93 |
| L3.PY/L3.KF/H3.TAQ | 2.01E+06 | 1.91E−03 | 6.05 | 0.95 |

TABLE 6C*

| | Human | | | Cyno | | |
|---|---|---|---|---|---|---|
| Antibody | ka (1/Ms) | kd (1/s) | KD (pM) | ka (1/Ms) | kd (1/s) | KD (pM) |
| P5A2_VHVL | 6.96E+06 | 3.87E−02 | 5567 | 1.61E+06 | 1.64E−02 | 10230 |
| A02_Rd4_0.6nM_C06 | 3.49E+06 | 7.37E−05 | 21 | 1.81E+06 | 1.05E−04 | 58 |
| A02_Rd4_0.6nM_C09 | 5.50E+06 | 9.75E−05 | 18 | 2.13E+06 | 1.74E−04 | 82 |
| A02_Rd4_6nM_C16 | 1.56E+06 | 1.41E−04 | 90 | 1.34E+06 | 1.58E−04 | 118 |
| A02_Rd4_6nM_C03 | 1.69E+06 | 1.26E−04 | 75 | 1.17E+06 | 1.85E−04 | 158 |
| A02_Rd4_6nM_C01 | 3.11E+06 | 9.20E−05 | 30 | 1.45E+06 | 5.83E−04 | 401 |
| A02_Rd4_6nM_C26 | 4.26E+06 | 1.39E−04 | 33 | 2.21E+06 | 4.48E−04 | 203 |
| A02_Rd4_6nM_C25 | 2.75E+06 | 1.80E−04 | 65 | 1.50E+06 | 3.30E−04 | 220 |
| A02_Rd4_6nM_C22 | 3.38E+06 | 1.82E−04 | 54 | 1.84E+06 | 3.24E−04 | 176 |
| A02_Rd4_6nM_C19 | 3.00E+06 | 1.48E−04 | 49 | 2.54E+06 | 6.61E−04 | 260 |
| A02_Rd4_0.6nM_C03 | 4.27E+06 | 1.82E−04 | 43 | 2.12E+06 | 4.26E−04 | 201 |
| A02_Rd4_6nM_C07 | 1.48E+06 | 1.89E−04 | 128 | 6.91E+05 | 7.86E−04 | 1138 |
| A02_Rd4_6nM_C23 | 1.22E+07 | 2.55E−04 | 21 | 2.63E+06 | 4.14E−04 | 157 |
| A02_Rd4_0.6nM_C18 | 4.73E+06 | 2.29E−04 | 48 | 3.24E+06 | 6.39E−04 | 197 |
| A02_Rd4_6nM_C10 | 4.51E+06 | 3.15E−04 | 70 | 1.90E+06 | 8.98E−04 | 472 |
| A02_Rd4_6nM_C05 | 3.10E+06 | 3.08E−04 | 99 | 1.36E+06 | 1.29E−03 | 950 |
| A02_Rd4_0.6nM_C10 | 2.30E+06 | 2.96E−04 | 129 | 8.83E+05 | 1.63E−03 | 1842 |
| A02_Rd4_6nM_C04 | 4.47E+06 | 6.03E−04 | 135 | 2.18E+06 | 8.31E−04 | 381 |
| A02_Rd4_0.6nM_C26 | 7.26E+06 | 4.43E−04 | 61 | 2.71E+06 | 2.56E−03 | 941 |
| A02_Rd4_0.6nM_C13 | 8.53E+06 | 5.66E−04 | 66 | 2.29E+06 | 1.28E−03 | 560 |
| A02_Rd4_0.6nM_C01 | 4.74E+06 | 9.15E−04 | 193 | 2.39E+06 | 1.57E−03 | 655 |
| A02_Rd4_6nM_C08 | 3.92E+06 | 7.38E−04 | 188 | 2.23E+06 | 1.13E−02 | 5072 |
| P5C1_VHVL | 1.16E+07 | 6.92E−02 | 5986 | 3.53E+06 | 5.38E−02 | 15231 |
| C01_Rd4_6nM_C24 | 7.47E+06 | 3.48E−03 | 467 | 3.17E+06 | 8.91E−04 | 281 |
| C01_Rd4_6nM_C26 | 1.50E+07 | 1.36E−03 | 90 | 4.75E+06 | 1.99E−03 | 419 |
| C01_Rd4_6nM_C02 | 1.61E+07 | 1.44E−03 | 89 | 5.12E+06 | 2.18E−03 | 426 |
| C01_Rd4_6nM_C10 | 1.31E+07 | 2.12E−03 | 162 | 4.44E+06 | 2.19E−03 | 493 |
| C01_Rd4_0.6nM_C27 | 1.23E+07 | 3.74E−03 | 303 | 3.34E+06 | 2.85E−03 | 852 |
| C01_Rd4_6nM_C20 | 6.02E+06 | 2.76E−03 | 459 | 3.60E+06 | 6.25E−03 | 1737 |
| C01_Rd4_6nM_C12 | 1.21E+07 | 6.49E−03 | 535 | 4.51E+06 | 3.70E−03 | 820 |
| C01_Rd4_0.6nM_C16 | 1.55E+07 | 6.30E−03 | 407 | 4.95E+06 | 4.64E−03 | 939 |
| C01_Rd4_0.6nM_C09 | 1.51E+07 | 8.25E−03 | 545 | 5.28E+06 | 9.36E−03 | 1773 |
| C01_Rd4_6nM_C09 | 1.58E+07 | 1.28E−02 | 811 | 3.73E+06 | 8.68E−03 | 2328 |
| C01_Rd4_0.6nM_C03 | 1.55E+07 | 1.50E−02 | 964 | 4.72E+06 | 1.19E−02 | 2528 |
| C01_Rd4_0.6nM_C06 | 1.82E+07 | 1.54E−02 | 847 | 6.22E+06 | 1.21E−02 | 1948 |
| C01_Rd4_6nM_C04 | 2.33E+07 | 4.97E−02 | 2134 | 6.34E+06 | 3.27E−02 | 5156 |
| COMBO_Rd4_0.6nM_C22 | 1.97E+06 | 7.15E−05 | 36 | 1.34E+06 | 6.66E−05 | 50 |
| COMBO_Rd4_6nM_C21 | 1.17E+07 | 7.34E−05 | 6 | 3.17E+06 | 2.48E−04 | 78 |
| COMBO_Rd4_6nM_C10 | 5.47E+06 | 9.72E−05 | 18 | 1.52E+06 | 1.60E−04 | 105 |
| COMBO_Rd4_0.6nM_C04 | 1.07E+07 | 1.58E−04 | 15 | 3.52E+06 | 1.37E−04 | 39 |
| COMBO_Rd4_6nM_C25 | 7.98E+06 | 1.13E−04 | 14 | 2.85E+06 | 2.26E−04 | 79 |
| COMBO_Rd4_0.6nM_C21 | 1.34E+07 | 1.15E−04 | 9 | 3.63E+06 | 3.04E−04 | 84 |
| COMBO_Rd4_6nM_C11 | 6.74E+06 | 1.24E−04 | 18 | 2.64E+06 | 4.12E−04 | 156 |
| COMBO_Rd4_0.6nM_C20 | 7.65E+06 | 1.46E−04 | 19 | 3.09E+06 | 2.84E−04 | 92 |
| COMBO_Rd4_6nM_C09 | 8.85E+06 | 1.43E−04 | 16 | 2.37E+06 | 3.18E−04 | 134 |
| COMBO_Rd4_6nM_C08 | 8.99E+06 | 1.69E−04 | 19 | 3.06E+06 | 4.28E−04 | 140 |
| COMBO_Rd4_0.6nM_C19 | 7.86E+06 | 1.55E−04 | 20 | 2.92E+06 | 9.79E−04 | 336 |
| COMBO_Rd4_0.6nM_C02 | 8.57E+06 | 1.85E−04 | 22 | 3.01E+06 | 4.94E−04 | 164 |
| COMBO_Rd4_0.6nM_C23 | 7.39E+06 | 2.10E−04 | 28 | 2.81E+06 | 5.31E−04 | 189 |
| COMBO_Rd4_0.6nM_C29 | 1.47E+07 | 2.77E−04 | 19 | 4.00E+06 | 3.36E−04 | 84 |
| COMBO_Rd4_0.6nM_C09 | 1.04E+07 | 3.19E−04 | 31 | 3.77E+06 | 3.46E−04 | 92 |
| COMBO_Rd4_6nM_C12 | 1.38E+07 | 2.70E−04 | 20 | 3.29E+06 | 4.86E−04 | 148 |
| COMBO_Rd4_0.6nM_C30 | 4.35E+06 | 2.82E−04 | 65 | 1.68E+06 | 8.08E−04 | 481 |
| COMBO_Rd4_0.6nM_C14 | 8.66E+06 | 3.28E−04 | 38 | 3.48E+06 | 6.45E−04 | 185 |
| COMBO_Rd4_6nM_C07 | 1.05E+07 | 3.71E−04 | 35 | 3.94E+06 | 9.34E−04 | 237 |
| COMBO_Rd4_6nM_C02 | 1.05E+06 | 4.43E−04 | 422 | 7.95E+05 | 1.36E−03 | 1714 |
| COMBO_Rd4_0.6nM_C05 | 4.32E+06 | 4.97E−04 | 115 | 1.94E+06 | 1.72E−03 | 886 |
| COMBO_Rd4_6nM_C17 | 8.68E+06 | 8.01E−04 | 92 | 3.06E+06 | 1.01E−03 | 330 |
| COMBO_Rd4_6nM_C22 | 3.03E+06 | 7.75E−04 | 256 | 1.70E+06 | 1.65E−03 | 972 |
| COMBO_Rd4_0.6nM_C11 | 5.11E+06 | 1.06E−03 | 207 | 2.20E+06 | 4.23E−03 | 1924 |

*The binding analysis was conducted at 37° C.

Example 2: Flow Cytometry of Human Anti-BCMA Antibodies on BCMA Positive Tumor Cells This example demonstrates binding of BCMA positive tumor cells by various BCMA antibodies of the present invention.

Binding of human anti-hBCMA expressed in mouse IgG2a were assessed on BCMA-expressing cells (KMS12BM, L363, MM1S and KMS12PE) by flow cytometry. 250,000 cells were incubated with 0.5 ug antibody in 100 uL binding buffer (PBS (Phosphate Buffered Saline)+ 0.2% BSA (Bovine Serum Albumin)), followed by incubation with Alex Fluor 647 conjugated anti-mouse IgG (Biolegend). Table 7 shows MFI (mean fluorescence intensity) on BCMA positive tumor cells by various BCMA antibodies (e.g., Combo_Rd4_0.6nM_C29, A02_Rd4_6nM_C01, A02_Rd4_6nM_C16, and P6E01/H3TAQ)

TABLE 7

| Cell Line | secondary only | Combo_Rd4_ 0.6 nM_C29 | A02_Rd4_ 6 nM_C01 MFI | A02_Rd4_ 6 nM | P6E01/ H3TAQ |
|---|---|---|---|---|---|
| KMS12PE (BCMA+++) | 26 | 6114 | 5862 | 3094 | 6018 |
| MM1S (BCMA++) | 22 | 2569 | 2539 | 1951 | 2715 |
| L363 (BCMA+) | 22 | 1667 | 1176 | 789 | 1457 |
| KMS12BM (BCMA+) | 22 | 583 | 580 | 421 | 634 |

Example 3: Cytotoxicity of Anti-BCMA ADCs in BCMA Positive Cells

This example illustrates the efficacy of the anti-BCMA ADCs in BCMA positive cells.

Human anti-BCMA (L3.PY/P6E01, L3.PY/H3.TAQ, Combo_Rd4_0.6nM_C29, A02_Rd4_6nM_C01, and A02_Rd4_6nM_C16) antibodies were expressed as human IgG1 subtypes engineered with glutamine-containing transglutaminase ("Q") tags (e.g. LCQ05, H7c, N297A, N297Q, N297A/H7c, N297Q/LCQ05) for drug antibody ratios (DAR) of 2, 4, and 6. TG17 corresponds to SEQ ID NO: 472 (LLQGPP); LCQ05 correspond to SEQ ID NO: 474 (GGLLQGPP), H7c correspond to SEQ ID NO: 454 (LLQG), respectively, and conjugated with AcLys-Val-Cit-PABC-Aur0101 (Acetyl-Lysine-Valine-Citrulline-p-aminobenzyloxycarbonyl), amino-PEG6-C2-Aur3377, or amino-PEG6-C2-Aur0131 as indicated in Table 8. In one instance, the transglutaminase tags can be engineered at the light chain, heavy chain, or a combination of light and heavy chains. In other instance, the transglutaminase tag (e.g., Q) is engineered at site of the antibody, such as at position 297 of the human IgG (EU numbering scheme). For example, the wild-type amino acid asparagine (N) is substituted with glutamine or alanine at position 297 of the BCMA antibody (N297Q or N297A) of the present invention. Anti-BCMA antibody conjugation to Aur0101, Aur3377, and Aur0131 was then achieved via microbial transglutaminase-catalyzed transamidation reaction between the anti-BCMA antibody carrying a targeted glutamine or glutamine tag at the specific site (e.g., carboxyl terminus or amino terminus of the heavy chain or light chain, position 297, or at another site of the antibody) and an amine-containing derivative of the payload (e.g., MMAD, Aur0101, Aur3377, or Aur0131). In some instances, the wild-type amino acid lysine at position 222, 340, or 370 (in accordance with EU numbering scheme) was replaced with amino acid arginine ("K222R", "K340R", or "K370R"). For example, the K222R substitution was found to have the surprising effect of resulting in more homogenous antibody and payload conjugate, better intermolecular crosslinking between the antibody and the payload, and/or significant decrease in interchain crosslinking with the glutamine tag on the C-terminus of the antibody light chain.

In the transamidation reaction, the glutamine on the antibody acted as an acyl donor, and the amine-containing compound acted as an acyl acceptor (amine donor). Purified anti-BCMA antibody in the concentration of 1-150 μM was incubated with a 5-100 molar excess acyl acceptor, ranging between 5 μM-15 mM, in the presence of 0.23-0.55% (w/v) *Streptoverticillium mobaraense* transglutaminase (AC-TIVA™, Ajinomoto, Japan) in 10-1000 mM NaCl, and 25 mM MES, HEPES [4-(2-hydroxyethyl)-1-piperazineethanesulfonic acid] or Tris HCl buffer at pH range 6.2-8.8. The reaction conditions were adjusted for individual acyl acceptor derivatives, and the optimal efficiency and specificity were typically observed for 33 μM antibody, 0.67 mM derivative, and 0.378% (w/v) transglutaminase in 75 mM NaCl, 25 mM Tris HCl, pH 8.5. Following incubation at 20-37 deg C. for 1-24 hours, the antibody was purified on Butyl Sepharose High Performance (Butyl HP) resin (GE Healthcare, Waukesha, Wis.) using standard chromatography methods known to persons skilled in the art, such as commercial hydrophobic interaction chromatography from GE Healthcare.

Target expressing (MM1.S, KMS12BM and L363) cells were then seeded on clear bottom plates at 3000 cells/well. Cells were treated with 4-fold serially diluted antibody-drug conjugates in triplicates. Cell viability was determined by CellTiter-Glo® Luminescent Cell Viability Assay 96 (Promega, Madison Wis.) 96 hours after treatment. Relative cell viability was determined as percentage of untreated control. EC50 was calculated by Prism software. Table 8 shows that all human anti-BCMA antibodies of the present invention conjugated to cytotoxic agent 0101, 3377, and 0131 through transglutaminase tags and linkers exert potent cell killing activity in BCMA expressing cells.

TABLE 8

| EC50 | | MM1.S LUCGFP (BCMA++) | | KMS12BM LUCGFP (+) | | L363 LUCGFP (+) | |
|---|---|---|---|---|---|---|---|
| ANTIBODY | DAR | nM | ug/mL | nM | ug/mL | nM | ug/mL |
| L3.PY/P6E01 N297Q/K222R AcLys vc0101 | 4 | 0.42 | 0.06 | 31.79 | 4.77 | 7.34 | 1.10 |
| L3PY/H3.TAQ N297Q/K222R Aclys vc0101 | 4 | 0.12 | 0.02 | 3.94 | 0.59 | 0.60 | 0.09 |

TABLE 8-continued

| ANTIBODY | DAR | MM1.S LUCGFP (BCMA++) | | KMS12BM LUCGFP (+) | | L363 LUCGFP (+) | |
|---|---|---|---|---|---|---|---|
| EC50 | | nM | ug/mL | nM | ug/mL | nM | ug/mL |
| A02_Rd4_6nM_C01 N297Q/K222R Aclys vc0101 | 3.91 | 0.26 | 0.04 | 18.67 | 2.80 | 2.53 | 0.38 |
| A02_Rd4_6nM_C16 N297Q/K222R Aclys vc0101 | 3.92 | 0.80 | 0.12 | 38.73 | 5.81 | 9.68 | 1.45 |
| Combo_Rd4_0.6nM_C29 LCQ05/K222R Aclys vc0101 | 2 | 0.13 | 0.02 | 10.91 | 1.64 | 1.67 | 0.25 |
| Combo_Rd4_0.6nM_C29 N297Q/K222R Aclys vc0101 | 3.9 | 0.11 | 0.02 | 0.99 | 0.15 | 0.66 | 0.10 |
| Combo_Rd4_0.6nM_C29 LCQ05/N297Q/K222R Aclys vc0101 | 5.98 | 0.34 | 0.05 | 1.19 | 0.18 | 1.05 | 0.16 |
| Combo_Rd4_0.6nM_C29 H7c/N297A/K222R AmPEG6 Aur0131 | 3.81 | 0.23 | 0.03 | 0.85 | 0.13 | 0.81 | 0.12 |
| Combo_Rd4_0.6nM_C29 H7c/N297A/K222R AmPEG6 Aur3377 | 3.88 | 0.30 | 0.05 | 5.01 | 0.75 | 1.36 | 0.20 |

Example 4: Anti-BCMA ADCs Induce Tumor Regression in an Orthotopic Multiple Myeloma Model This example illustrates the in vivo efficacy of the anti-BCMA ADCs in the MM1S orthotopic multiple myeloma model.

In vivo efficacy study of BCMA ADCs was performed with multiple myeloma cell line MM1.S expressing luciferase and GFP (Green Fluorescent Protein) in an orthotopic model. Ten million MM1.S LucGFP cells were injected intravenously through the tail vein into 6-8 weeks old female CB17/SCID animals. Intraperitoneal injection of D-luciferin (Regis Technologies, Morton Grove, Ill.) (200 uL per animal at 15 mg/mL), followed by anesthesia with isofluorane and subsequent whole body bioluminescence imaging (BLI) enable monitoring of tumor burden. Bioluminescent signals emitted by the interaction between luciferase expressed by the tumor cells and luciferin were captured by imaging using an IVIS Spectrum CT (Perkin Elmer, MA) and quantified as total flux (photons/sec) using Living Image 4.4 (Caliper Life Sciences, Alameda, Calif.). When the total flux reached an average of 1-3E6 for all animals, the animals were randomized into groups and a single dose of a human anti-BCMA antibody conjugated with 1) LCQ05/K222R-vc0101 at the C-terminus of the antibody light chain and control conjugates were administered through bolus tail vein injection. Animals were terminated when they exhibit hindlimb paralysis, an endpoint for MM1.S orthotopic models. FIG. 2 shows that a single dose at 3 mg/kg of various human anti-BCMA ADCs inhibits tumor progression as compared to the negative control (NNC), including P6E01/P6E01-AcLys-Val-Cit-PABC-Aur0101; P5A2_VHVL-AcLys-Val-Cit-PABC-Aur0101; P5C1_VHVL-AcLys-Val-Cit-PABC-Aur0101; P4G4-AcLys-Val-Cit-PABC-Aur0101; and P1A11-AcLys-Val-Cit-PABC-Aur0101.

This study demonstrates that treatment with a BCMA-ADC inhibits progression of multiple myeloma.

Example 5: Anti-BCMA ADCs Induce Tumor Regression and Inhibition in an Orthotopic Multiple Myeloma Model This example also illustrates the in vivo efficacy of the anti-BCMA ADCs in the MM1.S orthotopic multiple myeloma models.

In vivo efficacy study of BCMA ADCs was performed with multiple myeloma cell line MM1.S expressing luciferase and GFP in an orthotopic model. Ten million MM1.S LucGFP cells were injected intravenously through the tail vein into 6-8 weeks old female CB17/SCID animals. Intraperitoneal injection of D-luciferin (Regis Technologies, Morton Grove, Ill.) (200 uL per animal at 15 mg/mL), followed by anesthesia with isofluorane and subsequent whole body bioluminescence imaging (BLI) enable monitoring of tumor burden. Bioluminescent signals emitted by the interaction between luciferase expressed by the tumor cells and luciferin were captured by imaging using an IVIS Spectrum CT (Perkin Elmer, MA) and quantified as total flux (photons/sec) using Living Image 4.4 (Caliper Life Sciences, Alameda, Calif.). When the total flux reached an average of 1-3E6 for all animals, the animals were randomized into groups; 1) H7c/N297A/K222R-amino-PEG6-C2-3377, 2) N297Q/K222R-AcLys-Val-Cit-PABC-Aur0101, 3) LCQ05/K222R-AcLys-Val-Cit-PABC-Aur0101, 4) H7c/N297A/K222R-amino-PEG6-C2-0131, 5) N297Q/K222R/LCQ05-AcLys-Val-Cit-PABC-Aur0101, and 6) control conjugate LCQ04/K222R-AcLys-Val-Cit-PABC-Aur0101. A single dose of human anti-BCMA ADCs and control conjugate were administered through bolus tail vein injection. Animals were terminated when they exhibit hindlimb paralysis, an endpoint for MM1.S orthotopic model. FIG. 3 shows that a single dose of human anti-BCMA L3.PY/P6E01 antibody conjugated with 1) H7c/N297A/K222R-amino-PEG6-C2-0131 and 2) H7c/N297A/K222R-amino-PEG6-C2-3377 resulted in tumor regression. A single dose of human anti-BCMA L3.PY/P6E01 antibody conjugated with 1) N297Q/K222R-AcLys-Val-Cit-PABC-Aur0101, 2) LCQ05/K222R-AcLys-Val-Cit-PABC-Aur0101, and 3) N297Q/K222R/LCQ05-AcLys-Val-Cit-PABC-Aur0101 resulted in tumor inhibition.

Accordingly, this study demonstrates that treatment with a BCMA-ADC induces regression and inhibits progression of multiple myeloma.

Figure 1A:
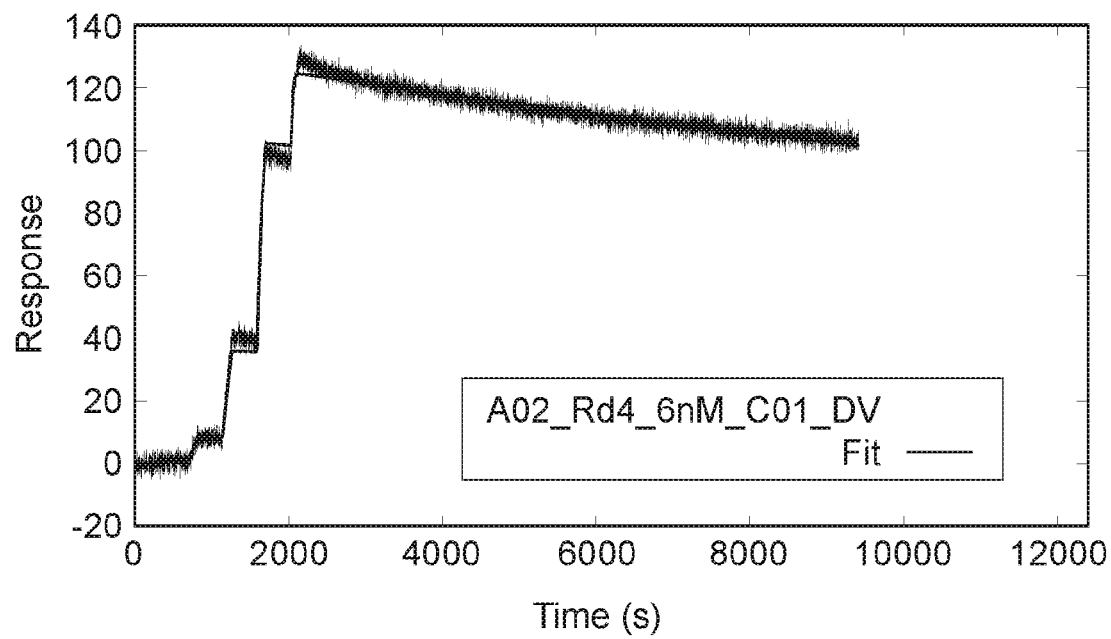
Figure 1B:
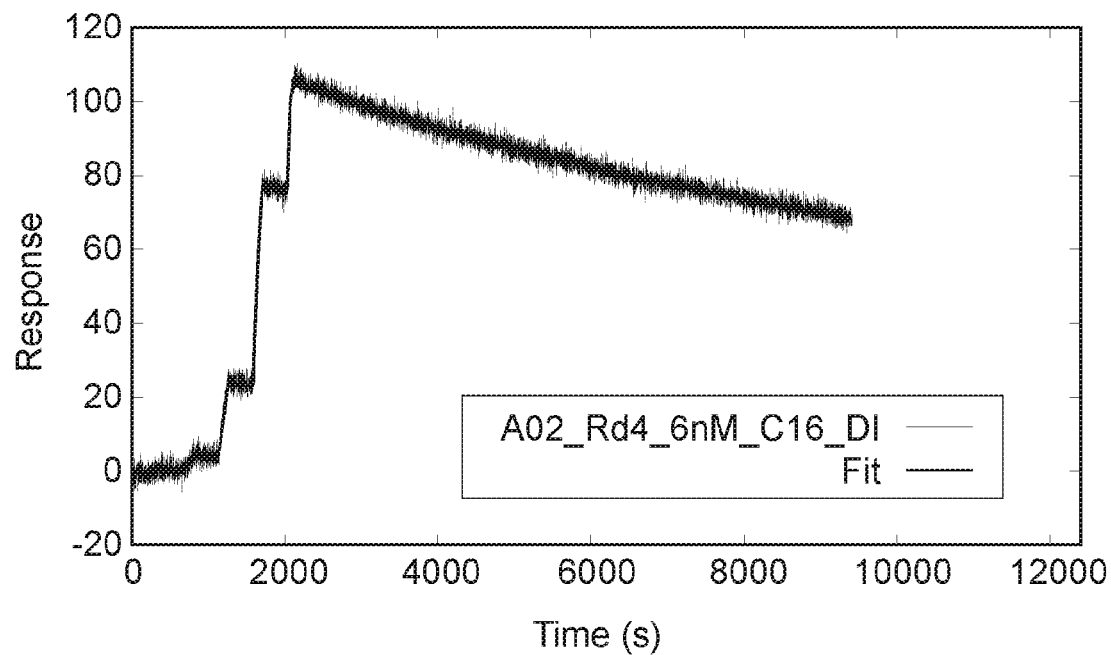
Figure 1C:
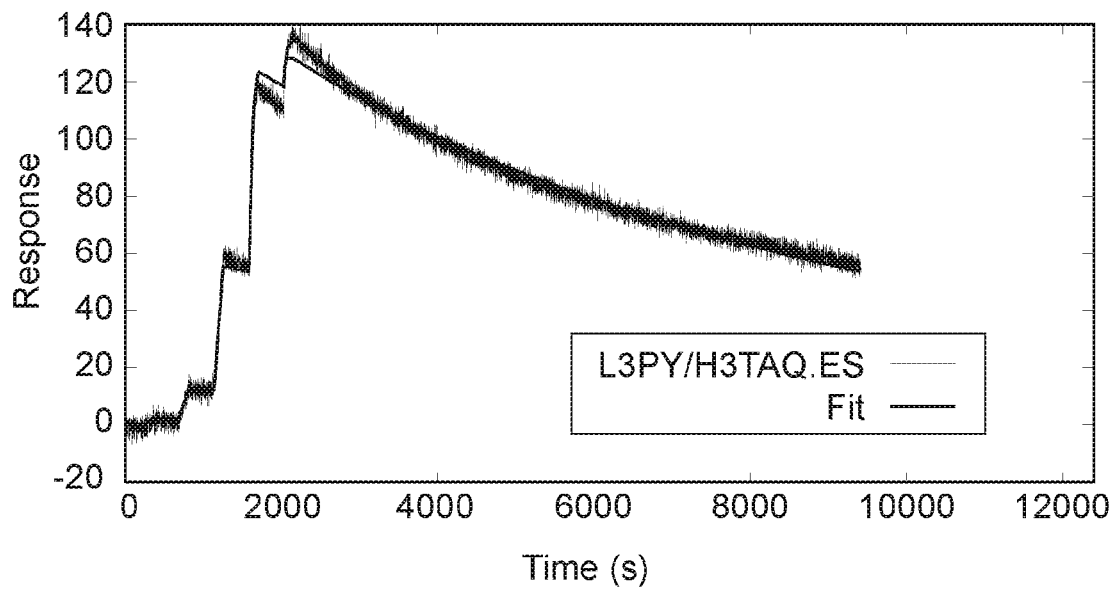
Figure 1D:
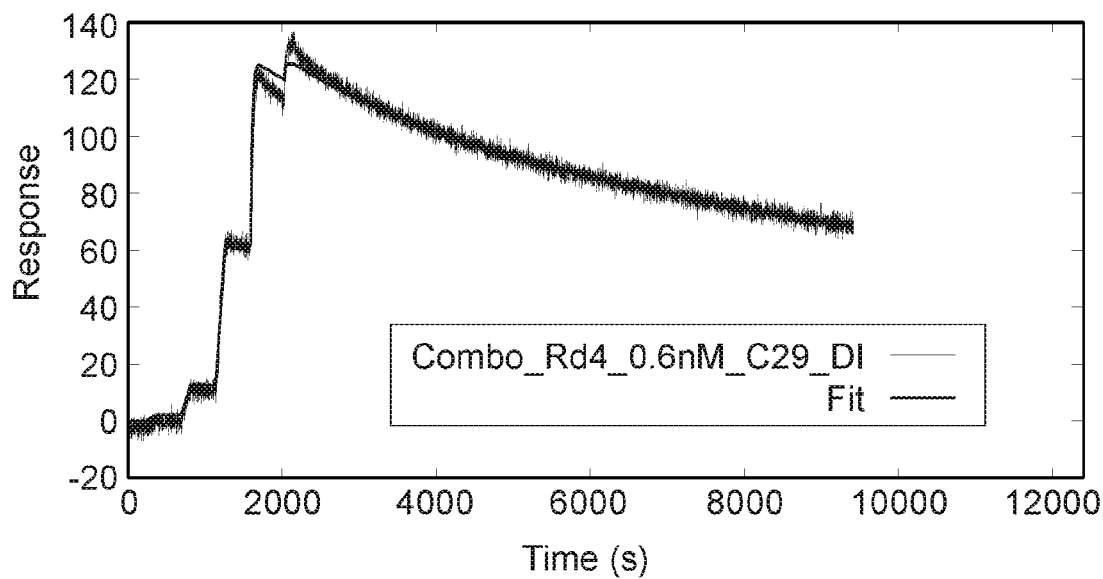
Figure 4:
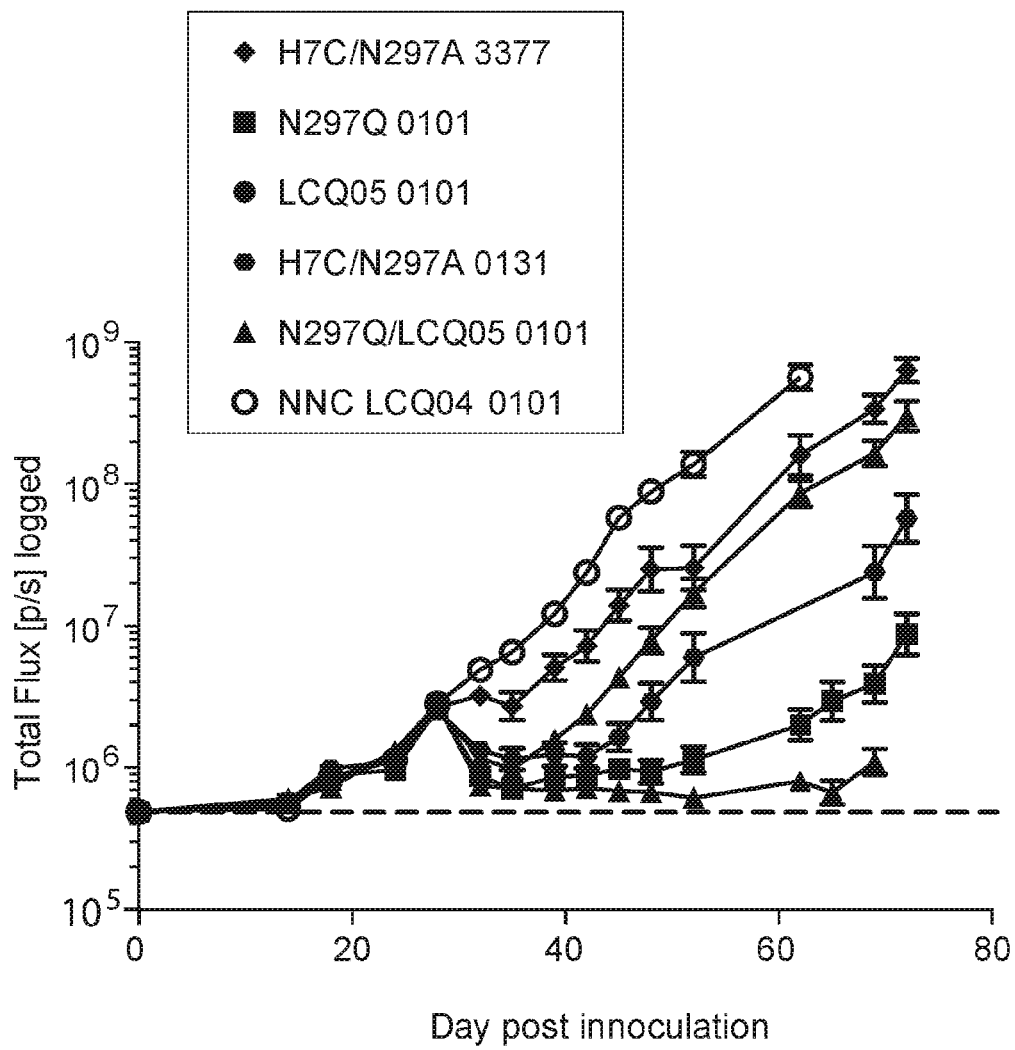

Example 6: Anti-BCMA ADCs Induce Tumor Inhibition in an Orthotopic Multiple Myeloma Model This example also illustrates the in vivo efficacy of the anti-BCMA ADCs in the KMS12BM orthotopic multiple myeloma models In vivo efficacy study of BCMA ADCs was performed with multiple myeloma cell line KMS12BM expressing luciferase and GFP in an orthotopic model. 6-8 weeks old female NSG animals were irradiated with 100 cGy and 24 hours post irradiation, ten million KMS12BM LucGFP cells were injected intravenously through the tail vein. Intraperitoneal injection of D-luciferin (Regis Technologies, Morton Grove, Ill.) (200 uL per animal at 15 mg/mL), followed by anesthesia with isofluorane and subsequent whole body bioluminescence imaging (BLI) enable monitoring of tumor burden. Bioluminescent signals emitted by the interaction between luciferase expressed by the tumor cells and luciferin are captured by imaging using an IVIS Spectrum CT (Perkin Elmer, MA) and quantified as total flux (photons/sec) using Living Image 4.4 (Caliper Life Sciences, Alameda, Calif.). When the total flux reached an average of 5E6 for all animals, the animals were randomized into groups; 1) H7c/N297A/K222R-amino-PEG6-C2-3377, 2) N297Q/K222R-AcLys-Val-Cit-PABC-Aur010, 3) LCQ05/K222R-AcLys-Val-Cit-PABC-Aur0101, 4) H7c/N297A/K222R-amino-PEG6-C2-0131, 5) N297Q/K222R/LCQ05-AcLys-Val-Cit-PABC-Aur0101, and 6) control conjugate LCQ04/K222R-AcLys-Val-Cit-PABC-Aur0101. A single dose of human anti-BCMA ADCs and control conjugate was administered through bolus tail vein injection. Animals were terminated when they lose more than 15% of total body weight, an endpoint for KMS12BM orthotopic models. FIG. 4 shows that a single dose of human anti-BCMA L3.PY/P6E01 antibody conjugated with 1) H7c/N297A/K222R-amino-PEG6-C2-3377, 2) N297Q/K222R-AcLys-Val-Cit-PABC-Aur0101, 3) LCQ05/K222R-AcLys-Val-Cit-PABC-Aur0101, 4) H7c/N297A/K222R-amino-PEG6-C2-0131, and 5) N297Q/K222R/LCQ05-AcLys-Val-Cit-PABC-Aur0101 resulted in tumor inhibition.

Accordingly, this study further demonstrates that treatment with a BCMA-ADC induces regression and inhibits progression of multiple myeloma.

Example 7: Dose Response Curve of Anti-BCMA ADC in MM1S Orthotopic Model

Figure 5:
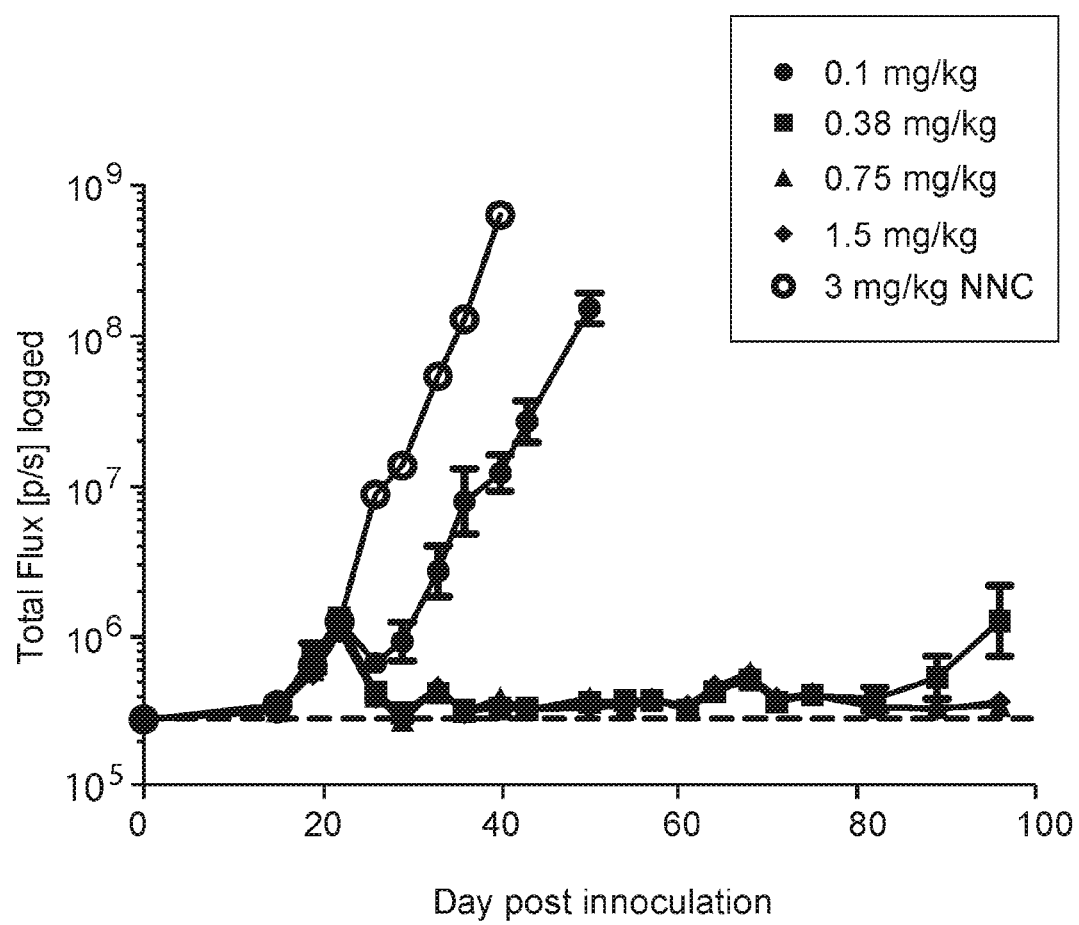
Figure 6A:
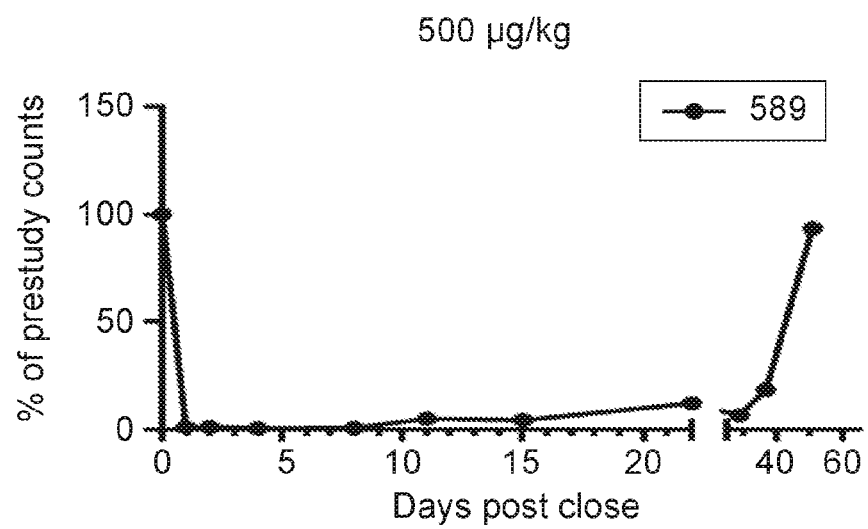
FIG. 6A-FIG. 6F depict the in vivo efficacy of an anti-CD3/anti-CD20 bispecific antibody in cynomolgus monkeys. B cell depletion following a single dose of bispecific antibody is shown as a percentage of prestudy counts.
Figure 6B:
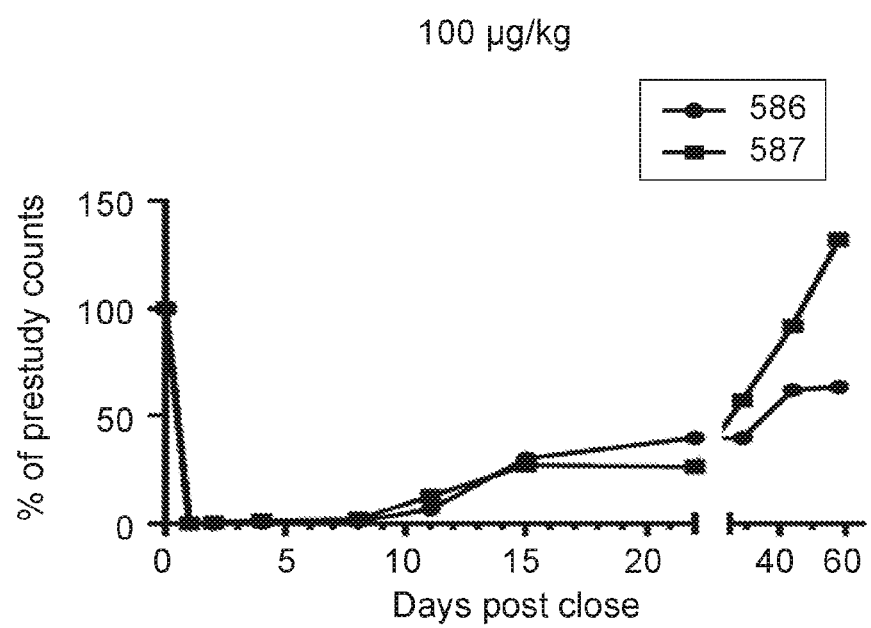
Figure 6C:
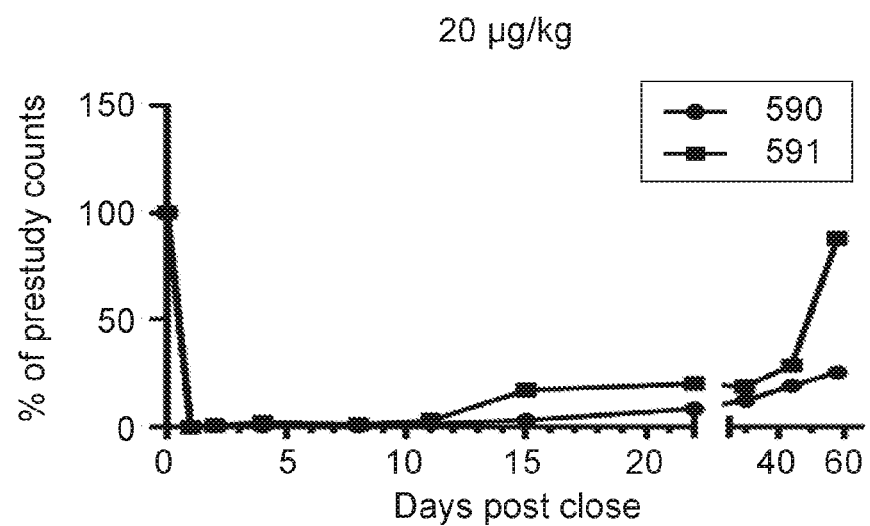
Figure 6D:
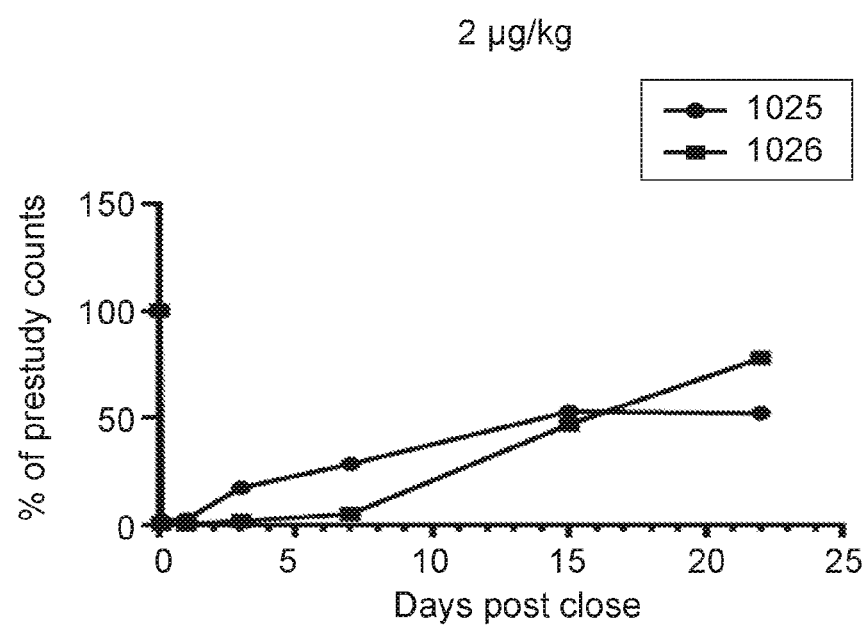
Figure 6E:
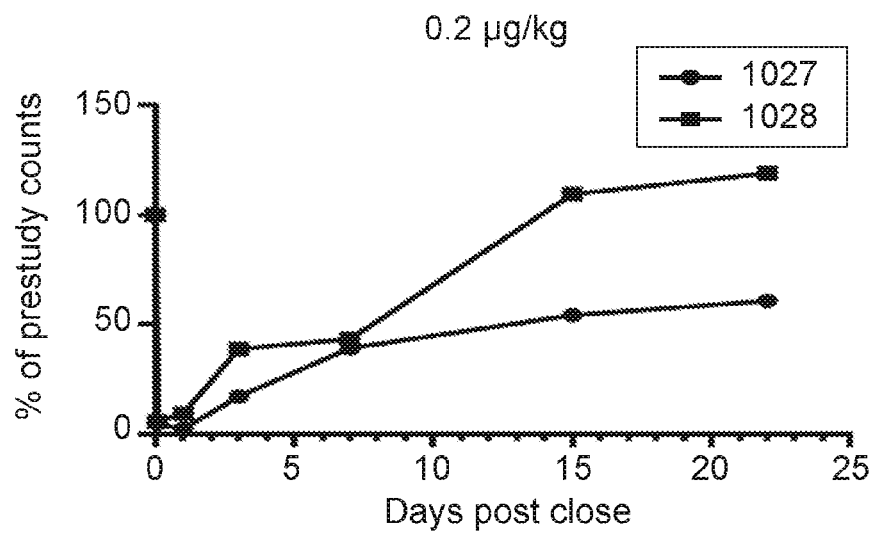
Figure 6F:
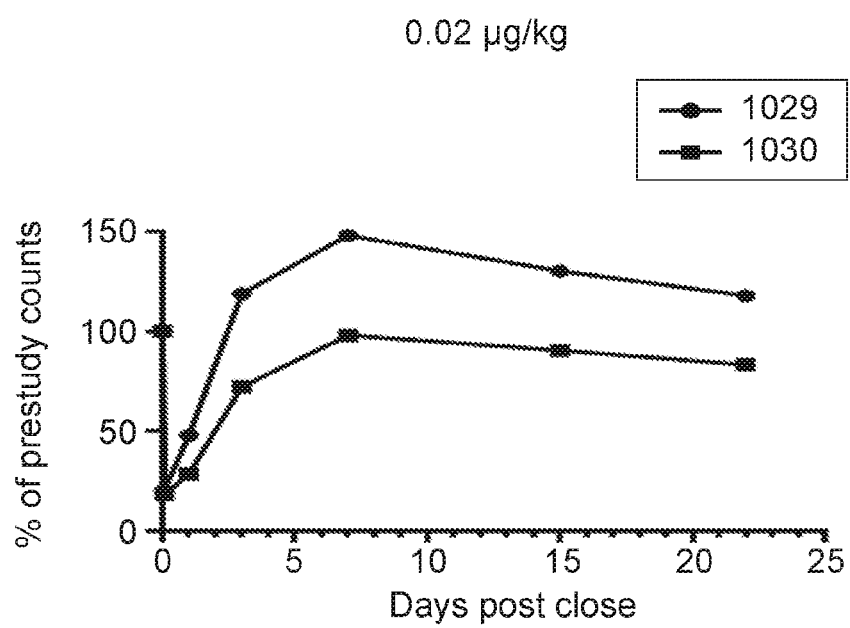
Figure 7A:
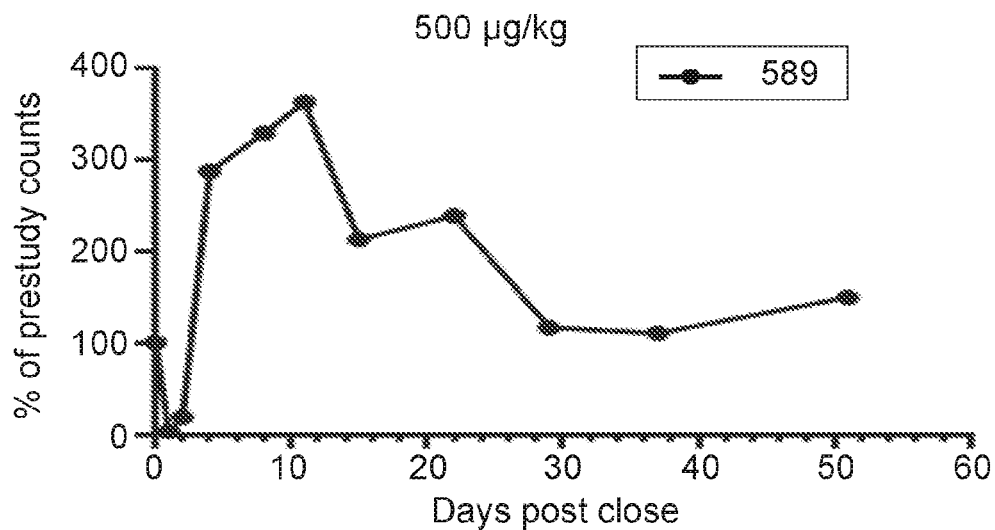
FIG. 7A-FIG. 7F depict the in vivo efficacy of an anti-CD3/anti-CD20 bispecific antibody in cynomolgus monkeys. CD8+ T cell kinetics were tracked following a single dose of bispecific antibody.
Figure 7B:
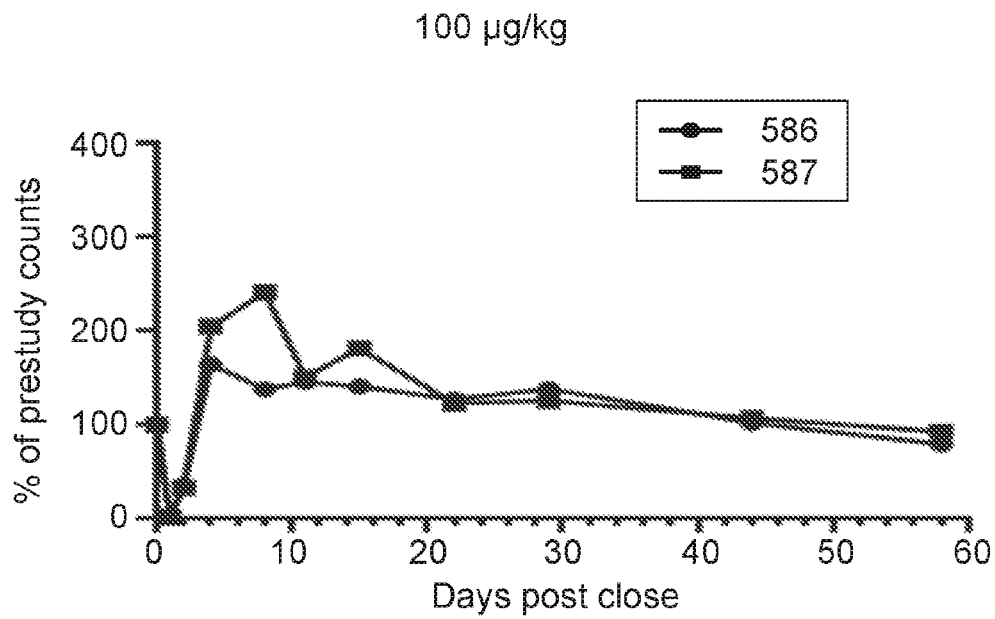
Figure 7C:
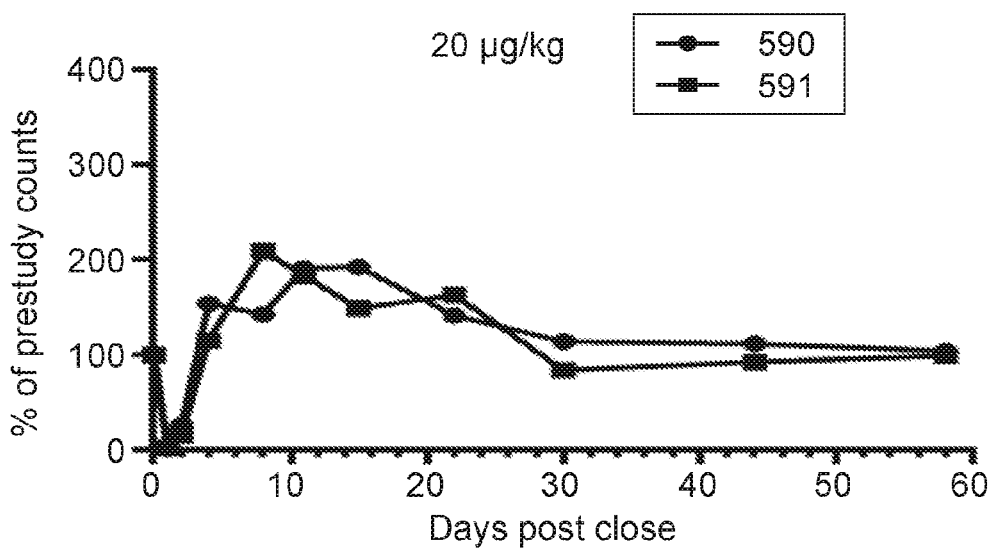
Figure 7D:
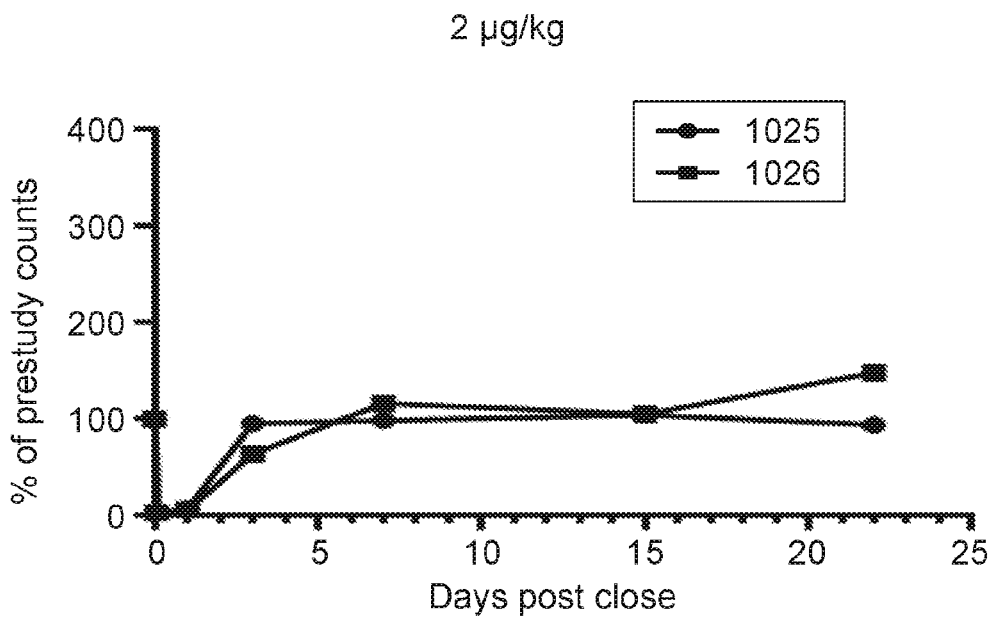
Figure 7E:
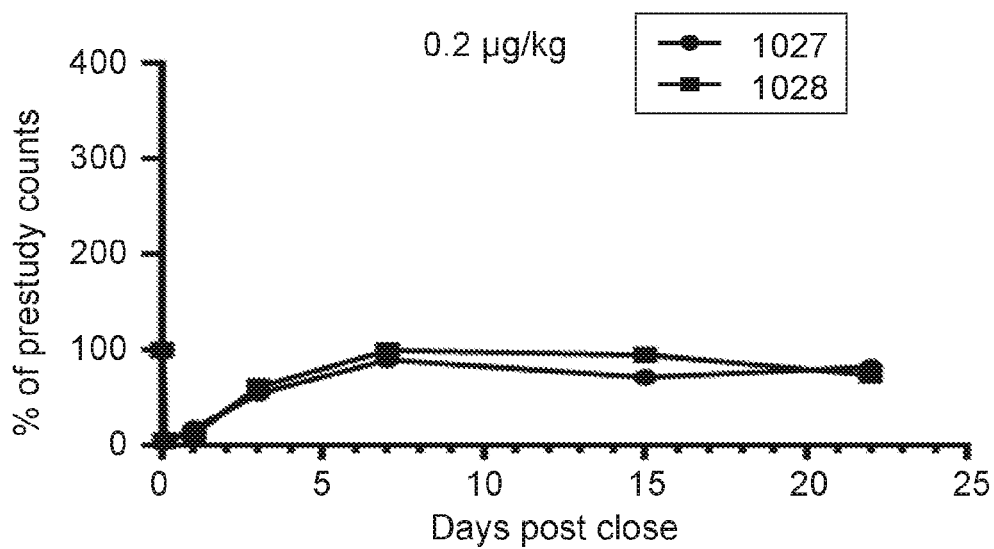
Figure 7F:
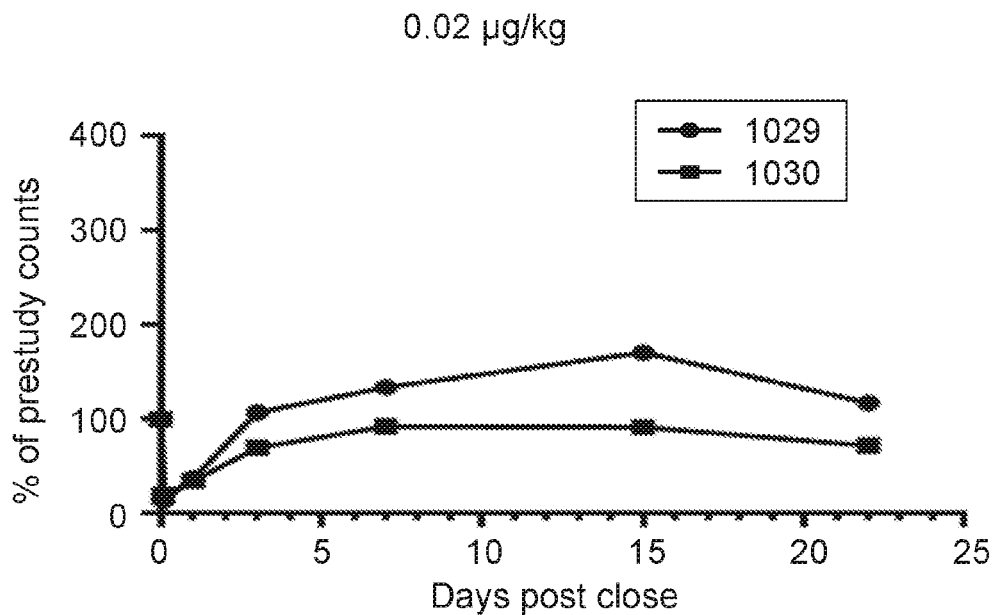

This example further illustrates the in vivo efficacy of the anti-BCMA ADCs in the MM1S orthotopic multiple myeloma models In vivo efficacy study of BCMA ADCs was performed with multiple myeloma cell line MM1.S expressing luciferase and GFP in an orthotopic model. Ten million MM1.S LucGFP cells were injected intravenously through the tail vein into 6-8 weeks old female CB17/SCID animals. Intraperitoneal injection of D-luciferin (Regis Technologies, Morton Grove, Ill.) (200 uL per animal at 15 mg/mL), followed by anesthesia with isofluorane and subsequent whole body bioluminescence imaging (BLI) enable monitoring of tumor burden. Bioluminescent signals emitted by the interaction between luciferase expressed by the tumor cells and luciferin were captured by imaging using an IVIS Spectrum CT (Perkin Elmer, MA) and quantified as total flux (photons/sec) using Living Image 4.4 (Caliper Life Sciences, Alameda, Calif.). When the total flux reached an average of 1.2E6 for all animals, the animals were randomized into groups; 1) 0.1 mg/kg H7c/N297A/K222R-amino-PEG6-C2-0131, 2) 0.38 mg/kg H7c/N297A/K222R-amino-PEG6-C2-0131, 3) 0.75 mg/kg H7c/N297A/K222-amino-PEG6-C2-0131, 4) 1.5 mg/kg H7c/N297A/K222R-amino-PEG6-C2-0131, and 5) 3 mg/kg control conjugate N297Q/K222R-AcLys-VC-0101. A single dose of human anti-BCMA ADCs and control conjugate were administered through bolus tail vein injection. Animals were terminated when they exhibit hindlimb paralysis, an endpoint for MM1.S orthotopic model. FIG. 5 shows that a single dose of human anti-BCMA COMBO_Rd4_0.6nM_C29 antibody conjugated with groups 1)-4) above resulted in tumor regression starting at 0.1 mg/kg and tumor inhibition up to 100 days starting at 0.75 mg/kg.

Accordingly, this study demonstrates that treatment with a BCMA-ADC induces tumor regression and tumor inhibition in multiple myeloma.

Example 8: Generation and Purification of Heterodimeric Antibodies

This example describes the generation and purification of the heterodimeric antibodies of the present application.

The variable region of the human specific anti-CD3 antibody was cloned into a human IgG1 or IgG2ΔA containing the following mutations 221R, 228R, and K409R; or 223R, 225R, 228R, and K409R, respectively, and referred as hIgG1 RRR or IgG2ΔA-RRRR.

The variable region of the anti-target antibody was cloned into a human IgG1 or IgG2ΔA containing the following mutations 221E, 228E, L368E or 223E, 225E, 228E and L368E, respectively, and referred as hIgG1EEE or hIgG2ΔA-EEEE.

Heterodimers were prepared by incubation of the anti-CD3 IgG1 or IgG2ΔA having hIgG1 RRR or IgG2ΔA-RRRR mutations with an anti-target antibody having hIgG1 EEE or hIgG2ΔA-EEEE mutations in PBS with 1 mM or 2 mM GSH for 24 hrs at 37° C. as described in International Patent Application No. PCT/US2011/036419 (WO2011/143545). The heterodimer was purified by ion exchange chromatography, as described below.

All the heterodimers were purified by ion exchange chromatography. Briefly, analytical ion exchange separation of the Fc-hetero and Fc-homodimers was carried out on Agilent 1100 quaternary pump LC system (Agilent Inc, Santa Clara, Calif., USA) equipped with weak cation exchange DIONEX Propac WCX-10G (4×50 mm) column. Proteins were injected in 5% buffer A (20 mM MES pH 5.4) and eluted in a gradient from 25% to 75% buffer B (20 mM MES pH 5.4 and 500 mM NaCl) over a 20 minute period with 1 ml/min flow rate. Larger scale Fc-heterodimer purification was performed on an Akta Explorer (GE) equipped with weak cation exchange DIONEX Propac WCX-10G (4×250 mm) column. Proteins were injected in 5% buffer A (20 mM MES pH 5.4) and eluted in a gradient from 15% to 75% buffer B (20 mM MES pH 5.4 and 500 mM NaCl) over a 60 minute period with 1 ml/m in flow rate.

Example 9: Determination of Kinetics and Affinity of hCD3/Human IgG Interactions at 25° C. and/or 37° C.

This example determines the kinetics and affinity of various anti-CD3 antibodies at 25° C. and 37° C.

All experiments were performed on a Bio-Rad Proteon XPR36 surface Plasmon resonance biosensor (Bio-Rad, Hercules, Calif.). An array of anti-CD3 antibodies was prepared using an amine-coupling method on a Bio-Rad GLC Sensor Chip similar to that described in Abdiche, et al., Anal. Biochem. 411, 139-151 (2011). The analysis temperature for the immobilization was 25° C. and the running buffer was HBS-T+(10 mM HEPES, 150 mM NaCl, 0.05% Tween-20, pH 7.4). Channels were activated in the analyte (horizontal) direction by injecting a mixture of 1 mM ECD and 0.25 mM NHS for 3 minutes at a flow rate of 30 µL/min. IgGs were immobilized on the activated spots by injecting them in the ligand (vertical) direction at 20 µg/mL in 10 mM Acetate pH 4.5 buffer for 1.5 minutes at 30 µg/m L. The activated surfaces were blocked by injecting 1M ethanolamine, pH 8.5 in the analyte direction for 3 minutes at 30 µL/m in.

The analysis temperature for the hCD3 binding analysis was 37° C. or 25° C. in a running buffer of HBS-T+, supplemented with 1 mg/mL BSA. A kinetic titration method was employed for the interaction analysis as described in Abdiche, et al. The hCD3 (human CD3) analyte was injected in the analyte direction using a series of injections from low to high concentration. The concentrations used were 0.08 nM, 0.4 nM, 2 nM, 10 nM and 50 nM (a 5-membered series, with a 5-fold dilution factor and top concentration of 50 nM). The association time for a given analyte dilution was two minutes. Immediately after the 50 nM hCD3 injection, dissociation was monitored for 2 hours. Prior to the hCD3 analyte injections, buffer was injected 5 times using the same association and dissociation times at the hCD3 analyte cycles to prepare a buffer blank sensorgram for double-referencing purposes (double referencing as described in Myszka, J. Mol. Recognit. 12, 279-284 (1999).

The sensorgrams were double-referenced and fit to a 1:1 Langmuir with mass transport kinetic titration model in BIAevaluation Software version 4.1.1 (GE Lifesciences, Piscataway, N.J.). The kinetics and affinity parameters for various anti-CD3 antibodies of the present invention are shown in Table 9.

Example 10: Flow Cytometry of Human Anti-CD3 Bispecific Antibodies on B Cells and CD8+ T Cells This example demonstrates the efficacy of the anti-CD3-anti-CD20 bispecific antibodies in CD20+ cells.

Cynomolgus monkey studies were conducted at Charles River Laboratories, Preclinical Services Nevada in accordance with the Institutional Animal Care and Use Committee. Animals (n=2) were dosed via intravenous bolus injection with the bispecific anti-CD20/h2B4 antibody at doses of 500 ug/kg, 100 ug/kg, 20 ug/kg, 2 ug/kg, 0.2 ug/kg or 0.02 ug/kg. Animals were observed twice daily and at each blood collection time point. Blood for flow cytometry and cytokine analysis was collected into K2EDTA tubes from a peripheral vessel not used for i.v. dosing.

Efficacy was determined by measuring B cells and T cells in peripheral blood by flow cytometry. Whole blood was collected at the time points indicated and kept at 4° C. until analysis. Erythrocytes were lysed with ACK buffer (Gibco) for 5 minutes at room temperature and white blood cells were pelleted by centrifugation. Cells were stained for 1 hr. at 4° C. with a cocktail containing fluorescently labeled antibodies recognizing cyno CD19 (Beckman Coulter), CD45, CD4, CD8, Ki67 (BD Biosciences) in PBS+2% FBS. For Ki67 analysis, cells were first stained with CD4 and CD8, then fix/permeabilized with BD cyotfix/cytoperm kit (BD Biosciences) according to manufacturer's instructions prior to intracellular staining for Ki67. Acquisition of cells on a BD LSRII flow cytometer was carried out immediately after staining.

The resulting B cell count was graphed as a percentage of the pre-study B cell count in FIGS. 6A-6F. Prolonged B cell depletion following a single dose was achieved with doses as low as 2 ug/kg. B cell depletion was seen at all doses. The duration of the depletion effect was dose dependent.

The resulting CD8+ T cell count was graphed as percentage of the pre-study CD8+ T cell count in FIGS. 7A-7F. After an initial relocalization, T cell levels were restored to baseline levels or above for the duration of the study.

Example 11: Flow Cytometry of Human Anti-CD3 Bispecific Antibodies on CD8+ T Cells This example demonstrates the efficacy of the monovalent anti-CD3 antibody on T cell kinetics and activation.

TABLE 9

| Antibody | ka (1/Ms) huCD3ed @25° C. | kd (1/s) huCD3ed @25° C. | T½ (min) to huCD3ed @25° C. | KD (nM) to huCD3ed @25° C. |
|---|---|---|---|---|
| H2B4 | 3.7E+05 | 2.0E−03 | 5.8 | 5.3 |

| Antibody | ka (1/Ms) huCD3ed @37° C. | kd (1/s) huCD3ed @37° C. | T½ (min) to huCD3ed @37° C. | KD (nM) to huCD3ed @37° C. |
|---|---|---|---|---|
| H2B4 | 4.37E+05 | 0.01369 | 0.84 | 3.14E−08 |
| h2B4-VH-wt VL_TK | 3.80E+05 | 1.40E−02 | 0.83 | 3.80E−08 |
| h2B4-VH-Hnps VL_TK | 3.90E+05 | 1.60E−02 | 0.72 | 4.10E−08 |
| h2B4-VH-yads VL_TK | 2.40E+05 | 2.10E−02 | 0.79 | 8.60E−08 |
| h2B4-VH-yaes VL_TK | 2.30E+05 | 2.30E−02 | 0.50 | 1.00E−07 |
| h2B4-VH-yaps VL_TK | 2.50E+05 | 2.30E−02 | 0.50 | 9.20E−08 |

| Antibody | ka (1/Ms) cyCD3ed @ 25° C. | kd (1/s) cyCD3ed @25° C. | T½ (min) to cyCD3ed @25° C. | KD (nM) to cyCD3ed @ 25° C. |
|---|---|---|---|---|
| H2B4 | 3.9E+05 | 1.5E−03 | 7.7 | 3.8 |

Cynomolgus monkey studies were conducted and efficacy was determined by measuring T cells in peripheral blood by flow cytometry as described in Example 3. Cynomolgus monkeys (n=2) were dosed weekly, i.v., at 0.2 ug/kg with anti-CD20/h2B4 or NNC (non-specific antibody)/h2B4. In contrast to the CD20 targeted bispecific antibody, the NNC/h2B4 has little to no effect on CD8+ T cell kinetics in the blood as measured by flow cytometry. Ki67 was used as a marker for T cell activation.

Figure 8A:
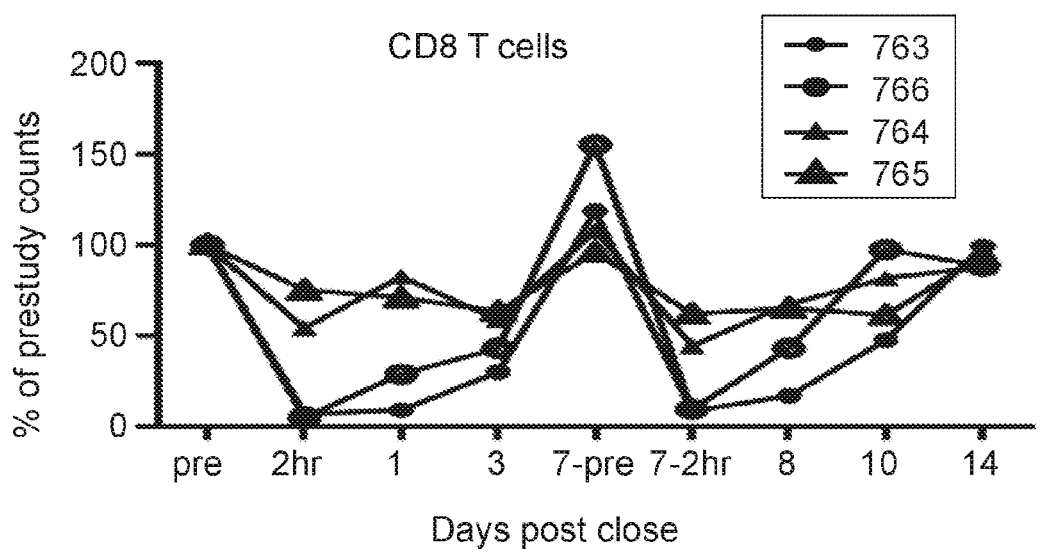
FIG. 8A and FIG. 8B depict the in vivo efficacy of an anti-CD3/anti-CD20 bispecific antibody in cynomolgus monkeys. The effect of the monovalent CD3 antibody on T cell kinetics and proliferation was analyzed.
Figure 8B:
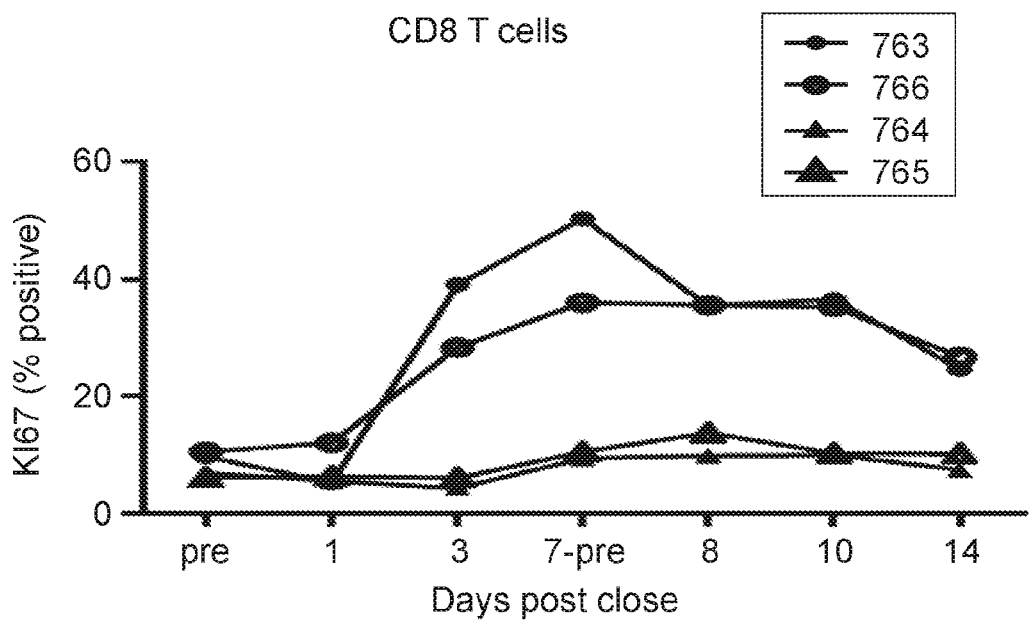
Figure 9A:
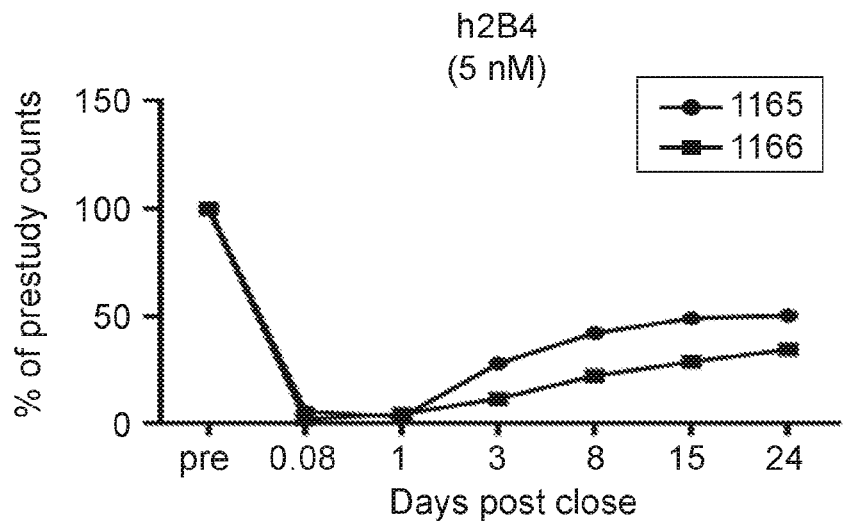
FIG. 9A-FIG. 9D depict the in vivo efficacy of an anti-CD3/anti-CD20 bispecific antibody in cynomolgus monkeys. The effect of anti-CD3 arm affinity on B cell depletion was analyzed.
Figure 9B:
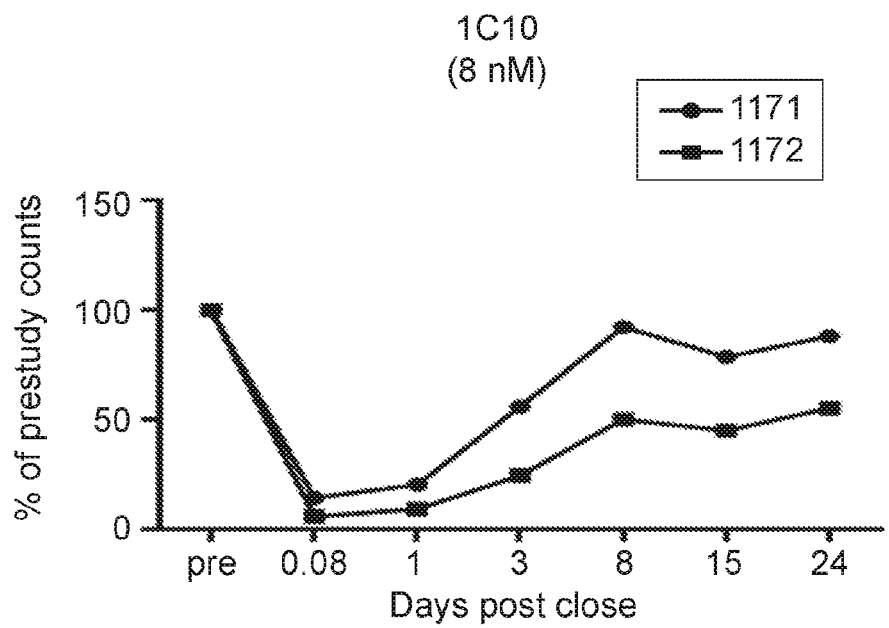
Figure 9C:
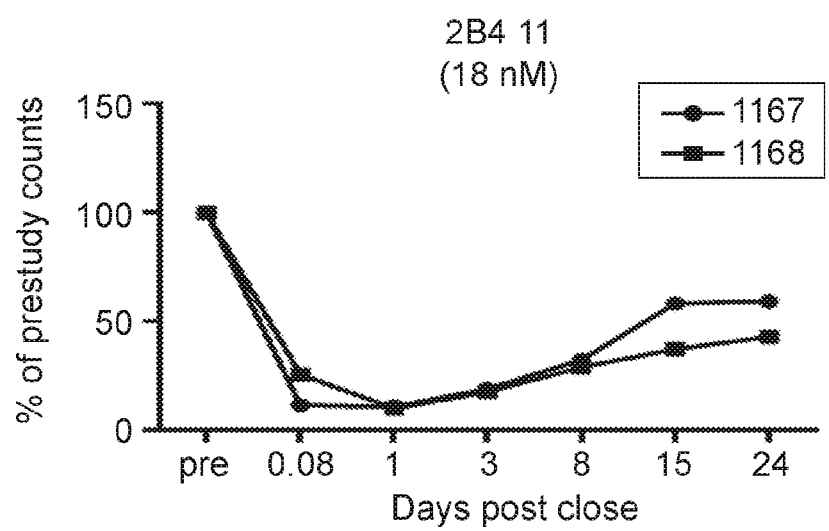
Figure 9D:
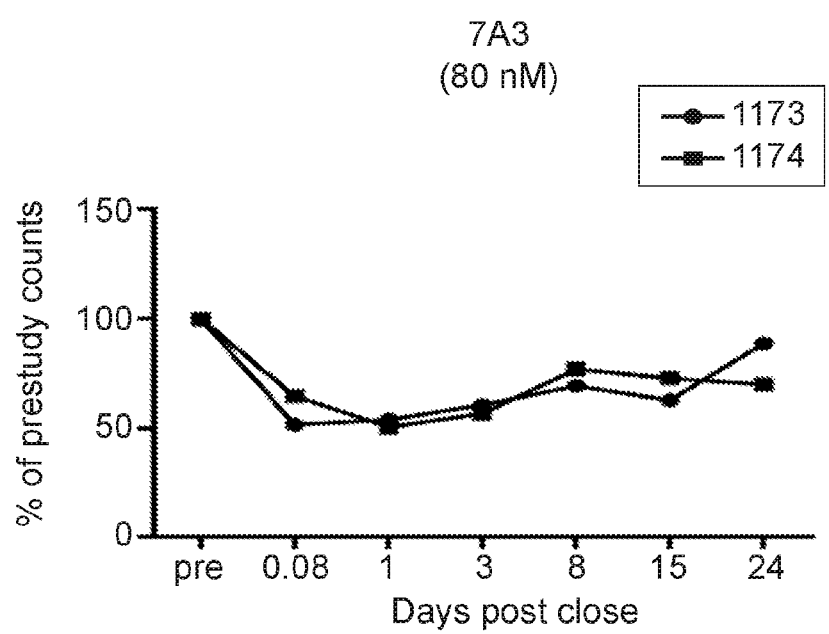

The resulting T cell count was graphed as percentage of the pre-study CD8+ T cell count in FIGS. 8A and 8B. In cynomolgus monkeys dosed with the CD20/h2B4 bispecific antibody, Ki67+ T cells increased and peaked between day 3 and day 7 post dose, indicating T cell activation. However, in cynomolgus monkeys dosed with NNC/h2B4, there was no increase in Ki67+ T cells.

Example 12: Flow Cytometry of Human Anti-CD3 Bispecific Antibodies on B Cells This example demonstrates the effect of anti-CD3 arm affinity on B cell depletion.

Cynomolgus monkey studies were conducted and efficacy was determined by measuring T cells in peripheral blood by flow cytometry as described in Example 10. Bispecific antibodies were made with an anti-CD20 arm paired with 4 anti-CD3 antibody arms with different affinities. Following a single, i.v. dose at 0.2 ug/kg, efficacy was determined by measuring B cells in peripheral blood by flow cytometry.

In FIGS. 9A-9D, the resulting B cell count was graphed as a percentage of the pre-study B cell count. Efficacy of B cell depletion correlates to anti-CD3 arm affinity.

Example 13: In Vitro Study of the Bispecific Antibody on T-Cell Mediated Killing of BCMA Positive Cells This example illustrates the in vitro cytotoxicity of the Anti-BCMA/CD3 hIgG2ΔA Bispecific in BCMA Positive Cells.

Human anti-BCMA (P5A2, A02_Rd4_0.6nM_C01, A02_Rd4_6nM_C16, P5C1, C01_Rd4_6nM_C12, COMBO_Rd4_0.6nM_C22, Combo_Rd4_0.6nM_C29, L3PY/H3TAQ and A02_Rd4_6nM_C01) and human anti-CD3 (H2B4) antibodies were expressed as human IgG2dA engineered with EEEE for bispecific exchange as described in Example 8.

CD3+ T cells from PBMC were negatively selected using Pan T Cell Isolation kit, human (Miltenyi, San Diego Calif.). Target expressing (KMS12PE, L363 and Molp8) cells and CD3+ T-cells were seeded on clear U-bottom plates at 20000 and 100000 cells/well respectively. Cells were treated with 10-fold serially diluted bispecific antibody in triplicates. Cell death was determined by CytoTox 96® Non-Radioactive Cytotoxicity Assay (Promega, Madison Wis.) 20 hours after treatment. Cell cytotoxicity was determined as percentage of untreated effector plus target control wells. EC50 was calculated by Prism software. Table 10 shows that all human anti-BCMA_H2B4 bispecific antibodies exert cell killing activity in BCMA expressing cells.

TABLE 10

| Anti-BCMA bispecific | KMS12PE (BCMA+++) | KMS12BM (BCMA+) | MOLP8 (MOLP8+) |
|---|---|---|---|
| P5A2 | 0.371 | 1.509 | 5.231 |
| A02_Rd4_0.6 nM_C01 | 0.073 | 0.078 | 0.550 |
| A02_Rd4_6 nM_C16 | 0.186 | 0.052 | 0.315 |
| P5C1 | 0.581 | 4.117 | N/A |
| C01_Rd4_6 nM_C12 | 0.189 | 0.415 | 0.850 |
| COMBO_Rd4_0.6 nM_C22 | 0.115 | 0.049 | 0.065 |
| Combo_Rd4_0.6 nM_C29 | 0.175 | 0.049 | 0.201 |
| L3PY/H3TAQ | 0.070 | 0.055 | 0.337 |
| A02_Rd4_6 nM_C01 | UND | 0.057 | 0.060 |

UND is undetermined;
N/A is EC50 could not be determined.

Example 14: In Vitro Characterization of the Mouse Hybridoma Cloned Anti-CD3 Antibody This example illustrates the in vitro T cell activation/proliferation of the anti-CD3 cloned from mouse hybridoma in human/cynomolgus PBMC cells for antibody screening.

Human anti-CD3 antibodies were cloned from immunized mouse, expressed as mouse IgG1, and purified by Protein A affinity beads. Human/Cynomolgus peripheral blood mononuclear cells (hu/cyPBMC) were prepared by Ficoll (Density: 1.083 g/mL, GE) density gradient centrifugation from blood filters obtained from local blood banks. Erythrocytes were removed by incubating in LCK buffer (155 mM NH4Cl, 10 mM KHCO3, 100 mM EDTA; Gibco) for 3 minutes at room temperature. Cells were centrifuged for 5 min at 600 g. The supernatant containing the lysed erythrocytes was discarded, and the PBMC were washed twice in 50 ml 1×PBS/1% BSA/1 mM EDTA. The pelleted cells were adjusted to $10^7$ cells per ml in culture media, X-VIVO-15, serum free media (Lonza), and the PBMC were seeded as $10^6$ (100 ul) per-well to round bottom 96 well tissue culture plates. Selected Abs are 10× serial diluted from 1000 ng to 1 ng per mL for mixing with human PBMC and 5× serial diluted from 5000 ng to 200 ng per mL for mixing with cynomolgus PBMC. For analysis of PBMC T cell proliferation by $^3$H-thymidine incorporation, 2 day cultures were performed in triplicate. During the final 16 h of culture $^3$H-thymidine (0.5 mCi/well) was added, and incorporation was measured. Cells are harvested and lysed, DNA is captured onto glass-fiber filter. Radioactivity (cpm) as measure for proliferation by counting on a scintillation beta-counter.

Figure 10A:
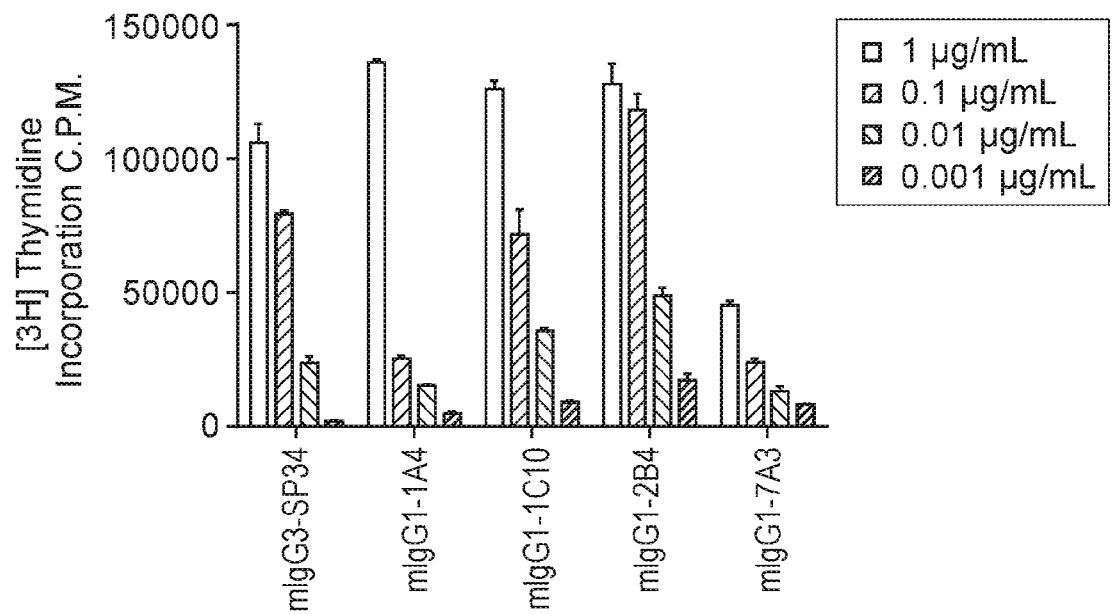
FIGS. 10A and 10B show that the selected anti-CD3 antibodies had Thymidine incorporation reading on human and cynomolgus PBMC.
Figure 10B:
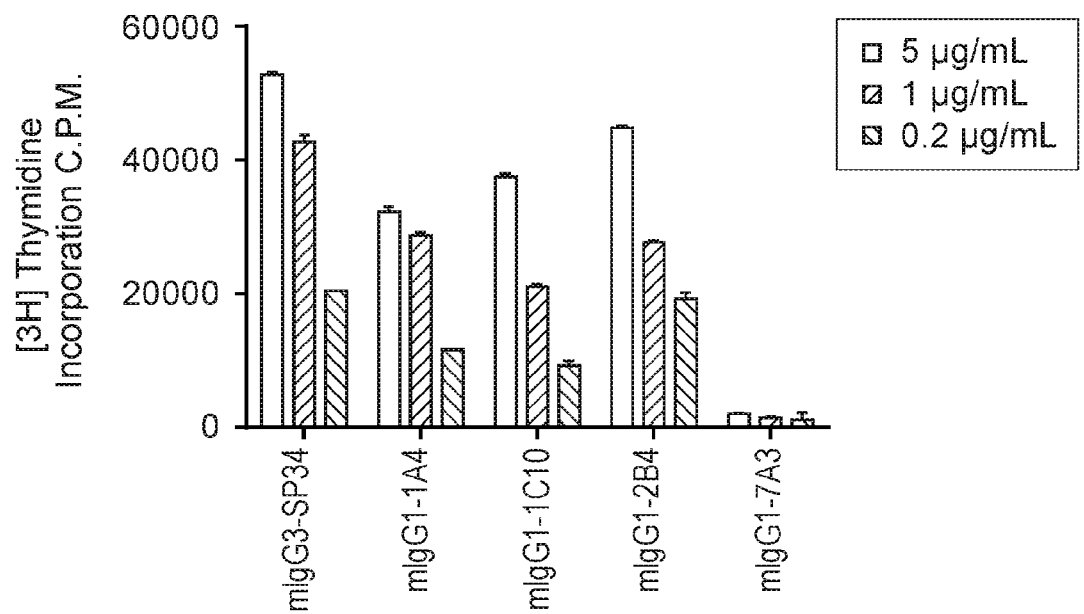

FIGS. 10A and 10B show that the selected anti-CD3 1A4, 1C10, 2B4, and 7A3 antibodies had Thymidine incorporation reading on human and cynomolgus PBMC (peripheral blood mononuclear cells). Table 11 shows their KDs by Biacore measurement. In vitro characterization shows anti-CD3 1C10 and 2B4 antibodies are similar to the positive control SP34 anti-CD3 antibody (BD Biosciences)

TABLE 11 anti-xCD3e ab/bsc_hCD3ed kinetic results for data fitted from 80 nM-0.64 nM

| Ligand | ka | kd | $t_{1/2}$ (min) | KD (nM) |
|---|---|---|---|---|
| UCHT1 (+) | 1.80E+05 | <8.55E−04 | >13.5 | <4.74 |
| 2B4 | 3.74E+05 | 2.74E−03 | 4.21 | 7.33 |
| 1C10 | 2.96E+05 | 2.37E−03 | 4.88 | 8.00 |
| SP34 (+) | 2.84E+05 | 3.04E−03 | 3.80 | 10.73 |
| 7A3* | | | | 82.70 |
| 1A4* | | | | 99.97 |

Note:
Data is only reported for satisfactory kinetic fits.
(+) = positive controls
*Kinetic determinations are rough estimates because antibody is heterogeneous. Only steady state affinity is measured

Example 15: In Vitro Study of the Bispecific Antibody on T Cell Mediated Killing This example illustrates the in vitro cytotoxicity of the anti-EpCam/CD3 Bispecific in SW480 mixed with healthy donor isolated Pan T cells.

A: Anti-CD Antibodies h2B4-1d, TK, hnpsTK, and yaesTK

Human anti-CD3 (h2B4-1d (or h2B4), h2B4-TK (or h2B4-VH-wt VL_TK), h2B4-hnpsTK (or h2B4-VH-hnps VL_TK), and h2B4-yaesTK (or h2B4-VH-yaes VL_TK)) antibodies and human anti-EpCam antibodies were expressed as human IgG2dA engineered with RRRR or EEEE for bispecific exchange as describe in Example 8.

The SW480 was selected as target cell line for cell killing assay and the effector cells and human T cells were purified from human peripheral blood mononuclear cells (huPBMC). Target and effector cells were seeded in 96-well, round bottom plates in cell culture medium containing 5% fetal bovine serum (FBS). The number of target cells was kept constant at $2 \times 10^4$ cells/well. A 10-fold serial dilution of bispecific antibody, from 3 ug to 3 µg per mL, was added in triplicate to the cells. Total reaction volume was 200 uL. The reactions were incubated for 48 and 72 hours. For the analysis of cytotoxicity, the lactate dehydrogenase (LDH), a stable cytosolic enzyme that was released upon cell lysis, was quantitatively measured by CytoTox 96® Non-Radioactive Cytotoxicity Assay kit (Promega, G1780). The plate was read on a Vmax kinetic microplate reader (Molecular Devices) at 490 nM. Optical density values were corrected for media background and spontaneous lysis of target and effector cells. Specific cytotoxicity was calculated according to the following formula:

[% spec. lysis=490 nM readout of sample−of $E+T$ mixed control)/(490 nM readout of total $T$ lysis−of media control)×100%]

Figure 11A:
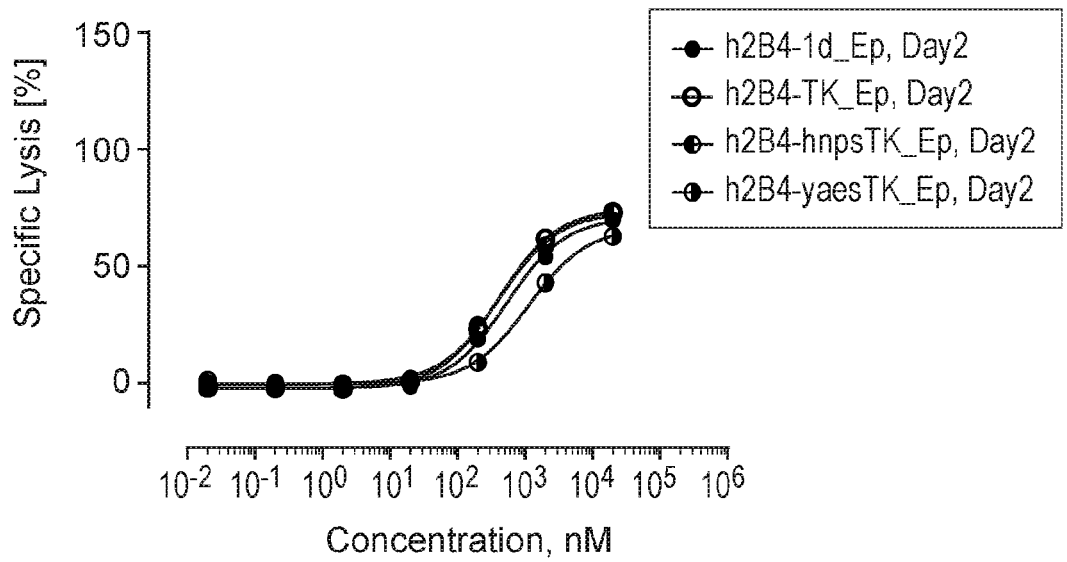
FIG. 11A-FIG. 11D show that all human anti-EpCam_h2B4 bispecific antibodies have cell killing activity on in vitro setting.
Figure 11B:
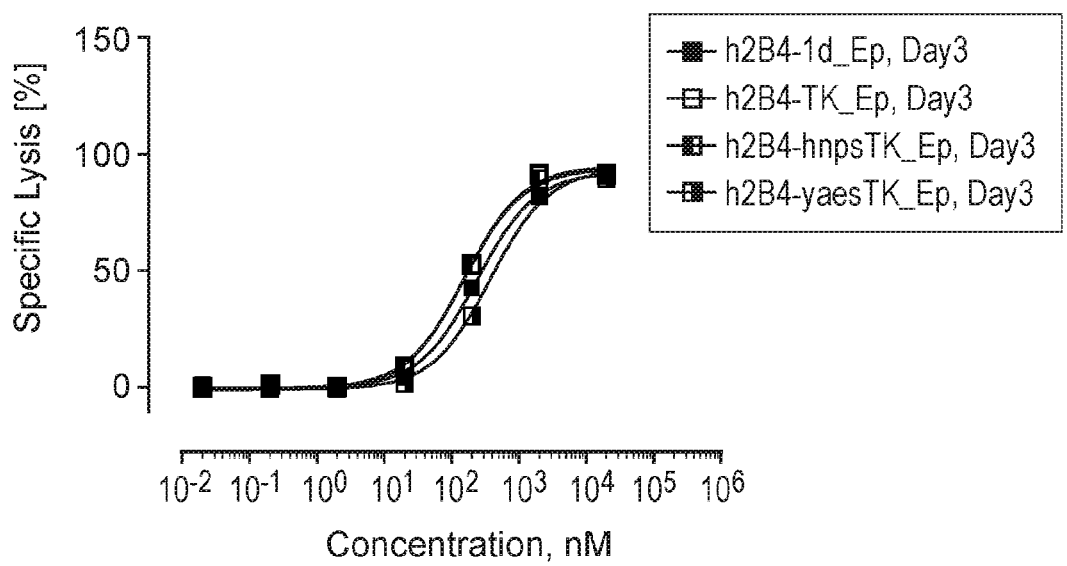

FIGS. 11A and 11B show that all human anti-EpCam_h2B4 bispecific antibodies had cell killing activity on in vitro setting, and antibody mediated T cell activation was monitoring by T cell activation marker. Table 12A shows their EC50. Table 12B shows Biacore KD on the bispecific antibody format.

TABLE 12A

| Day2: | EC50 (nM) |
|---|---|
| h2B4-1d_Ep | 537.1 |
| h2B4-TK_Ep | 405.3 |
| h2B4-hnpsTK_Ep | 424.7 |
| h2B4-yaesTK_Ep | 1126 |

TABLE 12B

Summary Table for anti-CD3 hIgG2dA bispecifics kinetics at 37° C.

| Sample ID-bschIgG2dA | ka (1/Ms) | kd (1/s) | t½ (min) | KD (nM) |
|---|---|---|---|---|
| h2B4-1d_Ep | 5.86E+05 | 2.37E−02 | 0.49 | 40.4 |
| h2B4-TK_Ep | 6.87E+05 | 2.13E−02 | 0.54 | 31.0 |
| h2B4-hnpsTK_Ep | 7.54E+05 | 2.35E−02 | 0.49 | 31.2 |
| h2B4-yaesTK_Ep | 4.74E+05 | 2.58E−02 | 0.45 | 54.4 |

B: Anti-CD Antibodies m25A8, h25A8-B12, and h25A8-B13

Human anti-CD3 h2B4 (h2B4_1 d) and h25A8 (m25A8, h25A8-B12, and h25A8-B13) and human anti-EpCam antibodies were expressed as human IgG2dA engineered with RRRR or EEEE for bispecific exchange as describe in Example 8.

Figure 11C:
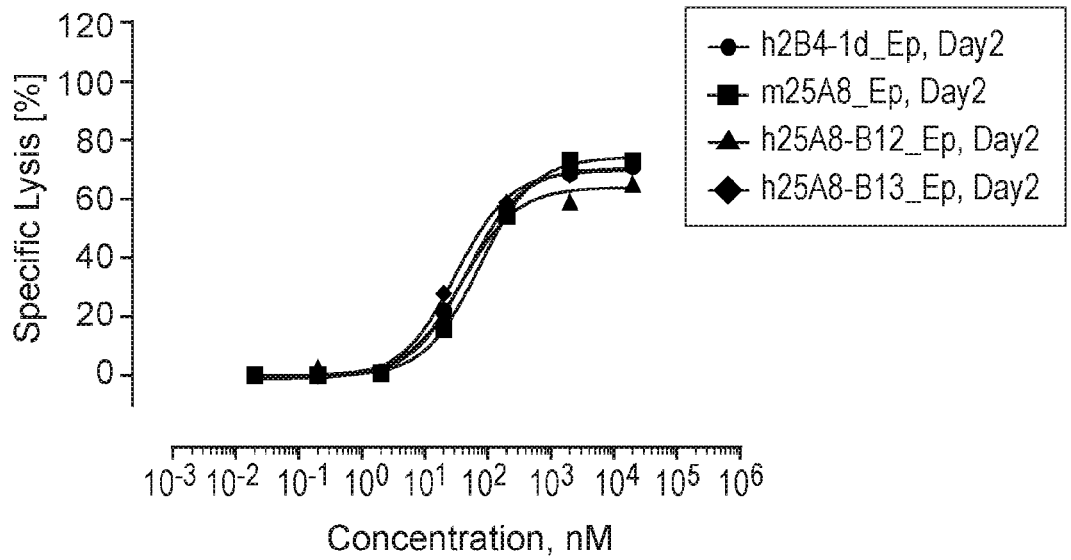
Figure 11D:
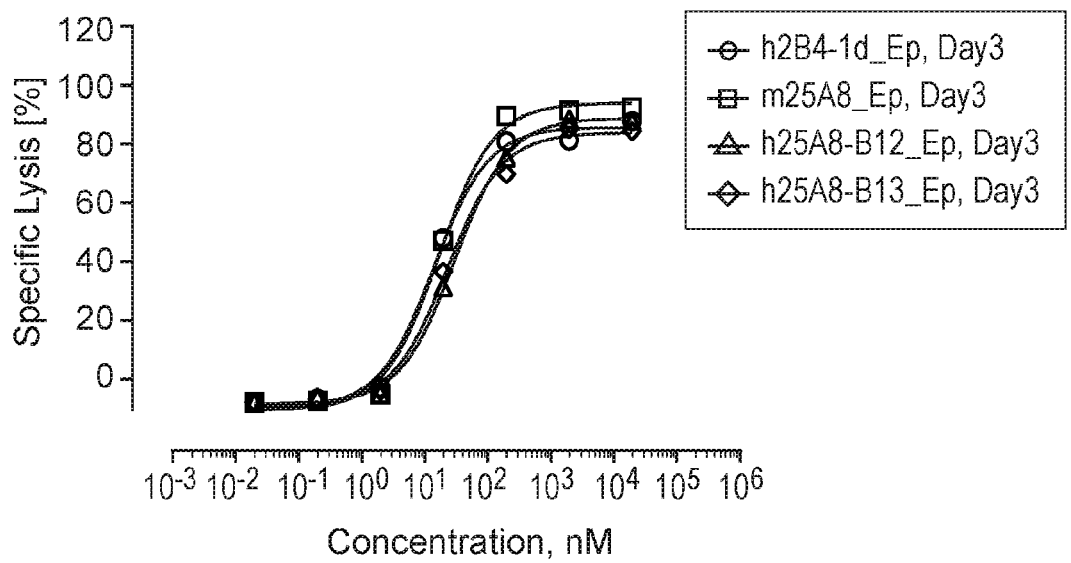

FIGS. 11C and 11D show that all human anti-EpCam_anti-CD3 bispecific antibodies had cell killing activity on in vitro setting, and antibody mediated T cell activation was monitoring by T cell activation marker. Table 12C shows the EC50 of in vitro cell killing. Table 12D shows the Biacore kinetics on the bispecific antibody format at 37° C. Table 12E shows in vitro characterization using SEC-MALS (Size Exclusion Chromatography with Multi-Angle Light Scattering) and DSC (Differential Scanning Calorimety).

TABLE 12C

EC50 of in vitro cell killing

| Day 1: | EC50 (nM) |
|---|---|
| h2B4-1d_Ep | 52.9 |
| m25A8_Ep | 127.6 |
| h25A8-B12_Ep | 99.36 |
| h25A8-B13_Ep | 57.11 |

TABLE 12D

Summary Table for anti-CD3 hIgG2dA bispecifics kinetics at 37° C.

| SampleID-bschIgG2dA | ka (1/Ms) | kd (1/s) | t½ (min) | KD (nM) |
|---|---|---|---|---|
| h25A8-B5_Ep | 1.29E+06 | 5.81E−02 | 0.20 | 45.0 |
| h25A8-B8_Ep | 1.19E+06 | 2.22E−02 | 0.52 | 18.7 |
| h25A8-B12_Ep | 1.15E+06 | 2.41E−02 | 0.48 | 21.0 |
| h25A8-B13_Ep | 1.20E+06 | 2.19E−02 | 0.53 | 18.3 |
| h25A8-C8_Ep | 1.20E+06 | 3.01E−02 | 0.38 | 25.1 |
| h2B4-1d_Ep | 5.86E+05 | 2.37E−02 | 0.49 | 40.4 |

TABLE 12E in vitro characterization

| | SEC-MALS | | DSC | | |
|---|---|---|---|---|---|
| | % Monomer | % Aggregate | Tm1 C (CH2) | Tm2 C (Fab) | Tm3 C (CH3) |
| m28A8 | 99.9 | 0.1 | 66.3 | 67.8 | 76.1 |
| hIgG2dA_h25A8-B12 | 99.2 | 0.8 | 70.91 | 73.06 | 78.31 |
| hIgG2dA_h25A8-B13 | 99.5 | 0.5 | 70.88 | 72.86 | 78.2 |
| hIgG2dA-h2B4TK | 98.8 | 1.4 | 70.2 | 74.5 | 79.4 |

Example 16: In Vitro Study of the Bispecific Antibody on T Cell Mediated Killing of Primary Myeloma Patient Samples This example illustrates the in vitro cytotoxicity of the anti-BCMA/CD3 Bispecific in primary myeloma cells.

Human anti-BCMA (P5A2, A02_Rd4_0.6nM_C01, A02_Rd4_6nM_C16, Combo_Rd4_0.6nM_C29, and P6E01 L3PY/H3TAQ) and human anti-CD3 (h2B4) antibodies were expressed as human IgG2dA engineered with EEEE or RRRR for bispecific exchange as describe in Example 8.

Total bone marrow mononuclear cells from myeloma patients were seeded in clear U-bottom plates at total bone marrow mononuclear cell numbers that resulted in 3000-5000 myeloma cells/well. Cells were treated with 10-fold serially diluted bispecific antibody. Five days after treatment, total viable cells were determined by flow cytometry using antibodies to CD138 and CD38 (Biolegend, CA). Cells were incubated with antibodies at 4° in PBS+0.5% FBS for 30 minutes. Cells were washed and Fixable Viability Dye eFluor 780 (eBioscience, Inc., CA) in PBS was added to the cells for 30 minutes at 4°. Prior to cell acquisition on a BD flow cytometer, cells were washed and CountBright Absolute Counting Beads (Molecular Probes, OR) were added. Percent live cells were determined as live cell count in treated vs untreated wells using counting beads. EC50 was calculated by Prism software.

Table 13A shows that all human anti-BCMA_h2B4 bispecific antibodies have cell killing activity on myeloma patient samples and patient T cells are functional effector cells. Table 13B shows killing of one anti-BCMA bispecific on multiple myeloma patient samples with different effector to target (E:T) ratio.

TABLE 13A

| Anti-BCMA bispecific (Patient MM00146) | EC50 (nM) |
|---|---|
| P6E01 L3PY/H3TAQ | 0.015 |
| P5A2 | 0.946 |
| A02_Rd4_0.6 nM_C01 | 0.064 |
| A02_Rd4_6 nM_C16 | 0.029 |
| NNC_2b41d hIgG2dA | 3.302 |

TABLE 13B

| Patient | Combo_Rd4_0.6 nM_C29 EC50 (nM) | E:T |
|---|---|---|
| MM00146 | 0.035 | 1:1 |
| MM00147 | 0.031 | 2:1 |
| MM00151 | 0.02 | 3:1 |
| MM00152 | 0.289 | 1:2 |

Example 17: ELISPOT of Antibody Secreting Cells from Cynomolgus Monkeys Administered with Anti-BCMA/CD3 Bispecific Antibodies This example illustrates the depletion of IgG secreting cells in cynomolgus monkey with anti-BCMA/CD3 bispecific antibodies.

Cynomolgus monkeys (n=2) were dosed via intravenous bolus injection with bispecific anti-BCMA_CD3 antibodies (h2B4-VH-hnps VL_TK), A02_Rd4_0.6nM_C01/H2B4 and Combo_Rd4_0.6nM_C29/H2B at two doses, day 1 and day 8, of 100 ug/kg and 300 ug/kg. Animals were observed twice daily and at each blood collection time point. Peripheral blood mononuclear cells (PBMC) were sampled on days −6, 4 and 10. Bone marrow samples were taken on day 10 when animals were necropsied.

Blood was collected into Becton Dickinson® CPT™ Cell Preparation Tubes containing sodium heparin and a density gradient, and then PBMCs were collected at the gradient interface following centrifugation.

A sample of bone marrow (from femur) was collected by flushing with approximately 5 mL of 100% fetal bovine serum (FBS) and then single cell suspensions were prepared by suspending flushed marrow in 50 ml of buffer.

Cells were counted using the Cellometer Vision and adjusted with complete RPMI 1640 culture medium to a concentration of $5\times10^6$ cells per mL for PBMC and $2\times10^6$ cells per mL for bone marrow cells. Total IgG-secreting cells were enumerated using the ELISpot$^{BASIC}$ kit from Mabtech (#3850-2HW-Plus). Briefly, PBMC or bone marrow cells were added to triplicate wells at specified concentrations (PBMCs at $5\times10^5$/well, and bone marrow cells at $2\times10^5$/well), and then cells were serially diluted in the plate. After an overnight incubation, plates were washed and a biotinylated detection antibody was added. Plates were incubated for 2 hours and streptavidin-HRP was added for 1 hour. IgG spots were visualized using TMB substrate solution and counted using the ImmunoSpot Imaging Analyzer system (CTL) and ImmunoSpot 5.1 software. Data were expressed as the mean (+/−SD) number of IgG-secreting cells from triplicate samples.

The resulting IgG-secreting cell count in PBMC and in bone marrow are listed in Tables 14A and 14B, respectively. Depletion of IgG-secreting cells was seen for both anti-BCMA/CD3 bispecific antibodies in PBMC as compared to pre-dose and bone marrow as compared to vehicle and negative control. A dose dependent effect was seen in the bone marrow.

TABLE 14A

| | Day | | |
|---|---|---|---|
| PBMC | −6 | 4 | 10 |
| Vehicle | 204, 320 | 323, 538 | 127, 137 |
| 0.1 mg/kg Combo_Rd4_0.6 nM_C29 | 107, 128 | 5, 0 | 0, 0 |
| 0.3 mg/kg Combo_Rd4_0.6 nM_C29 | 304, 362 | 0, 5 | 0, 0 |
| 0.1 mg/kg A02_Rd4_0.6 nM_C01 | 447, 672 | 16, 27 | 21, 10 |
| 0.3 mg/kg A02_Rd4_0.6 nM_C01 | 512, 224 | 25, 8 | 0, 0 |
| 0.3 mg/kg NNC_2b41d | 139, 361 | 1345, 1154 | 992, 928 |

TABLE 14B

| Bone Marrow | Day 10 |
|---|---|
| Vehicle | 2614, 8093 |
| 0.1 mg/kg Combo_Rd4_0.6 nM_C29 | 35, 18 |
| 0.3 mg/kg Combo_Rd4_0.6 nM_C29 | 35, 22 |
| 0.1 mg/kg A02_Rd4_0.6 nM_C01 | 996, 960 |
| 0.3 mg/kg A02_Rd4_0.6 nM_C01 | 2170, 93 |
| 0.3 mg/kg NNC_2b41d | 5980, 2893 |

Example 18: Anti-BCMA/CD3 Bispecific Induce Tumor Regression and Inhibition in MM1.S Tumor Model This example illustrates tumor regression and inhibition in an orthotopic MM1.S myeloma model.

Figure 12:
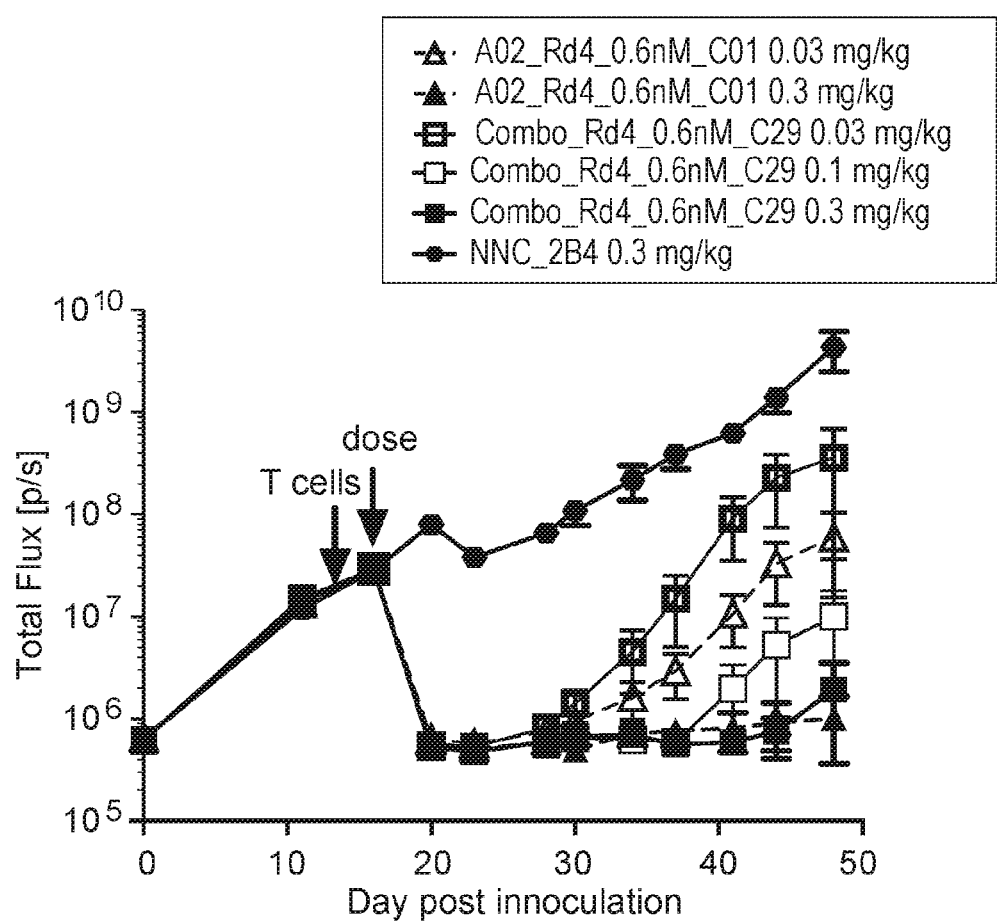
FIG. 12 shows that a single dose of human anti-BCMA/CD3 bispecific antibody resulted in tumor regression in a dose-dependent manner in an orthotopic MM1.S myeloma model.

In vivo efficacy study of BCMA bispecifics was performed with MM1.S, expressing luciferase and GFP, orthotopic model. One day prior to tumor cell injection, mice were irradiated with 100 cGy using RS 2000 Biological Research Irradiator (RAD Source Technolgies, GA). Five million MM1.S LucGFP cells were injected intravenously through the tail vein into 6-8 weeks old female Nod/Scid/IL2Rg$^{−/−}$ (NSG) animals. Intraperitoneal injection of D-luciferin (Regis Technologies, Morton Grove, Ill.) (200 uL per animal at 15 mg/mL), followed by anesthesia with isofluorane and subsequent whole body bioluminescence imaging (BLI) enabled monitoring of tumor burden. Bioluminescent signals emitted by the interaction between luciferase expressed by the tumor cells and luciferin were captured by imaging using an IVIS Spectrum CT (Perkin Elmer, MA) and quantified as total flux (photons/sec) using Living Image 4.4 (Caliper Life Sciences, Alameda, Calif.). When the total flux reached an average of 15E6 for all animals, the animals were injected through bolus tail vein with 20 million expanded T cells from PBMC. Briefly, pan-T cells purchased from AllCells (Alameda, Calif.) were activated with human T Cell Activation/Expansion Kit (Miltenyi, San Diego, Calif.). After three days, 15 U/mL of IL2 (ebioscience, San Diego, Calif.) was added every two days until day 11. Cells were harvested, activation/expansion beads were magnetically removed, and cells were washed and resuspended in PBS. One day post T cell injection, mice were imaged as described above and animals were randomized into groups of seven mice; A02_Rd4_0.6nM_C01 at 0.03 mg/kg and 0.3 mg/kg and Combo_Rd4_0.6nM_C29 at 0.03 mg/kg, 0.1 mg/kg and 0.3 mg/kg. A single dose of human anti-BCMA/CD3 (h2B4-VH-wt VL_TK) bispecific and negative (NNC) control bispecific antibody was administered through bolus tail vein injection. Animals were sacrificed when they exhibited hindlimb paralysis, an endpoint for MM1.S orthotopic model. FIG. 12 shows that a single dose of human anti-BCMA/CD3 bispecific antibody resulted in tumor regression in a dose-dependent manner.

Example 19: Two Doses of Anti-BCMA/CD3 Bispecific Induce Tumor Regression in Aggressive Molp8 Tumor Model This example illustrates tumor regression with two doses of anti-BCMA/CD3 bispecific antibodies in an orthotopic Molp8 myeloma model.

Figure 13:
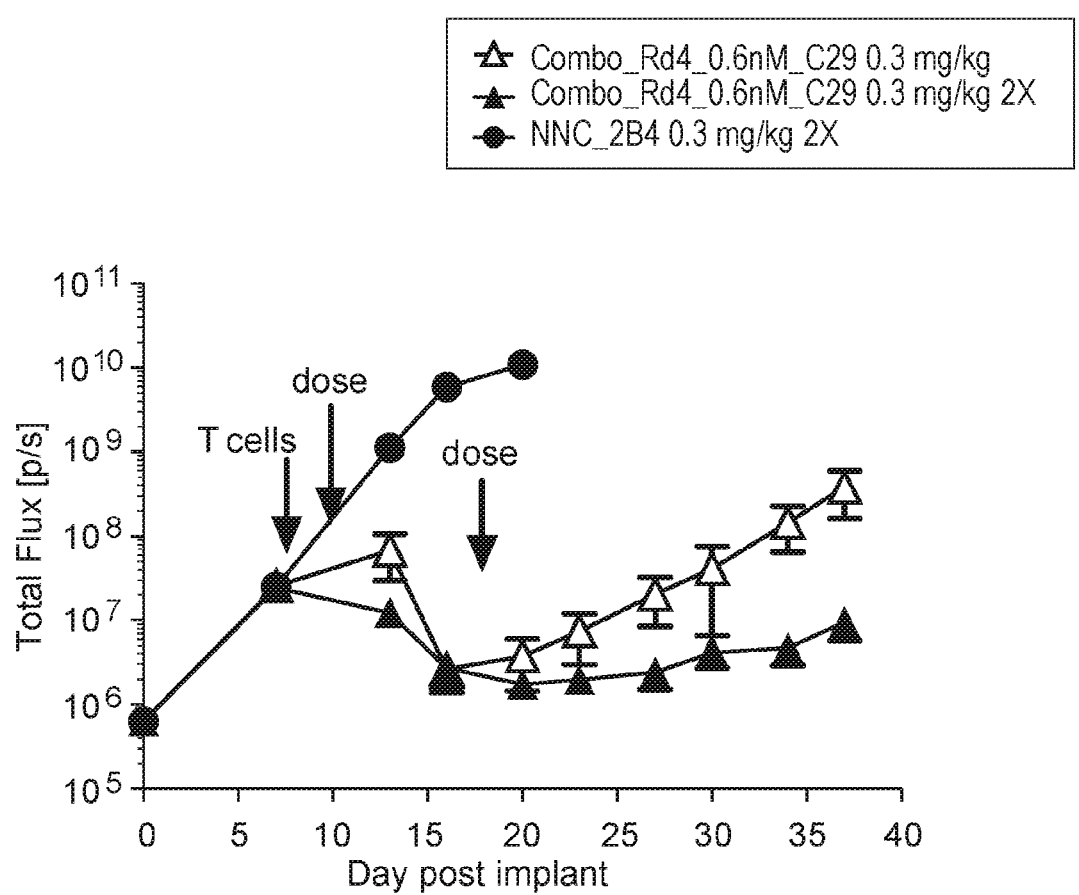
FIG. 13 shows that two doses of human anti-BCMA/CD3 bispecific antibody resulted in increased tumor regression in an orthotopic Molp8 myeloma model.

In vivo efficacy study of BCMA bispecifics was performed with Molp8, expressing luciferase and GFP, orthotopic model. Two million Molp8 LucGFP cells were injected intravenously through the tail vein into 6-8 weeks old female NSG animals. Intraperitoneal injection of D-luciferin (Regis Technologies, Morton Grove, Ill.) (200 uL per animal at 15 mg/mL), followed by anesthesia with isofluorane and subsequent whole body bioluminescence imaging (BLI) enabled monitoring of tumor burden. Bioluminescent signals emitted by the interaction between luciferase expressed by the tumor cells and luciferin were captured by imaging using an IVIS Spectrum CT (Perkin Elmer, MA) and quantified as total flux (photons/sec) using Living Image 4.4 (Caliper Life Sciences, Alameda, Calif.). When the total flux reached an average of 25E6 for all animals were randomized into three groups of seven mice; 1) Combo_Rd4_0.6nM_C29, 0.3 mg/kg, 2) Combo_Rd4_0.6nM_C29, 0.3 mg/kg, two doses and 3) NNC_2B4, 0.3 mg/kg, two doses. The animals were injected through bolus tail vein with 20 million expanded T cells as described in Example 18. Two days post T cell injection, mice were dosed with bispecific antibodies. Animals were sacrificed when they exhibited weight loss of more than 15%, an endpoint for Molp8 orthotopic model. FIG. 13 shows that two doses of human anti-BCMA/CD3 (h2B4-VH-wt VL_TK) bispecific antibody resulted in increased tumor regression.

Example 20: Anti-BCMA/CD3 Bispecific in Combination with Standard of Care for Multiple Myeloma in Orthotopic Molp8 Tumor Model This example demonstrates no opposing effects on anti-BCMA/CD3 bispecific antibodies when combined with bortezomib or lenalidomide and better potency with anti-BCMA/CD3 bispecific antibodies as compared to bortezomib and lenalidomie combined.

Figure 14:
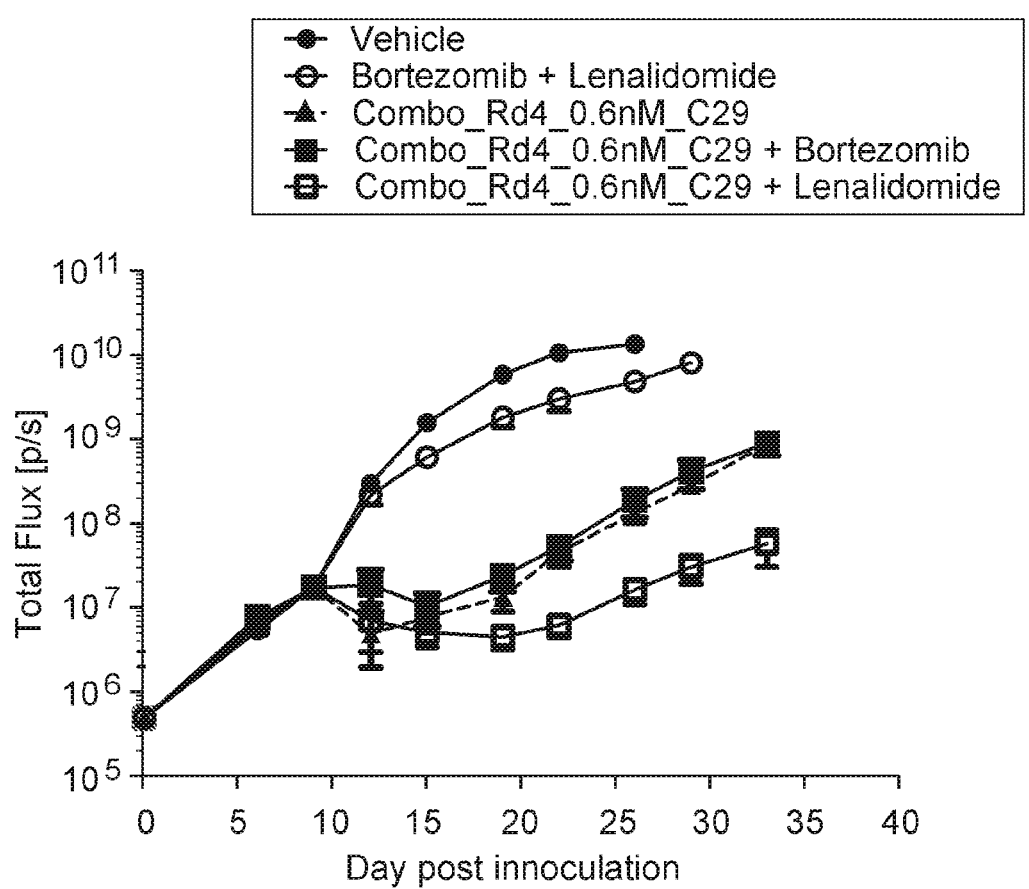
FIG. 14 shows that anti-BCMA/CD3 bispecific antibody alone or in combination with standard of care for multiple myeloma (lenalidomide or bortezomib) is more efficacious than lenalidomide and bortezomib combined in orthotopic Molp8 tumor model.

In vivo efficacy study of BCMA bispecifics was performed with Molp8, expressing luciferase and GFP, orthotopic model. Two million Molp8 LucGFP cells were injected intravenously through the tail vein into 6-8 weeks old female NSG animals. Intraperitoneal injection of D-luciferin (Regis Technologies, Morton Grove, Ill.) (200 uL per animal at 15 mg/mL), followed by anesthesia with isofluorane and subsequent whole body bioluminescence imaging (BLI) enabled monitoring of tumor burden. Bioluminescent signals emitted by the interaction between luciferase expressed by the tumor cells and luciferin were captured by imaging using an IVIS Spectrum CT (Perkin Elmer, MA) and quantified as total flux (photons/sec) using Living Image 4.4 (Caliper Life Sciences, Alameda, Calif.). The animals were injected through bolus tail vein on day 7 with 20 million expanded T cells as described in Example 18. Two days post T cell injection, mice were imaged and randomized into five groups of seven mice with an average of 17E6 total flux/group: 1) Combo_Rd4_0.6nM_C29, 0.3 mg/kg, 2) Combo_Rd4_0.6nM_C29, 0.3 mg/kg and 1 mg/kg bortezomib, 3) Combo_Rd4_0.6nM_C29, 0.3 mg/kg and 50 mg/kg lenalidomide, 4) 1 mg/kg bortezomib and 50 mg/kg lenalidomide and 5) vehicle. Anti-BCMA/CD3 (in PBS) was injected through bolus tail vein injection, bortezomib (in PBS) was administrated via intraperitoneal injection and lenalidomide (30% PEG400/5% propylene glycol/0.5% Tween80) via oral gavage. Vehicle consisted of 30% PEG400/5% propylene glycol/0.5% Tween80, which was administrated via oral gavage. Animals were sacrificed when they exhibit weight loss of more than 15%, an endpoint for Molp8 orthotopic model. FIG. 14 shows that combining an anti-BCMA/CD3 (h2B4-VH-hnps VL_TK) bispecific antibody with bortezomib or lenalidomide did not have a negative effect on the efficacy of the anti-BCMA/CD3 bispecific antibody. In this model, anti-BCMA/CD3 bispecific antibody alone or in combination with lenalidomide or bortezomib is more efficacious than lenalidomide and bortezomib combined.

Example 21: In Vitro Study of Anti-BCMA/CD3 Bispecific in Combination with Lenalidomide, Carfilzomib or Doxorubicin on OPM2 Cell Line This example illustrates no adverse effects on T cell function when combined with carfilzomib, doxorubicin, and lenalidomide for anti-BCMA/CD3 bispecific antibody activity as compared to the bispecific antibody alone.

CD3+ T cells from PBMC were negatively selected using Pan T Cell Isolation kit, human (Miltenyi, San Diego Calif.). OPM2 cells and CD3+ T-cells were seeded in clear U-bottom plates 20000 and 100000 cells/well, respectively. OPM2 and CD3+ T cells were first incubated with the standard of care for two hours at 37°. 1.56 nM carfilzomib and 6.25 nM doxorubicin were diluted in PBS containing 0.02% DMSO. Lenalidomide was diluted in PBS containing 0.1% DMSO at 195 nM. Cells were treated with 10-fold serially diluted bispecific antibody. Three days after treatment, total viable cells were determined by flow cytometry using antibodies to CD138, CD4, and CD8 (Biolegend). Cells were incubated with antibodies at 4° in PBS+0.5% FBS for 30 minutes. Cells were washed and Fixable Viability Dye eFluor 780 (eBioscience, Inc., CA) in PBS was added to the cells for 30 minutes at 4°. Prior to cell acquisition on a BD flow cytometer, cells were washed and CountBright Absolute Counting Beads (Molecular Probes, OR) were added. Percent live cells were determined as live cell count in treated vs untreated wells using counting beads. FIGS. 15A, 15B, and 15C, respectively, show that carfilzomib, lenalidomide, and doxorubicin do not have a negative effect on the function of Combo_Rd4_0.6nM_C29-CD3 (h2B4-VH-hnps VL-TK) bispecific antibody on OPM2 cells.

Example 22: In Vitro Study of Anti-BCMA/CD3 Bispecific in Combination with Lenalidomide and Carfilzomib on KMS12BM Cell Line This example illustrates synergistic effects on anti-BCMA/CD3 bispecific function when combined with carfilzomib and lenalidomide as compared to each molecule alone.

CD3+ T cells from PBMC were negatively selected using Pan T Cell Isolation kit, human (Miltenyi, San Diego Calif.). KMS12BM cells and CD3+ T-cells were seeded in clear U-bottom plates 20000 and 100000 cells/well, respectively. Cells were treated with 0.017 nM anti-BCMA/CD3 bispecific in combination with carfilzomib and a range of concentration for lenalidomide. 1.25 nM carfilzomib was diluted in PBS containing 0.02% DMSO. Lenalidomide was diluted in PBS containing 0.1% DMSO starting at 4 uM diluted 4-fold. Three days after treatment, total viable cells were determined by flow cytometry using antibodies to CD138, CD4, and CD8 (Biolegend, CA). Cells were incubated with antibodies at 4° in PBS+0.5% FBS for 30 minutes. Cells were washed and Fixable Viability Dye eFluor 780 (eBioscience, Inc., CA) in PBS was added to the cells for 30 minutes at 4°. Prior to cell acquisition on a BD flow cytometer, cells were washed and CountBright Absolute Counting Beads (Molecular Probes, OR) were added. Percent live cells were determined as live cell count in treated versus untreated wells using counting beads. FIG. 16 shows that at the concentrations tested, carfilzomib, lenalidomide, and anti-BCMA/CD3 (h2B4-VH-hnps VL-TK) bispecific antibody had very little single agent cytotoxic function. When all three agents were combined, a synergistic effect was observed at a dose-dependent lenalidomide concentration in KMS12BM cells.

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

---

It is claimed:

1. A bispecific antibody comprising a first antibody variable domain and a second antibody variable domain, wherein the first antibody variable domain specifically binds to Cluster of Differentiation 3 (CD3), the second antibody variable domain specifically binds to B-Cell Maturation Antigen (BCMA), and wherein
    (a) the first antibody variable domain comprises a heavy chain variable region complementarity determining region one (VH CDR1) comprising the sequence shown in SEQ ID NO: 333; a VH CDR2 comprising the sequence shown in SEQ ID NO: 417; a VH CDR3 comprising the sequence shown in SEQ ID NO: 335; a light chain variable region CDR1 (VL CDR1) comprising the sequence shown in SEQ ID NO: 343; a VL CDR2 comprising the sequence shown in SEQ ID NO: 341; and a VL CDR3 comprising the sequence shown in SEQ ID NO: 342; and the second antibody variable domain comprises a VH CDR1 comprising the sequence shown in SEQ ID NO: 157; a VH CDR2 comprising the sequence shown in SEQ ID NO: 159; a VH CDR3 comprising the sequence shown in SEQ ID NO: 155; a VL CDR1 comprising the sequence shown in SEQ ID NO: 209; a VL CDR2 comprising the sequence shown in SEQ ID NO: 221; and a VL CDR3 comprising the sequence shown in SEQ ID NO: 225;
(b) the first antibody variable domain comprises a heavy chain variable region complementarity determining region one (VH CDR1) comprising the sequence shown in SEQ ID NO: 331; a VH CDR2 comprising the sequence shown in SEQ ID NO: 336; a VH CDR3 comprising the sequence shown in SEQ ID NO: 335; a light chain variable region CDR1 (VL CDR1) comprising the sequence shown in SEQ ID NO: 343; a VL CDR2 comprising the sequence shown in SEQ ID NO: 341; and a VL CDR3 comprising the sequence shown in SEQ ID NO: 342; and the second antibody variable domain comprises a VH CDR1 comprising the sequence shown in SEQ ID NO: 156; a VH CDR2 comprising the sequence shown in SEQ ID NO:158; a VH CDR3 comprising the sequence shown in SEQ ID NO: 155; a VL CDR1 comprising the sequence shown in SEQ ID NO: 209; a VL CDR2 comprising the sequence shown in SEQ ID NO: 221; and a VL CDR3 comprising the sequence shown in SEQ ID NO: 225;
(c) the first antibody variable domain comprises a heavy chain variable region complementarity determining region one (VH CDR1) comprising the sequence shown in SEQ ID NO: 332; a VH CDR2 comprising the sequence shown in SEQ ID NO: 417; a VH CDR3 comprising the sequence shown in SEQ ID NO: 335; a light chain variable region CDR1 (VL CDR1) comprising the sequence shown in SEQ ID NO: 343; a VL CDR2 comprising the sequence shown in SEQ ID NO: 341; and a VL CDR3 comprising the sequence shown in SEQ ID NO: 342; and the second antibody variable domain comprises a VH CDR1 comprising the sequence shown in SEQ ID NO: 151; a VH CDR2 comprising the sequence shown in SEQ ID NO:159; a VH CDR3 comprising the sequence shown in SEQ ID NO: 155; a VL CDR1 comprising the sequence shown in SEQ ID NO: 209; a VL CDR2 comprising the sequence shown in SEQ ID NO: 221; and a VL CDR3 comprising the sequence shown in SEQ ID NO: 225; or
(d) the first antibody variable domain comprises a heavy chain variable region complementarity determining region one (VH CDR1) comprising the sequence shown in SEQ ID NO: 333; a VH CDR2 comprising the sequence shown in SEQ ID NO: 336; a VH CDR3 comprising the sequence shown in SEQ ID NO: 335; a light chain variable region CDR1 (VL CDR1) comprising the sequence shown in SEQ ID NO: 343; a VL CDR2 comprising the sequence shown in SEQ ID NO: 341; and a VL CDR3 comprising the sequence shown in SEQ ID NO: 342; and the second antibody variable domain comprises a VH CDR1 comprising the sequence shown in SEQ ID NO: 157; a VH CDR2 comprising the sequence shown in SEQ ID NO:158; a VH CDR3 comprising the sequence shown in SEQ ID NO: 155; a VL CDR1 comprising the sequence shown in SEQ ID NO: 209; a VL CDR2 comprising the sequence shown in SEQ ID NO: 221; and a VL CDR3 comprising the sequence shown in SEQ ID NO: 225.

2. The bispecific antibody of claim 1, wherein the second antibody variable domain comprises a VH CDR2 comprising the sequence shown in SEQ ID NO: 159.

3. The bispecific antibody of claim 1, wherein the bispecific antibody further comprises a human IgG2 heavy chain constant region.

4. The bispecific antibody of claim 3, wherein the human IgG2 heavy chain constant region is a modified human IgG2 heavy chain constant region, as compared to a wild type human IgG2 heavy chain constant region.

5. The bispecific antibody of claim 3, wherein the bispecific antibody comprises two human IgG2 heavy chain constant regions, wherein one heavy chain constant region comprises the sequence shown in SEQ ID NO: 496 and the other heavy chain constant region comprises the sequence shown in SEQ ID NO: 497.

6. The bispecific antibody of claim 1, further comprising two heavy chain constant regions, wherein one heavy chain constant region comprises the sequence shown in SEQ ID NO: 496.

7. The bispecific antibody of claim 1, further comprising two heavy chain constant regions, wherein one heavy chain constant region comprises the sequence shown in SEQ ID NO: 497.

8. The bispecific antibody of claim 1, wherein the first antibody variable domain comprises a heavy chain variable region comprising the sequence shown in SEQ ID NO: 324, and a light chain variable region comprising the sequence shown in SEQ ID NO: 323; and
the second antibody variable domain comprises a heavy chain variable region comprising the sequence shown in SEQ ID NO: 112, and a light chain variable region comprising the sequence shown in SEQ ID NO: 38.

9. The bispecific antibody of claim 1, wherein the first antibody variable domain comprises a heavy chain variable region comprising the sequence shown in SEQ ID NO: 324, and a light chain variable region comprising the sequence shown in SEQ ID NO: 323; and
the second antibody variable domain comprises a heavy chain variable region encoded by the polynucleotide sequence shown in SEQ ID NO: 486, and a light chain variable region encoded by the polynucleotide sequence shown in SEQ ID NO: 485.

10. The bispecific antibody of claim 9, further comprising two heavy chain constant regions, wherein one heavy chain constant region comprises the sequence shown in SEQ ID NO: 496 and the other heavy chain constant region comprises the sequence shown in SEQ ID NO: 497.

11. The bispecific antibody of claim 1, wherein
the first antibody variable domain comprises a heavy chain variable region comprising the sequence shown in SEQ ID NO: 324, and a light chain variable region comprising the sequence shown in SEQ ID NO: 323; and
the second antibody variable domain comprises a heavy chain variable region encoded by the polynucleotide having ATCC Accession No. PTA-122094, and a light chain variable region encoded by the polynucleotide having ATCC Accession No. PTA-122093.

12. The bispecific antibody of claim 11, further comprising two heavy chain constant regions, wherein one heavy chain constant region comprises the sequence shown in SEQ ID NO: 496 and the other heavy chain constant region comprises the sequence shown in SEQ ID NO: 497.

13. A bispecific antibody comprising a first antibody variable domain and a second antibody variable domain, wherein
the first antibody variable domain comprises a heavy chain variable region comprising the sequence shown in SEQ ID NO: 324, and a light chain variable region comprising the sequence shown in SEQ ID NO: 323; and the second antibody variable domain comprises a heavy chain variable region comprising the sequence shown in SEQ ID NO: 112, and a light chain variable region comprising the sequence shown in SEQ ID NO: 38.

14. A bispecific antibody comprising a first antibody variable domain and a second antibody variable domain, wherein the first antibody variable domain comprises a heavy chain variable region comprising the sequence shown in SEQ ID NO: 324, and a light chain variable region comprising the sequence shown in SEQ ID NO: 323; and the second antibody variable domain comprises a heavy chain variable region encoded by the polynucleotide sequence shown in SEQ ID NO: 486, and a light chain variable region encoded by the polynucleotide sequence shown in SEQ ID NO: 485.

* * * * *